(12) United States Patent
Kao et al.

(10) Patent No.: US 7,586,600 B2
(45) Date of Patent: Sep. 8, 2009

(54) NORMALIZATION OF DATA

(75) Inventors: H. Pin Kao, Fremont, CA (US); Ian A. Harding, San Mateo, CA (US); Achim Karger, Foster City, CA (US); Mark F. Oldham, Los Gatos, CA (US); Omead Ostadan, San Francisco, CA (US); Greg Young, Menlo Park, CA (US)

(73) Assignee: Applied Biosystem, LLC, Carlsbad, CA (US)

( * ) Notice: Subject to any disclaimer, the term of this patent is extended or adjusted under 35 U.S.C. 154(b) by 0 days.

(21) Appl. No.: 12/176,656

(22) Filed: Jul. 21, 2008

(65) Prior Publication Data
US 2008/0288179 A1 Nov. 20, 2008

Related U.S. Application Data

(63) Continuation of application No. 11/087,103, filed on Mar. 22, 2005, now Pat. No. 7,417,726, which is a continuation-in-part of application No. 10/913,601, filed on Aug. 5, 2004, now Pat. No. 7,233,393, and a continuation-in-part of application No. 10/944,673, filed on Sep. 17, 2004, now abandoned, and a continuation-in-part of application No. 10/944,691, filed on Sep. 17, 2004, now abandoned, said application No. 10/944,691 is a continuation-in-part of application No. 10/913,601, filed on Aug. 5, 2004, now Pat. No. 7,233,393.

(60) Provisional application No. 60/504,500, filed on Sep. 19, 2003, provisional application No. 60/504,052, filed on Sep. 19, 2003, provisional application No. 60/589,244, filed on Jul. 19, 2004, provisional application No. 60/589,225, filed on Jul. 19, 2004, provisional application No. 60/601,716, filed on Aug. 13, 2004, provisional application No. 60/504,052, filed on Sep. 19, 2003, provisional application No. 60/504,500, filed on Sep. 19, 2003, provisional application No. 60/589,224, filed on Jul. 19, 2004, provisional application No. 60/589,225, filed on Jul. 19, 2004.

(51) Int. Cl.
*G01N 31/00* (2006.01)
*G01J 1/10* (2006.01)

(52) U.S. Cl. .................. 356/243.1; 356/417; 356/418; 702/85; 436/8

(58) Field of Classification Search ................. 356/417, 356/418, 419
See application file for complete search history.

(56) References Cited

FOREIGN PATENT DOCUMENTS

WO  WO 02/052038 A2 * 7/2002

* cited by examiner

Primary Examiner—F. L Evans

(57) ABSTRACT

Methods for normalizing output from an instrument employing a reference standard or non-fluorescing substance disposed within at least one of a plurality of reaction chambers. The method comprises collecting and analyzing a signal associated with the reference standard or non-fluorescing substance to determine a normalizing bias. The normalizing bias is then applied to the data signal collected from a remainder of the plurality of reaction chambers.

17 Claims, 136 Drawing Sheets

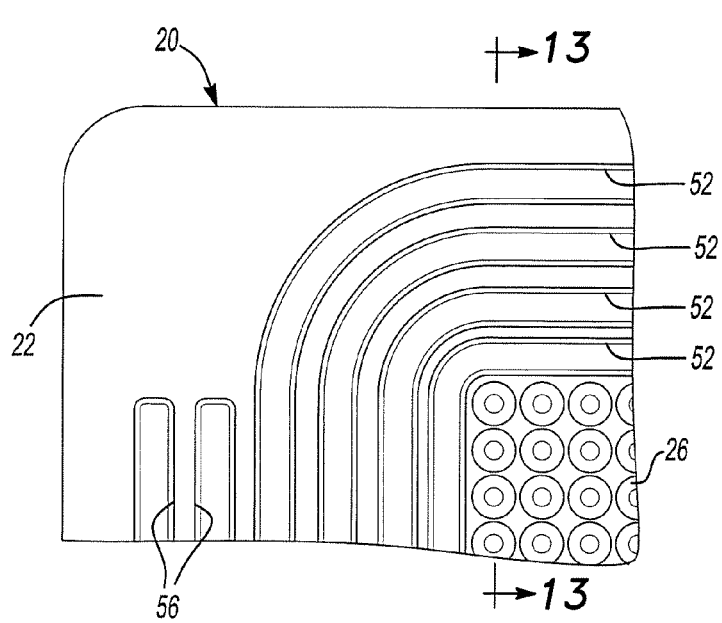
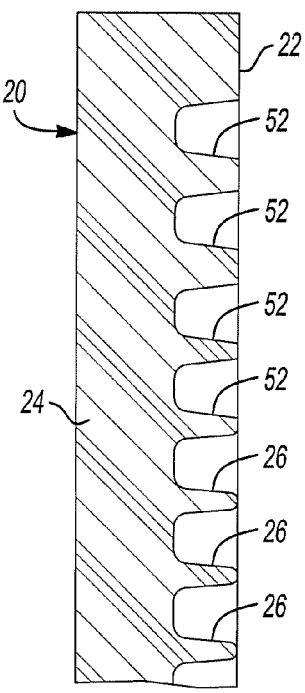
Fig-12
Fig-13
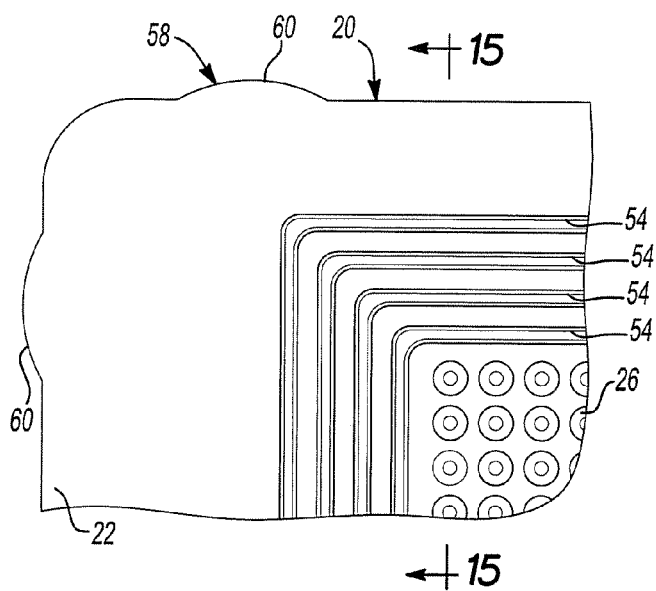
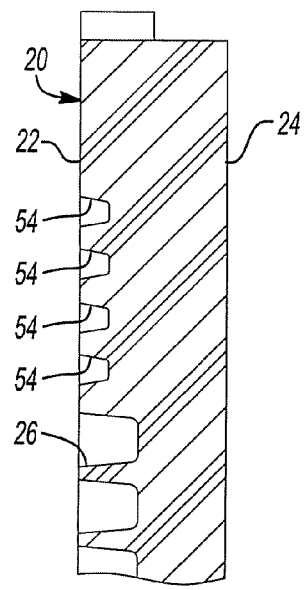
Fig-14
Fig-15

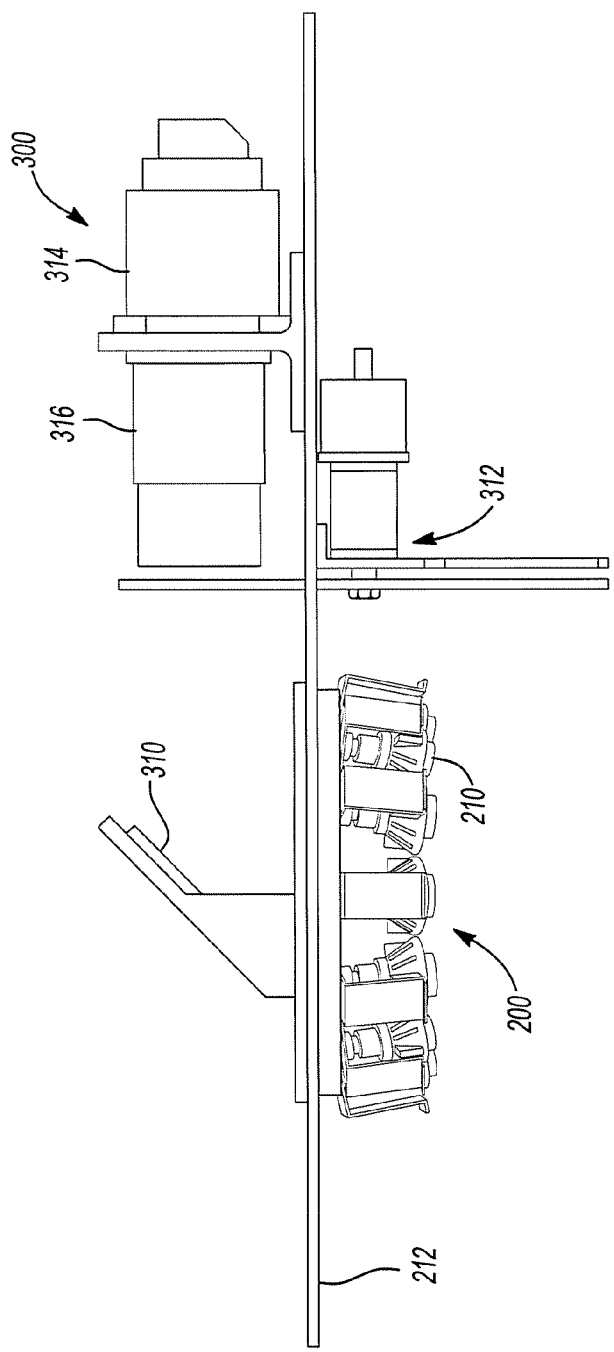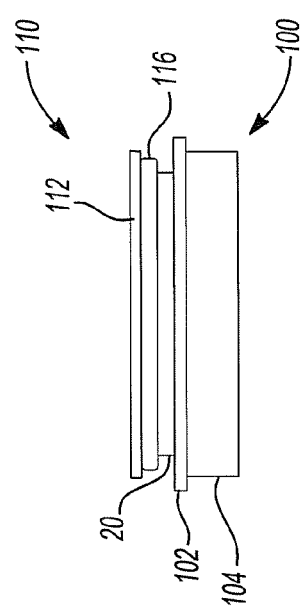
Fig-43

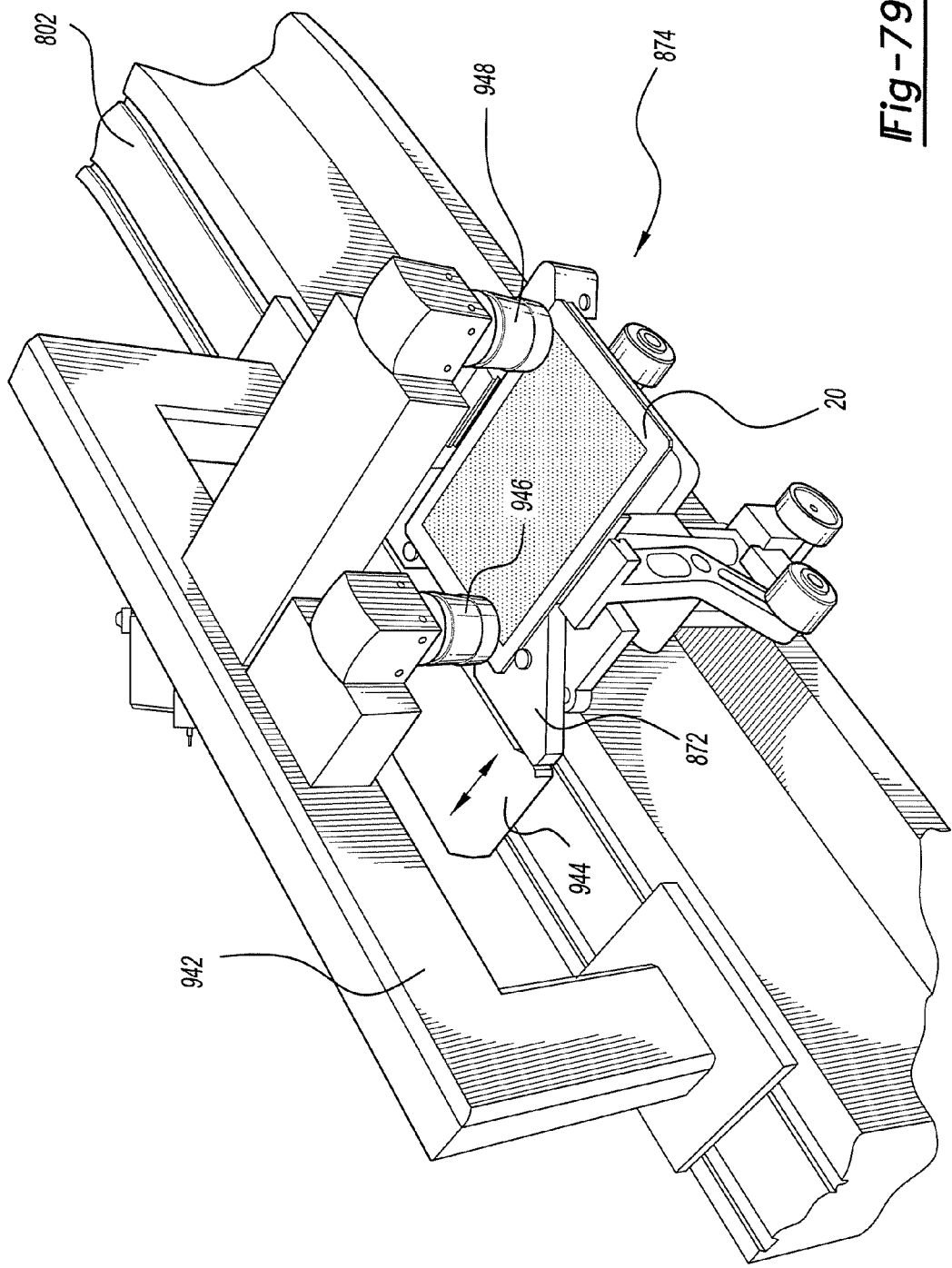

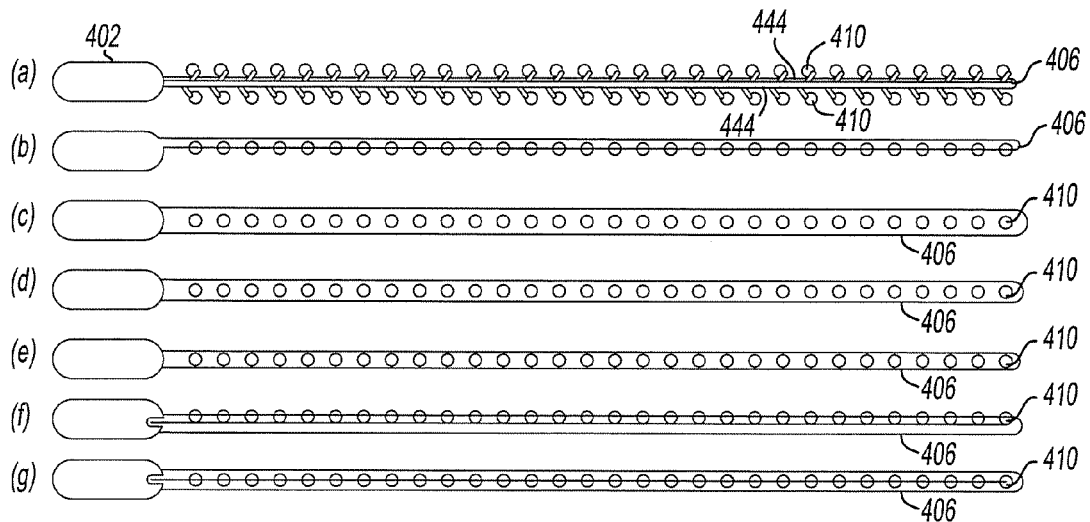
Fig-141
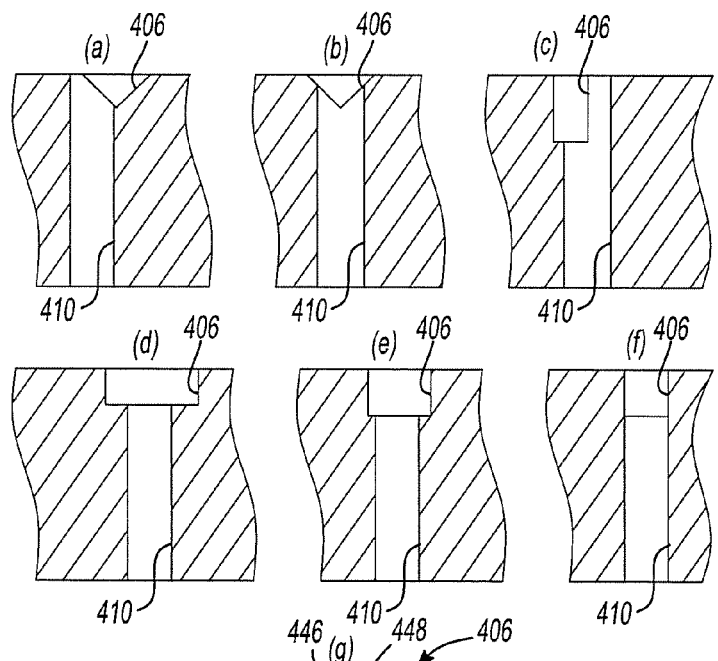
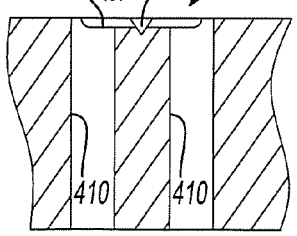
Fig-142

NORMALIZATION OF DATA

CROSS-REFERENCE TO RELATED APPLICATIONS

This application is a continuation of U.S. patent application Ser. No. 11/087,103 filed on Mar. 22, 2005, which is a continuation-in-part of U.S. patent application Ser. No. 10/913,601 filed on Aug. 5, 2004, U.S. patent application Ser. No. 10/944,673 filed on Sep. 17, 2004, now abandoned, and U.S. patent application Ser. No. 10/944,691 filed on Sep. 17, 2004, now abandoned. U.S. patent application Ser. No. 10/944,673 claims a benefit to U.S. Provisional Application No. 60/504,500 filed on Sep. 19, 2003; U.S. Provisional Application No. 60/504,052 filed on Sep. 19, 2003; U.S. Provisional Application No. 60/589,224 filed Jul. 19, 2004; U.S. Provisional Application No. 60/589,225 filed on Jul. 19, 2004; and U.S. Provisional Application No. 60/601,716 filed on Aug. 13, 2004. U.S. patent application Ser. No. 10/944,691 is a continuation-in-part of U.S. patent application Ser. No. 10/913,601 filed on Aug. 5, 2004, which further claims the benefit of U.S. Provisional Application No. 60/504,052 filed on Sep. 19, 2003; U.S. Provisional Application No. 60/504,500 filed on Sep. 19, 2003; U.S. Provisional Application No. 60/589,224 filed Jul. 19, 2004; U.S. Provisional Application No. 60/589,225 filed on Jul. 19, 2004; and U.S. Provisional Application No. 60/601,716 filed on Aug. 13, 2004.

All literature and similar materials cited in this application, including but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

INTRODUCTION

Currently, genomic analysis, including that of the estimated 30,000 human genes is a major focus of basic and applied biochemical and pharmaceutical research. Such analysis may aid in developing diagnostics, medicines, and therapies for a wide variety of disorders. However, the complexity of the human genome and the interrelated functions of genes often make this task difficult. There is a continuing need for methods and apparatus to aid in such analysis.

DRAWINGS

The skilled artisan will understand that the drawings, described herein, are for illustration purposes only. The drawings are not intended to limit the scope of the present teachings in any way.

FIG. 12 is an enlarged top view illustrating a corner of the microplate illustrated in FIG. 11;

FIG. 13 is a cross-sectional view of the microplate of FIG. 12 taken along Line 13-13;

FIG. 14 is an enlarged top view illustrating a corner of a microplate according to some embodiments;

FIG. 15 is a cross-sectional view of the microplate of FIG. 14 taken along Line 15-15;

Figure 26:
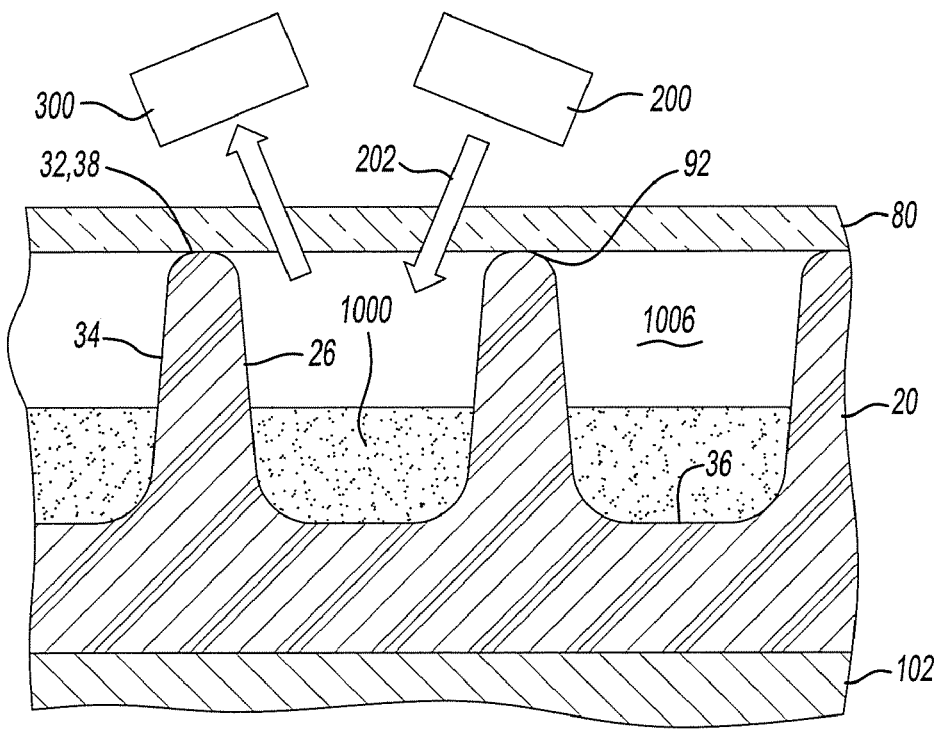
Figure 27:
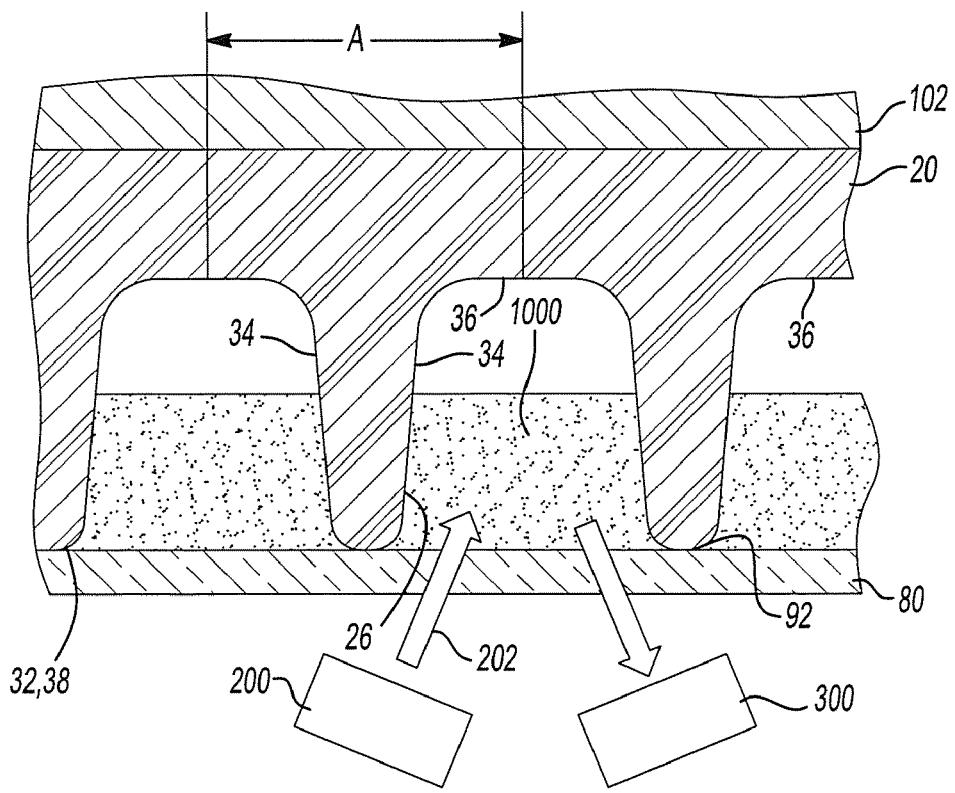
Figure 28:
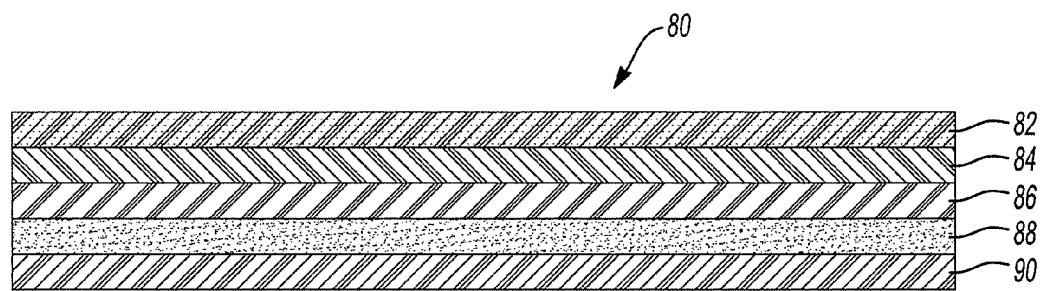
Figure 29:
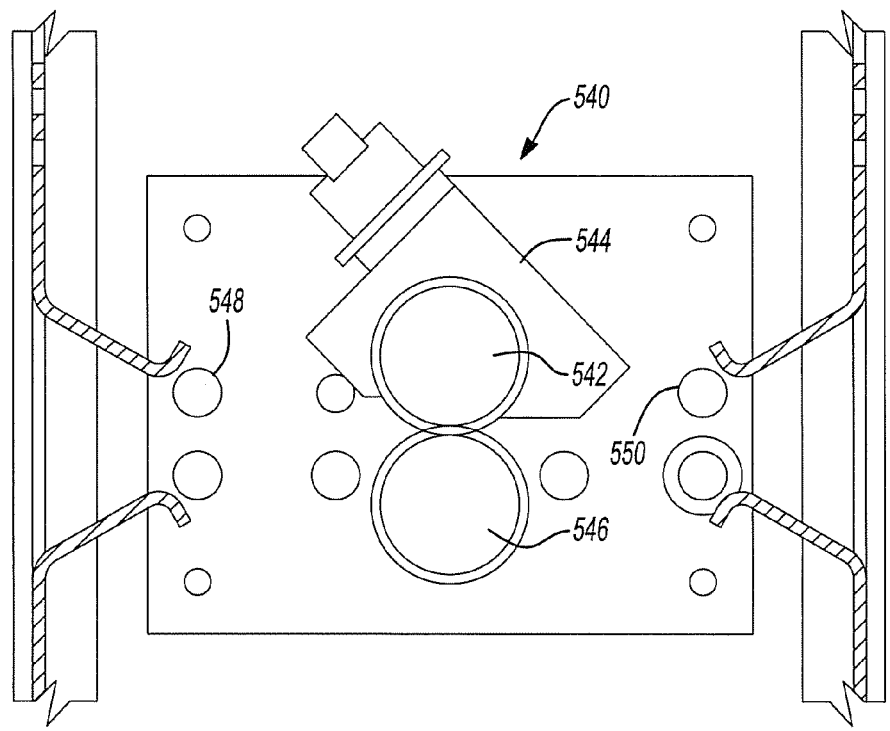
Figure 30:
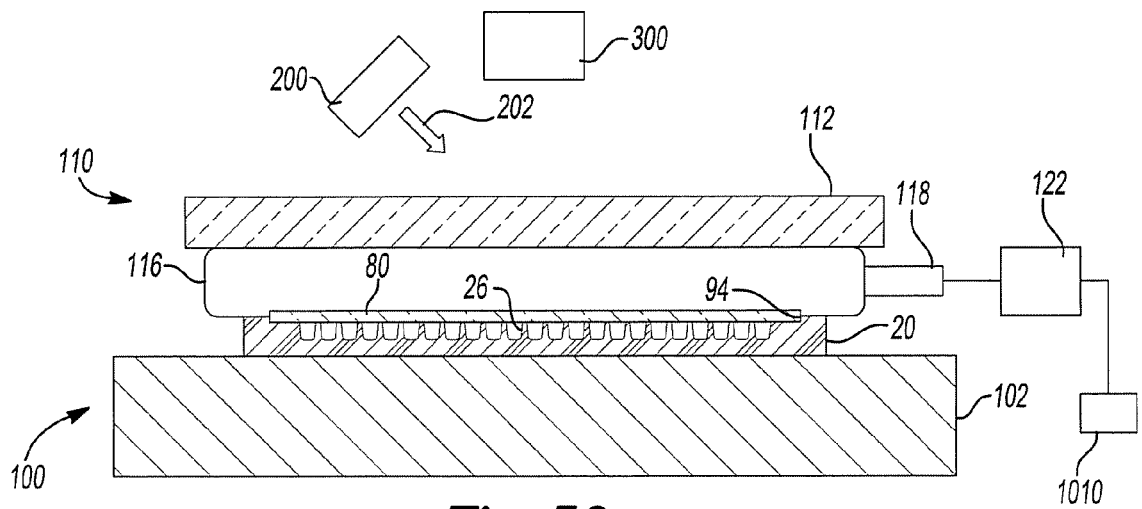
Figure 31:
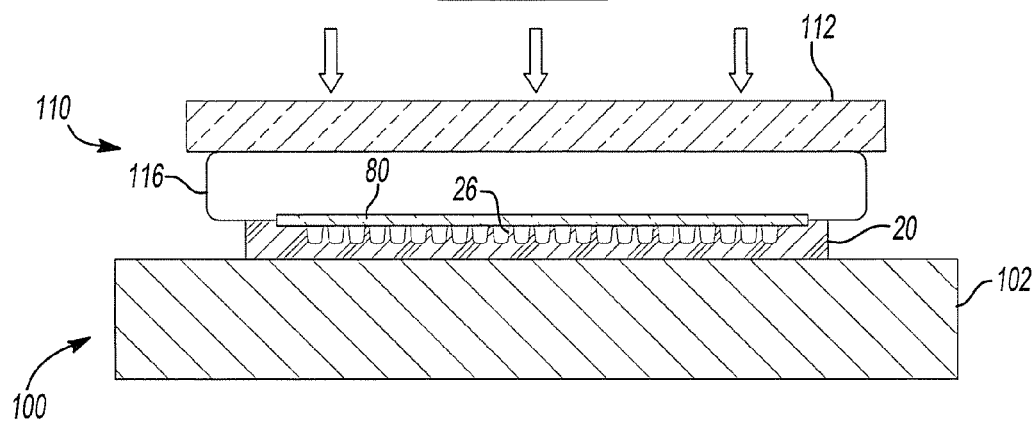
Figure 32:
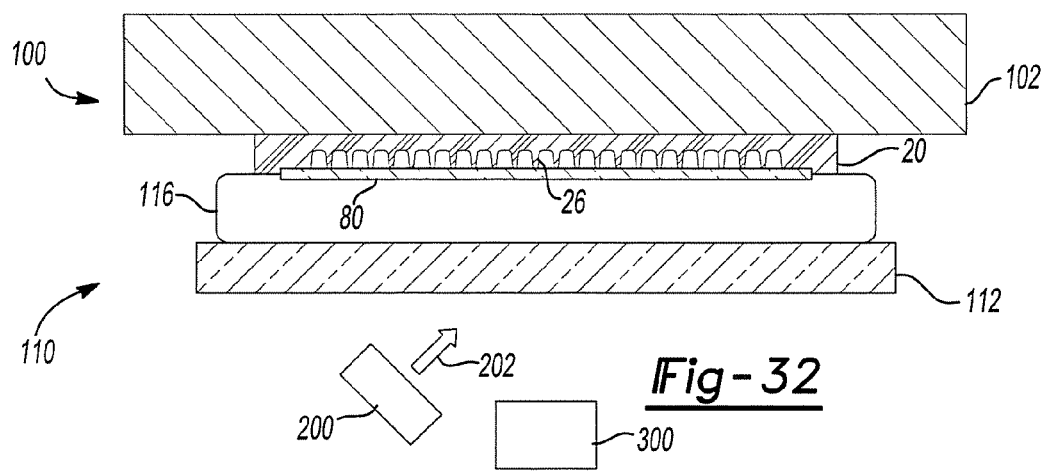
Figure 33:
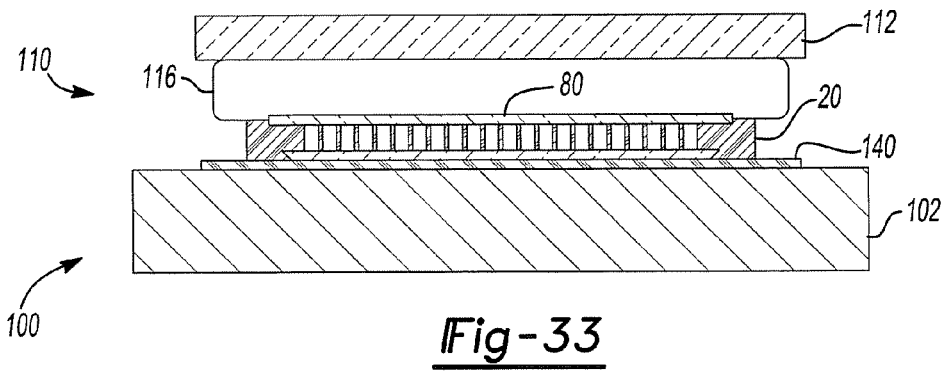
Figure 34:
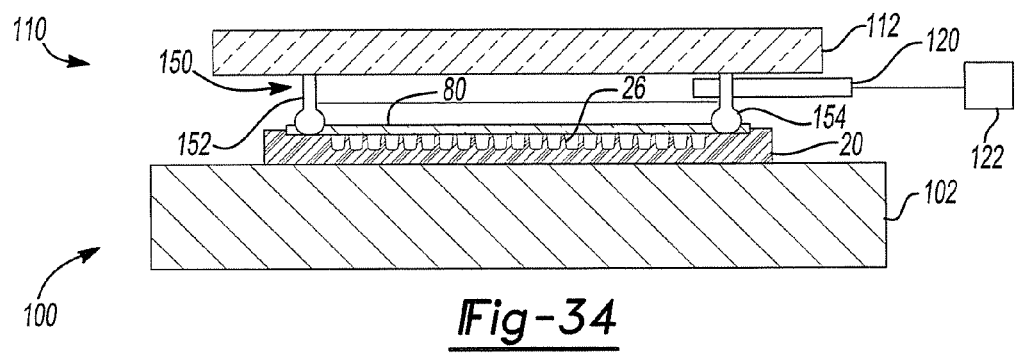
Figure 35:
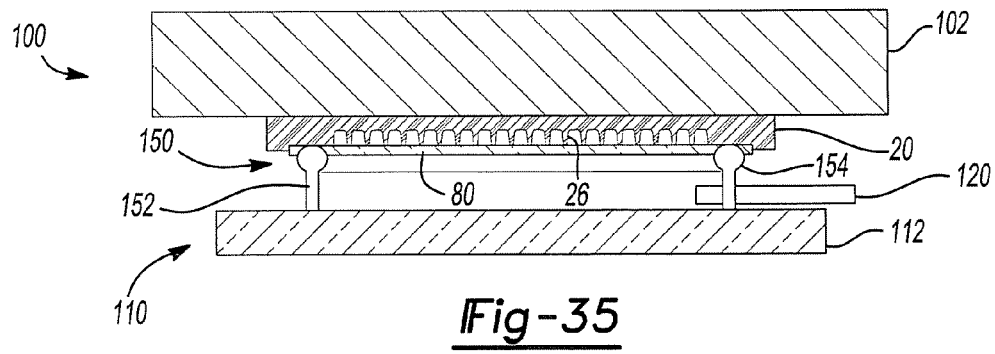
Figure 36:
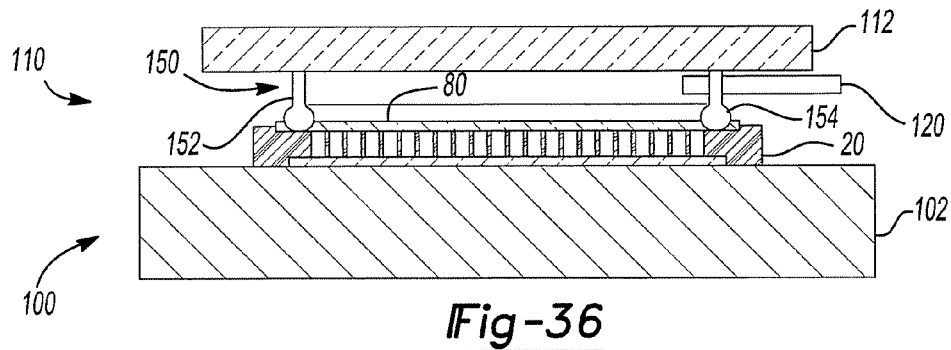
Figure 37:
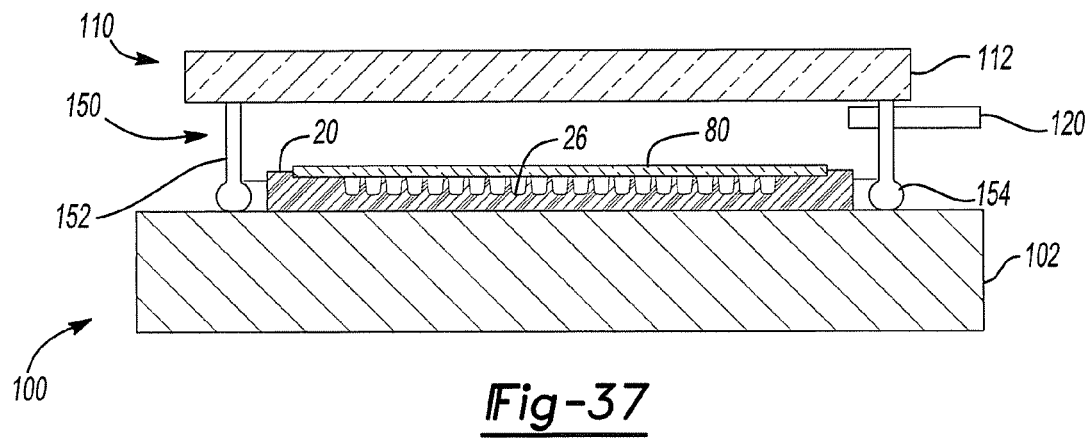
Figure 38:
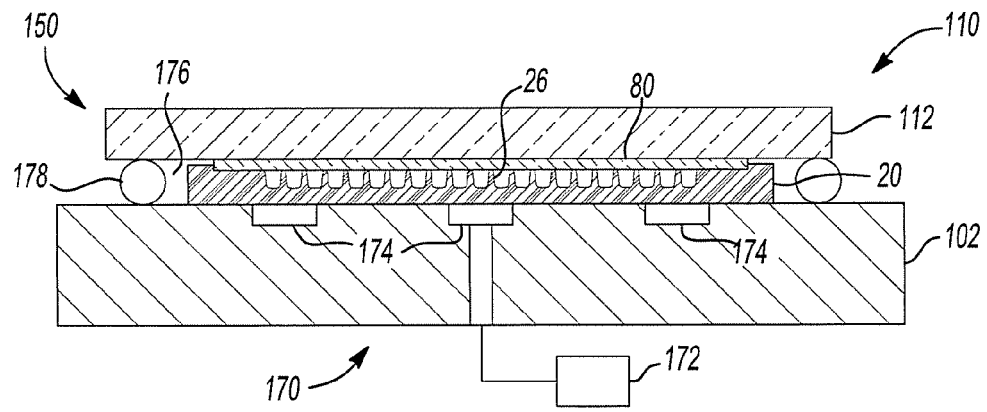
Figure 39:
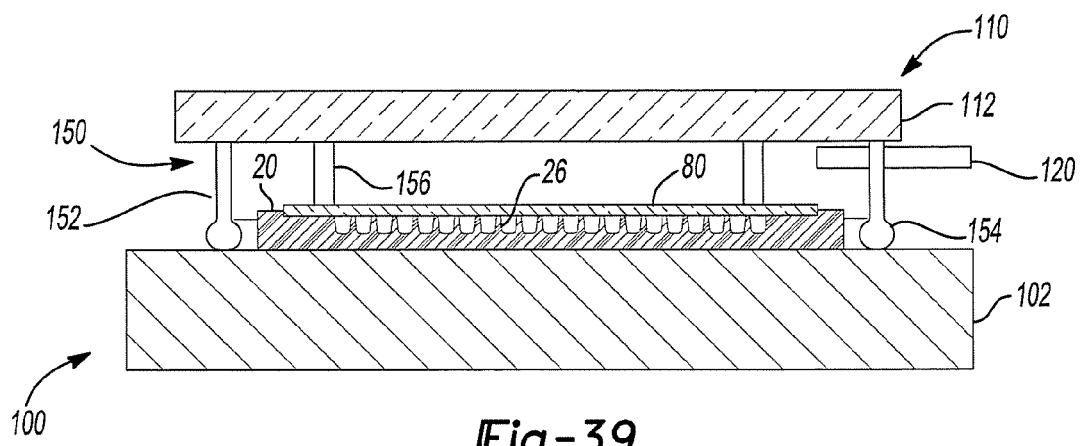
Figure 40:
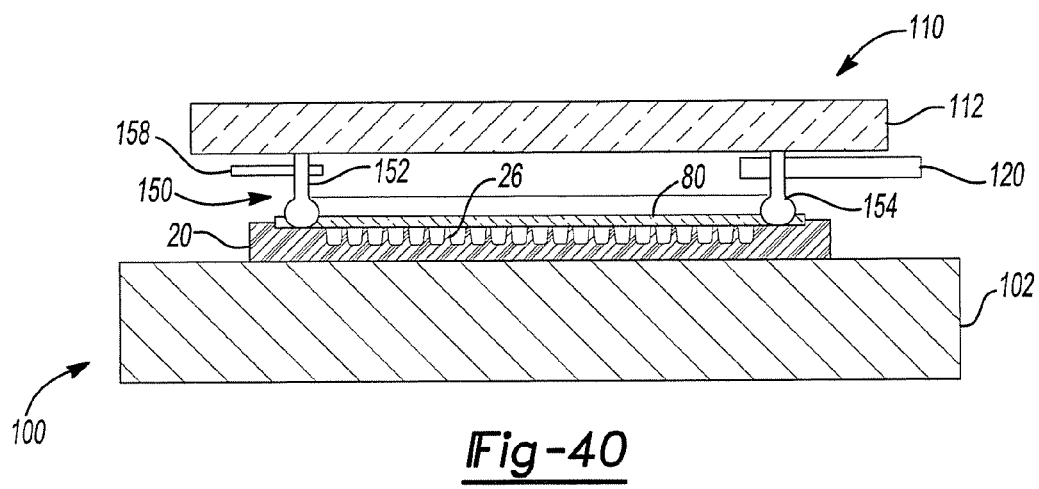
Figure 41:
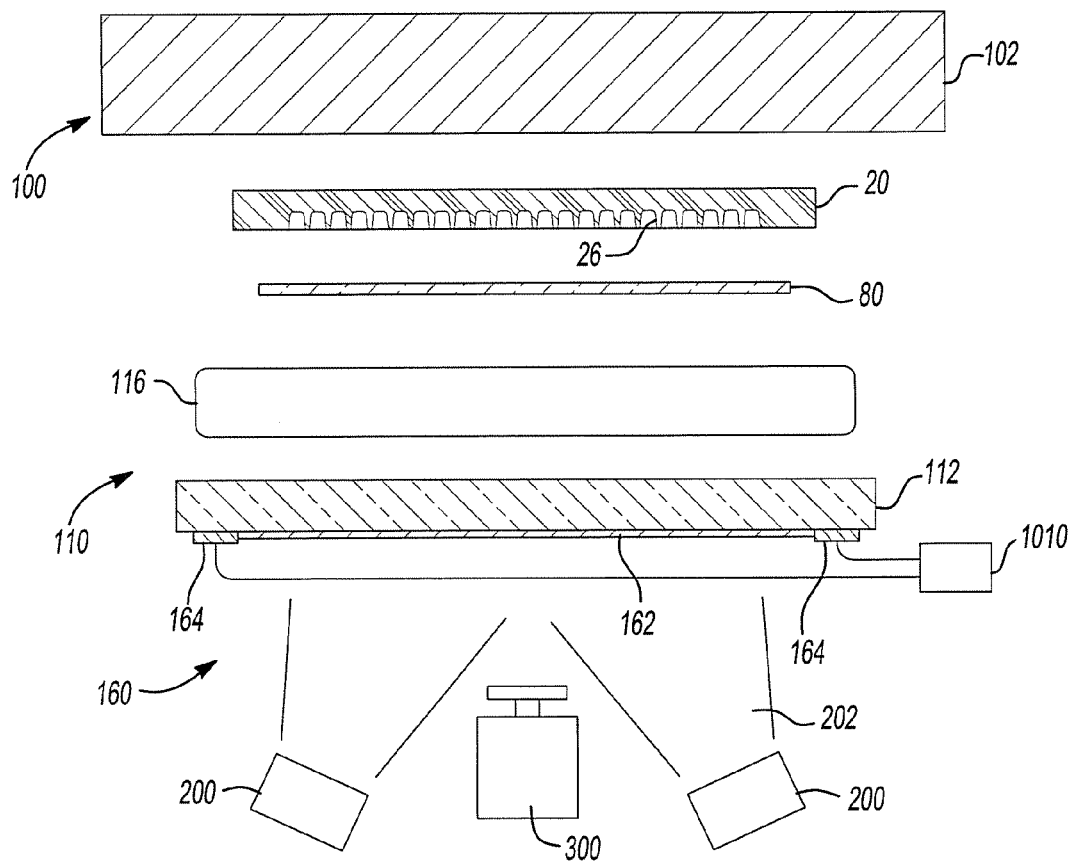
Figure 42:
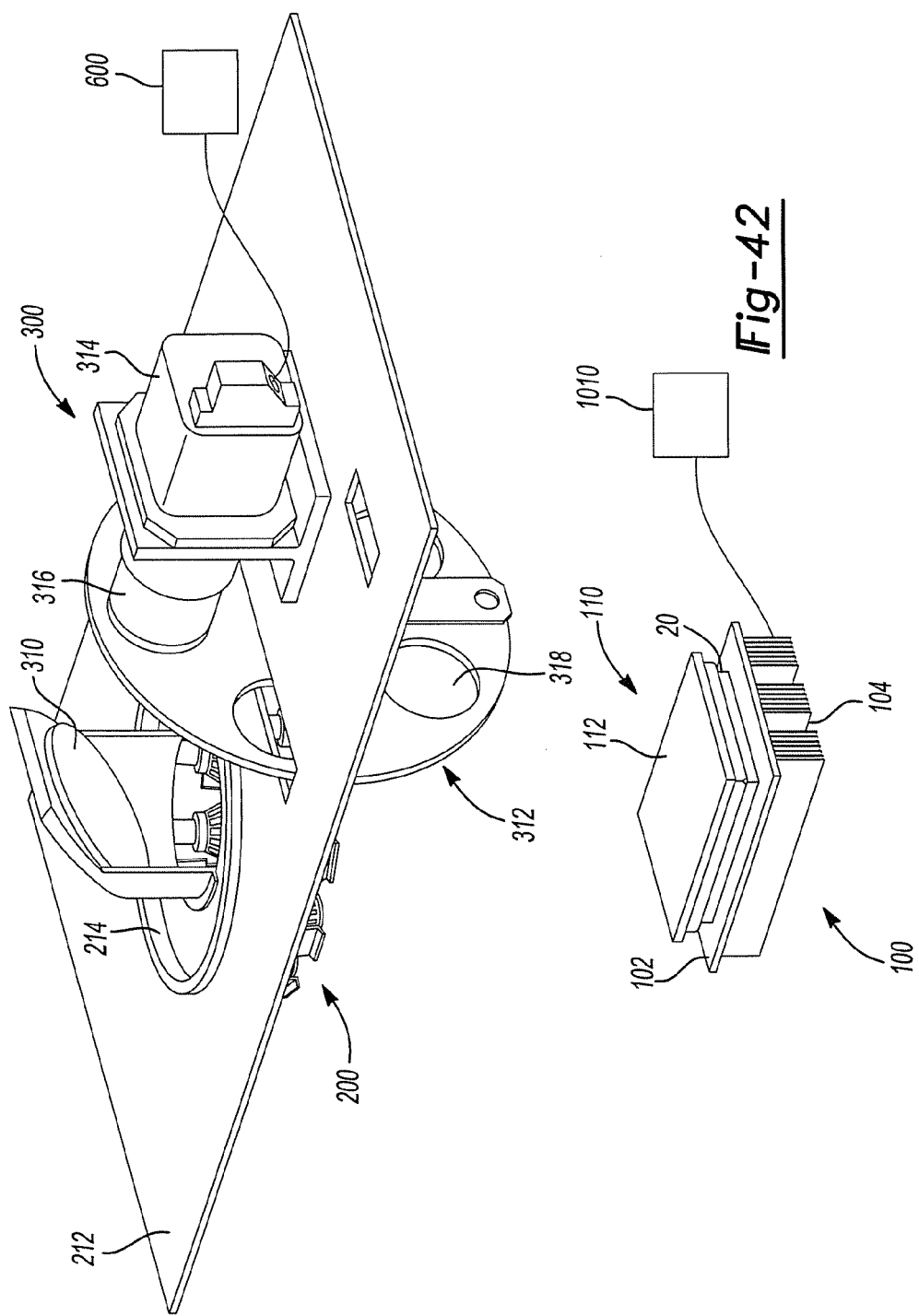
Figure 44:
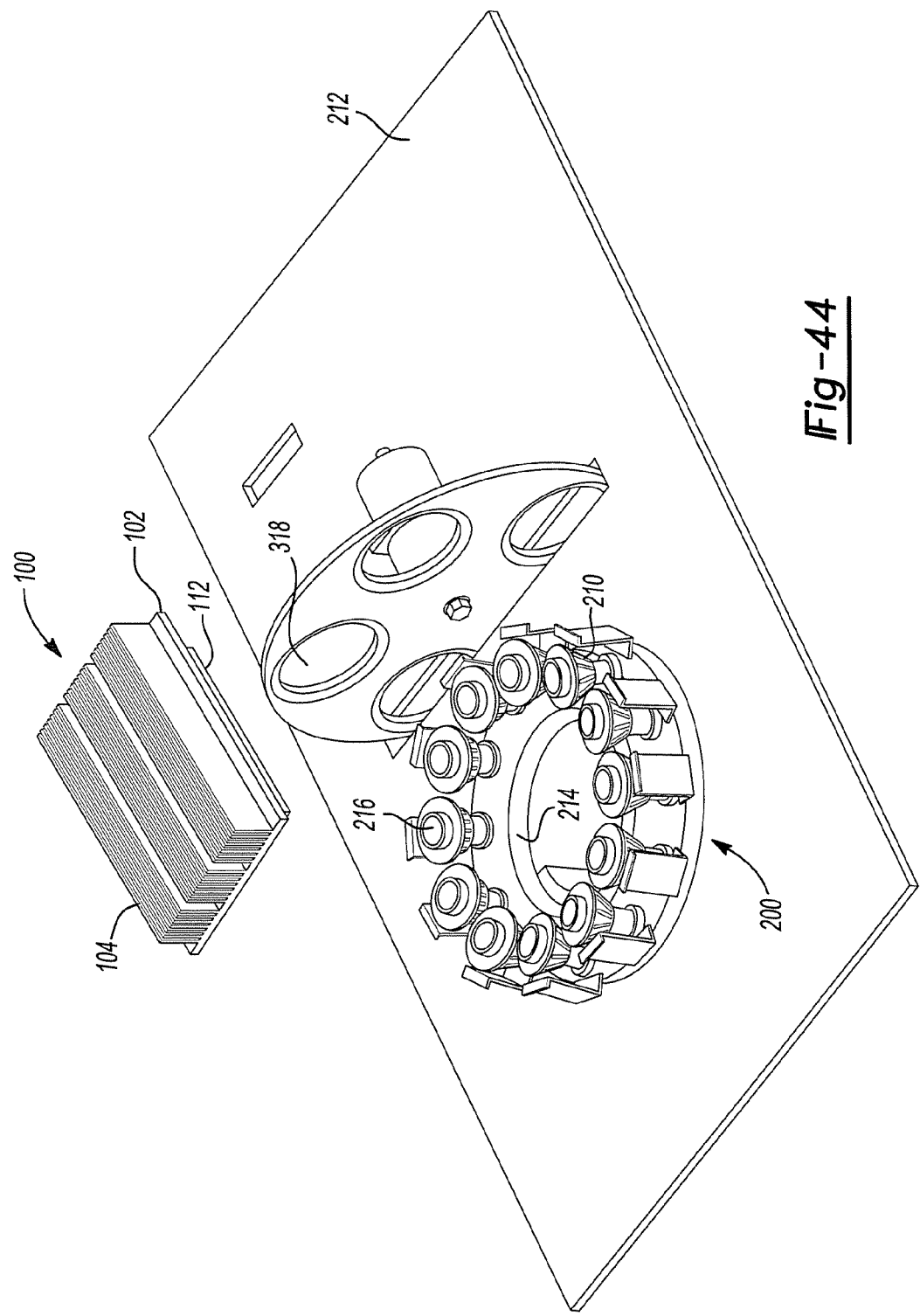
Figure 45:
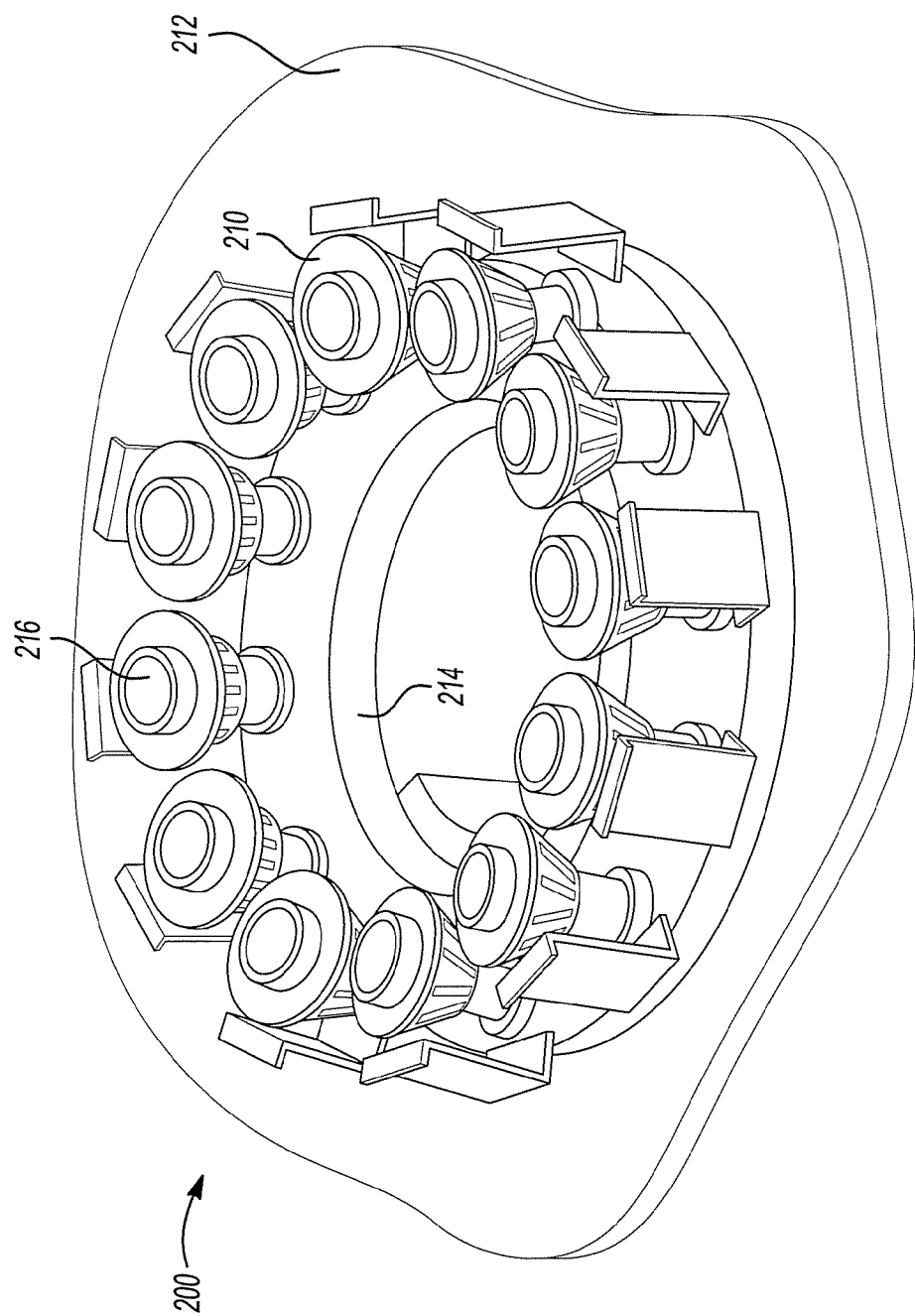
Figure 46:
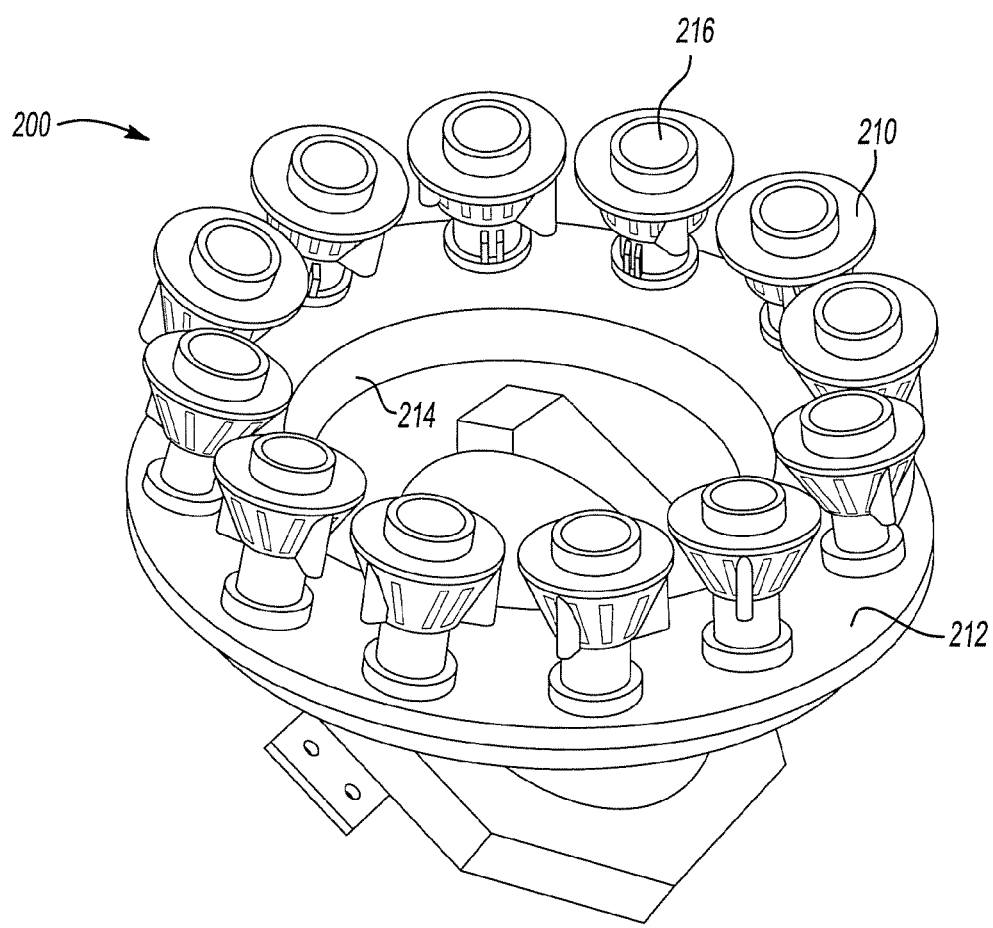
Figure 47:
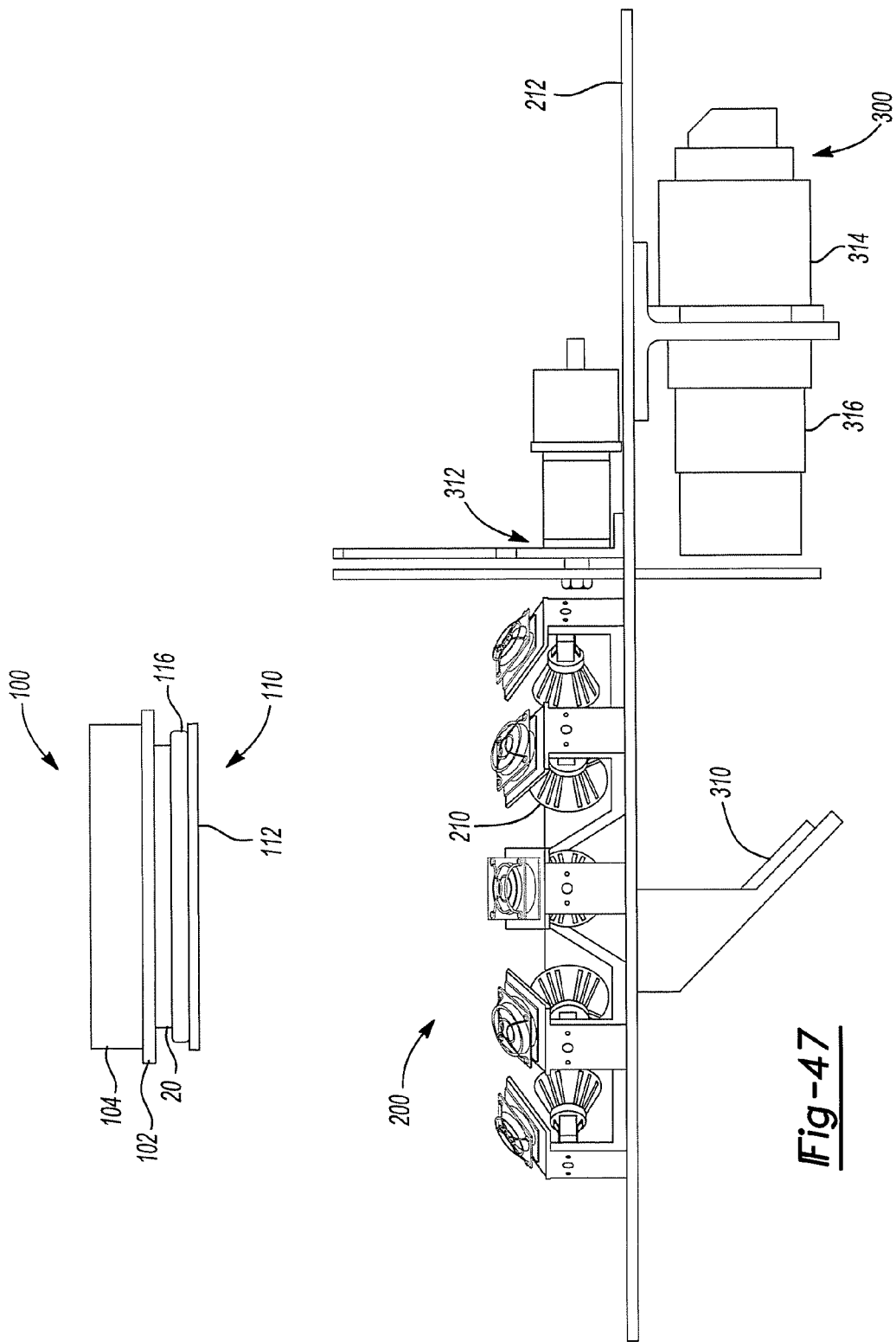
Figure 48:
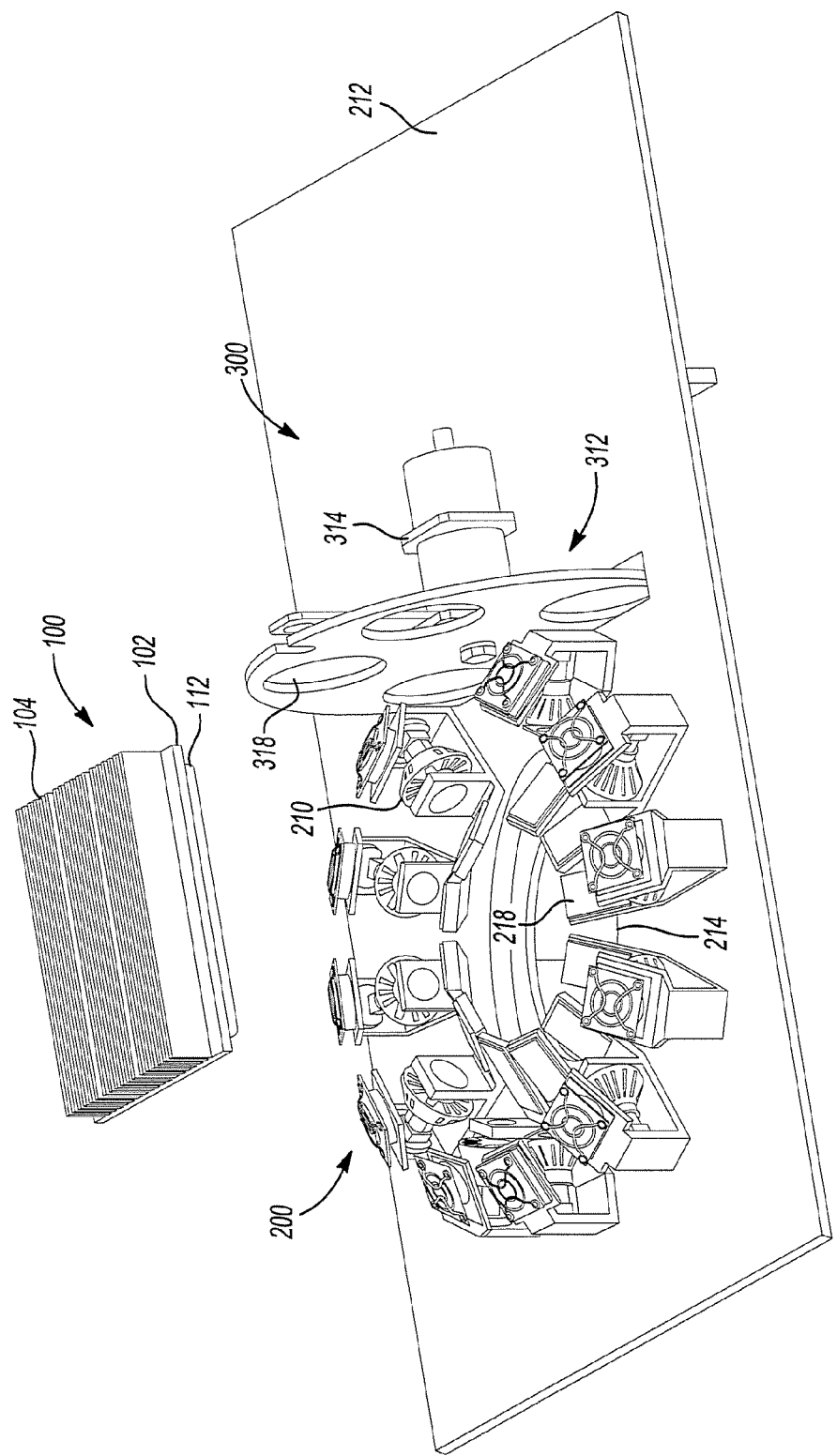
Figure 49:
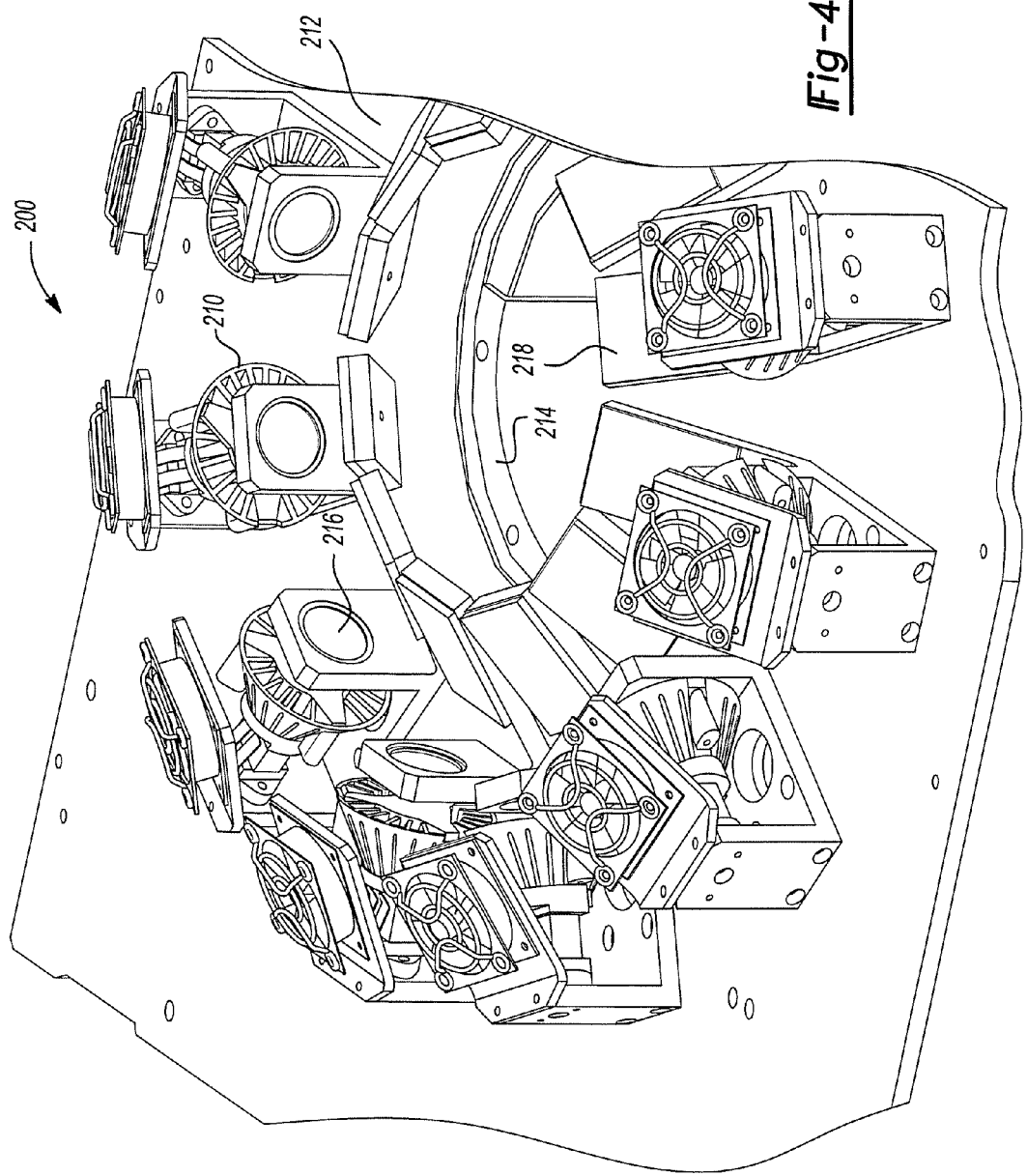
Figure 50:
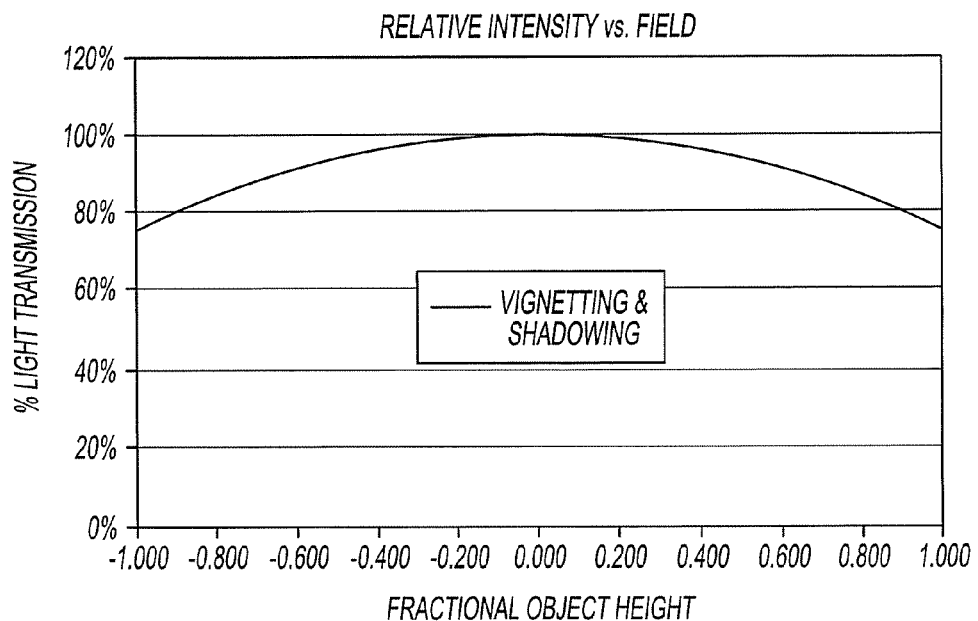
Figure 51:
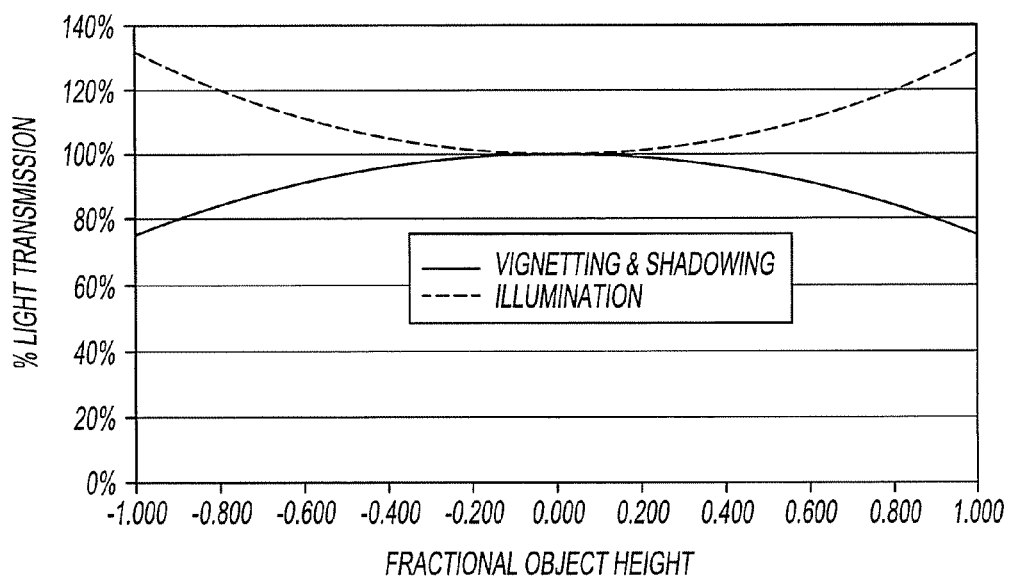
Figure 52:
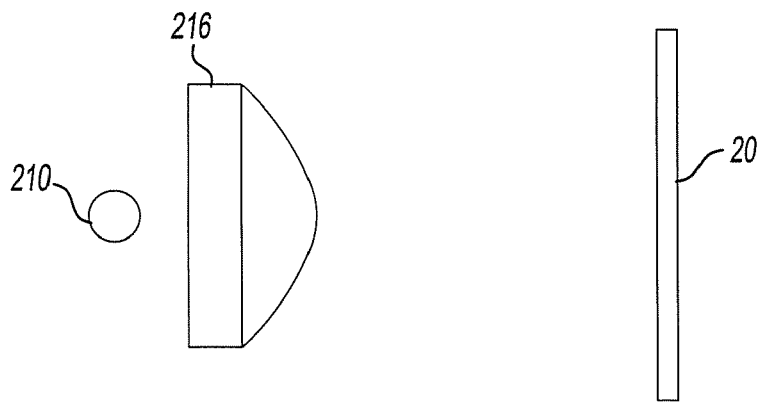
Figure 53:
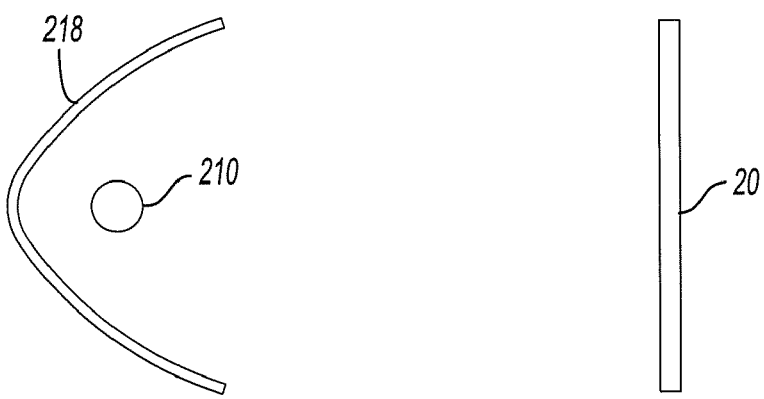
Figure 54:
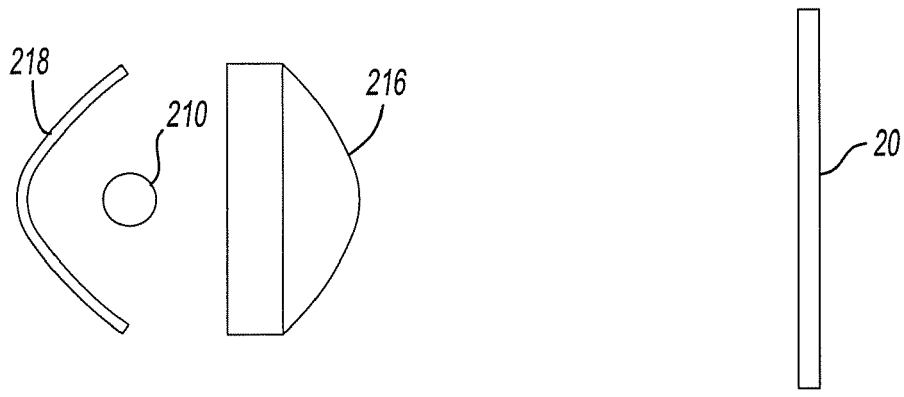
Figure 55:
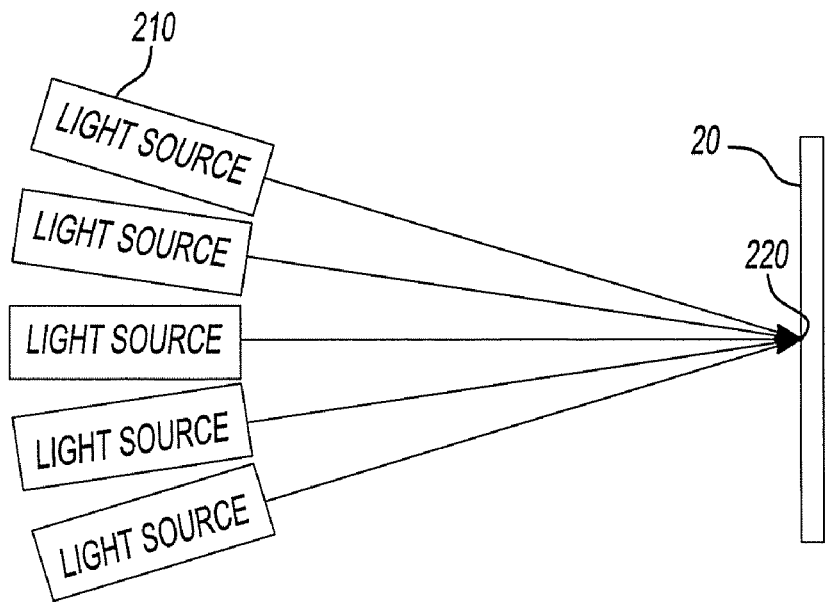
Figure 56:
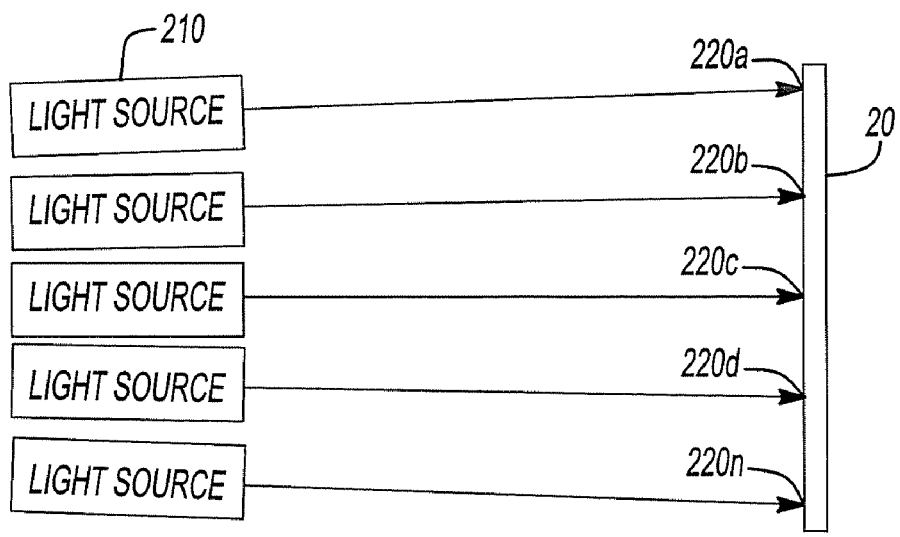
Figure 57:
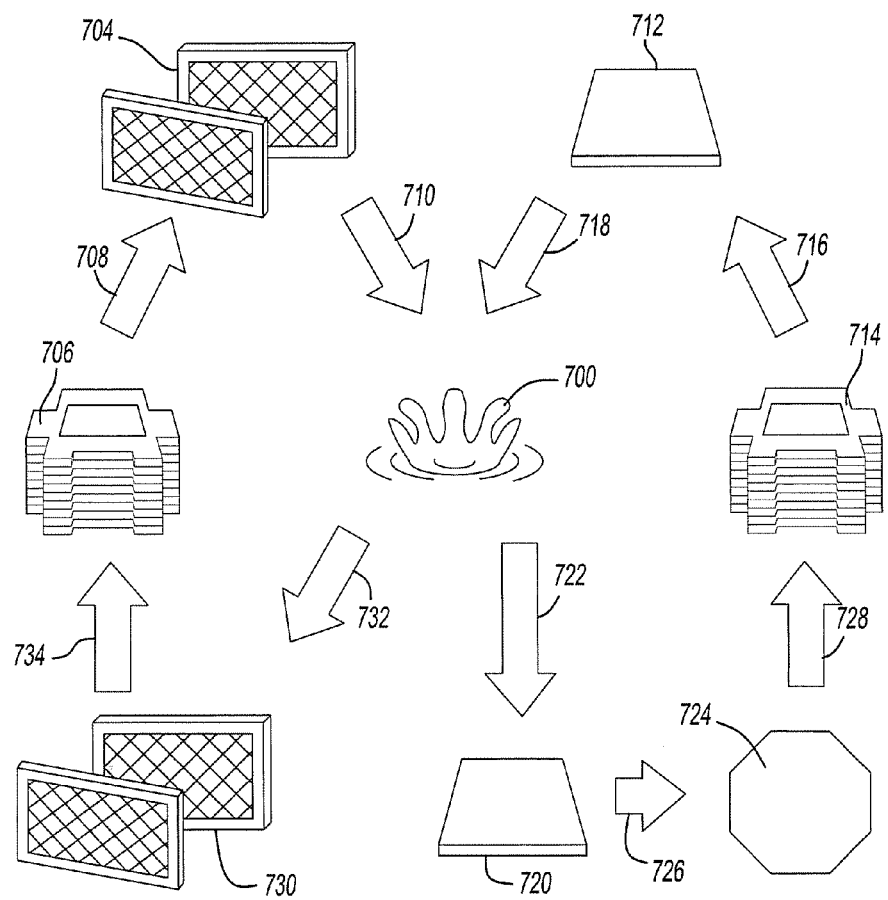
Figure 58:
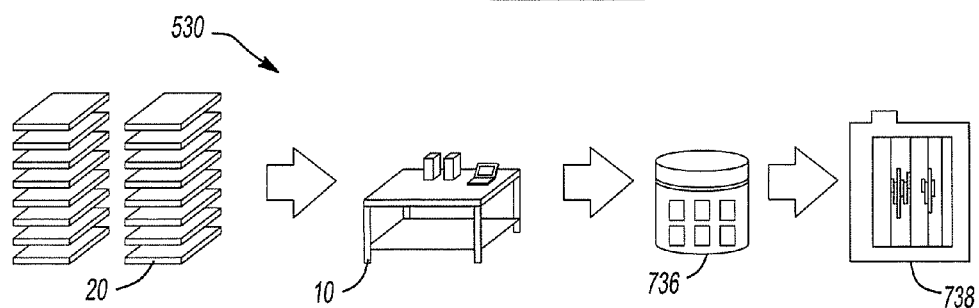
Figure 59:
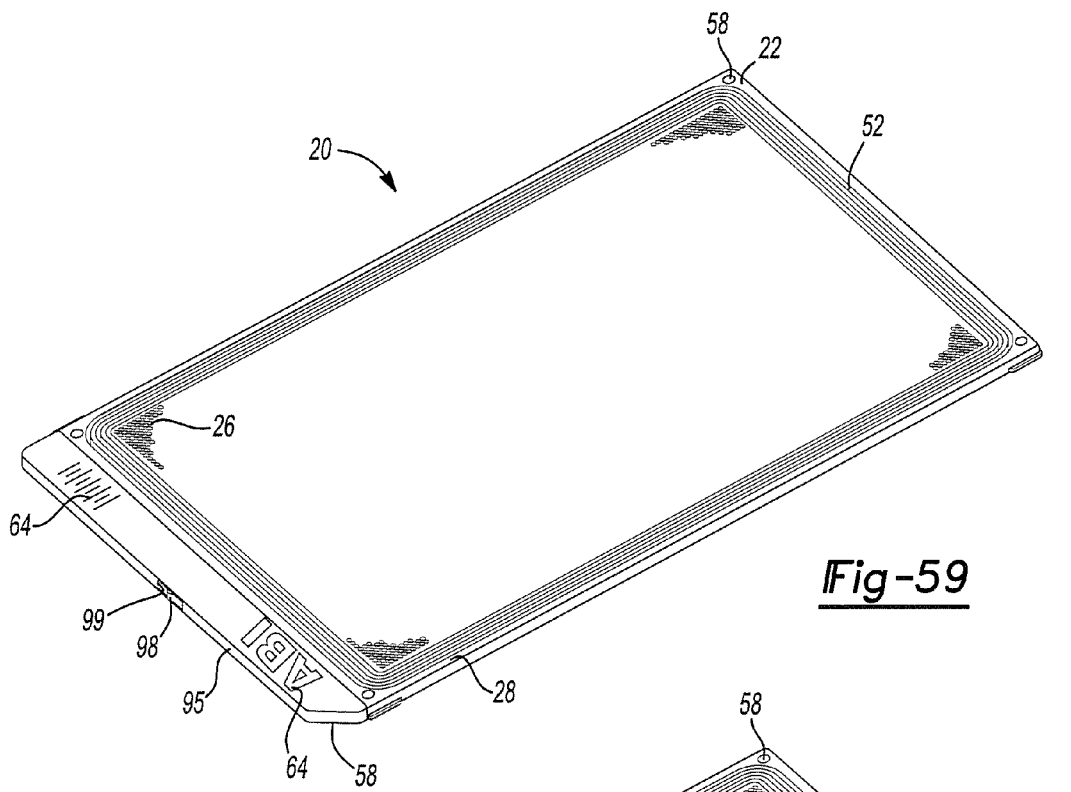
Figure 60:
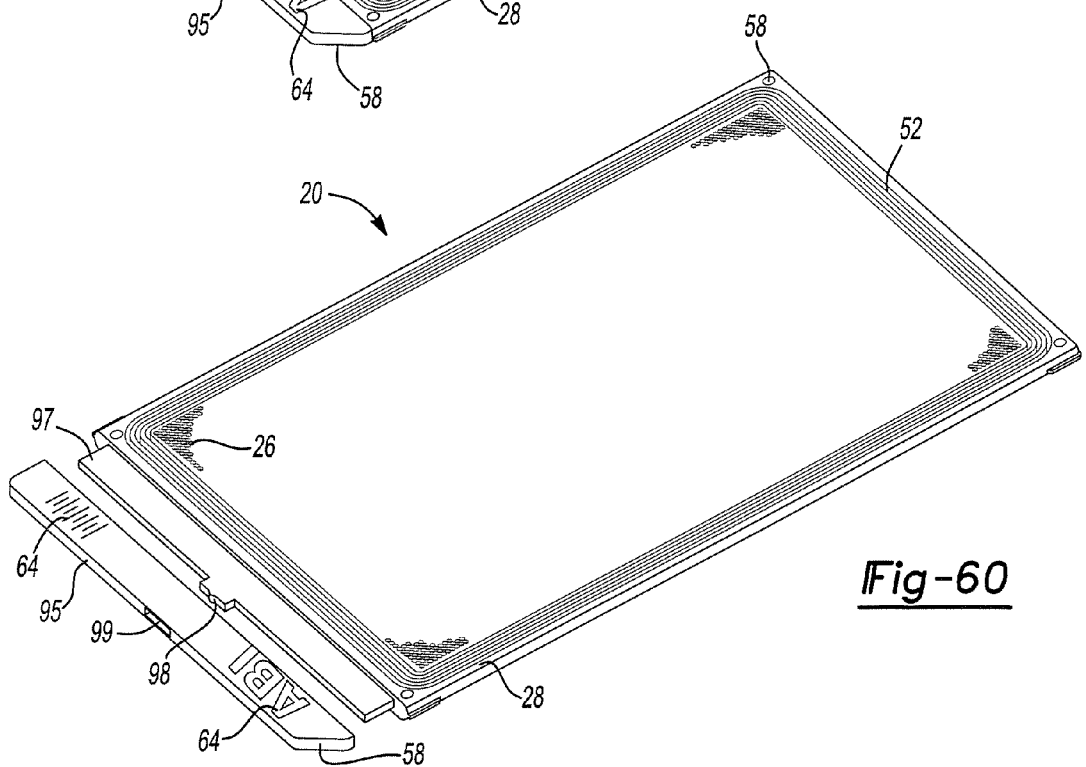
Figure 61:
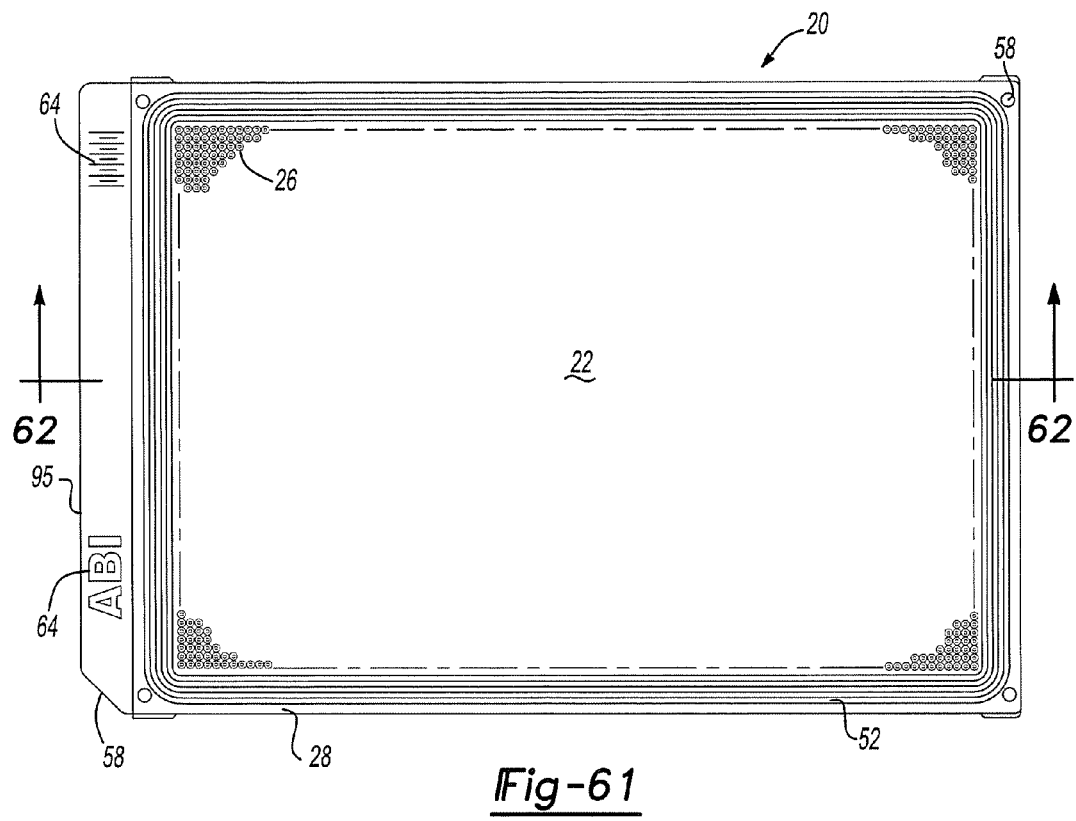
Figure 62:
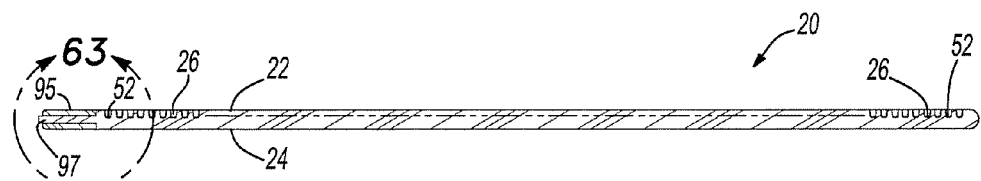
Figure 63:
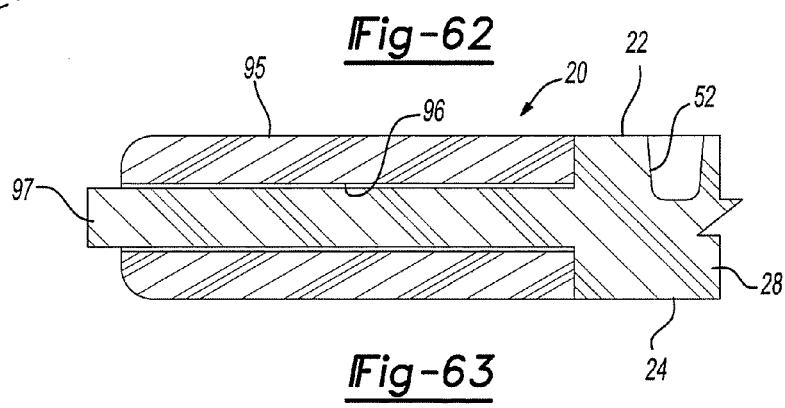
Figure 64:
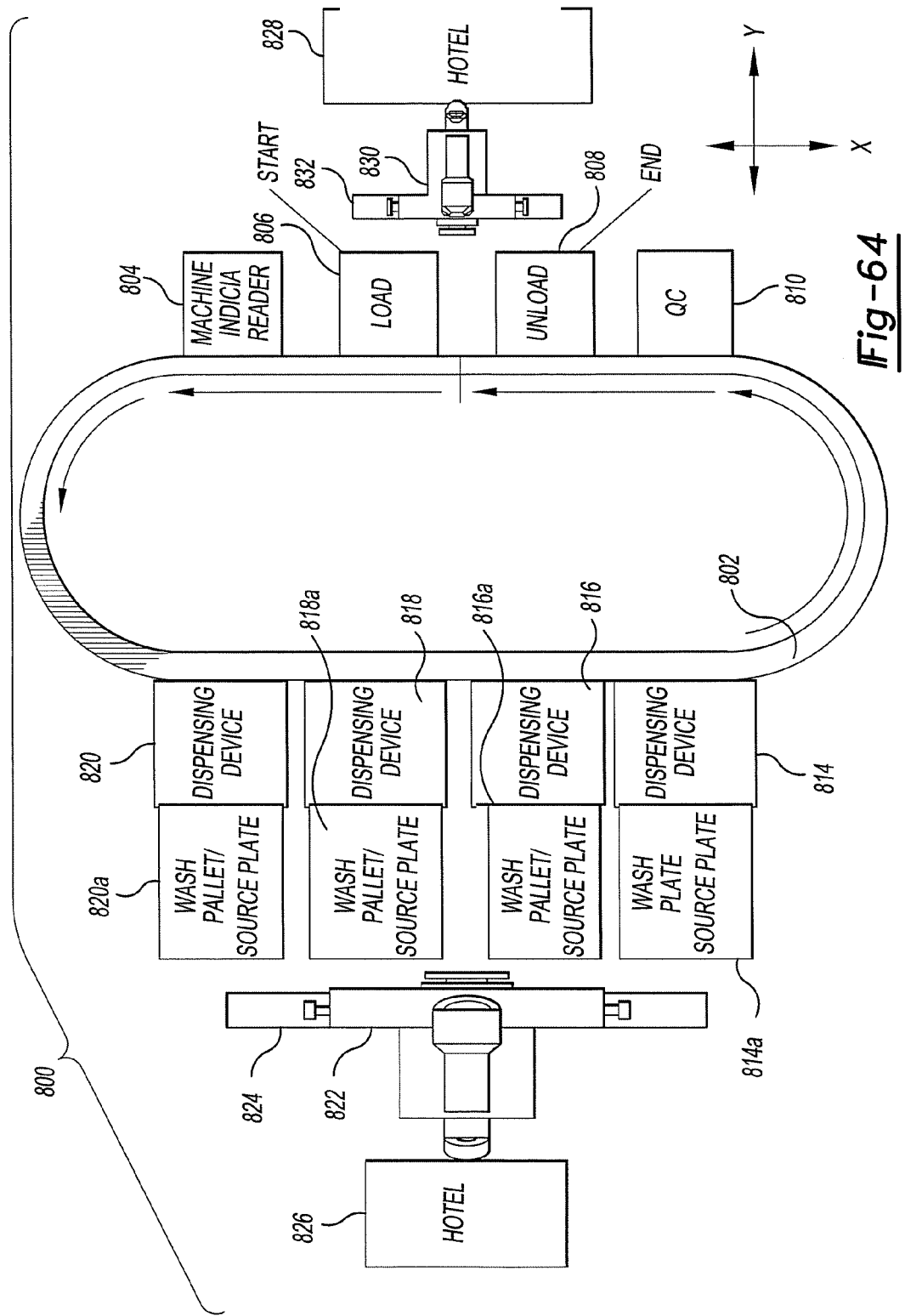
Figure 65:
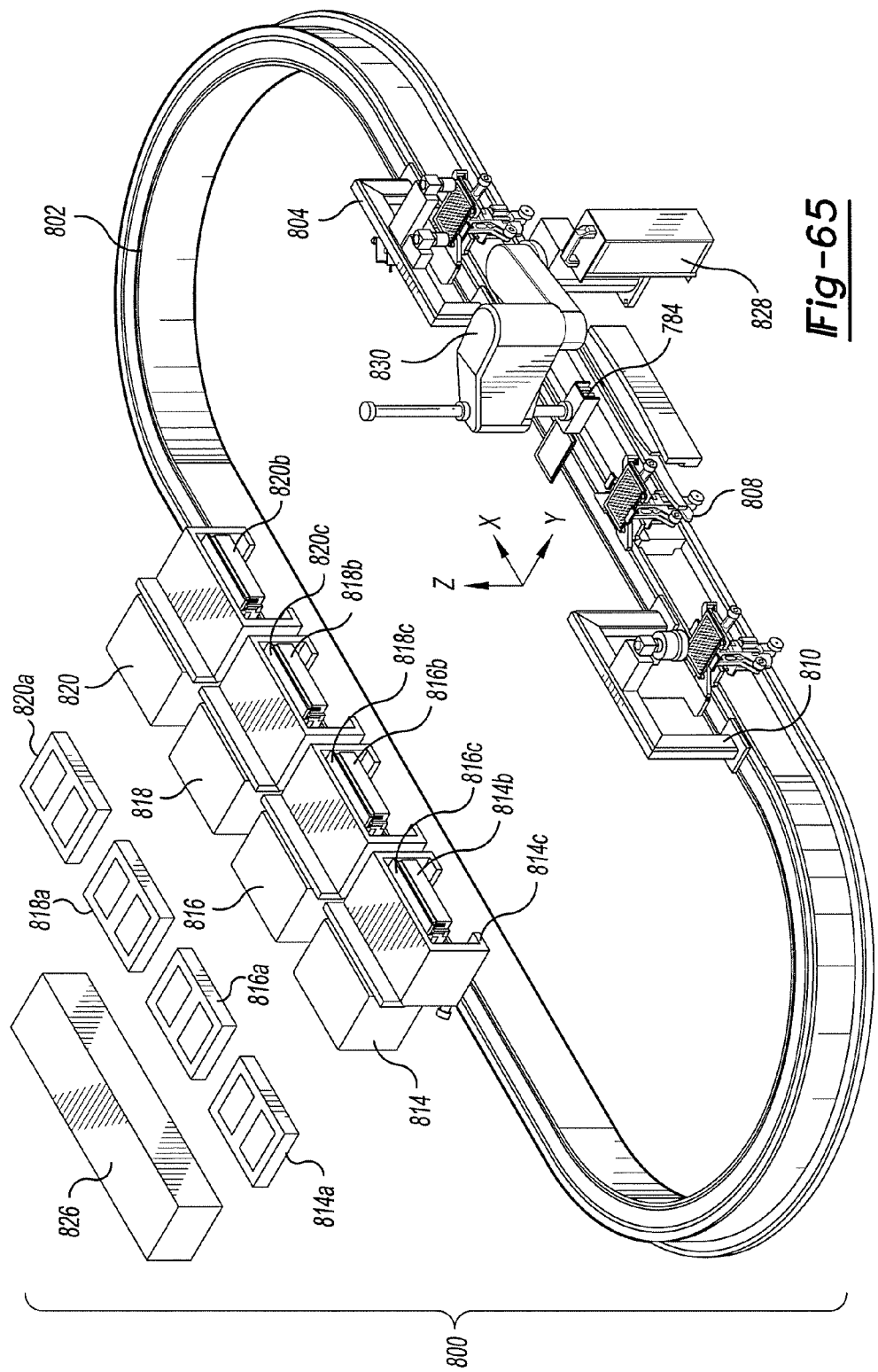
Figure 66:
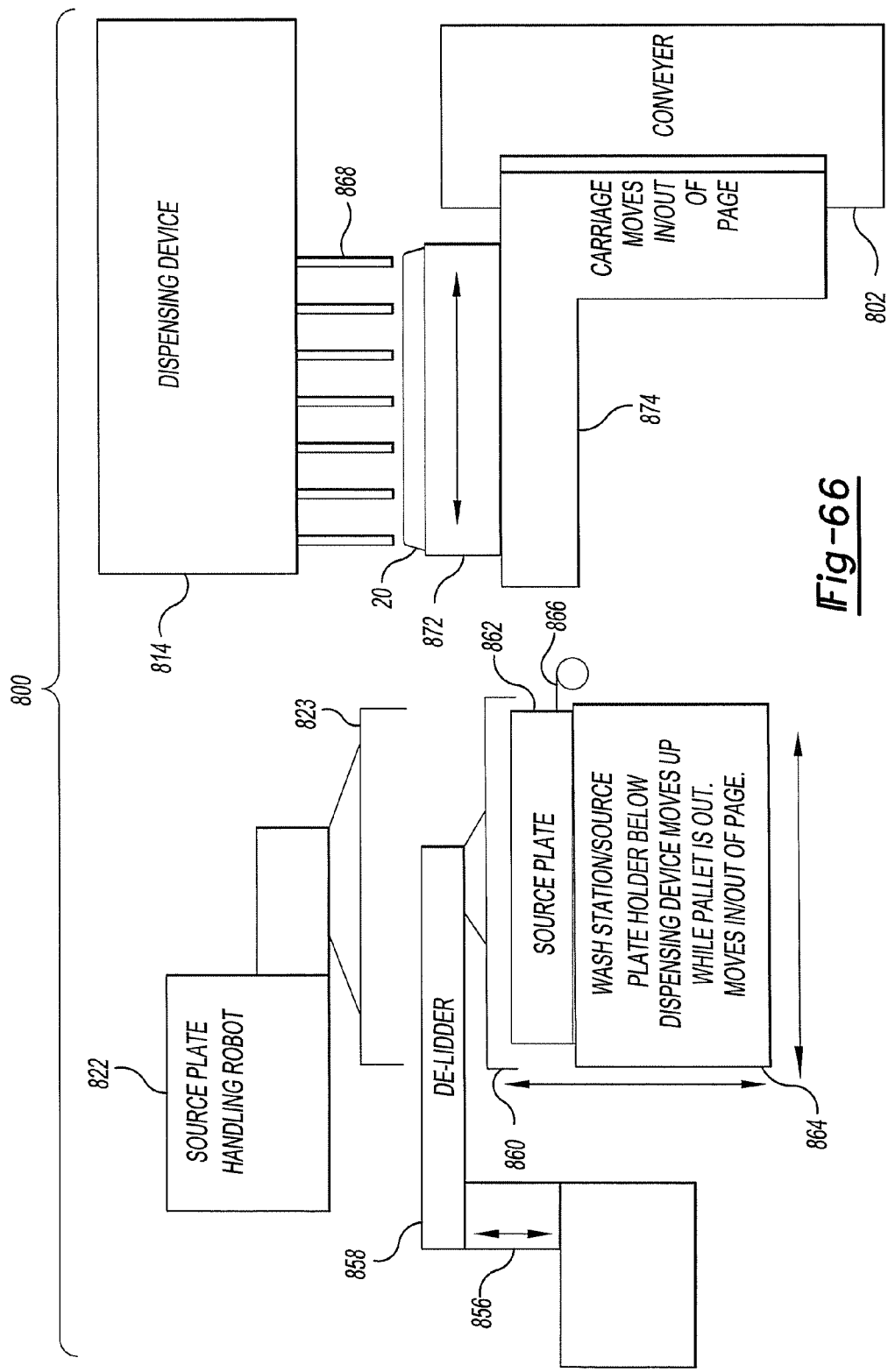
Figure 67:
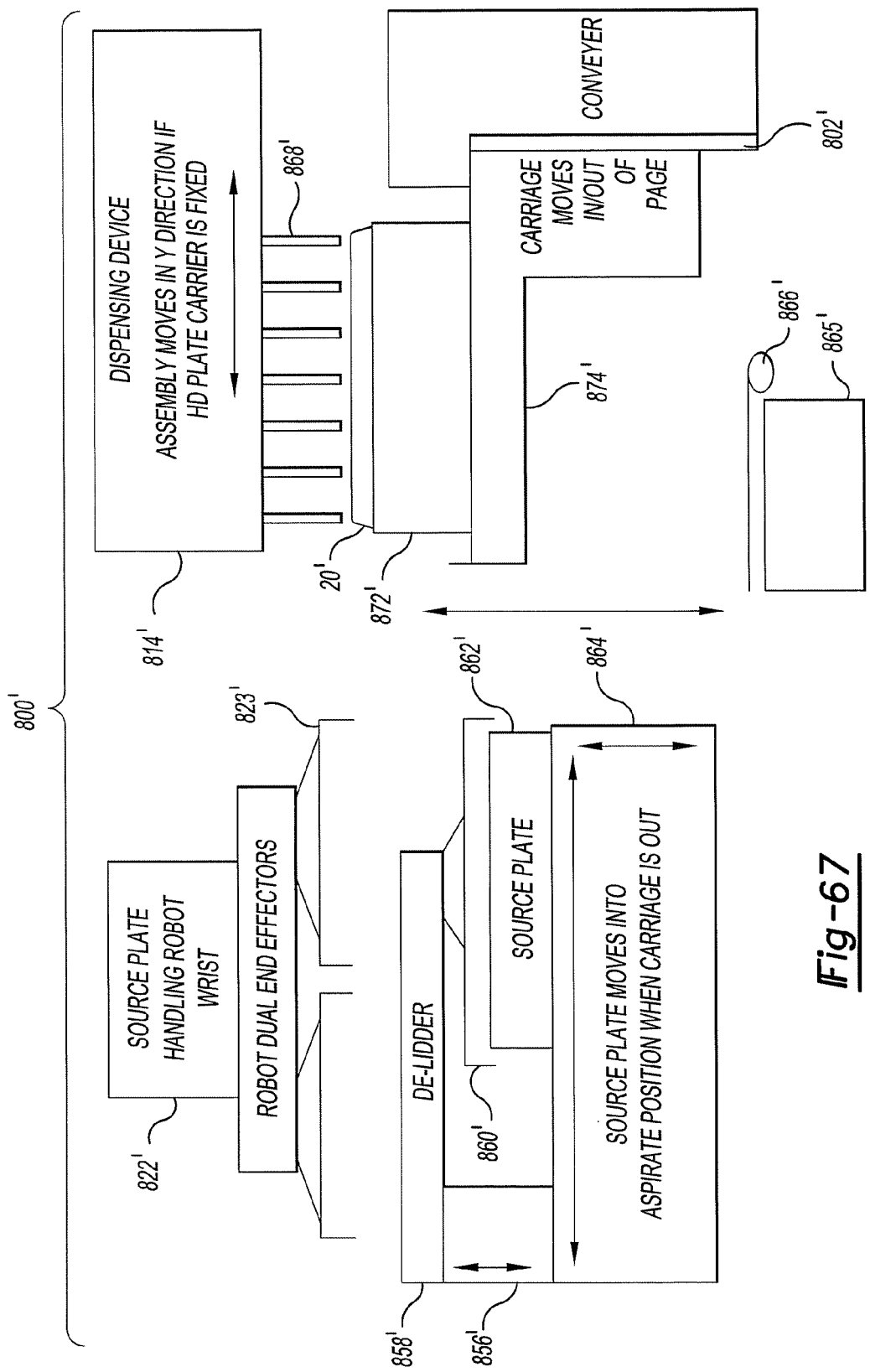
Figure 68:
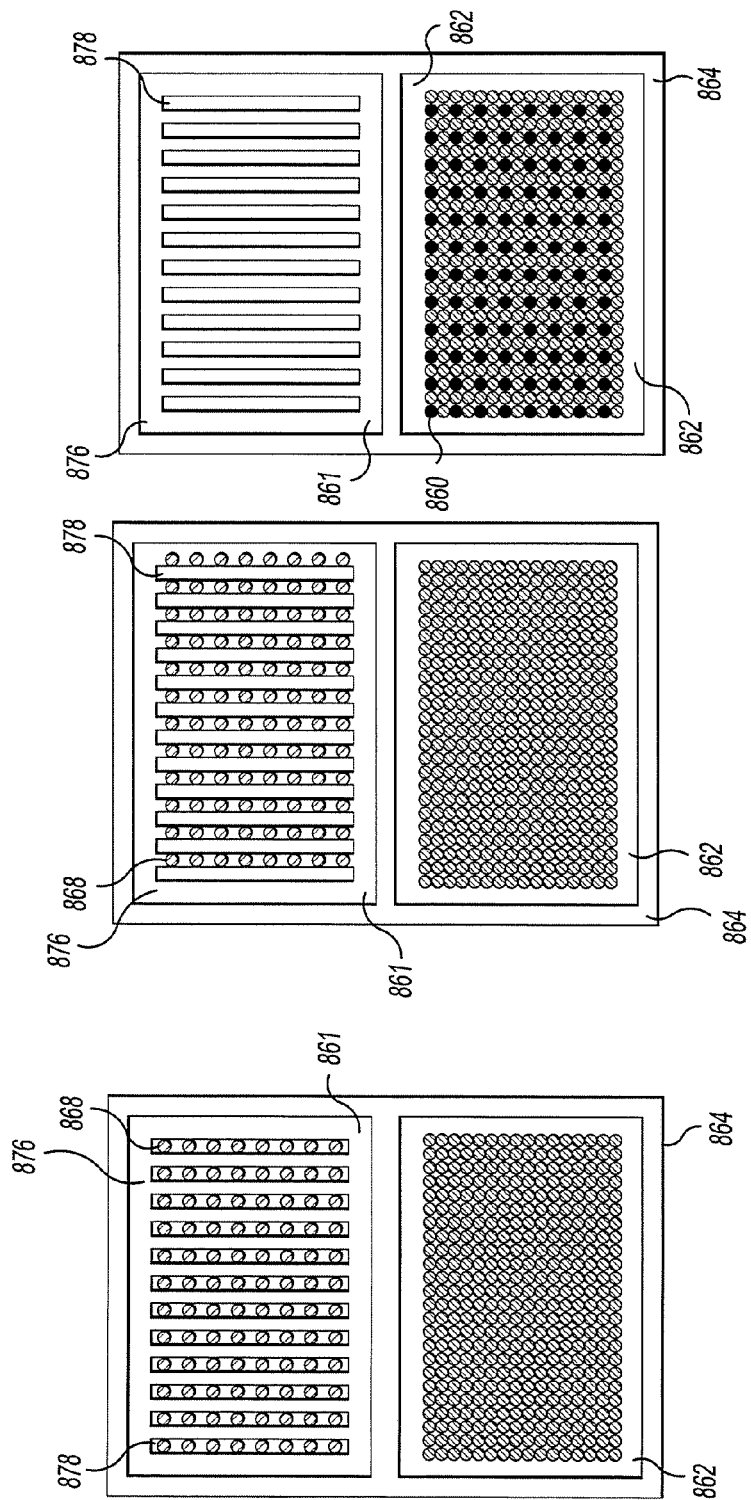
Figure 69:
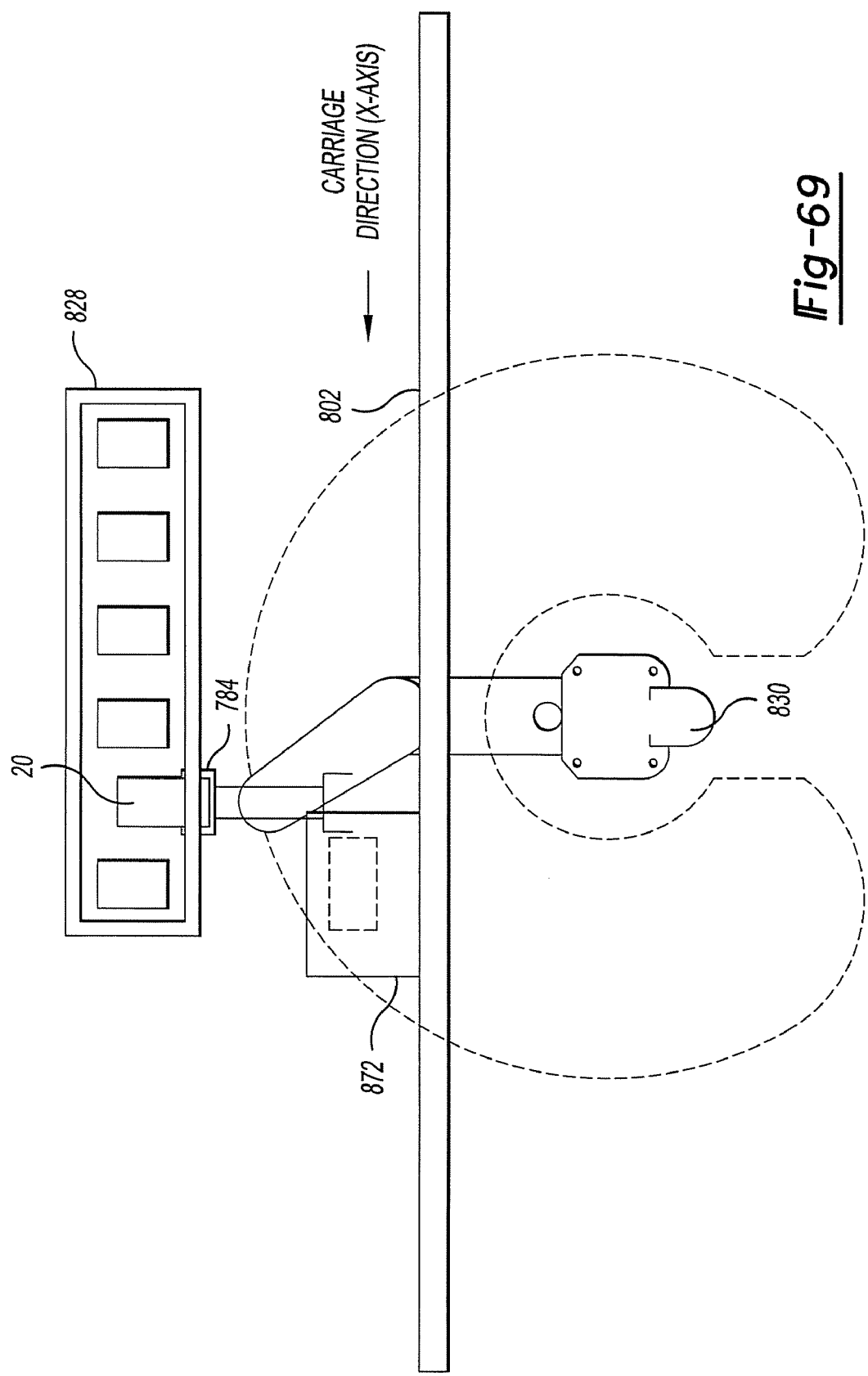
Figure 70:
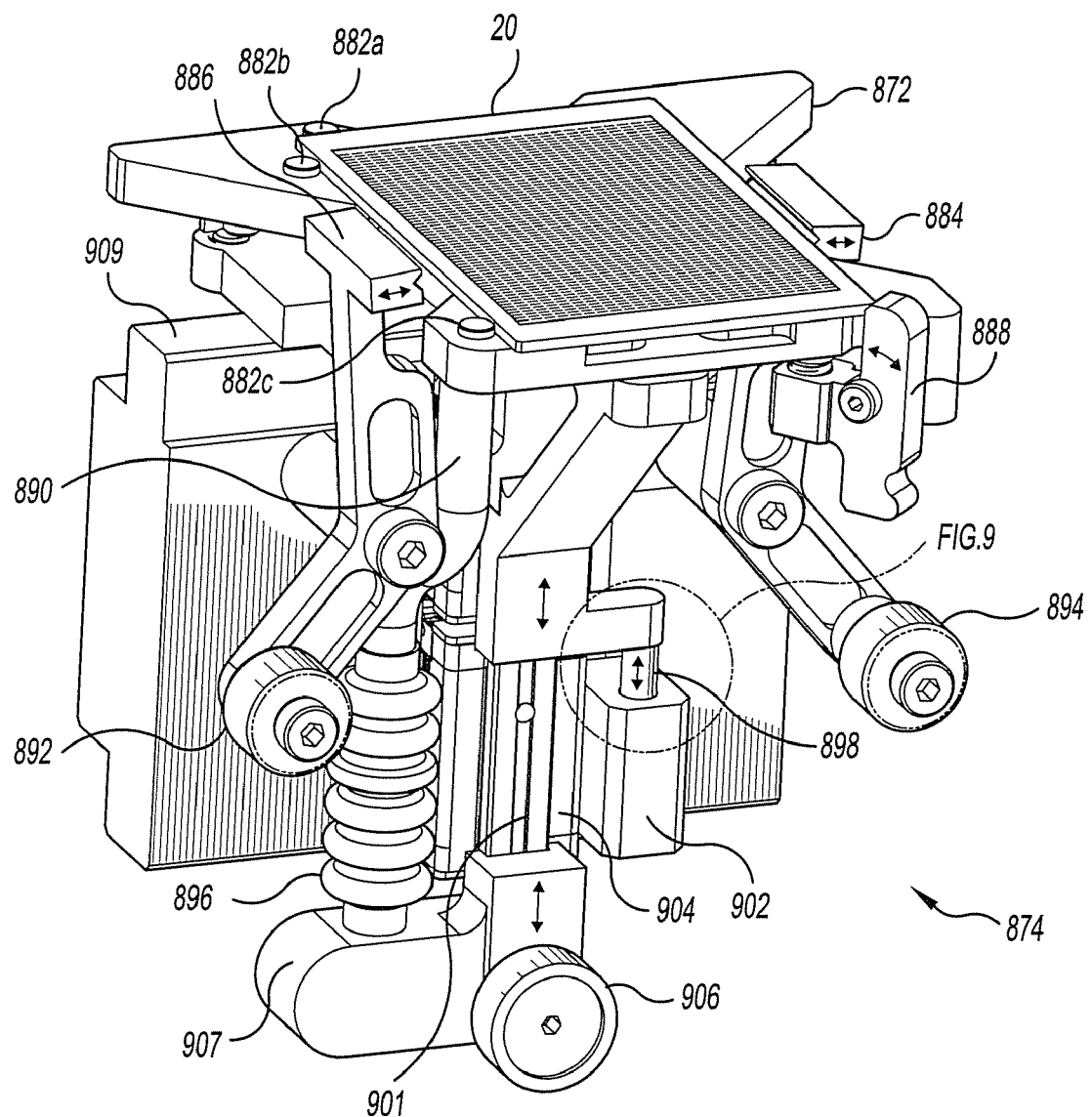
Figure 71:
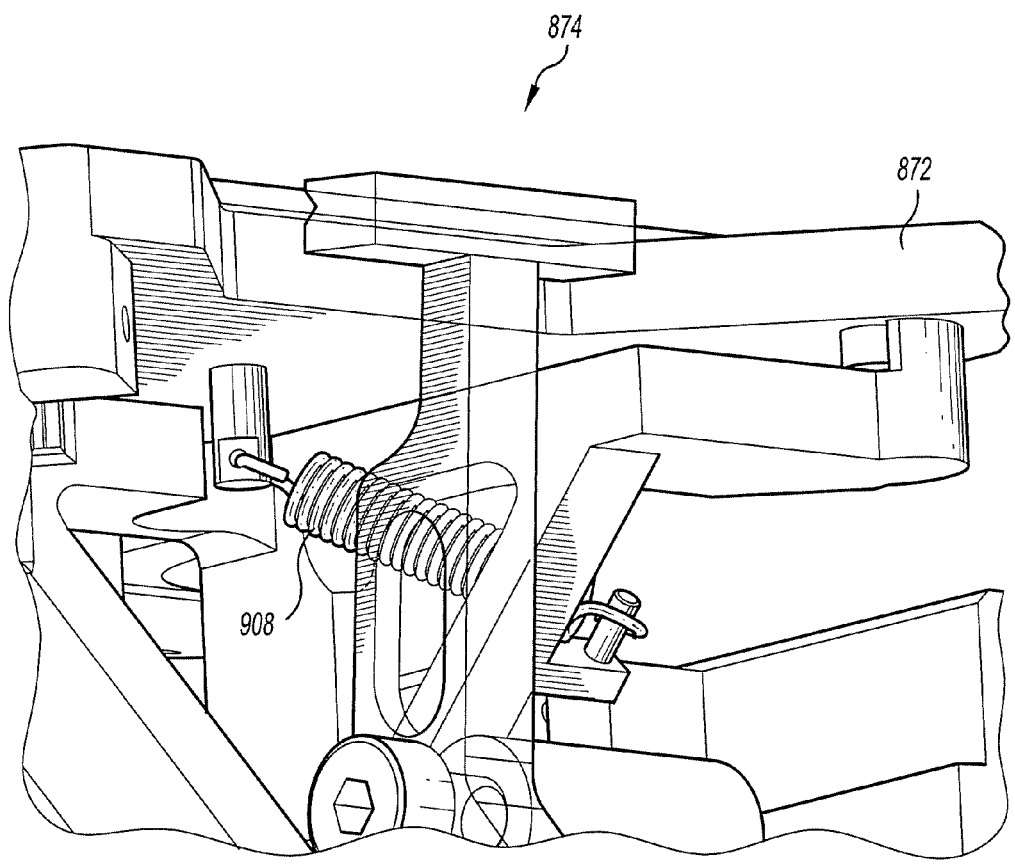
Figure 72:
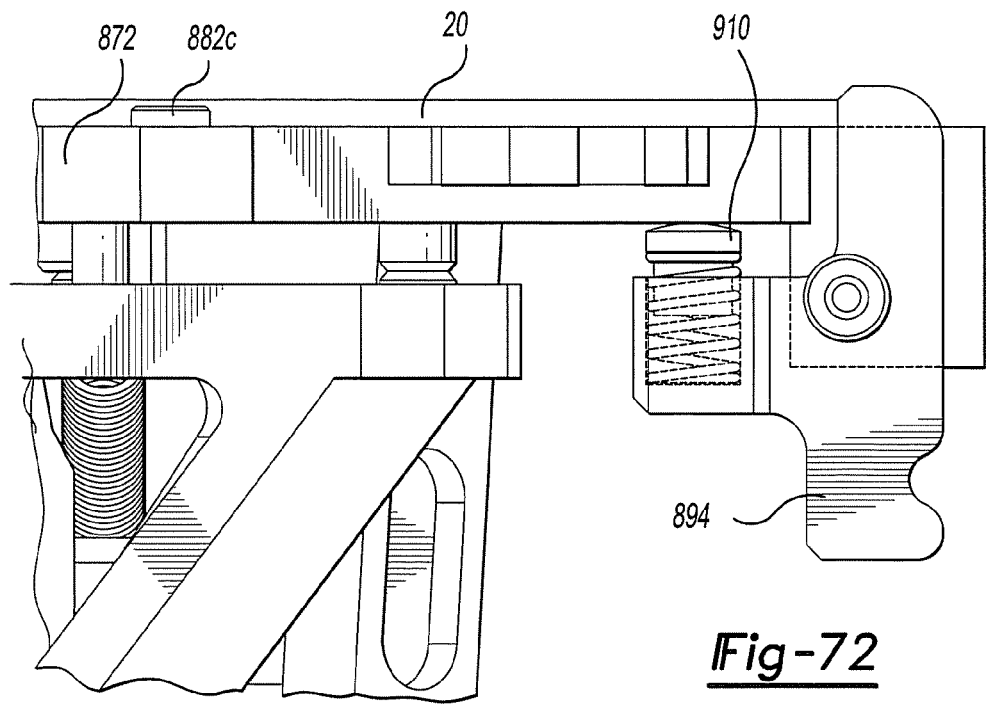
Figure 73:
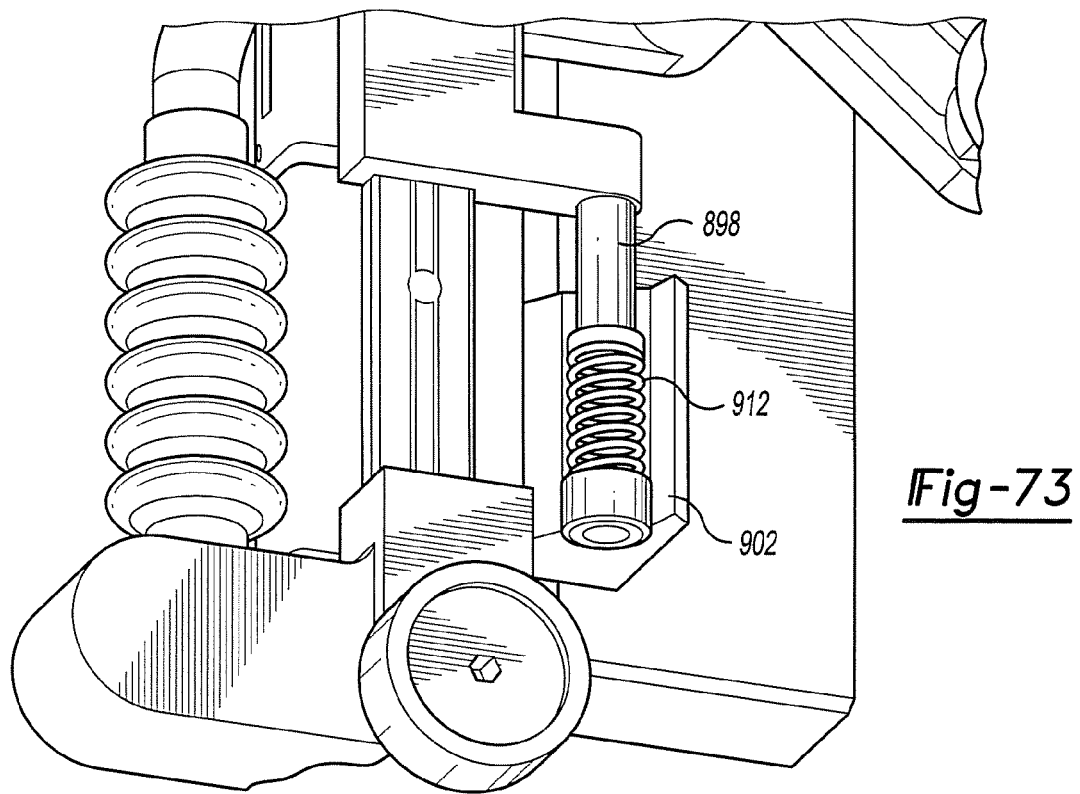
Figure 74:
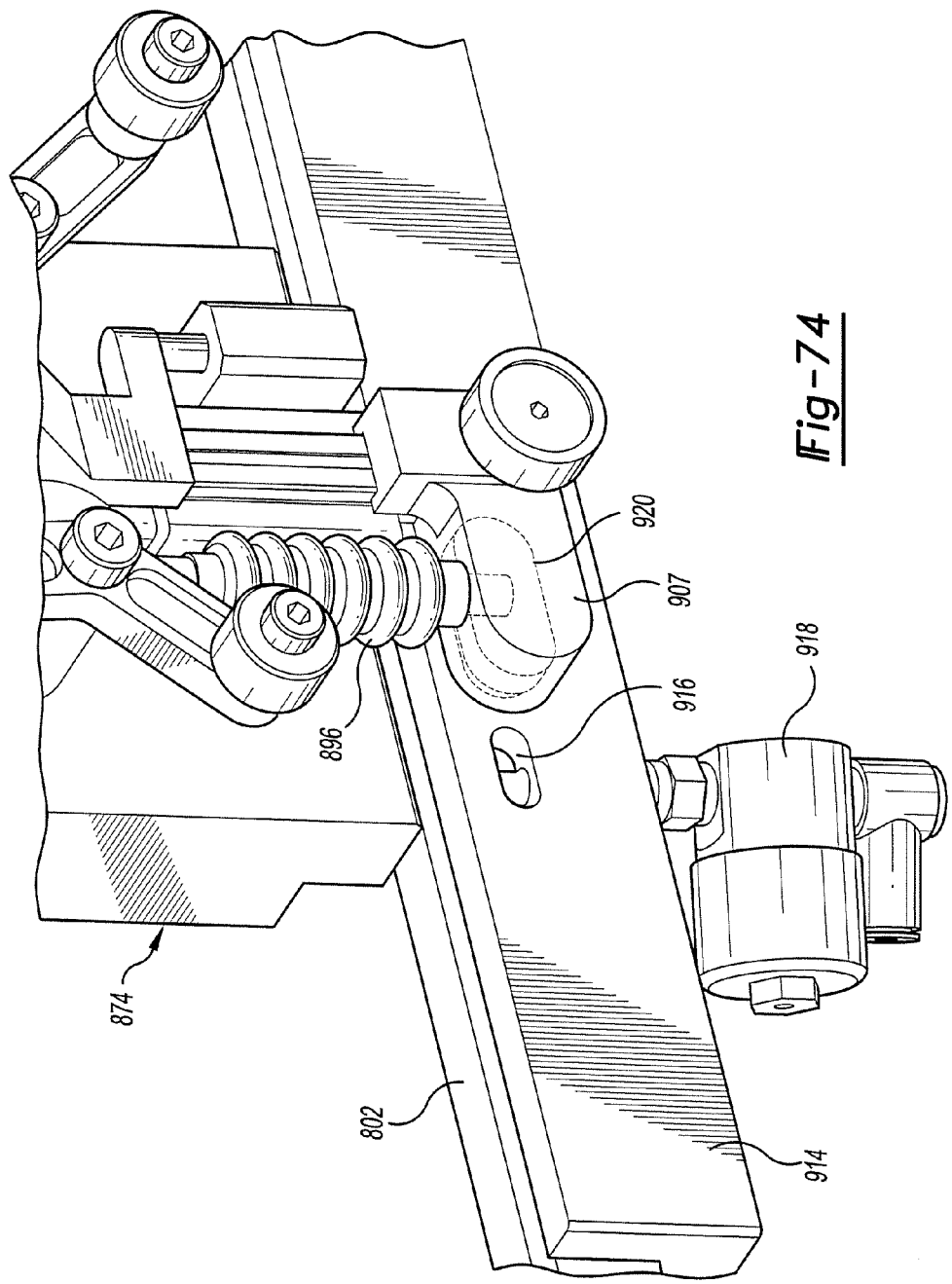
Figure 75:
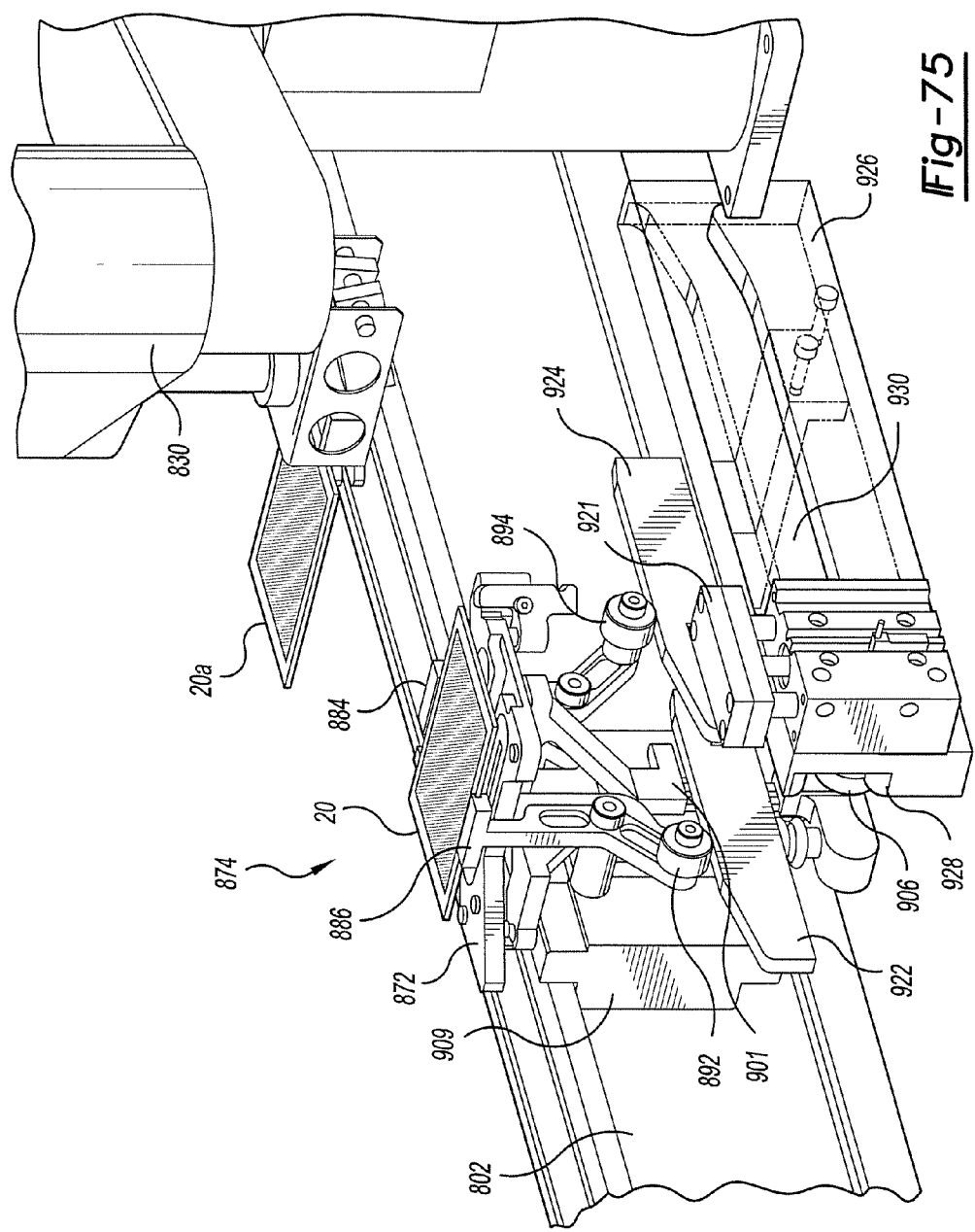
Figure 76:
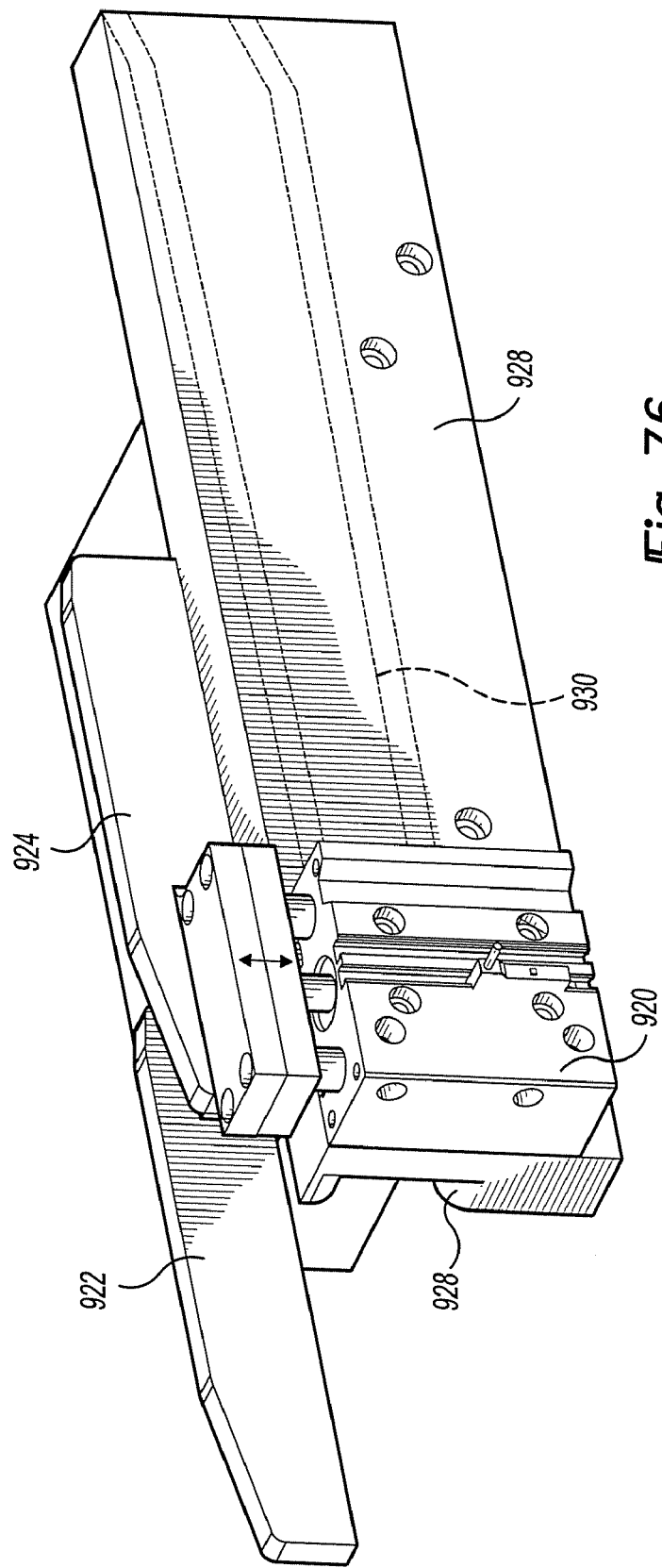
Figure 77:
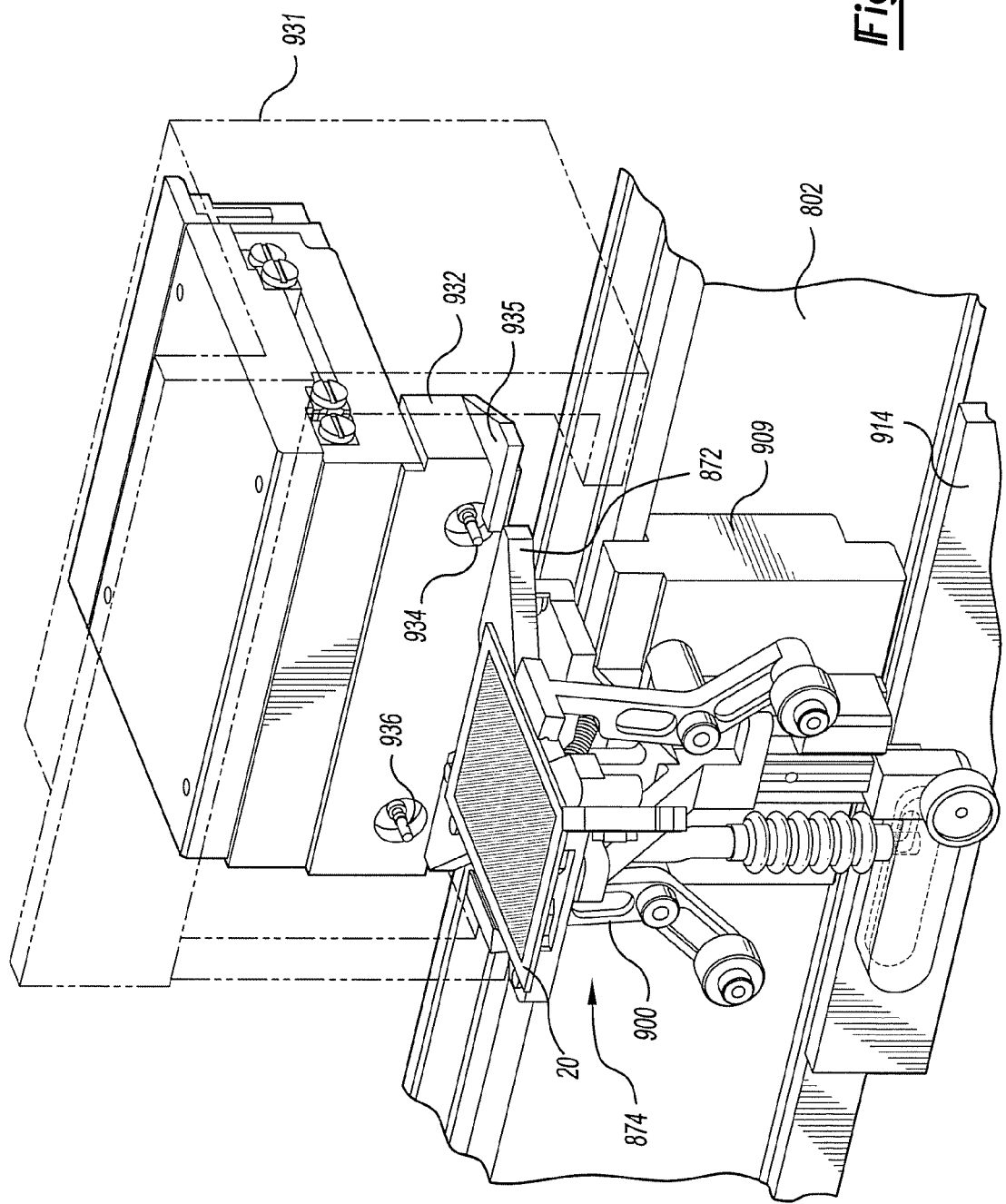
Figure 78:
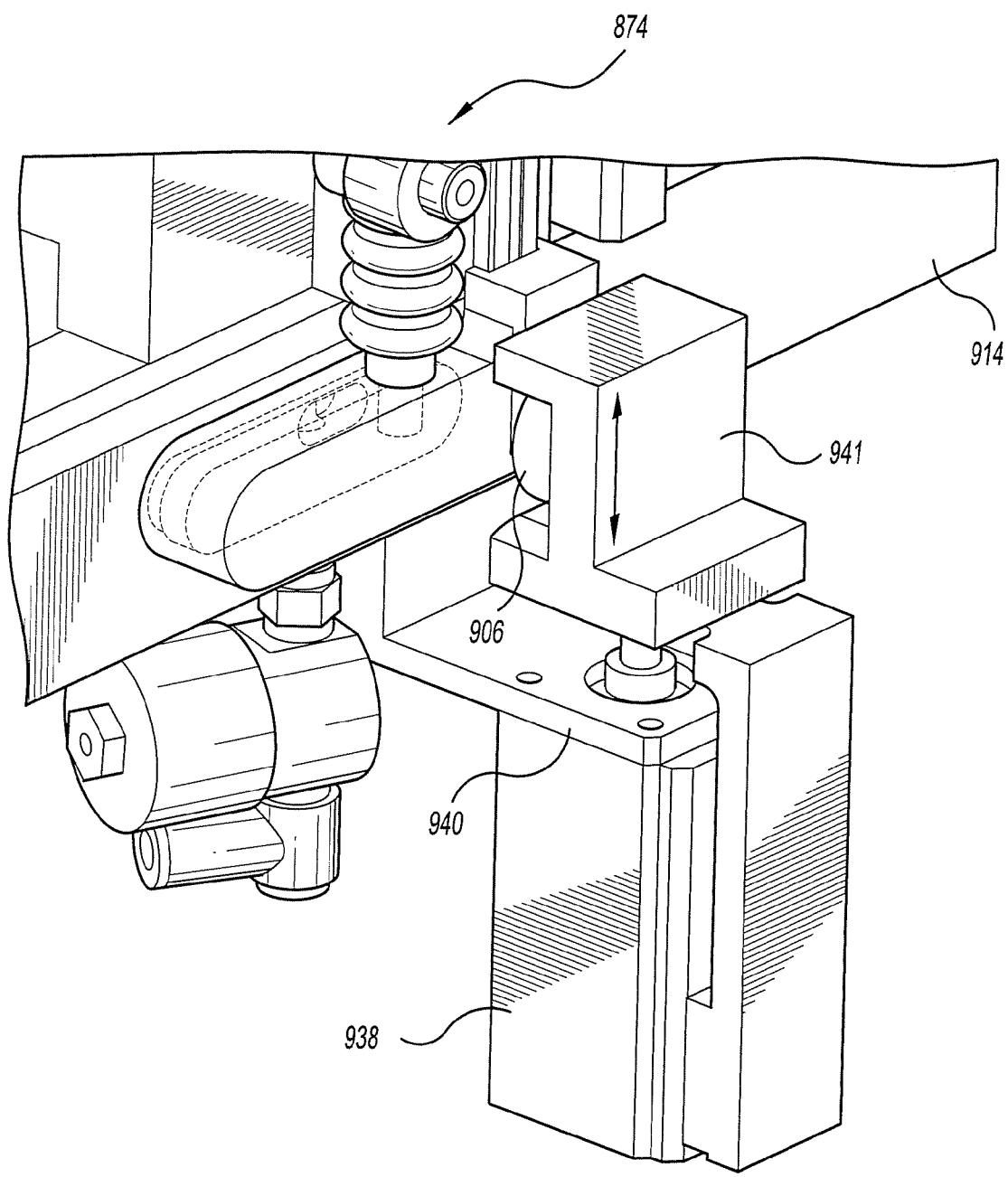
Figure 79A:
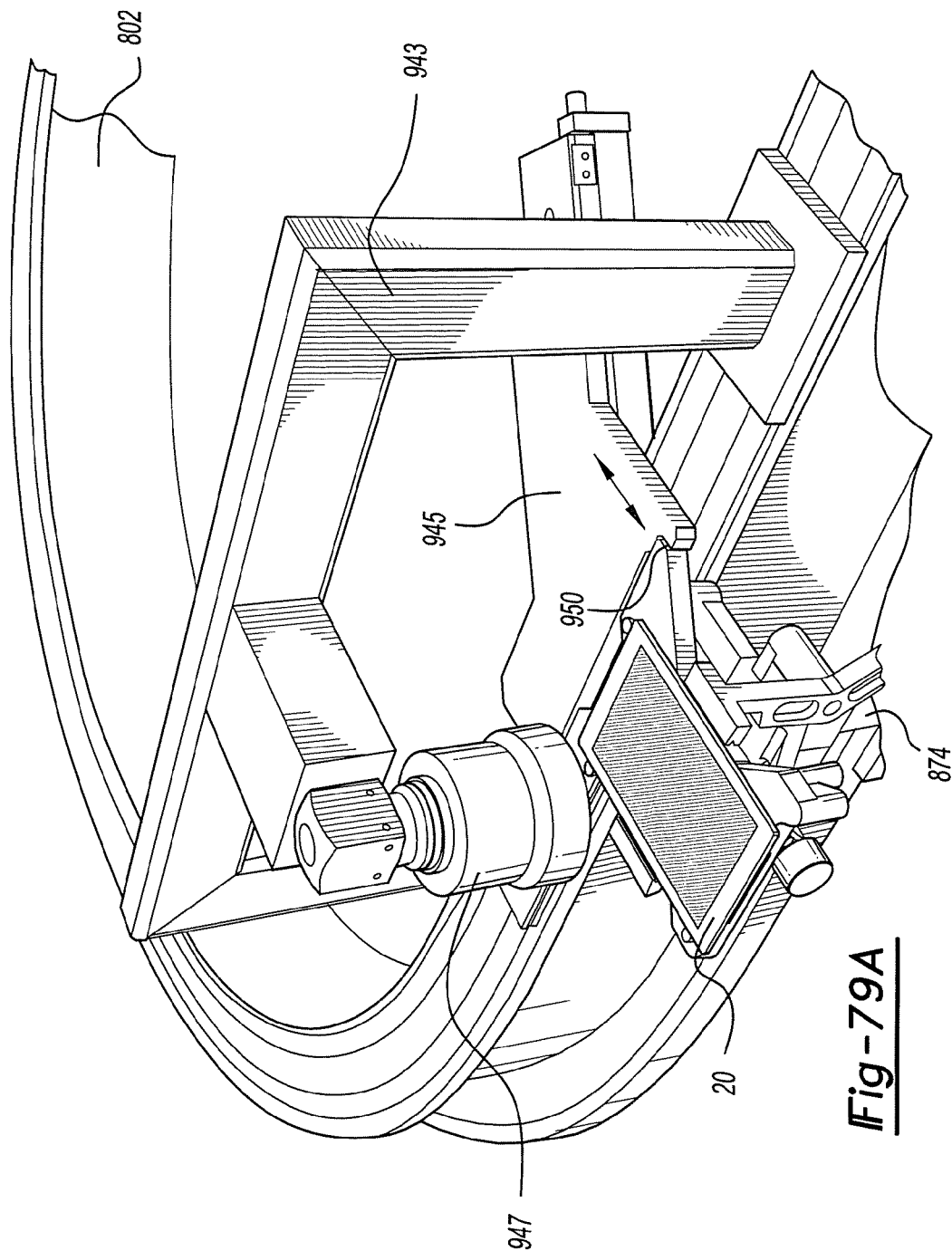
Figure 80:
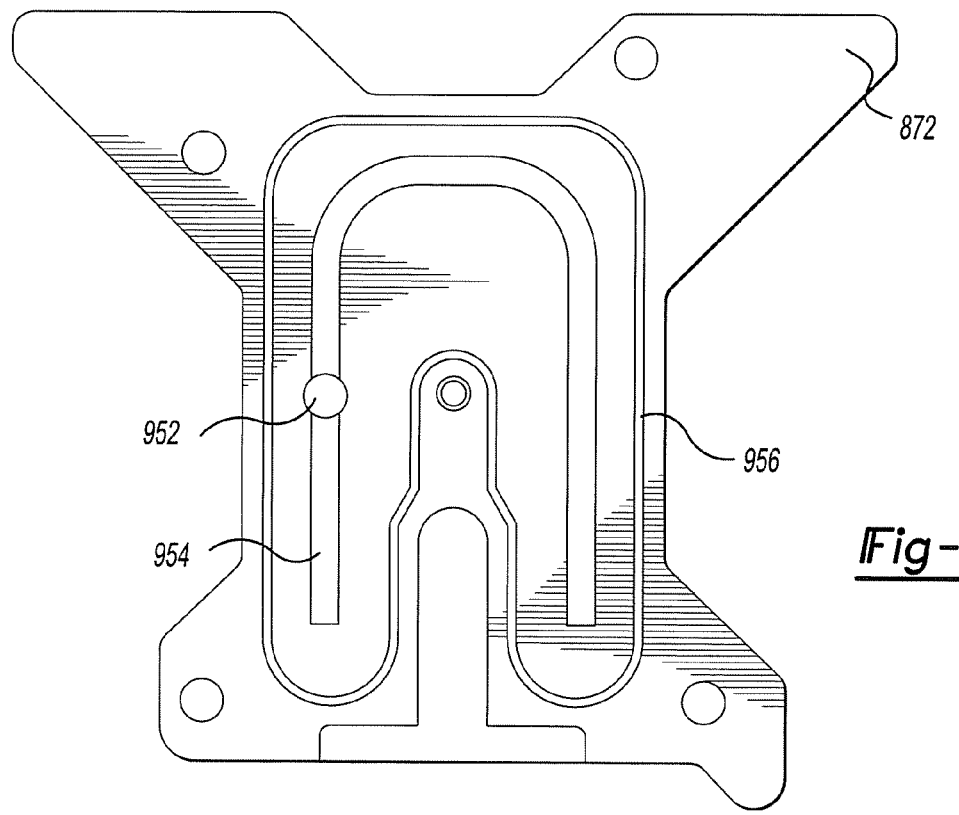
Figure 81:
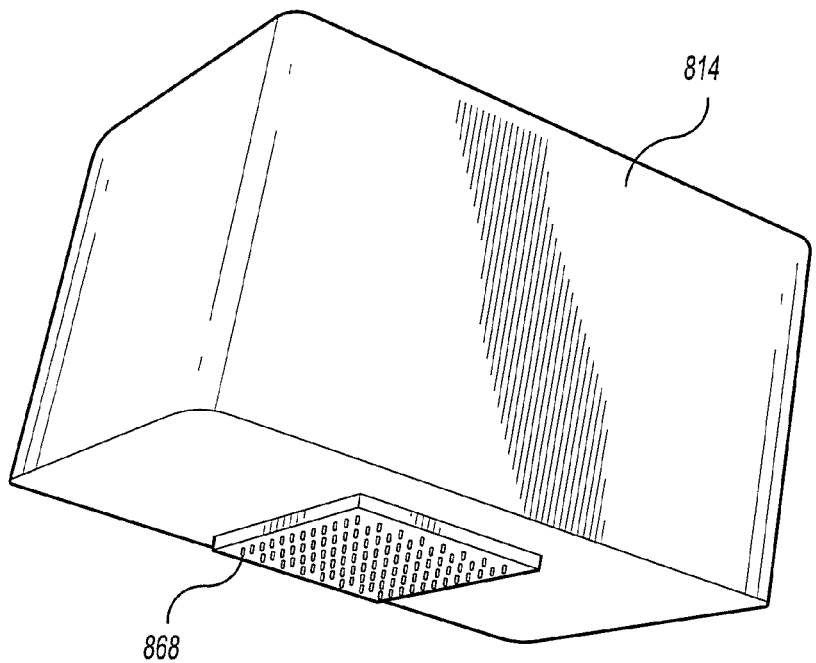
Figure 82:
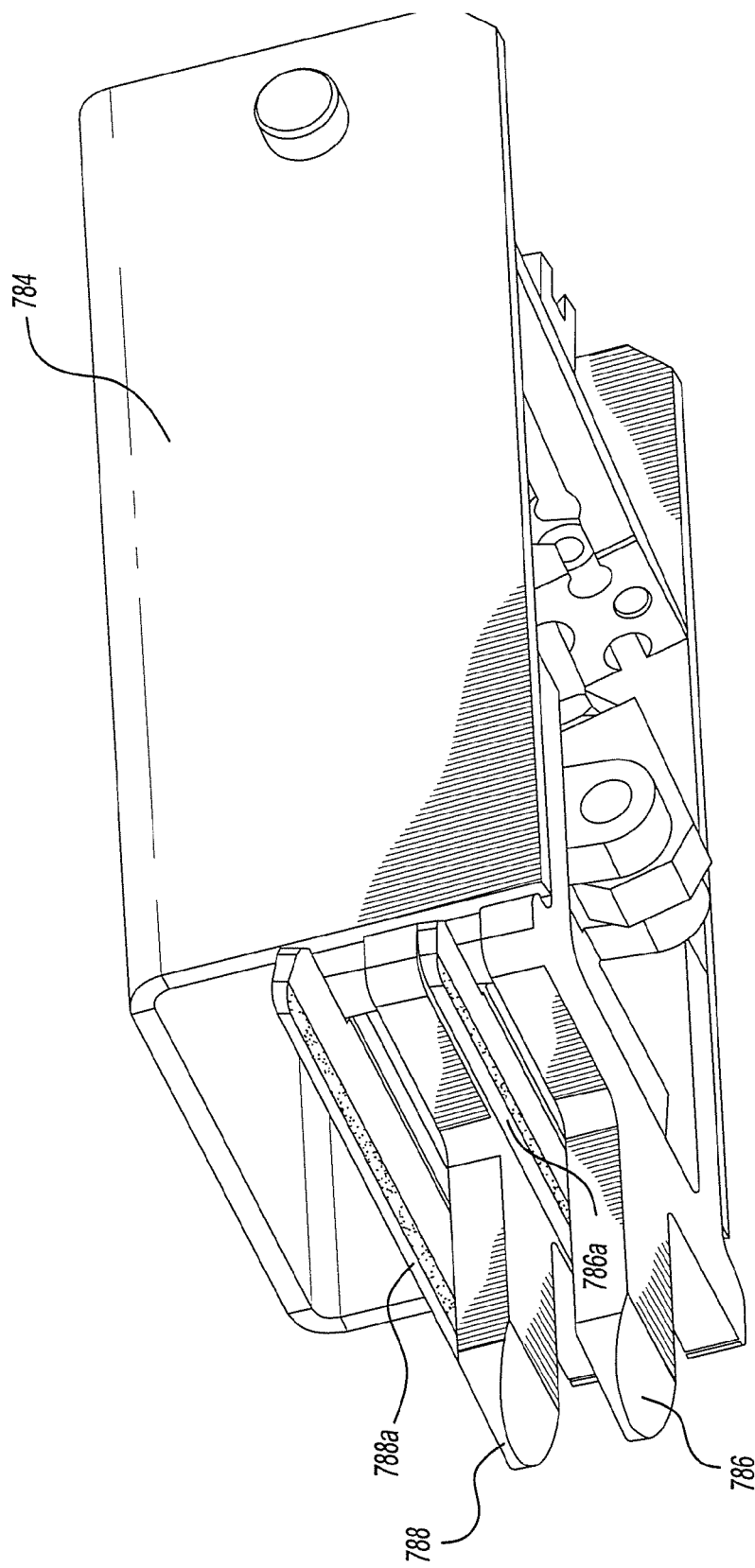
Figure 83:
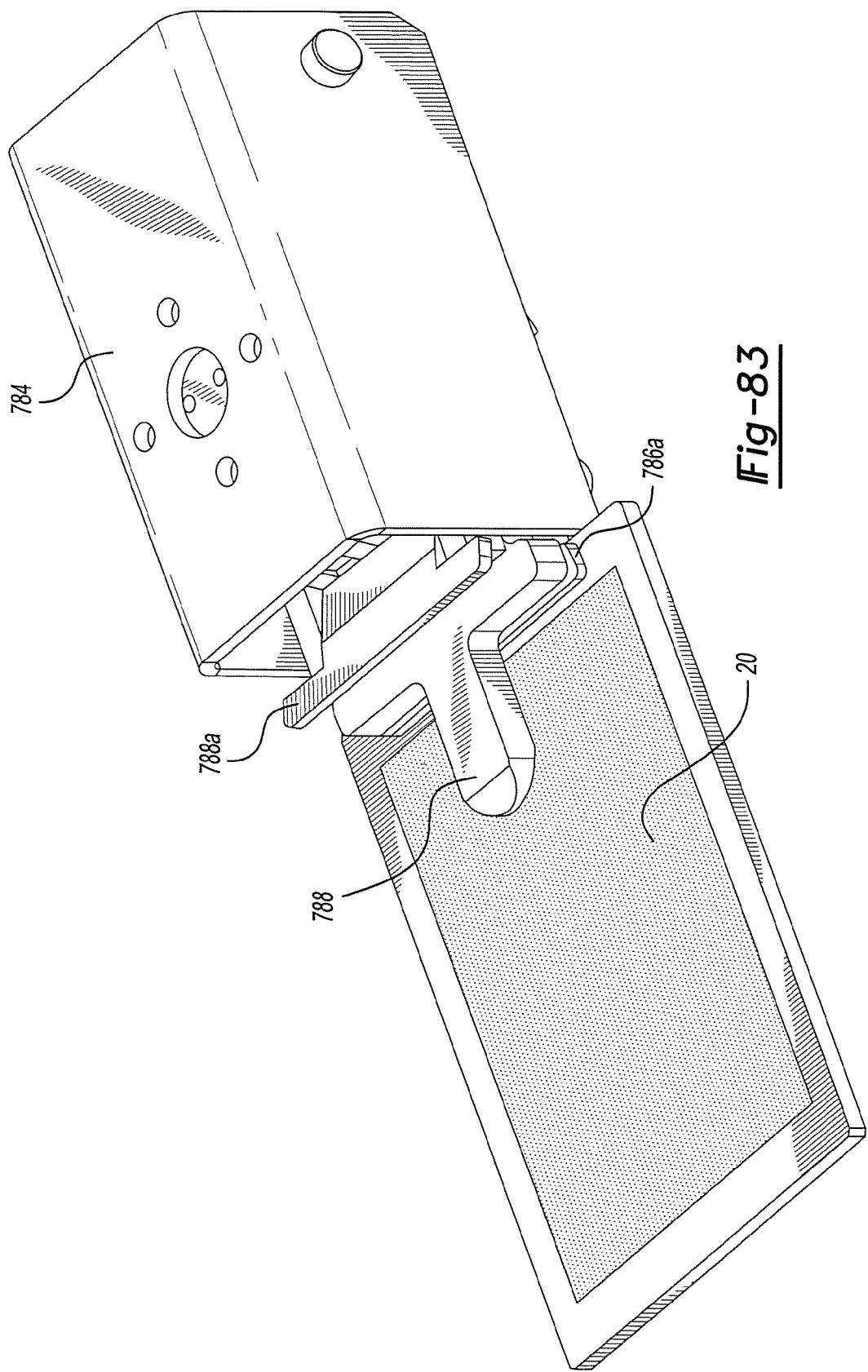
Figure 91:
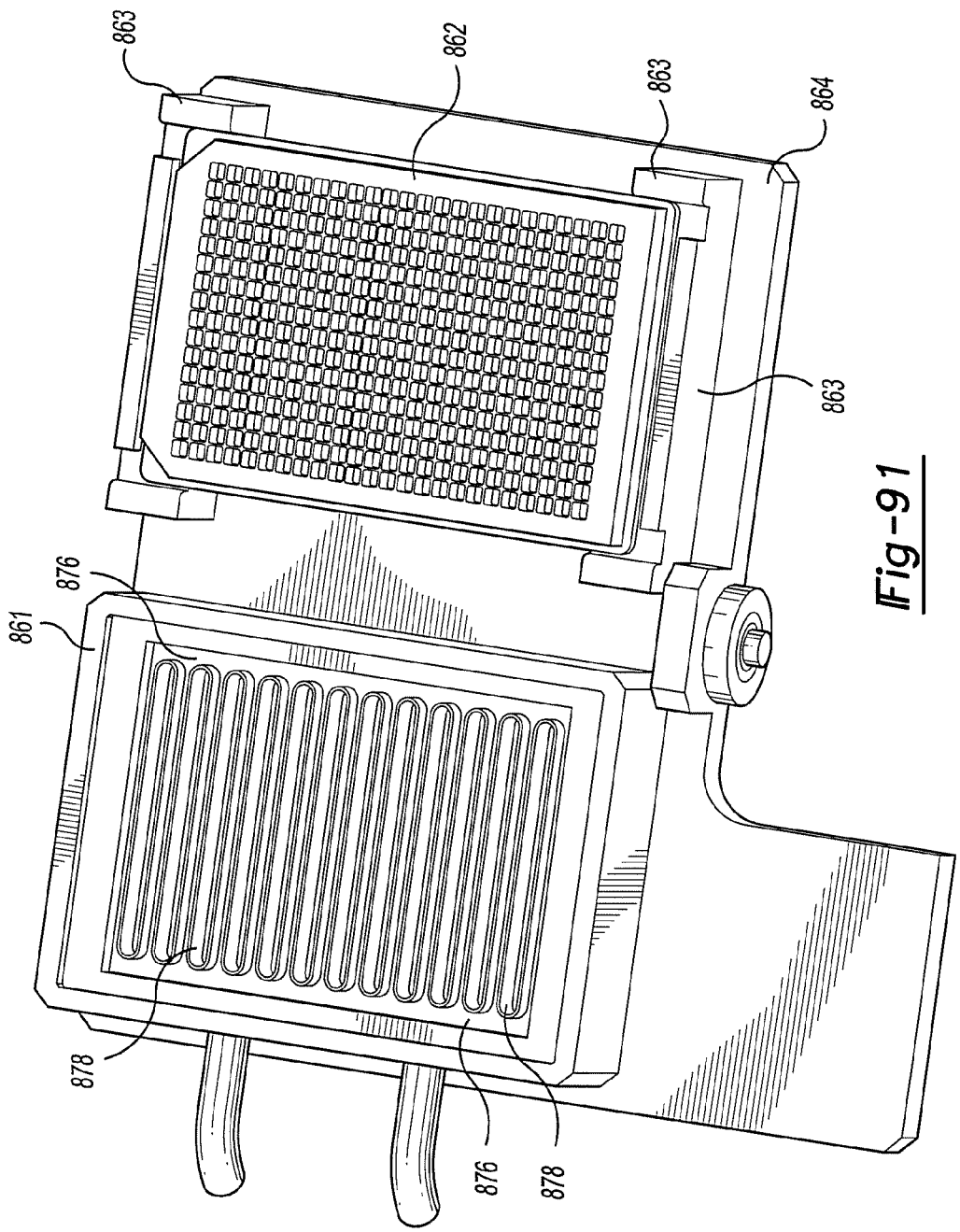
Figure 92:
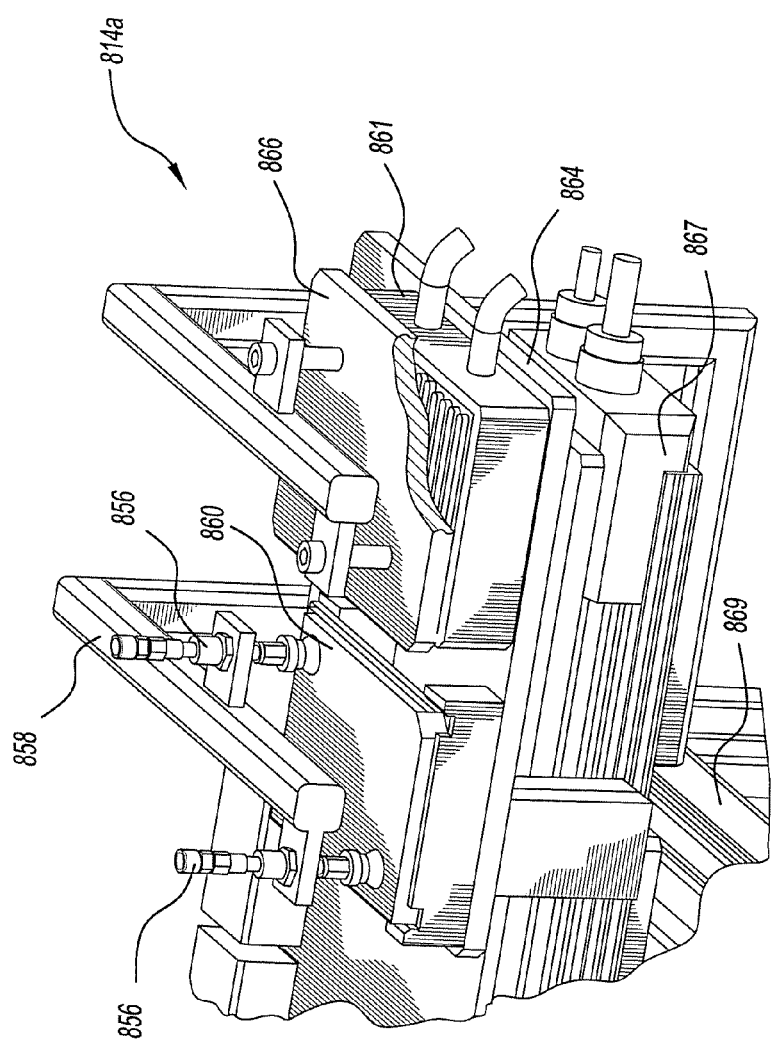
Figure 93:
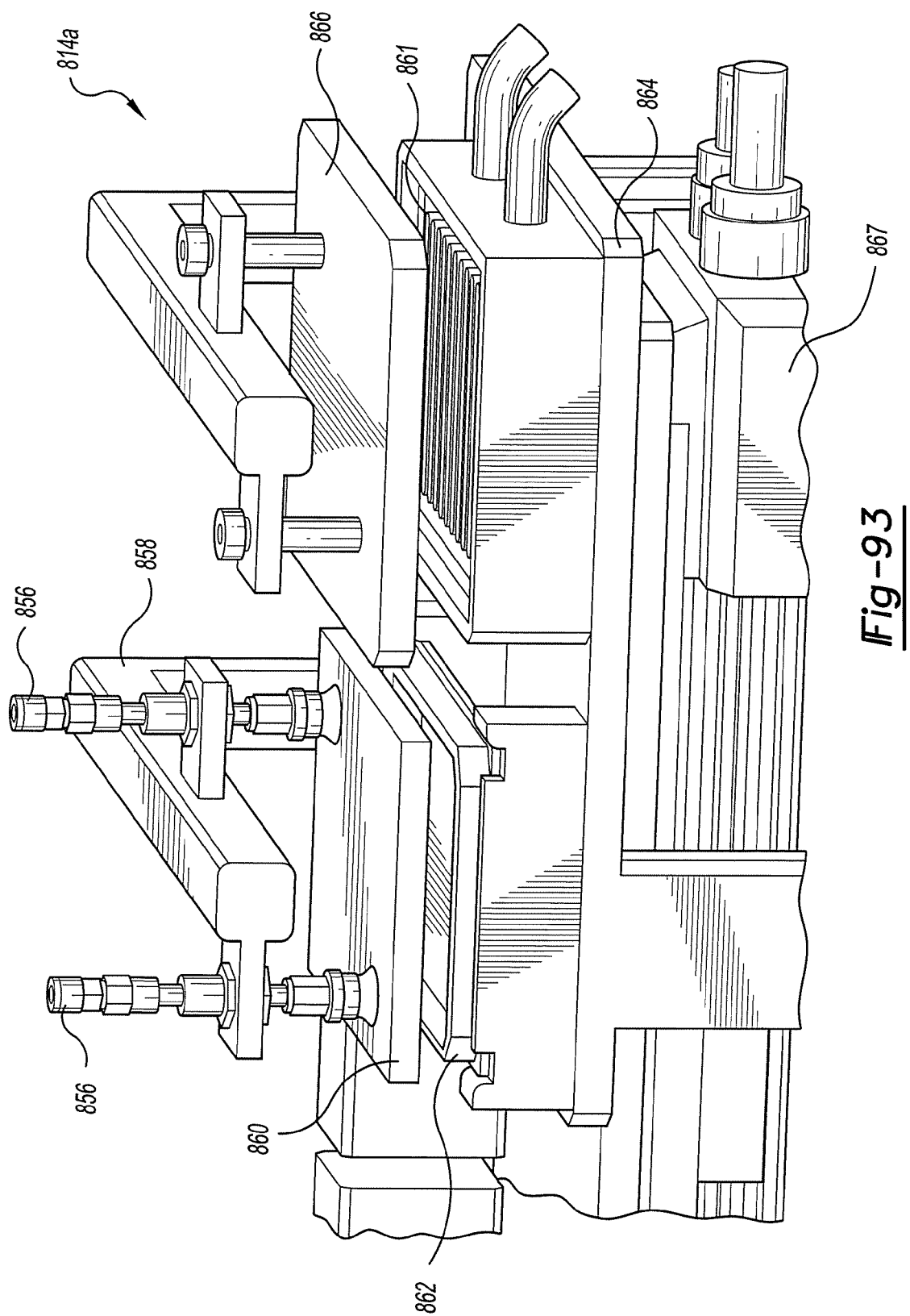
Figure 94:
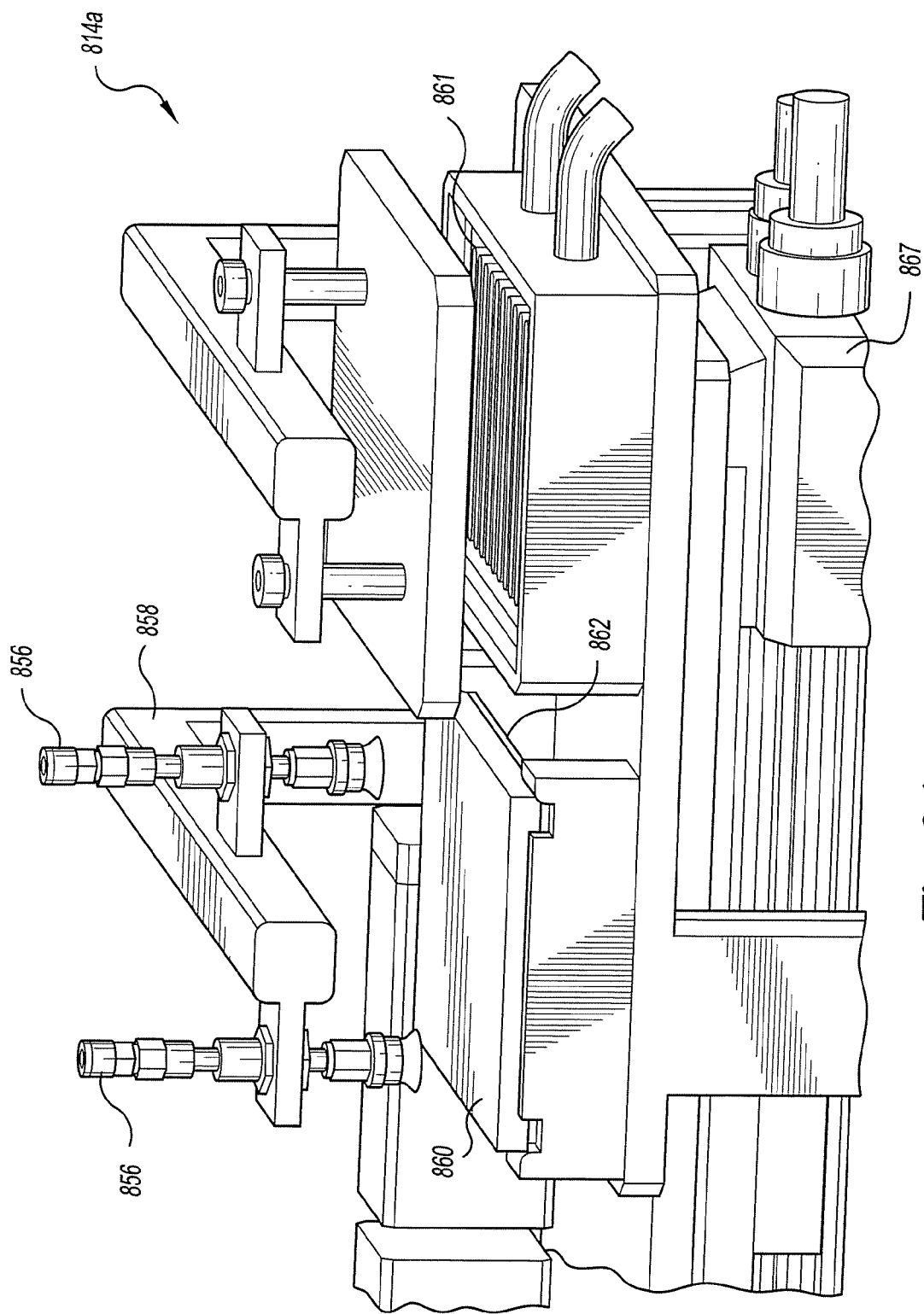
Figure 95:
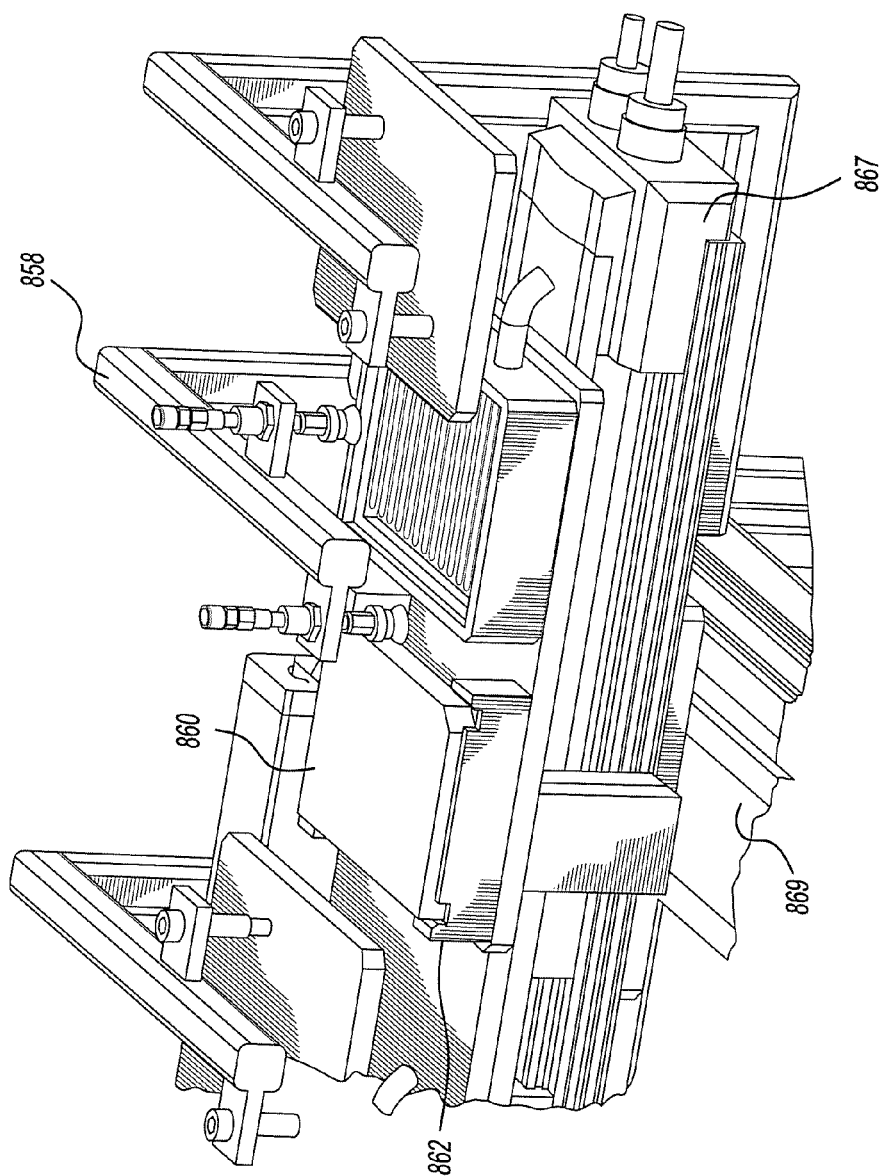
Figure 96:
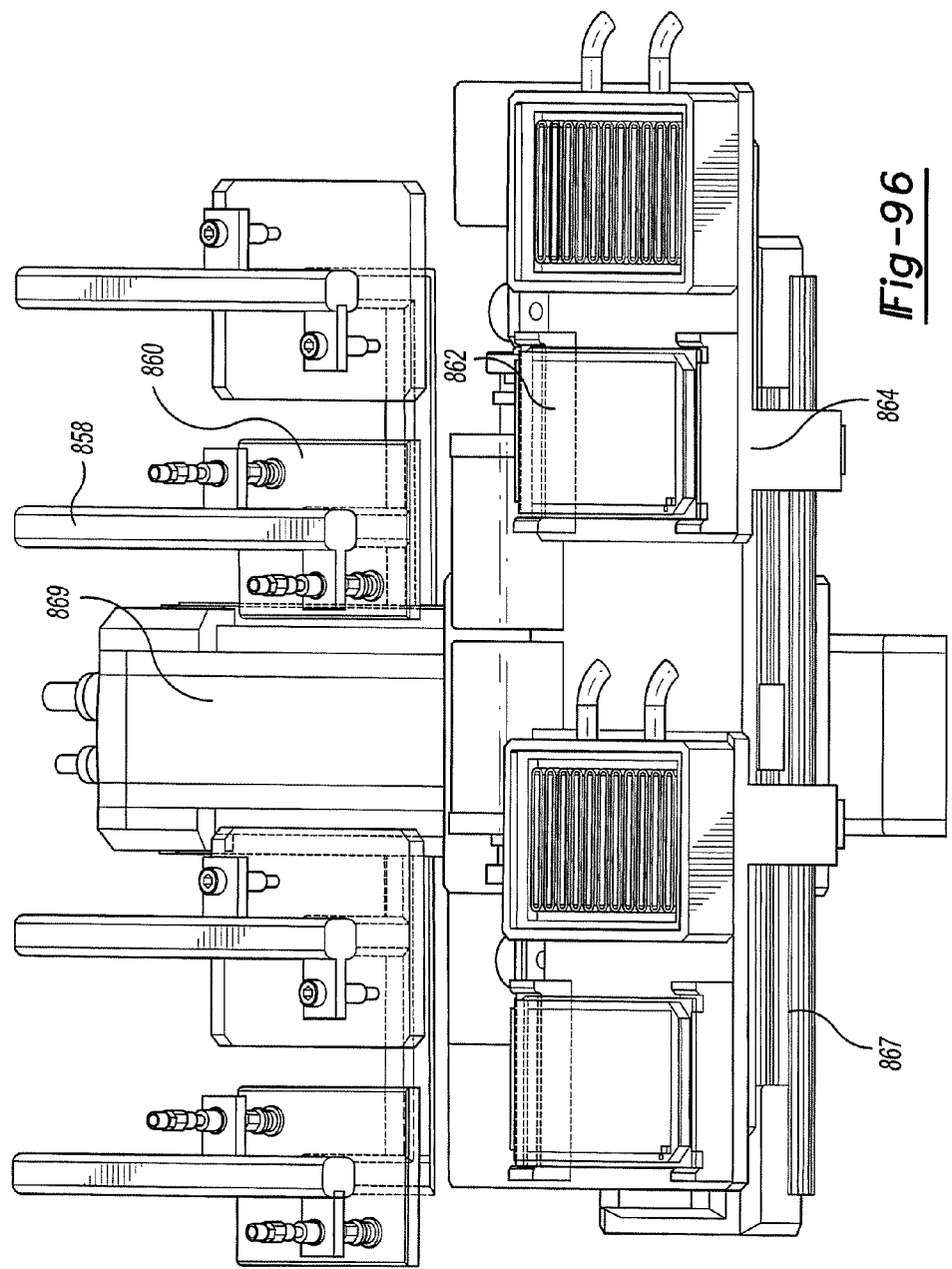
Figure 97:
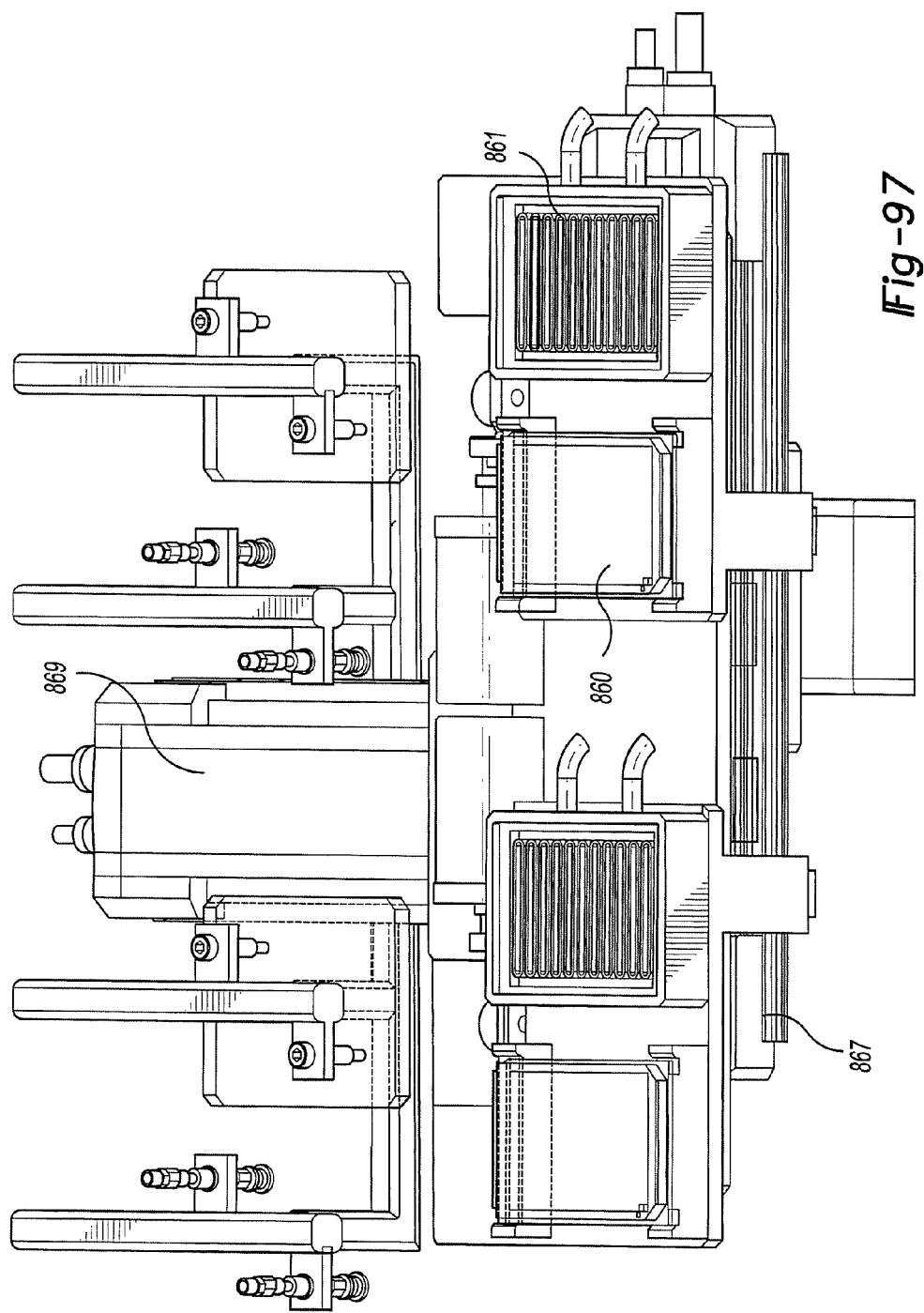
Figure 98:
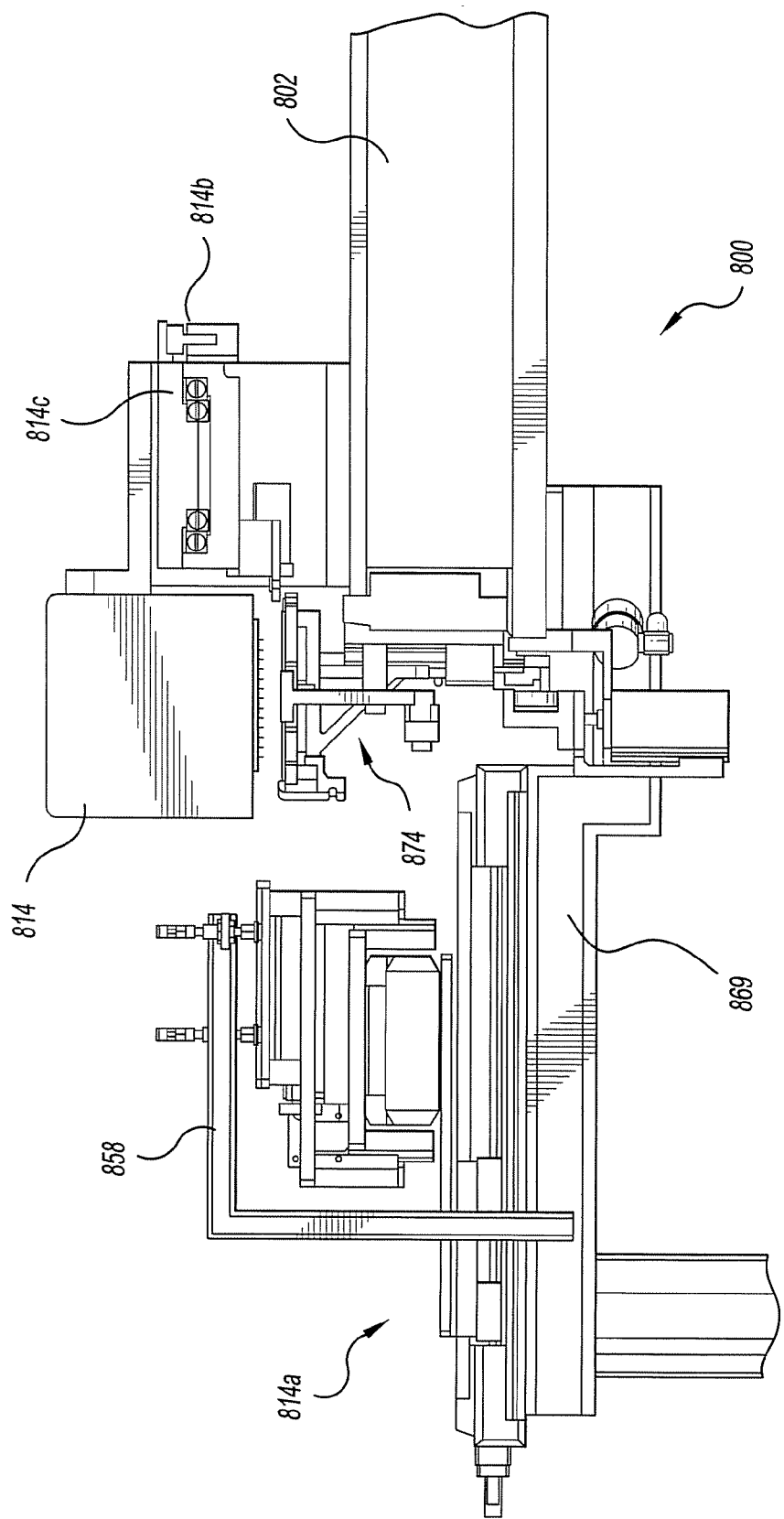
Figure 99:
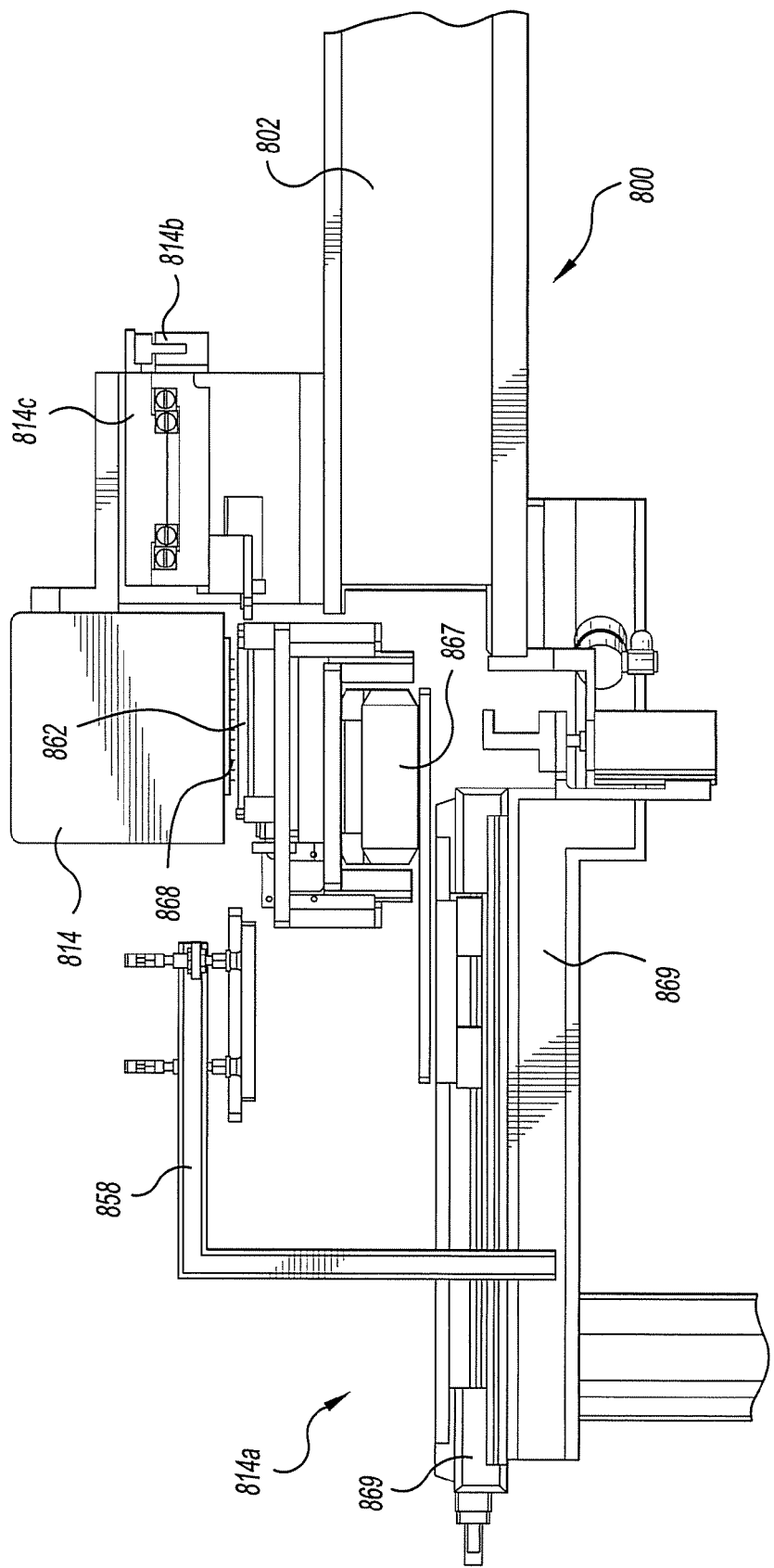
Figure 100:
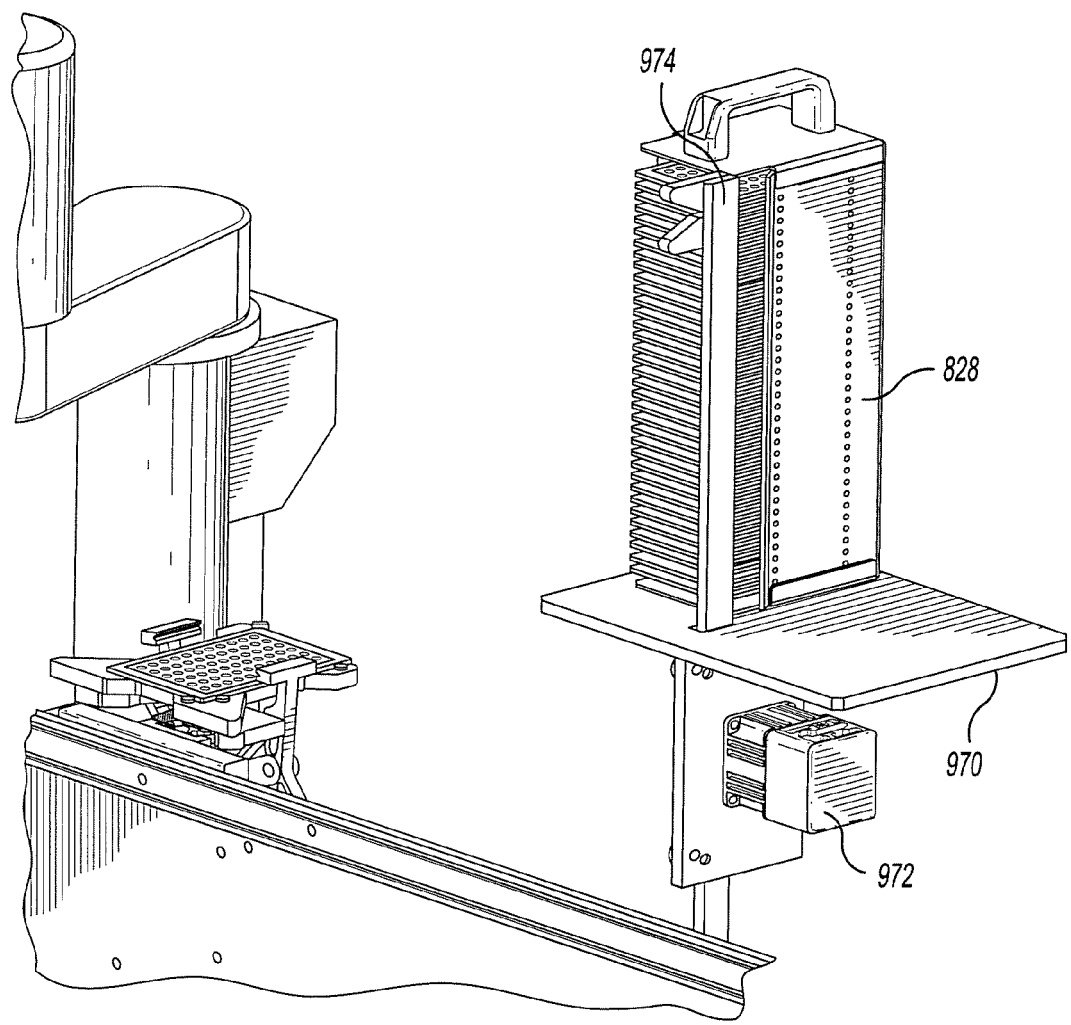
Figure 101:
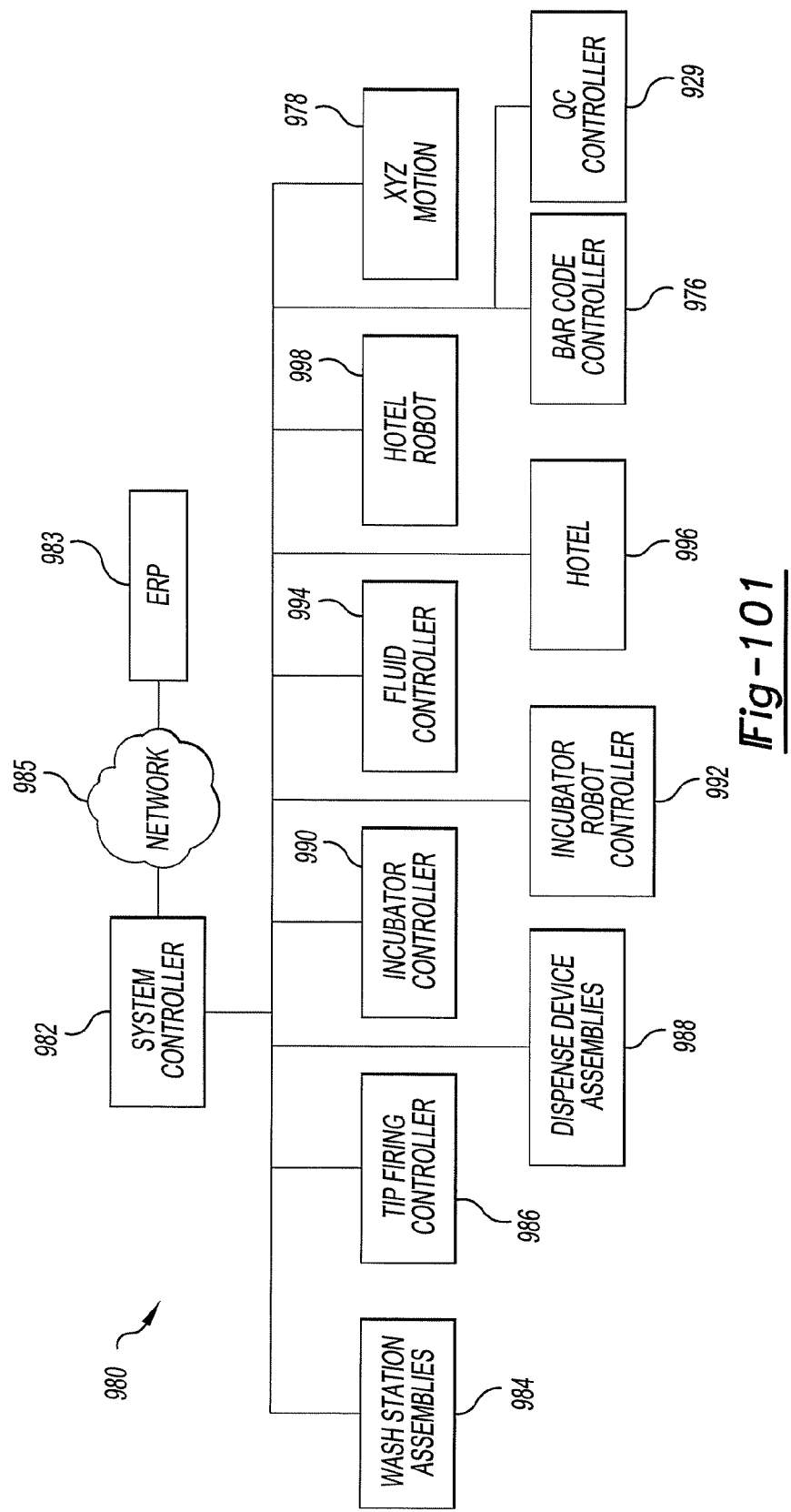
Figure 102:
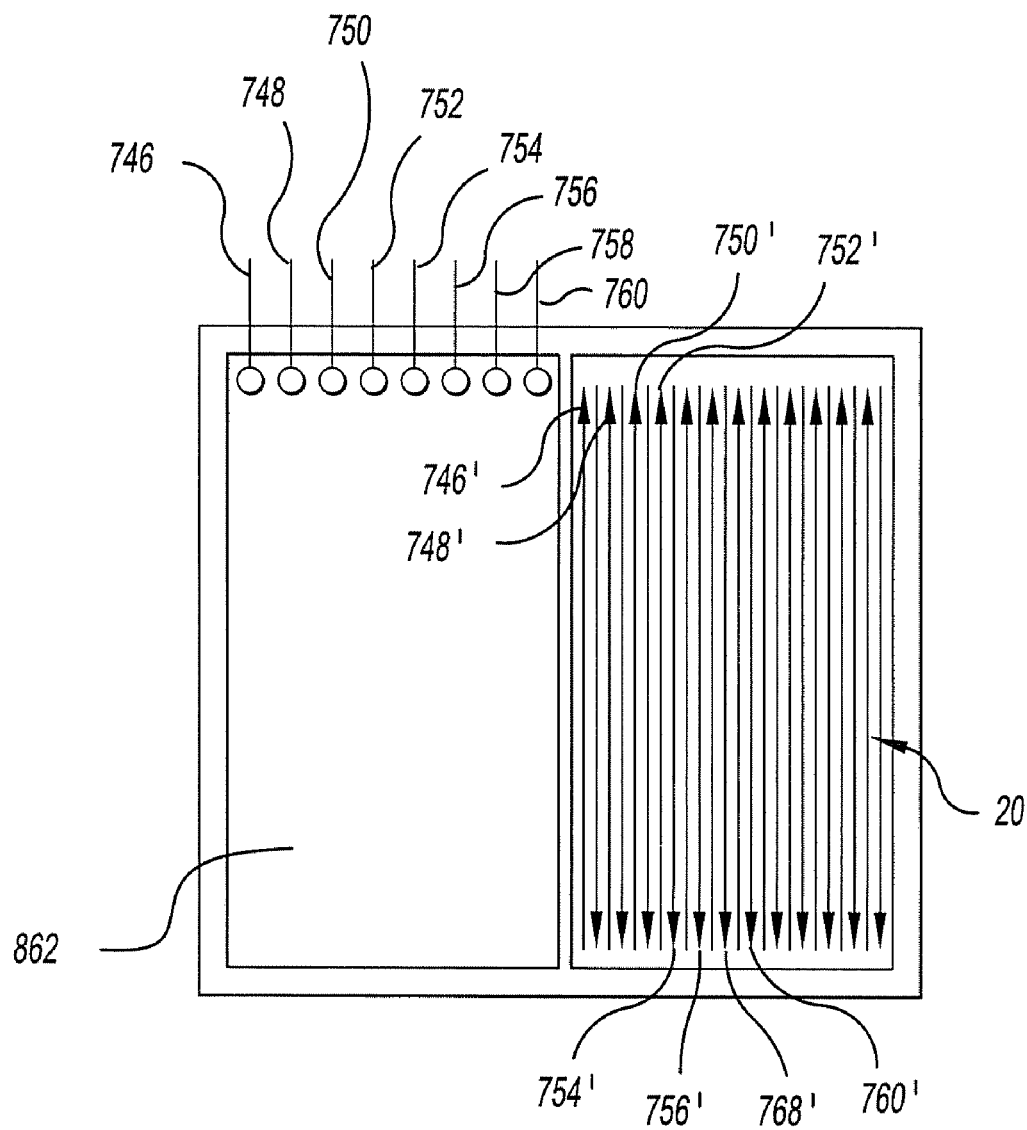
Figure 103:
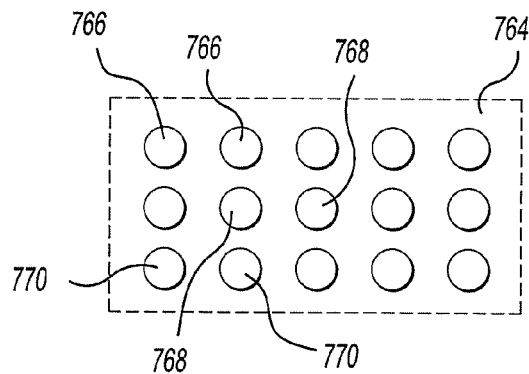
Figure 104:
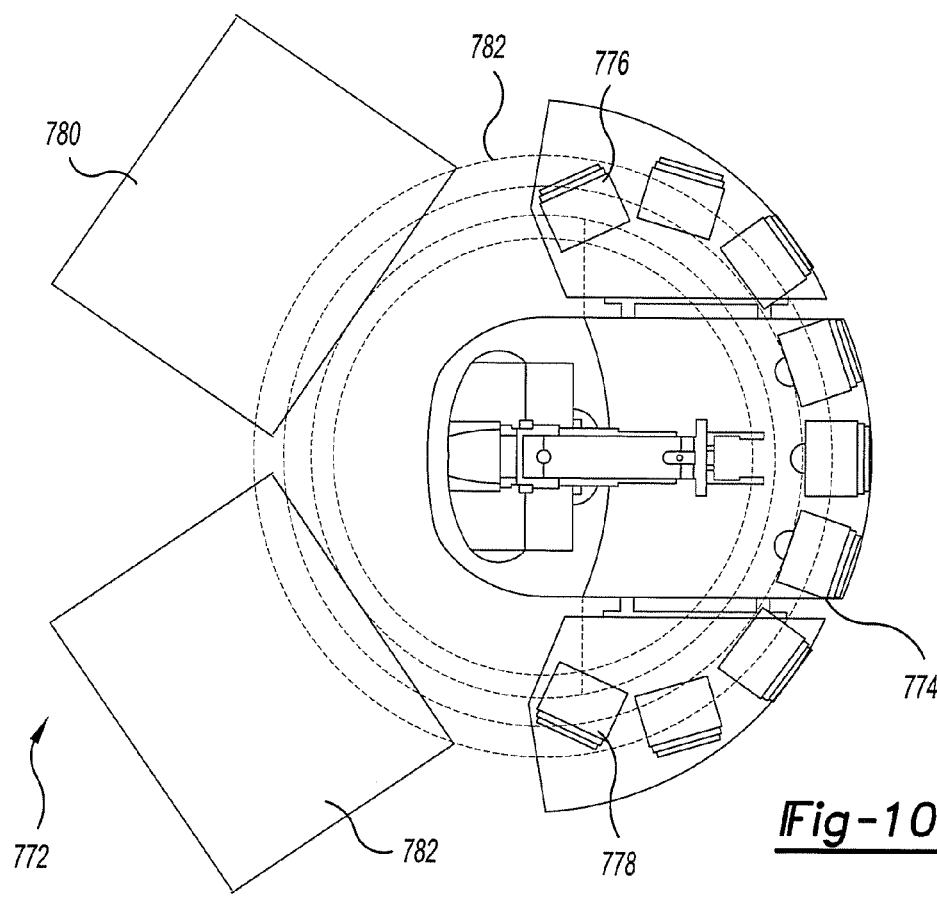
Figure 105:
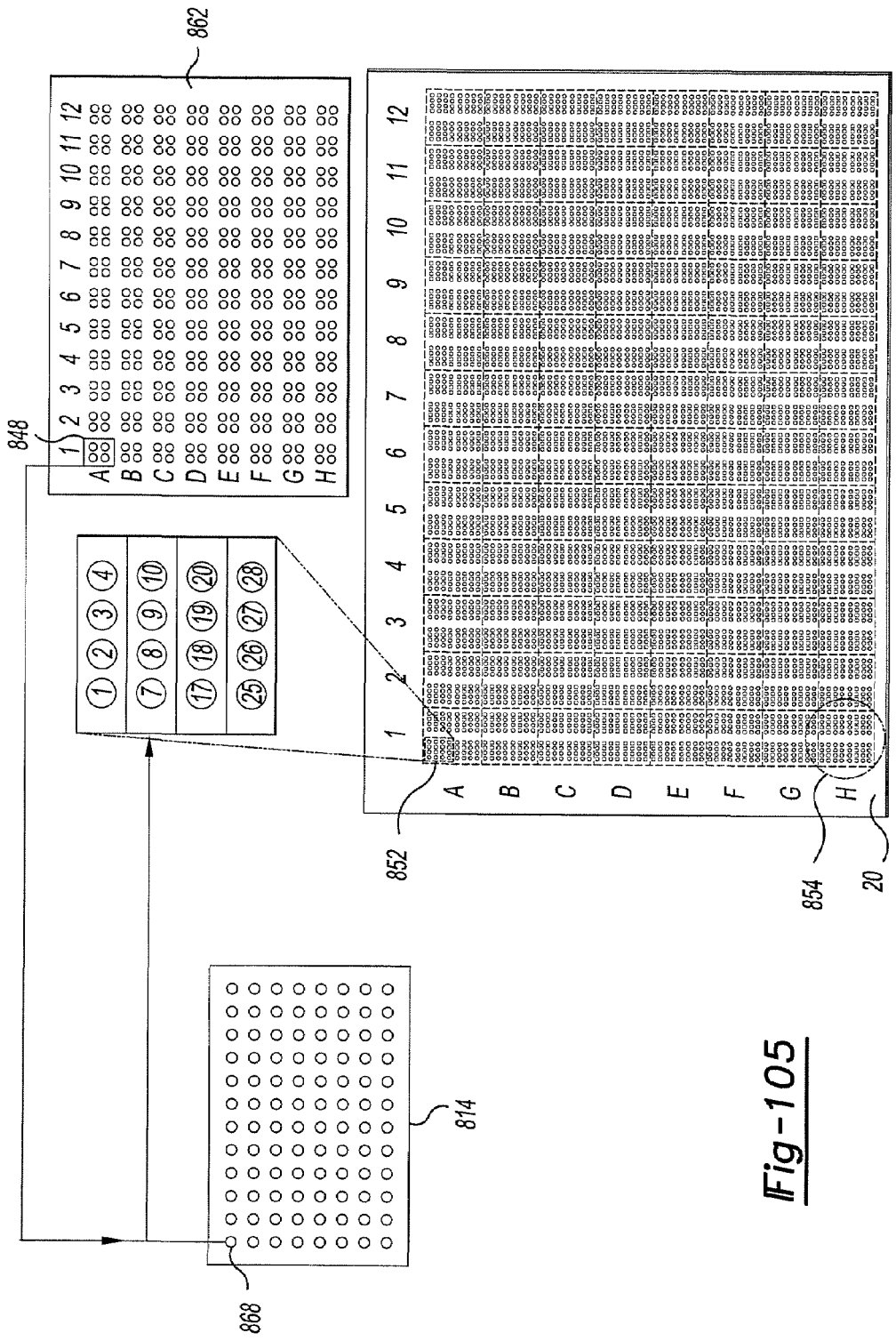
Figure 106:
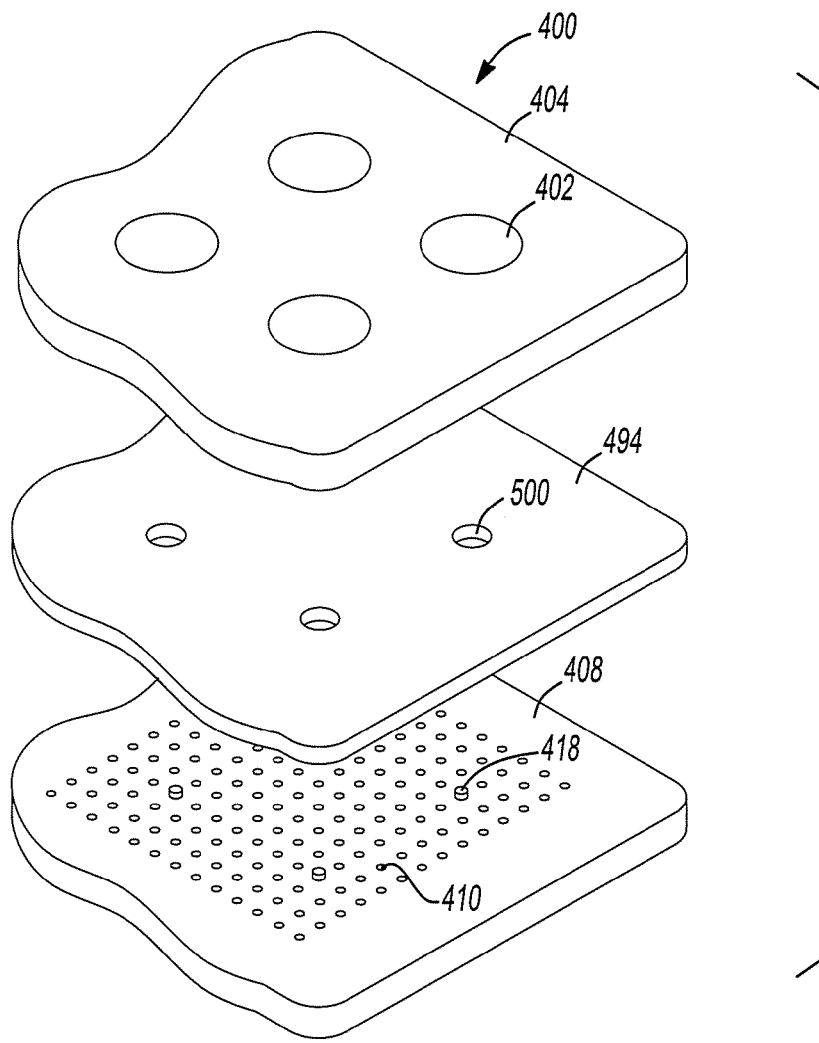
Figure 108:
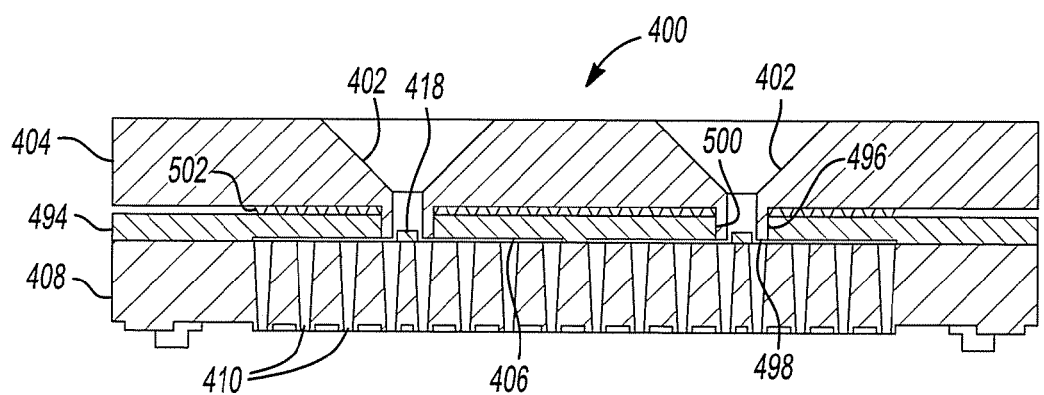
Figure 107:
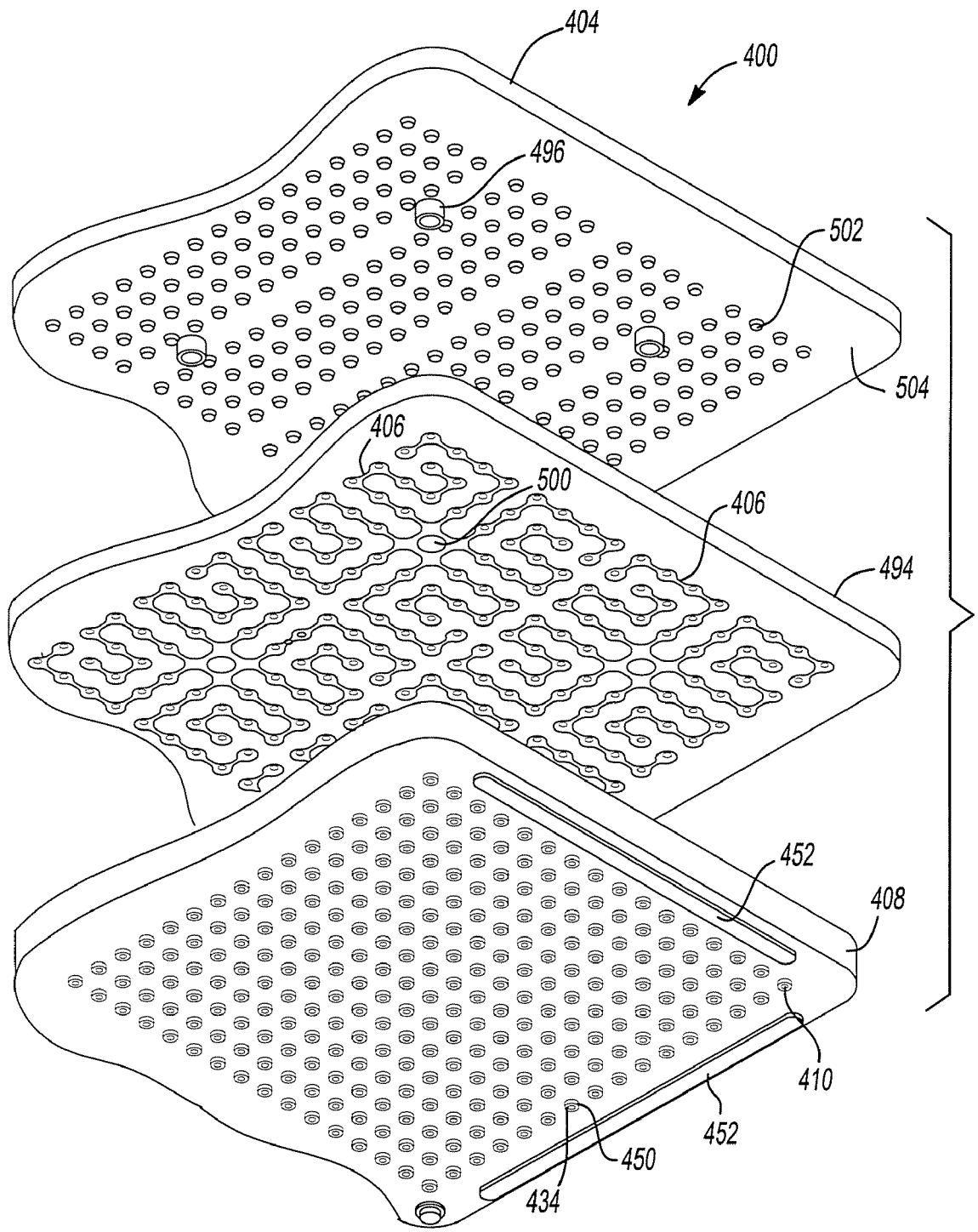
Figure 109:
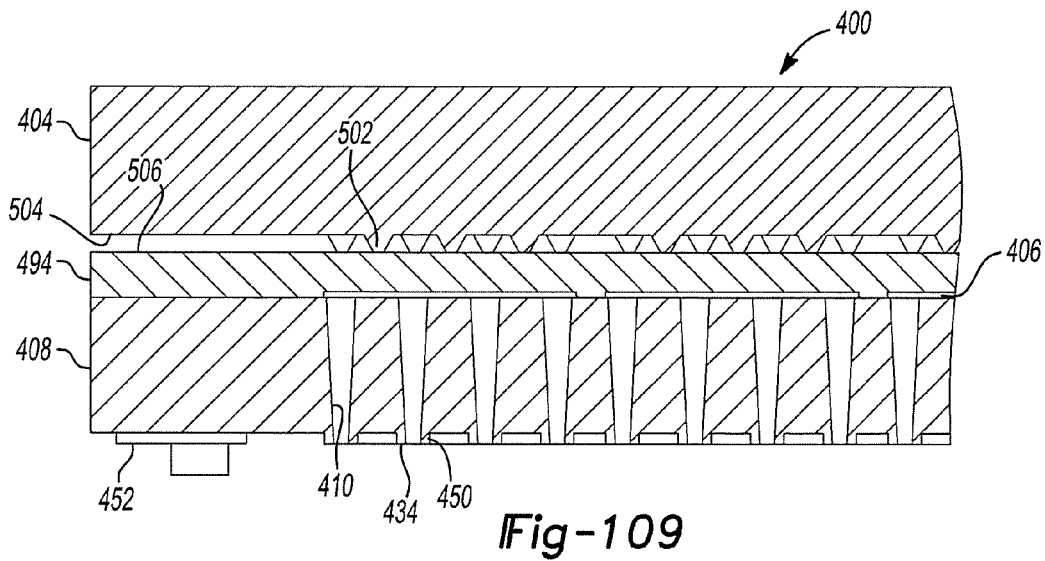
Figure 110:
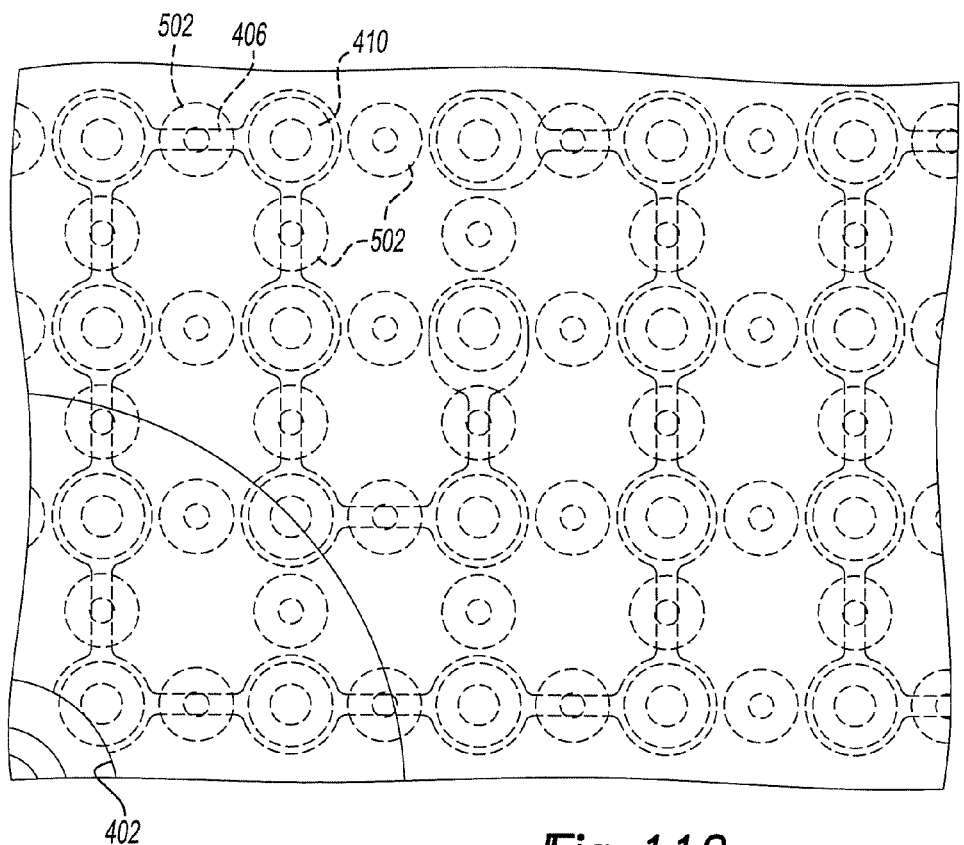
Figure 111:
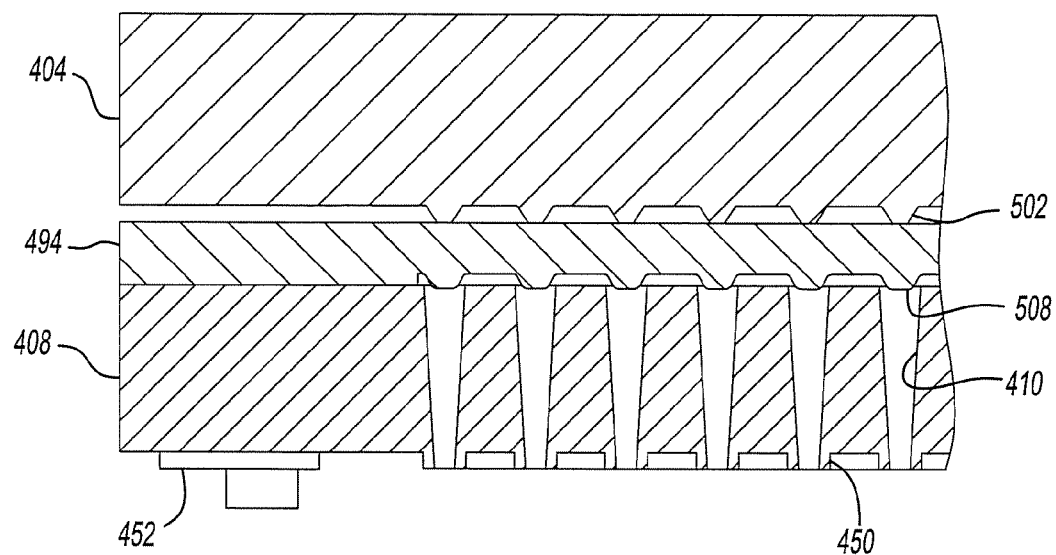
Figure 112:
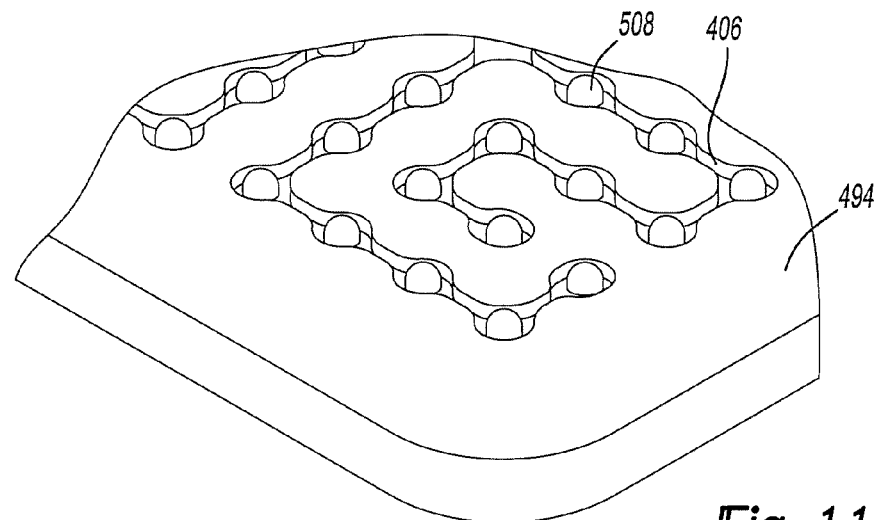
Figure 113:
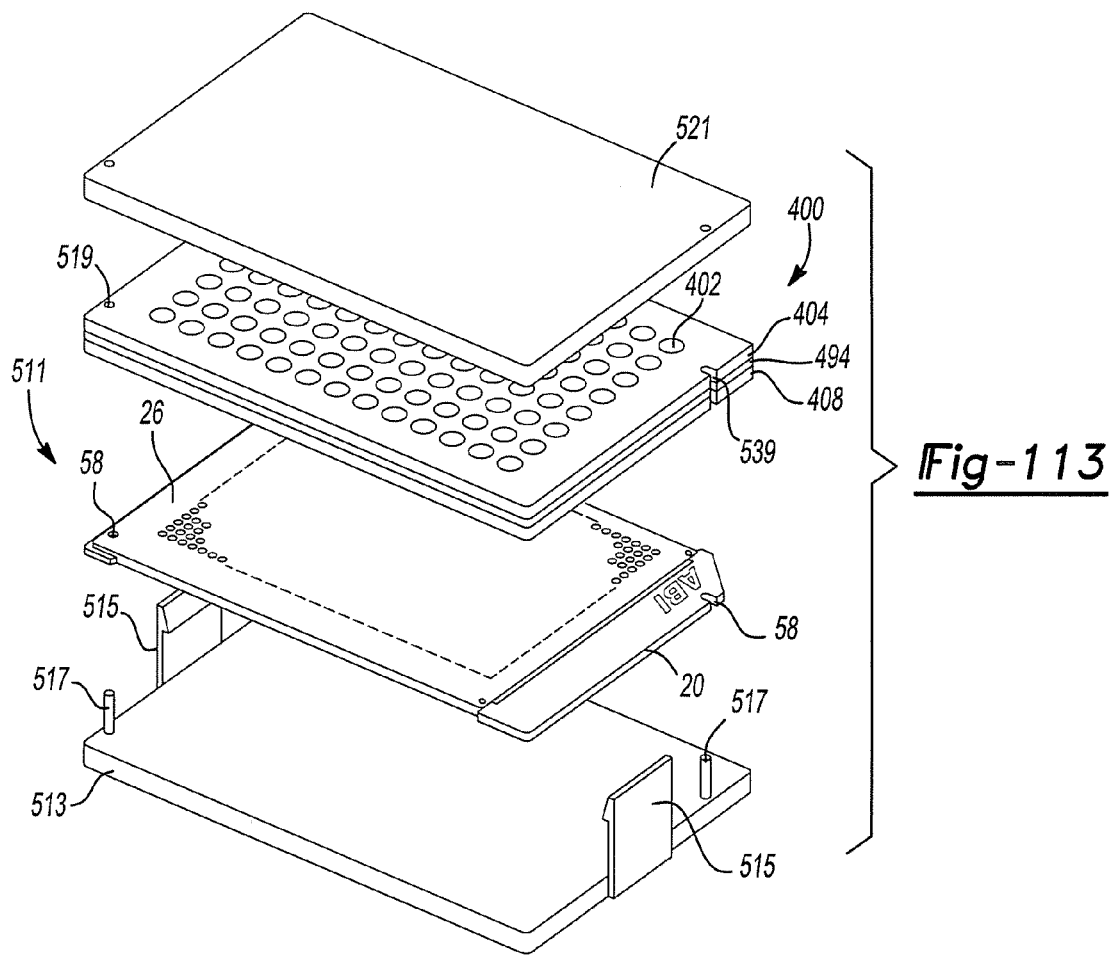
Figure 114:
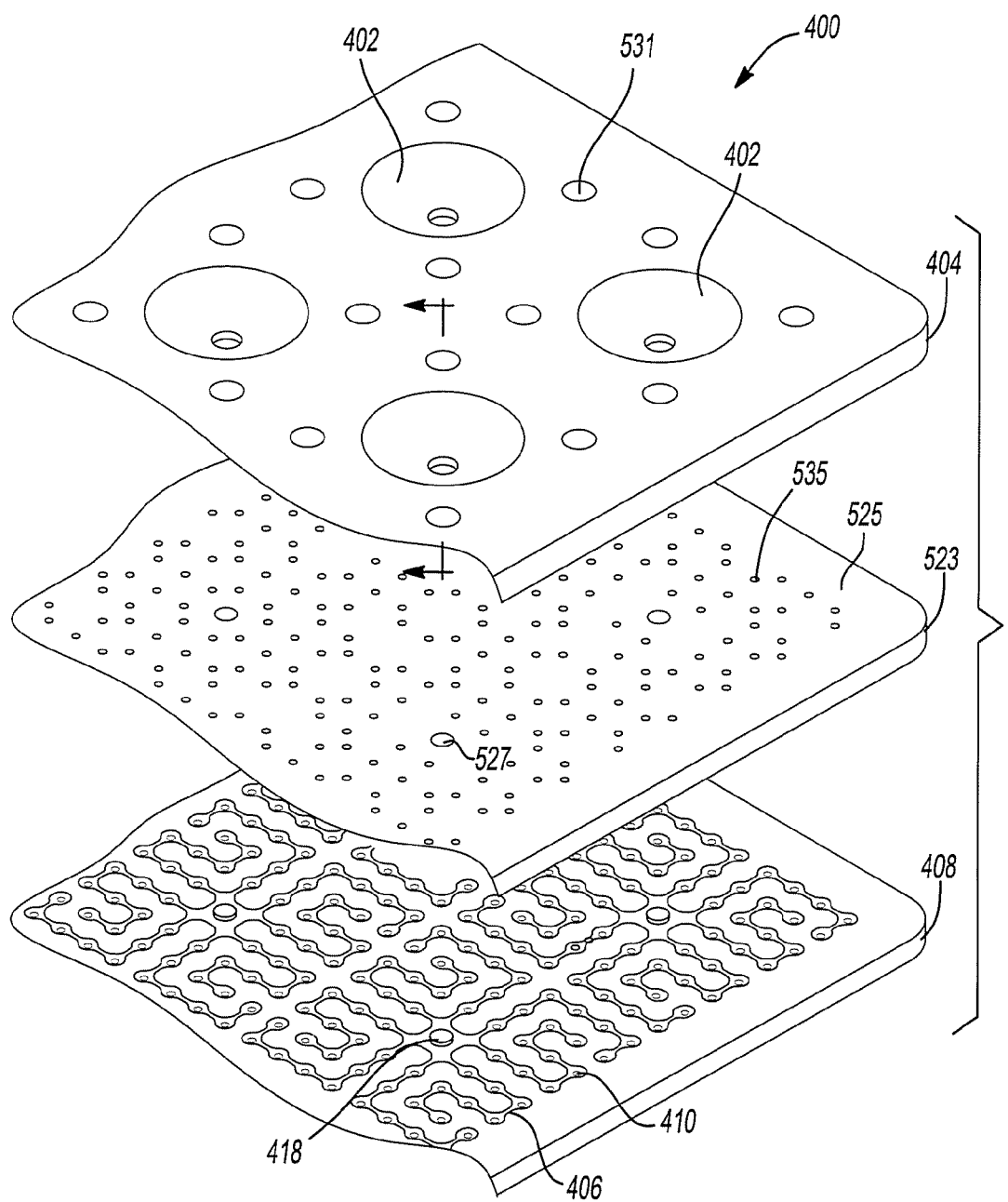
Figure 115:
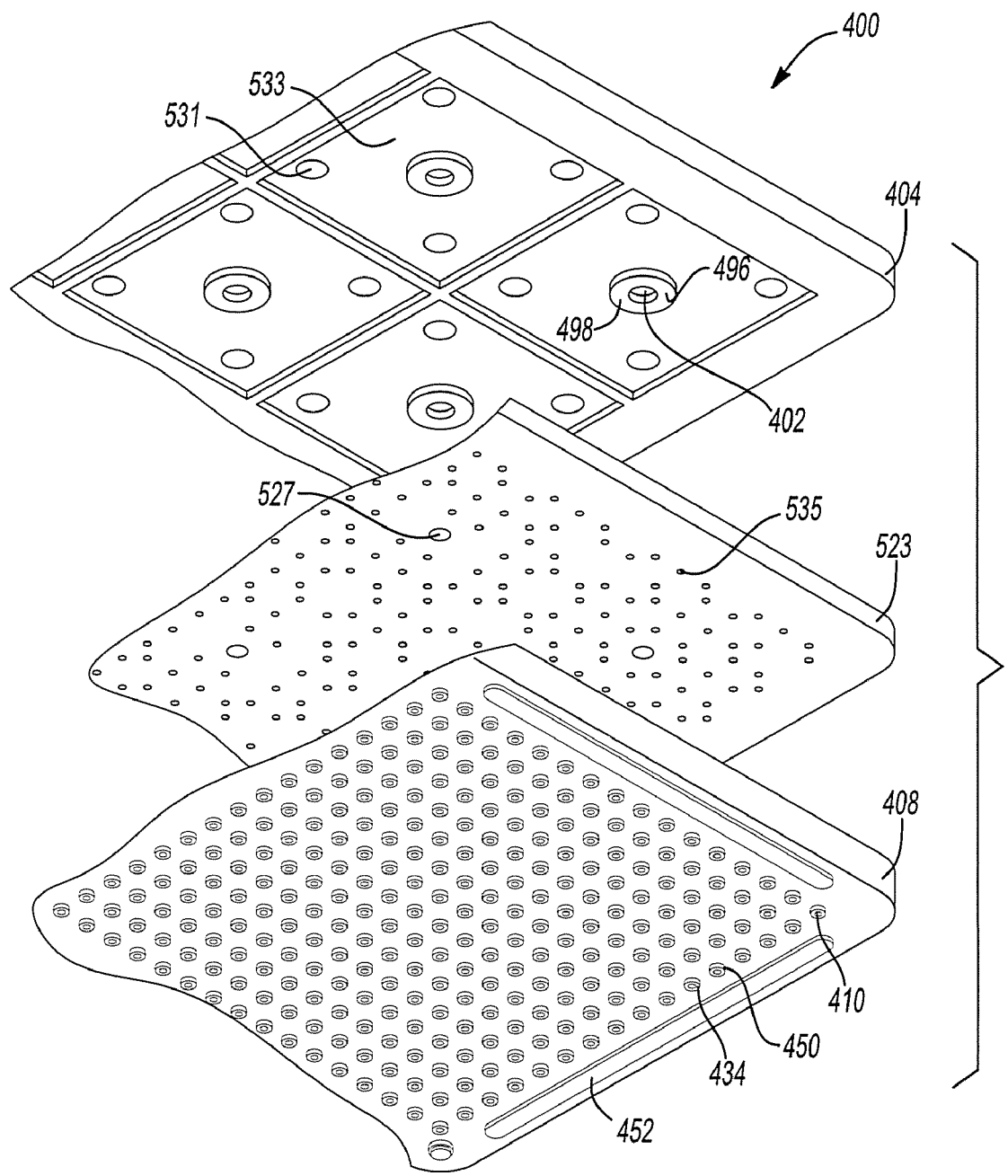
Figure 116:
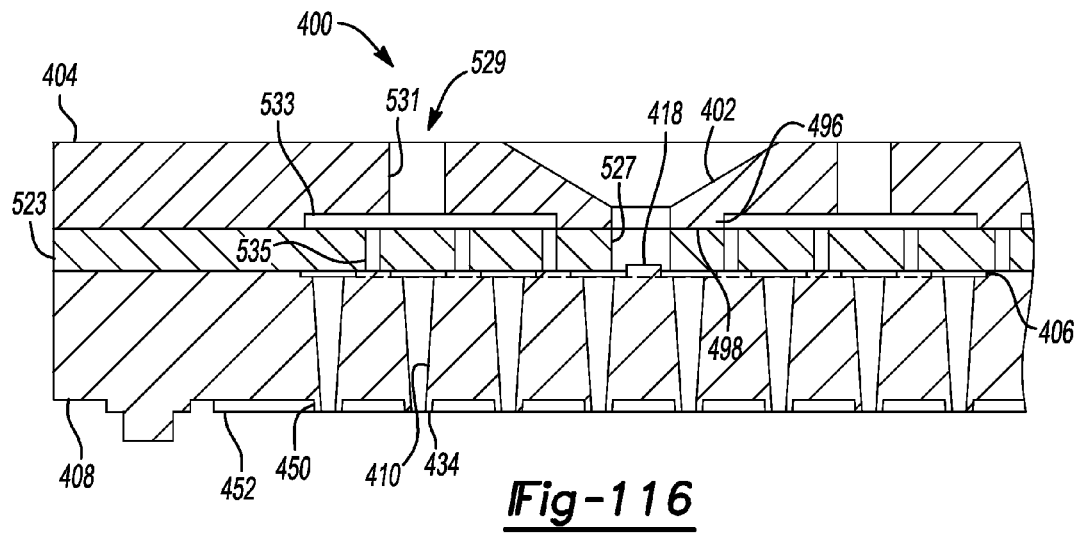
Figure 119:
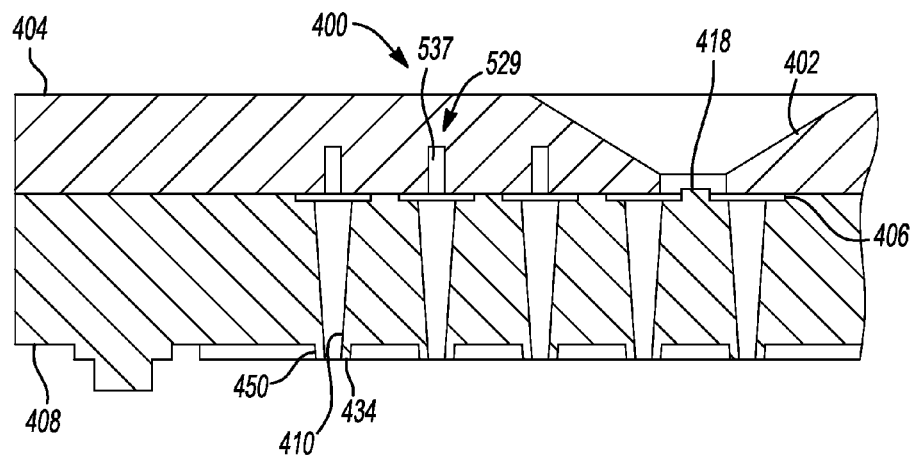
Figure 117:
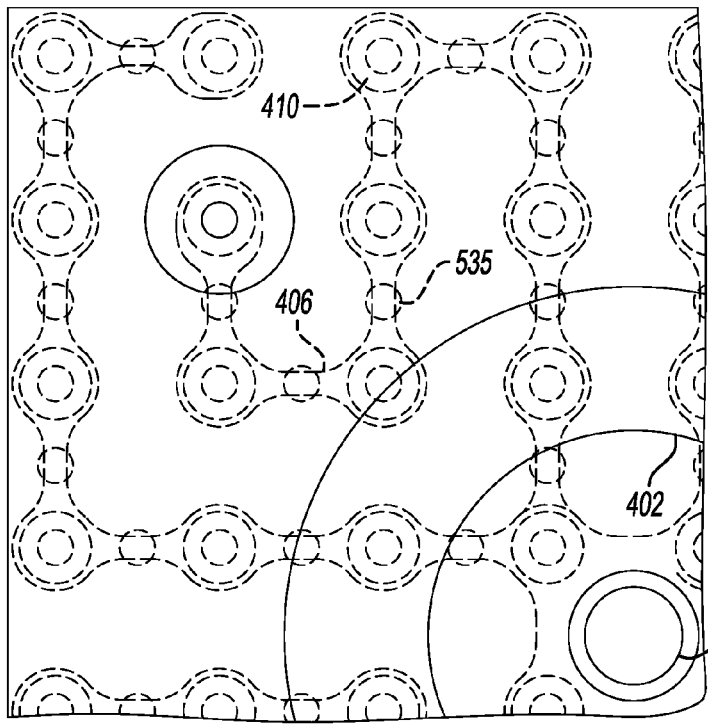
Figure 118:
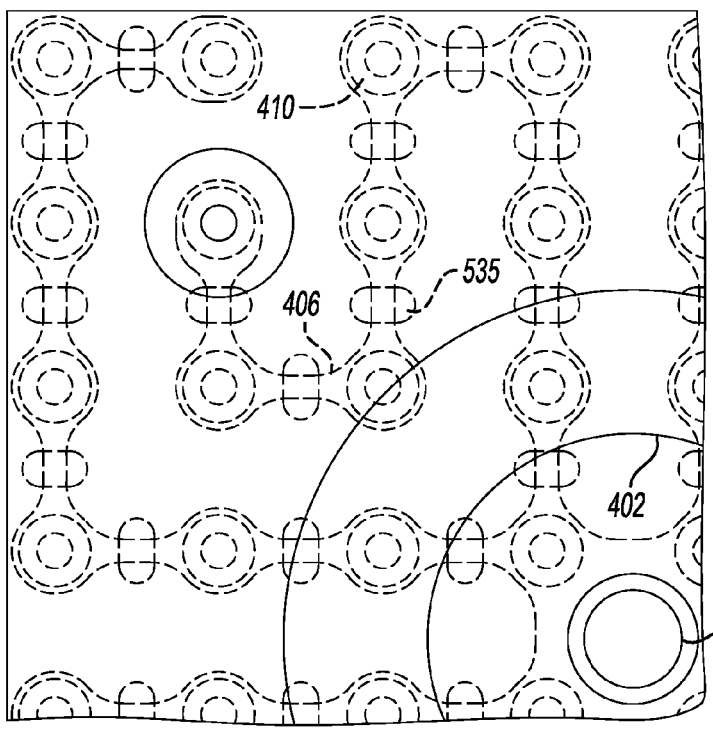
Figure 120:
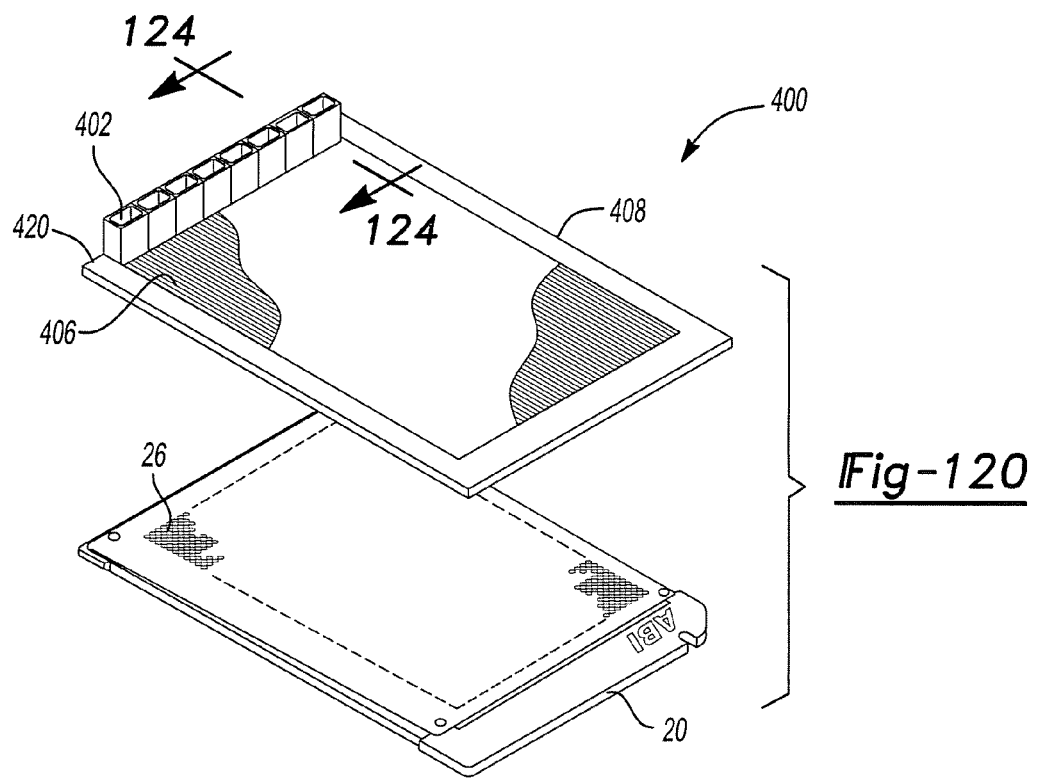
Figure 121:
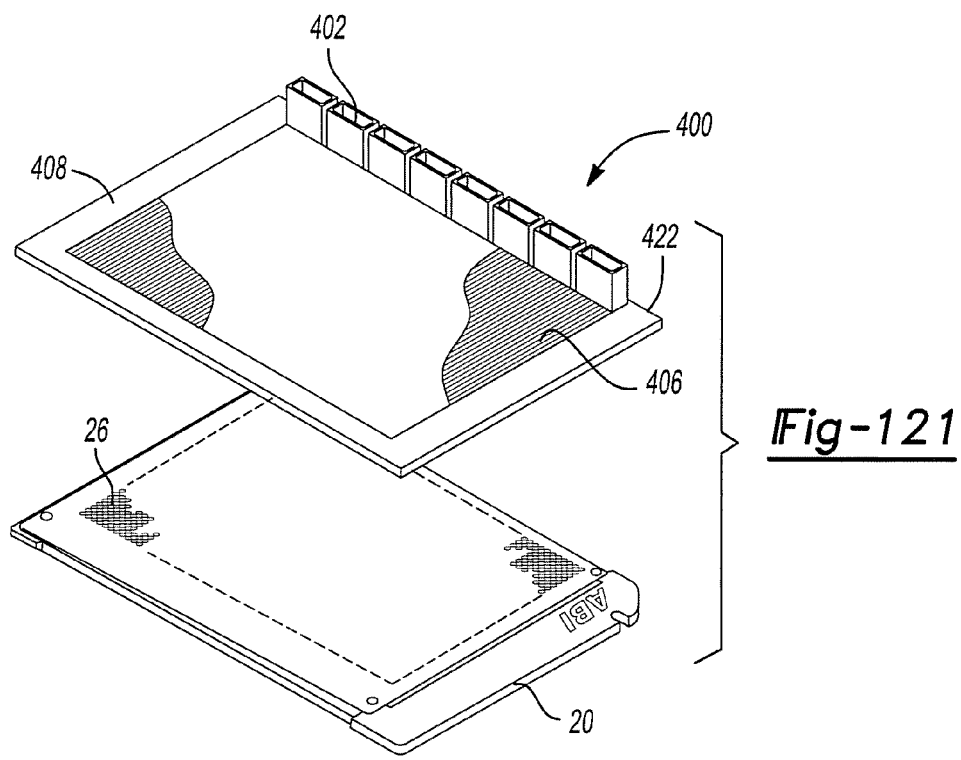
Figure 122:
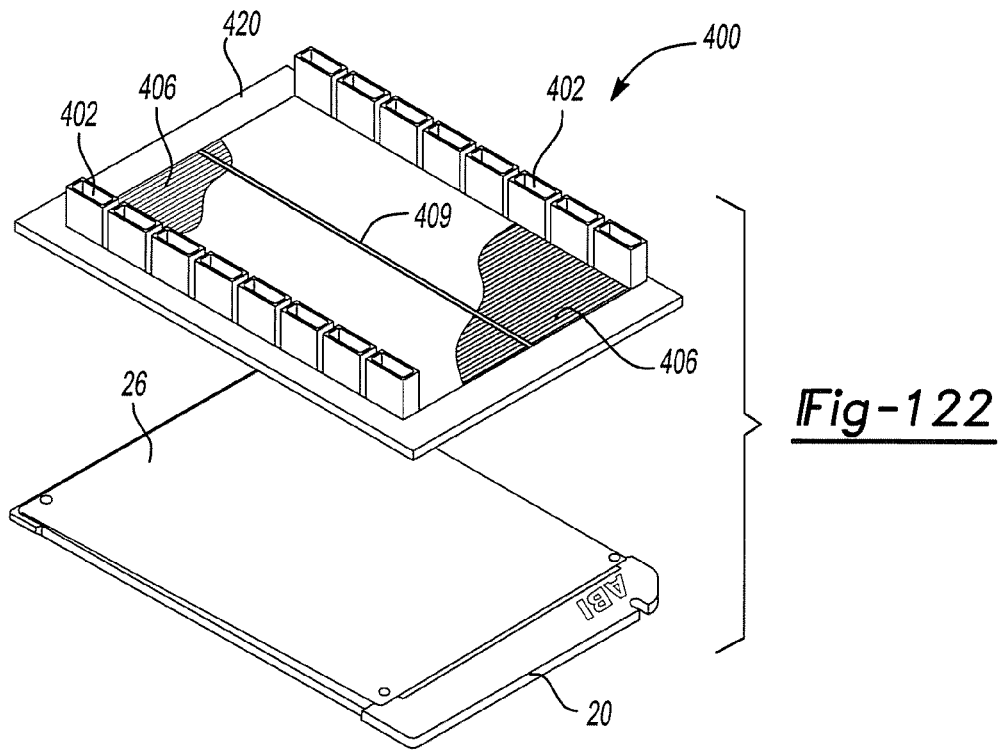
Figure 123:
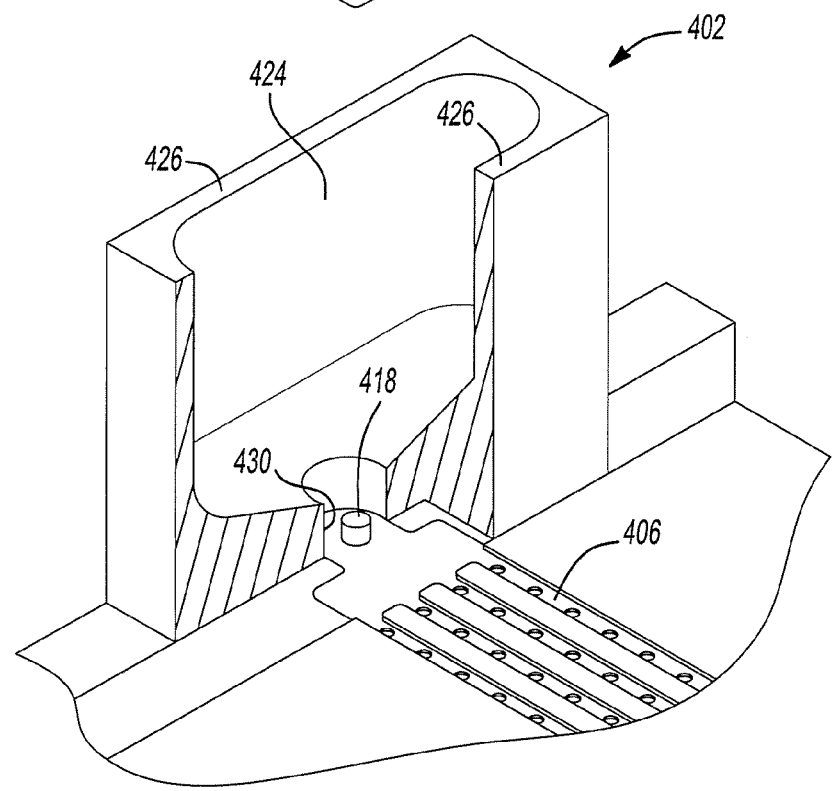
Figure 124:
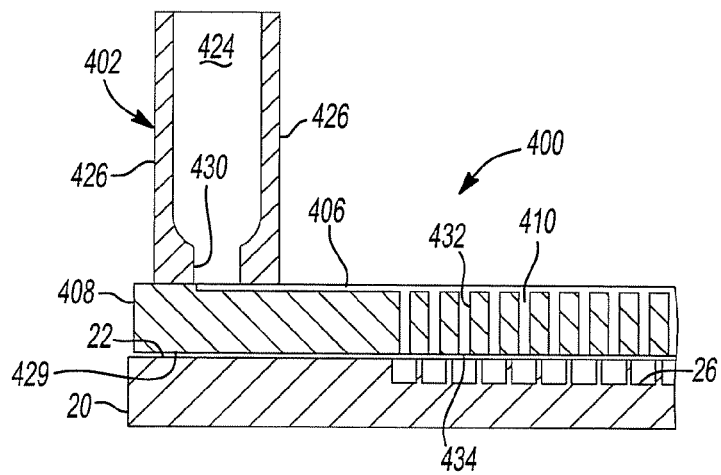
Figure 132:
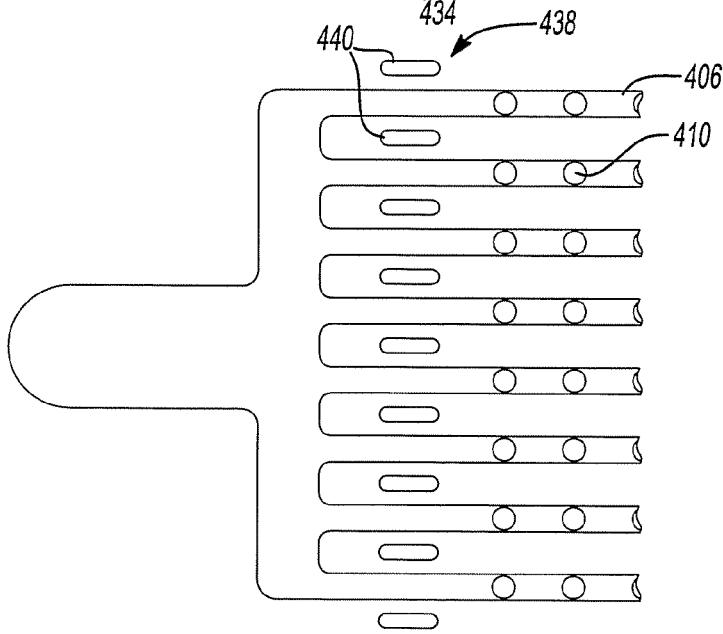
Figure 140:
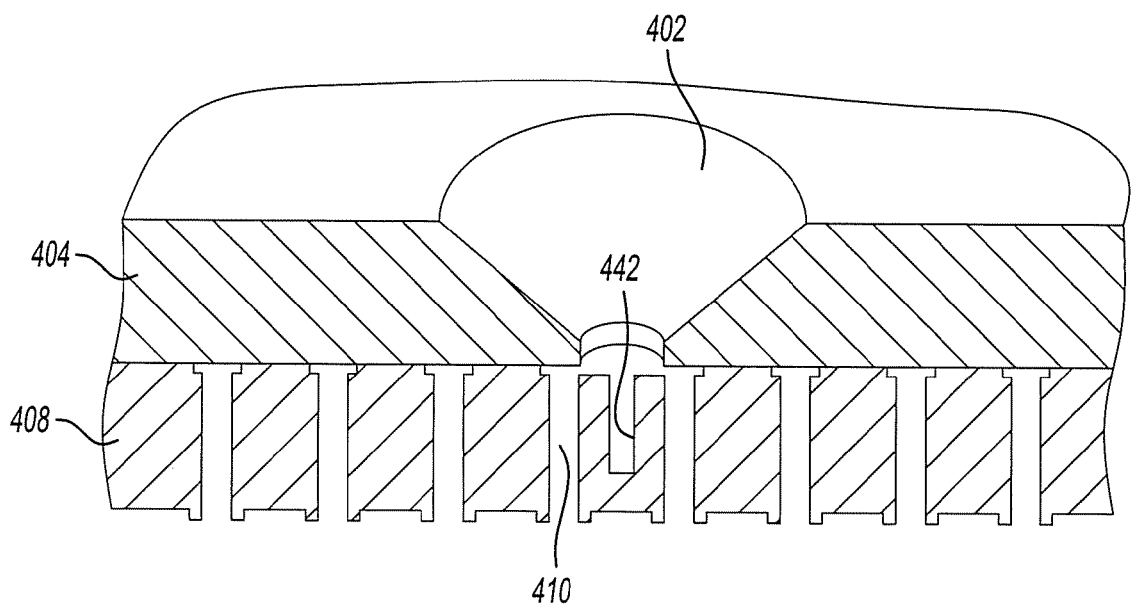
Figure 143:
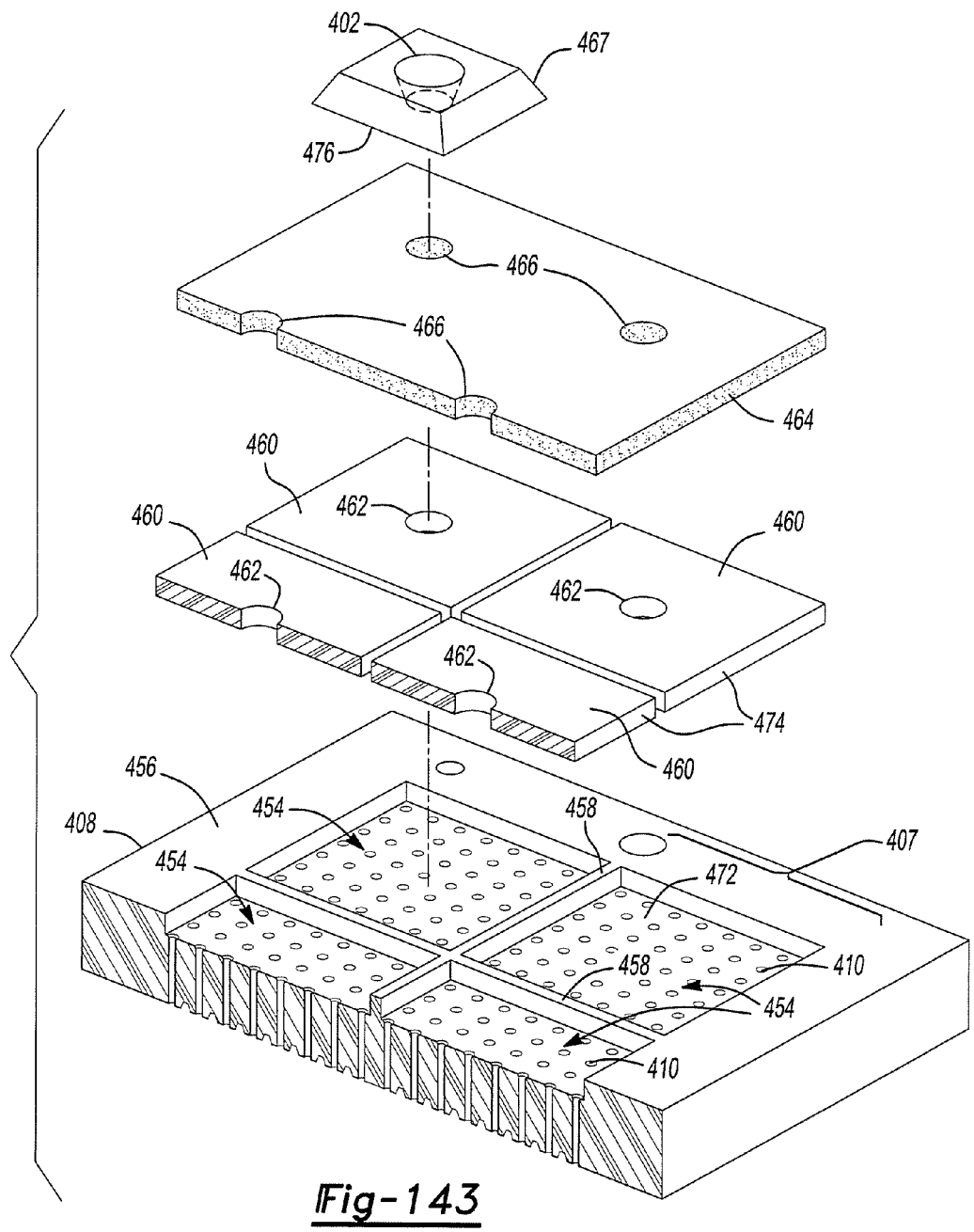
Figure 144:
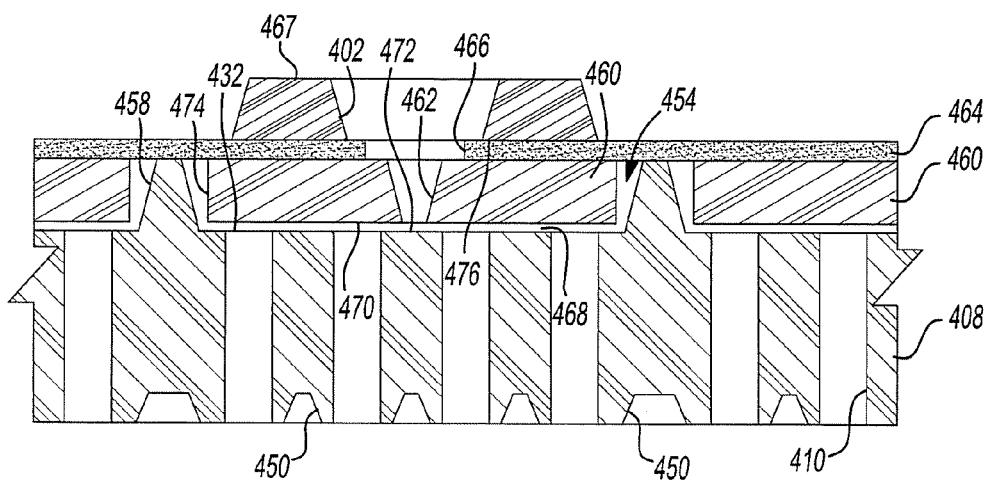
Figure 145:
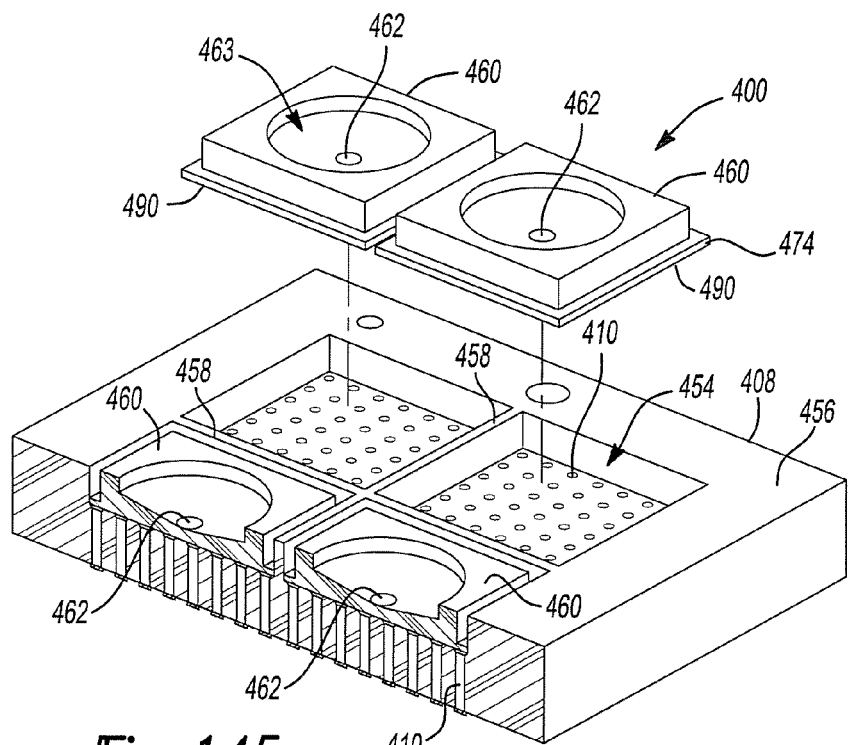
Figure 146:
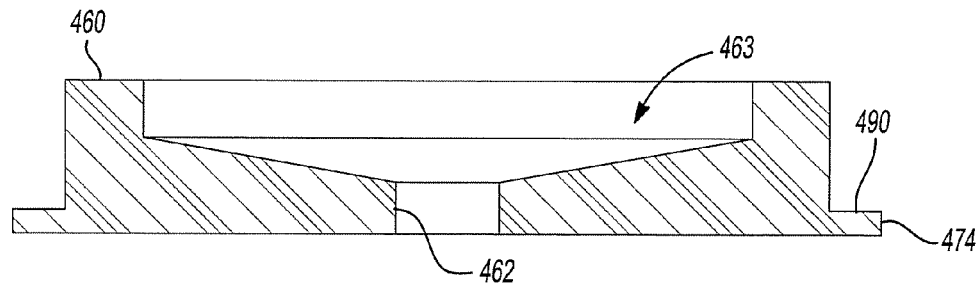
Figure 147:
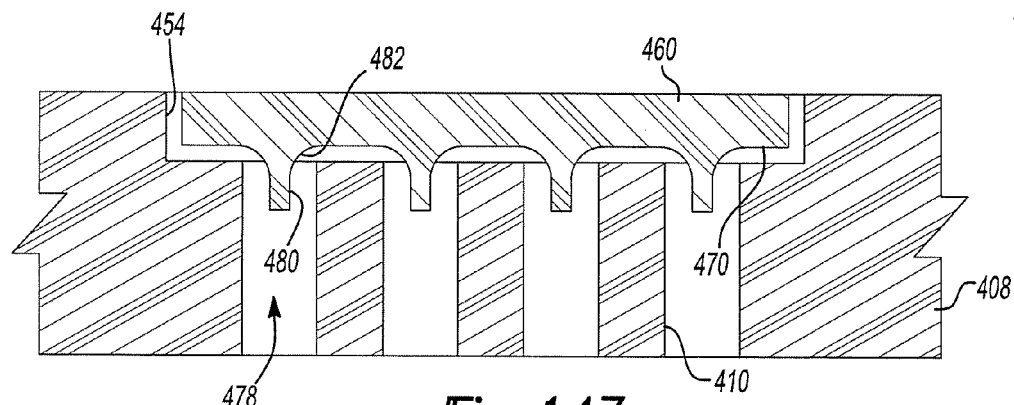
Figure 148:
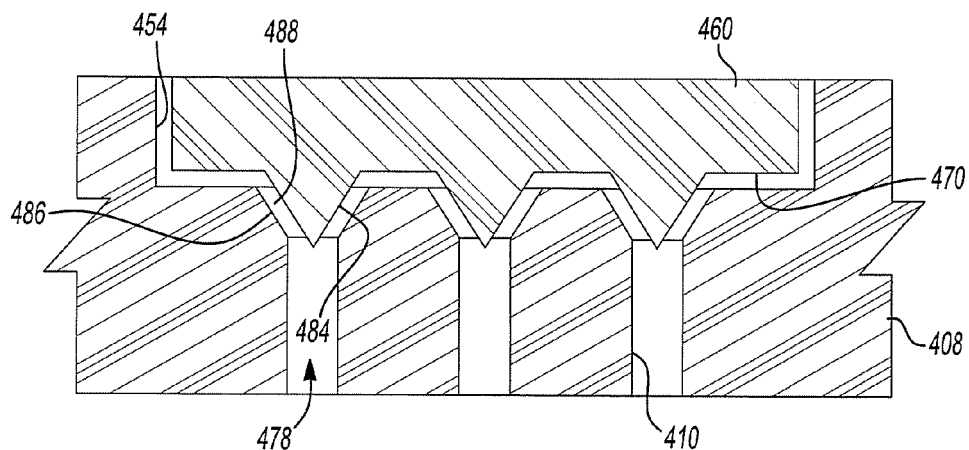
Figure 149:
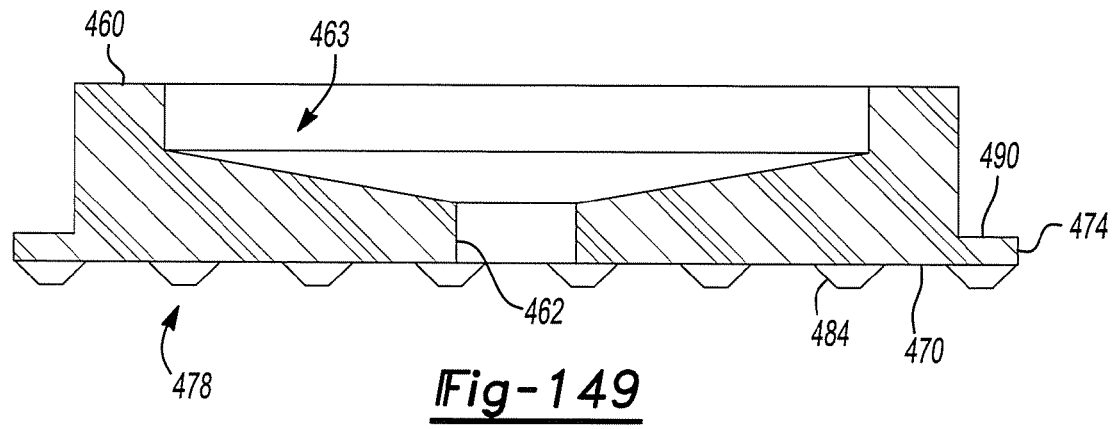
Figure 150:
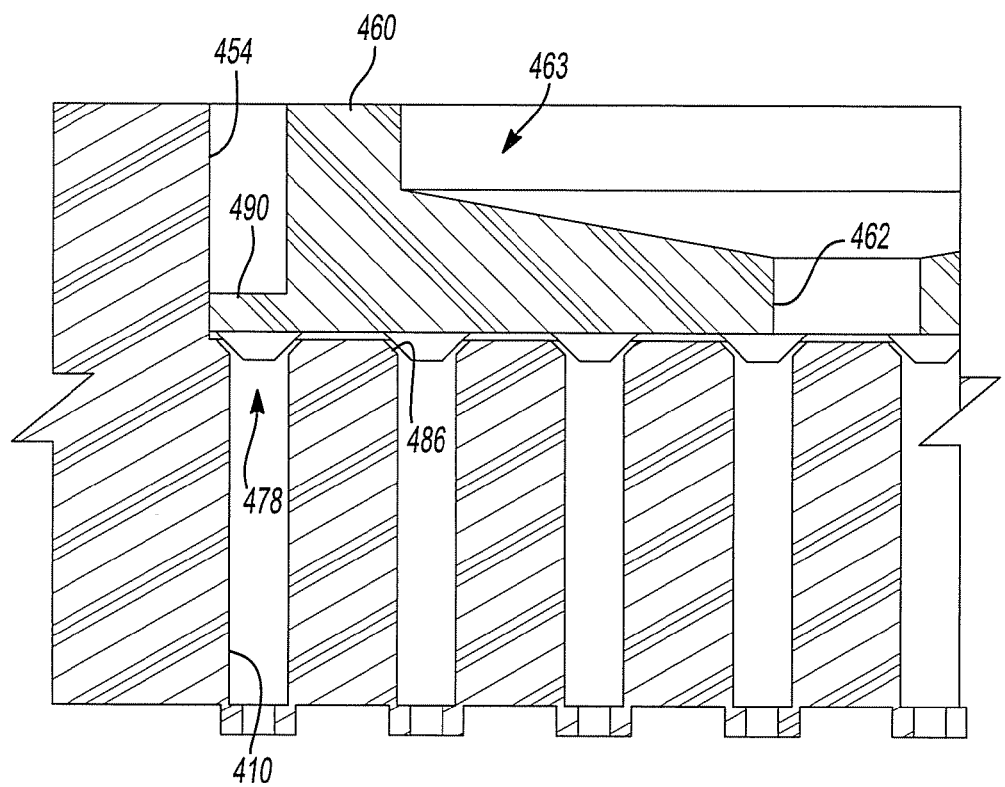
Figure 151:
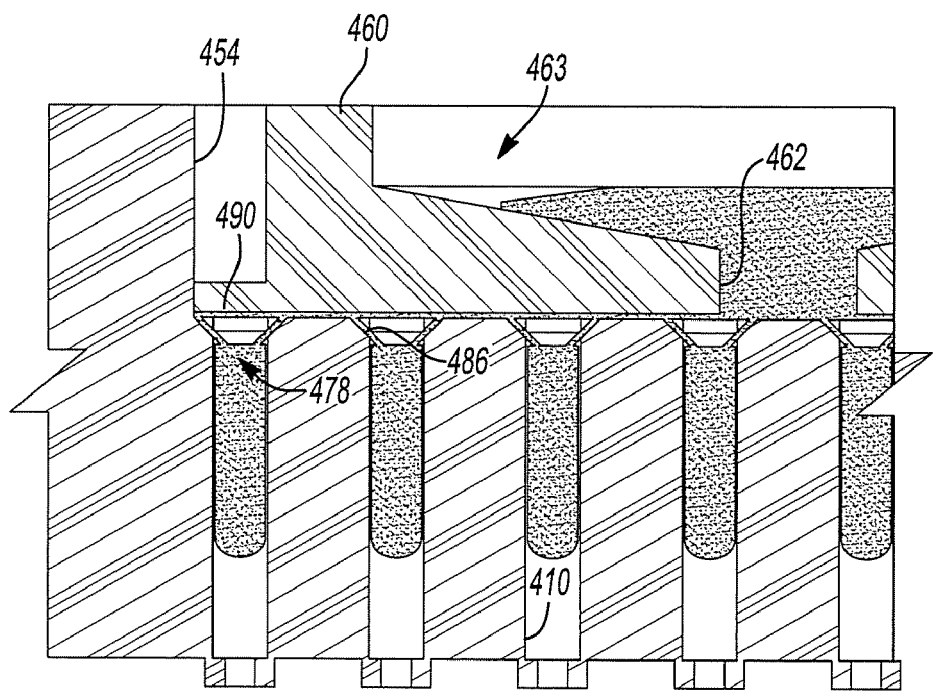
Figure 152:
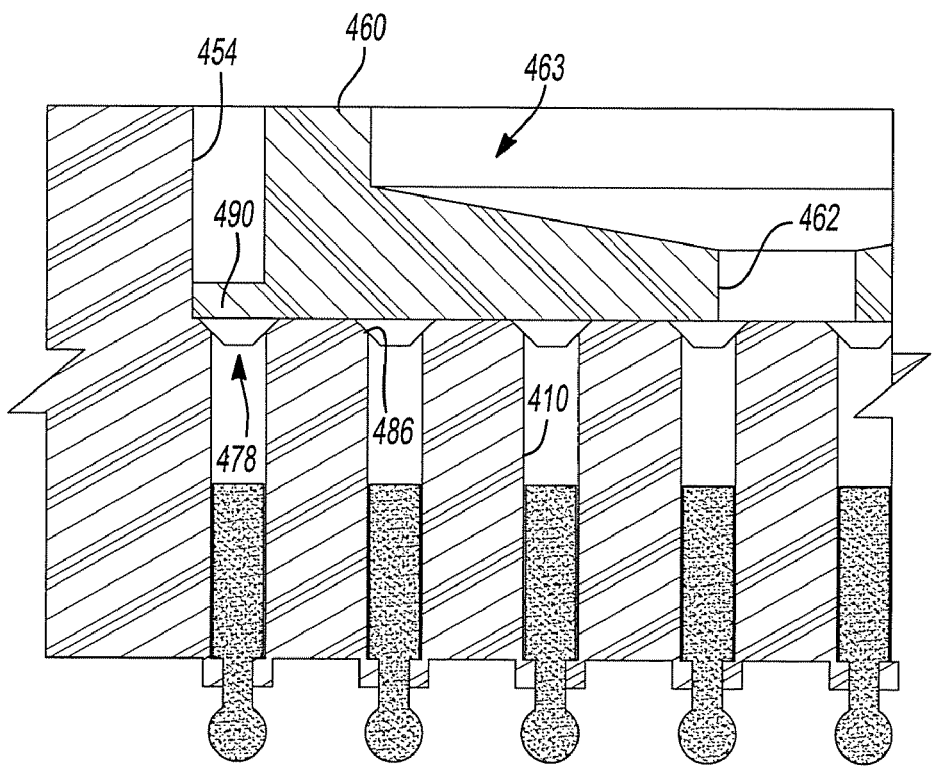
Figure 153:
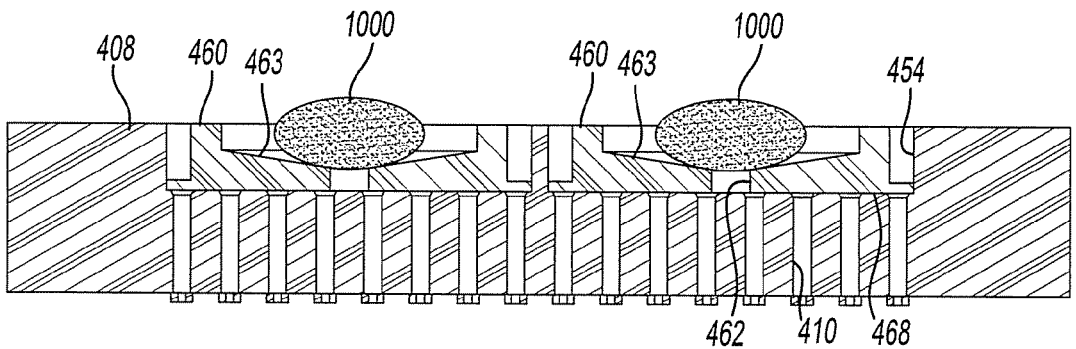
Figure 154:
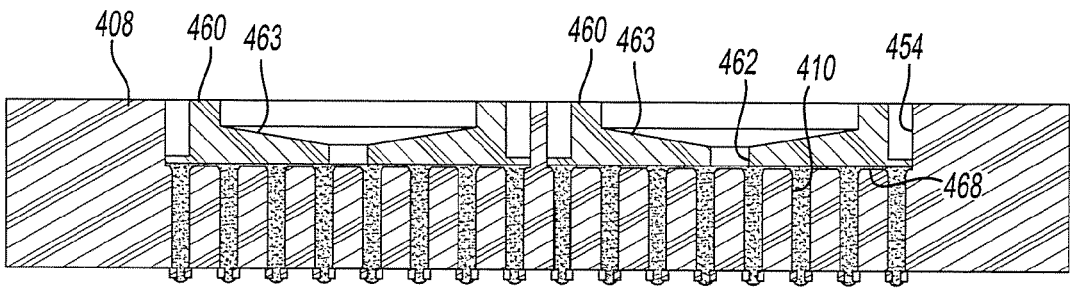
Figure 155:
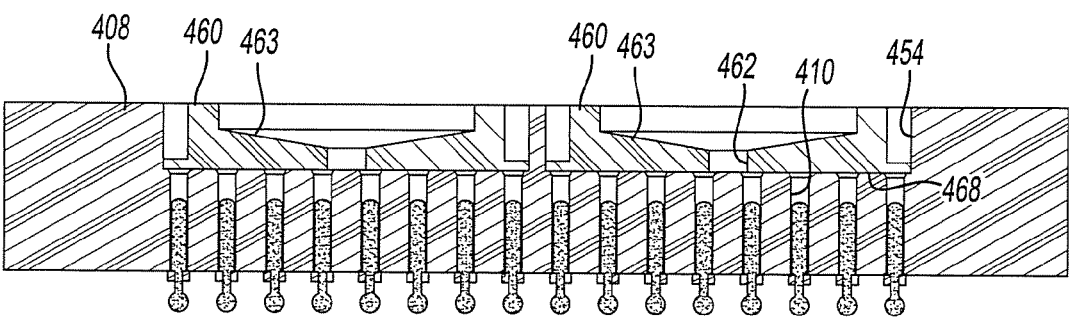
Figure 156:
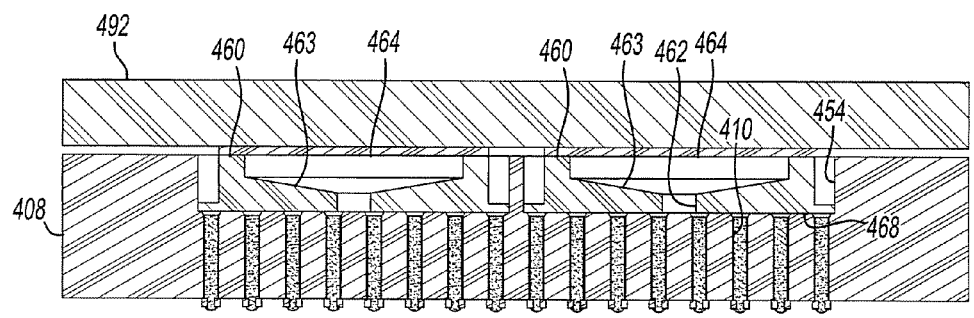
Figure 157:
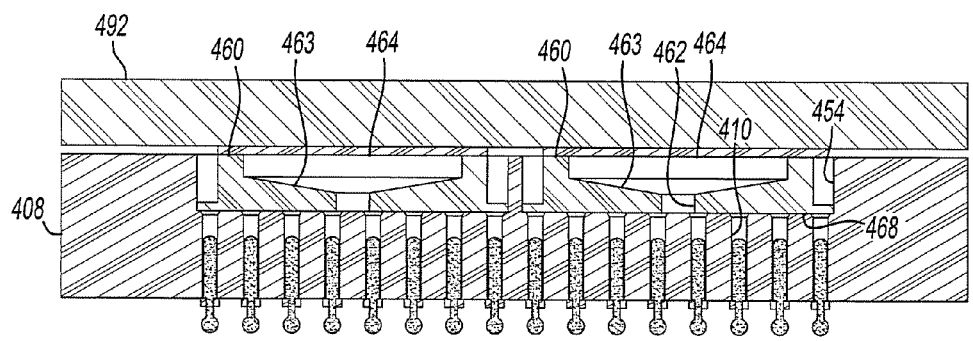
Figure 158:
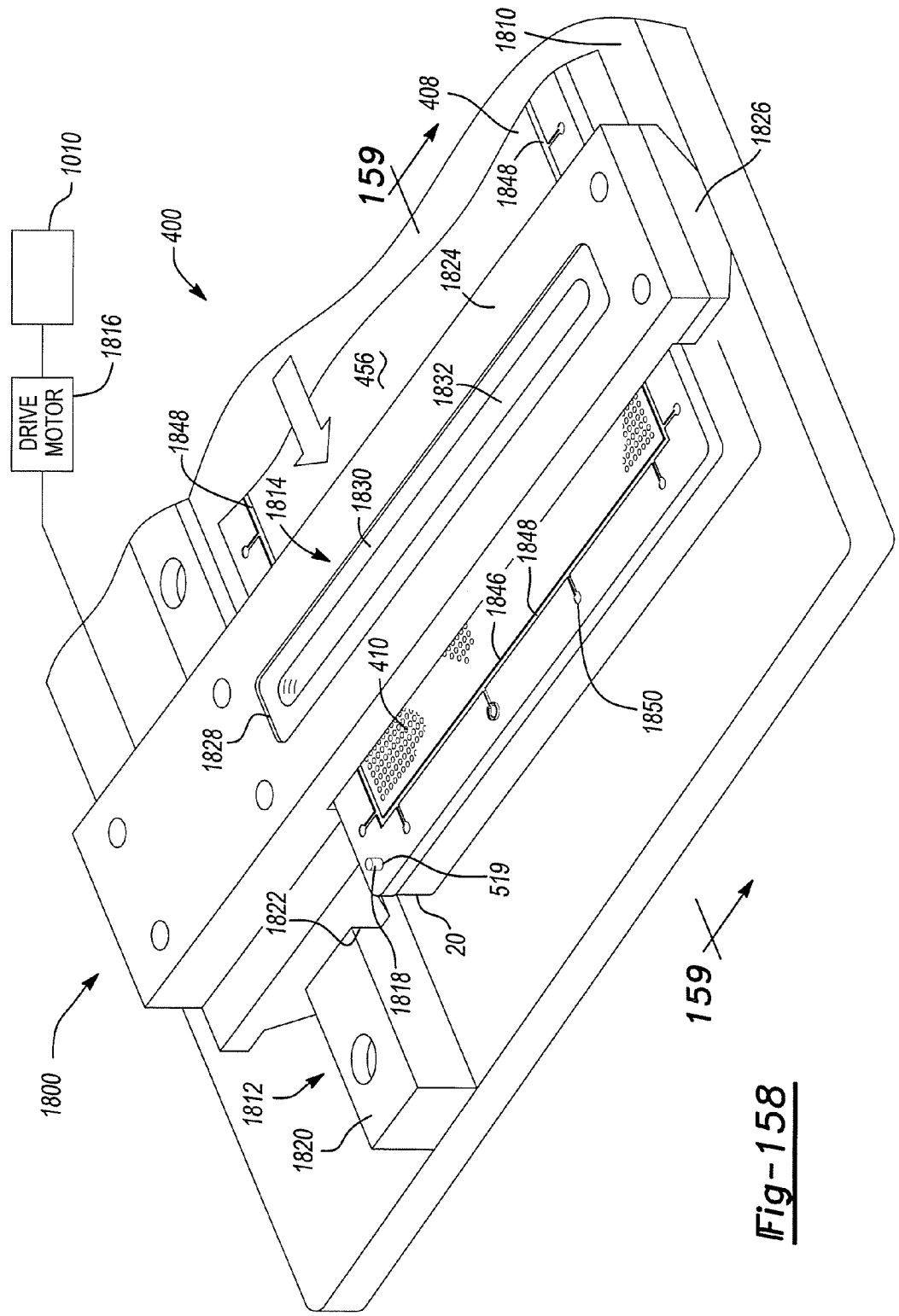
Figure 159:
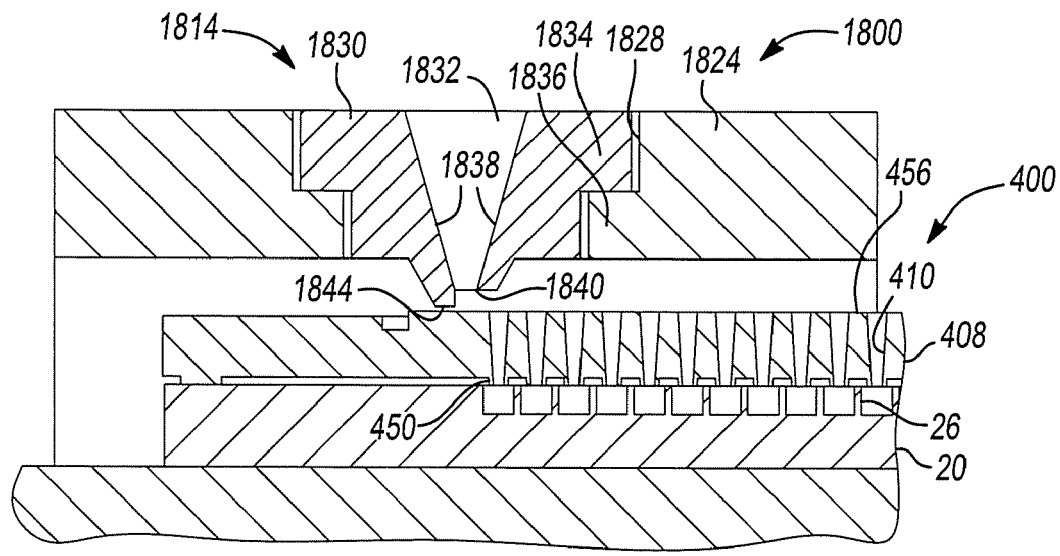
Figure 160:
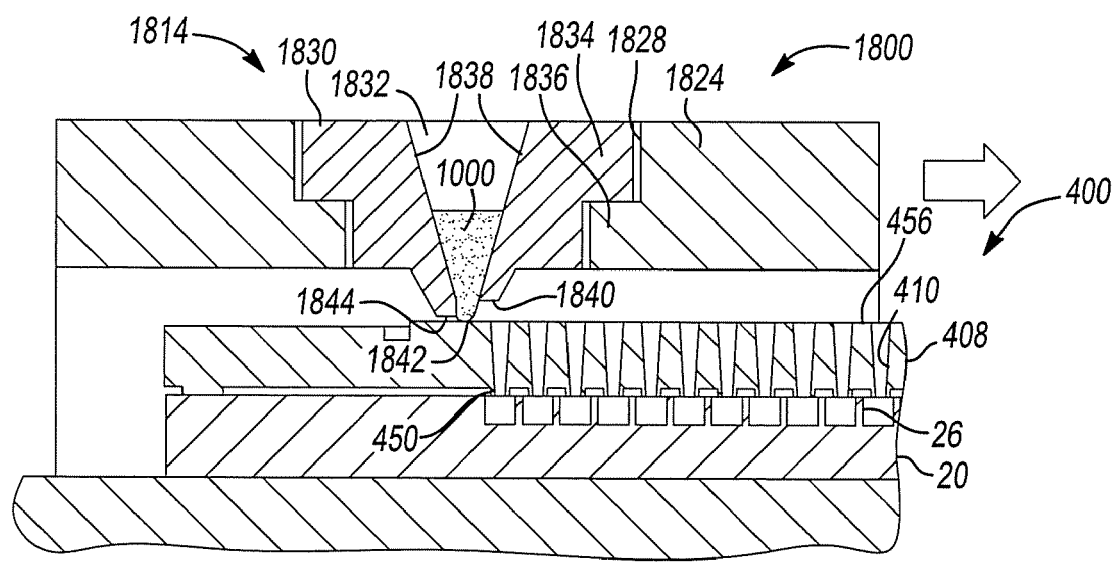
Figure 161:
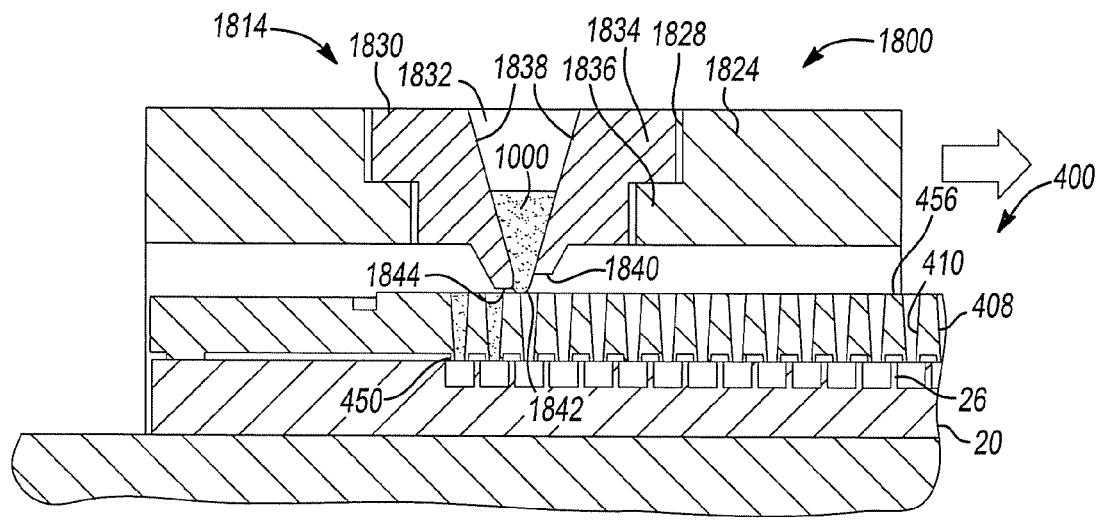
Figure 162:
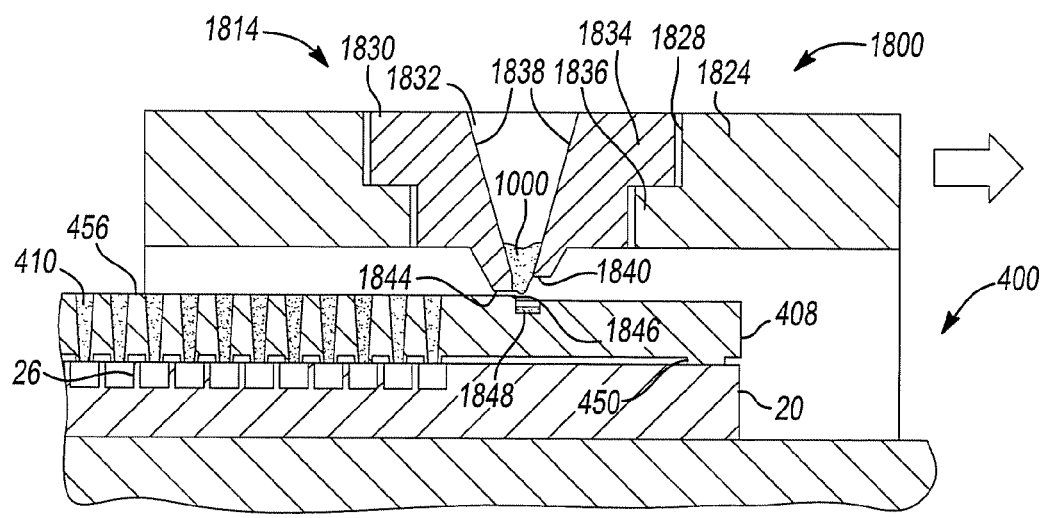
Figure 163:
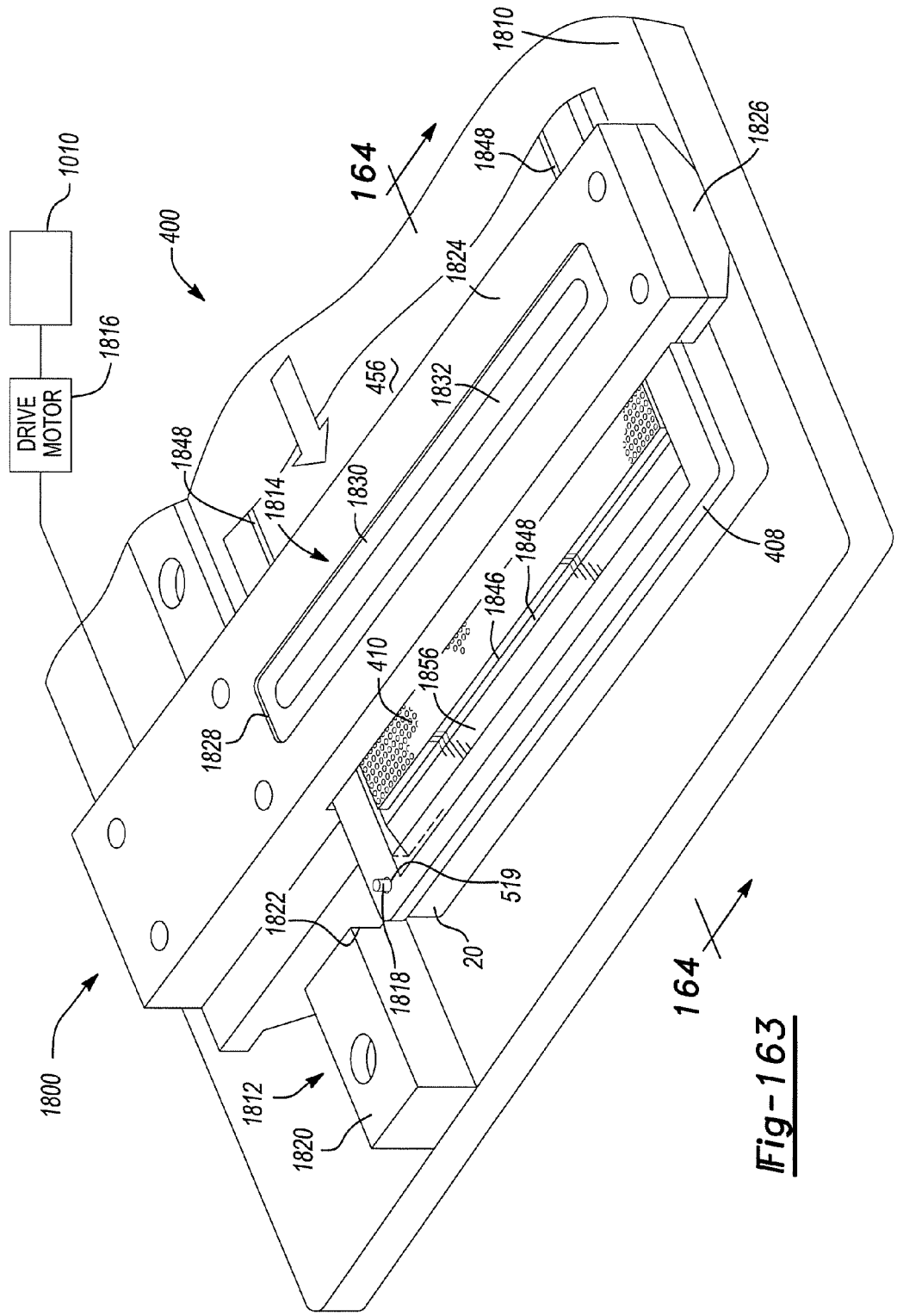
Figure 164:
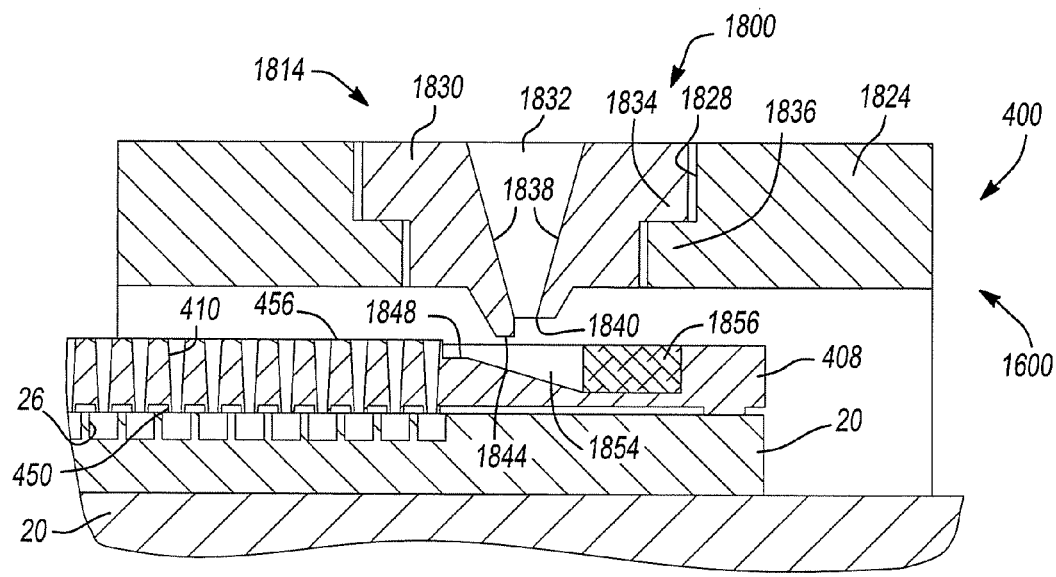
Figure 166:
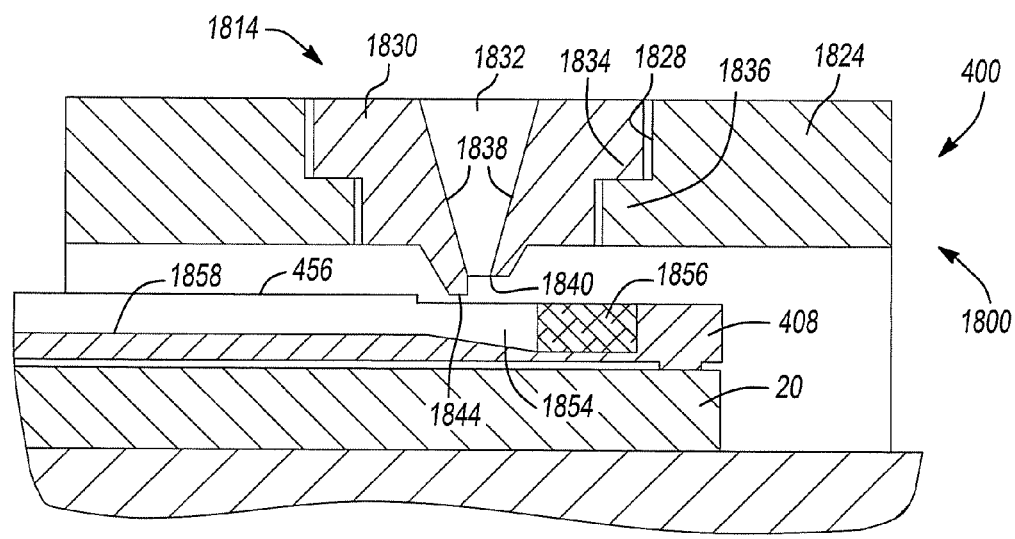
Figure 165:
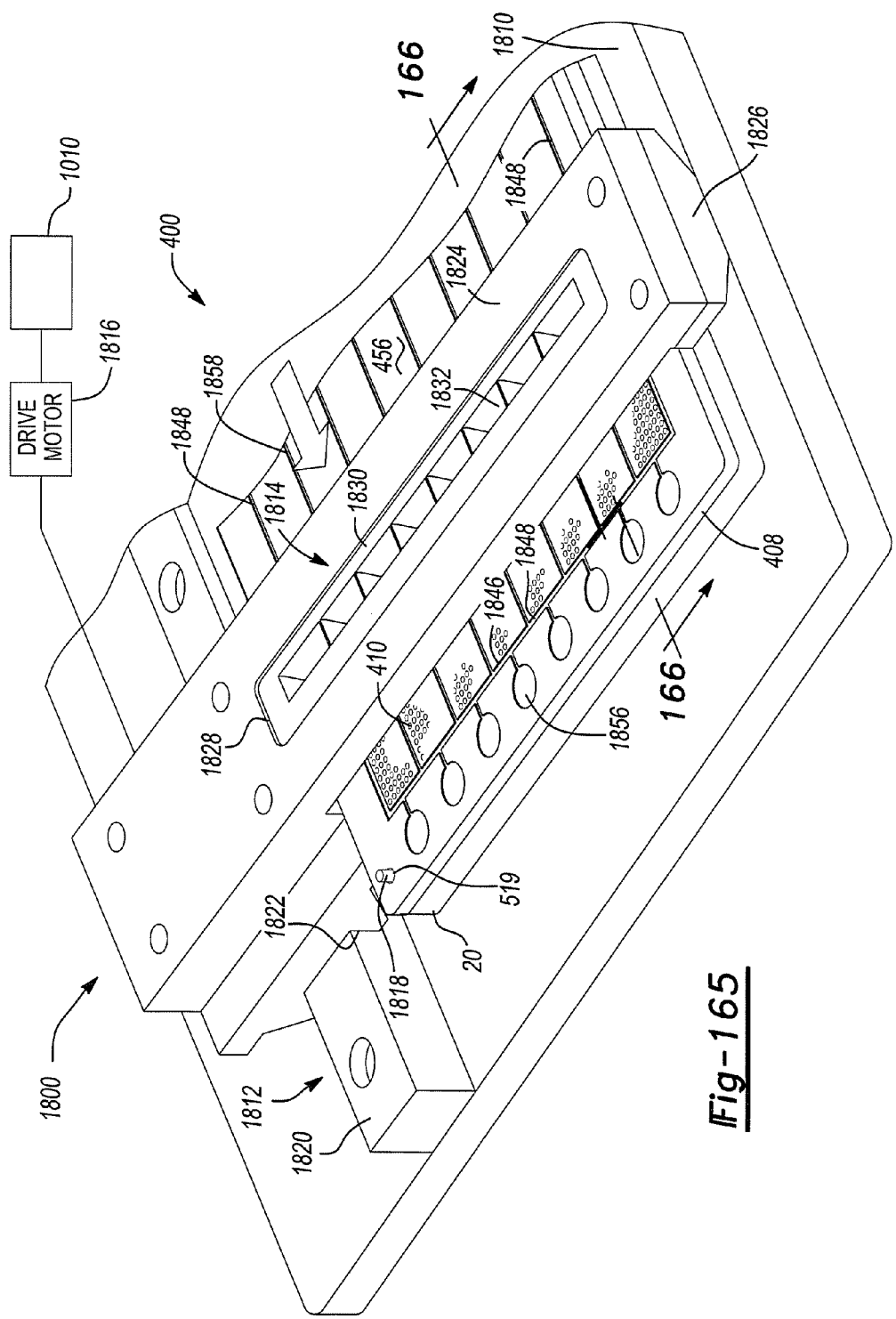
Figure 167:
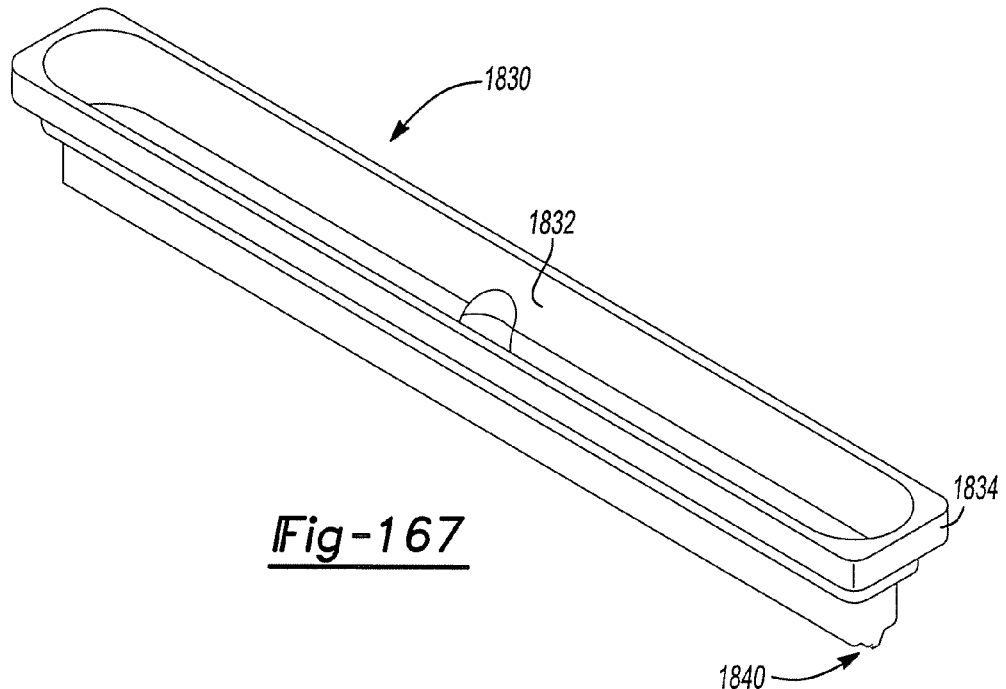
Figure 168:
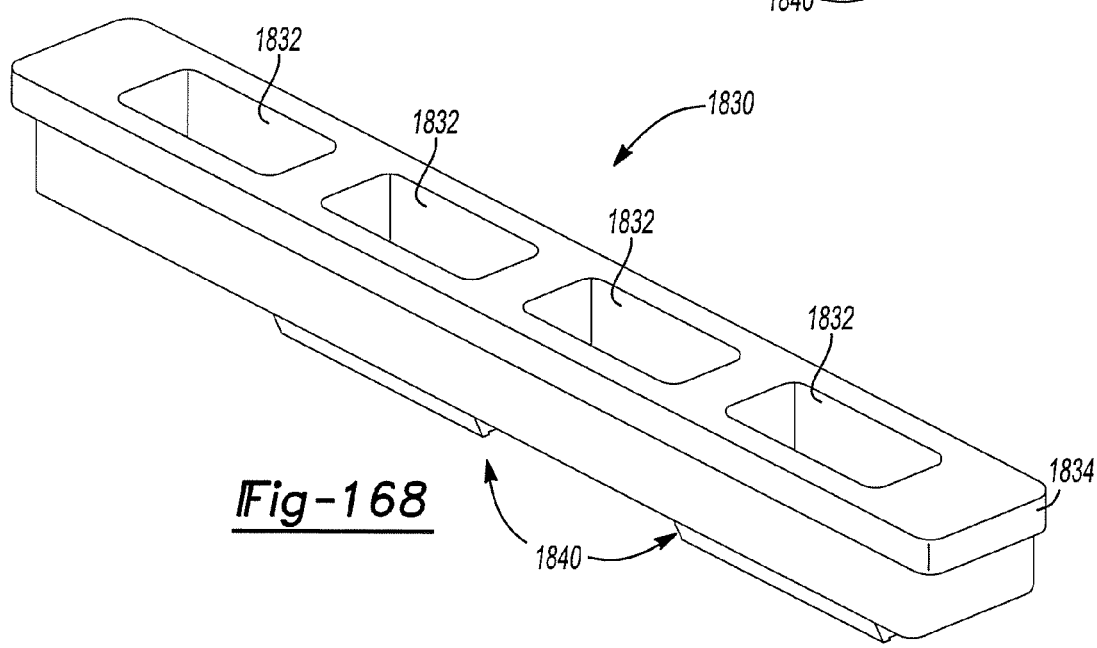
Figures 169, 170, 171:
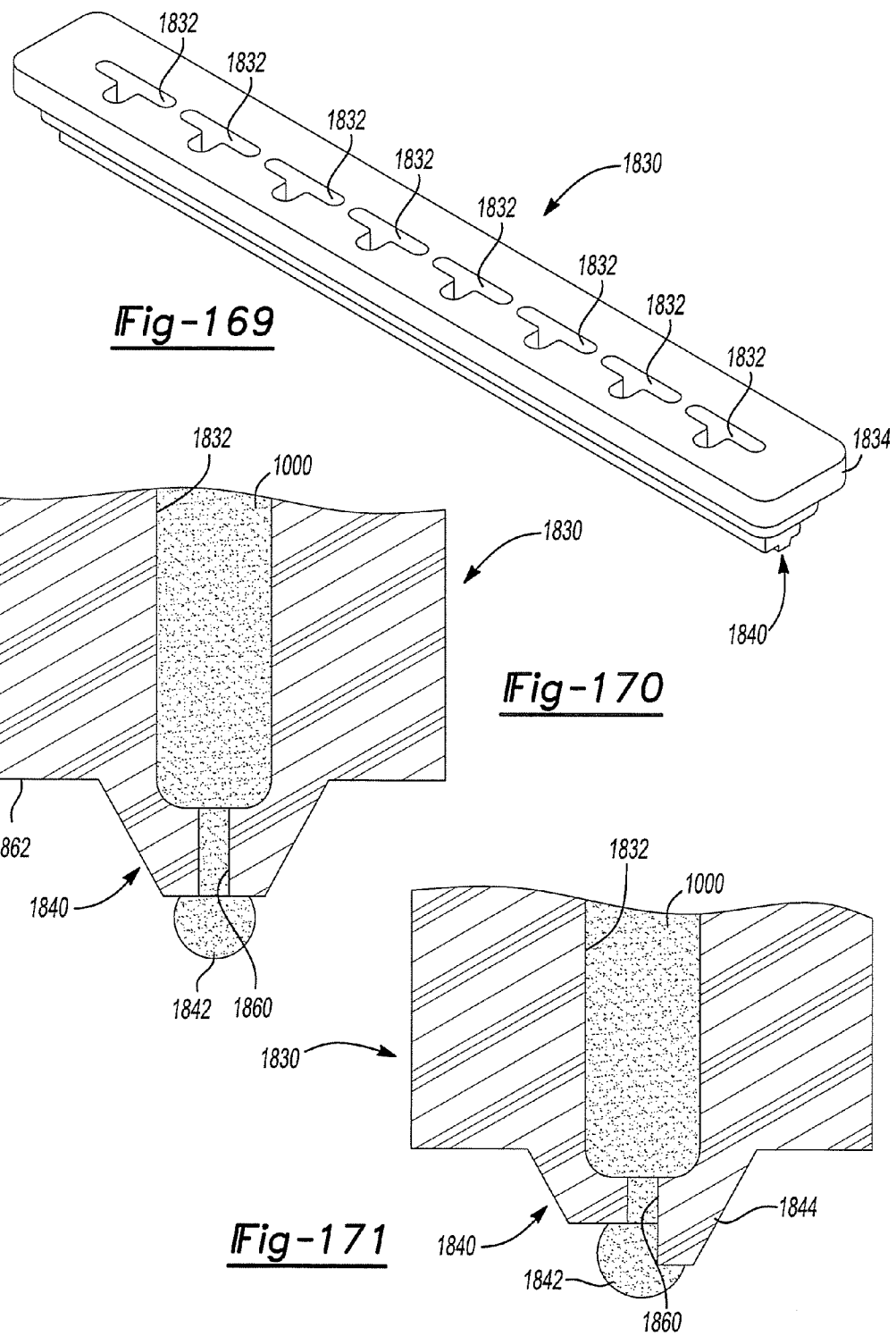
Figure 172:
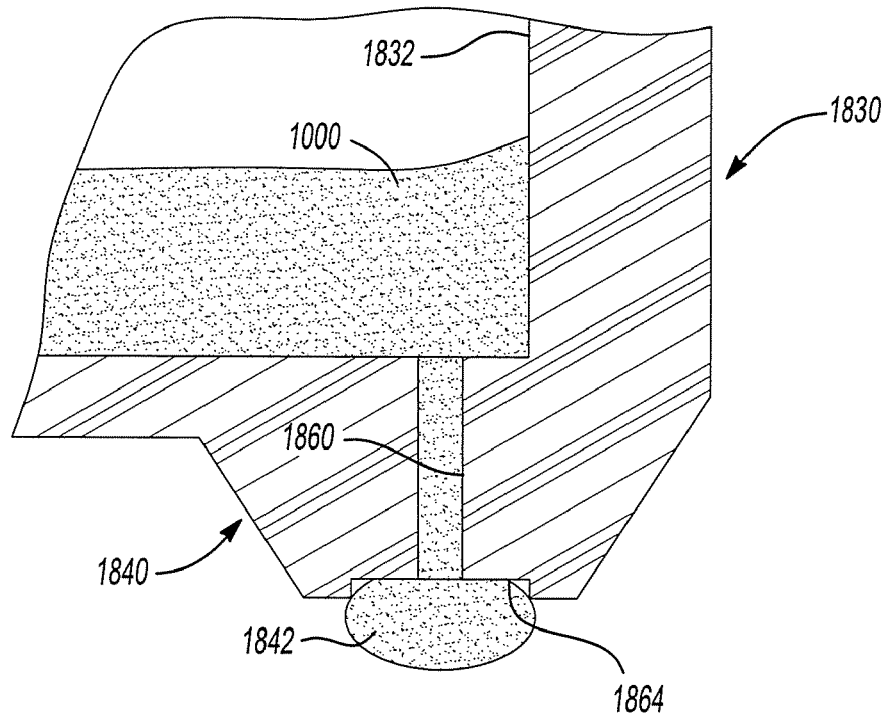
Figure 173:
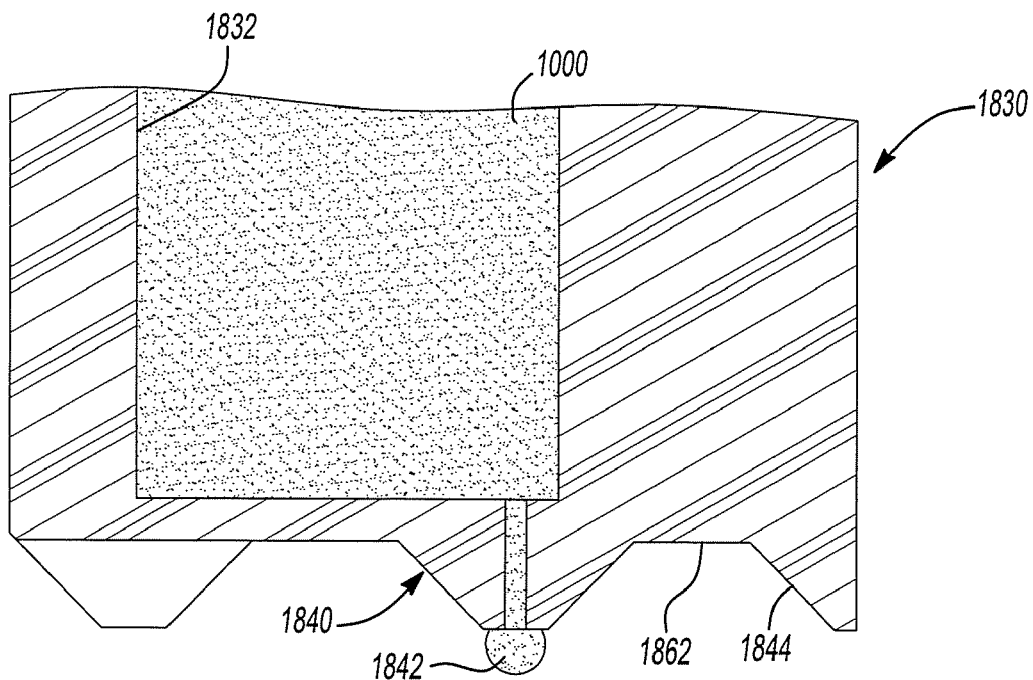
Figure 174:
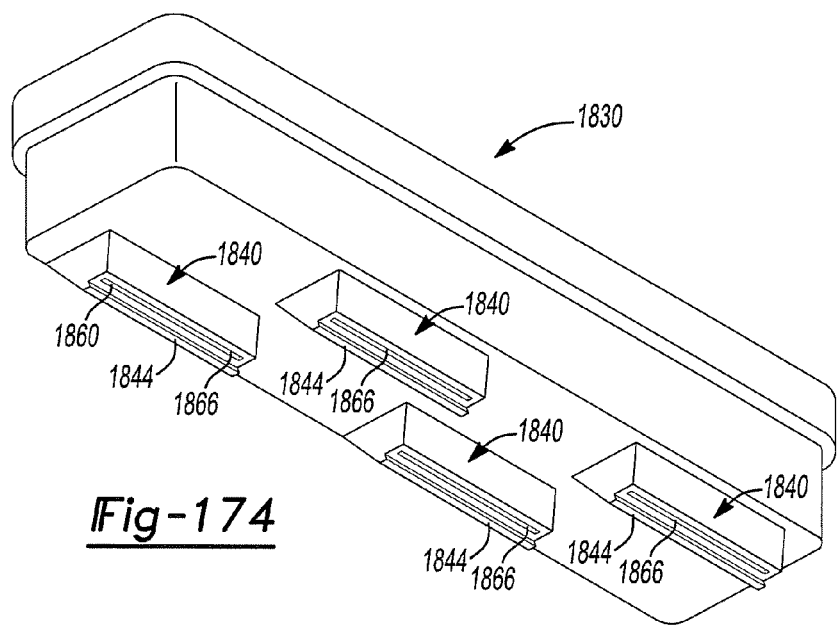
Figure 175:
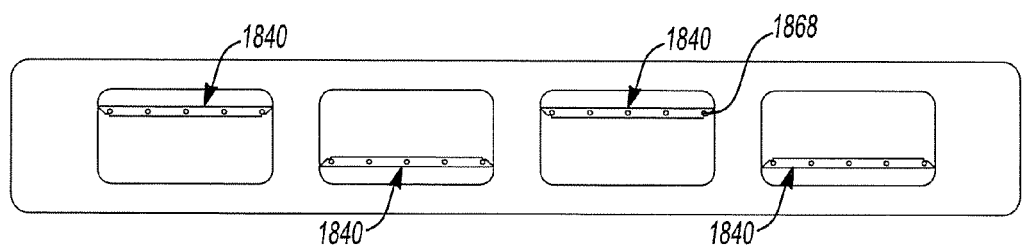
Figure 176:
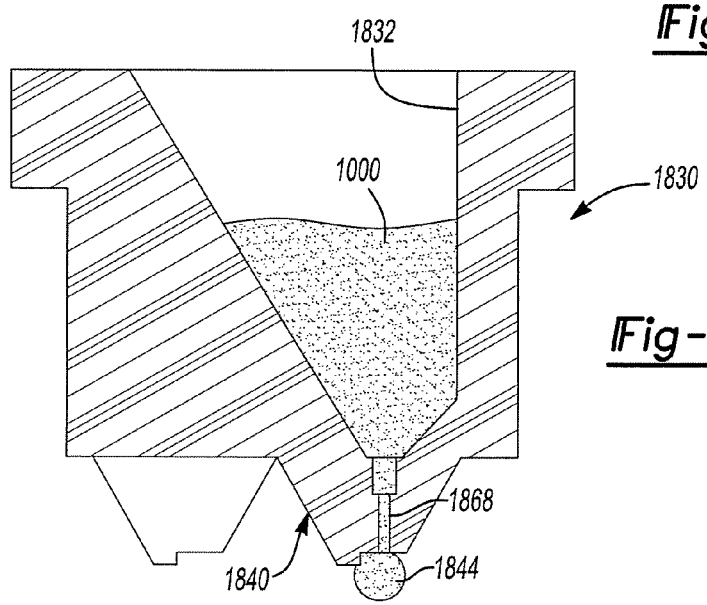
Figure 177:
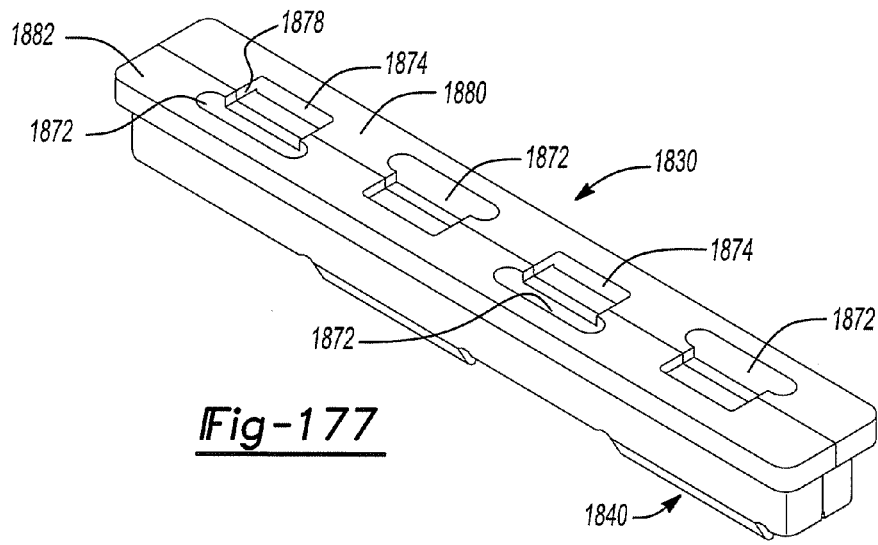
Figure 178:
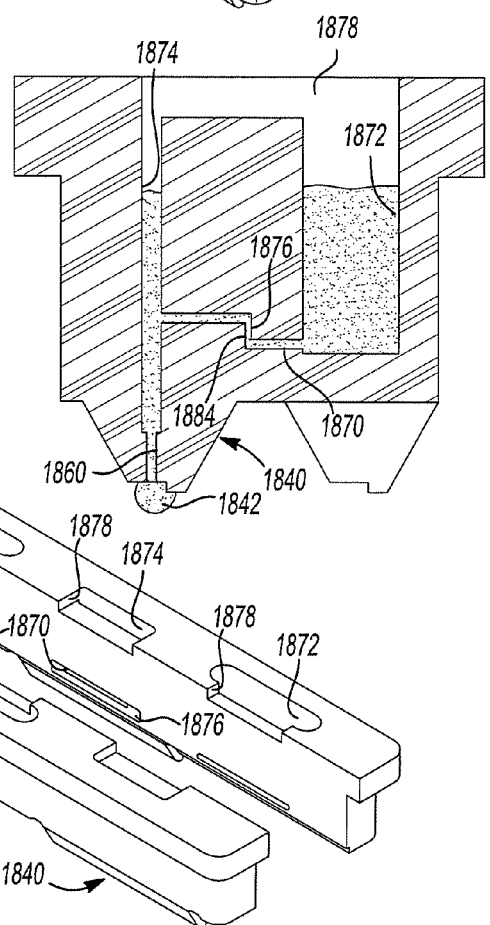
Figure 179:
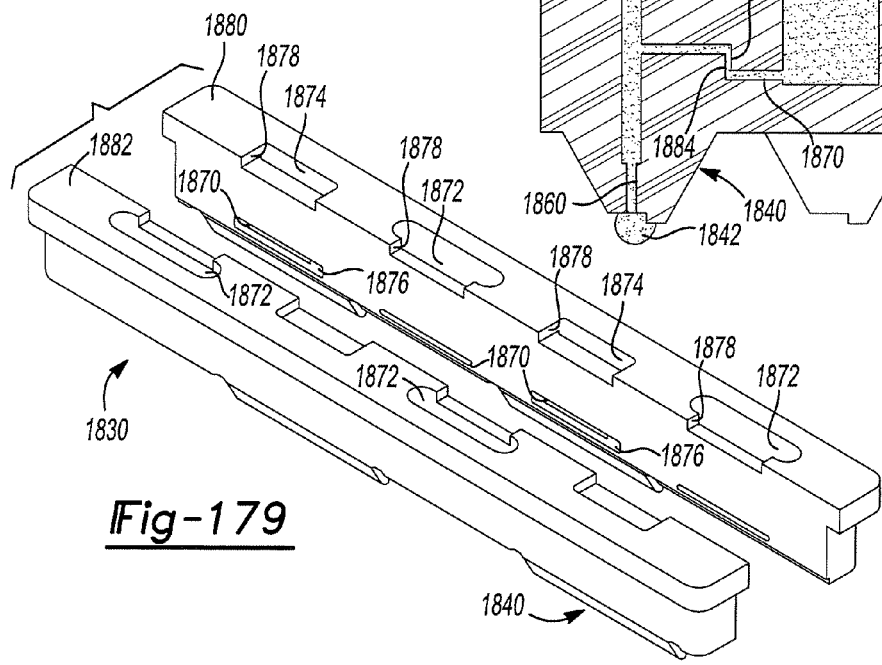
Figure 180:
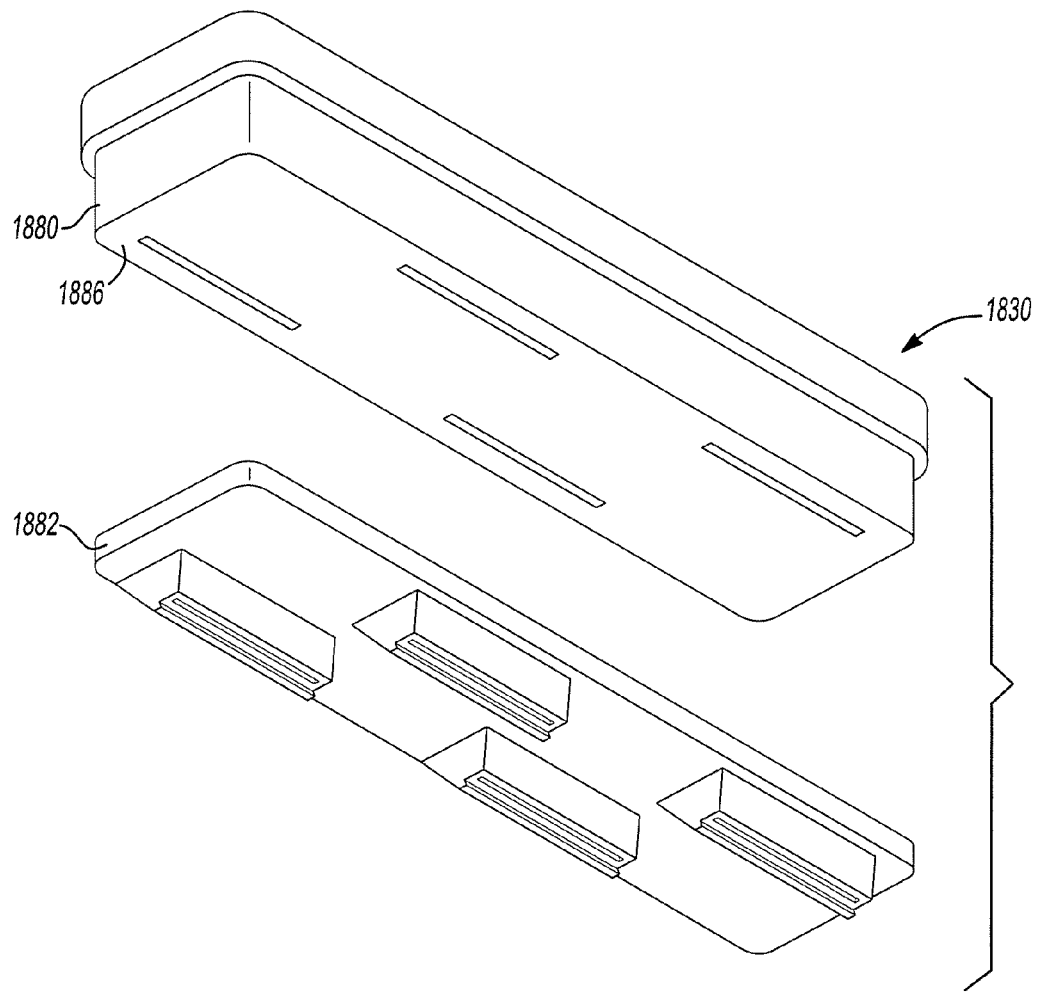
Figure 181:
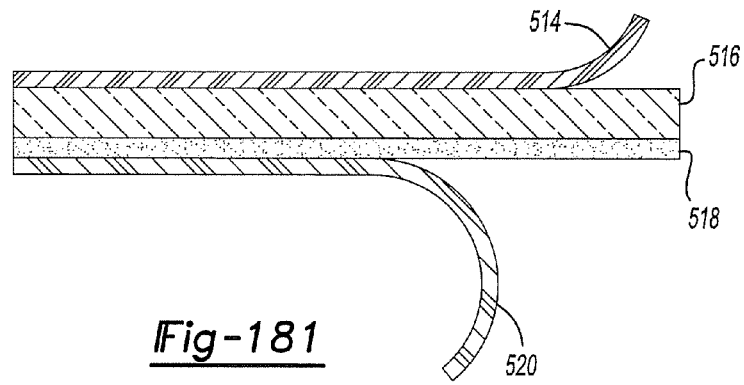
Figure 182:
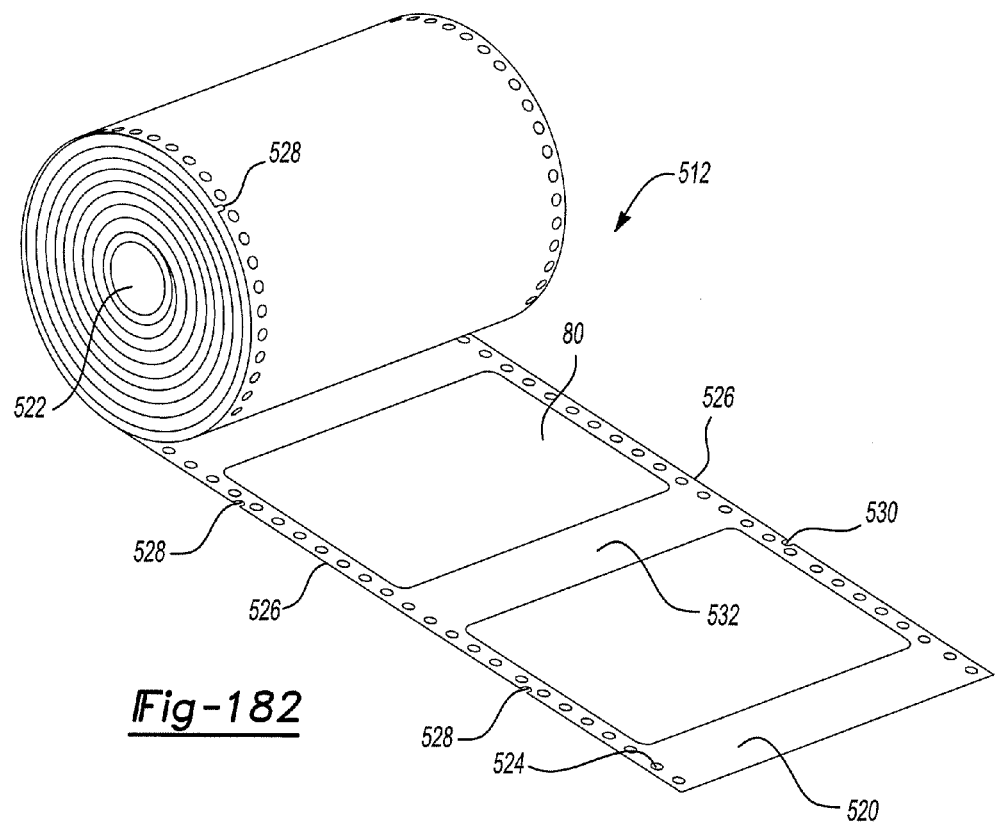
Figure 183:
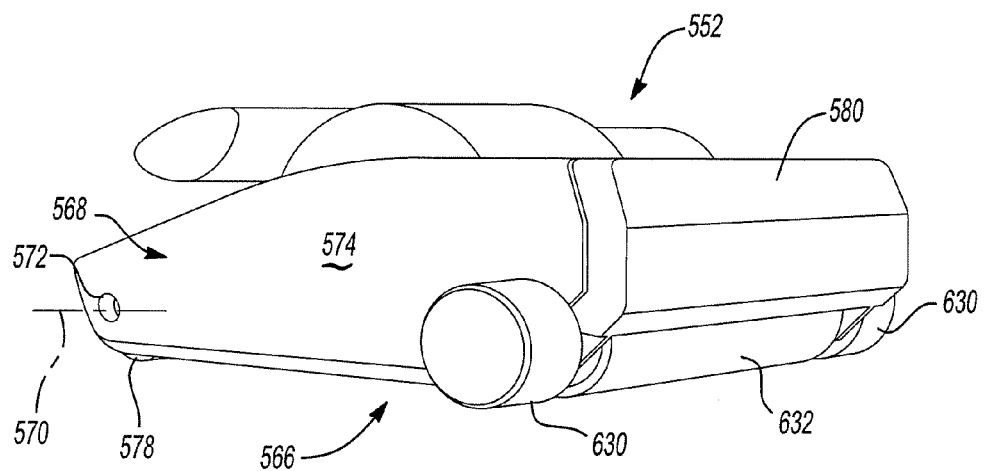
Figure 184:
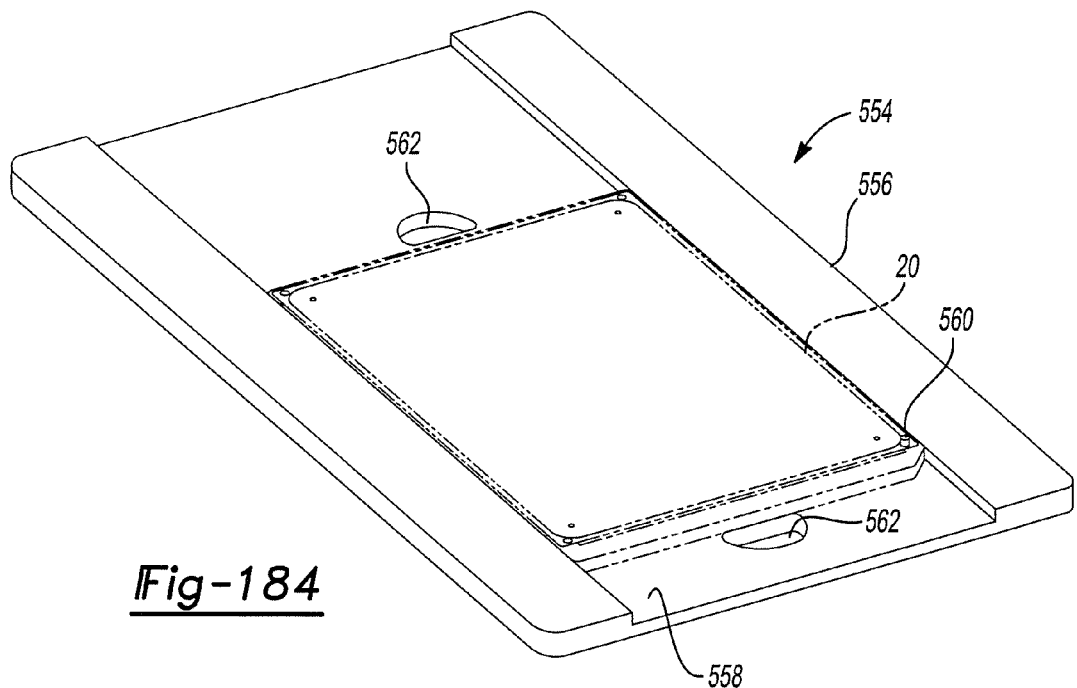
Figure 185:
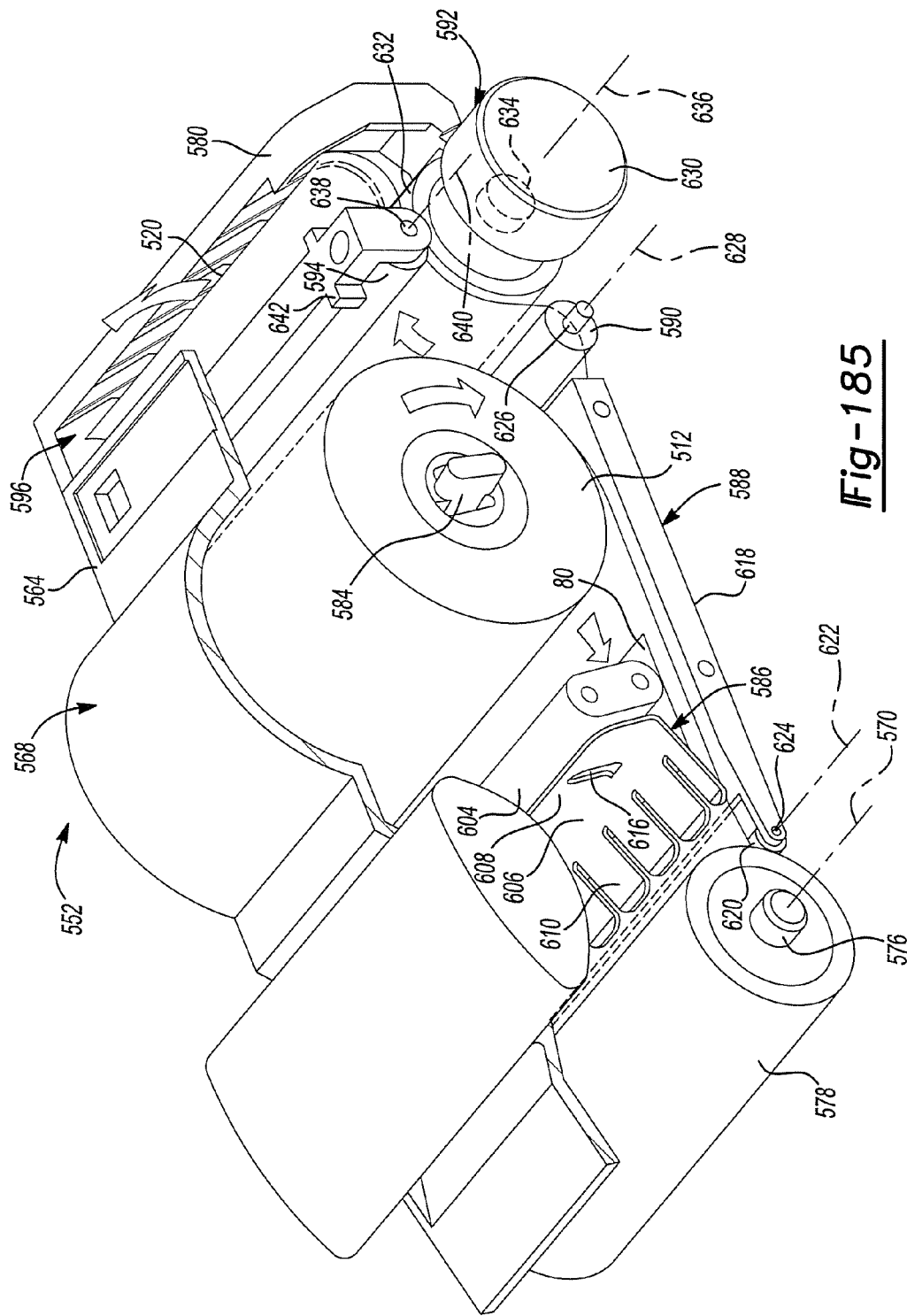
Figure 186:
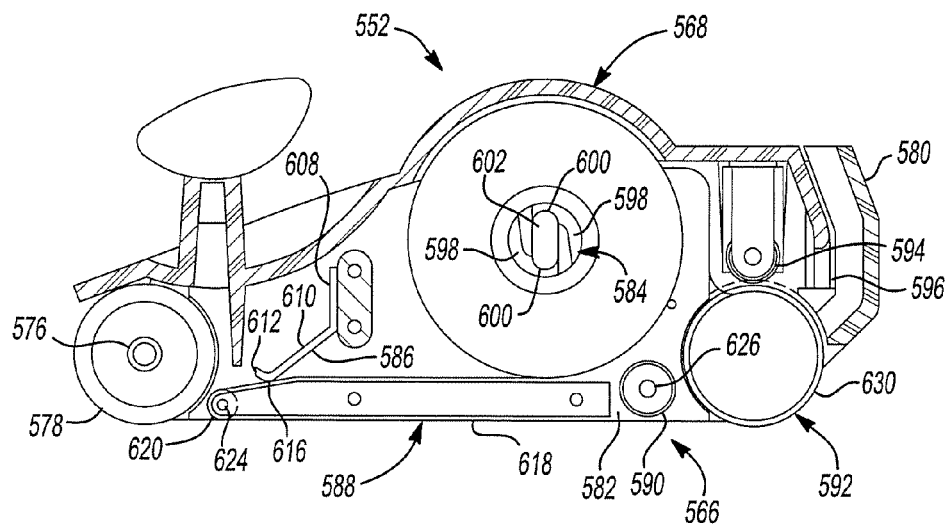
Figure 187:
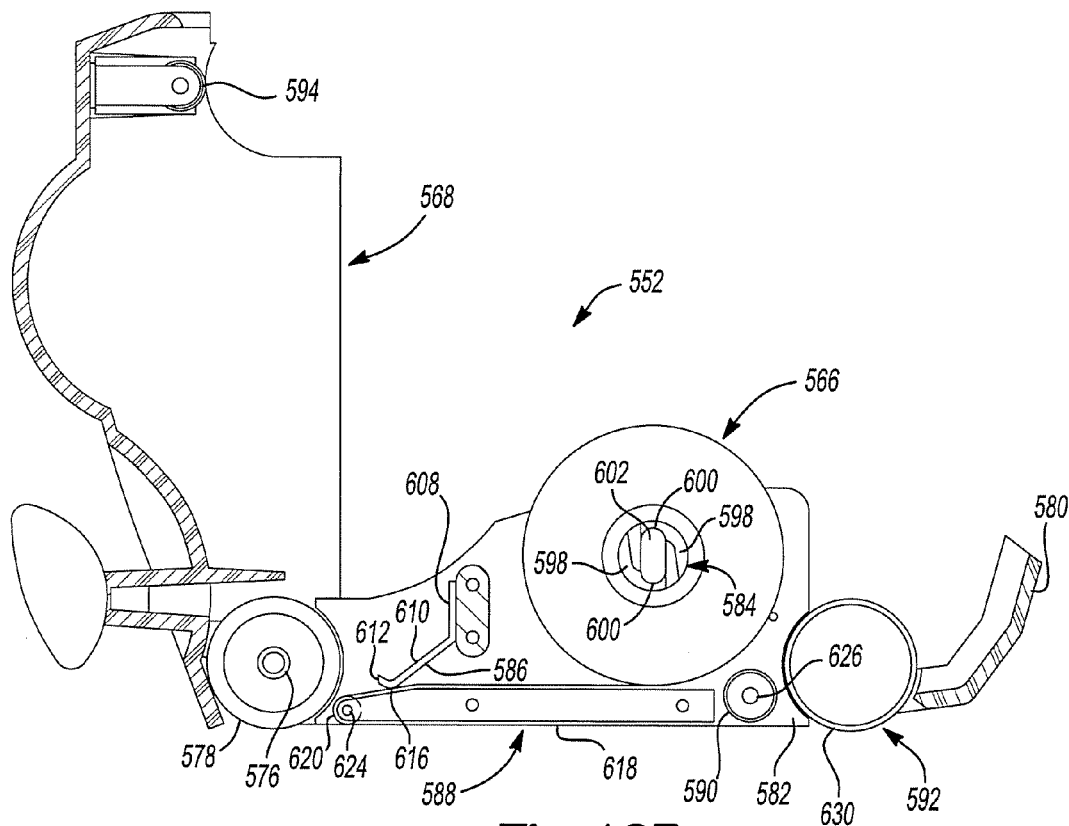
Figure 188:
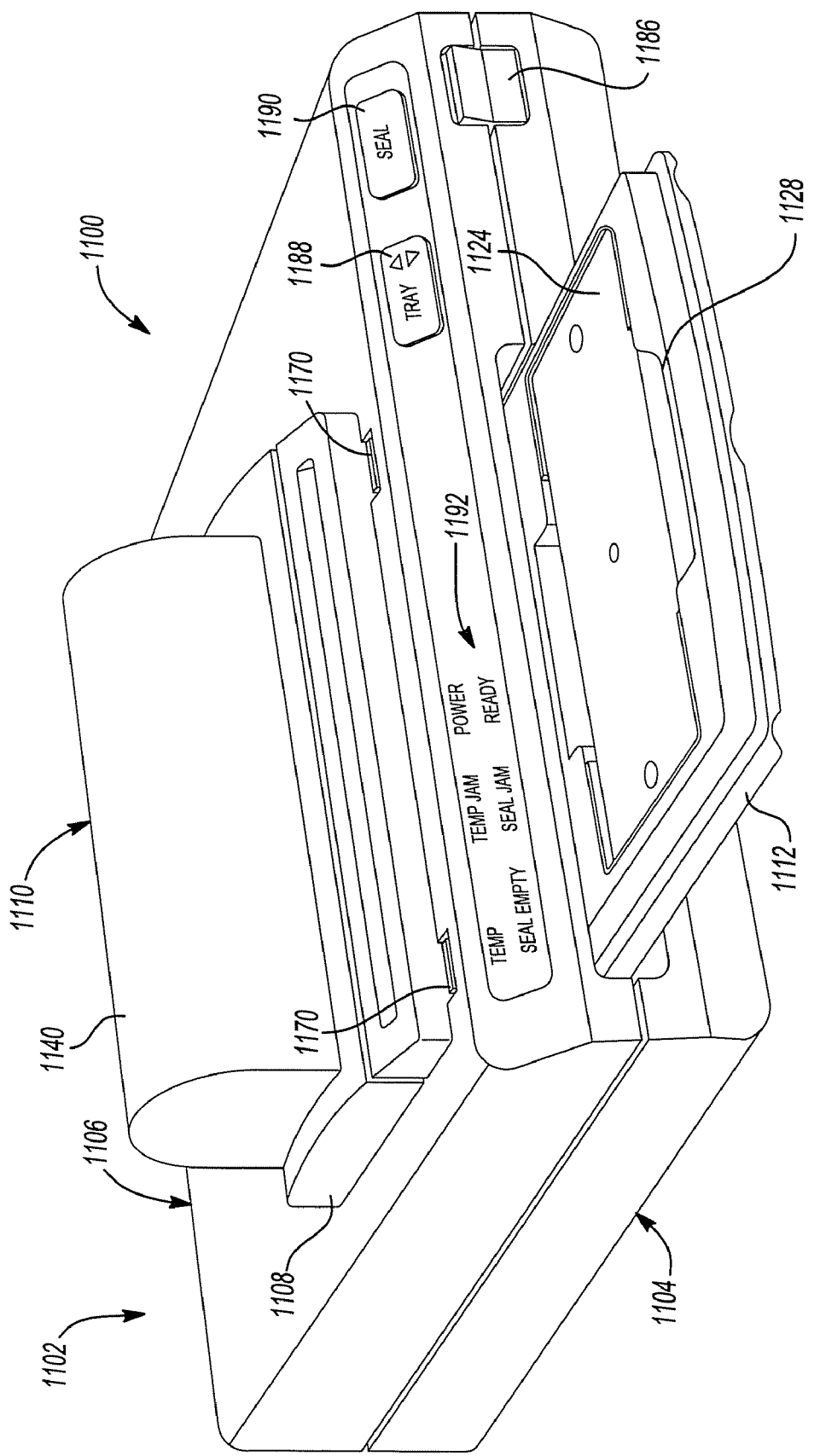
Figure 189:
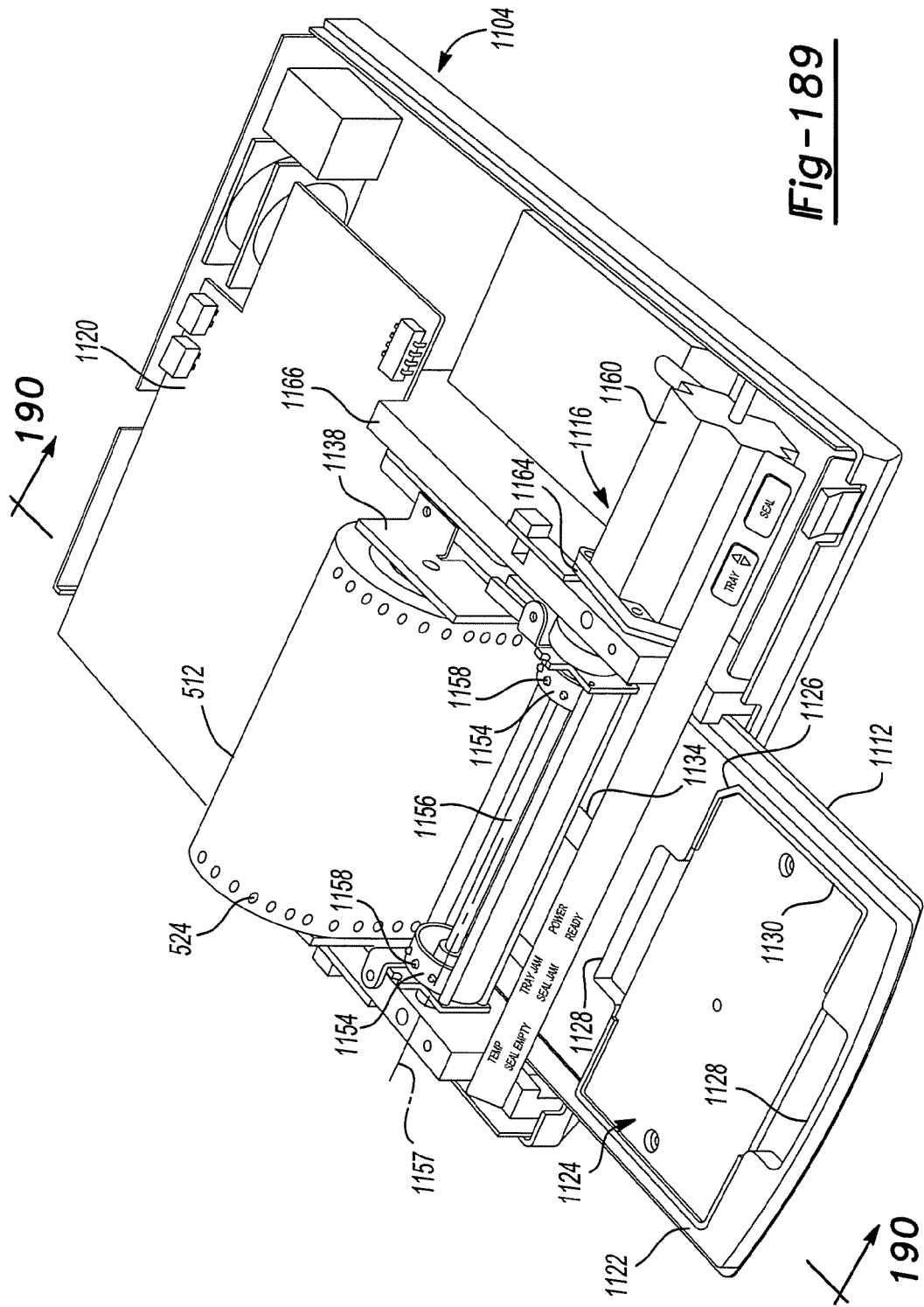
Figure 190:
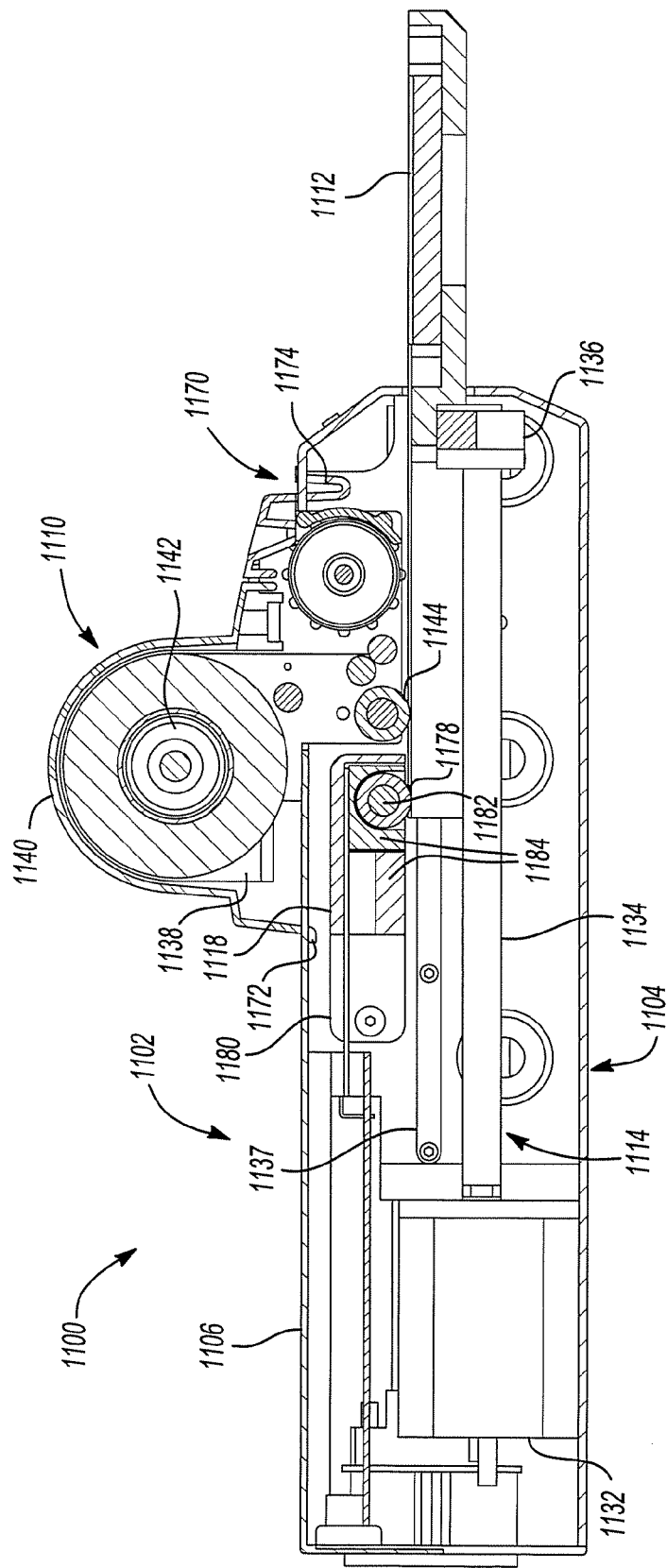
Figure 191:
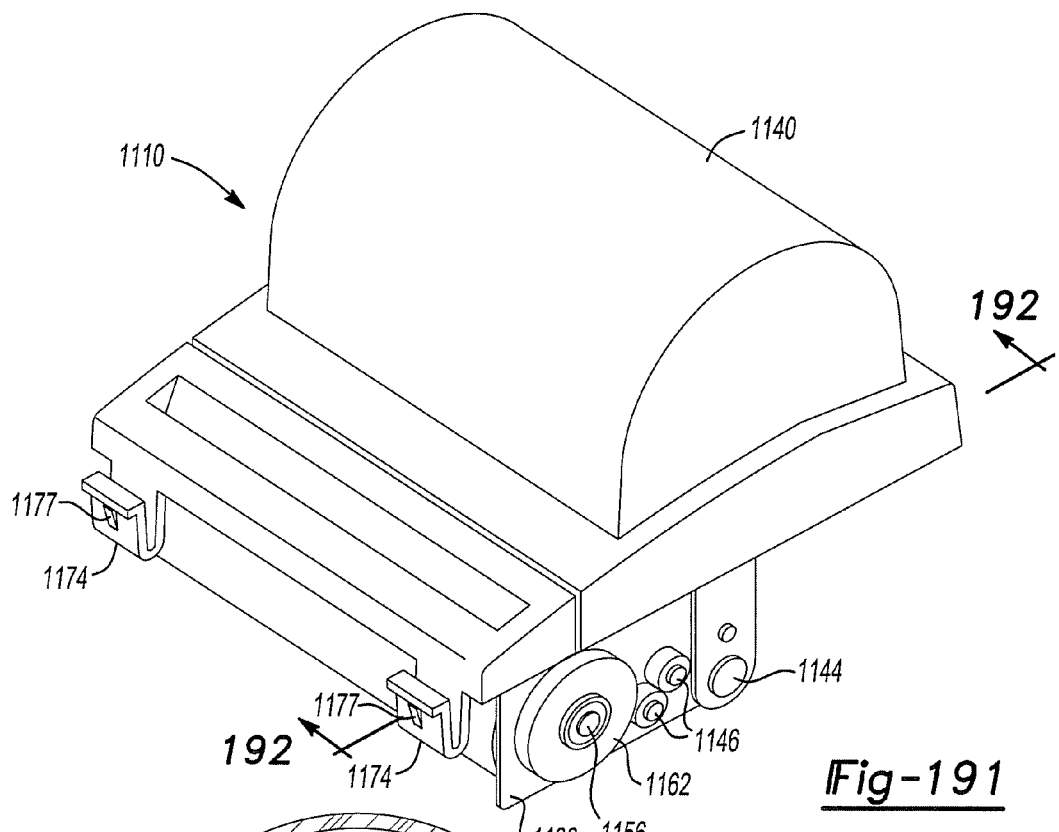
Figure 192:
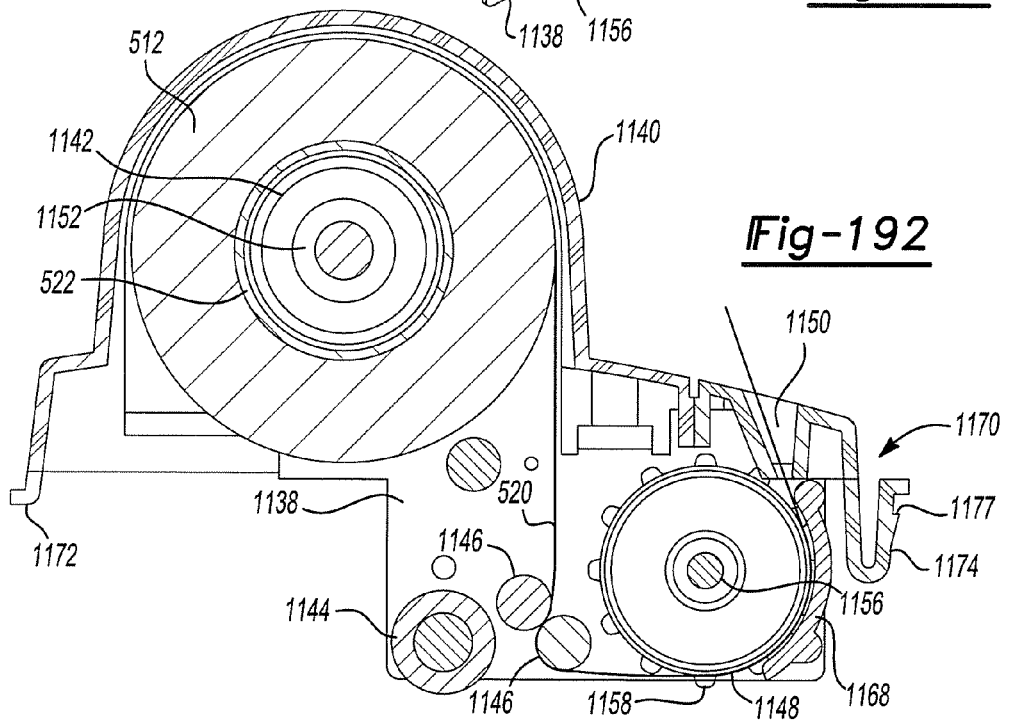
Figure 193:
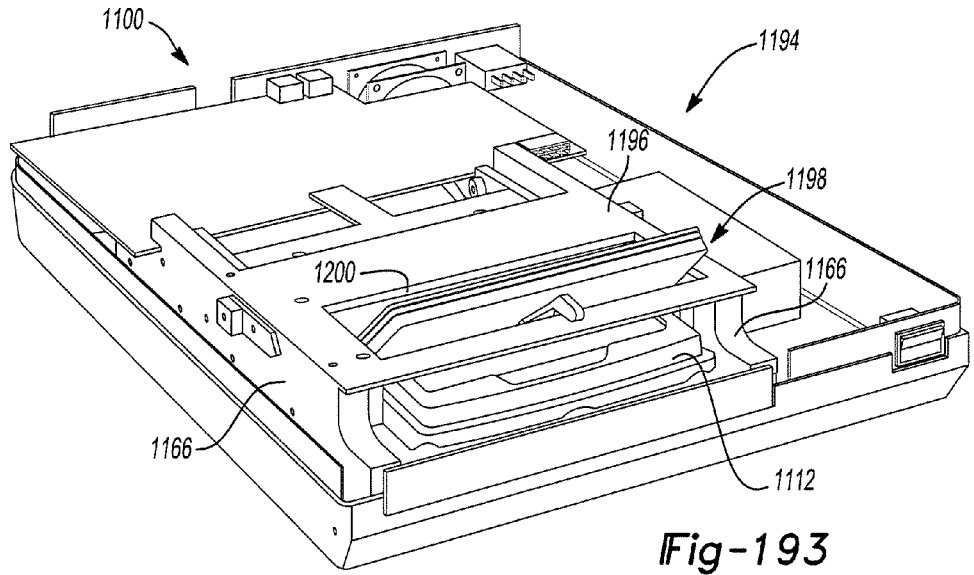
Figure 194:
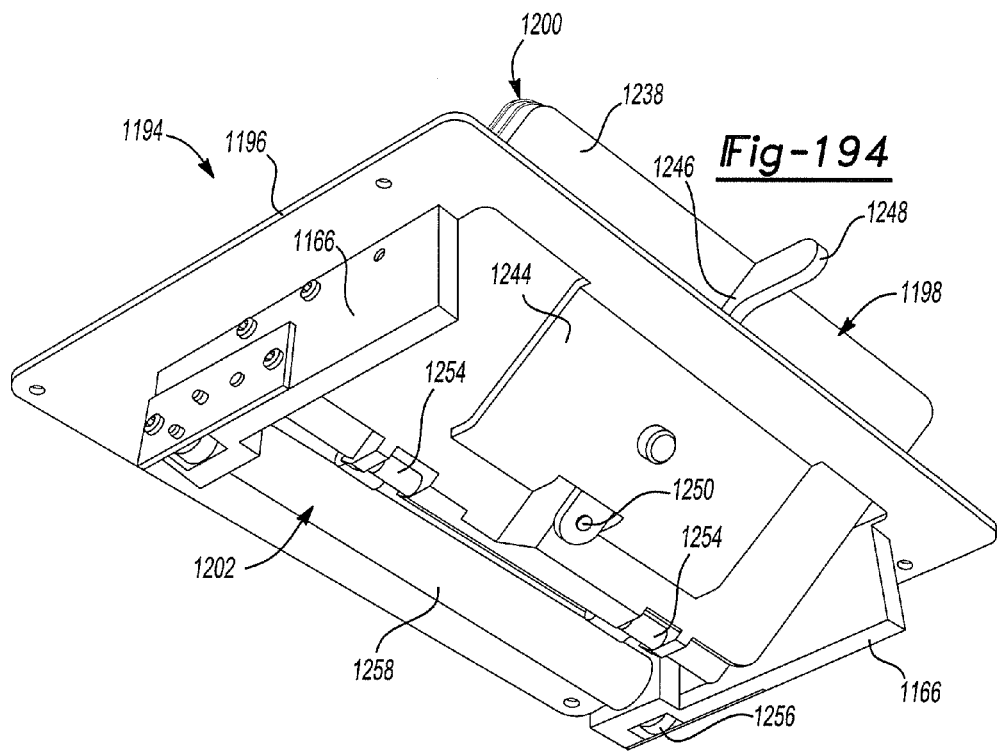
Figure 195:
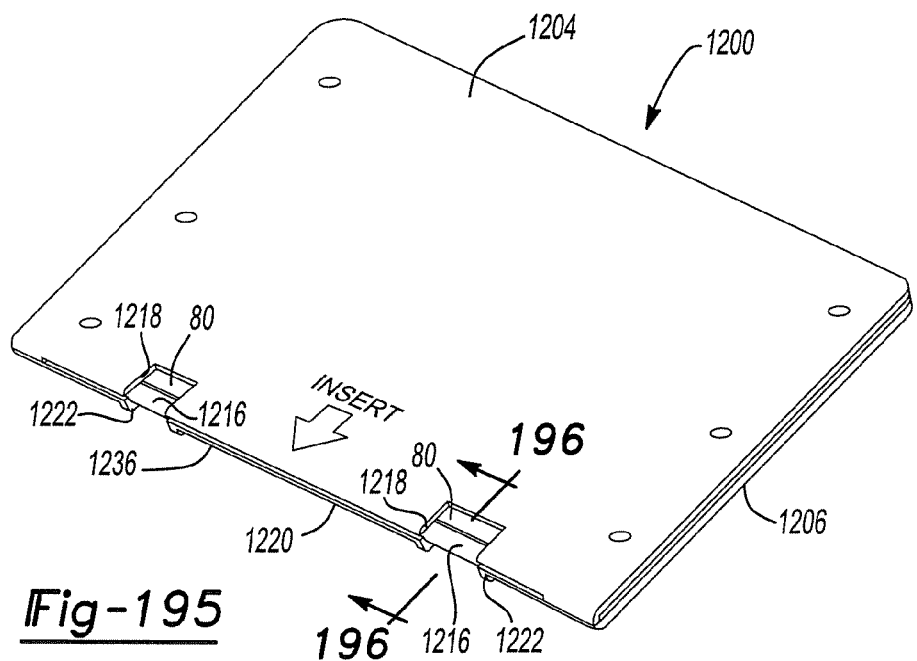
Figure 196:
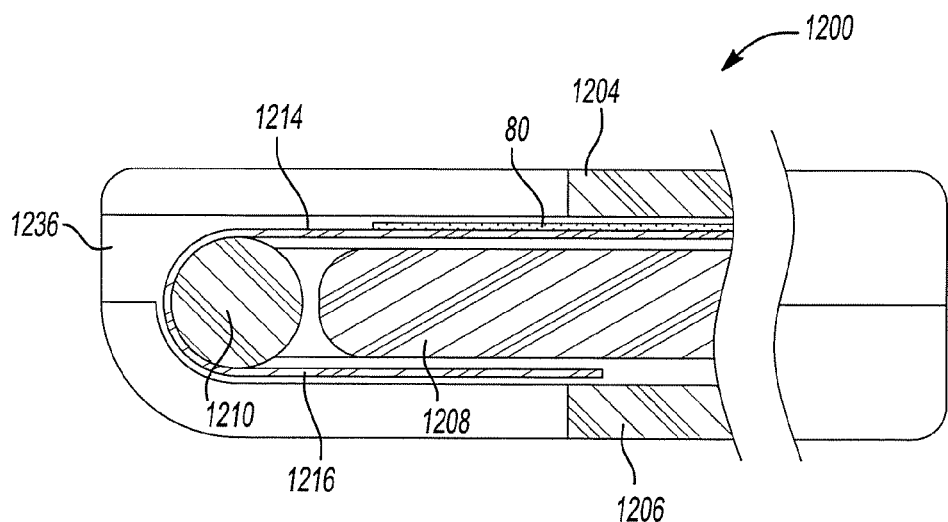
Figure 197:
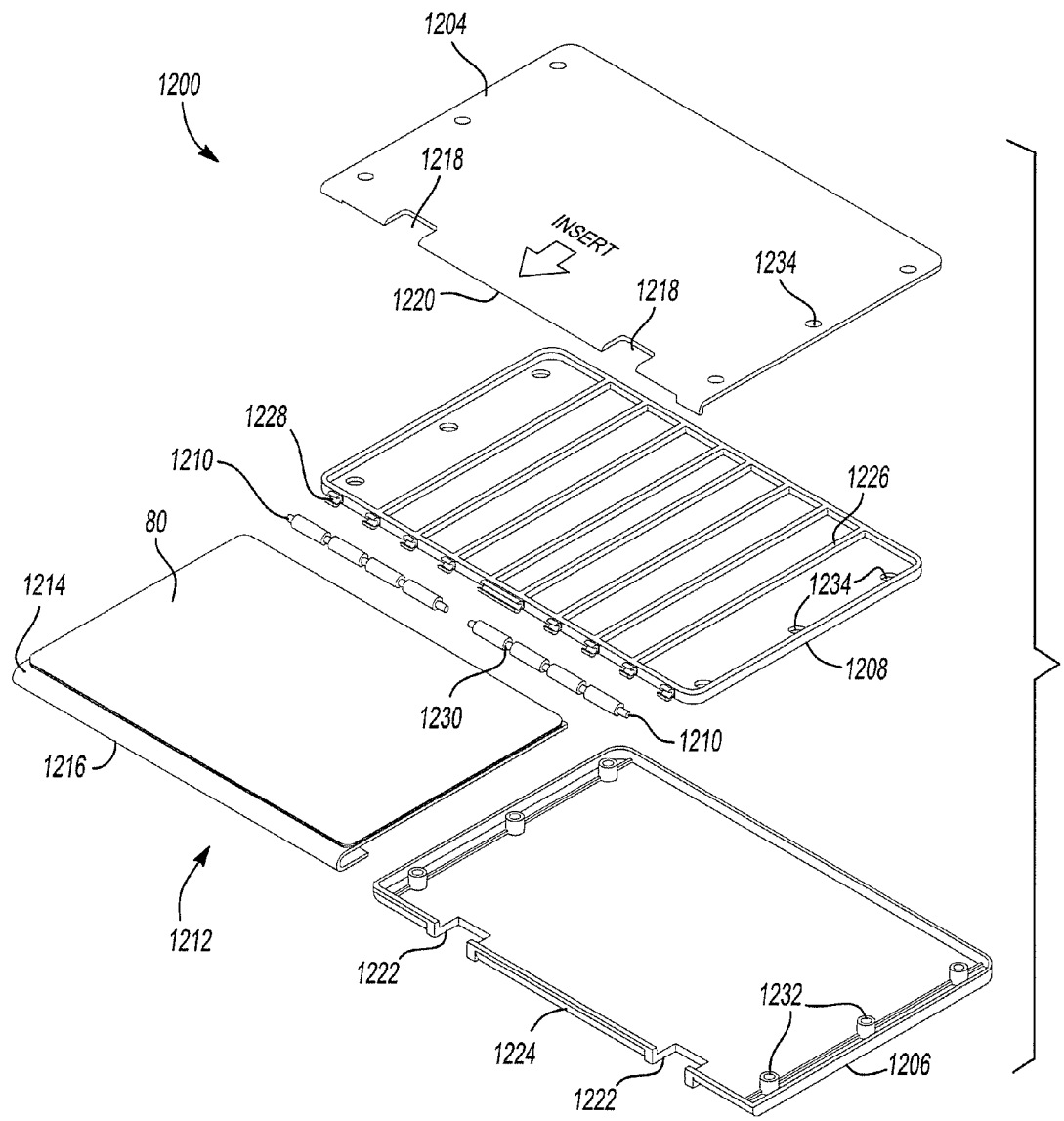
Figure 202:
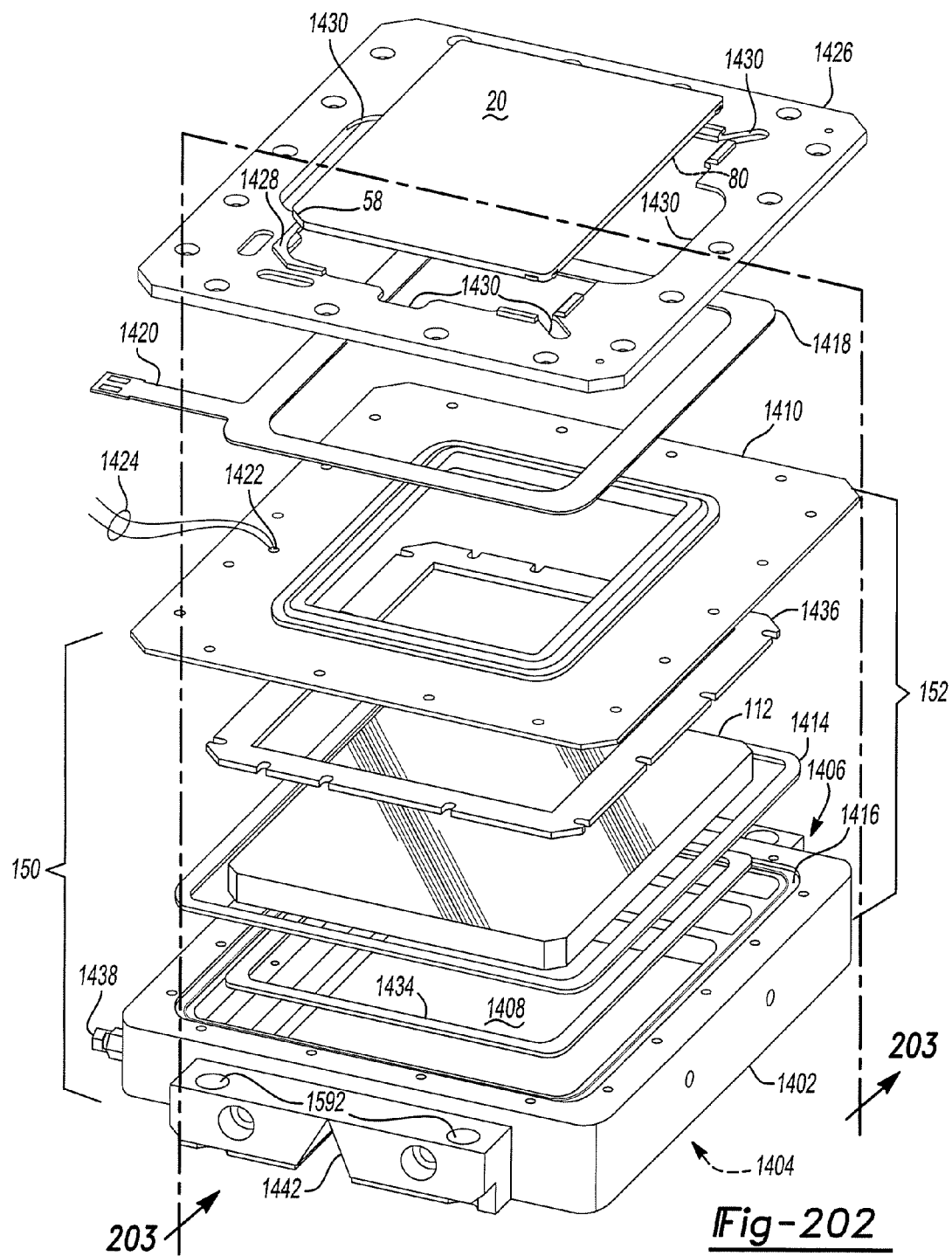
Figure 203:
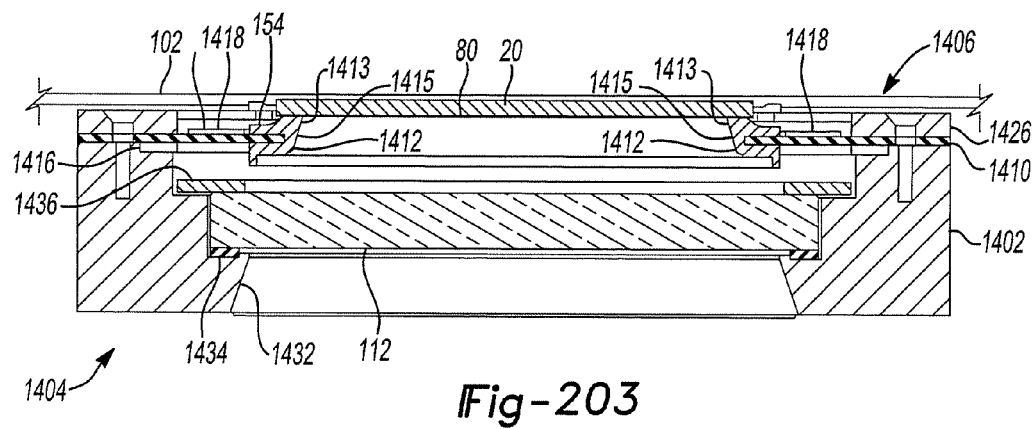
Figure 204:
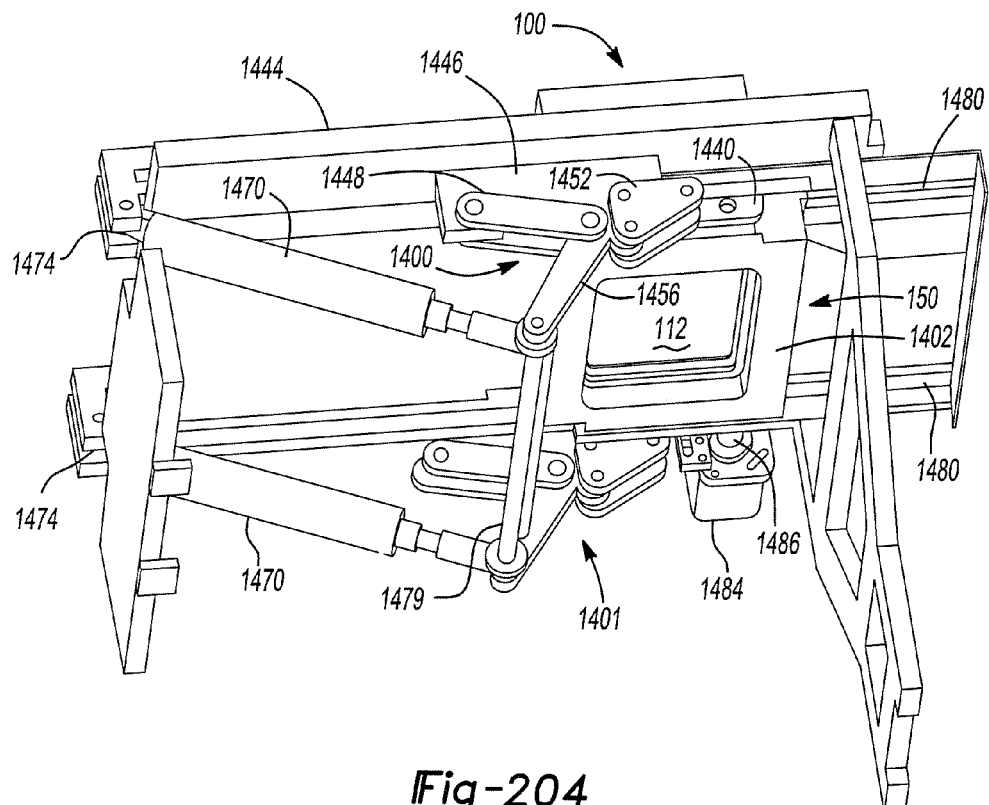
Figure 205:
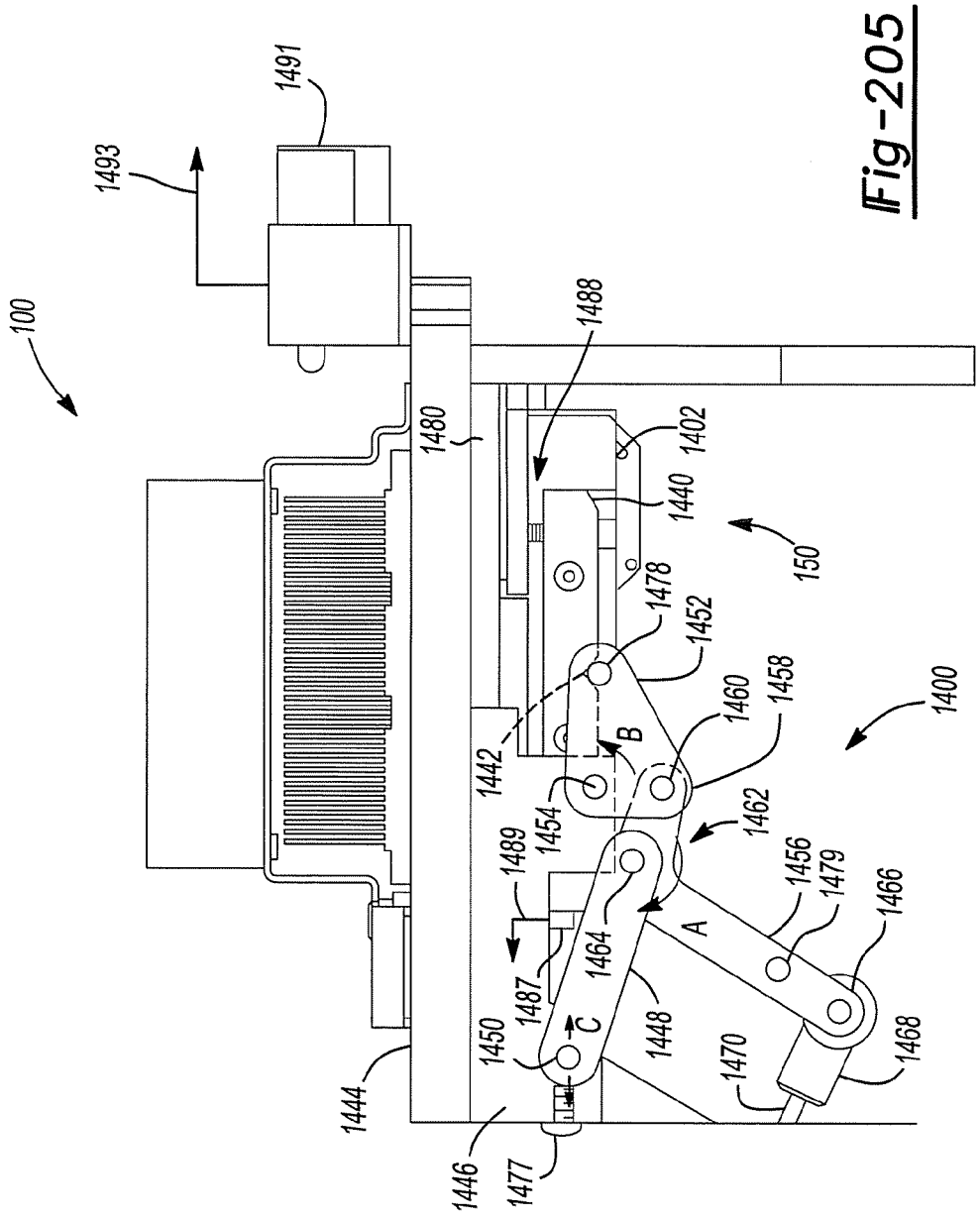
Figure 206:
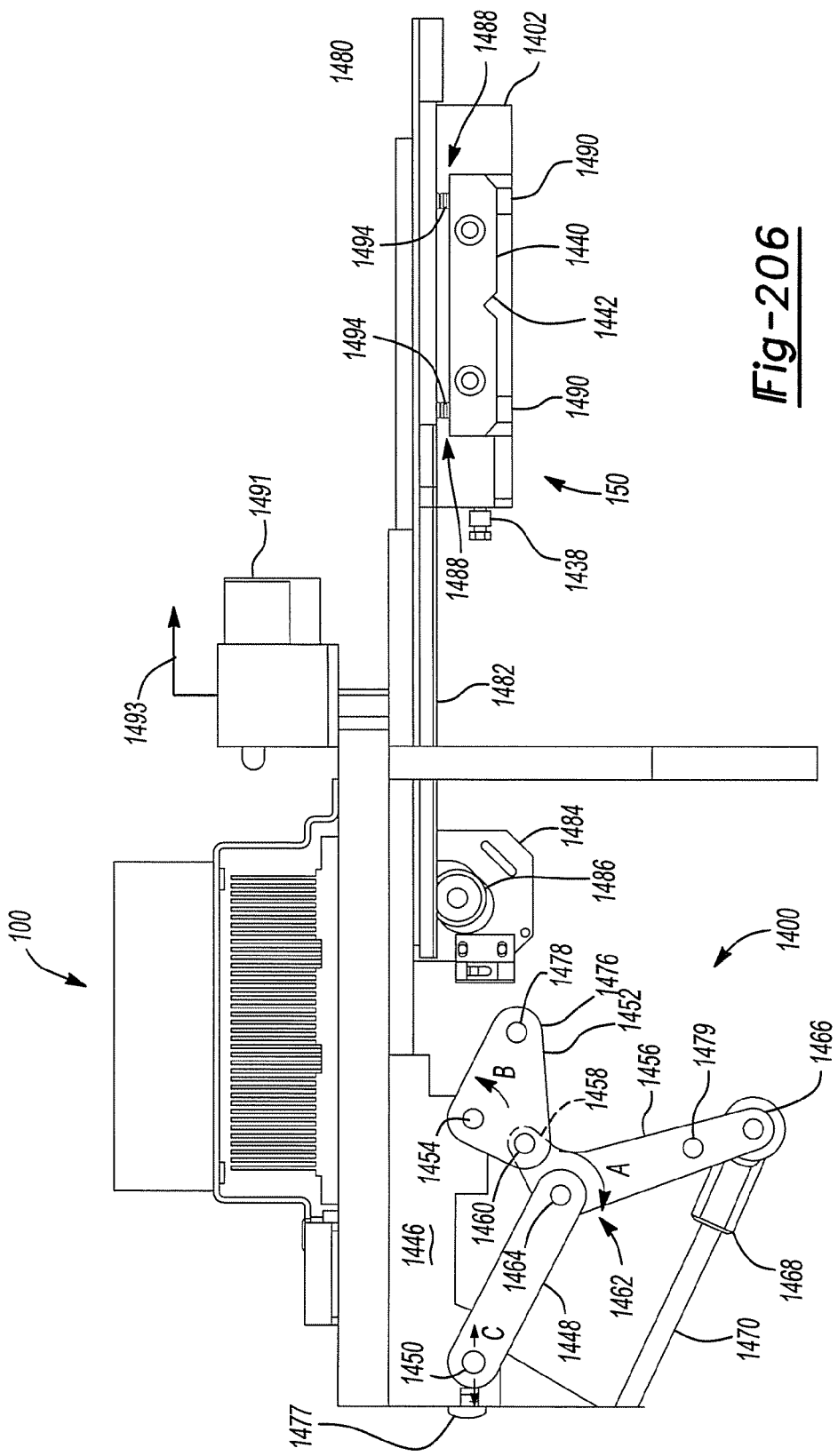
Figure 207:
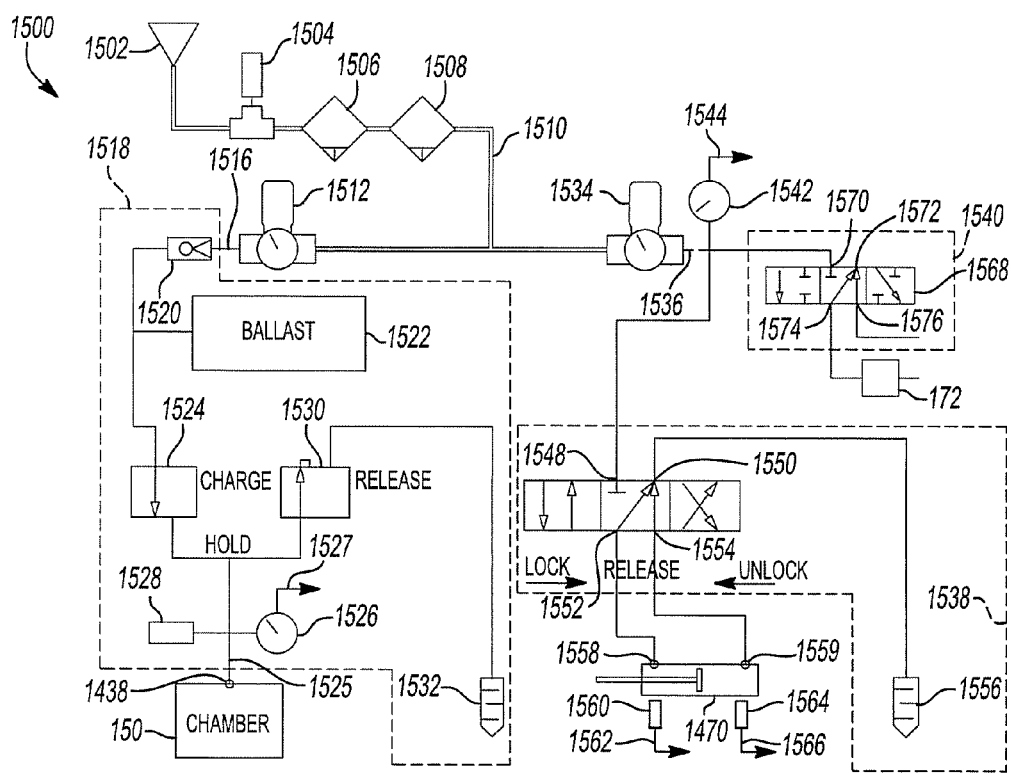
Figure 208:
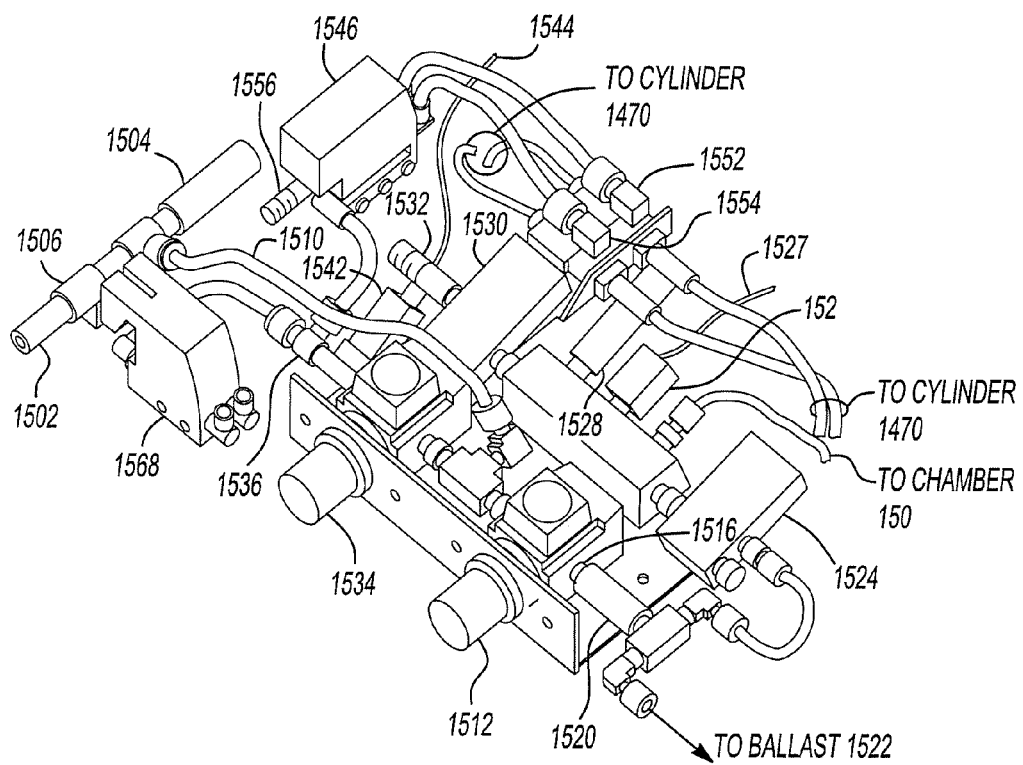
Figure 209:
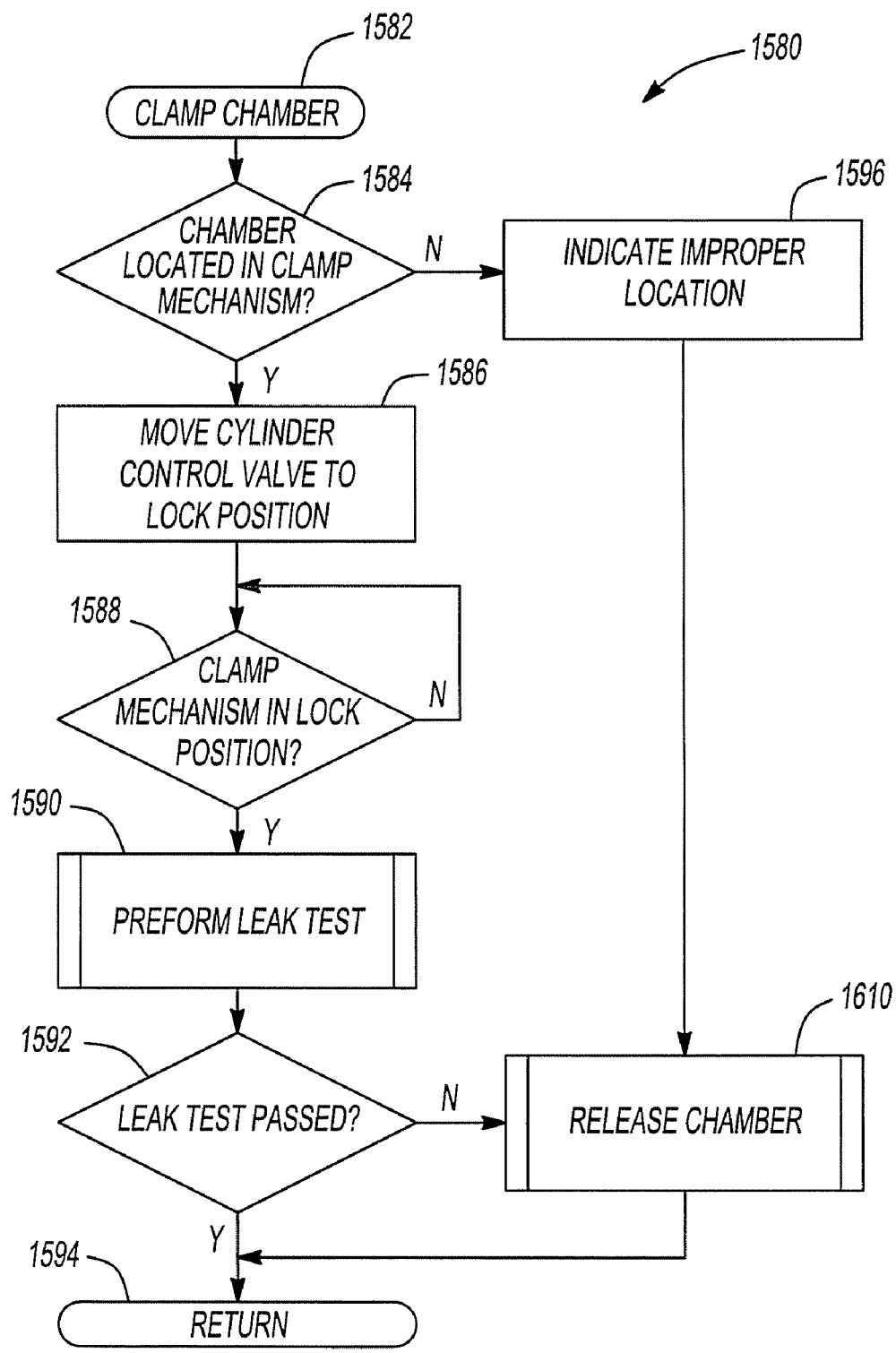
Figure 210:
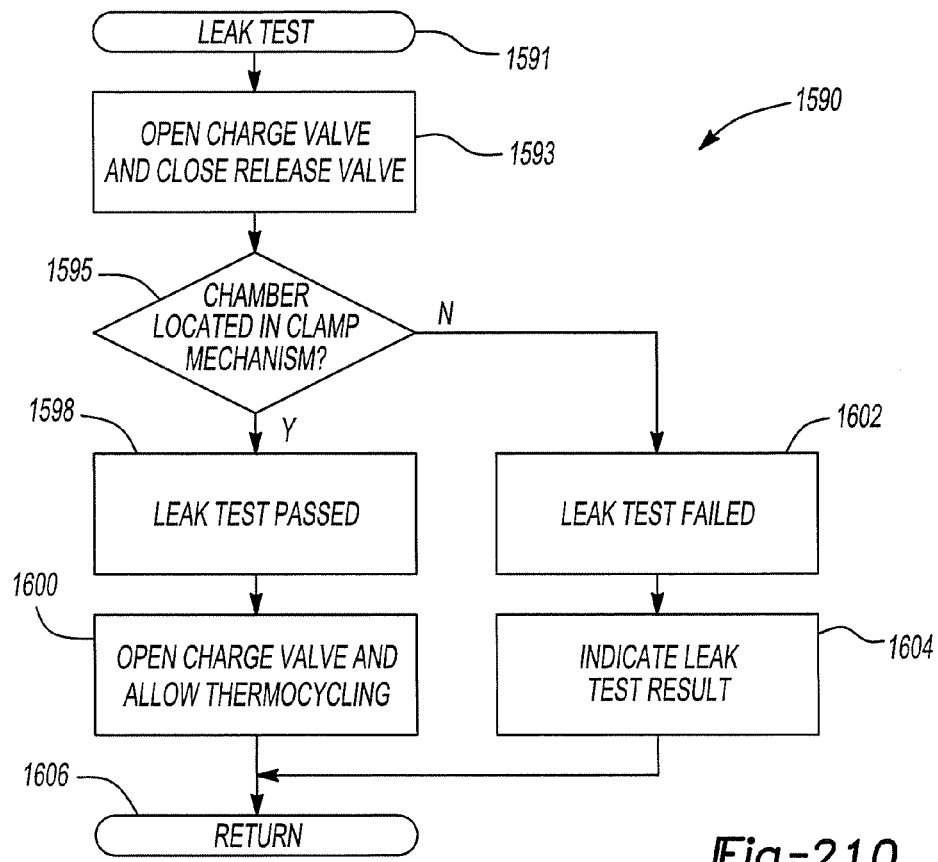
Figure 211:
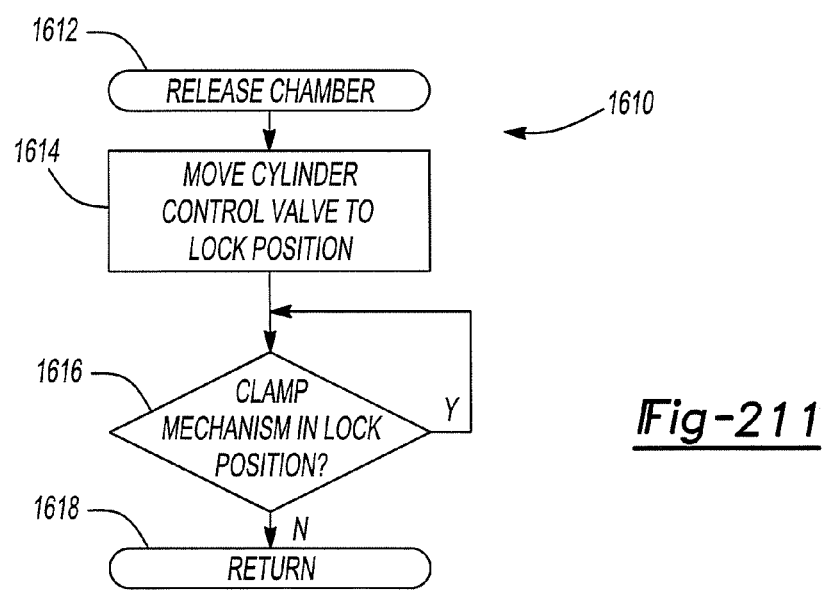
Figure 212:
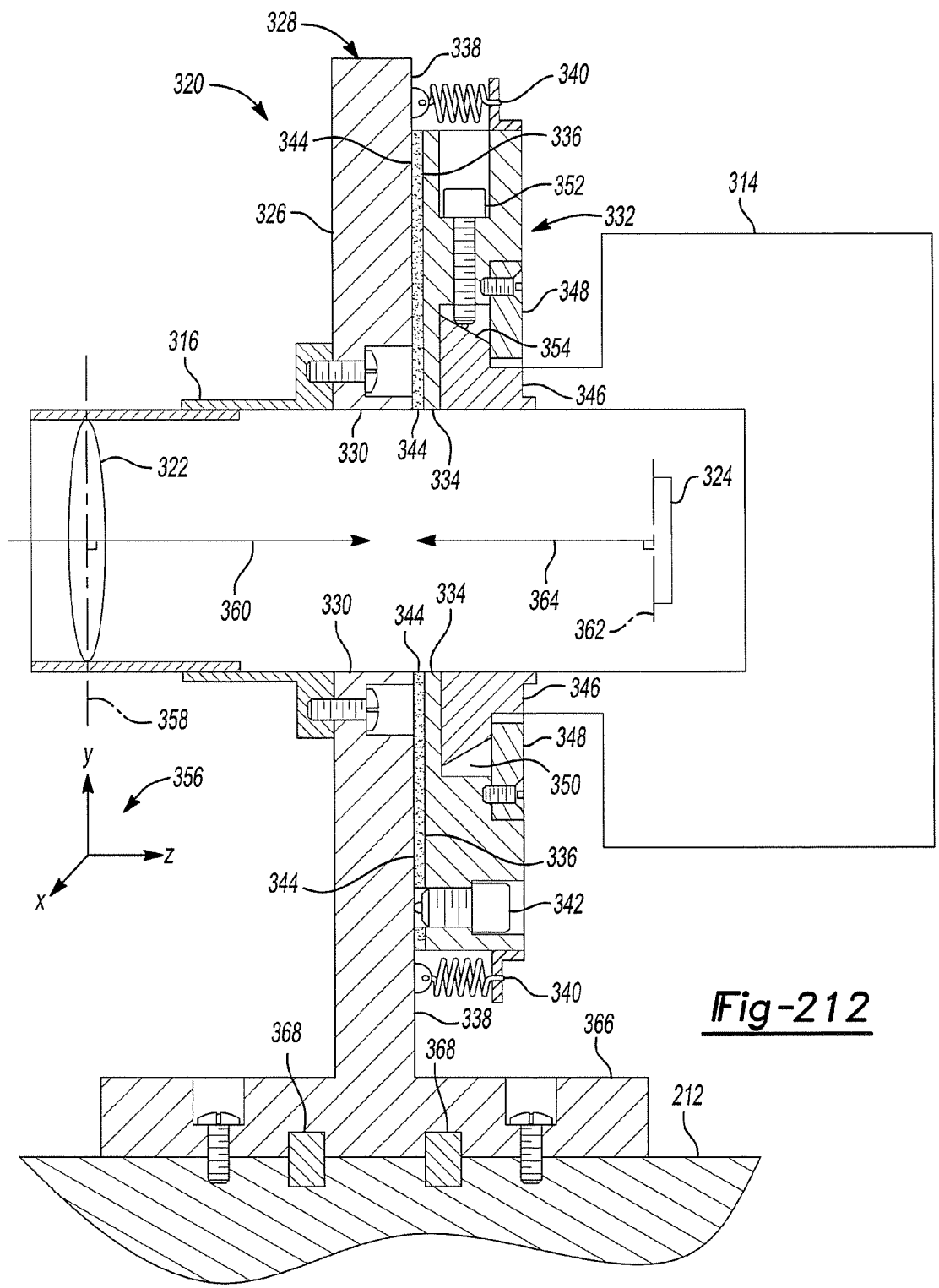
Figure 213:
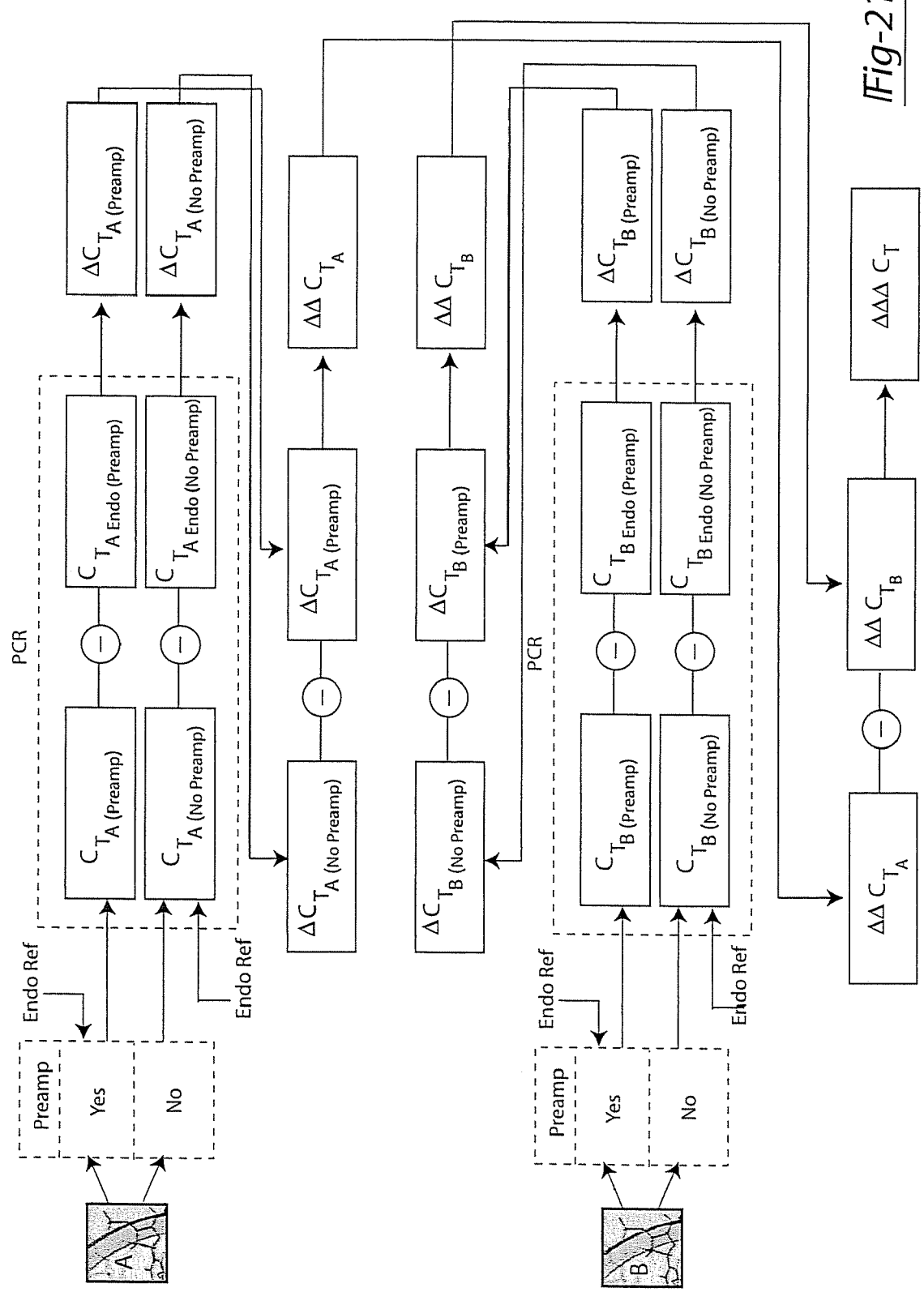

FIGS. 25(a)-(f) are top schematic views of a filling apparatus according to some embodiments;

FIG. 26 is a cross-sectional view illustrating a well of a microplate according to some embodiments;

FIG. 27 is a cross-sectional view illustrating a well of an inverted microplate according to some embodiments;

FIG. 28 is a cross-sectional view illustrating a sealing cover according to some embodiments;

FIG. 29 is a cross-sectional view illustrating a hot roller apparatus that can be used to seal a sealing cover to a microplate according to some embodiments;

FIG. 30 is a cross-sectional view illustrating a pressure clamp system according to some embodiments comprising an inflatable transparent bag;

FIG. 31 is a cross-sectional view illustrating a pressure clamp system according to some embodiments comprising a moveable transparent window;

FIG. 32 is a cross-sectional view illustrating a pressure clamp system according to some embodiments comprising an inverted microplate;

FIG. 33 is a cross-sectional view illustrating a pressure clamp system according to some embodiments comprising a plurality of apertures in a microplate;

FIG. 34 is a cross-sectional view illustrating a pressure clamp system according to some embodiments comprising a pressure chamber engaging a sealing cover;

FIG. 35 is a cross-sectional view illustrating a pressure clamp system according to some embodiments comprising a pressure chamber used together with an inverted microplate;

FIG. 36 is a cross-sectional view illustrating a pressure clamp system according to some embodiments comprising a pressure chamber used together with a microplate comprising a plurality of apertures;

FIG. 37 is a cross-sectional view illustrating a pressure clamp system according to some embodiments comprising a pressure chamber engaging a thermocycler block;

FIG. 38 is a cross-sectional view illustrating a pressure clamp system according to some embodiments comprising a vacuum assist system;

FIG. 39 is a cross-sectional view illustrating a pressure clamp system according to some embodiments comprising a pressure chamber engaging a thermocycler block and a microplate;

FIG. 40 is a cross-sectional view illustrating a pressure clamp system according to some embodiments comprising a pressure chamber and a relief port;

FIG. 41 is an exploded cross-sectional view illustrating a pressure clamp system according to some embodiments comprising a heatable transparent window;

FIG. 42 is a top perspective view illustrating an upright configuration, according to some embodiments, of a thermocycler system, an excitation system, a detection system, and a microplate;

FIG. 43 is a side view illustrating the upright configuration of the thermocycler system, the excitation system, the detection system, and the microplate of FIG. 42;

FIG. 44 is a perspective view illustrating an inverted configuration, according to some embodiments, of a thermocycler system, an excitation system, a detection system, and a microplate;

FIG. 45 is an enlarged perspective view illustrating an excitation system according to some embodiments comprising a plurality of LED excitation sources;

FIG. 46 is an enlarged perspective view illustrating an excitation system according to some embodiments comprising a plurality of LED excitation sources;

FIG. 47 is a side view illustrating the inverted configuration of the thermocycler system, the excitation system, the detection system, and the microplate of FIG. 44;

FIG. 48 is a perspective view illustrating an inverted configuration, according to some embodiments, of a thermocycler system, an excitation system comprising individually mirrored excitation sources, a detection system, and a microplate;

FIG. 49 is an enlarged perspective view illustrating the excitation system comprising individually mirrored excitation sources of FIG. 48;

FIG. 50 is a graph exemplifying vignetting and shadowing relative to excitation source position;

FIG. 51 is a graph exemplifying vignetting and shadowing and an illumination profile according to some embodiments;

FIG. 52 is a schematic view illustrating an excitation source comprising a lens according to some embodiments;

FIG. 53 is a schematic view illustrating an excitation source comprising a concave mirror according to some embodiments;

FIG. 54 is a schematic view illustrating an excitation source comprising a concave mirror and a lens according to some embodiments;

FIG. 55 is a schematic view illustrating multiple excitation sources focused to a point on a microplate according to some embodiments;

FIG. 56 is a schematic view illustrating multiple excitation sources focused to multiple points to achieve a desired irradiance profile according to some embodiments;

FIG. 57 is a flow chart illustrating a manufacturing procedure of preloaded microplates according to some embodiments;

FIG. 58 is a flow chart illustrating the use of a database system according to some embodiments;

FIG. 59 is a top perspective view illustrating a multipiece microplate in accordance with some embodiments;

FIG. 60 is an exploded perspective view illustrating the multipiece microplate of FIG. 59 in accordance with some embodiments;

FIG. 61 is a top view illustrating the multipiece microplate in accordance with some embodiments;

FIG. 62 is a cross-sectional view of the multipiece microplate of FIG. 61 taken along Line 62-62;

FIG. 63 is an enlarged cross-sectional view of cap portion and main body portion of the multipiece microplate of FIG. 62;

FIG. 64 is a top schematic view illustrating a loading distribution system comprising a conveyer, a plurality of dispensing stations, a plurality of robots, and a plurality of microplate hotels according to some embodiments;

FIG. 65 is a perspective view illustrating a loading distribution system according to some embodiments;

FIG. 66 is a side view illustrating a loading distribution system according to some embodiments, comprising a dispensing device, a source plate and wash station, and a carriage;

FIG. 67 is a side view illustrating a loading distribution system according to some embodiments, comprising a dispensing device, a source plate station, a wash station, and a carriage;

FIGS. 68(a)-(c) are top-plan views illustrating various uses of a source plate and wash pallet;

FIG. 69 is a top-plan view illustrating a ceiling mounted plate-handling device adapted to retrieve a microplate from a hotel according to some embodiments;

FIG. 70 is a perspective view illustrating a carriage capable of holding a microplate according to some embodiments;

FIG. 71 is a perspective view illustrating a table coupled to a carriage utilizing a spring allowing the table to float in X and Y axis with respect to the carriage according to some embodiments;

FIG. 72 is a perspective view illustrating an embodiment of a locating ratchet adapted to hold a microplate on the table according to some embodiments;

FIG. 73 is a perspective view illustrating a lifting device to allow the table to float in Z axis with respect to the carriage according to some embodiments;

FIG. 74 is a perspective view illustrating a pressure source adapted to communicate with a vacuum connection shoe according to some embodiments;

FIG. 75 is a perspective view illustrating of a loading distribution system comprising a pair of rails and a guide channel to lift the table off of the carriage according to some embodiments FIG. 76 is a perspective view illustrating an air slide connecting the pair of rails and a guide channel according to some embodiments;

FIG. 77 is a perspective view illustrating a loading distribution system comprising the carriage, the table, and an alignment stage according to some embodiments;

FIG. 78 is a perspective view illustrating a lifting stage adapted to lift a carriage according to some embodiments;

FIGS. 79(a)-(b) are perspective views illustrating a visual inspection station including a carriage alignment device according to some embodiments;

FIG. 80 is a top-plan view illustrating a table comprising a vacuum trench and a gasket according to some embodiments;

FIG. 81 is a perspective view illustrating a dispensing device including a plurality of dispensers according to some embodiments;

FIG. 82 is a perspective view illustrating a plate gripper robot according to some embodiments;

FIG. 83 is a perspective view illustrating a plate gripper robot, gripping a microplate in a lower jaw according to some embodiments;

FIGS. 84-90 are progressive perspective views illustrating a plate gripper robot depositing and picking-up microplates from a table and/or a plate storage unit according to some embodiments;

FIG. 91 is a perspective view illustrating a source plate and wash pallet according to some embodiments;

FIG. 92 is a perspective view illustrating a source plate and wash station, wherein a source plate and a washing tray each comprise a respective lid thereupon according to some embodiments;

FIG. 93 is a perspective view illustrating a source plate and wash station, wherein a de-lidded source plate allowing a dispensing device to access fluids stored in or on the source plate according to some embodiments;

FIG. 94 is a perspective view illustrating a source plate and wash station, wherein the source plate stays lidded and the washing tray can be accessed by a dispensing device according to some embodiments;

FIG. 95 is a perspective view illustrating a source plate and wash station positioned to enable a robot gripper to access a lidded source plate according to some embodiments;

FIG. 96 is a perspective view illustrating a source plate and wash station positioned to a allow a dispensing station to access a source plate according to some embodiments;

FIG. 97 is a perspective view illustrating a source plate and wash station positioned to a allow a dispensing station to access the washing tray according to some embodiments;

FIG. 98 is a front-plan view illustrating a source plate and wash station in a wait position alongside a dispensing device and a conveyer according to some embodiments;

FIG. 99 is a front-plan view illustrating a source plate and wash station in a deployed position alongside a dispensing device and a conveyer according to some embodiments;

FIG. 100 is a perspective view illustrating a hotel and a movable entry guide according to some embodiments;

FIG. 101 is a process flow diagram illustrating a software command and control architecture for a loading distribution system, according to some embodiments;

FIG. 102 is an illustration a sample distribution mapping for an eight dispenser sample filler, according to some embodiments;

FIG. 103 is an illustration of using a dead row to prevent cross-contamination in sample loadings from a filler according to some embodiments;

FIG. 104 is a top-plan view illustrating a robot accessing microplate hotels, source plate hotels, and a plurality of dispensing devices according to some embodiments;

FIG. 105 is a top-plan view illustrating a mapping of fluid locations of a 384-well source plate into a dispensing device comprising 96 dispensers and further into a 6,144-well microplate according to some embodiments;

FIG. 106 is an exploded top perspective view illustrating a filling apparatus comprising an intermediate layer according to some embodiments;

FIG. 107 is an exploded bottom perspective view illustrating the filling apparatus comprising the intermediate layer according to some embodiments;

FIG. 108 is a cross-sectional view illustrating the filling apparatus comprising the intermediate layer according to some embodiments;

FIG. 109 is a cross-sectional view illustrating the filling apparatus comprising the intermediate layer and nodules according to some embodiments;

FIG. 110 is a top schematic view of the filling apparatus comprising the intermediate layer and nodules according to some embodiments;

FIG. 111 is a cross-sectional view illustrating the filling apparatus comprising the intermediate layer, nodules, and sealing feature according to some embodiments;

FIG. 112 is a bottom perspective view of the intermediate layer of the filling apparatus according to some embodiments;

FIG. 113 is an exploded top perspective view illustrating a clamp system for a filling apparatus according to some embodiments;

FIG. 114 is an exploded top perspective view illustrating a filling apparatus comprising a vent layer according to some embodiments;

FIG. 115 is an exploded bottom perspective view illustrating the filling apparatus comprising the vent layer according to some embodiments;

FIG. 116 is a cross-sectional view illustrating the filling apparatus comprising the vent layer and a vent manifold according to some embodiments;

FIG. 117 is a top schematic view of the filling apparatus comprising the vent layer and vent apertures positioned between staging capillaries according to some embodiments;

FIG. 118 is a top schematic view of the filling apparatus comprising the vent layer and oblong vent apertures according to some embodiments;

FIG. 119 is a cross-sectional view illustrating the filling apparatus comprising the vent layer and pressure bores according to some embodiments;

FIG. 120 is a perspective view illustrating a filling apparatus comprising one or more assay input ports positioned on an end of an input layer according to some embodiments;

FIG. 121 is a perspective view illustrating a filling apparatus comprising one or more assay input ports positioned on a side of an input layer according to some embodiments;

FIG. 122 is a perspective view illustrating a filling apparatus comprising one or more assay input ports positioned on opposing sides of an input layer according to some embodiments;

FIG. 123 is a perspective view with portions illustrated in cross-section illustrating an assay input port according to some embodiments;

FIG. 124 is a cross-sectional view illustrating the filling apparatus of FIGS. 120-123 according to some embodiments;

FIGS. 125-131 and 133 are cross-sectional views illustrating the progressive filling of a microplate according to some embodiments;

FIG. 132 is a top schematic view of the filling apparatus comprising reduced material areas for, at least in part, use in staking according to some embodiments;

FIGS. 134-139 are cross-sectional views illustrating the progressive filling of a microplate using a filling apparatus employing fluid overfill reservoirs according to some embodiments;

FIG. 140 is a cross-sectional view illustrating a filling apparatus employing fluid overfill reservoirs disposed in an output layer according to some embodiments;

FIGS. 141(a)-(g) are top schematic views illustrating various possible positions of the staging capillaries relative to corresponding microfluidic channels according to some embodiments;

FIGS. 142(a)-(g) are cross-sectional views illustrating various possible positions and configurations microfluidic channels and staging capillaries according to some embodiments;

FIG. 143 is an exploded perspective view illustrating a filling apparatus comprising a floating insert and cover according to some embodiments;

FIG. 144 is a cross-sectional view illustrating the filling apparatus comprising the floating insert according to some embodiments;

FIG. 145 is an exploded perspective view illustrating a filling apparatus comprising a floating insert according to some embodiments;

FIG. 146 is a cross-sectional view illustrating a floating insert according to some embodiments;

FIG. 147 is a cross-sectional view illustrating a floating insert comprising post members according to some embodiments;

FIG. 148 is a cross-sectional view illustrating a floating insert comprising tapered members according to some embodiments;

FIG. 149 is a cross-sectional view illustrating a floating insert comprising tapered members and a flanged base portion according to some embodiments;

FIG. 150 is a cross-sectional view illustrating the floating insert comprising tapered members and the flanged base portion inserted into a corresponding depression according to some embodiments;

FIG. 151 is a cross-sectional view illustrating the floating insert comprising tapered members and the flanged base portion inserted into the corresponding depression and assay flow therebetween according to some embodiments;

FIG. 152 is a cross-sectional view illustrating the floating insert comprising tapered members and the flanged base portion being forced down onto the corresponding depression according to some embodiments;

FIGS. 153-155 are cross-sectional views illustrating the progressive filling and release of assay from the filling apparatus illustrated in FIG. 145 according to some embodiments;

FIGS. 156 and 157 are cross-sectional views illustrating the filling and release of assay from a filling apparatus comprising weight members according to some embodiments;

FIG. 158 is a perspective view illustrating a filling apparatus comprising a surface wire assembly and reservoir pockets according to some embodiments;

FIG. 159 is a cross-sectional view illustrating the filling apparatus comprising the surface wire assembly according to some embodiments;

FIGS. 160-162 are cross-sectional views illustrating the progressive filling of a plurality of staging capillaries according to some embodiments;

FIG. 163 is a perspective view illustrating a filling apparatus comprising a surface wire assembly, a reservoir trough, and absorbent member according to some embodiments;

FIG. 164 is a perspective view illustrating the filling apparatus comprising the surface wire assembly, the reservoir trough, and absorbent member further comprising a sloping portion according to some embodiments;

FIG. 165 is a perspective view illustrating a filling apparatus comprising a surface wire assembly, reservoir pockets, and absorbent members according to some embodiments;

FIG. 166 is a perspective view illustrating the filling apparatus comprising the surface wire assembly, reservoir pockets, and absorbent members further comprising a sloping overflow channel portion according to some embodiments;

FIG. 167 is a perspective view illustrating a funnel member comprising an assay chamber according to some embodiments;

FIG. 168 is a perspective view illustrating a funnel member comprising multiple discrete assay chambers according to some embodiments;

FIG. 169 is a perspective view illustrating a funnel member comprising multiple discrete assay chambers according to some embodiments;

FIG. 170 is a cross-sectional view illustrating a funnel member comprising a tip portion according to some embodiments;

FIG. 171 is a cross-sectional view illustrating a funnel member comprising a tip portion and a wiper member according to some embodiments;

FIG. 172 is a cross-sectional view illustrating a funnel member comprising a tip portion and a planar cavity according to some embodiments;

FIG. 173 is a cross-sectional view illustrating a funnel member comprising a tip portion and a wiper member spaced apart from the tip portion according to some embodiments;

FIG. 174 is a bottom perspective view illustrating a funnel member comprising multiple offset discrete assay chambers according to some embodiments;

FIG. 175 is a top plan view illustrating a funnel member comprising multiple offset discrete assay chambers and one or more apertures according to some embodiments;

FIG. 176 is a cross-sectional view illustrating a funnel member comprising multiple offset discrete assay chambers and one or more apertures according to some embodiments;

FIG. 177 is a top perspective view illustrating a multipiece funnel member comprising multiple offset discrete assay chambers and an internal siphon passage according to some embodiments;

FIG. 178 is a cross-sectional view illustrating the multipiece funnel member comprising multiple offset discrete assay chambers and the internal siphon passage according to some embodiments;

FIG. 179 is an exploded top perspective view illustrating a multipiece funnel member comprising portions separated generally vertically according to some embodiments;

FIG. 180 is an exploded top perspective view illustrating a multipiece funnel member comprising portions separated generally horizontally according to some embodiments;

FIG. 181 is a cross-sectional view illustrating a sealing cover according to some embodiments;

FIG. 182 is a perspective view illustrating a sealing cover roll according to some embodiments;

FIG. 183 is a perspective view illustrating a manual sealing cover applicator according to some embodiments;

FIG. 184 is a perspective view illustrating a fixture for use with a manual sealing cover applicator according to some embodiments;

FIG. 185 is a perspective view, with portions illustrated in cross-section, illustrating the manual sealing cover applicator according to some embodiments;

FIG. 186 is a side view, with portions illustrated in cross-section, illustrating the manual sealing cover applicator in a closed position according to some embodiments;

FIG. 187 is a side view, with portions illustrated in cross-section, illustrating the manual sealing cover applicator in an opened position according to some embodiments;

FIG. 188 is a perspective view illustrating an automated sealing cover applicator employing a sealing cover roll according to some embodiments;

FIG. 189 is a perspective view, with portions removed for clarity, illustrating the automated sealing cover applicator employing the sealing cover roll according to some embodiments;

FIG. 190 is a cross-sectional view illustrating the automated sealing cover applicator employing the sealing cover roll according to some embodiments;

FIG. 191 is a perspective view illustrating a sealing cover roll cartridge according to some embodiments;

FIG. 192 is a cross-sectional view illustrating the sealing cover roll cartridge according to some embodiments;

FIG. 193 is a perspective view, with portions removed for clarity, illustrating the automated sealing cover applicator employing a single sheet cartridge according to some embodiments;

FIG. 194 is a perspective view, with portions removed for clarity, illustrating a single sheet applicator assembly according to some embodiments;

FIG. 195 is a perspective view, with portions removed for clarity, illustrating a single cover cartridge according to some embodiments;

FIG. 196 is an enlarged cross-sectional view illustrating the single cover cartridge according to some embodiments;

FIG. 197 is an exploded perspective view illustrating the single cover cartridge according to some embodiments;

FIGS. 198-201 are cross-sectional views illustrating progressive steps of applying a single sealing cover to a microplate according to some embodiments;

FIG. 202 is an exploded view illustrating an inverted configuration of a pressure chamber according to some embodiments;

FIG. 203 is a cross-sectional view illustrating section A-A of the pressure chamber of FIG. 202 in combination with a thermocycler system according to some embodiments;

FIG. 204 is a side view illustrating a clamp mechanism in a locked condition according to some embodiments;

FIG. 205 is a side view illustrating a clamp mechanism in an unlocked condition according to some embodiments;

FIG. 206 is a bottom perspective view illustrating a clamp mechanism in a locked condition according to some embodiments;

FIG. 207 is a pneumatic diagram illustrating a pneumatic system for a pressure chamber and a clamp mechanism according to some embodiments;

FIG. 208 is a perspective view illustrating the pneumatic system of FIG. 207 according to some embodiments;

FIG. 209 is a flow diagram illustrating a method of clamping a chamber to a thermocycler system according to some embodiments;

FIG. 210 is a flow diagram illustrating a method of performing a leak test on a chamber according to some embodiments;

FIG. 211 is a flow diagram illustrating a method of unclamping a chamber from a thermocycler system according to some embodiments;

FIG. 212 is a cross-sectional view illustrating an adjustable lens and camera mount according to some embodiments; and FIG. 213 is a flowchart illustrating a process for determining bias.

DESCRIPTION OF SOME EMBODIMENTS

The following description of some embodiments is merely exemplary in nature and is in no way intended to limit the present teachings, applications, or uses. Although the present teachings will be discussed in some embodiments as relating to polynucleotide amplification, such as PCR, such discussion should not be regarded as limiting the present teaching to only such applications.

The section headings and sub-headings used herein are for general organizational purposes only and are not to be construed as limiting the subject matter described in any way.

High-Density Sequence Detection System

In some embodiments, a high density sequence detection system comprises one or more components useful in an analytical method or chemical reaction, such as the analysis of biological and other materials containing polynucleotides. Such systems are, in some embodiments, useful in the analysis of assays, as further described below. High density sequence detection systems, in some embodiments, comprise an excitation system and a detection system which can be useful for analytical methods involving the generation and/or detection of electromagnetic radiation (e.g., visible, ultraviolet or infrared light) generated during analytical procedures. In some embodiments, such procedures include those comprising the use of fluorescent or other materials that absorb and/or emit light or other radiation under conditions that allow quantitative and/or qualitative analysis of a material (e.g., assays among those described herein). In some embodiments useful for polynucleotide amplification and/or detection, a high density sequence detection system can further comprise a thermocycler. In some embodiments, a high density sequence system can further comprise microplate and components for, e.g., filling and handling the microplate, such as a pressure clamp system. It will be understood that, although high density sequence detection systems are described herein with respect to specific microplates, assays and other embodiments, such systems and components thereof are useful with a variety of analytical platforms, equipment, and procedures.

Figure 1A:
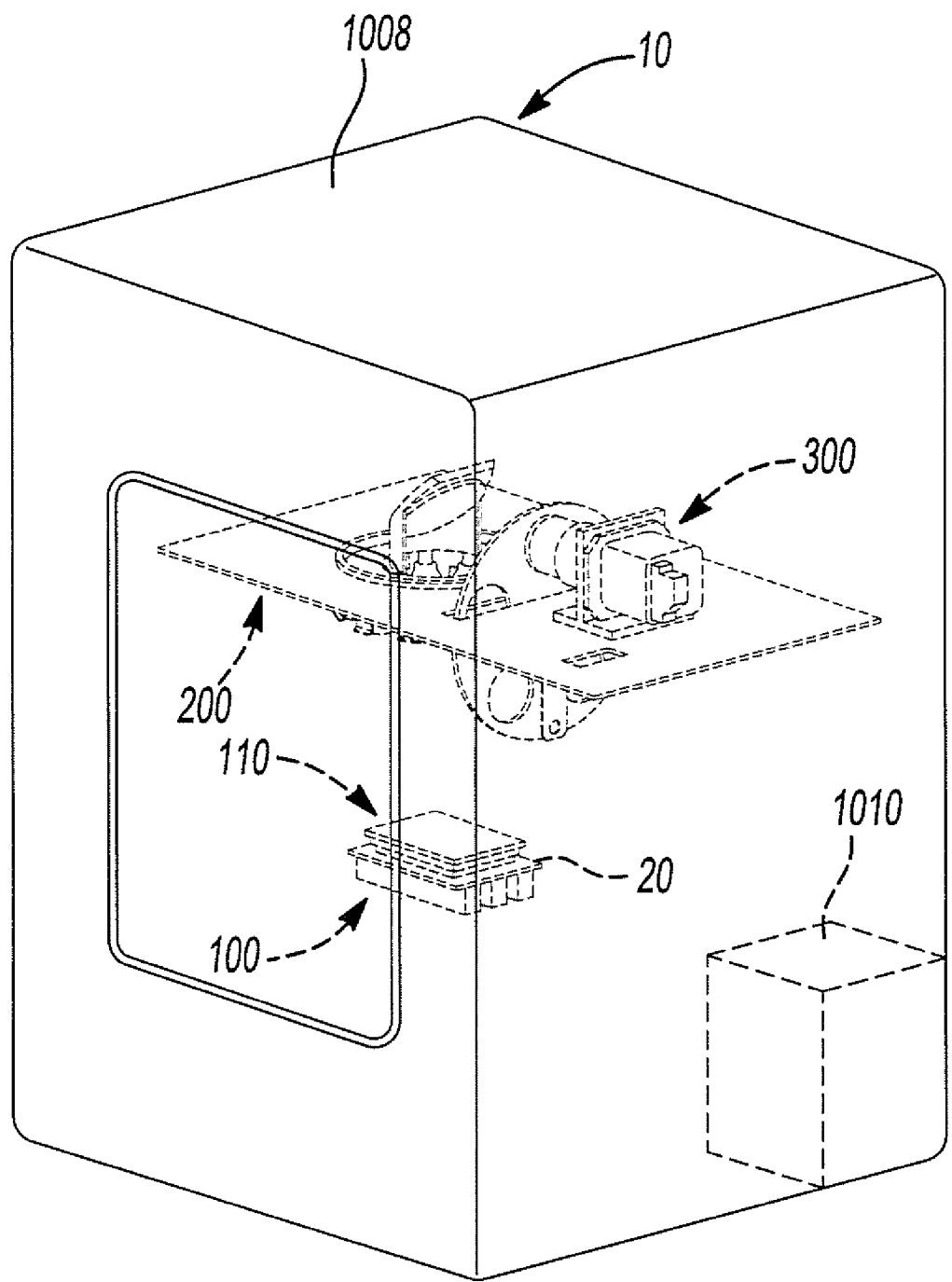
FIG. 1(a) is a perspective view illustrating a high-density sequence detection system according to some embodiments of the present teachings.
Figure 1B:
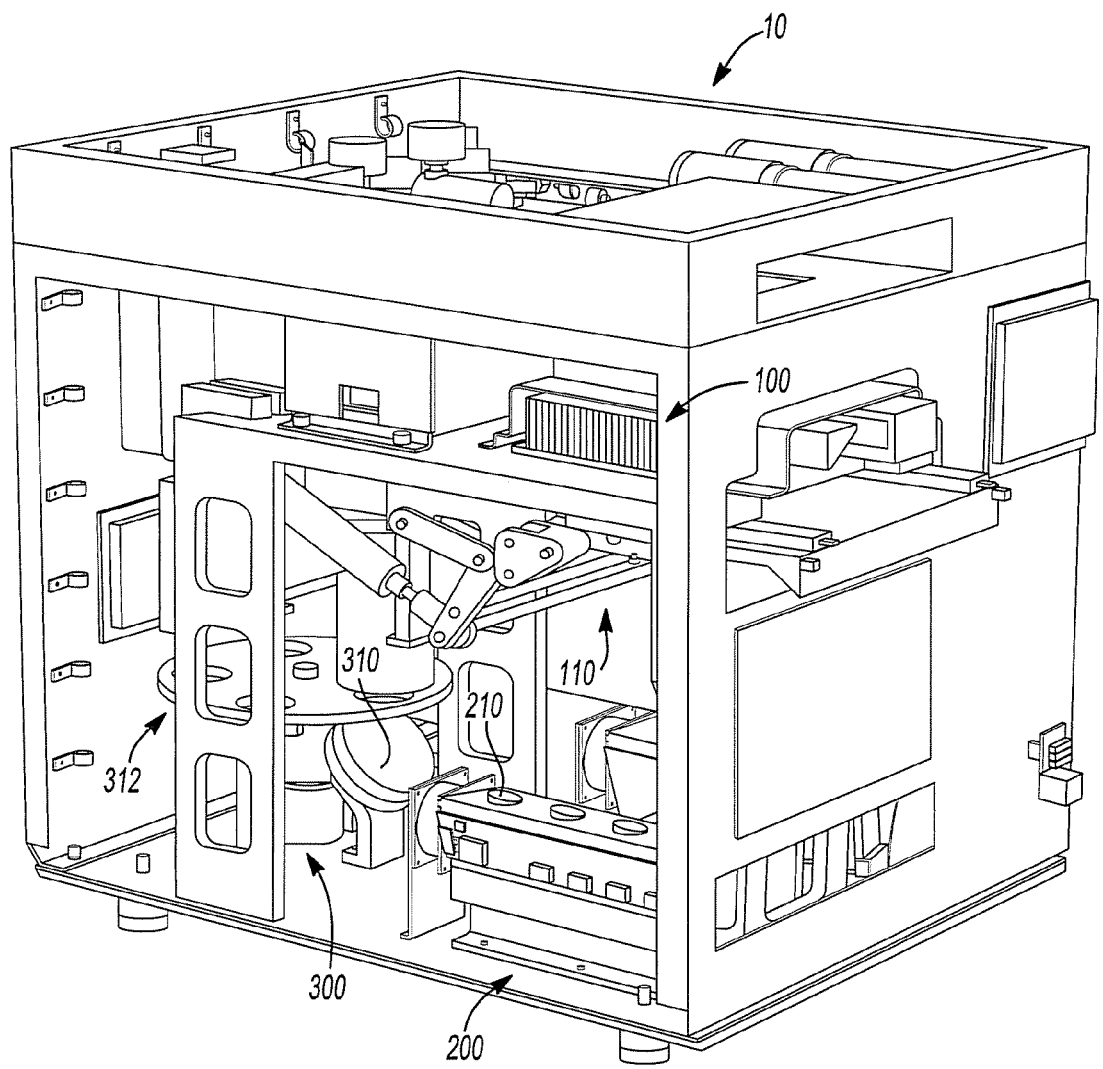
FIG. 1(b) is a perspective view illustrating a high-density sequence detection system according to some embodiments of the present teachings.
Figure 1C:
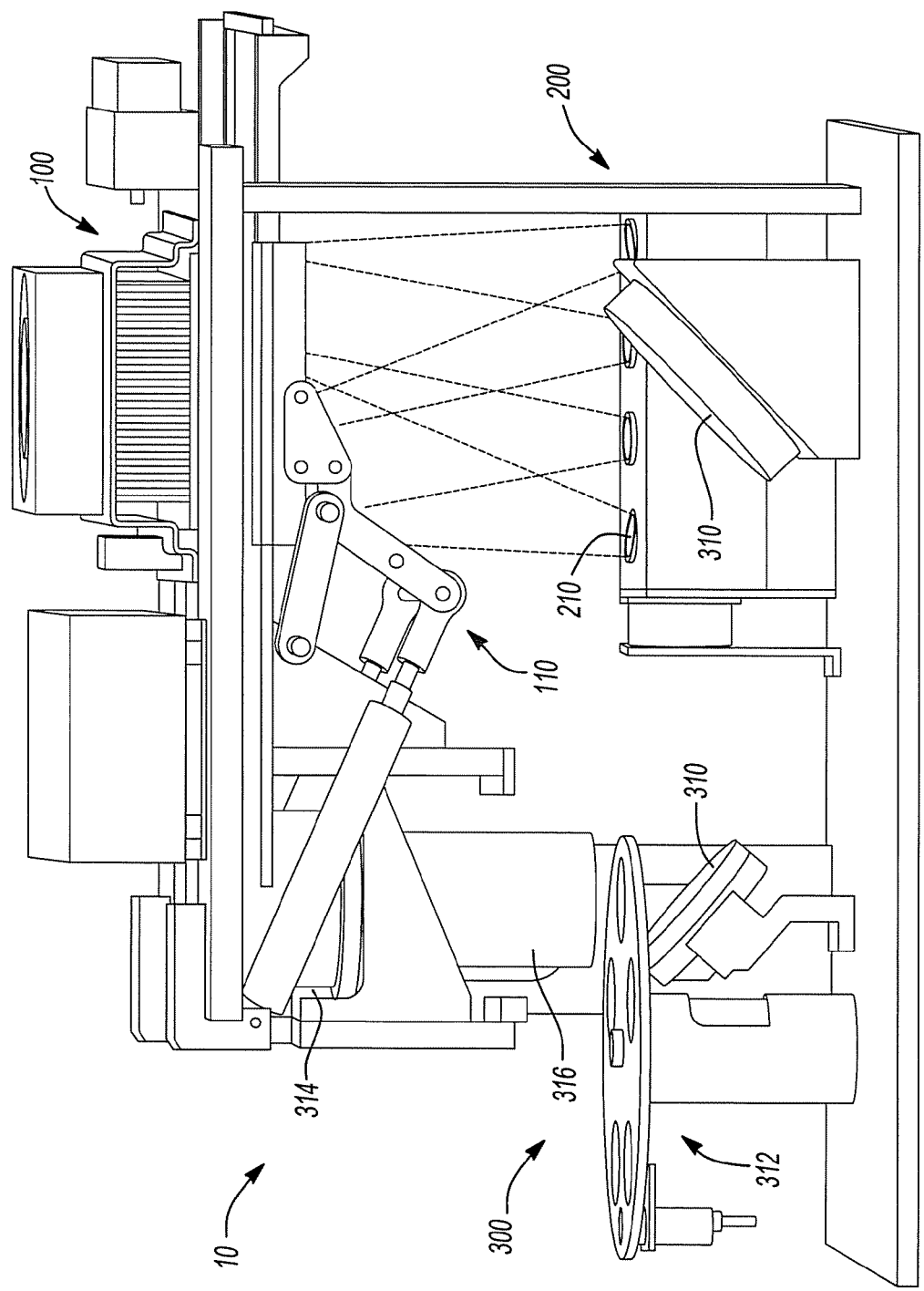
FIG. 1(c) is a side view illustrating the high-density sequence detection system of FIG. 1(b)

Referring to FIG. 1, a high-density sequence detection system 10 is illustrated in accordance with some embodiments of the present teachings. In some embodiments, high-density sequence detection system 10 comprises a microplate 20 containing an assay 1000 (see FIGS. 26 and 27), a thermocycler system 100, a pressure clamp system 110, an excitation system 200, and a detection system 300 disposed in a housing 1008.

In some embodiments, assay 1000 can comprise any material that is useful in, the subject of, a precursor to, or a product of, an analytical method or chemical reaction. In some embodiments for amplification and/or detection of polynucleotides, assay 1000 comprises one or more reagents (such as PCR master mix, as described further herein); an analyte (such as a biological sample comprising DNA, a DNA fragment, cDNA, RNA, or any other nucleic acid sequence), one or more primers, one or more primer sets, one or more detection probes; components thereof; and combinations thereof. In some embodiments, assay 1000 comprises a homogenous solution of a DNA sample, at least one primer set, at least one detection probe, a polymerase, and a buffer, as used in a homogenous assay (described further herein). In some embodiments, assay 1000 can comprise an aqueous solution of at least one analyte, at least one primer set, at least one detection probe, and a polymerase. In some embodiments, assay 1000 can be an aqueous homogenous solution. In some embodiments, assay 1000 can comprise at least one of a plurality of different detection probes and/or primer sets to perform multiplex PCR, which can be useful, for example, when analyzing a whole genome (e.g., 20,000 to 30,000 genes, or more) or other large numbers of genes or sets of genes.

Microplate

In some embodiments, a microplate comprises a substrate useful in the performance of an analytical method or chemical reaction. In some embodiments, a microplate can comprise one or more material retention regions, configured to hold or support a material (e.g., an assay, as discussed below, or other solid or liquid) at one or more locations on or in the microplate. In some embodiments, such material retention regions can be wells, through-holes, hydrophilic spots or pads, and the like. In some embodiments, such as shown in FIG. 2-19, material retention regions comprise wells, as at 26. In some embodiments, such wells can comprise a feature on or in the surface of the microplate wherein assay 1000 is contained at least in part by physical separation from adjacent features. Such well features can include, in some embodiments, depressions, indentations, ridges, and combinations thereof, in regular or irregular shapes. In some embodiments a microplate is single-use, wherein it is filled or otherwise used with a single assay for a single experiment or set of experiments, and is thereafter discarded. In some embodiments, a microplate is multiple-use, wherein it can be operable for use in a plurality of experiments or sets of experiments.

Referring now to FIGS. 2-19, in some embodiments, microplate 20 comprises a substantially planar construction having a first surface 22 and an opposing second surface 24 (see FIG. 12-19). First surface 22 comprises a plurality of wells 26 disposed therein or thereon. The overall positioning of the plurality of wells 26 can be referred to as a well array. Each of the plurality of wells 26 is sized to receive assay 1000 (FIGS. 26 and 27). As illustrated in FIGS. 26 and 27, assay 1000 is disposed in at least one of the plurality of wells 26 and sealing cover 80 (FIG. 26) is disposed thereon (as will be discussed herein). In some embodiments, one or more of the plurality of wells 26 may not be completely filled with assay 1000, thereby defining a headspace 1006 (FIG. 26), which can define an air gap or other gas gap.

In some embodiments, the material retention regions of microplate 20 can comprise a plurality of reaction spots on the surface of the microplate. In such embodiments, a reaction spot can be an area on the substrate which localizes, at least in part by non-physical means, assay 1000. In such embodiments, assay 1000 can be localized in sufficient quantity, and isolation from adjacent areas on the microplate, so as to facilitate an analytical or chemical reaction (e.g., amplification of one or more target DNA) in the material retention region. Such localization can be accomplished by physical and chemical modalities, including, for example, physical containment of reagents in one dimension and chemical containment in one or more other dimensions.

In some embodiments, the surface of the microplate 20 comprises an enhanced surface which can comprise a physical or chemical modality on or in the surface of the microplate so as to enhance support of, or filling of, assay 1000 in a material retention region (e.g., a well or a reaction spot). Such modifications can include chemical treatment of the surface, or coating the surface. In some embodiments, such chemical treatment can comprise chemical treatment or modification of the surface of the microplate so as to form relatively hydrophilic and hydrophobic areas. In some embodiments, a surface tension array can be formed comprising a pattern of hydrophilic sites forming reaction spots on a hydrophobic matrix, such that the hydrophilic sites can be spatially segregated by hydrophobic regions. Reagents delivered to the array can be constrained by surface tension difference between hydrophilic and hydrophobic sites.

In some embodiments, the chemical modality can comprise chemical treatment or modification of the surface or other material of microplate 20 so as to affix one or more components of assay 1000 to the microplate. In such embodiments, assay 1000 can be affixed to microplate 20, directly or indirectly, so that assay 1000 is operable for analysis or reaction, but is not removed or otherwise displaced from the microplate prior to the analysis or reaction during routine handling of the microplate. In some embodiments, assay 1000 can be affixed to the surface so as form a patterned array (immobilized reagent array) of reaction spots. In some embodiments, an immobilization reagent array can comprise a hydrogel affixed to the microplate. Such hydrogels can include, for example, cellulose gels, such as agarose and derivatized agarose (e.g., low melting agarose, monoclonal anti-biotin agarose, and streptavidin derivatized agarose); xanthan gels; synthetic hydrophilic polymers, such as crosslinked polyethylene glycol, polydimethyl acrylamide, polyacrylamide, polyacrylic acid (e.g., cross-linked with dysfunctional monomers or radiation cross-linking), and micellar networks; and combinations thereof.

In some embodiments, one or more components of assay 1000 can be affixed to microplate 20 by covalent or non-covalent bonding to the surface of the microplate. In certain embodiments, assay 1000 an be bonded, anchored or tethered to a second moiety (immobilization moiety) which, in turn, can be anchored to the surface of the microplate. In some embodiments, such anchoring is through a chemically releasable or cleavable moeity, such that assay 1000 can be released or made available for analysis or reaction after reacting with a cleaving reagent prior to, during, or after the microplate assembly. Such release methods can include a variety of enzymatic, or non-enzymatic means, such as chemical, thermal, or photolytic treatment. In some embodiments, chemical moieties for immobilization moieties can include those comprising carbamate, ester, amide, thiolester, (N)-functionalized thiourea, functionalized maleimide, amino, disulfide, amide, hydrazone, streptavidin, avidin/biotin, and gold-sulfide groups.

Microplate Footprint

With reference to FIGS. 2-19, microplate 20 generally comprises a main body or substrate 28. In some embodiments, main body 28 is substantially planar. In some embodiments, microplate 20 comprises an optional skirt or flange portion 30 disposed about a periphery of main body 28 (see FIG. 2). Skirt portion 30 can form a lip around main body 28 and can vary in height. Skirt portion 30 can facilitate alignment of microplate 20 on thermocycler block 102. Additionally, skirt portion 30 can provide additional rigidity to microplate 20 such that during handling, filling, testing, and the like, microplate 20 remains rigid, thereby ensuring assay 1000, or any other components, disposed in each of the plurality of wells 26 does not contaminate adjacent wells. However, in some embodiments, microplate 20 can employ a skirtless design (see FIGS. 3-5) depending upon user preference.

In order to facilitate use with existing equipment, robotic implements, and instrumentation, the footprint dimensions of main body 28 and/or skirt portion 30 of microplate 20, in some embodiments, can conform to standards specified by the Society of Biomolecular Screening (SBS) and the American National Standards Institute (ANSI), published January 2004 (ANSI/SBS 3-2004). In some embodiments, the footprint dimensions of main body 28 and/or skirt portion 30 of microplate 20 are about 127.76 mm (5.0299 inches) in length and about 85.48 mm (3.3654 inches) in width. In some embodiments, the outside corners of microplate 20 comprise a corner radius of about 3.18 mm (0.1252 inches). In some embodiments, microplate 20 comprises a thickness of about 0.5 mm to about 3.0 mm. In some embodiments, microplate 20 comprises a thickness of about 1.25 mm. In some embodiments, microplate 20 comprises a thickness of about 2.25 mm. One skilled in the art will recognize that microplate 20 and skirt portion 30 can be formed in dimensions other than those specified herein.

Plurality of Wells

In order to increase throughput of genotyping, gene expression, and other assays, in some embodiments, microplate 20 comprises an increased quantity of the plurality of wells 26 beyond that employed in prior conventional microplates. In some embodiments, microplate 20 comprises 6,144 wells. According to the present teachings, microplate 20 can comprise, but is not limited to, any of the array configurations of wells described in Table 1.

TABLE 1

| Total Number of Wells | Rows × Columns | Approximate Well Area |
|---|---|---|
| 96 | 8 × 12 | 9 × 9 mm |
| 384 | 16 × 24 | 4.5 × 4.5 mm |
| 1536 | 32 × 48 | 2.25 × 2.25 mm |
| 3456 | 48 × 72 | 1.5 × 1.5 mm |
| 6144 | 64 × 96 | 1.125 × 1.125 mm |
| 13824 | 96 × 144 | 0.75 × .075 mm |
| 24576 | 128 × 192 | 0.5625 × 0.5625 mm |
| 55296 | 192 × 288 | 0.375 × 0.375 mm |
| 768 | 24 × 32 | 3 × 3 mm |
| 1024 | 32 × 32 | 2.25 × 3 mm |
| 1600 | 40 × 40 | 1.8 × 2.7 mm |
| 1280 | 32 × 40 | 2.25 × 2.7 mm |
| 1792 | 32 × 56 | 2.25 × 1.714 mm |
| 2240 | 40 × 56 | 1.8 × 1.714 mm |
| 864 | 24 × 36 | 3 × 3 mm |
| 4704 | 56 × 84 | 1.257 × 1.257 mm |
| 7776 | 72 × 108 | 1 × 1 mm |
| 9600 | 80 × 120 | 0.9 × .09 mm |
| 11616 | 88 × 132 | 0.818 × 0.818 mm |
| 16224 | 104 × 156 | 0.692 × 0.692 mm |
| 18816 | 112 × 168 | 0.643 × 0.643 mm |
| 21600 | 120 × 180 | 0.6 × 0.6 mm |
| 27744 | 136 × 204 | 0.529 × 0.529 mm |
| 31104 | 144 × 216 | 0.5 × 0.5 mm |
| 34656 | 152 × 228 | 0.474 × 0.474 mm |
| 38400 | 160 × 240 | 0.45 × 0.45 mm |
| 42336 | 168 × 252 | 0.429 × 0.429 mm |
| 46464 | 176 × 264 | 0.409 × 0.409 mm |
| 50784 | 184 × 256 | 0.391 × 0.391 mm |

Well Shape

Figure 4:
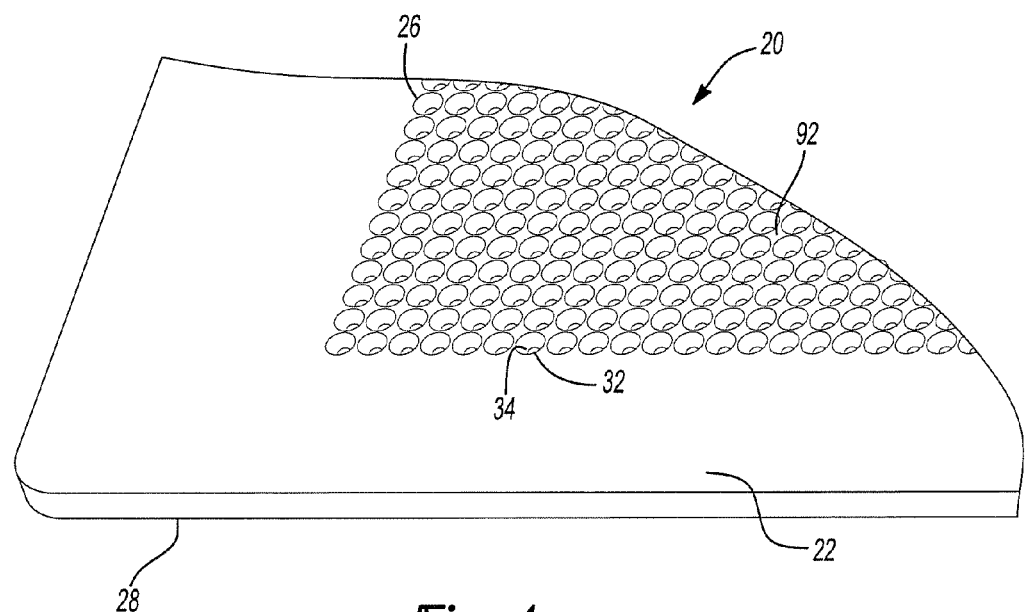
FIG. 4 is an enlarged perspective view illustrating a microplate in accordance with some embodiments comprising a plurality of wells comprising a circular rim portion.
Figure 5:
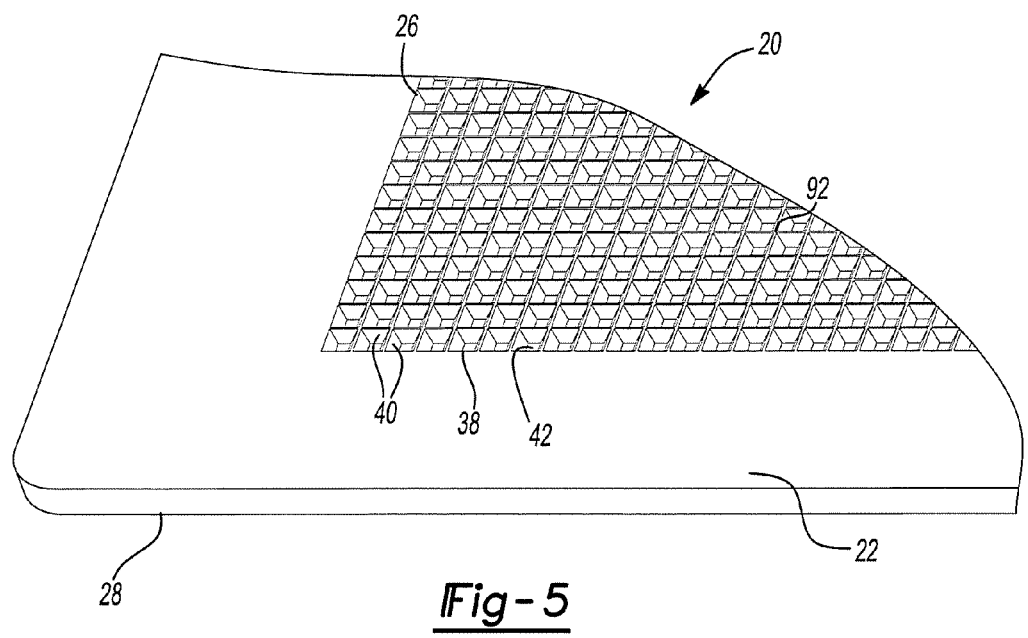
FIG. 5 is an enlarged perspective view illustrating a microplate in accordance with some embodiments comprising a plurality of wells comprising a square-shaped rim portion.
Figure 6:
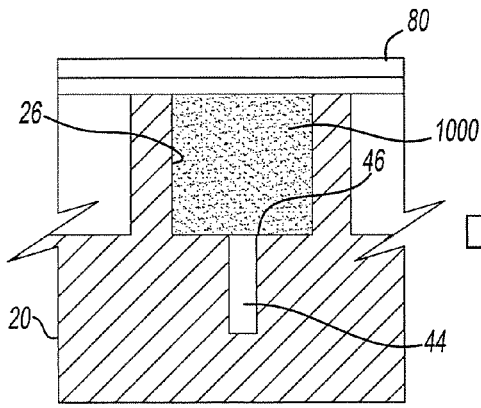
FIG. 6 is a cross-sectional view illustrating a well comprising a pressure relief bore according to some embodiments.

According to some embodiments, as illustrated in FIGS. 4 and 5, each of the plurality of wells 26 can be substantially equivalent in size. The plurality of wells 26 can have any cross-sectional shape. In some embodiments, as illustrated in FIGS. 4, 26, and 27, each of the plurality of wells 26 comprises a generally circular rim portion 32 (FIG. 4) with a downwardly-extending, generally-continuous sidewall 34 that terminate at a bottom wall 36 interconnected to sidewall 34 with a radius. A draft angle of sidewall 34 can be used in some embodiments. In some embodiments, the draft angle provides benefits including increased ease of manufacturing and minimizing shadowing (as discussed herein). The particular draft angle is determined, at least in part, by the manufacturing method and the size of each of the plurality of wells 26. In some embodiments, circular rim portion 32 can be about 1.0 mm in diameter, the depth of each of the plurality of wells 26 can be about 0.9 mm, the draft angle of sidewall 34 can be about 1° to 5° or greater and each of the plurality of wells 26 can have a center-to-center distance of about 1.125 mm. In some embodiments, the volume of each of the plurality of wells 26 can be about 500 nanoliters.

According to some embodiments, as illustrated in FIG. 5, each of the plurality of wells 26 comprises a generally square-shaped rim portion 38 with downwardly-extending sidewalls 40 that terminate at a bottom wall 42. A draft angle of sidewalls 40 can be used. Again, the particular draft angle is determined, at least in part, by the manufacturing method and the size of each of the plurality of wells 26. In some embodiments of wells 26 of FIG. 5, generally square-shaped rim portion 38 can have a side dimension of about 1.0 mm in length, a depth of about 0.9 mm, a draft angle of about 1° to 5° or greater, and a center-to-center distance of about 1.125 mm, generally indicated at A (see FIG. 27). In some embodiments, the volume of each of the plurality of wells 26 of FIG. 5 can be about 500 nanoliters. In some embodiments, the spacing between adjacent wells 26, as measured at the top of a wall dividing the wells, is less than about 0.5 m. In some embodiments, this spacing between adjacent wells 26 is about 0.25 mm.

In some embodiments, and in some configurations, the plurality of wells 26 comprising a generally circular rim portion 32 can provide advantages over the plurality of wells 26 comprising a generally square-shaped rim portion 38. In some embodiments, during heating, it has been found that assay 1000 can migrate through capillary action upward along edges of sidewalls 40. This can draw assay 1000 from the center of each of the plurality of wells 26, thereby causing variation in the depth of assay 1000. Variations in the depth of assay 1000 can influence the emission output of assay 1000 during analysis. Additionally, during manufacture of microplate 20, in some cases cylindrically shaped mold pins used to form the plurality of wells 26 comprising generally circular rim portion 32 can permit unencumbered flow of molten polymer thereabout. This unencumbered flow of molten polymer results in less deleterious polymer molecule orientation. In some embodiments, generally circular rim portion 32 provides more surface area along microplate 20 for improved sealing with sealing cover 80, as is discussed herein.

Pressure Relief Bores

Figure 7:
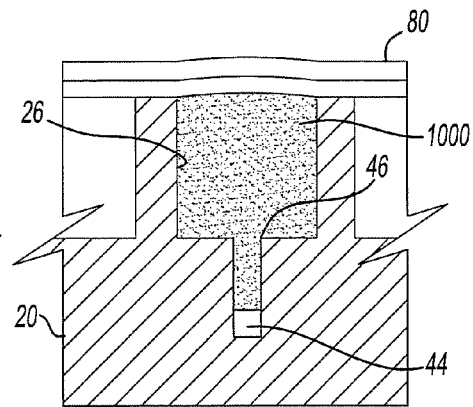
FIG. 7 is a cross-sectional view illustrating the well of FIG. 6 wherein the pressure relief bore is partially filled.

Referring now to FIGS. 6-9, in some embodiments, each of the plurality of wells 26 of microplate 20 can comprise a pressure relief bore 44. In some embodiments, pressure relief bore 44 is sized such that it does not initially fill with assay 1000 due to surface tension. However, when assay 1000 is heated during thermocycling, assay 1000 expands, thereby increasing an internal fluid pressure in each of the plurality of wells 26. This increased internal fluid pressure is sufficient to permit assay 1000 to flow into pressure relief bore 44 as illustrated in FIG. 7, thereby minimizing the pressure exerted on sealing cover 80. In some embodiments, each of the plurality of wells 26 can have one or a plurality of pressure relief bores 44.

Figure 8:
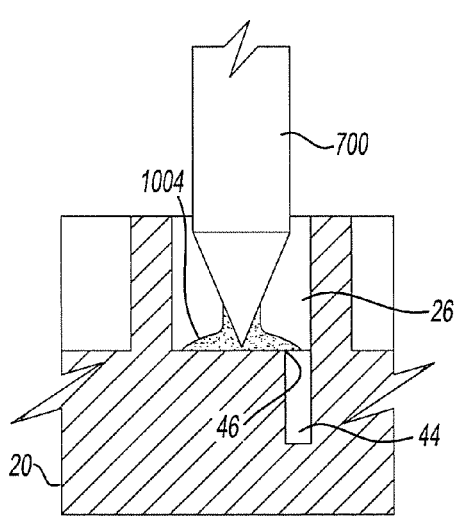
FIG. 8 is a cross-sectional view illustrating a well comprising an offset pressure relief bore according to some embodiments, being filled by a spotting device.
Figure 9:
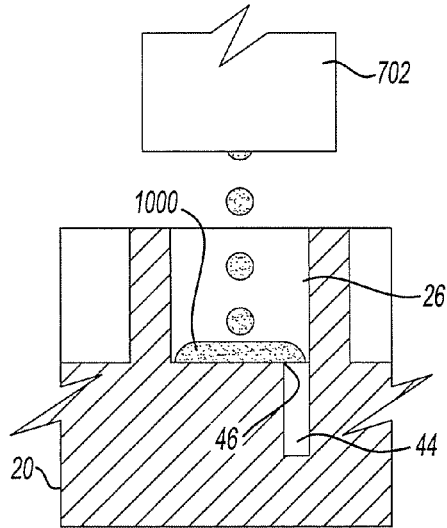
FIG. 9 is a cross-sectional view illustrating the well of FIG. 8 being filled by a micro-piezo dispenser.

In some embodiments, as illustrated in FIGS. 8 and 9, pressure relief bore 44 can be offset within each of the plurality of wells 26 so that each of the plurality of wells 26 can be filled with assay 1000 or other material 1004 via a spotting device 700 (FIG. 8) or a micro-piezo dispenser 702 (FIG. 9). In some embodiments, a top edge 46 of pressure relief bore 44 can be generally square and have minimal or no radius. This arrangement can reduce the likelihood that assay 1000 or other material 1004 will enter pressure relief bore 44 prior to thermocycling.

Through-Hole Wells

Figure 10:
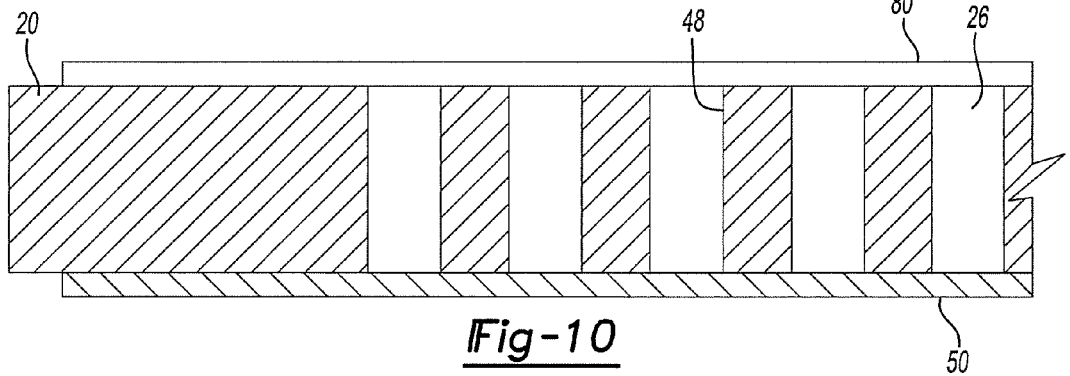
FIG. 10 is a cross-sectional view illustrating a microplate employing a plurality of apertures, a foil seal, and a sealing cover according to some embodiments.
Figure 11:
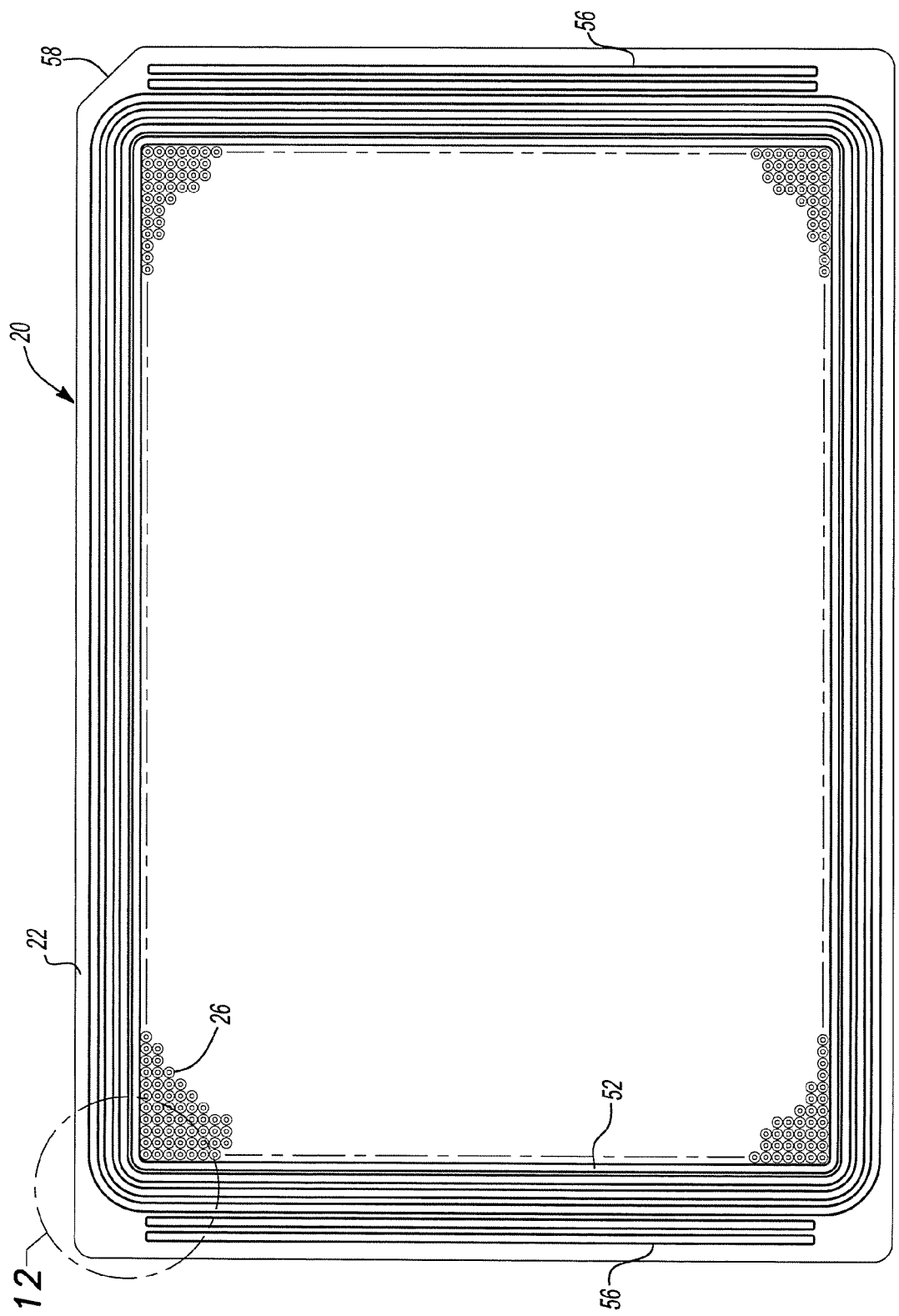
FIG. 11 is a top view illustrating a microplate in accordance with some embodiments comprising one or more grooves.

Turning now to FIGS. 10, 33, and 36, in some embodiments, each of the plurality of wells 26 of microplate 20 comprises a plurality of apertures 48 being sealed at least on one end by sealing cover 80. In some embodiments, each of the plurality of apertures 48 is sealed on an opposing end with a foil seal 50, which can have a clear or opaque adhesive. In these embodiments, foil seal 50 can be placed against thermocycler block 102 to aid in thermal conductivity and distribution.

In some embodiments, a layer of mineral oil can be placed at the top of each of the plurality of apertures 48 before, or as an alternative to, placement of sealing cover 80 on microplate 20. In several of such embodiments, the mineral oil can fill a portion of each of the plurality of apertures 48 and provide an optical interface and can control evaporation of assay 1000.

Grooves

Referring to FIGS. 11-15, in some embodiments, microplate 20 can comprise grooves 52 and grooves 54 disposed about a periphery of the plurality of wells 26. In some embodiments, grooves 52 can have depth and width dimensions generally similar to the depth and width dimensions of the plurality of wells 26 (FIGS. 12 and 13). In some embodiments, grooves 54 can have depth and width dimensions less than the depth and width dimensions of the plurality of wells 26 (FIGS. 14 and 15). In some embodiments, as illustrated in FIG. 12, additional grooves 56 can be disposed at opposing sides of microplate 20. In some embodiments, grooves 52, 54, and 56 can improve thermal uniformity among the plurality of wells 26 in microplate 20. In some embodiments, grooves 52, 54, and 56 can improve the sealing interface formed by sealing cover 80 and microplate 20. Grooves 52, 54, and 56 can also assist in simplifying the injection molding process of microplate 20. In some embodiments, a liquid solution similar to assay 1000 can be disposed in grooves 52, 54, and 56 to, in part, improve thermal uniformity during thermocycling.

Alignment Features

In some embodiments, as illustrated in FIGS. 2, 3, 11, and 14, microplate 20 comprises an alignment feature 58, such as a corner chamfer, a pin, a slot, a cut corner, an indentation, a graphic, or other unique feature that is capable of interfacing with a corresponding feature formed in a fixture, reagent dispensing equipment, and/or thermocycler. In some embodiments, alignment feature 58 comprises a nub or protrusion 60 as illustrated in FIG. 14. Additionally, in some embodiments, alignment features 58 are placed such that they do not interfere with sealing cover 80 or at least one of the plurality of wells 26. However, locating alignment features 58 near at least one of the plurality of wells 26 can provide improved alignment with dispensing equipment and/or thermocycler block 102.

Thermally Isolated Portion

In some embodiments, as illustrated in FIGS. 16-19, microplate 20 comprises a thermally isolated portion 62. Thermally isolated portion 62 can be disposed along at least one edge of main body 28. Thermally isolated portion 62 can be generally free of wells 26 and can be sized to receive a marking indicia 64 (discussed in detail herein) thereon. Thermally isolated portion 62 can further be sized to facilitate the handling of microplate 20 by providing an area that can be easily gripped by a user or mechanical device without disrupting the plurality of wells 26.

Still referring to FIGS. 16-19, in some embodiments, microplate 20 comprises a first groove 66 formed along first surface 22 and a second groove 68 formed along an opposing second surface 24 of microplate 20. First groove 66 and second groove 68 can be aligned with respect to each other to extend generally across microplate 20 from a first side 70 to a second side 72. First groove 66 and second groove 68 can be further aligned upon first surface 22 and second surface 24 to define a reduced cross-section 74 between thermally isolated portion 62 and the plurality of wells 26. This reduced cross-section 74 can provide a thermal isolation barrier to reduce any heat sink effect introduced by thermally isolated portion 62, which might otherwise reduce the temperature cycle of some of the plurality of wells 26.

Marking Indicia

Figure 2:
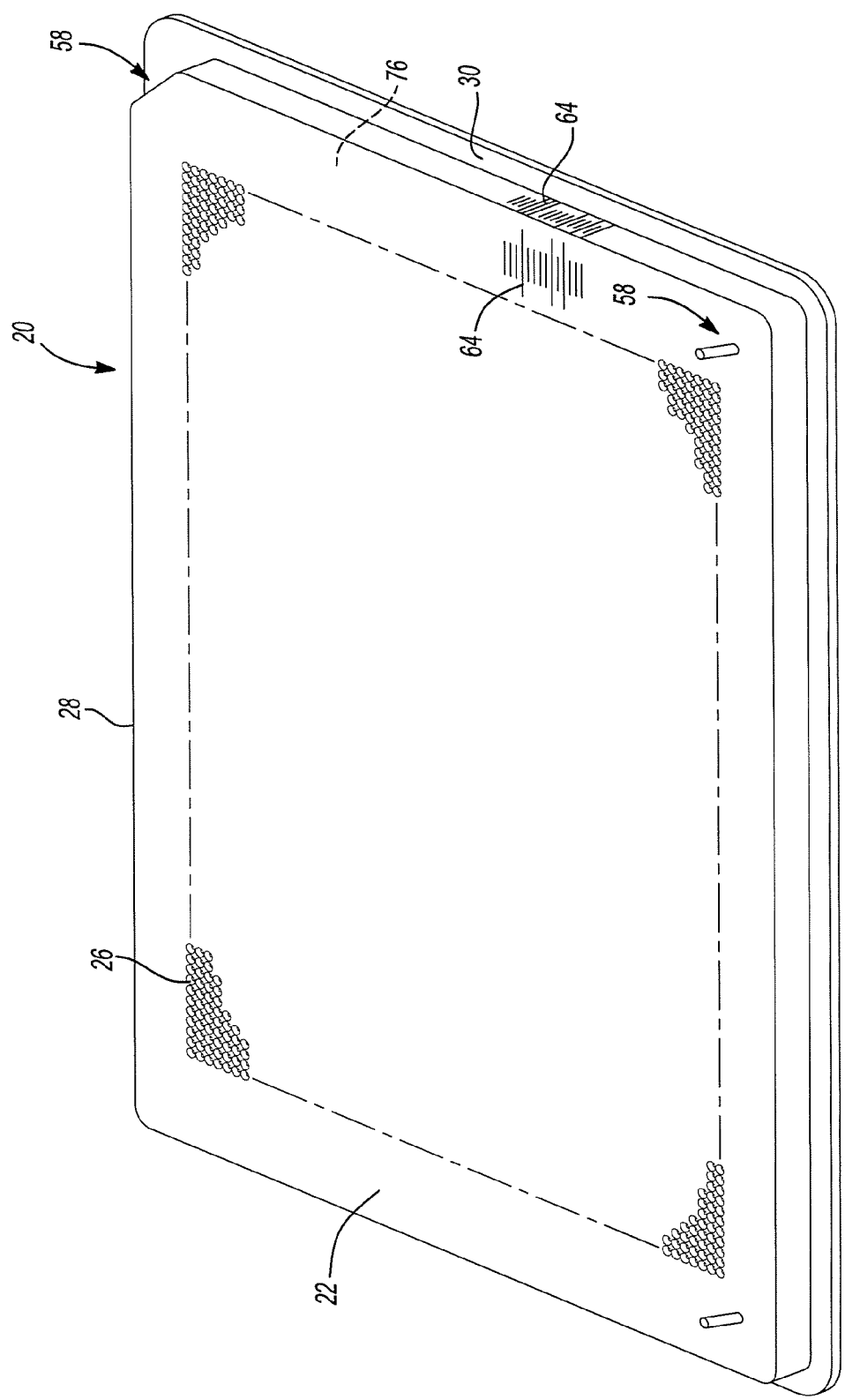
FIG. 2 is a top perspective view illustrating a microplate in accordance with some embodiments.
Figure 3:
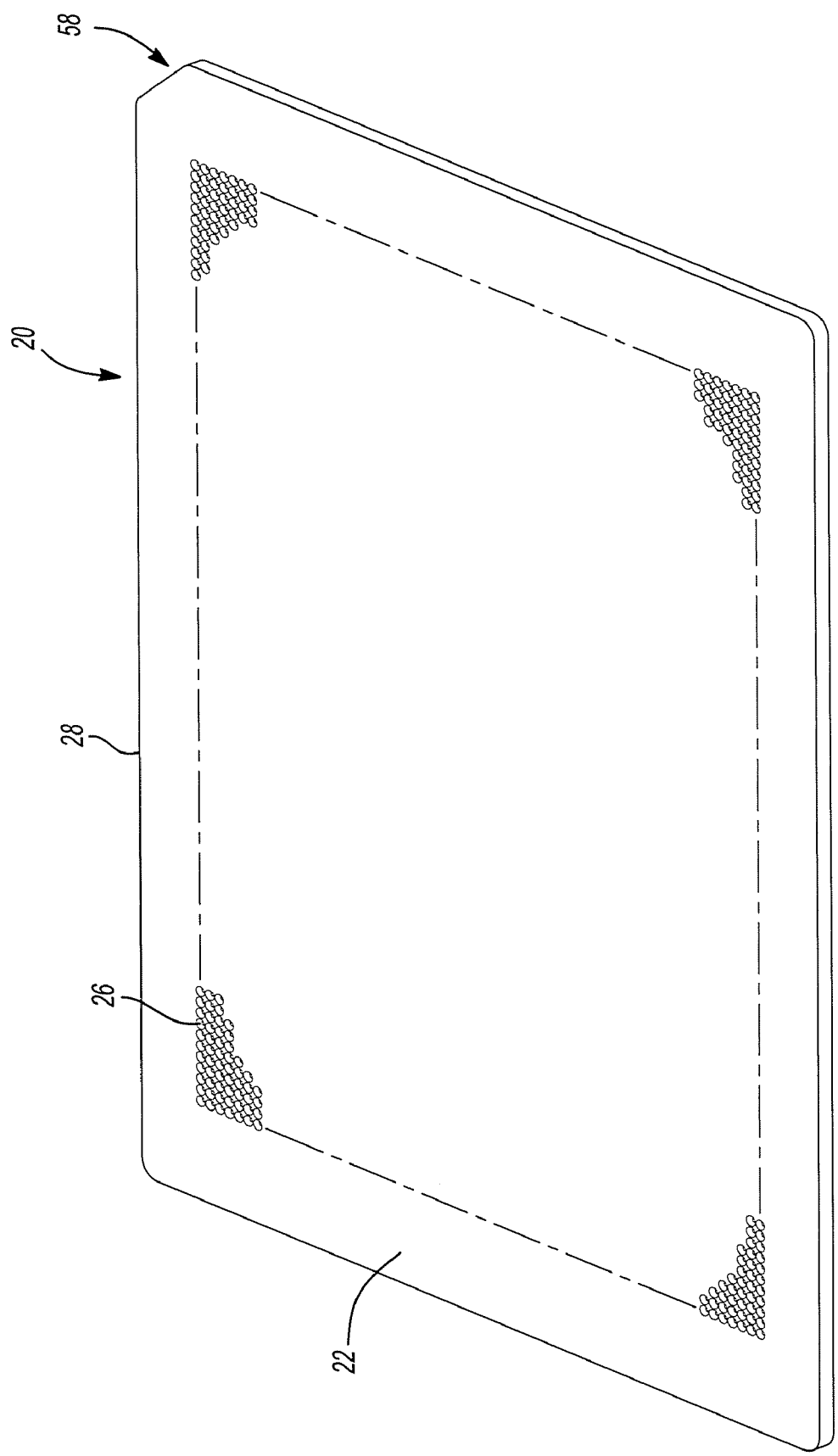
FIG. 3 is a top perspective view illustrating a microplate in accordance with some embodiments.
Figure 16:
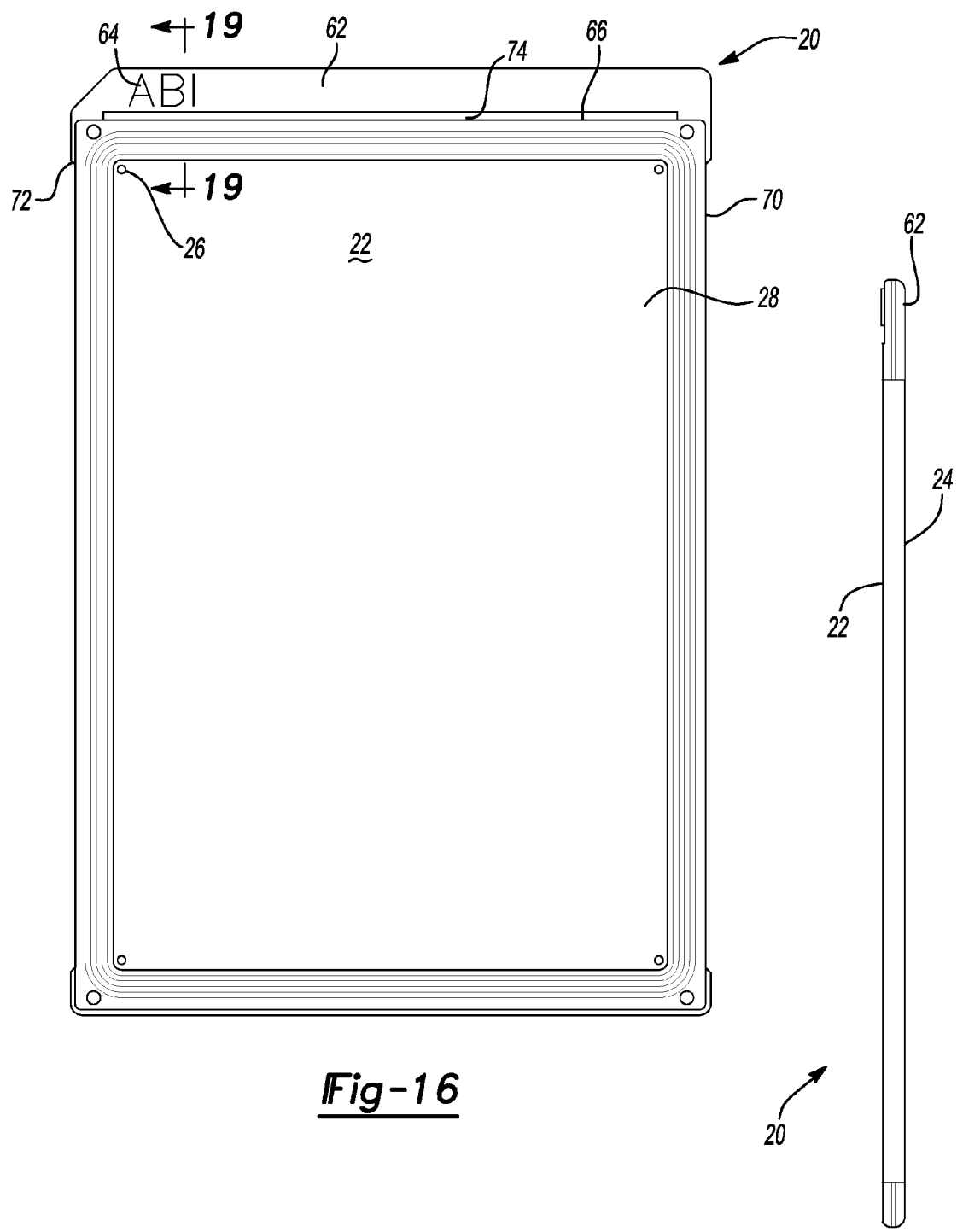
FIG. 16 is a top view illustrating a microplate in accordance with some embodiments comprising at least one thermally isolated portion.
Figure 17:
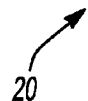
FIG. 17 is a side view illustrating the microplate of FIG. 16.
Figures 18, 19:
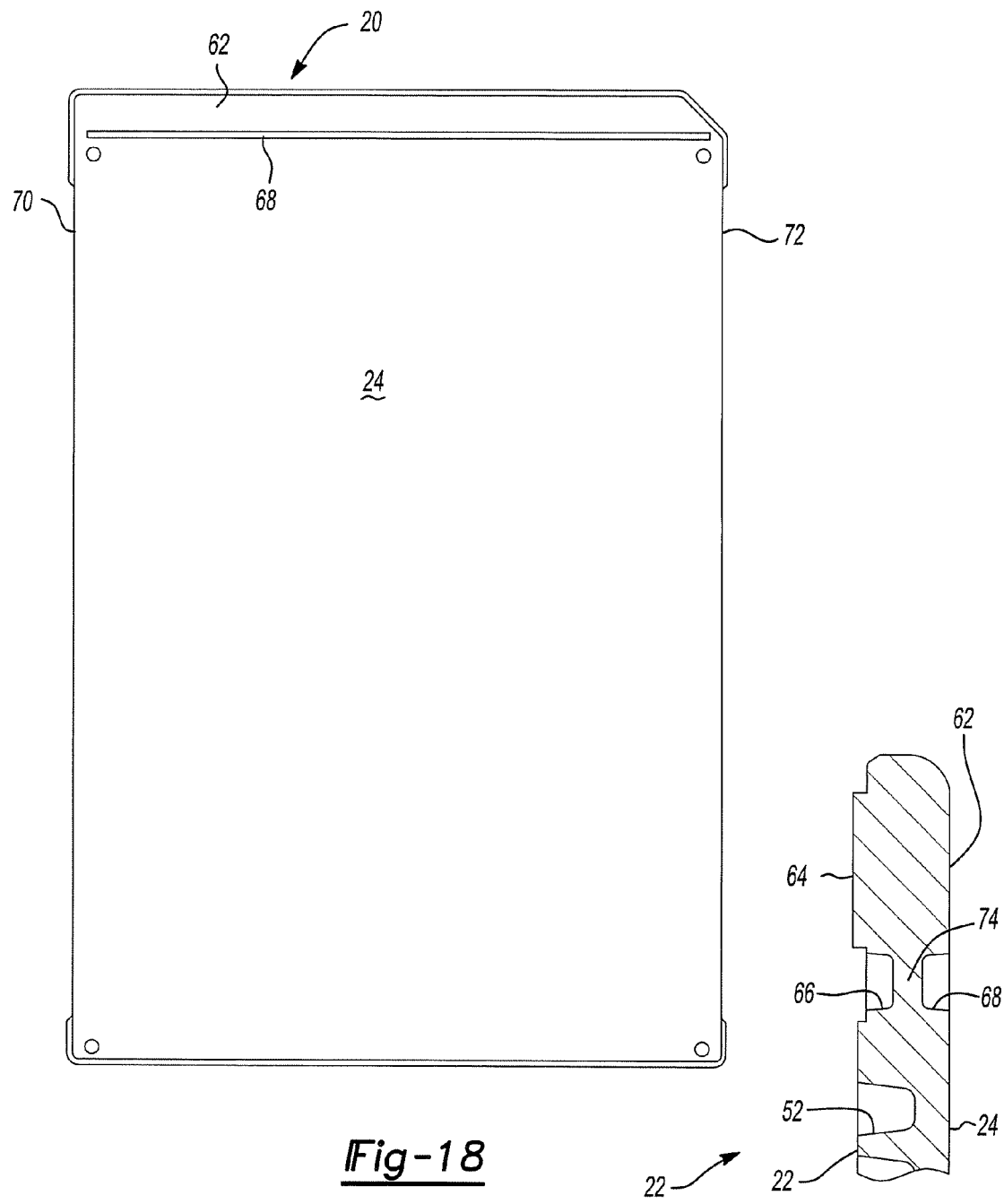
FIG. 18 is a bottom view illustrating the microplate of FIG. 16.
FIG. 19 is an enlarged cross-sectional view illustrating the microplate of FIG. 16 taken along Line 19-19.

In some embodiments, as illustrated in FIGS. 2, 16 and 17, microplate 20 comprises marking indicia 64, such as graphics, printing, lithograph, pictorial representations, symbols, bar codes, handwritings or any other type of writing, drawings, etchings, indentations, embossments or raised marks, machine readable codes (i.e. bar codes, etc.), text, logos, colors, and the like. In some embodiments, marking indicia 64 is permanent.

In some embodiments, marking indicia 64 can be printed upon microplate 20 using any known printing system, such as inkjet printing, pad printing, hot stamping, and the like. In some embodiments, such as those using a light-colored microplate 20, a dark ink can be used to create marking indicia 64 or vice versa.

In some embodiments, microplate 20 can be made of polypropylene and have a surface treatment applied thereto to facilitate applying marking indicia 64. In some embodiments, such surface treatment comprises flame treatment, corona treatment, treating with a surface primer, or acid washing. However, in some embodiments, a UV-curable ink can be used for printing on polypropylene microplates.

Still further, in some embodiments, marking indicia 64 can be printed upon microplate 20 using a $CO_2$ laser marking system. Laser marking systems evaporate material from a surface of microplate 20. Because $CO_2$ laser etching can produce reduced color changes of marking indicia 64 relative to the remaining portions of microplate 20, in some embodiments, a YAG laser system can be used to provide improved contrast and reduced material deformation.

In some embodiments, a laser activated pigment can be added to the material used to form microplate 20 to obtain improved contrast between marking indicia 64 and main body 28. In some embodiments, an antimony-doped tin oxide pigment can be used, which is easily dispersed in polymers and has marking speeds as high as 190 inches per second. Antimony-doped tin oxide pigments can absorb laser light and can convert laser energy to thermal energy in embodiments where indicia are created using a YAG laser.

In some embodiments, marking indicia 64 can identify microplates 20 to facilitate identification during processing.

Furthermore, in some embodiments, marking indicia 64 can facilitate data collection so that microplates 20 can be positively identified to properly correlate acquired data with the corresponding assay. Such marking indicia 64 can be employed as part of Good Laboratory Practices (GLP) and Good Manufacturing Practices (GMP), and can further, in some circumstances, reduce labor associated with manually applying adhesive labels, manually tracking microplates, and correlating data associated with a particular microplate.

In some embodiments, marking indicia 64 can assist in alignment by placing a symbol or other machine-readable graphic on microplate 20. An optical sensor or optical eye 1491 (FIG. 204) can detect marking indicia 64 and can determine a location of microplate 20. In some embodiments, such location of microplate 20 can then be adjusted to achieve a predetermined position using, for example, a drive system of high-density sequence detection system 10, sealing cover applicator 1100, or other corresponding systems.

In some embodiments, the type (physical properties, characteristics, etc.) of marking indicia employed on a microplate can be selected so as to reduce thermal and/or chemical interference during thermocycling relative to what might otherwise occur with other types of marking indicia (e.g., common prior indicia designs, such as adhesive labels). For example, adhesive labels can, in some circumstances, interfere (e.g., chemically interact) with one or more reagents (e.g., dyes) being used.

Referring to FIG. 2, in some embodiments, a radio frequency identification (RFID) tag 76 can be used to electronically identify microplate 20. RFID tag 76 can be attached or molded within microplate 20. An RFID reader (not illustrated) can be integrated into high-density sequence detection system 10 to automatically read a unique identification and/or data handling parameters of microplate 20. Further, RFID tag 76 does not require line-of-sight for readability. It should be appreciated that RFID tag 76 can be variously configured and used according to various techniques, such as those described in commonly-assigned U.S. patent application Ser. No. 11/086,069, entitled "SAMPLE CARRIER DEVICE INCORPORATING RADIO FREQUENCY IDENTIFICATION, AND METHOD" filed herewith.

Multi-Piece Construction

In some embodiments, such as illustrated in FIGS. 59-63, microplate 20 can comprise a multi-piece construction. In some embodiments, microplate 20 can comprise main body 28 and a separate cap portion 95 that can be connected with main body 28. In some embodiments, cap portion 95 can be sized and/or shaped to mate with main body 28 such that the combination thereof results in a footprint that conforms to the above-described SBS and/or ANSI standards. Alternatively, main body 28 and/or cap portion 95 can comprise non-standard dimensions, as desired.

Cap portion 95 can be coupled with main body 28 in a variety of ways. In some embodiments, cap portion 95 comprises a cavity 96 (FIG. 63), such as a mortis, sized and/or shaped to receive a support member 97, such as a tenon, extending from main body 28 to couple cap portion 95 with main body 28. In some embodiments, cavity 96 of cap portion 95 and support member 97 of main body 28 can comprise an interference fit or other locking feature, such as a hook member, to at least temporarily join main body 28 and cap portion 95 during assembly. In some embodiments, support member 97 of main body 28 can comprise a cap alignment feature 98 that can interface with a corresponding feature 99 on cap portion 95 to properly align cap portion 95 relative to main body 28. In some embodiments, cap portion 95 can comprise alignment feature 58 for use in later alignment of microplate 20 as described herein. In some embodiments, alignment feature 58 can be disposed on main body 28 to reduce tolerance buildup caused by the interface of cap portion 95 and main body 28.

In some embodiments, cap portion 95 can be formed directly on main body 28, such as through over-molding. In such embodiments, main body 28 can be placed within a mold cavity that generally closely conforms to main body 28 and defines a cap portion cavity generally surrounding support member 97 of main body 28. Over-molding material can then be introduced about support member 97 within cap portion cavity to form cap portion 95 thereon.

In some embodiments, cap portion 95 comprises marking indicia 64 on any surface(s) thereon (e.g. top surface, bottom surface, side surface). In some embodiments, cap portion 95 can comprise an enlarged print area thereon relative to embodiments employing first groove 66 (FIG. 16-19). In some embodiments, cap portion 95 can be made of a material different from main body 28. In some embodiments, cap portion 95 can be made of a material that is particularly conducive to a desired form of printing or marking, such as through laser marking. In some embodiments, a laser-activated pigment can be added to the material used to form cap portion 95 to obtain improved contrast between marking indicia 64 and cap portion 95. In some embodiments, an antimony-doped tin oxide pigment can be used. In some embodiments, cap portion 95 can be color-coded to aid in identifying a particular microplate relative to others.

In some embodiments, cap portion 95 can serve to provide a thermal isolation barrier through the interface of cavity member 96 and support member 97 to reduce any heat sink effect of cap portion 95 relative to main body 28 to maintain a generally consistent temperature cycle of the plurality of wells 26. Cap portion 95 can be made, for example, of a non-thermally conductive material, such as one or more of those set forth herein, to, at least in part, help to thermally isolate cap portion 95 from main body 28.

In some embodiments, cap portion 95 can serve to conceal any injection molding gates coupled to support member 97 during molding. During manufacturing, as such gates are removed from any product, aesthetic variations can result. Any such aesthetic variations in main body 28 can be concealed in some embodiments using cap portion 95. In some case, injection-molding gates can lead to a localized increase in flourescence. In some embodiments, such localized increase in flourescence can be reduced using cap portion 95.

Microplate Material

In some embodiments, microplate 20 can comprise, at least in part, a thermally conductive material. In some embodiments, a microplate, in accordance with the present teachings, can be molded, at least in part, of a thermally conductive material to define a cross-plane thermal conductivity of at least about 0.30 W/mK or, in some embodiments, at least about 0.58 W/mK. Such thermally conductive materials can provide a variety of benefits, such as, in some cases, improved heat distribution throughout microplate 20, so as to afford reliable and consistent heating and/or cooling of assay 1000. In some embodiments, this thermally conductive material comprises a plastic formulated for increased thermal conductivity. Such thermally conductive materials can comprise, for example and without limitation, at least one of polypropylene, polystyrene, polyethylene, polyethyleneterephthalate, styrene, acrylonitrile, cyclic polyolefin, syndiotactic polystyrene, polycarbonate, liquid crystal polymer, conductive fillers or plastic materials; and mixtures or combinations thereof. In some embodiments, such thermally conductive materials include those known to those skilled in the art with a melting point greater than about 130° C. For example, microplate 20 can be made of commercially available materials such as RTP199X104849, COOLPOLY E1201, or, in some embodiments, a mixture of about 80% RTP199X104849 and 20% polypropylene.

In embodiments, microplate 20 can comprise at least one carbon filler, such as carbon, graphite, impervious graphite, and mixtures or combinations thereof. In some cases, graphite has an advantage of being readily and cheaply available in a variety of shapes and sizes. One skilled in the art will recognize that impervious graphite can be non-porous and solvent-resistant. Progressively refined grades of graphite or impervious graphite can provide, in some cases, a more consistent thermal conductivity.

In some embodiments, one or more thermally conductive ceramic fillers can be used, at least in part, to form microplate 20. In some embodiments, the thermally conductive ceramic fillers can comprise boron nitrate, boron nitride, boron carbide, silicon nitride, aluminum nitride, and mixtures or combinations thereof.

In some embodiments, microplate 20 can comprise an inert thermally conductive coating. In some embodiments, such coatings can include metals or metal oxides, such as copper, nickel, steel, silver, platinum, gold, copper, iron, titanium, alumina, magnesium oxide, zinc oxide, titanium oxide, and mixtures thereof.

In some embodiments, microplate 20 comprises a mixture of a thermally conductive material and other materials, such as non-thermally conductive materials or insulators. In some embodiments, the non-thermally conductive material comprises glass, ceramic, silicon, standard plastic, or a plastic compound, such as a resin or polymer, and mixtures thereof to define a cross-plane thermal conductivity of below about 0.30 W/mK. In some embodiments, the thermally conductive material can be mixed with liquid crystal polymers (LCP), such as wholly aromatic polyesters, aromatic-aliphatic polyesters, wholly aromatic poly(ester-amides), aromatic-aliphatic poly(ester-amides), aromatic polyazomethines, aromatic polyester-carbonates, and mixtures thereof. In some embodiments, the composition of microplate 20 can comprise from about 30% to about 60%, or from about 38% to about 48% by weight, of the thermally conductive material.

The thermally conductive material and/or non-thermally conductive material can be in the form of, for example, powder particles, granular powder, whiskers, flakes, fibers, nanotubes, plates, rice, strands, hexagonal or spherical-like shapes, or any combination thereof. In some embodiments, the microplate comprises thermally conductive additives having different shapes to contribute to an overall thermal conductivity that is higher than any one of the individual additives alone.

In some embodiments, the thermally conductive material comprises a powder. In some embodiments, the particle size used herein can be between 0.10 micron and 300 microns. When mixed homogeneously with a resin in some embodiments, powders provide uniform (i.e. isotropic) thermal conductivity in all directions throughout the composition of the microplate.

As discussed above, in some embodiments, the thermally conductive material can be in the form of flakes. In some such embodiments, the flakes can be irregularly shaped particles produced by, for example, rough grinding to a desired mesh size or the size of mesh through which the flakes can pass. In some embodiments, the flake size can be between 1 micron and 200 microns. Homogenous compositions containing flakes can, in some cases, provide uniform thermal conductivity in all directions.

In some embodiments, the thermally conductive material can be in the form of fibers, also known as rods. Fibers can be described, among other ways, by their lengths and diameters. In some embodiments, the length of the fibers can be, for example, between 2 mm and 15 mm. The diameter of the fibers can be, for example, between 1 mm and 5 mm. Formulations that include fibers in the composition can, in some cases, have the benefit of reinforcing the resin for improved material strength.

In some embodiments, microplate 20 can comprise a material comprising additives to promote other desirable properties. In some embodiments, these additives can comprise flame-retardants, antioxidants, plasticizers, dispersing aids, marking additives, and mold-releasing agents. In some embodiments, such additives are biologically and/or chemically inert.

In some embodiments, microplate 20 comprises, at least in part, an electrically conductive material, which can improve reagent dispensing alignment. In this regard, electrically conductive material can reduce static build-up on microplate 20 so that the reagent droplets will not go astray during dispensing. In some embodiments, a voltage can be applied to microplate 20 to pull the reagent droplets into a predetermined position, particularly with a co-molded part where the bottom section can be electrically conductive and the sides of the plurality of wells 26 may not be electrically conductive. In some embodiments, a voltage field applied to the electrically conductive material under the well or wells of interest can pull assay 1000 into the appropriate wells.

In some embodiments, microplate 20 can be made, at least in part, of non-electrically conductive materials. In some embodiments, non-electrically conductive materials can at least in part comprise one or more of crystalline silica (3.0 W/mK), aluminum oxide (42 W/mK), diamond (2000 W/mK), aluminum nitride (150-220 W/mK), crystalline boron nitride (1300 W/mK), and silicon carbide (85 W/mK).

Microplate Molding

In some embodiments, microplate 20 can be molded by first extruding a melt blend comprising a mixture of a polymer and one or more thermally conductive materials and/or additives. In some embodiments, the polymer and thermally conductive additives can be fed into a twin-screw extruder using a gravimetric feeder to create a well-dispersed melt blend. In some embodiments, the extruded melt blend can be transferred through a water bath to cool the melt blend before being pelletized and dried. The pelletized melt blend can then be heated above its melting point by an injection molding machine and then injected into a mold cavity. The mold cavity can generally conform to a desired shape of microplate 20. In some embodiments, the injection-molding machine can cool the injected melt blend to create microplate 20. Finally, microplate 20 can be removed from the injection-molding machine.

In some embodiments, two or more material types of pellets can be mixed together and the combination then placed in the injection molding machine to be melt blended during the injection molding process. In some embodiments, microplate 20 can be molded by first receiving pellet material from a resin supplier; drying the pellet material in a resin dryer; transferring the dried pellet material with a vacuum system into a hopper of a mold press; molding microplate 20; trimming any resultant gates or flash; and packaging microplate 20. In some embodiments, the mold cavity can be centrally gated along the second surface 24 of microplate 20. In some embodiments, the mold cavity can be gated along a perimeter of main body 28 and/or skirt portion 30 of microplate 20.

Microplate Spotting, Filling, and Sealing

In some embodiments, one or more devices can be used to facilitate the placement of one or more components of assay 1000 within at least some of the plurality of wells 26 of microplate 20.

Microplate Spotting

In some embodiments, as illustrated in FIG. 57, microplate 20 can be preloaded with at least some component materials of assay 1000, such as reagents. In some embodiments, as described further herein, such reagents can comprise at least one primer and at least one detection probe. In some embodiments, such reagents can comprise elements facilitating analysis of a whole genome or a portion of a genome. Still further, in some embodiments, such reagents can comprise buffers and/or additives useful for coating, stability, enhanced rehydration, preservation, and/or enhanced dispensing of reagents.

In some embodiments, such reagents can be delivered (e.g. spotted) into at least one of the plurality of wells 26 of microplate 20 in very small, e.g. nanoliter, increments using a spotting device 700 (FIG. 8). In some embodiments, spotting device 700 employs one or more piezoelectric pumps, acoustic dispersion, liquid printers, micropiezo dispensers, or the like to deliver such reagents to each of the plurality of wells. In some embodiments, spotting device 700 employs an apparatus and method like or similar to that described in commonly assigned U.S. Pat. Nos. 6,296,702, 6,440,217, 6,579,367, and 6,849,127, issued to Vann et al.

According to some embodiments, in operation, as schematically illustrated in FIG. 57, reagents, e.g. in an aqueous form or bead form, can be stored on one or more storage plates 704 in a high-humidity storage unit 706. In some embodiments, high-humidity storage unit 706 can comprise a relative humidity in the range of about 70-100%. However, in some embodiments, high-humidity storage unit 706 can comprise a relative humidity in the range of about 70-85%. The bead form can be like or similar to that described in commonly assigned U.S. Pat. No. 6,432,719 to Vann et al. Some of the plurality of storage plates 704 can be moved out of high-humidity storage unit 706, as indicated by 708, and can be placed onto spotting device 700, as indicated by 710. A separate unspotted microplate 712 can then be moved out of a low-humidity storage unit 714, as indicated by 716. In some embodiments, low-humidity storage unit 714 can comprise a relative humidity in the range of about 0-30%. Unspotted microplate 712 can then be placed on spotting device 700, as indicated by 718. Reagents from storage plate 704 can then be spotted onto at least some of the plurality of wells 26 on unspotted microplate 712. Once at least some of the plurality of wells 26 are spotted, the spotted microplate 720 can then be moved from spotting device 700, as indicated by 722. Spotted microplate 720 can then be moved to an optional quality-control station 724, as indicated by 726. After quality-control station 724, spotted microplate 720 can then be moved back to low-humidity storage unit 714, as indicated by 728. This procedure of spotting microplates 20 can continue until a desired number (e.g. all) of microplates in storage unit 714 have been spotted with reagents from storage plate 704. It should be noted that unspotted microplate 712 and spotted microplate 720 are each similar to microplate 20, however different numerals are used for simplicity in the above description.

In some embodiments, the spots of reagents on spotted microplate 720 can be partially or fully dried down, as desired, in the low-humidity of storage unit 714. In some embodiments, storage unit 714 can also be heated to facilitate this drying. Once the microplates from storage unit 714 have been spotted with reagents from storage plate 704, storage plate 704 can be removed and designated as a used storage plate 730. Used storage plate 730 can be removed from spotting device 700 as indicated by 732. Used storage plate 730 can be returned to high-humidity storage unit 706 as indicated by 734. The process can continue as the next storage plate 704 is moved out of high-humidity storage unit 706 and into spotting device 700. In some embodiments, this next storage plate 704 can contain a different set of reagents. The aforementioned process can then be repeated, as desired. This process can continue until all of the plurality of wells 26 on spotted microplate 720 have been spotted or, in some cases, a portion of the plurality of wells 26 have been spotted, while leaving the remaining wells 26 empty.

It should be appreciated that this preloading process can vary as desired to accommodate user needs. For instance, in some embodiments, the reagents spotted in each of the plurality of wells 26 can be encapsulated with a material. Such encapsulation can prevent or reduce moisture at room temperature from interacting with the reagents. In some embodiments, each of the plurality of wells 26 can be spotted several times with reagents, such as for multiplex PCR. In some embodiments, these multiple spotted reagents can form layers. In some embodiments of this preloading process, primer sets and detection probes for a whole genome can be spotted from storage plates 704 onto spotted microplate 720. In other embodiments, a portion of a genome, or subsets of selected genes, can be spotted from source plates 704 onto spotted microplate 720.

In some embodiments, spotted microplate 720 can be sealed with a protective cover, stored, and/or shipped to another location. In some embodiments, the protective cover is releasable from spotted microplate 720 in one piece without leaving adhesive residue on spotted microplate 720. In some embodiments, the protective cover is visibly different (e.g., a different color) from sealing cover 80 to aid in visual identification and for ease of handling.

In some embodiments, the protective cover can be made of a material chosen to reduce static charge generation upon release from spotted microplate 720. When it is time for spotted microplate 720 to be used, the package seal can be broken and the protective cover can be removed from spotted microplate 720. In some embodiments, the protective cover can be a pierceable film, a slitted film, or a duckbilled closure to, at least in part, reduce contamination and/or evaporation. An analyte (such a biological sample comprising DNA) can then be added to spotted microplate 720, along with other materials such as PCR master mix, to form assay 1000 in at least some of the plurality of wells 26. Spotted microplate 720 can then be sealed with sealing cover 80 as described above. High-density sequence detection system 10 can then be actuated to collect and analyze data.

In some embodiments, the filling apparatus comprises a device for depositing (e.g., spotting or spraying) of assay 1000 to specific wells, wherein one or more of the plurality of wells 26 of microplate 20 contains a different assay material than other wells 26 of microplate 20. In some embodiments, the device can include piezoelectric pumps, acoustic dispersion, liquid printers, or the like. According to some embodiments, a pin spotter can be employed, such as described in PCT Publication No. WO 2004/018104. In some embodiments, a fiber and/or fiber-array spotter can be employed, such as described in U.S. Pat. No. 6,849,127.

In some embodiments, the filling apparatus comprises a device for depositing assay 1000 to a plurality of wells, wherein two or more wells contain the same assay material. In some embodiments, microplate 20 comprises two more groups of wells 26. Each of the groups of wells 26 can comprise a different assay material than at least one other group of wells 26 on microplate 20.

Loading Distribution System

Referring to FIG. 64, a loading distribution system 800 comprising a conveyer or a track 802 can be used to set up an expandable and flexible microplate loading distribution system. For example, FIG. 64 depicts four dispensing devices 814, 816, 818, and 820, disposed adjacent a corresponding source plate and wash station 814*a*, 816*a*, 818*a*, and 820*a*, respectively. Dispensing devices 814, 816, 818, and 820 can each comprise a plurality of dispensers, for example, 24-dispensers, 48-dispensers, 96-dispensers, 384-dispensers. FIG. 81 is a perspective view illustrating dispensing device 814 including a plurality of dispensers 868, for example, in a SBS standard micro-titer format. One or more of dispensing devices 814, 816, 818, and 820 can comprise, for example, the Aurora Scout MPD (MultiTip Piezo Dispenser) available from Aurora Discovery as, for example, a 96-tip dispensing device and/or a 384-tip dispensing device. In some embodiments, the dispensing device can comprise at least 96 dispensing tips in loading distribution system 800. The dispensing device can comprise, for example, at least 96 dispensing tips, at least 384 dispensing tips, at least 768 dispensing tips, at least 1536 dispensing tips, or more. The dispensing device can comprise a plurality of dispensers and each dispenser can comprise a piezo-electric dispenser. The dispensing device in loading distribution system 800 can comprise a plurality of dispensers and a respective plurality of storage reservoirs. Each dispenser can be designed to dispense a first volume of fluid per dispensing action, and each reservoir can be adapted to store many times the first volume, for example, at least 15 times the first volume, at least 25 times the first volume, at least 50 times the first volume, or at least 100 times the first volume.

In some embodiments, each of the plurality of dispensers can be adapted to dispense about 100 nanoliters of liquid or fluid, per dispensing action. The dispensing device can comprise a plurality of spotting devices. The dispensing devices can comprise, for example, piezo-electric devices, acoustic devices, ink-jet devices, pump-action devices, pin spotters, or the like, or a combination thereof.

In some embodiments, the number of dispensing devices 814, 816, 818, and 820 disposed around a conveyer 802 can be increased or decreased so as to address a desired throughput target. In some embodiments, conveyer 802 can expand (be lengthened) in an X-direction. This can allow more dispensing devices to be disposed around conveyer 802. Conveyer 802 can comprise a track, for example, SuperTrak™ available from ATS Automation Tooling Systems Inc. However, it should be understood that other tracks can be used.

In some embodiments, loading distribution system 800 can comprise a load position 806 on conveyer 802. Loading distribution system 800 can comprise an unload position 808 on conveyer 802. Load position 806 and unload position 808 can, according to some embodiments, be a same position along conveyer 802.

The plurality of stations can also include, for example, one or more of an inspection station, a plurality of inspection stations, a tracking station, an identifying tag reader station, or the like, as further described herein. According to some embodiments and as further described below, the table described herein can comprise a plurality of tables, with the number of tables, and corresponding carriages if used, being greater than or equal to the number of processing stations. In some embodiments, the plurality of processing stations in loading distribution system 800 can comprise an inspection station adapted to check an alignment of a microplate on the table. The inspection station can comprise, for example, one or more of a camera, a CCD, a laser, a pattern analyzer, an edge analyzer, and a combination thereof. The plurality of processing stations can comprise, for example, an inspection station adapted to perform a quality control analysis of a spot disposed on the microplate, wherein the inspection station can comprise, for example, one or more of a camera, a CCD, a laser, a pattern analyzer, an edge analyzer, and a combination thereof. In some embodiments, loading distribution system 800 can further comprise, for example, a tracking device adapted to track dispensation of fluid from the dispensing device. The tracking device can track a microplate and be adapted to determine whether and which locations of a microplate have been processed, spotted, or otherwise prepared. The tracking device can, in some embodiments, be adapted to track the use of components of an assay. The tracking device can be adapted, for example, to communicate with an identifying tag reader or with an identifying tag to track the progress of a preparation procedure, for example, to track loading and/or spotting operations at each of many loading and/or spotting sites. The tracking device can be adapted to communicate with machine indicia reader 804 and inspection station 810 illustrated in FIG. 64. In some embodiments, a dispensing device can comprise a plurality of dispensing devices and the tracking device can be adapted to track dispensation of fluids from each of the dispensing devices to a microplate. Methods of tracking are further discussed in more detail below.

In some embodiments, the plurality of processing stations can comprise a tracking station, for example, an identifying tag reader station adapted to read marking indicia 64 disposed on or in microplate 20. The identifying tag can be a bar code, a two-dimensional barcode, or other marking indicia reader station adapted to read the identifying tag. The reader station can comprise a reader device or apparatus appropriate to the type of marking indicia employed, e.g., a bar code reader. The identifying tag can, in some embodiments, be a radio frequency identification (RFID) tag and the reader station can comprise a RFID reader. In some embodiments, a marking indicia reader station in loading distribution system 800 can comprise one or more of a bar code reader, a one-dimensional bar code reader, a two-dimensional bar code reader, and an RFID reader. In some embodiments, a marking indicia reader station in loading distribution system 800 can be adapted to read marking indicia on the same surface of the microplate that can engage the table when the microplate is on the table.

In some embodiments, loading distribution system 800 can comprise a machine indicia reader 804 disposed along conveyer 802. Machine indicia reader 804 can, according to some embodiments, comprise a plurality of machine indicia readers, one each disposed prior to every dispensing device along conveyer 802. In some embodiments, machine indicia reader 804 can be disposed past load position 806 along conveyer 802.

In some embodiments, a method of tracking a microplate is provided. The method can comprise, for example, a first dispensing operation that comprises spotting components of an assay to one or more locations or material retention regions of a microplate, for example, one or more wells of a multiwell microplate, to form a partially loaded microplate. Each well can be spotted with a different set of components of a different respective assay. The method can comprise storing information about the at least partially loaded microplate by writing information into a memory using a value of the machine-readable identifier as an index. The method can comprise storing information about the at least partially loaded microplate by writing information into a memory that is addressable by a value associated with the machine-readable identifier. The stored information can comprise information pertaining to the wells and which wells have been spotted and with what respective components of an assay. By tracking such information, subsequent dispensing operations can be directed to wells that have not been spotted and assay components that have not yet been spotted into respective wells.

In some embodiments, the method of tracking can comprise subjecting a microplate to two or more, for example, five or more, dispensing operations and to two or more, for example, five or more, information reading steps with at least one information reading step being conducted prior to or subsequent to each dispensing operation. According to some embodiments, the method of tracking can comprise a reading step followed by a plurality of dispensing operations at a respective plurality of dispensing stations. The method can comprise storing information about the at least partially loaded microplate by writing information to the radio frequency identification tag. The method can comprise: reading information from a machine-readable identifier on a microplate; subjecting the microplate to a first dispensing operation by a first multi-tip dispenser to at least partially load one or more material retention regions of the microplate and form an at least partially loaded microplate; storing information about the at least partially loaded microplate; reading the information stored about the at least partially loaded microplate; and determining, based on the information read about the at least partially loaded microplate, whether to subject the microplate to a subsequent dispensing operation by second multi-tip dispenser that differs from the first multi-tip dispenser. The determining can comprise determining that the at least partially loaded microplate should be subjected to a subsequent dispensing operation, and the method can then further comprise subjecting the microplate to an additional dispensing operation by the second multi-tip dispenser, to further load the microplate.

The method of tracking can be used in connection with a system comprising a first multi-tip dispenser located at a first station, a second multi-tip dispenser located at a second station, and a conveyer device connecting the two stations. The method can comprise conveying the microplate from the first station to the second station, along, on, or with, the conveyer device. The conveyer device can comprise, for example, a track and/or a belt or chain. The conveyer device illustrated in FIGS. 64 and 65 comprises a track along which a carriage and table can ride or traverse.

The method of tracking can comprise, for example, reading the information stored about the at least partially loaded microplate by reading the information at a third station. The third station can be located between the first station and the second station, along the conveyer device, or it can be located upstream or downstream of both the first and second stations. The first station and the second station can be located adjacent each other along a track and the method can comprise disposing the microplate on a carriage and conveying the carriage along the track from the first station to the second station.

In some embodiments, and as described further below, a system controller 982 (FIG. 101) can manage and track microplates at various locations. Locations for a microplate can comprise, for example, in one or more plate storage units, in or on one or more tables, or in one or more jaws of one or more plate handling devices. In some embodiments, system controller 982 (FIG. 101) can, for example, manage and track microplates at various locations in loading distribution system 800 (FIGS. 64 and 65). Locations for a microplate can comprise, for example, in one or more plate storage units, in or on one or more tables, or in one or more jaws of one or more plate handling devices. In some embodiments, system controller 982 (FIG. 101) can, for example, manage and track source plates at various locations in loading distribution system 800 (FIGS. 64 and 65). Locations for a source plate can comprise, for example, in a source plate storage unit like an incubator, in one or more source plate holders, or in one or more grippers of one or more source plate handling devices. System controller 982 described below with reference to FIG. 101 can also, for example, track and trace the contents of one or more dispensers, each disposed in one or more respective dispensing devices. For example, system controller 982 can track and trace the contents of one or more dispensers, each disposed in one or more respective dispensing devices.

With reference to the perspective views of FIGS. 64 and 65, a number of the above-described features of the present teachings can be seen embodied in a high-throughput system for fabricating a microplate. Generally, conveyer 802 transports, in serial fashion, empty microplates from a hotel or storage unit 828 to a position adjacent a load position 806. Handling device 830 places the microplate on a table and carriage assembly for movement along conveyer 802. The microplate is then moved by the table and carriage assembly along conveyer 802 to machine indicia reader 804. The method of tracking can comprise scanning indicia on the bottom of the microplate. This operation can serve, for example, to ensure that the card has been properly placed on the table and to read identifying information into a control computer (not illustrated). Next, the table translates the microplate to dispensing stations 820, 818, 816, 814, serially, for spotting operations.

Having received components of an assay from the dispensing stations, the microplate can then be advanced to a position below an inspection station 810 that inspects each well of the microplate for the presence of spotted components of an assay. If the inspection operations indicate that the microplate has been properly loaded with components of an assay, the microplate is then moved along conveyer 802 to an unload position 808 where the microplate can be unloaded, for example, by handling device 830, and moved back to the storage unit 828. If a failure is indicated, on the other hand, unloading at unload position 808 can comprise depositing the microplate in a reject bin.

In a subsequent operation, for example, after a new set of respective assay components has been aspirated or loaded in dispensing heads of dispensing stations 820, 818, 816, and 814, a partially loaded microplate can again be moved by handling device 830 onto a table of a carriage on conveyer 802, and then conveyed again to machine indicia reader 804. The method of tracking can then comprise reading information stored about the microplate as a result of previous quality control inspection at inspection station 810 and indexed by marking indicia on the microplate. If further spotting of assay components is required, the microplate can then be conveyed to dispensing stations 820, 818, 816, 814 for further dispensing operations, this time with the newly-loaded assay components. After the further dispensing operations, the procedure can be repeated, starting, for example, with another quality control inspection at inspection station 810. Stored information corresponding to a marking indicia can be compared to predetermined values to determine whether additional spotting is needed or whether the microplate has been completely spotted with all desired assay components.

According to some embodiments, the method of tracking can use a control computer (not illustrated) that can integrate the operation of the various assemblies, for example through a program written in an event driven language such as LABVIEW.RTM. or LABWINDOWS.RTM. (National Instruments Corp., Austin, Tex.). In particular, the LABVIEW software provides a high level graphical programming environment for controlling instruments. U.S. Pat. Nos. 4,901,221; 4,914,568; 5,291,587; 5,301,301; 5,301,336; and 5,481,741 (each expressly incorporated herein in its entirety by reference) disclose various aspects of the LABVIEW graphical programming and development system. The graphical programming environment disclosed in these patents allows a user to define programs or routines by block diagrams, or "virtual instruments." As this is done, machine language instructions are automatically constructed which characterize an execution procedure corresponding to the displayed procedure. Interface cards for communicating the computer with the motor controllers are also available commercially, for example, from National Instruments Corp.

In some embodiments, loading distribution system 800 can comprise an inspection station 810 disposed along conveyer 802. Inspection station 810 can comprise, according to some embodiments, a plurality of inspection stations, one disposed after each dispensing device along conveyer 802. In some embodiments, a single inspection station 810 can be disposed after all the dispensing devices along conveyer 802.

In some embodiments, loading distribution system 800 can comprise a plate-handling device 830 disposed on a plate-handling device pathway 832 to access a storage unit 828 adapted to store microplates. Storage unit 828 can also be called a hotel. Loading distribution system 800 can comprise a source plate-handling device 822. Source plate-handling device 822 can be disposed on a source plate-handling device pathway 824 to access a source plate storage unit 826 housing a plurality of source plates (not illustrated). Source plate storage unit 826 can comprise an incubator, for example, Kendro Cytomat 6001 available from Kendro Laboratory Products. Storage unit 828 can comprise a hotel, for example, one or more 120 Nest Landscape Carousels. Plate-handling device 830 and source plate-handling device 822 can each comprise a Select Compliant Articulated Robot Arm (SCARA) robot, respectively, available, for example, from IAI America, Inc. The SCARA robots can be movable in 4-axis or 5-axis. However, it should be understood that other robot mechanisms can be used.

In some embodiments, loading distribution system 800 can comprise a storage unit 828. Storage unit 828 can comprise a hotel, a carousel, or another rack adapted to hold a plurality of microplates. In some embodiments, storage unit 828 can be accessible by the plate-handling device so that the plate-handling device can retrieve microplates, for example, one at a time, or store microplates therein, for example, one at a time. Loading distribution system 800 can further comprise a plurality of microplates arranged in the storage unit.

As illustrated in FIG. 65, in some embodiments, dispensing devices 814, 816, 818, and 820 can be disposed along conveyer 802 using a respective dispensing device mount 814c, 816c, 818c, and 820c. Each dispensing device 814, 816, 818, and 820 can be disposed, for example, adjacent a respective alignment station 814b, 816b, 818b, and 820b. Alignment stations 814b, 816b, 818b, and 820b can be adapted to move a table (not illustrated) in a Y-direction.

In some embodiments, when an alignment station is not provided to move a table in the Y-direction, a dispensing device can be moved in the Y-direction to align a microplate disposed on the table with the dispensing device.

As illustrated in FIG. 66, in some embodiments, dispensing device 814 can comprise a plurality of dispensers 868. A carriage 874 can be disposed on conveyer 802. Carriage 874 can be positioned under dispensers 868, when dispensing of a fluid in or on microplate 20 is desired. Microplate 20 can be disposed on a table 872. Table 872 can comprise a vacuum chuck; see FIG. 80, adapted to hold microplate 20. Table 872 can move to align microplate with dispensers 868. Conveyer 802 can translate carriage 874 away from the dispensing position. Carriage 874 can move along conveyer 802.

In some embodiments, table 872 can be adapted to move along the Y-axis and the alignment stage can be adapted to align the microplate with the dispensing device. Table 872 can be adapted to be rotatable about the Y-axis direction. As described herein, table 872 can comprise a vacuum chuck adapted to apply a vacuum to a surface of a microplate when a microplate is disposed on the table. Loading distribution system 800 can comprise a vacuum source in fluid communication with the vacuum chuck. A vacuum retainment valve can be disposed in fluid communication with the vacuum chuck and can be adapted to maintain a vacuum between the vacuum chuck and the surface of a microplate when a microplate is disposed on the table, for example, when the vacuum chuck is not in fluid communication with the vacuum source. Loading distribution system 800 can comprise a vacuum detector adapted to verify the formation of a vacuum between the surface of a microplate disposed on the table, and the vacuum chuck.

In some embodiments, loading distribution system 800 can further comprise an accessory carriage configured to engage a source plate comprising a source of fluids to be loaded into the spotting or other dispensing station. The accessory carriage can be adapted to move the source plate to the dispensing station for aspiration of the fluids from the source plate into the dispensing device. Loading distribution system 800 can further comprise an incubator adapted to store the source plate, for example, to keep it in a cooler and more humid environment relative to the immediately surrounding atmosphere. Loading distribution system 800 can comprise a source plate-handling device adapted to translate a source plate from the incubator to the dispensing station. The incubator can comprise a de-lidder adapted to remove a lid from a source plate in loading distribution system 800. The de-lidder in loading distribution system 800 can further be adapted to place a lid on a source plate.

In some embodiments, when carriage 874 is not positioned beneath dispensing device 814, a source plate and wash pallet 864 can be positioned under dispensing device 814. As illustrated in FIG. 91, source plate and wash pallet 864 can comprise a washing tray 861 and a source plate holder 863. Source plate-handling device 822 can pick-up and deposit a source plate 862 from source plate holder 863 using a gripper 823. Source plate 862 can be covered using a lid 860. Lid 860 can be placed on source plate 862 by a de-lidder 858. De-lidder 858 can comprise a lifting device 856 adapted to lift and hold lid 860. Source plate and wash pallet 864 can be disposed on an elevator mechanism (not illustrated) to move source plate and wash pallet 864 within range of dispensers 868. Source plate and wash pallet 864 can be in a rest position or a washing position. While in a rest position, washing tray 861 can be covered using a dust cover 866. Dust cover 866 can be hinged. In some embodiments, loading distribution system 800 can further comprise a plurality of source plates in the incubator, wherein the dispensing device comprises a plurality of multi-tip dispensing heads, and the source plate handling device can be adapted to translate one or more of the plurality of source plates from the incubator to each of the plurality of multi-tip dispensing heads.

In FIG. 66(b), a washing tray can be disposed on a washing tray pallet 865' adapted to elevate the washing tray under dispensers 868' of a dispensing device 814'. A source plate 862' can be disposed on a source plate pallet 864' that can be positioned under dispensing device 814'. Source plate-handling device 822' can comprise dual end effectors to pick-up and deposit a source plate 862' on source plate pallet 864'.

As illustrated in FIGS. 68(a)-(c), source plate and wash pallet 864 can comprise washing tray 861 and holding source plate 862. As illustrated in FIGS. 68(a)-(c) a dispensing device can comprise 96-fixed dispensers. FIG. 68(a) illustrates an internal dispenser wash. Dispensers 868 can be immersed in a fluid disposed in internal wash slots 878. FIG. 68(b) illustrates an external dispenser wash. Dispensers 868 can be immersed in a fluid disposed in external wash slots 876. FIG. 68(c) illustrates aspiration by dispensers 868. The illustration depicts 96-dispensers into a 384-well source plate. Each respective dispenser can be illustrated disposed in every other well along every row and every column. In some embodiments, each dispensing device can be adapted to be loaded by aspirating fluid from a fluid source. The fluid source can be disposed in loading distribution system 800, for example, in the storage unit or in a separate, second storage unit. Each storage unit can comprise an incubator.

As illustrated in FIG. 69, a ceiling mounted plate-handling device 830 can be adapted to retrieve microplate 20 from a plate storage unit 828. Plate-handling device 830 can pick-up and remove microplate 20 from a table 872. Table 872 can be moved along a conveyer 802. The ceiling mount configuration can provide for an unobstructed range of motion by plate-handling device 830. The ceiling mount configuration can provide clearance for an arm of plate-handling device 830. Plate storage unit 828 can be adapted to translate racks of microplates allowing plate-handling device 830 to access microplates 20 stacked in each rack of plate storage unit 828. Plate storage unit 828 can provide environmental control. Plate storage unit 828 can be designed for mobility. Plate storage unit 828 can be designed for off-line operator loading and unloading. Microplates 20 can be stored in plate storage unit 828 in a landscape orientation with respect to conveyer 802. Microplates 20 can be stored in plate storage unit 828 in a portrait orientation with respect to conveyer 802.

In some embodiments, an interval required to unload and reload a microplate from loading distribution system 800 can be a rate-limiting factor when determining throughput of loading distribution system 800. A plate gripper, automated and robotic, in combination with a carriage adapted to allow simultaneous or substantially simultaneous, unloading and reloading of microplates on the carriage, in a minimum amount of time, can be provided.

Referring now to FIG. 70, a carriage 874 comprising a table 872 is illustrated. Microplate 20 can be disposed on table 872. Carriage 874 can comprise locating pins 882a, 882b, and 882c disposed on table 872. A ratchet 888 can be disposed on table 872. As illustrated in FIG. 72, ratchet 888 can be spring-loaded by a spring 910. When microplate 20 is disposed on table 872, spring 910 can secure microplate 20 against locating pins 882a, 882b, and 882c. Spring 910 can be automated. Spring 910 can be actuated and/or released by a manufacturing control system. Spring 910 can be used to position microplate 20 on table 872, allowing stations disposed along conveyer 902 to be correctly oriented. A self-conveyance device 909 can propel carriage 874 around conveyer 802 (not illustrated). In some embodiments, loading distribution system 800 can further comprise a conveyer on which or with which the table and/or the alignment stage can be moved or translated. Loading distribution system 800 can comprise a carriage, for example, that can ride on, along, and/or with the conveyer. The carriage can be adapted to be translated to one or more of the plurality of processing stations. The carriage can be adapted to translate the table along the conveyer to one or more of the plurality of processing stations.

According to some embodiments, table 872 can comprise a plurality of tables and the carriage can comprise a plurality of carriages each respectively adapted to translate one or more of the plurality of tables. Each carriage can comprise a self-conveyance device, for example, a translation motor or servomotor, and the plurality of carriages can be disposed on or along a conveyer. In some embodiments, each of the plurality of carriages can comprise a plurality of automated actuators and a self-conveyance device, for example, wherein the self-conveyance device can comprise a conduit for transferring control signals to the plurality of automated actuators. The conveyer can comprise a track, for example, in the form of a circle, oval, or other loop. The loop can be endless.

In some embodiments, loading distribution system 800 can be adapted to convey the table along the X-axis direction. The conveyance can be repeatably positionable to within about 100 micrometers of a predefined location. A conveyer can be used that serially translates one or more of a plurality of tables, for example, with each table being disposed on a respective carriage. The plurality of tables can be translated, for example, consecutively translated, to each of the plurality of processing stations.

In some embodiments, a vacuum line supply 890 can provide communication from table 872 to a bellows 896. Bellows 896 can communicate with a vacuum connection shoe 907.

In some embodiments, carriage 874 can comprise a mechanism to lift or raise a first microplate, allowing a second microplate to be placed under the first microplate. Carriage 874 that transports microplate 20 between stations of loading distribution system 800 can comprise a set of grippers comprising a first cam 884 and a second cam 886, which can hold up microplate 20 without microplate 20 resting on table 872 of carriage 874. First cam 884 and second cam 886 can be pivotally attached to self-conveyance device 909. Table 872 of carriage 874 can move up and down vertically. The normal resting position of table 872 can be at a midpoint of travel for table 872, rather than a bottom point of travel for table 872. Table 872 normally rests on a spring plunger 902 via a pin 898. Table 872 can be lifted off spring plunger 902 for an upward motion. Table 872 can be forced down, in a downward motion, and depress pin 892 into spring plunger 902. The downward motion can allow first cam 884 and second cam 886 to grab microplate 20 on table 872 and lift microplate 20 up off a surface of table 872.

In some embodiments, rollers 894 and 892 can be attached to first cam 884 and second cam 886, respectively. A tripod 901 can be disposed in a linear bearing 904. Linear bearing 904 can be disposed vertically. A travel of tripod 901 can raise and/or lower table 872. A roller 906 can be attached to tripod 901.

FIG. 71 illustrates a spring 908 that holds table 872 of carriage 874 against one corner.

FIG. 73 illustrates a sectioned view of spring plunger 902 that holds table 872 (not illustrated) at an intermediate position in the Z-axis. Table 872 can be lifted off pin 898 to raise table 872 for dispensing or spring 912 can be overpowered to depress table 872 for microplate swapping operation as described herein.

FIG. 74 is a perspective view illustrating an embodiment of a pressure source 918 adapted to communicate with vacuum connection shoe 907. Vacuum connection shoe 907 can comprise a port 920 on the opposite side that can engage with a vacuum supply port 916 disposed in a frame 914 attached to conveyer 902. Bellows 896, or other means known in the art, can allow a flexible connection between vacuum connection shoe 907 and table 872 that can move up and down, and shift sideways.

In FIG. 74, vacuum connection shoe 907 can be disposed next to vacuum port 916 on frame 914. When a carriage is at a station, for example, a loading station, or a dispensing device station, a valve (not illustrated) opens where vacuum port 916 is disposed on frame 914. A vacuum retainment valve (not illustrated) can be disposed on carriage 874 along bellow 896 or vacuum line supply 890.

In some embodiments, vacuum connection shoe 907 can be elongated so that a vacuum connection is established before table 872 can reach the stop position at a station. This elongated vacuum connection shoe can make a significant difference in cycle time, as a final deceleration prior to stopping a carriage at a station can be a large part of total transit time for a carriage.

FIGS. 75 and 76 illustrate cam rails 922, 924 and a slotted rail 926 comprising a slot 930 for vertical motion of first cam 884 and second cam 886 and tripod 901, respectively. Cam rails 922, 924 can be attached to conveyer 802. Cam rails 922, 924 can control the timing of first cam 884 and second cam 886 when performing a grip operation. Slotted rail 926 can control a drop operation of table 872. The two operations can occur automatically during the motion of carriage 874. The two operations can occur simultaneously or substantially simultaneously. Carriage 874 transfer speed can take into consideration a use of cam rails 922, 924 and slotted rail 926. First cam 884 and second cam 886 can be fixed to carriage 874. When a station, for example, a dispensing device station, needs a final registration of microplate 20, table 872 can float relative to carriage 874. Table 872 need not float relative to carriage 874 at some stations, for example, a load station or an unload station.

Slotted rail 926 that controls the Z-axis movement of table 872 can be fixed to conveyer 802. Cam rails 922, 924 can be mounted to an air-operated slide 921. Air-operated slide 921 can be attached to slotted rail 926. When carriage 874 approaches cam rails 922, 924, table 872 can be floating at a midpoint, and first cam 884 and second cam 886 can be open. Cam rails 922, 924 can be elevated when carriage 874 approaches a station. Cam rails 922, 924 can be rising up, for example, by activating air-operated glide 921, to meet carriage 874 as it enters a station as long as cam rails 922, 924 are in position when roller 906, a Z-axis control roller, engages with slotted rail 926. When roller 906 enters slot 930, tripod 901 can drop. As table 872 rests on tripod 901, table 872 can drop down with tripod 901. Prior to dropping tripod 901, rollers 894 and 892 can engage cam rails 922, 924. As rollers 894 and 892 rise on a ramp of cam rails 922, 924, first cam 884 and second cam 886 attached to rollers 894 and 892, respectively, close and grip microplate 20. As a ramp of cam rails 922, 924 continues to rise, first cam 884 and second cam 886 can lift microplate 20 off table 872. When a release of a gripped microplate is desired, first cam 884 and second cam 886 can be dropped, by lowering air-operated slide 921 that in turn lowers cam rails 922, 924. The lowering of cam rails 922, 924 can disengage rollers 894 and 892 from cam rails 922, 924, which in turn can open first cam 884 and second cam 886 releasing a gripped microplate 20. The release can performed when, for example, a plate gripper robot 784 is ready to remove a microplate. Plate gripper robot 784 is illustrated in FIGS. 82-90 described below.

FIG. 77 is a perspective view illustrating an embodiment of a loading distribution system comprising carriage 874, table 872, and an alignment stage 932. Alignment stage 932 can be disposed under a dispensing device mount 931. A dispensing device (not illustrated) can be attached to dispensing device mount 930. Table 872 of carriage 874 can engage with alignment stage 932 when carriage 874 lifts. A set of actuators 934, 936 engages with three points on table 872 after carriage 874 enters a dispensing station and table 872 has been raised. Alignment stage 932 can comprise a long stroke actuator 935 for the X-axis since microplate 20 disposed on table 872 can index over a substantial distance for some kinds of dispensing, for example, dispensing of fluids for Focused Genome dispensing. The X-axis carries two short stroke Y-axis actuators 934, 936. The Y-axis actuators 934, 936 can operate independently from each other to compensate for skew.

In some embodiments, loading distribution system 800 can comprise the table, the alignment stage, and a plurality of processing stations. The table can be configured to engage at least one of a plurality of microplates and be movable at least in an X-axis direction. The table can be moved together with a carriage that in-turn can be adapted to move in the X-axis direction. The an alignment stage can be configured to move the table and/or carriage at least in a Y-axis direction that differs from the X-axis direction, for example, that can be perpendicular or at least substantially perpendicular, to the X-axis direction. In some embodiments, substantially perpendicular can mean within about 15 degrees of being perpendicular. The plurality of processing stations can comprise at least one or more dispensing stations and a plate-handling station. Each of the one or more dispensing stations can comprise a dispensing device adapted to dispense fluid into or onto one or more of a plurality of microplates. The plate-handling station can comprise a plate-handling device. The plate-handling device can be adapted to selectively pick up and deposit on the table individual microplates from a plurality of microplates, at least one at a time. In an exemplary embodiment, loading distribution system 800 can further comprise a microplate disposed on the table, wherein the dispensing device comprises at least 24 or more dispensers, and the microplate comprises 768 or more wells, for example, 96 or 384 dispensers and 6,144 wells.

In some embodiments, alignment stage 932 works in cooperation with locating pins 882a, 882b, and 882c. A location of microplate 20 can be offset in varying degrees from the center of dispensing device 814 to satisfy a need to interleave subsets of dot patterns or dispensing locations, and to form stripe pattern offsets for Focused Genome dispensing. A system requiring operator intervention to mechanically align dispensing device 814 with the independent axes of motion, for example, X, Y, and Z-axis, can be very difficult to maintain. In some embodiments, loading distribution system 800 can work without a need for precision alignment by an operator after maintenance on loading distribution system 800 has been performed. Alignment stage 932 can be enhanced with a vision system based adaptive alignment system. A camera (not illustrated) can form an image of microplate 20. The image can be processed to derive X, Y, and/or Z movement specifications for alignment stage 932. Table 872 can comprise reference markings (not illustrated) to determine offsets needed to compute the movement specifications.

FIG. 78 is a perspective view illustrating an embodiment of a lifting stage 940 adapted to lift carriage 874 in the Z-axis. A motorized slide 938 moves a block 941 with a slot in block 941, lifting carriage 874 up and down. Roller 906 that controls the Z-axis engages with a slot in block 941 to move table 872 of carriage 874 up for dispensing. Lifting stage 940 can be disposed underneath a dispensing device to allow a Z-direction movement of carriage 874.

FIG. 79(a) and FIG. 79(b) are perspective views illustrating two visual inspection station, according to some embodiments. The visual inspection stations can provide an ability to compensate for a large number of potential errors, assist in quality control, and alignment of microplates.

FIG. 79(a) illustrates a full scan vision station disposed on conveyer 802. The full scan vision station can perform a full scan of microplate 20 disposed of table 872. A camera mount 941 can extend from conveyer 802 to position a camera 947 over microplate 20 as it moves around conveyer 802. A carriage alignment device 945 can engage and properly align table 872 with camera 947. Carriage alignment device 945 can be a mechanical device to push table 872 into a fixed position by contacting three points on a perimeter of table 872. This can eliminate servo errors to provide a consistent reference measurement. Carriage alignment device 945 can retract from above conveyer 802, thus disengaging table 872 from the full scan vision station. Carriage 874 can be docked at a station where camera 947 takes a picture of a fluid pattern deposited on microplate 20. The full scan vision station can provide quality control. The full scan vision station can be used to provide measurements to alignment system 932. The full scan vision station can be downstream of the dispensing devices for quality control of microplate 20.

A periphery scan vision system or plate check vision system can be disposed upstream of a dispensing device to check the position and accuracy of microplate 20, prior to a dispensing by a dispensing device. The periphery scan vision system can utilize a camera mount 941 to hold two cameras 946, 948. Cameras 946, 948 can be narrow focus cameras. Cameras 946, 948 can check the location of two or three dispensing locations. The periphery scan vision system can comprise a carriage alignment 944 similar in functionality to carriage alignment device 945 described above. The periphery scan vision system can comprise a marker indicia reader station.

In some embodiments, a reference microplate can be disposed on table 932. The reference microplate can comprise an accurately machined microplate mimicking a microplate. The reference microplate can comprise a pattern of etched dots or location that matches the desired pattern on microplates to be manufactured.

In some embodiments, a test target microplate can be disposed on table 932. Flat blank plates can be used for making test patterns of dots. The test target microplate can comprise, for example, a plastic material or a cardboard material. The test target microplate does not need to comprise wells. The test target microplate can comprise a surface providing good contrast with the dot pattern. The surface can comprise a coating that can change color when liquid contacts the coating.

In some embodiments, the following sequence of operations can be used adjust loading distribution system 800. The reference microplate can be placed on a first carriage and the first carriage can be moved to the full scan vision system. The dot pattern on the reference microplate can teach the camera of the full scan vision station, the desired dot locations. Next, a test target microplate can be placed on a second carriage. The second carriage can be moved under a dispensing device. The alignment stage can move the table of the second carriage to the position that the alignment stage guesses to be the correct position. The guess can be based on previous runs. A single test target microplate can be used for one or more of the dispensing devices since the patterns from the individual dispensing stations can be disposed far enough apart so that they do not overlap. Lastly, the second carriage with the test target microplate can be moved to the full scan vision system and the dot pattern of the test target microplate can be compared to the stored memory of the desired pattern. Offsets can be computed to adjust the position of the alignment stages for the next cycle.

The above process can be repeated by running another test target microplate through loading distribution system 800 to verify the results of the previous run, until achieving a desired or satisfactory run. The above process need not be repeated. When it is determined that the dot pattern from a particular dispensing device does not or cannot fitted to a desired pattern by adjusting the X, Y and rotary axes, then aiming of dispensers of the dispensing device can be checked and adjusted, if desired. Loading distribution system 800 can alert an operator or it can devise another offset for the off-target dispenser or a subset of the off-target dispensers. The alignment stage can move the table to one position and fire one set of dispensers. The alignment stage can then make a slight adjustment of the alignment of the table and the dispensing device, and fire another dispenser or set of dispensers. The alignment can be dynamic while loading distribution system 800 can be dispensing fluids to the microplates. The slight penalty of a microplate that fails quality control and/or a slight increase in the overall cycle time can be preferable to stopping loading distribution system 800 for maintenance. This process can be useful for expediting, for example, small orders of custom microplates.

In some embodiments, once loading distribution system 800 adjusts for a production operation, a microplate can be loaded onto a carriage. The carriage can be moved to the periphery scan vision system. The location of two or more wells can be checked and a new offset for this carriage and microplate set can be added to loading distribution system 800 offsets. This new offset can adjust for variations in carriages, variations in how a microplate is placed on a carriage, and molding variations in the microplates. If the dispensing locations wells are too far or too close to each other or to the edge of the microplate, the microplate can be rejected and the microplate need not be spotted. If the well spacing is within limits but substantially off from the ideal, the error can tend to be cumulative rather than random. This means that each dispensing location can be almost perfectly spaced relative to adjacent dispensing locations, but that this spacing can be always slightly larger or smaller than specification. This can imply that the farthest dispensing locations on the microplate can be out of specification in relation to each other. Loading distribution system 800 can divide the microplate into halves or quadrants, compute an offset for each quadrant, and then dispense to each quadrant with a respective offset.

According to some embodiments, a fluid distribution system can comprise: a table configured to engage at least one of a plurality of microplates and movable at least in an X-axis direction and in a Y-axis direction that differs from the X-axis direction; a dispensing device adapted to dispense fluid into or onto one or more of a plurality of microplates; a plate-handling station comprising a plate-handling device adapted to selectively pick-up microplates from and deposit microplates on the table; an inspection station adapted to image a microplate when a microplate is disposed on the table; a calculating device adapted to compute offsets that can comprise at least an X-axis direction offset and a Y-axis direction offset, based on an image provided by the inspection station;

and a control device adapted to control an adjustment of a relative position of the table based on offsets computed by the calculating device.

According to some embodiments, the calculating device can be adapted to compute positions of at least two dispensing locations on a microplate from an image of the microplate. The calculating device can reject a microplate if the computed positions are not within a predetermined specification. The calculating device can be adapted to divide the image into portions and compute positions of at least two dispensing locations in each image portion. The calculating device can reject a microplate if respective computed positions of an image portion are not within at least one predetermined specification. The control device can be adapted to control movement of the table with the respective offset for each image portion being dispensed to by the dispensing station. The microplate can comprise a reference target plate.

According to some embodiments, the system can comprise a marking indicia reader such as marking indicia reader 804 adapted to read a marking indicia disposed on a microplate when a microplate is disposed on the table. The system can comprise a memory or storage device capable of storing offsets indexed by the marking indicia for one or more of a plurality of microplates. The system can comprise an alignment stage configured to move the table in the X-axis direction and in the Y-axis direction.

According to some embodiments, the calculating device can compute offsets. Either retrieving from the storage device offsets indexed to a respective marking indicia, or computing and saving into the storage device offsets indexed by the respective marking indicia, for one or more of a plurality of microplates.

According to some embodiments, the table can comprise a plurality of tables and each table can comprise a respective table identifier. The storage device can store offsets by the table identifier and marking indicia pair. The computing device can retrieve offsets by the table identifier and marking indicia pair.

According to some embodiments, the system can comprise a quality control inspection device adapted to inspect an image of two or more dispensings onto a microplate. The quality control inspection device can be adapted to reject a microplate if an image of two or more dispensings is not within at least one predetermined specification. The quality control inspection device can be adapted to compute dispensing station offsets that can comprise at least an X-axis direction offset and a Y-axis direction offset, based on the image.

According to some embodiments, the quality control inspection device can be adapted to inspect an image of a microplate. The quality control inspection device can be adapted to divide the image into portions. The quality control inspection device can be adapted to compute positions of two or more dispensings in each image portion. The quality control inspection device can be adapted to reject a microplate if positions for each image portion of the microplate are not within at least one predetermined specification. The quality control inspection device can be adapted to adjust a dispenser of a dispensing device if positions and volumes for each image portion of the microplate are not within at least one predetermined specification. The microplate can comprise a test target microplate.

In some embodiments, loading distribution system 800 can be used dispense dry beads. Loading distribution system 800 can use dry beads rather than fluids to deposit probes. The dry dispensing can face the same issues of how to align a series of interleaved dispensing devices. Dropping dry beads on a test microplate does not provide a useful test pattern. The individual dispensing devices can comprise ink jet heads or sharp pins that can be machined in a fixed pattern relative to the bead outlet points. A test microplate can be run through loading distribution system 800 and the jets or pins can be activated to create a visible dot pattern that can be checked by a vision system.

FIG. 80 is a top-plan view illustrating table 872 comprising a vacuum trench 954 and a gasket 956. When a microplate is disposed on table 872, a pressure source (not illustrated) can be connected to a vacuum inlet 952, to form a vacuum between a surface of microplate 20 and table 972. FIG. 74 illustrates an embodiment of a pressure source communicating with table 872. FIG. 80 illustrates an embodiment of table 872 comprising four locating pins and no ratchet, in contrast to table 872 of FIG. 70.

In some embodiments, a table can provide for initial microplate registration to a carriage at a load station. Vacuum formed between a microplate surface and a table can be used to flatten a microplate. The vacuum can also hold a microplate in place for a dispensing operation. Loading distribution system 800 can operate under a tight tolerance window. A dispensing device and a microplate can be aligned by various devices described to be within, for example, about 100 µm, about 40 µm, or within about 10 µm. These tolerances can allow dispensing into microplates, for example, high-density microplates. The alignment devices can be supplemented with vision and/or laser based active alignment systems, for additional accuracy if desired. Alignment to the tight tolerances can compensate for potential molding errors, head alignment errors, track variability, and table on carriage errors.

FIG. 81 is a perspective view illustrating a dispensing device 814 including a plurality of dispensers 868.

Figure 84:
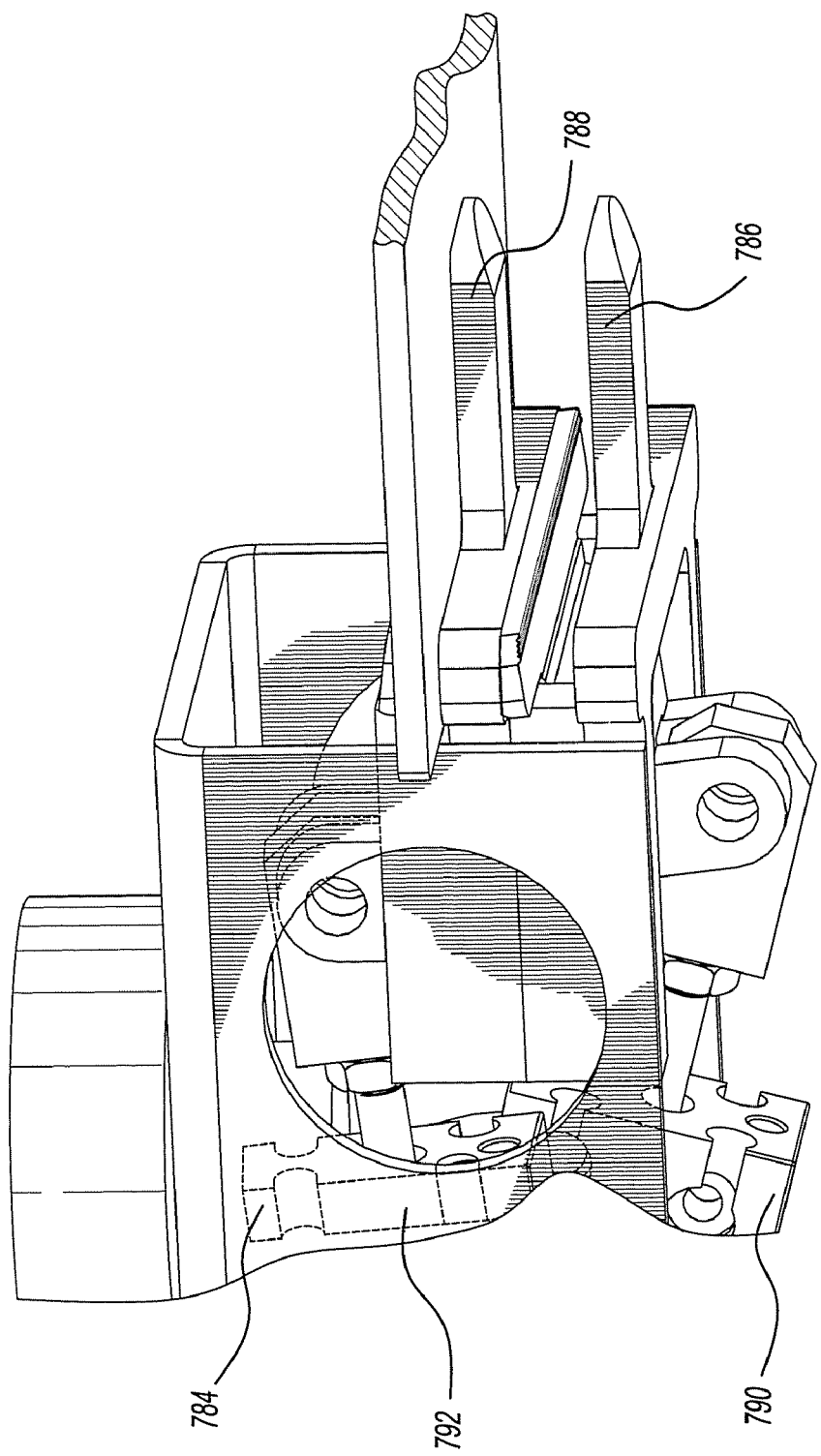

FIGS. 82-84 are perspective views illustrating plate gripper robot 784. Plate gripper robot 784 can comprise a pair of jaws—a lower jaw 786 and an upper jaw 788. Upper jaw 788 can be mounted above lower jaw 786. Plate gripper robot 784 can include actuators 784 and 790 to pivotally move an upper jaw-clamping portion 788a and a lower jaw-clamping portion 786a, respectively.

Figure 85:
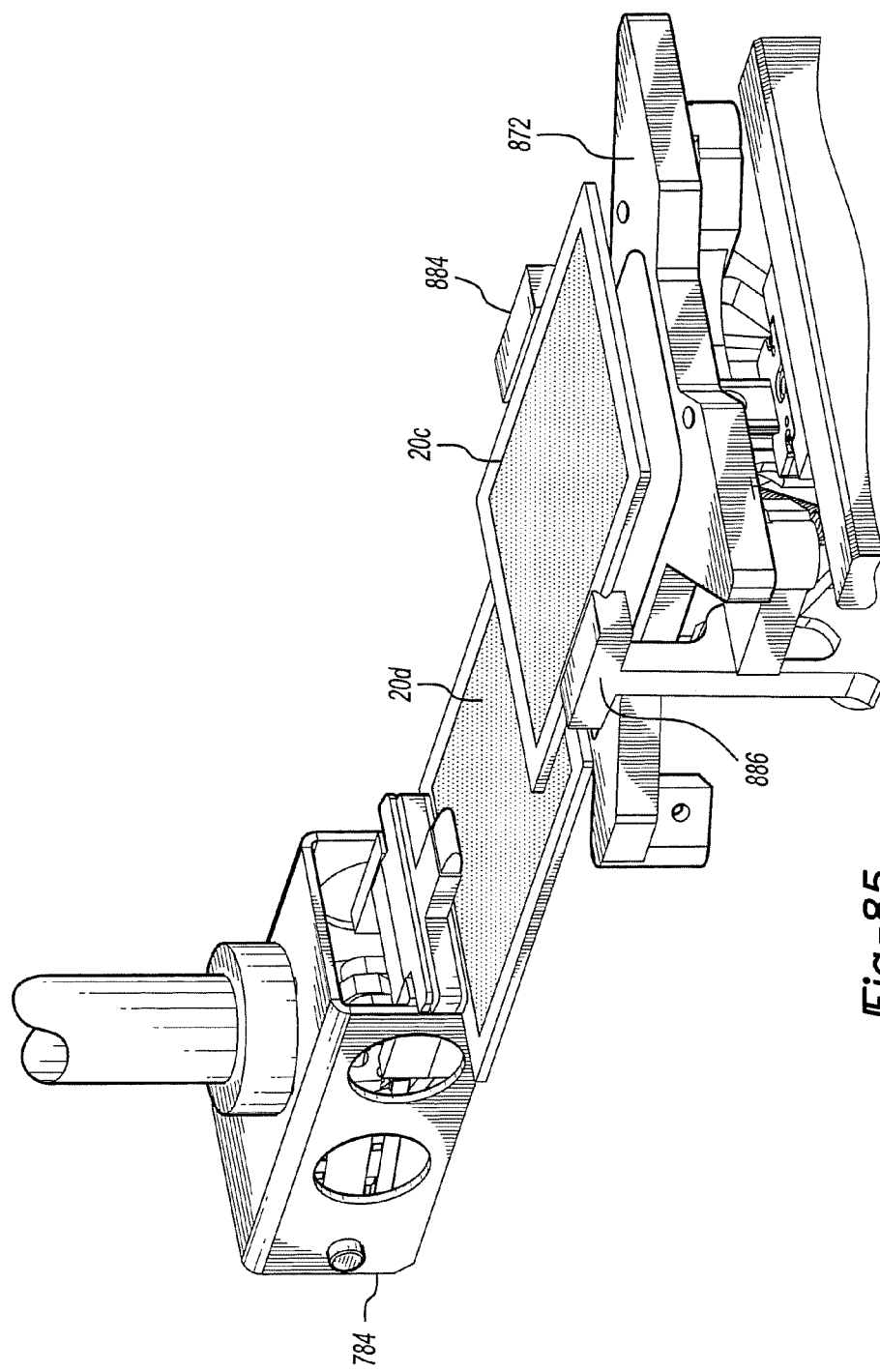
Figure 86:
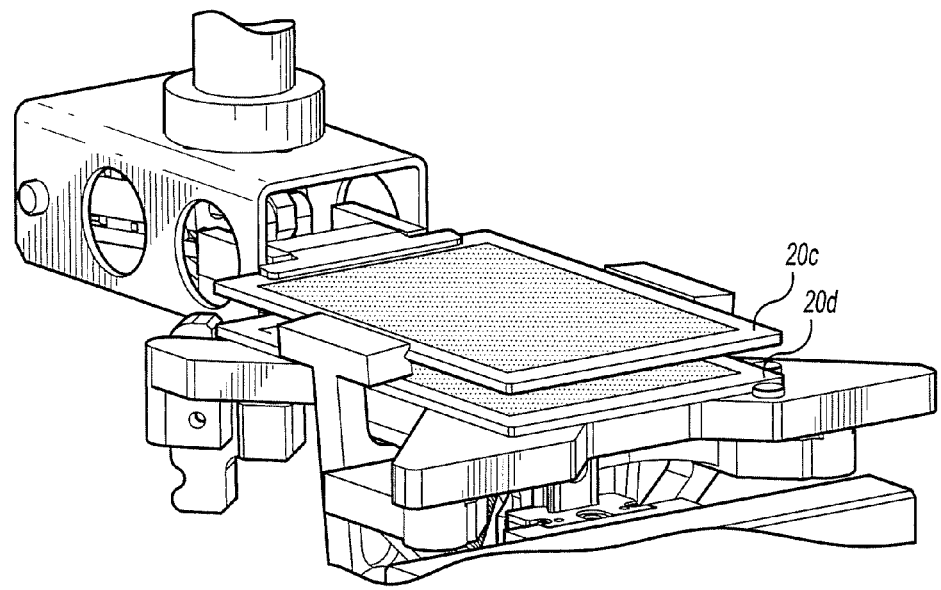
Figure 87:
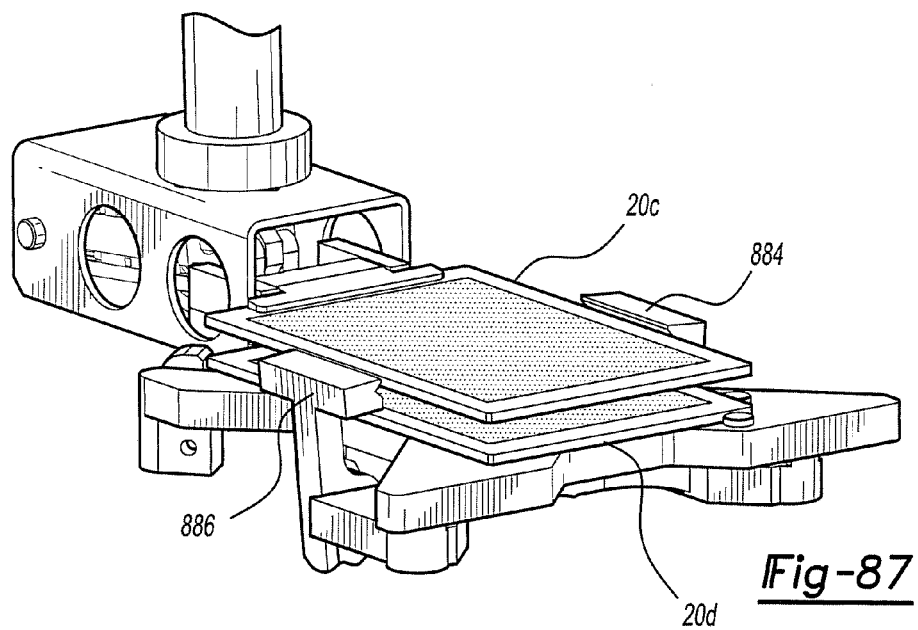

In some embodiments, as illustrated in FIG. 85 lower jaw 786 can bring a first microplate 20d to table 872 and can place first microplate 20d on table 872 under a second microplate 20c that carriage 874 can be holding above table 872 using first cam 884 and second cam 886. As illustrated in FIG. 86, plate gripper robot 784 can release first microplate 20d from lower jaw 786, placing first microplate 20d on table 872. As illustrated in FIG. 87, first cam 884 and second cam 886 can release, and upper jaw 788 can grab second microplate 20c. First cam 884 and second cam 886 can release second microplate 20c as described in FIG. 75 and FIG. 76.

Figure 88:
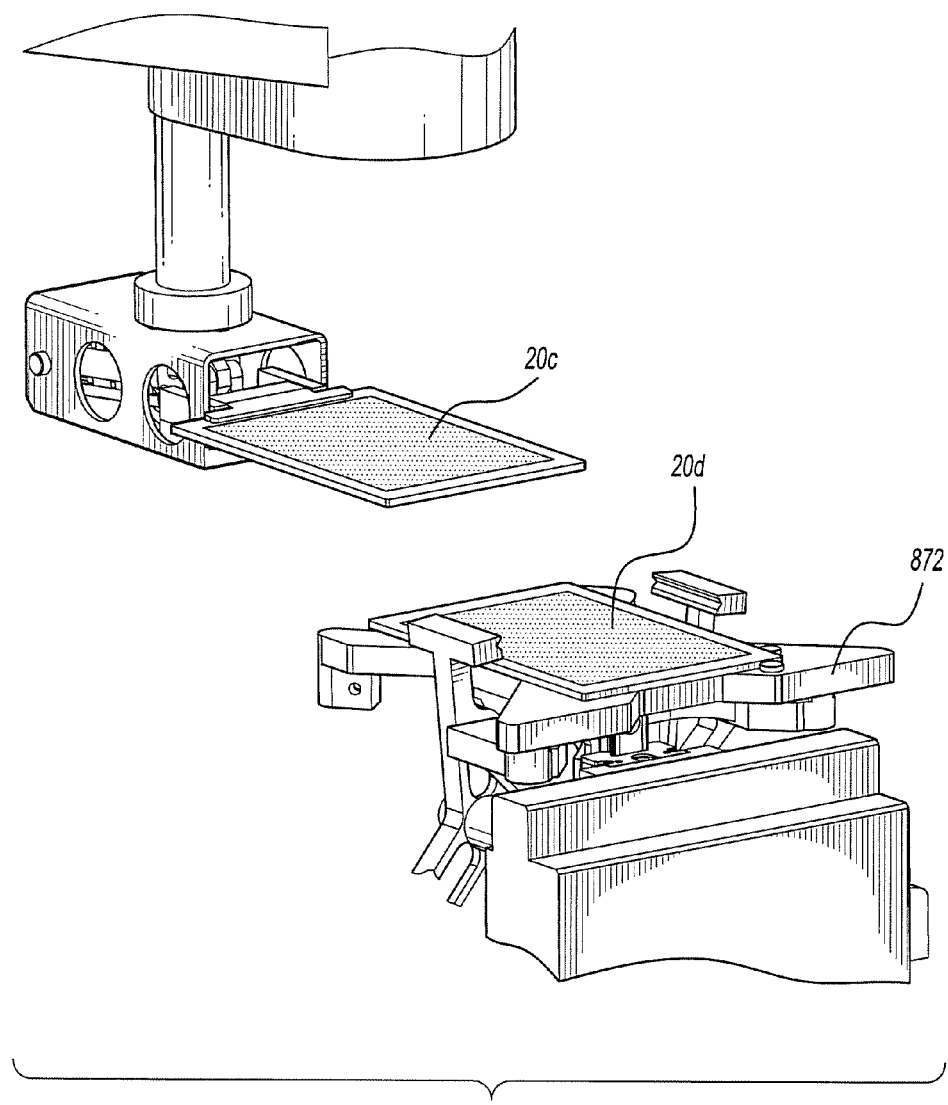
Figure 89:
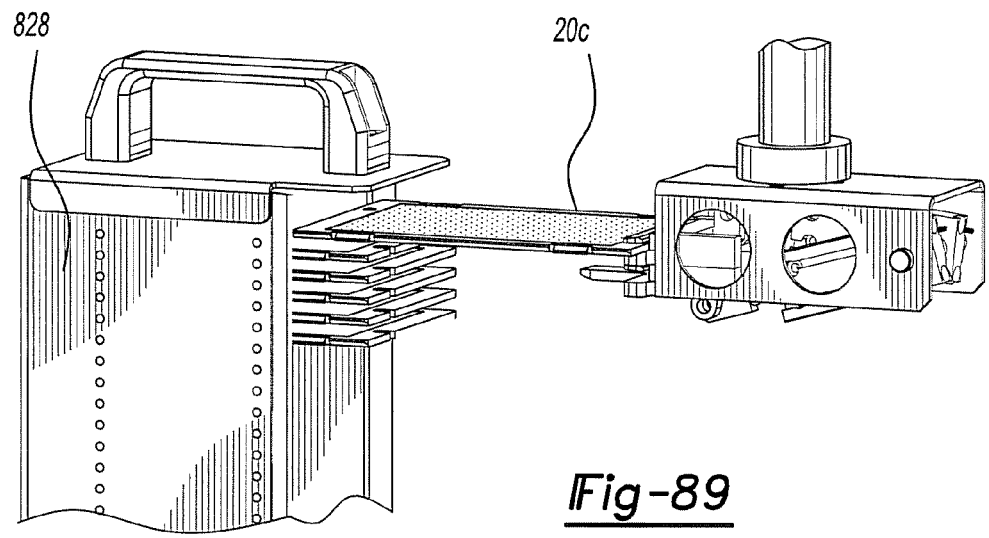

FIG. 88 illustrates plate gripper robot 784 removing second microplate 20c from table 872. As illustrated in FIG. 89, plate gripper robot 784 can transfer second microplate 20c to plate storage unit 828. At plate storage unit 828, plate gripper robot 784 can place second microplate 20c on an empty shelf. The next lower shelf in plate storage unit 828 can be empty to provide clearance for lower jaw 786.

Figure 90:
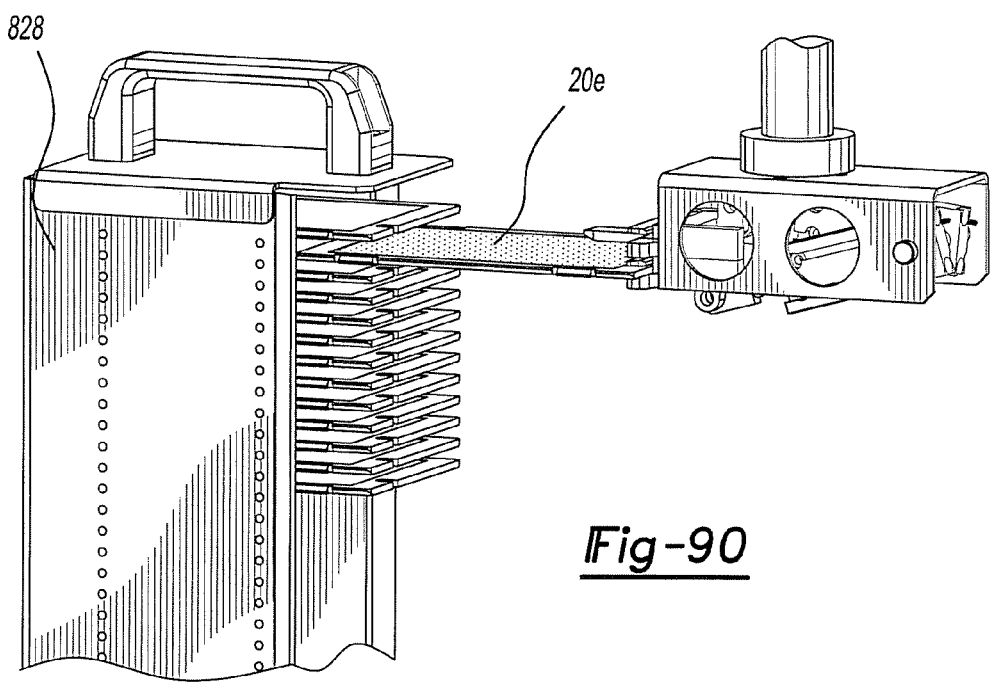

As seen in FIG. 90, lower jaw 786 grasps a third microplate 20e on from plate storage unit 828 without plate gripper robot 784 needing to shift to another position. Third microplate 20e can now be treated as first microplate 20c of FIG. 85 and the process can be repeated again.

In some embodiments, after a stack in plate storage unit 828 has been processed, plate gripper robot 784 can shift two microplates from the top of the stack to the bottom of the stack. This can provide empty spaces for the process, and can allow the process to repeat during a next pass. In some embodiments, the table can comprise a plate gripper. The plate gripper can be adapted to grip and/or, lift to an elevated position, a first microplate. Starting with a first microplate disposed on the table, the plate-handling device can be adapted to lift the first microplate and deposit a second microplate underneath the first microplate while the first microplate is in the elevated position. Loading distribution system 800 can comprise a plate gripper release device that can be adapted to release the plate gripper from gripping the first microplate. The plate gripper release device can enable the removal of a first microplate from the plate gripper.

Even further details regarding various other uses and configurations of the plate gripper and systems using the same can be found in U.S. patent application entitled "Dual Nest Microplate Spotter" to Lehto, (Ser. No. 11/086,072), filed the same day as the present application.

In some embodiments, a plate gripper robot can approach a table with a new microplate. The plate gripper robot can dispose the new microplate on the table. The plate gripper robot can grip the top microplate. The plate gripper robot can then release the new or bottom microplate. The plate gripper robot can then remove the top microplate. At the plate storage unit, the plate gripper can place the microplate in its top jaws on an empty shelf. There can be two empty adjacent shelves in a hotel, for example, the top empty shelf can receive a microplate, and the next empty shelf can be unused, for example, for gripper clearance. The shelf below the two empty shelves can hold a next microplate. The lower jaws of the plate gripper robot can than grab a microplate from the shelf holding the next microplate without needing to shift to another position along the plate storage unit. The cycle can then be repeated to (1) place a microplate gripped by the lower jaws on the table, (2) grip and remove a microplate raised above the table using the upper jaws, (3) return the microplate in the upper jaws to the plate storage unit, and (4) grab a microplate in the lower jaw from the next shelf holding a microplate. In some embodiments, the plate-handling device in loading distribution system 800 can comprise a two-jaw plate gripper device. The two jaws can be positioned one over the other. Each jaw can be adapted to grip a microplate. The plate-handling device can be adapted to grip and remove a first microplate from the table and substantially simultaneously deposit a second microplate on the table.

In some embodiments, a carriage or pallet can move microplates along a conveyer in a portrait orientation. It can be desirable to include as many of the carriage functions as possible off board of the carriage for design simplicity. In some embodiments, a register plate function can be off carriage. A vacuum pallet function applied to chuck can be on carriage. A Z-motion can be off carriage. A Y-motion can be off carriage. A vacuum sensor can be off carriage. A register sensor can be off carriage. A bar code reader can be off carriage. A Docking, Command and Data Acquisition (CDA), signal, and power function can be provided on a carriage. In some embodiments, loading distribution system 800 can comprise a lift. The lift can be configured to move the table in a Z-axis direction. The Z-axis direction can be different from both the X-axis direction and the Y-axis direction. The Z-axis direction can be, for example, perpendicular or substantially perpendicular, to both the X-axis direction and the Y-axis direction. In some embodiments, substantially perpendicular can mean within about 15 degrees of being perpendicular.

In some embodiments, the microplate can be pushed at a corner while on a load station of the conveyer. A vacuum chuck can be onboard every carriage. A Z-motion actuator can be disposed beneath the carriage. This can provide clearance and can move the vacuum chuck up to meet a dispensing device. A Y-motion actuator can reside outside of the carriage. The actuator can utilize a ram to drive a table to a reference location. A vacuum sensor can be disposed on the vacuum line supply proximate a carriage docking mechanism. A register sensor-can determine correct microplate placement, for example, by checking a pressure on the vacuum line supply. A machine indicia reader, for example, a bar code reader, can be used with a mirror to reflect a bar code on a microplate to separate reader assembly. In some embodiments, 50-micron repeatability can be desired for X, Y, and Z direction movements at a dispensing station. The carriage can be driven on a conveyer or track by a linear stepper motor. The dispensing device and dispensers therein can be held stationary. Various components, for example, the conveyer, of loading distribution system 800 can be provided with EMI shielding.

FIG. 91 is a perspective view illustrating source plate and wash pallet 864 comprising washing tray 861 and source plate holder 863. A source plate 862 can be disposed in source plate holder 863. Washing tray 861 can comprise internal wash slots 878 and external wash slots 876. Washing tray 861 can be available from Aurora Discovery, Inc.

Source plate-handling device 822 can pick-up and deposit a source plate 862 from source plate holder 863 using a gripper 823. Source plate 862 can be covered using a lid 860. Lid 860 can be placed on source plate 862 by a de-lidding device 868. De-lidding device 868 can comprise a lifting device 856 adapted to lift and hold lid 860. Source plate and wash pallet 864 can be disposed on an elevator mechanism (not illustrated) to move source plate and wash pallet 864 within range of dispensers 868. Source plate and wash station 814a can be in a rest position or a washing position, when an elevator mechanism is used. While in a rest position, washing tray 861 can be covered using a dust cover 866. Dust cover 866 can be hinged.

FIG. 92 is a perspective view illustrating a source plate and wash station 814a comprising at least one source plate and wash pallet 864. This embodiment of source plate and wash station 814a can service two dispensing stations simultaneously or substantially simultaneously. Washing tray 861 and source plate holder 863 can be placed next to each other on a platform or source plate and wash pallet 864. Source plate and wash pallet 864 can be disposed on a first slide 867. Vacuum cups 856 can grab and hold lid 860, a standard plate cover. Dust cover 866 can cover washing tray 861. A support 858 can be used to hold vacuum cups 856. Source plate and wash pallet 864 can normally wait in a position that presses washing tray 861 and source plate 862 up against their respective lids. Washing tray 861 can be covered by dust cover 866 that can be permanently attached to a frame. FIG. 98 is a side-plan view of source plate and wash station 814a in a wait position with respect to conveyer 802 and dispensing device 814.

As illustrated in FIG. 93, if source plate and wash station 814a can be extended to aspirate a dispensing device from source plate 862, then source plate and wash pallet 864 drops and vacuum cups 856 retain lid 860.

As illustrated in FIG. 94, if source plate and wash station 814a is going to extend to wash dispensers of a dispensing stations, vacuum cups 856 do not turn on and lid 860 stays with source plate 872. FIG. 99 is a side-plan view of source plate and wash station 814a in the wash position with respect to conveyer 802 and dispensing device 814.

As illustrated in FIG. 95, to swap source plate 872 out with a fresh source plate from source plate storage unit 826, a second slide 869 stays retracted. First slide 867 slides crossways, and shifts to one-side so that source plate 872 is not under lid 860 holding mechanism and an external SCARA or 5-axis robot, like store plate-handling unit 822 can load and unload the source plate 872.

As illustrated in FIG. 96, source plate and wash station 814*a* can extend on second slide 869 to position source plate 862 for aspiration by a dispensing device.

As illustrated in FIG. 97, source plate and wash station 814*a* can extend on first slide 867 and second slide 869 to position washing tray 861 to wash dispensers.

In some embodiments, for a wash operation carriages can be stopped along the conveyer at locations away from the dispensing devices to allow clearance of a washing tray moving mechanism. The moving mechanism can travel along a fixed linear track that can bring the washing tray to the conveyer. Initially, the washing tray can be located beneath a fixed cover plate that can include an embedded seal surface that the edges of the washing tray can seal against when the bath is in the up or wait position under the fixed cover. The washing tray can be lowered slightly in the Z-direction to unseal the washing tray. The washing tray can then move along a linear track towards the conveyer. When the washing tray is clear of the fixed cover, the washing tray can be raised to present the washing tray to the dispensers of a dispensing station. The washing tray can move down and can index in the Y-direction to accomplish both internal and external tip washing operations. When a wash cycle is complete, the tray can move down and back towards the rest position along the linear track.

In some embodiments, for an aspirate operation, a robot arm can remove a correct source plate from an incubator and place it onto a source plate location. The source plate can be moved to a de-lidder that can be mounted under a dust cover. The lid of the source plate can be removed using the de-lidder.

FIG. 100 is a perspective view illustrating a hotel and a movable entry guide. In some embodiments, reliable insertion of microplates into shelves can be facilitated by adding an entry guide 974 that captures a leading edge of a microplate. The vertical position of the edge can vary from microplate warping and/or variation in how a microplate can be gripped by a jaw of a plate gripper robot. A shelf 970 can provide support for plate storage unit 828. Entry guide 974 can be indexed using a linear motor 972.

FIG. 101 is a process flow diagram illustrating a software command and control architecture for a loading distribution system, according to some embodiments. A system controller 982 can networked to an enterprise resource planning (ERP) system 983, using an inter or intra network 985. ERP system 983 can provide work order requests to system controller.

In some embodiments, system controller 982 (FIG. 101) can manage and track source plates and microplates at various locations in loading distribution system 800 (FIGS. 64 and 65). Locations for a source plate can comprise, for example, in a source plate storage unit like an incubator, in one or more source plate holders, or in one or more grippers of one or more source plate handling devices. Locations for a microplate can comprise, for example, in one or more plate storage units, in or on one or more tables, or in one or more jaws of one or more plate handling devices. System controller 982 can be adapted to track and trace the contents of one or more dispensers, each disposed in one or more respective dispensing devices.

When processing a work order or manufacturing microplates, system controller 982 provides control, control, and communication for wash station assemblies module 984, a tip firing controller 986, a dispensing assemblies module 988, an incubator controller 990 also known as a source storage unit controller, an incubator robot controller 992 also known as a storage plate handling device controller, a fluidics controller 994, a hotel module 996 also known as a storage unit controller, a hotel robot controller 998 also known as a plate handling device controller, a bar code controller 976 also known as a marking indicia reader controller, a XYZ motion controller 978, and a quality control controller 929. Wash station assemblies module 984, tip firing controller 986, dispensing assemblies module 988, incubator controller 990, incubator robot controller 992, fluidics controller 994, hotel module 996, hotel robot controller 998, and bar code controller 976 can be provided as part of one or more Original Equipment Manufacturer (OEM) packages including Application Protocol Interfaces (API) for all subassemblies. System controller 982 and XYZ motion controller 978 can be provided using real-time manufacturing protocols, for example, Supervisory Control And Data Acquisition (SCADA), a computer system for gathering and analyzing real time data. Quality control controller 929 can comprise a decision maker. QC controller 929 can gather data and status from various systems comprising a loading distribution system, to render a decision for each microplate processed by loading distribution system.

In some embodiments, the array of dispensers can be aligned to a microplate, in order to accomplish parallel dispensing of different reagents into different locations at the same time. Dispensers can dispense spots of an assay reagent into one or more locations of a microplate by, for example, aspirating a volume of assay reagent sufficient for multiple spots. The aspirated volume can subsequently be dispersed as spots into multiple locations, where each location receives substantially the same mass of assay reagent.

A dilution problem can be observed using arrayed dispensers. Dilution can occur because a dispenser system fluid can dilute an assay reagent, as it is dispensed. Because a dispenser can dispense a volume of the reagent and system fluid, a reduced mass of assay reagent can be deposited into each location from dispensing action to dispensing action.

In some embodiments, a dispenser can be programmed to compensate for the dilution affect. The aspirate and dispense arrayed liquid handling technologies, can dispense different amounts of assay reagents for each nozzle for each dispense action. The level of dilution can be measured, and the measured curves can be used to calibrate the effect of dilution. In some embodiments, a method for calibrating the observed diffusion on a tip-by-tip basis, and compensating for the loss of dispensed assay reagent per nozzle from dilution by programming dispensing to dispense more solution per spot, is provided. A required increase in spot volumes can be calculated by mathematically integrating an area under a fluorescence-dispense calibration curve. In some embodiments, dynamic programming of the dispense volumes can provide microplate to microplate reproducibility of dispensed mass of assay reagents (spots), and can reduce assay reagent waste by allowing the use of highly diluted assay reagents from the dispensing device.

In some embodiments, methods of spotting assay reagents based on dispenser arrays, into microplates, consistent with the banded format of filling devices, and the production of source plates for spotting, are provided.

In some embodiments, assay 1000 can be distributed on microplate 20 using a filling apparatus, such as filling apparatus 400, a robotic filler, or a manual filler to distribute one or more components of assay 1000 across microplate 20 in columns or bands, for example, as illustrated in FIG. 102. For microplates that accommodate more than one sample, the sample distribution can map to this columnar or banded format.

FIG. 102 illustrates sample distribution in a banded format using a robotic or manual filler head. The head comprises tips

746, 748, 750, 752, 754, 756, 758, and 760, respectively. Tips 746, 748, 750, 752, 754, 756, 758, and 760 can aspirate fluids from source plate 862. Source plate 862 can comprise, for example, a 96 or a 384-location plate, including, for example, biological reagents or pre-amplified samples. Tips 746, 748, 750, 752, 754, 756, 758, and 760 can distribute the aspirated samples across microplate 20 to form bands or columns across microplate 20, for example, bands about 9 mm wide, bands about 4.5 mm wide, bands about 2.25 mm wide, or bands about 1.125 mm wide. The microplate can include, for example, 6,144 wells. Tips 746, 748, 750, 752, 754, 756, 758, and 760 can dispense individual samples in bands across a plurality of rows of microplate 20. As illustrated in FIG. 102, tip 746 can correspond to band 746', tip 748 can correspond to band 748', tip 750 can correspond to band 750', tip 752 can correspond to band 752', tip 754 can correspond to band 754', tip 756 can correspond to band 756', tip 758 can correspond to band 758', tip 760 can correspond to band 760', and tip 762 can correspond to band 762'. In an exemplary embodiment, tip 746 can load an eight-row column that is a total of 9 mm wide, from one end to the other end of the card, to include band 746' illustrated in FIG. 102. With a number of sweeps along the card, back-and-forth, a band of sample can be loaded into the microplate, and with an 8-tip dispenser, the entire 6144 wells of a 6144 well microplate can be loaded with eight motions of the filler to achieve loading one respective well at a time, for each dispenser tip.

FIG. 31 illustrates the use of a dead row between sample-loaded wells that can be used to avoid cross-contamination of two rows to be tested, taking advantage of a banded format. FIG. 103 illustrates a microplate 764. In the following discussion, rows run from left to right. Microplate 764 includes three rows, illustrated from left to right in the figure, including a first row into which a first sample is loaded and including sample wells 766. A second row into which a second sample is loaded includes sample wells 770. The row containing sample wells 768, located in between the rows respectively containing sample wells 766 and sample wells 770, can be used as a dead row and can be skipped during a sample loading process. If any of the first or second samples might stray from its intended row, it can be captured in the dead row. That is, if a sample deposited in well or location 766 or well or location 770 of microplate 764, carries over to an adjacent location 768, no problem arises because the results of any assays in wells 768 would not be analyzed. For example, when using a robotic or manual filler, any possible cross-contamination between samples can be prevented by leaving approximately one unused row (a "dead row") between each band of loaded samples in the microplate. The dead row can comprise one or more rows.

In some embodiments, a method of avoiding cross-contamination of a plurality of samples disposed in locations of a microplate can be provided. The method can include loading a filling device that can include a plurality of dispensers, each dispenser can include a fluid; translating the filling device along a translation path traversing a microplate that can include rows of locations; and dispensing a band of a respective fluid from each of the dispensers along a portion of the translation path to load rows of the locations, where the bands do not contact one another and the rows include loaded rows and a dead row between otherwise adjacent loaded rows.

Bands can contain the same set of samples or assay reagents across the microplate. One row can be eliminated from each band on the microplate. Where one band or one sample is provided on the microplate, there can be no need for a dead row to prevent sample cross-contamination.

In some embodiments, the dead rows of a microplate can be left empty or can be spotted with one or more components of assay. A buffer, for example, a TaqMan buffer, comprising no templates in common with the assay reagents in the bands, can be used to fill locations in a dead row. In some embodiments, each microplate can comprise an m×n configuration. Dead rows do not have to comprise wells or fluid locations. Dead rows can comprise other markings or features, for example, mold ejector pins can be disposed in the dead rows to improve a release of the microplate from a mold. Dead row wells or locations can be loaded with a calibrating dye or other marker or control substance useful in calibrating, for example, with respect to fluorescence or background noise. Dead row wells or locations can be loaded with a dye or other marker useful in providing identifiable locations on the microplate.

FIG. 104 illustrates a system according to some embodiments for manufacturing source plates and spotted microplates. Loading distribution system 800 can include: a plate-handling station 774 for moving at least one microplate; a first dispensing station 780 and a second dispensing station 782; a source incubator 776; and a microplate incubator 778. Each dispense station can dispense fluid, for example, into or onto a microplate. Each dispense station can aspirate fluid from one or more source plate. Plate-handling station 774 can move source plates (not illustrated) in and out of source incubators 778. Plate-handling station 774 can move and microplates in and out of dispensing stations 780, 782. The source plates can be stored in incubators when not in use.

In some embodiments, source plates can be stored, optionally lidded, in source incubator 776 that can circulate, for example, high humidity filtered air around the source plates. This can, for example, prevent evaporation of the assay reagents. There can be a delay between when source plates are prepared and when they are used for spotting destination microplates. The delay can be problematic because evaporation can adversely change the concentration of the reagents.

In some embodiments, the spotted assay reagents can be dried and the microplates can be protected from dust during production. Drying of microplates can take place in microplate incubator 778. The destination microplates can be stored, optionally lidded, in microplate incubator 778 that can circulate low humidity filtered air around the microplates. Because the spotted assay reagents can be dried within microplate incubator 778, a post-batch drying step for the microplates can be eliminated. In some embodiments, loading distribution system 800 can be housed in an enclosure such that the housing can enclose loading distribution system 800. The housing can comprise a class 1000 or cleaner clean room.

Plate-handling station 774 can be adapted to selectively pick up and deposit in dispensing station 780, 782, individual microplates, at least one at a time. The plate-handling station 774 can include, for example, a robotic arm. The plate-handling station 774 can be adapted to simultaneously remove a first microplate from an incubator and deposit a second microplate an incubator. Dispensing stations 780 and 782 can include at least 96 dispensing tips, or at least 384 dispensing tips. Each dispensing station can include a plurality (two or more) of dispensers. Dispensing stations 780 and 782 can further include a plurality of (two or more) storage reservoirs. The source incubator 776 can store a source plate. The microplate incubator 778 can store a microplate that is unspotted, partially spotted, or fully spotted. The source incubator 776 can include circulated high humidity filtered air in order to prevent evaporation of the source assay reagents from the stored source plate. Microplate incubator 778 can include circulated low humidity filtered air to dry the spotted assay reagents. Microplate incubator 778 can maintain the spotted dried assay reagents in a dried state on the spotted microplate. Microplate incubator 778 can prevent a post-batch drying step.

The plate-handling station 774 can be adapted to selectively pick up and deposit individual source plates from the source hotel 776, microplates from the microplate hotel 778, or microplates and/or source plates from dispensing station 780, 782. The plate-handling station can transfer source plates from the dispensing station 780 and 782 to the appropriate source incubator 776. The plate-handling station can transfer microplates from the dispensing station 780 and 782 to the appropriate microplate incubator 778. The source plates and/or the microplates can optionally be lidded. The incubators can include a device for lidding and de-lidding a source plate.

In some embodiments, methods and systems are provided that improve the manufacturing of microplates by: increasing microplate to microplate reducibility and reducing assay reagent waste; preventing sample cross-contamination from the use of robotic and manual fillers; reducing evaporation loss of assay reagents from source plates; assisting in the drying of spotted assay reagents on microplates, and avoiding a post-batch step of drying the microplates; and reducing dust contamination of both source and microplates.

FIG. 105 is a top-plan view illustrating a mapping of fluid locations of a 384-location source plate into a dispensing device comprising 96 dispensers, further into a 6,144-microplate. Microplate 20 can comprise a plurality of grids, for example, 96-grids. A grid 854 can comprise 64 locations. Each of the locations in a grip of microplate 20 can be dispensed into or onto by a respective dispenser 868 of dispensing device 814, when dispensing device 814 comprises 96-dispensers. A quarter of a grid 852, 16 locations, illustrates a location map pattern. The locations in quarter of a grid 852 can be addresses as 1, 2, 3, and 4 for a first row; 7, 8, 9, and 10 for a second row; 17, 18, 19, and 20 for a third row; and 25, 26, 27, and 28 for a fourth row. Loading distribution system 800 can dispense into a location number 1 during a first pass over microplate 20, location number 2 during a second pass over microplate 20, and so on so forth. To accomplish this, loading distribution system 800 can control the X and Y placement of microplate 20 using X-Y alignment, for example, as provided by alignment stage 932 as described above when dispensing device 814 is fixed or stationary with relative to microplate 20, or by offsetting each dispenser 868 of dispensing device 814.

In some embodiments, source plate 862 can be divided into 96-grids, each grid 848 comprising 4-locations for fluid aspiration. Loading distribution system 800 can aspirate from a location number 1 during a first pass over source plate 862, location number 2 during a second pass over source plate 862, and so on so forth. To accomplish this, loading distribution system 800 can control the X and Y placement of source plate 862 using X-Y alignment, for example, as provided by source plate and wash station 814a as described above when dispensing device 814 is fixed or stationary with relative to microplate 20, or by offsetting each dispenser 868 of dispensing device 814 while holding source plate 862 in fixed position.

In some embodiments, a system and method for manufacturing a microplate comprising a plurality of fluid samples, for example, about 768 or more samples, about 1536 or more fluids, about 3072 or more fluids, about 6,144 or more fluids, about 12,288 or more fluids, are described. In some embodiments the plurality of fluids can all be the same fluid and in some embodiments each fluid can be different from all the other fluids. The plurality of fluids can reside in or on a microplate.

In some embodiments, fluids to loading distribution system 800 can be provided using a source plate, for example, a multiwell source plate. The source plate can comprise 24 or more wells, for example, 48 or more wells, 96 or more wells, 192 or more wells, 384 or more wells, or 768 or more wells.

In some embodiments, a dispensing device comprising a plurality of dispensers can be used in the present teachings. The dispensers can number 24 or more tips, for example, 48 or more tips, 96 or more tips, 192 or more tips, 384 or more tips. The dispensers can be, for example, piezo-electric spotting tips. The dispensers can be disposed in an SBS microtiter footprint, for example, the footprint and pitch distribution of a standard 96 well microtiter plate, a 192 well microtiter footprint pitch, a 384 well microtiter footprint, etc. In some embodiments, the dispensers can be fixed in position. In some embodiments, the dispensers can be moveable within a subportion of the dispensing device.

According to some embodiments, a system utilizing a 384-well source plate using a 96-dispenser device can be used to manufacture a microplate comprising, for example, 6,144 wells. Loading distribution system 800 can utilize, for example, 16, 384 well source plates, to access 6,144 unique fluids from the 36 times 384 or 6,144 wells. A 96-dispenser device can access a 384-source plate four times, each time drawing 96 unique fluids into corresponding 96-dispensers. Thus, the dispensing device can aspirate from a 384 well source plate 4 times. Sixteen source plates and 64 aspirations can be utilized to aspirate 6,144 unique fluids. A dispenser can be positioned over a target microplate comprising 6,144 wells, 64 times. For a 96 tip dispenser spotting a 6144 well microplate, each of the 64 dispensations per dispenser tip can be offset from the other dispensations so that each dispenser tip dispenses to 64 different combinations of X and Y coordinates, for example, so each tip spots 64 different wells.

In some embodiments, a method of dispensing can comprise: (a) loading a dispensing device comprising n fixed dispensers with a first plurality of fluids from a first source plate, wherein the source plate comprises m fluids, wherein n is an integer greater than or equal to two, and m is a positive whole number multiple of n; (b) moving a first microplate into a receiving position with respect to the fixed dispensers; (c) dispensing n fluids from the dispensers onto or into a first set of n locations on or in the first microplate, (d) moving at least one additional microplate into receiving position with respect to the dispensers; (e) dispensing n fluids from the dispensers onto or into a first set of n locations on or in the at least one additional microplate; (f) loading the n dispensers with a second plurality of fluids from a second source plate, wherein the second source plate comprises m fluids; (g) moving the first microplate into a receiving position with respect to the fixed dispensers; (h) dispensing n fluids from the dispensers onto or into a second set of n locations on or in the first microplate; (i) moving the at least one additional microplate into receiving position with respect to the dispensers; and (j) dispensing n fluids from the dispensers onto or into a second set of n locations on or in the at least one additional microplate. The first source plate can be the same as the second source plate, or they can be different source plates.

The method of dispensing can further involve loading from a plurality of source plates, for example, four, eight, 16, 32, 64, 96, 384, or more. In some embodiments, the first and second source plates can be the same and the first plurality of fluids can be a different plurality of fluids than the second plurality of fluids. In some embodiments, the first plurality of fluids can be the same plurality of fluids as the second plurality of fluids. In some embodiments, the first plurality of fluids can comprise a first plurality of mixtures, and each mixture can comprise two or more reagents for a nucleic acid sequence reaction. The method can comprise spotting a microplate that comprises, for example, 6,144 or more wells.

In some embodiments, a method of dispensing fluids is provided that comprises: (a) aspirating a first fluid volume into a dispenser adapted to dispense fluid volumes of one microliter or less; (b) dispensing a desired amount of the fluid volume, to form a dispensed portion, (c) calculating the volume of the dispensed portion, and (d) calculating an adjusted desired volume that compensates for a difference between the desired volume and the volume of the dispensed portion. The method can further comprise: (e) dispensing an adjusted desired volume of the fluid volume, to form a second dispensed portion, (f) calculating the volume of the second dispensed portion, and (g) calculating an adjusted desired volume that compensates for a difference between the adjusted desired volume and the volume of the dispensed portion. The method can comprise repeating the dispensing and two calculating steps for each dispensation of the dispenser. The method can be used on a piezo-electric dispenser, on an acoustic dispenser, or the like.

The method of dispensing a fluid can comprise calculating the volume by remembering a count of the number of dispensings per aspiration, and looking up in a table a level of dilution determined by the count. As fluid can be dispensed from the dispenser, the loss of volume can comprise an effect on the dispensed amount and the method can improve dispensing accuracy. A computer control unit and a memory can be used to track the dispensing and determine adjustments to be made if compensation is needed for a loss of volume per dispensation. The dispenser can comprise a plurality of dispensers and the calculating can comprise calculating a level of dilution of the dispensed volume for each dispenser of the plurality of dispensers. The dispenser can comprise a plurality of dispensers and the adjusting can comprise adjusting the dispensed volume of each dispenser of the plurality of dispensers.

In some embodiments, a method of loading a microplate is provided that comprises: translating a filling device comprising a plurality of dispensers, each dispenser comprising a fluid, along a translation path traversing a microplate comprising rows of wells, wherein the wells can comprise an average minimum dimension equal to a first dimension; and dispensing a band of a respective fluid from each of the dispensers along a portion of the translation path to load rows of the wells, wherein the bands do not contact one another and the rows include at least two adjacent loaded rows of wells which can be spaced apart from one another by a dimension that is about the same as or greater than the first dimension. The at least two adjacent loaded rows of wells can be separated from one another by at least one dead row of wells, that is, at least one row of wells that has not purposefully been loaded, but rather, that may receive some overspray or overshoot of fluids intended to be dispensed into the loaded wells. In place of a dead row of wells, the method can comprise dispensing to a microplate that includes a thickened sidewall between the two adjacent loaded rows, wherein the sidewall can be at least as wide as the average width of each of the well. The sidewall can be as high as all of the other sidewalls between adjacent wells of the microplate.

The method of loading a microplate can comprise the dispensation of, for example, one or more biological sample. The method can comprise the dispensation of, for example, a biological reagent, an assay, a probe, a primer, an oligonucleotide, and a combination thereof. The plurality of the wells of the microplate can each be preloaded with components for a same kind of assay or for respective different kinds of assays. Each well in each row of wells loaded by one of the bands can comprise components for a same kind of assay. In some embodiments, the method can comprise dispensing a marker fluid in the at least one dead row of wells, for example, a control liquid, dye, or optical marker. The marker fluid can be used to calibrate fluorescence signals and/or to provide for location identification like a milepost or landmarker.

In some embodiments, loading distribution system 800 can be used to transfer assay components such as oligonucleotides from source plates, for example, 384-well source plates, to microplates 20. Loading distribution system 800 can produce a plurality of microplates 20 simultaneously in batches. Batches can comprise a plurality of source plates, for example, 2, 4, 8, 16, 32, or more source plates. Batches can comprise a plurality of target microplates, for example, about 5 or more, about 10 or more, about 100 or more, or about 200 or more, microplates per batch. Loading distribution system 800 can be integrated into a manufacturing system. The manufacturing system can provide, for example, work orders, a manufacturing historian, or logger. The manufacturing system can comprise an enterprise resource planning (ERP) system. Loading distribution system 800 can maintain queues for source and target microplates. Loading distribution system 800 can provide different temperature and humidity control environments for the source and the target microplates. A cache of source and target microplates can be disposed in appropriate stations of loading distribution system 800. This can allow for the unattended operation of loading distribution system 800.

In some embodiments, control software and/or a dispensing device can be utilized that is configurable for a list of variables. Exemplary variables can be found herein in the EXAMPLE section. Loading distribution system 800 can utilize, for example, a 96-dispenser dispensing device, or a 384-dispenser dispensing device. Loading distribution system 800 can utilize, for example, 1, 2, 4, 8, 16, or more than 16 dispensing devices. Loading distribution system 800 can be designed to mitigate a throughput bottleneck at a dispensing device.

In some embodiments, Incoming Quality Control (IQC) requirements for microplate 20 can be used for a Whole Genome Array (WGA), a Focused Gene Set(s) (FGS) system, or a custom gene-set(s) system. The IQC can require, for example, a 100% inspection of a microplate in from about 1 second to about 60 seconds, from about 1 second to about 10 seconds, or from about 3 seconds to about 6 seconds. The inspection can comprise tests for, for example, an absence or presence of spots, spot metrics, and/or volume and concentration measurements (CPM). The IQC system can comprise hardware and/or software. In some embodiments, the IQC station can comprise a fluorescence detection system using, for example, infrared dye spiking or blue LED excitation of spots. The IQC station can be a data logger. The IQC can be a decision maker.

In some embodiments, a dispensing device can be configured to disable rows of dispensers. For example, a 96 dispenser-dispensing device can mimic 12, 24, and 48 dispenser configurations. In some embodiments, the unused dispensers can be disabled, for example, using software. In some embodiments, the unused dispensers can be physically removed from a dispense position. A manifold in the dispensing device can be reconfigured to gang disabled tips. A common valve disposed on the manifold can shut-off unused dispensers to prevent them from aspirating air. The different dispensing devices can be swapped manually or robotically.

An exemplary loading distribution system can provide many different combinations of variables as exemplified in the table below:

| Variable | Counts | Unit |
|---|---|---|
| number of tips per head | 96 | |
| number of spotting heads | 4 | |
| number of replicates per tip per source plate well | 1 | |
| moving time between 2 stations | 1 | sec |
| move time between replicates on microplate | 0.5 | sec |
| tip firing cycle time for each spotting | 1 | sec |
| number of stations for other functions | 4 | |
| number of dispenses per tip per source plate | 1 | |
| number of high-density microplates per batch | 150 | |
| number of source plates per batch | 16 | |
| number of passes for each microplate | 16 | |
| volume in tip per aspirate | 3 | μl |
| volume per dispense | 0.03 | μl |
| percent of volume dispensed per aspirate | 50% | |
| number of dispenses per aspirate | 50 | |
| number of aspirates per source plate well per tip per batch | 3 | |
| number of total aspirate cycles per head per batch | 12 | |
| number of spotting cycles per tip per batch | 2400 | |
| number of spotting cycles per head per batch | 2400 | |
| number of index cycles to ramp up and down | 14 | |
| Total aspirate time per batch | 5280 | sec |
| Total spotting time per batch | 16898 | sec |
| Aspirate Serial Actions | | |
| move wash station in position | 5 | sec |
| wash tips | 45 | sec |
| move wash station out | 5 | sec |
| load source plate in aspirate position | 5 | sec |
| aspirate time | 15 | sec |
| unload source plate from aspirate position | 5 | sec |
| Aspirate cycle time | 80 | sec |
| Dispense Spotting Station Actions | | |
| move shuttle in dispense position | 1 | sec |
| position plate for spotting under head | 4 | sec |
| tip firing time per high-density plate per source plate | 1 | sec |
| reposition plate after dispense | 1 | sec |
| Spotting Cycle Times | 7 | sec |
| Actions | | |
| load per unload source plate @ incubator | 40 | sec |
| handling time per plate | 40 | sec |
| Other Station Actions | | |
| move shuttle in dispense position | 1 | sec |
| unload shuttle high-density plate @ hotel | 4 | sec |
| load high-density plate in shuttle @ hotel | 4 | sec |
| inline QC | 4 | sec |
| barcode reading and writing of high-density plate | 2 | |
| Station process time per pass | 5 | sec |

Loading distribution system 800 can provide the following throughput for spotting with four 96-tip dispense devices.

| | | |
|---|---|---|
| number of 384-well source plates = | 16 | 16 |
| number of unique assay = | 384 × 16 = | 6144 |
| number of tips per head = | 4 | 96 |
| number of heads = | 4 | 4 |
| number of total tips = | 96 × 4 | 384 |
| number of passes for each high-density plate = | 6144/4/96 = | 64 |
| number of source wells per tip = | 6144/384 = | 16 |

Microplate Filling

In some embodiments, a filling apparatus 400 can be used to fill at least some of the plurality of wells 26 of microplate 20 with one or more components of assay 1000. It should be understood that filling apparatus 400 can comprise any one of a number of configurations.

Figure 20:
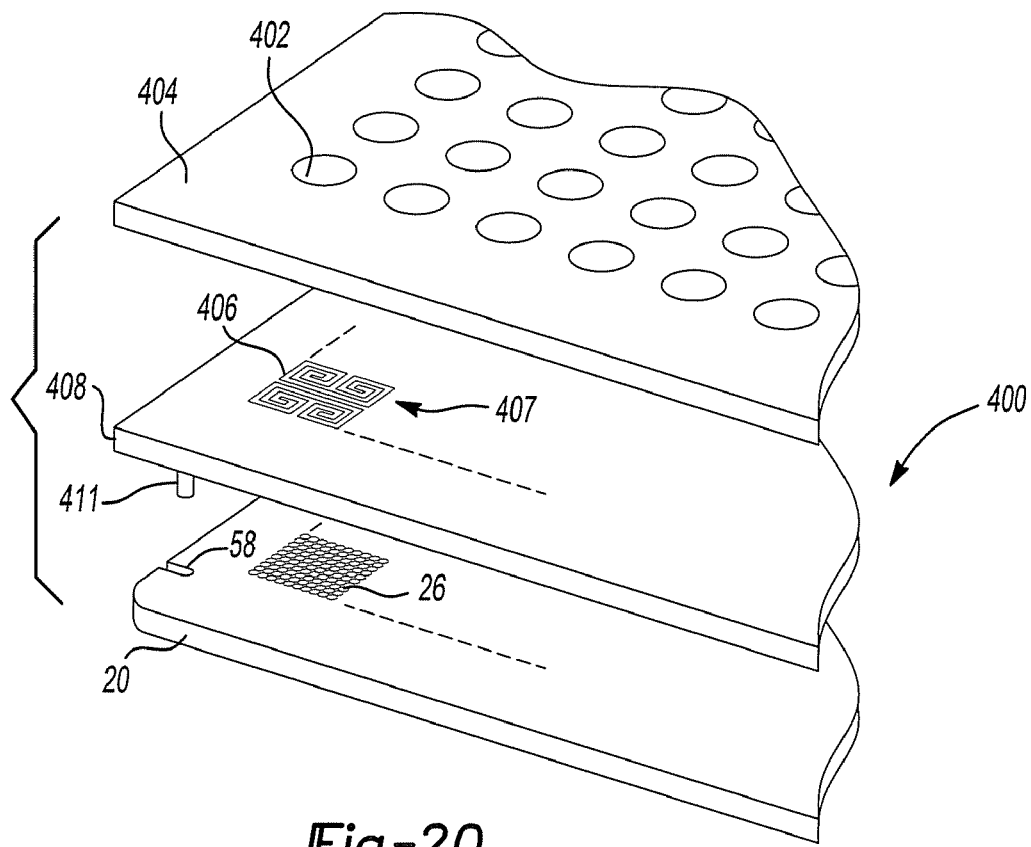
FIG. 20 is an exploded perspective view illustrating a filling apparatus according to some embodiments.

In some embodiments, referring to FIGS. 20-22(b), filling apparatus 400 comprises one or more assay input ports 402, such as about 96 input ports, disposed in an input layer 404. In some embodiments, assay input ports 402 of input layer 404 can be in fluid communication with a plurality of microfluidic channels 406 disposed in input layer 404, an output layer 408, or any other layer of filing apparatus 400. In some embodiments, the plurality of microfluidic channels 406 can be formed in an underside of input layer 404 and a seal member can be placed over the underside of input layer 404. In some embodiments, the seal member can comprise a perforation (e.g. hole) positioned over a desired location in microplate 20 to permit a discrete fluid communication passage to extend therethrough. In some embodiments, the plurality of microfluidic channels 406 can be arranged as a grouping 407 (FIG. 20). In some embodiments, assay input ports 402 can be positioned at a predetermined pitch (e.g. 9 mm) such that each assay input port 402 can be aligned with a center of each grouping 407. In some embodiments, the plurality of microfluidic channels 406 can be in fluid communication with a plurality of staging capillaries 410 formed in output layer 408 (FIGS. 21-22(b)).

In some embodiments, input layer 404 and output layer 408 can be bonded or otherwise joined together to form a single unit. This bond can be made with, among other things, a double-stick tape, a laser weld, an ultrasonic weld, or an adhesive. However, it should be appreciated that the bonding or otherwise joining of input layer 404 and output layer 408 is not required.

During filling, assay 1000 can be put into at least one assay input port 402 and can be fluidly channeled toward at least one of the plurality of microfluidic channels 406, first passing a surface tension relief post 418 in some embodiments. In some embodiments, surface tension relief post 418 can serve, at least in part, to evenly spread assay 1000 throughout the plurality of microfluidic channels 406 and/or engage a meniscus of assay 1000 to encourage fluid flow. Assay 1000 can be fluidly channeled through the plurality of microfluidic channels 406 and can collect in the plurality of staging capillaries 410 (FIG. 22(b)). Assay 1000 can then be held in the plurality of staging capillaries 410 by capillary or surface tension forces.

Figure 21:
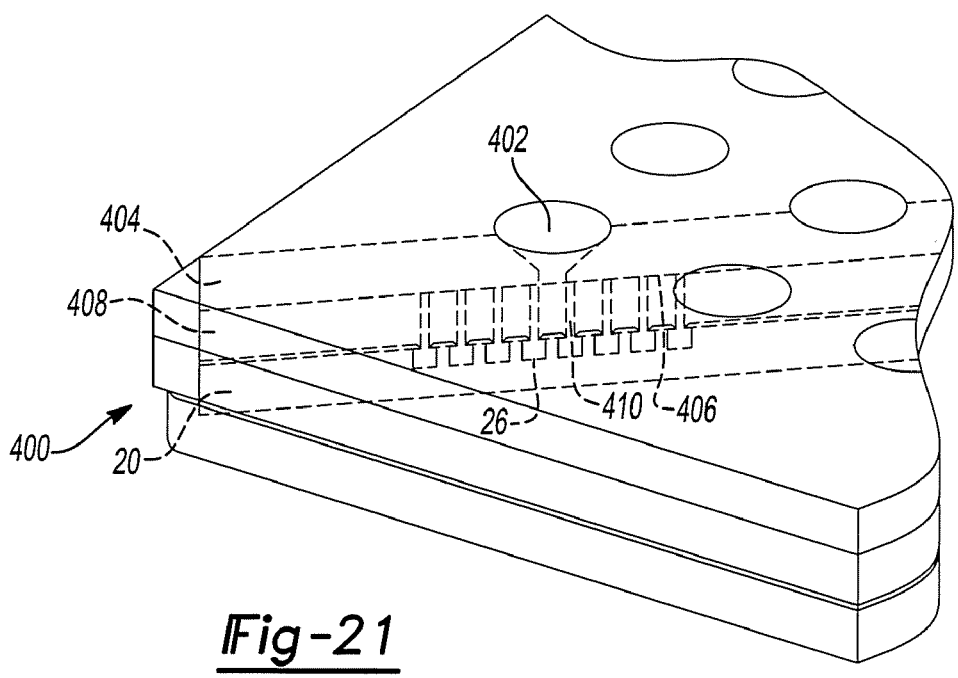
FIG. 21 is a cross-sectional perspective view of the filling apparatus of FIG. 20.
Figure 22A:
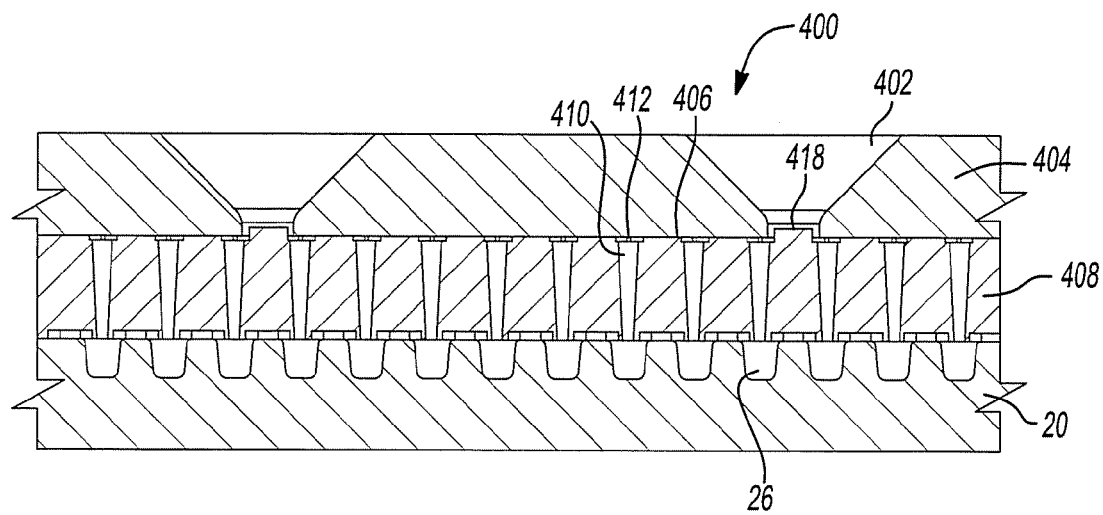
FIG. 22(a) is a cross-sectional perspective view of a filling apparatus according to some embodiments.
Figure 22B:
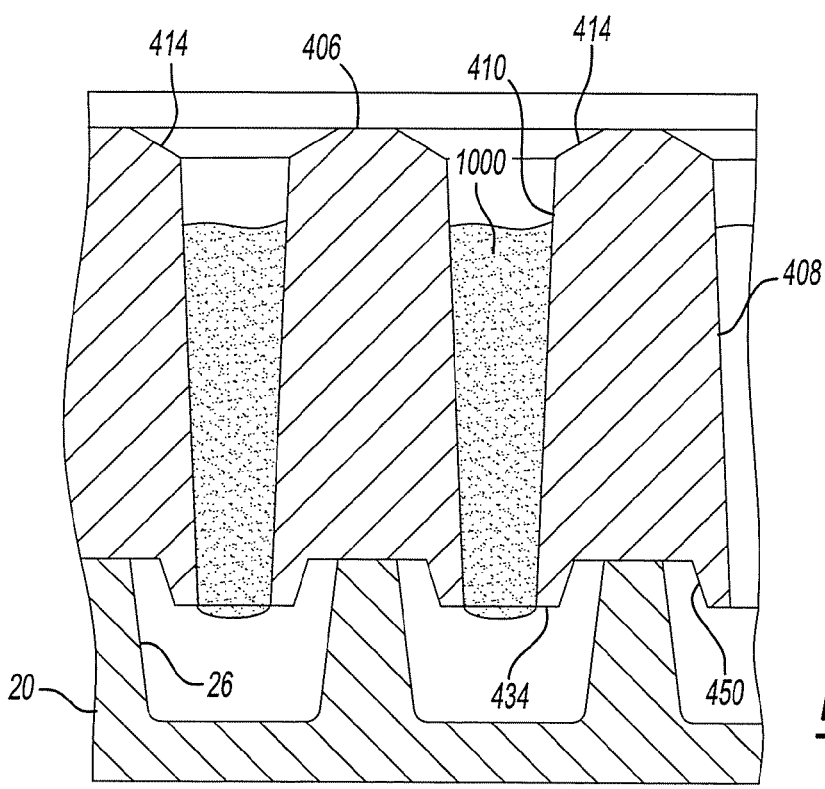
FIG. 22(b) is a cross-sectional view of a portion of a filling apparatus comprising a plurality of staging capillaries, microfluidic channels, and ramp features according to some embodiments.

In some embodiments, as illustrated in FIGS. 21 and 22(a)-(b), microplate 20 can be attached to filling apparatus 400 so that each of the plurality of staging capillaries 410 is generally aligned with each of the plurality of wells 26. In some embodiments, filling apparatus 400 comprises alignment features 411 (FIG. 20) operably sized to engage corresponding alignment feature 58 on microplate 20 to, at least in part, facilitate proper alignment of each of the plurality of staging capillaries 410 with a corresponding (respective) one of the plurality of wells 26. In some embodiments, the combined unit of filling apparatus 400 and microplate 20 can then be placed in a centrifuge. The centrifugal force of the centrifuge can, at least in part, urge assay 1000 from the plurality of staging capillaries 410 into each of the plurality of wells 26 of microplate 20. Filling apparatus 400 can then be removed from microplate 20. In some embodiments, microplate 20 can then receive additional reagents and/or be sealed with sealing cover 80, or other sealing feature such as a layer of mineral oil, and then placed into high-density sequence detection system 10.

In some embodiments, capillary or surface tension forces encourage flow of assay 1000 through staging capillaries 410. In this regard, staging capillaries 410 can be of capillary size, for example, staging capillaries 410 can be formed with an exit diameter less than about 500 micron, and in some embodiments less than about 250 microns. In some embodiments, staging capillaries 410 can be formed, for example, with a draft angle of about 1-5° and can define any thickness sufficient to achieve a predetermined volume. To further encourage the desired capillary action in staging capillaries 410, staging capillaries 410 can be provided with an interior surface that is hydrophilic, i.e., wettable. For example, the interior surface of staging capillaries 410 can be formed of a hydrophilic material and/or treated to exhibit hydrophilic characteristics. In some embodiments, the interior surface comprises native, bound, or covalently attached charged groups. For example, one suitable surface, according to some embodiments, is a glass surface having an absorbed layer of a polycationic polymer, such as poly-l-lysine.

Ramps

Figure 23A:
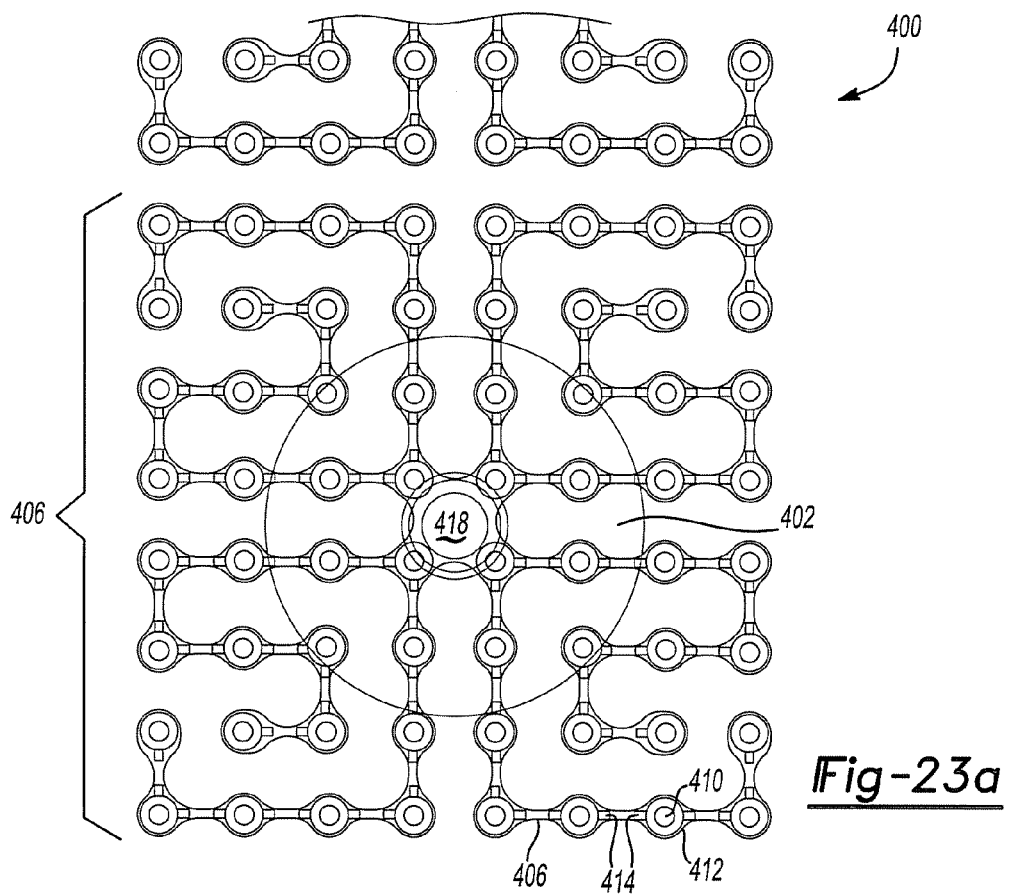
FIG. 23(a) is a top schematic view of a filling apparatus according to some embodiments.
Figure 23B:
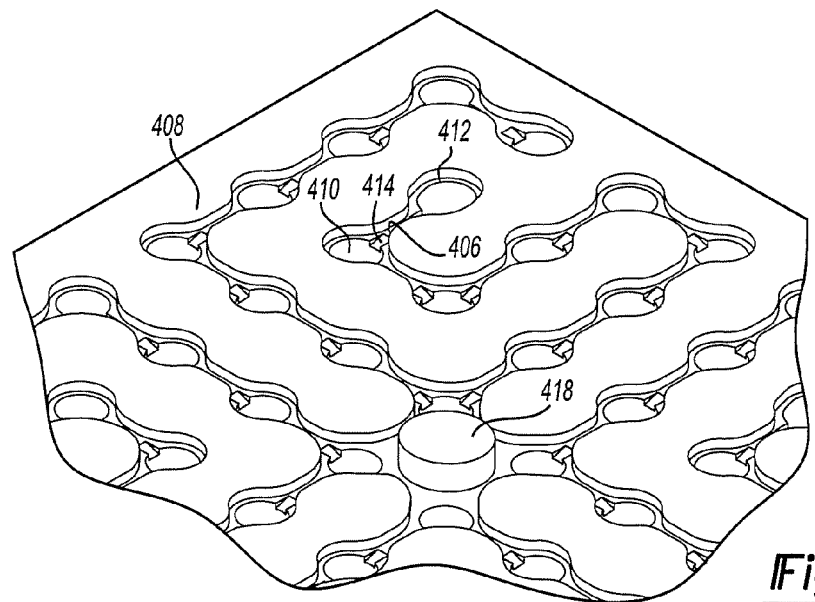
FIG. 23(b) is a top perspective view of a portion of a filling apparatus comprising a plurality of staging capillaries, microfluidic channels, and ramp features according to some embodiments.

In some embodiments, as illustrated in FIGS. 22(b) and 23(a)-(b), each of the plurality of staging capillaries 410 can comprise a ramp feature 414 disposed at an entrance thereof to achieve a predetermined capillary action. It should be appreciated that ramp feature 414 can be formed on one or more edges of the entrance to each of the plurality of staging capillaries 410. In some embodiments, ramp feature 414 can comprise a countersink lip or chamfered rim formed about the entire entrance. In some embodiments that do not employ the plurality of microfluidic channels 406, ramp feature 414 can be used to reduce an angle between staging capillary 410 and an upper surface 456 (to be described herein) of output layer 408 to aid in capillary flow and/or exposure time to a fluid bead moving thereby.

Nozzles Bottom Features

Figure 24:
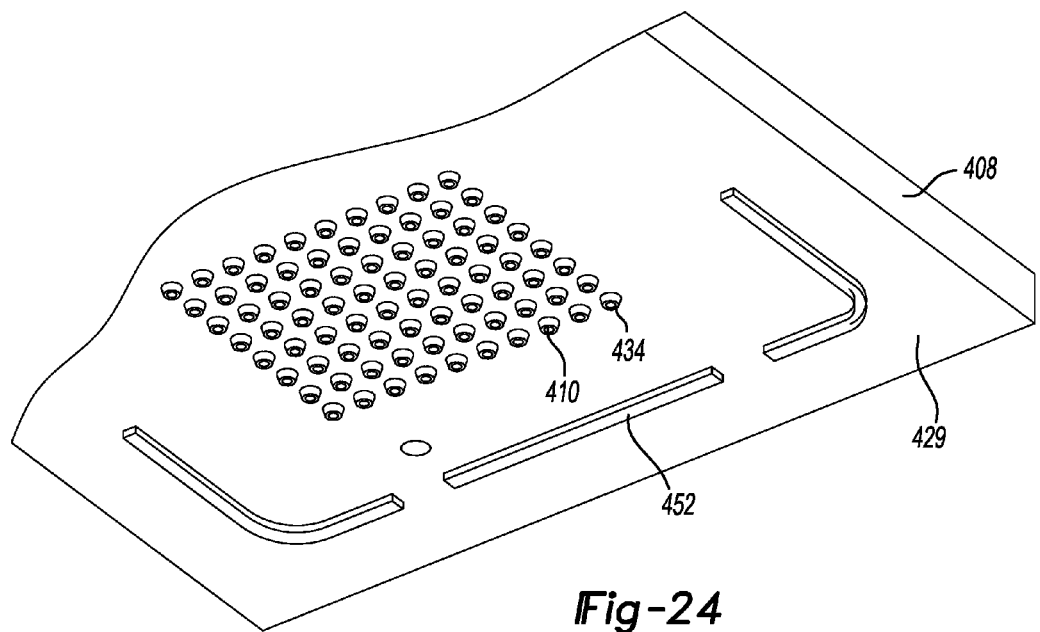
FIG. 24 is a bottom perspective view of an output layer of a filling apparatus comprising spacer features according to some embodiments.

In some embodiments, with reference to FIGS. 22(b) and 24, output layer 408 can comprise a protrusion 450 formed on an outlet 434 of staging capillary 410. In some embodiments, protrusion 450 can be shaped to cooperate with a corresponding shape of each of the plurality of wells 26. In some embodiments, protrusion 450 can be conically shaped to be received within circular rim portion 32 of each of the plurality of wells 26. In some embodiments, protrusion 450 can be square-shaped to be received within square-shaped rim portion 38 of each of the plurality of wells 26. Protrusion 450, in some embodiments, can define a sufficiently sharp surface such that the capillary force within staging capillary 410 can retain assay 1000 and protrusion 450 can inhibit movement of assay 1000 to adjacent wells 26. In some embodiments, protrusion 450 of output layer 408 can be positioned above microplate 20, flush with first surface 22 of microplate 20 (FIG. 22(a)), or disposed within well 26 of microplate 20 (FIG. 22(b)). In some embodiments, protrusion 450 can define a nozzle feature that comprises a diameter that is less than the diameter of the plurality of wells 26 to aid, at least in part, in capillary retention of assay 1000 within staging capillary 410.

Protrusion 450 can be provided with an exterior surface that is hydrophobic, i.e., one that causes aqueous medium deposited on the surface to bead. For example, protrusion 450 can be formed of a hydrophobic material and/or treated to exhibit hydrophobic characteristics. This can be useful, for example, to prevent spreading of a drop, formed at tip portion 1840. A variety of known hydrophobic polymers, such as polystyrene, polypropylene, and/or polyethylene, can be utilized to obtain desired hydrophobic properties. In addition, or as an alternative, a variety of lubricants or other conventional hydrophobic films can be applied to tip portion 1840.

Bottom Feature—Spacer

In some embodiments, as illustrated in FIG. 24, one or more spacer members 452 can be formed along bottom surface 429 of output layer 408 to, at least in part, achieve a desired spacing between output layer 408 and microplate 20. In some embodiments, spacer member 452 can be formed as an elongated member (FIG. 24), a post (FIG. 107), one or more spaced-apart members, or the like.

Fluidic Patterns

Figure 25A:
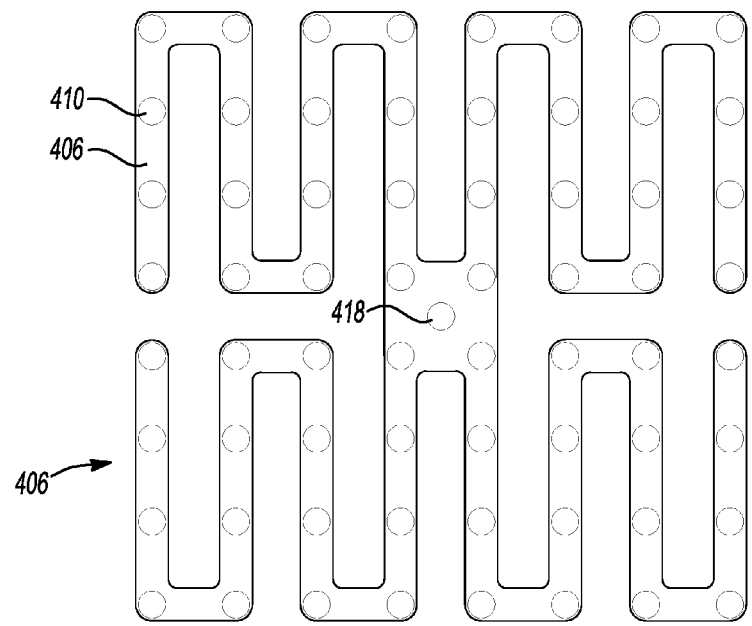
Figure 25B:
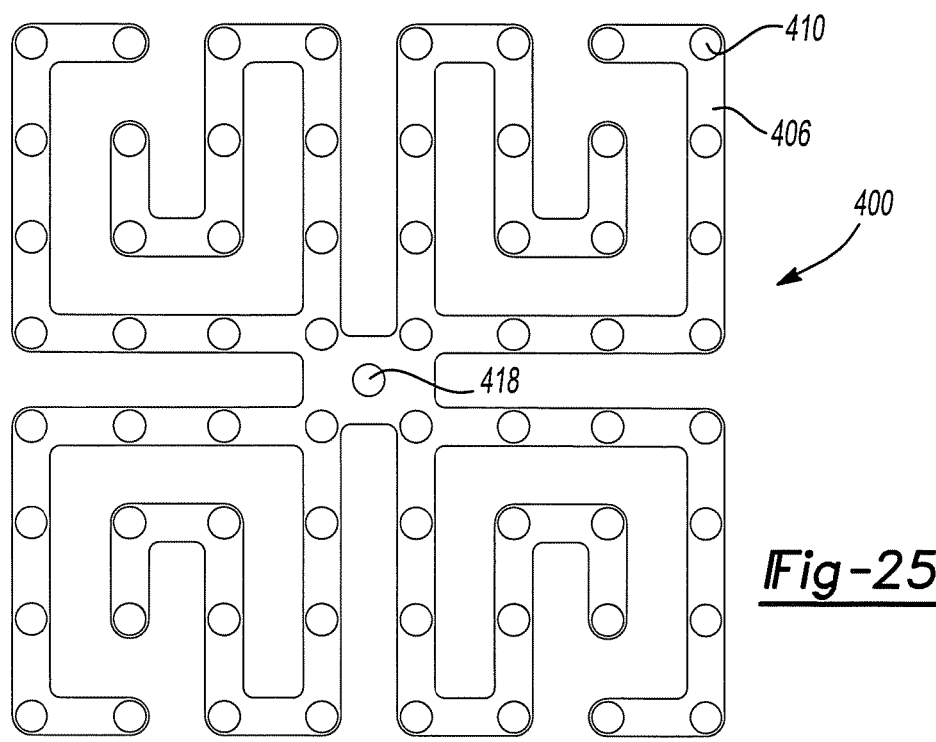
Figure 25C:
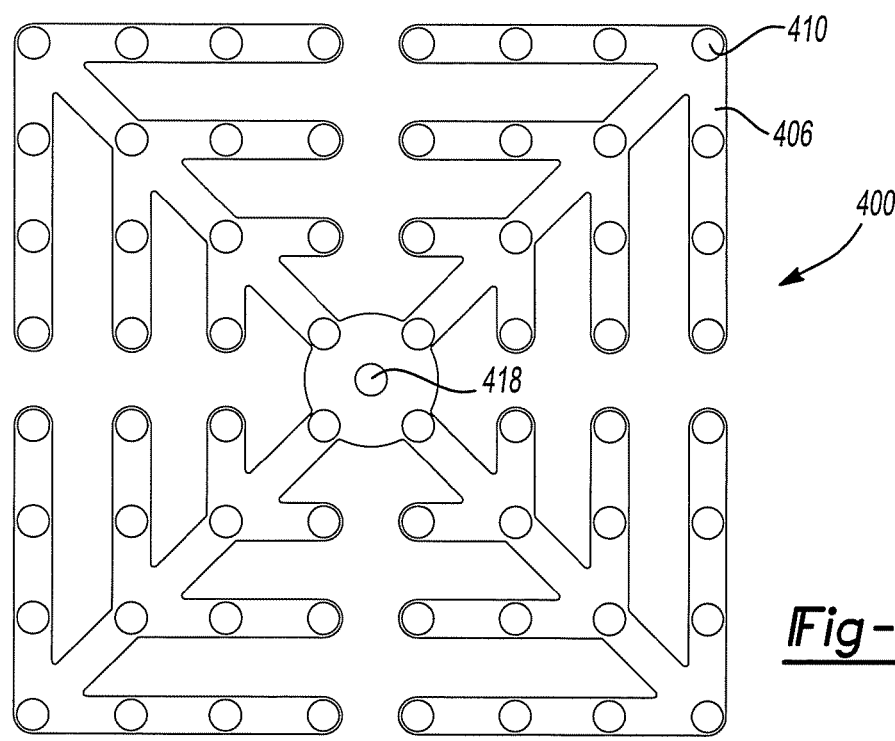
Figure 25D:
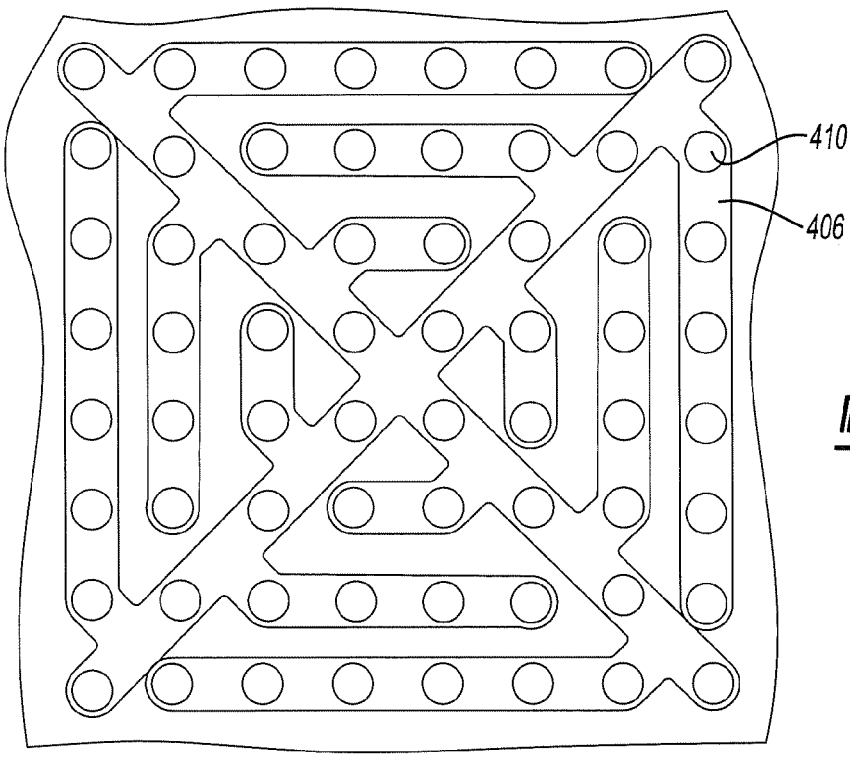
Figure 25E:
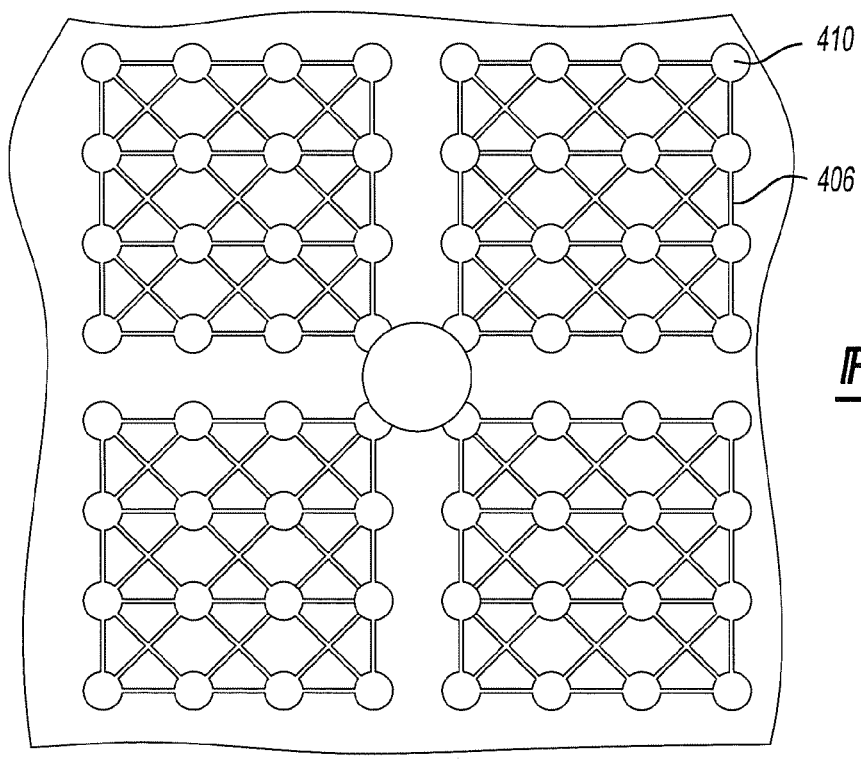
Figure 25F:
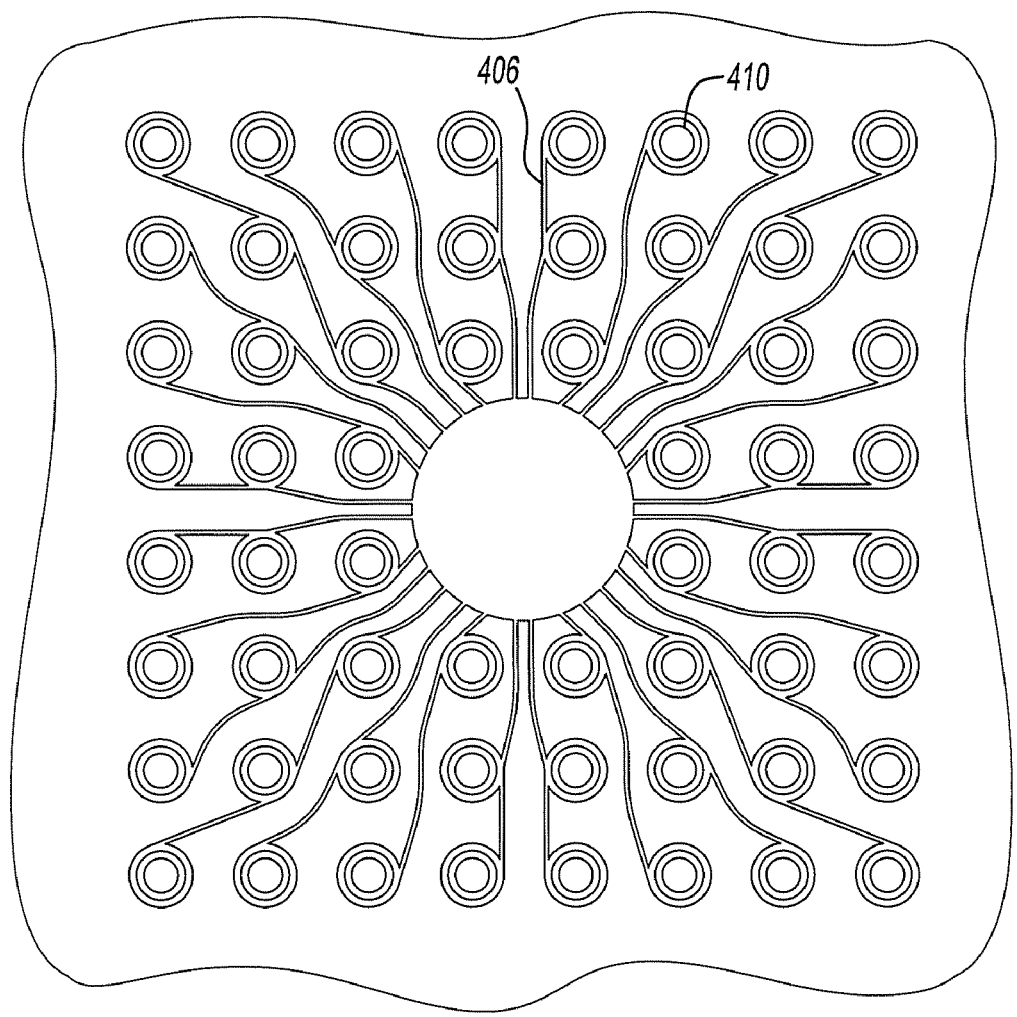

In some embodiments, as illustrated in FIGS. 23(a)-(b) and 25(a)(f), the plurality of microfluidic channels 406 can have any one of a plurality of configurations for carrying assay 1000 to each of the plurality of staging capillaries 410. In some embodiments, each of the plurality of staging capillaries 410 can be in fluid communication with only one of the plurality of microfluidic channels 406 (FIGS. 23(a)-(b), 25(a)-(d), and 25(f)) in a series-type configuration. In some embodiments, each of the plurality of staging capillaries 410 can be in fluid communication with two or more of the plurality of microfluidic channels 406 (FIG. 25(e)) in a multi-path or parallel-type configuration. In such parallel-type configurations, fluid can flow along the path of least resistance to fill each of the plurality of staging capillaries 410 in the least amount of time. In any configuration, the time required to fill each of the plurality of staging capillaries 410 can be reduced by reducing the length of each microfluidic channel 406. In some embodiments, a hybrid of the series-type and the parallel-type configurations can be used. In some embodiments, as illustrated in FIG. 25(f), each of the plurality of microfluidic channels 406 can be in fluid communication with only one edge of each of the plurality of staging capillaries 410 to provide pass-by and filling action simultaneously.

In some embodiments, each of the plurality of microfluidic channels 406 can exert, at least in part, a capillary force to draw fluid (e.g. assay 1000) therein to aid in reducing the time required to fill. The capillary force of each of the plurality of microfluidic channels 406 can be varied, at least in part, by varying at least the dimensional properties of the plurality of microfluidic channels 406 according to capillary principles.

Pressure Nodules

In some embodiments, as illustrated in FIGS. 106-113, filling apparatus 400 comprises input layer 404, output layer 408, and an intermediate layer 494, or any combination thereof for filling one or more components of assay 1000 into at least some of the plurality of wells 26 in microplate 20.

In some embodiments, intermediate layer 494 can be positioned and aligned between input layer 404 and output layer 408. In some embodiments, input layer 404 comprises assay input ports 402 extending therethrough. As illustrated in FIGS. 107 and 108, in some embodiments, each assay input port 402 can extend through input layer 404 and terminate at an extended outlet 496. In some embodiments, extended outlet 496 can be sized to extend from input layer 404 such that an end 498 of extended outlet 496 is spaced a predetermined distance from output layer 408 (FIG. 108). Extended outlet 496 can extend through a corresponding aperture 500 (FIG. 106) formed through intermediate layer 494.

In some embodiments, as illustrated in FIG. 108, extended outlet 496 can be aligned with surface tension relief post 418 extending upward from output layer 408. In some embodiments, an internal diameter of extended outlet 496 can be larger than an outer diameter of surface tension relief post 418 to permit surface tension relief post 418 to be at least partially received within extended outlet 496. Surface tension relief post 418, in some embodiments, can be sufficiently sized to facilitate even spreading of assay 1000 throughout the plurality of microfluidic channels 406 and/or engage a meniscus of assay 1000 within assay input port 402 to encourage flow. In some embodiments, extended outlet 496 and surface tension relief post 418 can cooperate to facilitate alignments of input layer 404, output layer 408, and intermediate layer 494.

In some embodiments, intermediate member 494 comprises microfluidic channels 406 extending there along (e.g., etched or otherwise formed in one major side thereof) in fluid communication with the plurality of staging capillaries 410 in output layer 408. For example, microfluidic channels 406, extending along a lower surface of intermediate layer 494, can communicate with upper-end openings of staging capillaries 410. It should be appreciated that the particular route configuration of microfluidic channels 406 can be any one of a number of configurations selected by one skilled in the art or one of those described herein. In some embodiments, intermediate member 494 can be compliant, or resiliently deformable, to permit flexing of intermediate member 494 in response to an external force. In some embodiments, intermediate member 494 can be made of polymeric materials, such as but not limited to rubber or silicone (PDMS).

As illustrated in FIGS. 107-111, in some embodiments, input layer 404 comprises one or more nodules 502 extending from a bottom surface 504. In some embodiments, nodules 502 can be patterned along bottom surface 504 such that each nodule 502 can engage a top surface 506 of compliant intermediate layer 494. During centrifugation, centripetal force exerted on input layer 404 can cause nodules 502 to engage compliant intermediate layer 494 to at least partially collapse or depress a segment of intermediate layer 494 against output layer 408 to minimize fluid communication between adjacent staging capillaries 410. In some embodiments, as illustrated in FIGS. 109 and 110, nodules 502 can be patterned such that each nodule 502 is positioned adjacent each of the plurality of staging capillaries 410. For example, nodules 502 can be disposed so that each nodule aligns, or corresponds, with a respective one of staging capillaries 410. In some embodiments, nodules 502 can be patterned over portions of microfluidic channels 406 to close microfluidic channel 406 during centrifugation. In some embodiments, as illustrated in FIG. 111, nodules 502 can be patterned over each of the plurality of staging capillaries 410 to seal each of the plurality of staging capillaries 410 during centrifugation. For example, upon being depressed by nodules 502 during centrifugation, segments of intermediate layer 494 can seal the upper end openings of respective, corresponding staging capillaries 410.

In some embodiments, as illustrated in FIGS. 111 and 112, a sealing feature 508 can extend from intermediate layer 494 that can be sized to fit into the corresponding staging capillary 410 by nodule 502 acting upon intermediate layer 494. These, and substantially equivalent, embodiments can be used to define a shut-off valve during centrifugation or anytime a force is applied to input layer 404 and/or intermediate layer 494.

It should be appreciated that the physical size and/or compliancy of one of more of input layer 404, intermediate layer 494, nodules 502, and sealing features 508 can be tailored to achieve a predetermined sealing engagement upon application of a predetermined amount of force. Additionally, it should be appreciated that nodules 502 and/or sealing feature 508 can be of any shape conducive to applying a force and sealing an opening, respectively, such as, but not limited to, triangular, square, or conical.

In some embodiments, to load each of the plurality of staging capillaries 410, a predetermined amount of assay 1000 can be placed at each assay input port 402. Capillary force, at least in part, can draw at least a portion of assay 1000 from assay input port 402 into microfluidic channels 406 and further fill at least some of the plurality of staging capillaries 410. In some embodiments, once at least some of the plurality of staging capillaries 410 are filled, output layer 408 and microplate 20 can be placed into a swing-arm centrifuge. In some embodiments, the centripetal force of the swing-arm centrifuge can be sufficient to overcome the surface tension of assay 1000 in each the plurality of staging capillaries 410, thereby forcing a metered volume of assay 1000 into each of the plurality of wells 26 of microplate 20. In some embodiments, the centripetal force of the centrifuge can be sufficient to exert a clamping force on at least one of input layer 404 and intermediate layer 494 to fluidly seal adjacent staging capillaries 410, either at the entrance thereof or therebetween, to prevent residual assay 1000 left in assay input port 402 or assay 1000 from an undesired one of the plurality of wells 26 of microplate 20 from overfilling a particular staging capillary. In some embodiments, an external force (e.g. mechanical, pneumatic, hydraulic, electro-mechanical, and the like) can be applied to exert a clamping force on at least one of input layer 404 and intermediate layer 494 to fluidly seal adjacent staging capillaries 410, either at the entrance thereof or therebetween.

In some embodiments, as illustrated in FIG. 113, at least some of input layer 404, intermediate layer 494, and output layer 408 can be used in conjunction with a clamp system 511. In some embodiments, clamp system 511 comprises a base structure 513 and one or more locking features 515 extending therefrom. In some embodiments, base structure 513 comprises at least one alignment feature 517 operably sized to engage a corresponding alignment feature 58 on microplate 20 to, at least in part, facilitate proper alignment of each of the plurality of staging capillaries 410 relative to each of the plurality of wells 26. In some embodiments, alignment feature 517 can further engage a corresponding alignment feature 519 formed in at least one of input layer 404, intermediate layer 494, and output layer 408. In some embodiments, at least some of microplate 20, input layer 404, intermediate layer 494, and output layer 408 can be coupled with base structure 513 such that locking feature 515 engages input layer 404 to exert a preload on intermediate layer 494 to prevent fluid flow and/or leakage of assay 1000 prior to achieving sufficient centrifugal speed in the centrifuge. In some embodiments, a top plate 521 can be used in conjunction with base structure 513 to ensure equal pressure application across input layer 404 by locking feature 515.

Venting

In some embodiments, as illustrated in FIGS. 114-119, filling apparatus 400 comprises input layer 404, output layer 408, and a vent layer 523, or any combination thereof for loading assay 1000 into at least some of the plurality of wells 26 in microplate 20. In some embodiments, output layer 408 comprises microfluidic channels 406 formed in a side thereof and extending there along in fluid communication with the plurality of staging capillaries 410 in output layer 408.

In some embodiments, input layer 404 comprises assay input ports 402 extending therethrough. As illustrated in FIGS. 115-116, in some embodiments, each assay input port 402 can extend through input layer 404 and terminate at extended outlet 496. In some embodiments, extended outlet 496 can be sized to extend from input layer 404 such that an end 498 of extended outlet 496 is generally flush to a top surface 525 of vent layer 523 and aligned to a flow aperture 527 extending through vent layer 523.

In some embodiments, input layer 404 comprises one or more vent features 529 (FIGS. 116-119). In some embodiments, vent feature 529 can be sized to have a capillary force associated therewith that is lower than a capillary force within microfluidic channels 406 and/or each of the plurality of staging capillaries 410 to reduce the likelihood of assay 1000 flow through or into vent feature 529. In some embodiments, vent feature 529 comprises a vent hole 531 extending through input layer 404 (FIGS. 114-118) and in communication with atmosphere. In some embodiments, vent hole 531 can be coupled to a chamber or manifold 533 (FIGS. 115 and 116) that can couple two or more vent apertures 535 formed in vent layer 523 to atmosphere.

In some embodiments, vent feature 529 comprises a pressure bore 537 (FIG. 117) associated with one or more of the plurality of staging capillaries 410. In some embodiments, pressure bore 537 can be formed in input layer 404. For example, pressure bore 537 can extend from a lower surface of input layer 404 toward, but stopping short of, an opposing surface. In some embodiments, plural pressure bores 537 are disposed in an array corresponding to an array defined by staging capillaries 410. Pressure bores 537, in some embodiments, can be sized to act as an air capacitor trapping a portion of air therein that can contract or expand during filling of assay 1000 into filling apparatus 400 and/or centrifuging assay 1000 into each of the plurality of wells 26, respectively.

Vent feature 529, in some embodiments, can at least partially relieve vacuum created when assay 1000 is centrifuged from each of the plurality of staging capillaries 410 into each of the corresponding plurality of wells 26 of microplate 20 and permit improved loading. In some embodiments, vent feature 529 can at least partially interrupt fluid flow between adjacent staging capillaries 410 by introducing an air gap therebetween. In some embodiments, such an air gap can provide consistent metering of assay 1000 loaded into each of the plurality of wells 26.

In some embodiments, vent layer 523 can be positioned and aligned between input layer 404 and output layer 408. In some embodiments, as illustrated in FIG. 116, flow aperture 527 of vent layer 523 can be aligned with surface tension relief post 418 extending upward from output layer 408. In some embodiments, an internal diameter of flow aperture 527 can be larger than the outer diameter of surface tension relief post 418 to permit surface tension relief post 418 to be at least partially received within flow aperture 527. Surface tension relief post 418, in some embodiments, can be sufficiently sized to facilitate even spreading of assay 1000 throughout the plurality of microfluidic channels 406 in output layer 408 and/or engage a meniscus of assay 1000 within assay input port 402 and/or flow aperture 527 to encourage flow. In some embodiments, extended outlet 496, flow aperture 527, and surface tension relief post 418 can cooperate to facilitate alignments of input layer 404, output layer 408, and vent layer 523.

As illustrated in FIGS. 116-118, in some embodiments, vent layer 523 can be aligned with input layer 404 and output layer 408 such that vent apertures 535 are positioned above or between each of the plurality of staging capillaries 410. In some embodiments, vent apertures 535 can be a circular bore (FIG. 117) or any other shape, such as oblong (FIG. 118), to accommodate for potential misalignment between input layer 404 and vent layer 523 and/or potential misalignment between vent layer 523 and output layer 408.

In some embodiments, vent layer 523 can be made of any material conducive to joining with input layer 404 and/or output layer 408. In some embodiments, vent layer 523 can comprise PDMS, which can aid in joining vent layer 523 to input layer 404 due to the intrinsic tackiness properties of PDMS. In some embodiments, vent layer 523 can be made using a double stick adhesive tape. In such embodiments, the double stick adhesive tape can be first applied to input layer 404 and then laser cut to accurately place vent apertures 535 to simplify assembly of input layer 404 and vent layer 523.

In some embodiments, to load each of the plurality of staging capillaries 410, a predetermined amount of assay 1000 can be placed at each assay input port 402. Such placement can be effected, for example, using an automated pipette system (e.g., a Biomek) or hand-operated single- or multi-channel pipette device (e.g., a Pipetman). Capillary force, at least in part, can draw at least a portion of assay 1000 from assay input port 402 into microfluidic channels 406 and further fill at least some of the plurality of staging capillaries 410. In some embodiments, outlet 434 of each of the plurality of staging capillaries 410 permits venting of air within each of the plurality of staging capillaries 410 during filling. In some embodiments, once at least some of the plurality of staging capillaries 410 are filled, input layer 404, vent layer 523, output layer 408, and microplate 20 can be placed into a swing-arm centrifuge. In some embodiments, the venting features 529 can reduce vacuum effects on assay 1000 during centrifugation to more easily meter a volume of assay 1000 into each of the plurality of wells 26 of microplate 20.

Assay Ports on Sides

In some embodiments, as illustrated in FIGS. 120-131, filling apparatus 400 can comprise assay input ports 402 positioned within and/or upon output layer 408. In some embodiments, as illustrated in FIG. 120, assay input ports 402 can be positioned at an end 420 of output layer 408. For example, such assay input ports can be positioned along a short dimension of a major surface (e.g., a top surface) of the output layer, adjacent and parallel to an end thereof. In some embodiments, as illustrated in FIG. 121, assay input ports 402 can be positioned at a side 422 of output layer 408. For example, such assay input ports can be positioned along a long dimension of a major surface (e.g., a top surface) of the output layer, adjacent and parallel to a side thereof. Still further, in some embodiments, as illustrated in FIG. 122, assay input ports 402 can be positioned at opposing ends 420 or opposing sides 422 (not illustrated) of output layer 408. In some embodiments, assay input ports 402 can be positioned at opposing ends 420 or opposing sides 422 (not illustrated) of output layer 408 with a fluid interrupt 409 (e.g. wall or barrier) to fluidly isolate those assay input ports 402 on one end or side from the remaining assay input ports 402 on the other end or side.

As illustrated in FIG. 123, in some embodiments, assay input ports 402 can each comprise a fluid well 424 bound by a plurality of upstanding walls 426. In some embodiments, fluid well 424 of each assay input port 402 can be in fluid communication with one or more corresponding microfluidic channels 406 through a throat 430 formed in fluid well 424. For example, such a throat can be formed in a lower region of the fluid well, so as to fluidly communicate the fluid well with the microfluidic channels. Throat 430 can comprise a diameter of, for example, 2 mm or less, 1 mm or less, 0.5 mm or less, or 0.25 mm or less. In some embodiments, such as illustrated in FIG. 123, throat 430 comprises a reservoir in fluid communication with one or more microfluidic channel 406. In some embodiments, surface tension relief post 418 can be disposed in throat 430 to, at least in part, evenly spread assay 1000 throughout the plurality of microfluidic channels 406 and/or engage a meniscus of assay 1000 to encourage fluid flow. Surface tension relief post can, according to some embodiments, comprise a hydrophilic surface in order to further encourage fluid flow into the throat and, thus, the microchannels.

In some embodiments, as illustrated in at least FIGS. 124-131, microfluidic channels 406 can be in fluid communication with the plurality of staging capillaries 410 extending from microfluidic channel 406, through output layer 408, to a bottom surface 429. In some embodiments, bottom surface 429 can be spaced apart from first surface 22 of microplate 20 (FIG. 124) or can be in contact with first surface 22 of microplate 20. In some embodiments, each of the plurality of staging capillaries 410 can be generally aligned with a corresponding one of the plurality of wells 26 of microplate 20. In some embodiments, a protective covering (not shown) can be disposed over microfluidic channels 406 to provide, at least in part, protection from contamination, reduced evaporation, and the like. It should be understood that such protective covering can be used with any of the various configurations set forth herein.

Figure 125:
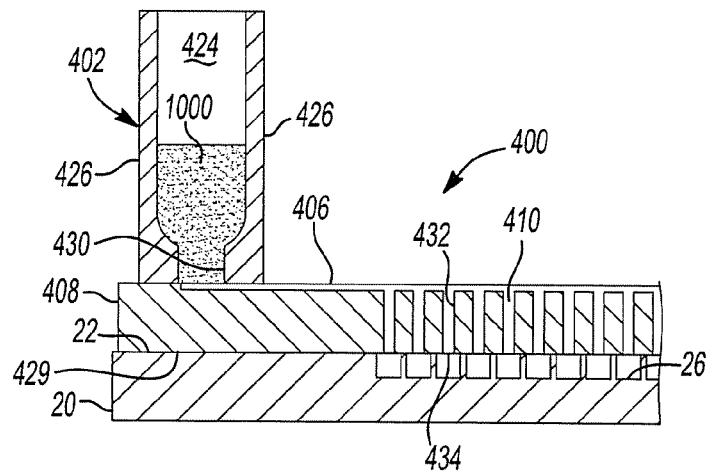
Figure 126:
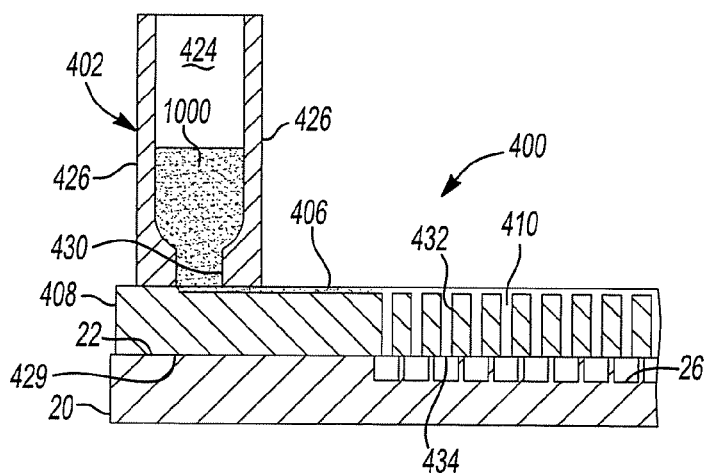
Figure 127:
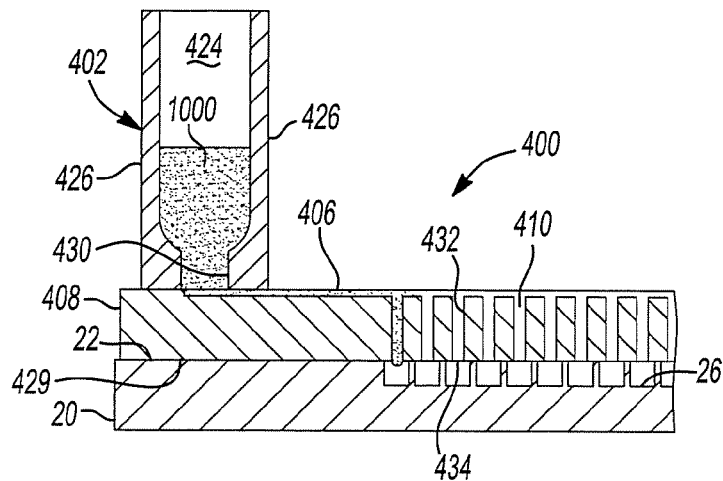
Figure 128:
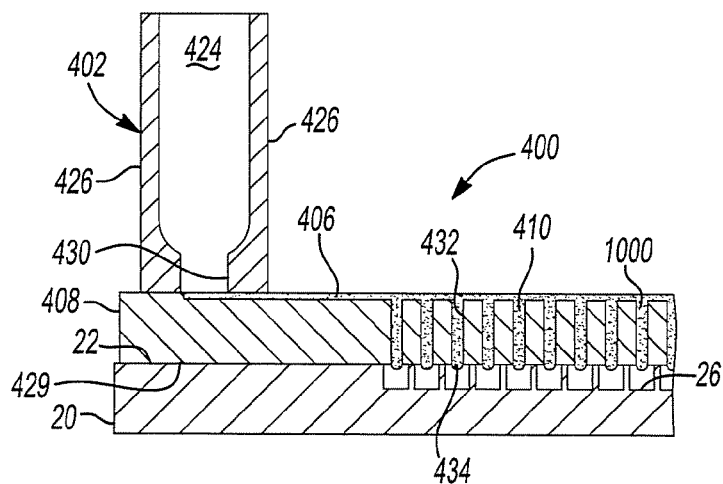

Referring to FIGS. 125-131, to perform a filling operation, each assay input port 402 can be at least partially filled with assay 1000 or different assays or fluids (FIG. 125). At least in part through hydraulic pressure and/or capillary force, assay 1000 can flow from fluid well 424 of each assay input port 402 through throat 430 into the one or more microfluidic channels 406 (FIG. 126). As assay 1000 flows across an end-opening or mouth 432 of each of the plurality of staging capillaries 410, capillary action, at least in part, draws a metered amount of assay 1000 therein (FIG. 127). Assay 1000 can continue to flow down the one or more microfluidic channels 406 until each of the plurality of staging capillaries 410 can be at least partially filled with assay 1000 (FIG. 128). In some embodiments, assay 1000 in each of the plurality of staging capillaries 410 can be held therein by capillary or surface tension forces to aid in the equal metering of assay 1000 to be loaded in each of the plurality of wells 26. In some embodiments, outlet 434 of each of the plurality of staging capillaries 410 permits venting of air within each of the plurality of staging capillaries 410 during filling.

Figure 129:
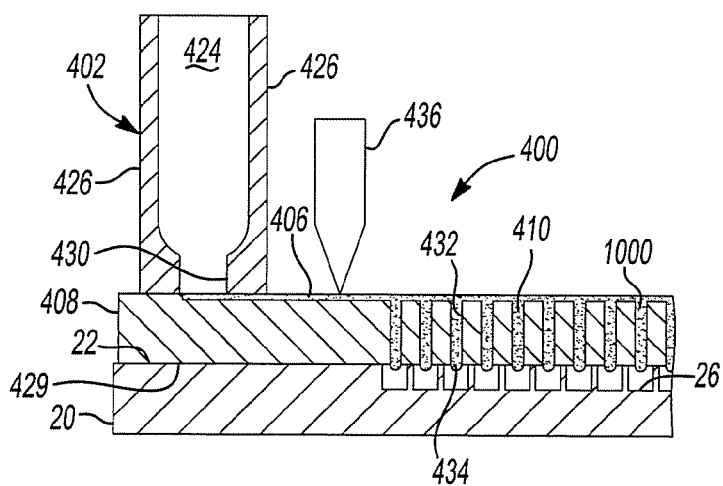
Figure 130:
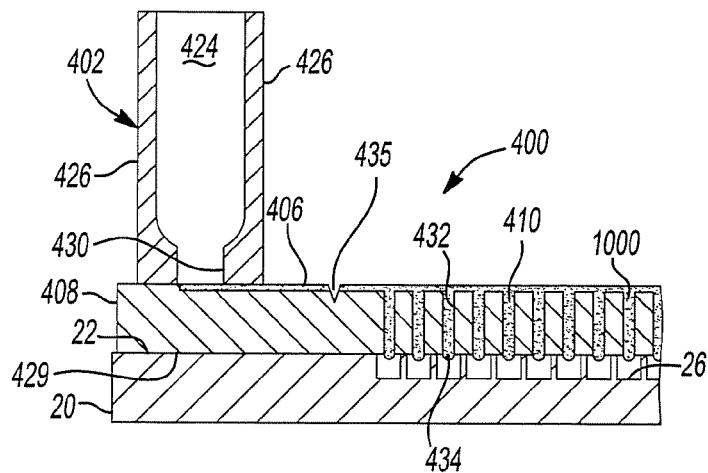

As illustrated in FIGS. 129 and 130, in some embodiments, filling apparatus 400 can be stake cut, generally indicated at 435, via device 436 along a portion of one or more microfluidic channels 406. In some embodiments, stake-cutting serves to, at least in part, aid in metering of assay 1000 in each well 26 by isolating the plurality of staging capillaries 410 from any excess assay 1000 left in each assay input port 402. This arrangement can minimize additional assay 1000 left within each assay input port 402 from overfilling each of the plurality of wells 26 during later centrifugation. In some embodiments, stake cutting can be completed through mechanical and/or thermal deformation (e.g. heat staking) of output layer 408. It should be appreciated that a Zbig valve can be used to achieve fluid isolation between the plurality of staging capillaries 410 and assay input port 402, such as those described in commonly-assigned U.S. patent application Ser. No. 10/336,274, filed Jan. 3, 2003 and PCT Application No. WO 2004/011147 A1.

Figure 131:
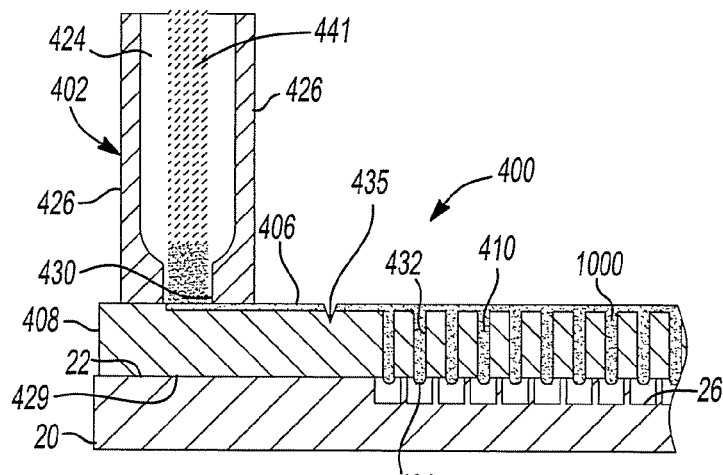

As illustrated in FIG. 132, in some embodiments, filling apparatus 400 can comprise reduced material areas 438 disposed in output layer 408. In some embodiments, reduced-material areas 438 comprise one or more cutout portions 440 (e.g. voids, slots, holes, grooves) formed in output layer 408 on opposing sides of microfluidic channels 406. The use of reduced material areas 438 can provide, among other things, reduced thermal capacity in the localized areas, which can increase the rate of heat staking and/or stake cutting. In some embodiments, the elongated shape of cutout portion 440 can accommodate any misalignment of the staking tool relative to output layer 408. In some embodiments, following staking, excess assay 1000 in assay input ports 402 and/or the upstream portion of microfluidic channels 406 relative to stake cut 435 can be removed, if desired. In some embodiments, this can be accomplished by employing a wicking member 441, as illustrated in FIG. 131.

Figure 133:
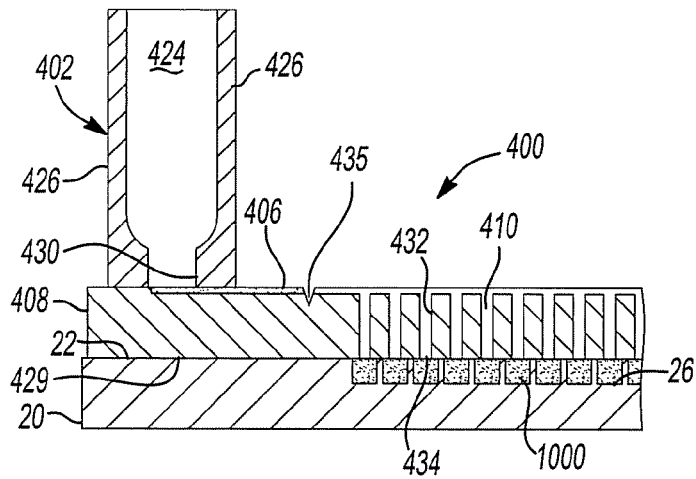

In some embodiments, once at least some of the plurality of staging capillaries 410 are filled, output layer 408 and microplate 20 can be placed into a swing-arm centrifuge. In some embodiments, the centripetal force of the swing-arm centrifuge can be sufficient to overcome the surface tension of assay 1000 in each the plurality of staging capillaries 410, thereby forcing a metered volume of assay 1000 into each of the plurality of wells 26 of microplate 20 (FIG. 133).

Referring again to FIGS. 120-122, filling apparatus 400 can be configured in any one of a number of configurations as desired. As described above, as illustrated in FIG. 120, assay input ports 402 can be positioned at end 420 of output layer 408. When this configuration is used with a microplate comprising 6,144 wells, filling apparatus 400 can comprise, for example, eight assay input ports 402 that can each be in fluid communication with eight respective microfluidic channels 406. Each of the eight microfluidic channels 406 can be in fluid communication with ninety-six respective staging capillaries 410. In some embodiments, as illustrated in FIG. 121, assay input ports 402 can be positioned at side 422 of output layer 408. When this configuration is used with a microplate comprising 6,144 wells, filling apparatus 400 can comprise, for example, eight assay input ports 402 that can each be in fluid communication with twelve respective microfluidic channels 406. Each of the twelve microfluidic channels 406 can be in fluid communication with sixty-four respective staging capillaries 410. This configuration can provide shorter channel lengths, which, in some circumstances, can have more rapid capillary filling times relative to the configuration of FIG. 120.

In some embodiments, as illustrated in FIG. 122, assay input ports 402 can be positioned at opposing ends 420 or opposing sides 422 (configuration not illustrated) of output layer 408. When the configuration illustrated in FIG. 122 is used with a microplate comprising 6,144 wells, filling apparatus 400 can comprise, for example, sixteen assay input ports 402 that can each be in fluid communication with twelve respective microfluidic channels 406. Each of the twelve microfluidic channels 406 can be in fluid communication with thirty-two respective staging capillaries 410. Likewise, when sixteen assay input ports 402 are positioned along opposing sides 422, sixteen assay input ports 402 can each be in fluid communication with eight respective microfluidic channels 406. Each of the eight microfluidic channels 406 can be in fluid communication with forty-eight respective staging capillaries 410. These configurations can provide shorter channel lengths, which, in some circumstances, can have more rapid capillary filling times relative to the configurations of FIGS. 120 and 121.

In some embodiments, the plurality of microfluidic channels 406 can be oriented such that, during centrifugation, they are perpendicular to an axis of revolution of the centrifuge. In some embodiments, this orientation can limit the flow of assay 1000 along the plurality of microfluidic channels 406 during centrifugation.

Overfill Solutions

In some embodiments, metering a predetermined amount of assay 1000 into each of the plurality of staging capillaries 410 and finally into each of the plurality of wells 26 can be achieved using a plurality of overfill reservoirs disposed in output layer 408. Referring to FIGS. 134-139, in some embodiments, filling apparatus 400 comprises fluid well 424 in fluid communication with one or more corresponding microfluidic channels 406 in fluid communication with the plurality of staging capillaries 410. In some embodiments, at least one microfluidic channel 406 comprises one or more fluid overfill reservoir 442 in fluid communication therewith. In some embodiments, the one or more fluid overfill reservoir 442 can be a bore opened at one end (e.g., a bore extending into output layer 408 from a surface thereof; with the bore having an open upper-end and a closed bottom end.)

Figure 134:
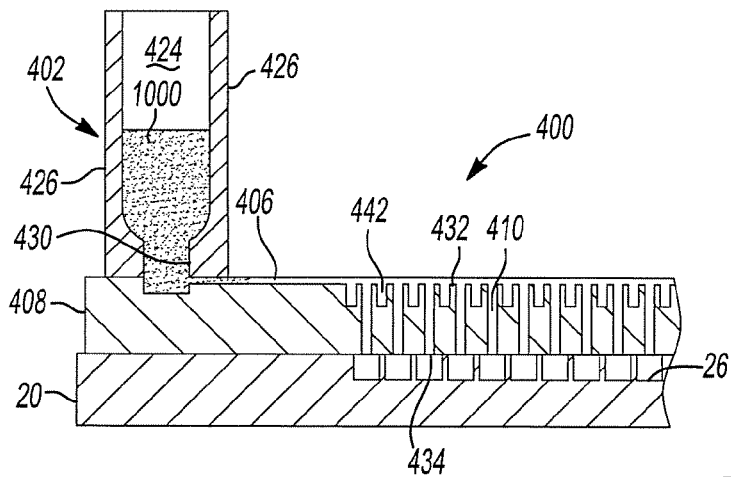
Figure 135:
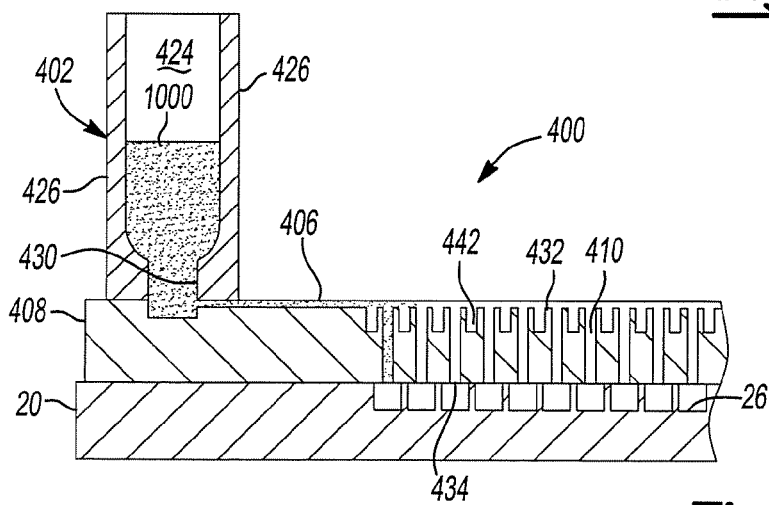
Figure 136:
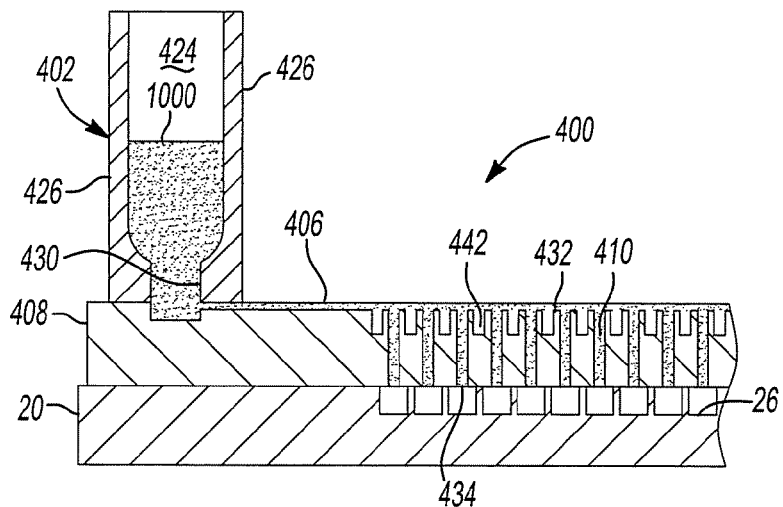

As illustrated in FIGS. 134-139, to perform a filling operation, each assay input port 402 can be at least partially filled with assay 1000 or other desired fluid (FIG. 134). At least in part through hydraulic pressure and/or capillary force, assay 1000 can flow from fluid well 424 of each assay input port 402 into the one or more microfluidic channels 406 (FIG. 134). As assay 1000 flows across an upper-end opening or mouth 432 of each of the plurality of staging capillaries 410, capillary action, at least in part, draws a metered amount of assay 1000 therein (FIG. 135). Assay 1000 can continue to flow down the one or more microfluidic channels 406 until each of the plurality of staging capillaries 410 can be at least partially filled with assay 1000 (FIG. 136). In some embodiments, fluid overfill reservoir 442 can generally inhibit assay 1000 from flowing into fluid overfill reservoir 442, at least in part because of the single opening therein generally preventing air within fluid overfill reservoir 442 from exiting. In some embodiments, fluid overfill reservoir can have a diameter equal to that of staging capillaries 410 and a depth of about 0.05 inch, or less.

In some embodiments, assay 1000 in each of the plurality of staging capillaries 410 can be held therein by capillary or surface tension forces to aid in the equal metering of assay 1000 to be loaded in each of the plurality of wells 26. In some embodiments, a lower-end opening or open-air outlet 434 of each of the plurality of staging capillaries 410 permit venting of air within each of the plurality of staging capillaries 410 during filling.

Figure 137:
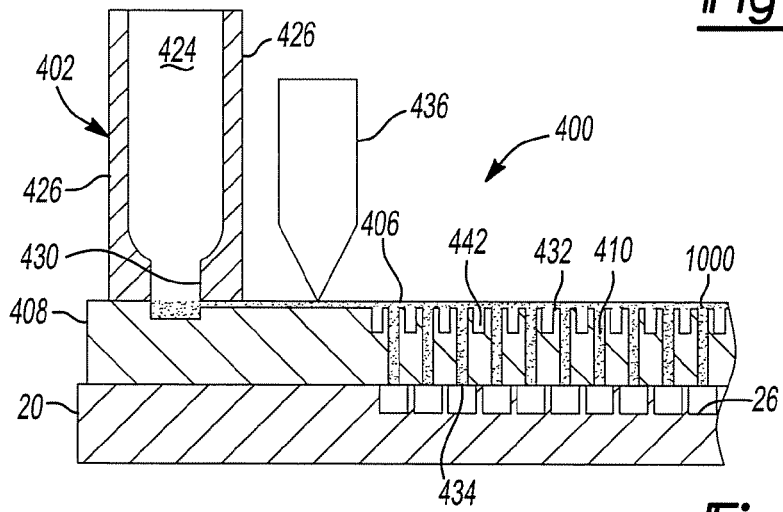
Figure 138:
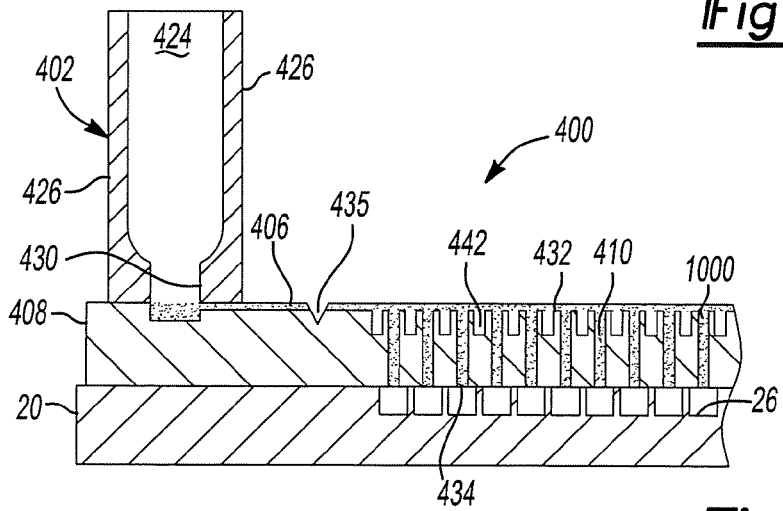

As illustrated in FIGS. 137 and 138 and described above, in some embodiments, filling apparatus 400 can be stake cut, generally indicated at 435, via device 436 along a portion of one or more microfluidic channels 406. It should be appreciated that stake-cutting or staking can be carried out, as previously described.

Figure 139:
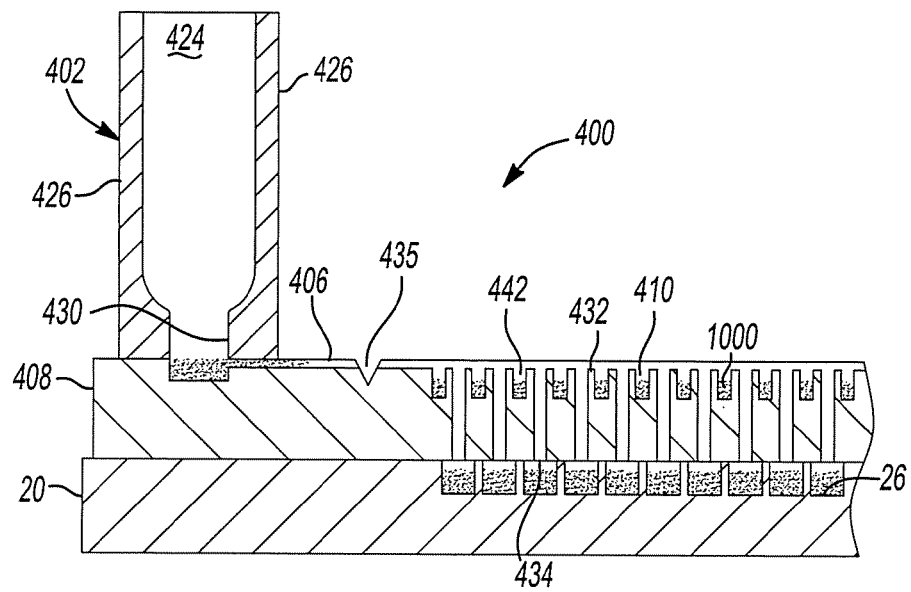

In some embodiments, once at least some of the plurality of staging capillaries 410 are filled, at least output layer 408 and microplate 20 can be placed into a swing-arm centrifuge. In some embodiments, the centripetal force of the centrifuge can be sufficient to overcome the capillary force and/or surface tension of assay 1000 in each the plurality of staging capillaries 410, thereby forcing a metered volume of assay 1000 into each of the plurality of wells 26 of microplate 20 (FIG. 139). In some embodiments, the centripetal force of the centrifuge can be sufficient to force overfill fluid (e.g. assay 1000 still remaining in microfluidic channels 406) into overfill reservoir 442, thereby displacing the air within overfill reservoir 442, rather than into the plurality of staging capillaries 410. In some embodiments, this air can serve to isolate one staging capillary 410 from an adjacent staging capillary 410. In some embodiments, overfill reservoir 442 can act as a reservoir for excess assay 1000. As illustrated in FIG. 140, in some embodiments, overfill reservoir 442 can be disposed within output layer 408 and generally aligned with and positioned below at least one assay input port 402 in output layer 408.

Microfluidic Channel Shapes

As illustrated in FIGS. 141(*a*)-(*g*) and 142(*a*)-(*g*), in some embodiments, microfluidic channels 406 can have any one or a combination of various configurations. In some embodiments, as illustrated in FIG. 141(*a*), each microfluidic channel 406 can be in fluid communication with a pair of rows of the plurality of staging capillaries 410 via feeder channels 444. In some embodiments, as illustrated in FIGS. 141(*b*), 142(*a*), and 142(*c*), microfluidic channel 406 can be in fluid communication with a row of staging capillaries 410 that can be offset to one side of microfluidic channel 406. In some embodiments, as illustrated in FIGS. 141(*c*)-(*e*) and 142(*d*)-(*f*), a cross dimension, e.g., width, of microfluidic channel 406 can vary relative to a diameter of each of the plurality of staging capillaries 410 ranging from larger than the diameter of each staging capillaries 410 to about equal to the diameter of each staging capillaries 410 to less than the diameter of each staging capillary (FIGS. 25(*e*)-(*f*)). In some embodiments, as illustrated in FIGS. 141(*f*), 141(*g*), 142(*a*), and 142(*b*), microfluidic channel 406 can have a generally triangular cross-section that can be either aligned with or offset from staging capillaries 410. In some embodiments, as illustrated in FIG. 142(*g*), microfluidic channel 406 can have a single channel portion 446 fluidly coupled to two or more rows of staging capillaries 410. In some embodiments, single channel portion 446 comprises a centrally disposed feature 448 to, in part, aid in fluid splitting between adjacent rows of staging capillaries 410.

In some embodiments, capillary or surface tension forces encourage flow of assay 1000 through microfluidic channels 406. In this regard, microfluidic channels 406 can be of capillary size, for example, microfluidic channels 406 can be formed with a width of less than about 500 micron, and in some embodiments less than about 125 microns, less than about 100 microns, or less than about 50 microns. In some embodiments, microfluidic channels 406 can be formed, for example, with a depth of less than about 500 micron, and in some embodiments less than about 125 microns, less than about 100 microns, or less than about 20 microns. To further encourage the desired capillary action in microfluidic channels 406, microfluidic channels 406 can be provided with an interior surface that is hydrophilic, i.e., wettable. For example, the interior surface of microfluidic channels 406 can be formed of a hydrophilic material and/or treated to exhibit hydrophilic characteristics. In some embodiments, the interior surface comprises native, bound, or covalently attached charged groups. For example, one suitable surface, according to some embodiments, is a glass surface having an absorbed layer of a polycationic polymer, such as poly-l-lysine.

Floating Inserts

In some embodiments, as illustrated in FIGS. 143-157, filling apparatus 400 comprises output layer 408, a floating insert 460, a cover 464, port member 467, or any combination thereof for loading assay 1000 into at least some of the plurality of wells 26 in microplate 20.

In some embodiments, output layer 408 comprises one or more recessed regions or depressions 454 formed in an upper surface 456 of output layer 408. Each depression 454 can be, in some embodiments, sized and/or shaped to receive floating insert 460 therein. In some embodiments comprising two or more depressions 454, at least one wall 458 can be used to separate each depression 454 to define grouping 407 of staging capillaries 410 of any desired quantity and orientation.

In some embodiments, as illustrated in FIG. 144, floating insert 460 and depression 454 can together define a capillary gap 468 between a bottom surface 470 of floating insert 460 and a top surface 472 of depression 454. In some embodiments, capillary gap 468 can result from surface variations in bottom surface 470 of floating insert 460 and/or top surface 472 of depression 454 and/or spacing gaps formed therebetween. It should be appreciated that capillary gap 468 can be quite small; therefore, the drawings of the present application may exaggerate this feature for ease of printing and understanding. In some embodiments, capillary gap 468 exhibits a capillary force sufficient to draw assay 1000 there along and to mouth 432 of each staging capillary 410. In some embodiments, bottom surface 470 of floating insert 460 and/or top surface 472 of depression 454 can be treated and/or coated to enhance the hydrophilic properties of capillary gap 468. In some embodiments, capillary gap 468 can be in fluid communication with an aperture 462 extend through floating insert 460. Aperture 462 can be centrally located relative to floating insert 460 or can be located to one side and/or corner thereof. In some embodiments, aperture 462 comprises an assay receiving well 463 (FIG. 145-157). In such embodiments, port member 467 is optional.

As illustrated in FIG. 144, in some embodiments, to reduce capillary force between a sidewall 474 of floating insert 460 and wall 458 of depression 454, the thickness of floating insert 460 and the depth of depression 454 can be minimized to shorten the length of any resulting capillary channel and, thus, reduce the overall capillary force in this region. In some embodiments, as illustrated in FIGS. 145-157, floating insert 460 comprises a flanged base portion 490 to reduce the potential capillary surface between sidewall 474 of floating insert 460 and wall 458 of depression 454. In some embodiments, a hydrophic surface can be employed between floating insert 460 and wall 458 of depression 454 to reduce capillary force therebetween. In some embodiments, this hydrophic surface can result from native material characteristics, treatments, coatings, and the like.

In some embodiments, as illustrated in FIGS. 147-152, floating insert 460 can be shaped to, at least in part, achieve any particular capillary and/or flow characteristics. In some embodiments, as illustrated in FIGS. 147-149, floating insert 460 can comprise a plurality of flow features 478 to, at least in part, extend the capillary surface to facilitate capillary flow. In some embodiments, for example, each of the plurality of flow features 478 comprises a post member 480 (FIG. 147) extending orthogonally from bottom surface 470 of floating insert 460. In some embodiments, post member 480 comprises a radiused root portion 482 to facilitate capillary flow, if desired. In some embodiments, post member 480 can be offset within the corresponding staging capillary 410 and can, if desired, contact a sidewall of staging capillary 410. In some embodiments, each of the plurality of flow features 478 comprises a tapered member 484 (FIGS. 148-152) extending from bottom surface 470 of floating insert 460. In some embodiments, each of the plurality of staging capillaries 410 comprises a corresponding mating entrance feature 486 (FIGS. 148, 150, and 151) to closely conform to each flow feature 478 to define a transition capillary gap 488. Tapered member 484 can be conically shaped (FIGS. 148-149) to closely conform to the complementarily-shaped mating entrance feature 486 in staging capillary 410. It should be appreciated that in some embodiments, the plurality of flow features 478 can further serve to individually plug or seal each corresponding capillary 410 during centrifugation (FIG. 152).

In some embodiments, floating insert 460 can comprise any material conducive to encourage capillary action along capillary gap 468, such as but not limited to plastic, glass, elastomer, and the like. In some embodiments, floating insert 460 can be made of at least two materials, such that an upper portion can be made of a first material and a lower portion can be made of a second material. In some embodiments, the second material can provide a desired compliancy, hydrophilicity, or any other desire property for improved fluid flow and/or sealing of staging capillaries 410. In some embodiments, the tapered members can include a seal-facilitating film, coating, or gasket thereon.

In some embodiments, as seen in FIG. 144, cover 464 can be used, at least in part, to retain floating insert 460 within each depression 454, if desired. In some embodiments, cover 464 comprises an aperture 466 generally aligned with an aperture 462 of floating insert 460. In some embodiments, cover 464 comprises a pressure sensitive adhesive to, at least in part, retain floating insert 460 within depression 454.

As illustrated in FIGS. 143 and 144, in some embodiments, port member 467 comprises assay input port 402. In some embodiments, port member 467 can comprise a material comprising sufficient weight such that during centrifugation, the centripetal force of port member 467 exerted upon floating insert 460 and output layer 408 can aid in closing off cross-communication of fluid between adjacent staging capillaries 410, as the upper-end openings of staging capillaries 410 can be covered and sealed by the lower surface of floating insert 460. In some embodiments, port member 467 can be sized such that its footprint (e.g. the surface area of a bottom surface 476 of port member 467) can be smaller than the opening of depression 454 to aid in the exertion of centripetal force on floating insert 460 during centrifuge.

In some embodiments, as illustrated in FIG. 153-155, to load each of the plurality of staging capillaries 410, a predetermined amount of assay 1000 can be placed at each assay input port 402 when used with port member 467 or receiving well 463. Capillary gap 468 can be sized to provide sufficient capillary force to draw at least a portion of assay 1000 from assay input port 402 or receiving well 463 into capillary gap 468. The capillary force of capillary gap 468 can be, at least in part, due to the non-rigid connection between floating insert 460 and output layer 408. As illustrated in FIG. 154, as assay 1000 is drawn into and spreads about capillary gap 468, each of the plurality of staging capillaries 410 in fluid communication with capillary gap 468 can begin to fill, at least in part, by capillary force as described herein.

In some embodiments, once at least some of the plurality of staging capillaries 410 are filled, at least output layer 408 and microplate 20 can be placed into a centrifuge. For example, the pieces can be clamped or otherwise held together, and then placed in a bucket centrifuge as a unit. In some embodiments, the centripetal force of the centrifuge can be sufficient to overcome the capillary force and/or surface tension of assay 1000 in each the plurality of staging capillaries 410, thereby forcing a metered volume of assay 1000 into each of the plurality of wells 26 of microplate 20. In some embodiments, the centripetal force of the centrifuge can also cause floating insert 460 to be forced and, thus, pressed against top surface 472 of depression 454. In some embodiments, where port member 467 is installed (FIGS. 143 and 144) or any additional weight member 492 (FIGS. 156 and 157), this additional weight can further apply a force upon floating insert 460 to force floating insert 460 against top surface 472 of depression 454. This force on floating insert 460 against top surface 472 of depression 454 can help to fluidly isolate each staging capillaries 410 from adjacent staging capillaries 410 for improved metering.

It should be appreciated that any component of filling apparatus 400, such as input layer 404, output layer 408, floating insert 460, cover 464, port member 467, intermediate layer 494, vent layer 523, etc., can comprise a plate, tile, disk, chip, block, wafer, laminate, and any combinations thereof, and the like.

Surface Wipe

As illustrated, for example, in FIGS. 158-166, in some embodiments, filling apparatus 400 does include the plurality of microfluidic channels 406. In some embodiments, for example, filling apparatus 400 comprises output layer 408 and a surface wipe assembly 1800 for loading assay 1000 into at least some of the plurality of wells 26 in microplate 20. In some embodiments, surface wipe assembly 1800 comprises one or more of a base support 1810, a drive assembly 1812, a funnel assembly 1814, or any combination thereof.

In some embodiments, such as illustrated in FIG. 158, base support 1810 can be a generally planar support member operable to support microplate 20 and output layer 408 thereon. In some embodiments, base support 1810 comprises an alignment feature 1818 that can engage corresponding alignment feature 58 (refer to previous figures) of microplate 20 and/or alignment feature 519 of output layer 408 to maintain microplate 20 and output layer 408 in a predetermined alignment relative to each other and/or funnel assembly 1814.

In some embodiments, drive assembly 1812 comprises a drive motor 1816; a guide member 1820, coupled to or formed in base support 1810; a tracking member 1822, coupled to or formed in funnel assembly 1814; and control system 1010. In some embodiments, guide member 1820 and tracking member 1822 are sized and/or shaped to slidingly engage with each other to provide guiding support for funnel assembly 1814 as it moves relative to base support 1810. In some embodiments, drive motor 1816 can be operably coupled to tracking member 1822 or base support 1810 to move tracking member 1822 relative to guide member 1820 via known drive transmission interfaces, such as mechanical drives, pneumatic drives, hydraulic drives, electromechanical drives, and the like. In some embodiments, drive motor 1816 can be controlled in response to control signals from control system 1010 or a separate control system. In some embodiments, drive motor 1816 can be operably controlled in response to a switch device controlled by a user.

In some embodiments, funnel assembly 1814 comprises a spanning portion 1824 generally extending above output layer 408. In some embodiments, spanning portion 1824 can be supported on opposing ends by tracking member 1822 of drive assembly 1812 and a foot member 1826. Tracking member 1822 and foot member 1826 can each be coupled to spanning portion 1824 via conventional fasteners in some embodiments. Foot member 1826 can be generally arcuately shaped so as to reduce the contact area between foot member 1826 and base support 1810. In some embodiments, foot member 1826 can be made of a reduced friction material, such as Delrin®.

In some embodiments, spanning portion 1824 of funnel assembly 1814 comprises a slot 1828 formed vertically therethrough that can be sized and/or shaped to receive a funnel member 1830 therein. As illustrated in FIGS. 158-166, funnel member 1830 can comprise one or more assay chambers 1832 for receiving one or more different assays therein. It should be appreciated that drive assembly 1812 and funnel assembly 1814 can be configured to track in a direction perpendicular to that illustrated in the accompanying figures to provide an increased number of assay chambers 1832 and reduced track distances. In some embodiments, such as illustrated in FIG. 159, funnel member 1830 can comprise a flange portion 1834 extending about a top portion thereof. Flange portion 1834 of funnel member 1830 can be sized and/or shaped to rest upon a corresponding flange portion 1836 of slot 1828 of spanning portion 1824 to support funnel member 1830. However, it should be appreciated that funnel member 1830 can comprise any outer profile complementary to slot 1828.

Assay chambers 1832, in some embodiments, can be shaped to provide a predetermined assay capacity for filling all of a predetermined number and/or grouping of the plurality of staging capillaries 410 in output layer 408. In some embodiments, assay chamber 1832 comprises converging sidewalls 1838 that terminate at a tip portion 1840.

In some embodiments, such as illustrated in FIG. 160-162, to load each of the plurality of staging capillaries 410, a predetermined amount of assay 1000 can be placed in each assay chamber 1832. In some embodiments, each assay chamber 1832 comprises a different assay. Assay 1000 is drawn down along sidewalls 1838 to tip portion 1840 to form a fluid bead 1842 extending from tip portion 1840 that can be in contact with upper surface 456 of output layer 408. In some embodiments, fluid bead 1842 can be bound by a lip or wiper member 1844 extending downwardly from tip portion 1840 of funnel member 1830. In some embodiments, wiper member 1844 can, at least in part, wipe and/or remove excess assay 1000 on upper surface 456 of output layer 408 as funnel member 1830 moves thereabout. In some embodiments, drive assembly 1812 can be actuated to advance funnel assembly 1814 across output layer 408 at a predetermined rate, as illustrated in FIG. 161. However, it should be appreciated that funnel assembly 1814 can be advanced manually across output layer 408. As funnel assembly 1814 is advanced across output layer 408, in some embodiments, fluid bead 1842 can contact the upper-end opening or entrance of each of the plurality of staging capillaries 410 and begin to fill, at least in part, by capillary force as described herein.

In some embodiments, such as illustrated in FIGS. 158 and 162, as funnel assembly 1814 continues past the last of the plurality of staging capillaries 410, some assay 1000 can be forced off upper surface 456 of output layer 408 at an edge 1846 into at least one overflow channel 1848. In some embodiments, once at least some of the plurality of staging capillaries 410 are filled, at least output layer 408 and microplate 20 can be placed into a centrifuge. In some embodiments, the centripetal force of the centrifuge can be sufficient to overcome the capillary force and/or surface tension of assay 1000 in each the plurality of staging capillaries 410, thereby forcing a metered volume of assay 1000 into each of the plurality of wells 26 of microplate 20.

In some embodiments, such as illustrated in FIG. 158, the excess assay 1000 in overflow channel 1848 can be contained using one or more reservoir pockets 1850. In some embodiments, reservoir pocket 1850 can be in fluid communication with at least one overflow channel 1848. In some embodiments, reservoir pocket 1850 can be deeper than overflow channel 1848 to encourage flow of assay 1000 to reservoir pocket 1850. During centrifugation, centripetal force can further encourage assay 1000 to flow to reservoir pocket 1850, thereby reducing the likelihood of any contamination or cross-feed between adjacent staging capillaries 410. In some embodiments, an extended wall member 1852 can be positioned about reservoir pocket 1850 to further contain assay 1000.

In some embodiments, such as illustrated in FIGS. 163 and 164, the excess assay 1000 in overflow channel 1848 can be contained using a reservoir trough 1854. In some embodiments, an absorbent member 1856 can be disposed in reservoir trough 1854 to absorb excess assay 1000 therein. In some embodiments, absorbent member 1856 can be a hydrophilic fiber membrane. As illustrated in FIG. 164, reservoir trough 1854 can be sloped toward absorbent member 1856 to facilitate absorption of excess assay 1000. In some embodiments, absorbent member 1856 can be removable to permit removal and relocating of the excess assay 1000 prior to centrifugation.

In some embodiments, such as illustrated in FIGS. 165 and 166, funnel member 1830 can comprise two or more discrete assay chambers 1832 for delivering one or more different assays. In such embodiments, for example, output layer 408 can comprise one or more central overflow channels 1858 extending along upper surface 456 of output layer 408 to receive at least some overflow assay 1000. In some embodiments, central overflow channels 1858 are each disposed between each separate grouping of staging capillaries 410 served by each discrete assay chamber 1832. In some embodiments, as illustrated in FIG. 166, central overflow channel 1858 can be sloped down to at least one of overflow channel 1848 (FIG. 158), reservoir pocket 1850 (FIG. 158), reservoir trough 1854 (FIG. 163), or absorbent member 1856 (FIG. 166). As illustrated in FIG. 165, in some embodiments, absorbent member 1856 can be sized and/or shaped to fit with an enlarged reservoir pocket 1850.

Funnel Member

As illustrated in FIGS. 167-180, in some embodiments, funnel member 1830 of funnel assembly 1814 can be any one of a number of configurations sufficient to maintain fluid bead 1842 in contact with upper surface 456 of output layer 408. In some embodiments, a predetermined shape of fluid bead 1842 and/or a predetermined flowrate of assay 1000 through tip portion 1840 can be achieved through the particular configuration of funnel member 1830.

As illustrated in FIG. 167-169, in some embodiments, funnel member 1830 comprises one or more assay chambers 1832 in fluid communication with tip portion 1840. As described above, in embodiments comprising two or more assay chambers 1832 (FIG. 168), multiple assays can be used such that a different assay can be disposed in each assay chamber 1832. It should be understood that any number of assay chambers 1832 can be used (e.g., 2, 4, 6, 8, 10, 12, 16, 20, 32, 64, or more).

In some embodiments, tip portion 1840 can be configured to define a capillary force and/or surface tension sufficient to prevent assay 1000 from exiting assay chamber 1832 prior to fluid bead 1842 engaging upper surface 456 and to permit assay 1000 to be pulled into each of the plurality of staging capillaries 410 during filling of the staging capillaries. As illustrated in FIG. 170, tip portion 1840 comprises a restricted orifice 1860 that is sized to increase surface tension to retain assay 1000 with assay chamber 1832. In some embodiments, tip portion 1840 can be spaced apart from an underside surface 1862 to, at least in part, inhibit assay 1000 from collecting between funnel member 1830 and output layer 408. In some embodiments, as illustrated in FIG. 171, restricted orifice 1860 can be used with wiper member 1844 to increase surface tension to retain assay 1000 and to wipe and/or remove excess assay 1000 on upper surface 456 of output layer 408. In some embodiments, such as illustrated in FIG. 172, tip portion 1840 can comprise a planar cavity 1864 disposed in fluid communication with restricted orifice 1860. In some embodiments, planar cavity 1864 can encourage the formation of wider and/or shallower fluid bead 1842 relative to similar configurations not employing planar cavity 1864. In some configurations, the wider and/or shallower fluid bead 1842 can, at least in part, prolong the time fluid bead 1842 is in contact with each of the plurality of staging capillaries 410.

As illustrated in FIG. 173, in some embodiments, funnel member 1830 can comprise wiper 1844 spaced apart from tip portion 1840 to wipe and/or remove excess assay 1000 on upper surface 456 of output layer 408. In some embodiments, wiper 1844 can extend a distance from underside surface 1862 of funnel member 1830 equal to about a distance from underside surface 1862 to a distal end of tip portion 1840. As illustrated in FIGS. 174-176, each tip portion 1840 associated with each assay chamber 1832 can be offset relative to adjacent tip portions 1840. In some embodiments, this offset relationship between adjacent tip portions 1840 can permit the plurality of staging capillaries 410 to be closely spaced with reduced likelihood for crosstalk between adjacent fluid beads 1842.

Still referring to FIGS. 174-176, in some embodiments, restricted orifice 1860 comprises an elongated slot 1866 (FIG. 174) generally extending from one edge of tip portion 1840 to the opposing edge to define an elongated fluid bead 1842. However, in some embodiments, restricted orifice 1860 comprises one or more apertures 1868. In some embodiments, the reduced cross-sectional area of apertures 1868 relative to that of elongated slot 1866 can serve to withstand a fluid head pressure exerted by assay 1000 in assay chamber 1832 that would otherwise overcome the surface tension of fluid bead 1842 exiting elongated slot 1866 and possibly lead to premature discharge of assay 1000. In some embodiments, the restricted orifice 1860 can be collinear as well as offset as illustrated in (FIG. 174).

In some embodiments, such as illustrated in FIGS. 177-179, funnel member 1830 can comprise an internal siphon passage 1870 to, at least in part, control the flowrate of assay 1000 from restricted orifice 1860. In some embodiments, funnel member 1830 comprises a main chamber 1872 fluidly coupled to a delivery chamber 1874 via siphon passage 1870. In some embodiments, siphon passage 1870 can be positioned along a bottom of main chamber 1872. Siphon passage 1870 can comprise an upturned section 1876 that can require assay 1000 in main chamber 1872 to flow, at least in part, against the force of gravity. In some embodiments, main chamber 1872 and delivery chamber 1874 can be fluidly coupled at the top thereof by a top chamber 1878. When main chamber 1872 is filled at least partially above top chamber 1878, the excess assay 1000 can flow across top chamber 1878 into delivery chamber 1874. During filling, as the level of assay 1000 drops below the bottom surface of top chamber 1878 and assay 1000 flows from restricted orifice 1860, assay 1000 within delivery chamber 1874 can be replaced through the siphoning action of siphon passage 1870 at the bottom of main chamber 1872. This arrangement can reduce the fluid head pressure exerted at restricted orifice 1860. Accordingly, the fluid head pressure exerted at restricted orifice 1860 can be generally to about the fluid head pressure of assay 1000 contained in delivery chamber 1874.

In some embodiments, as illustrated in FIGS. 179 and 180, funnel member 1830 can be formed with a two- or more-piece construction. As illustrated in FIG. 179, funnel member 1830 can comprise a first section 1880 and a second section 1882. First section 1880 can comprise one or more desired features.

For example, as illustrated in FIG. 179, upturned section 1876 of FIG. 178 can be formed in first section 1880. First section 1880 and second section 1882 can then be joined or otherwise mated along a generally vertical joining line 1884 (FIG. 178) to form funnel member 1830. In some embodiments, first section 1880 and second section 1882 can be joined or otherwise mated along a generally horizontal joining line 1886 (FIG. 180). In some embodiments, first section 1880 and second section 1882 can be made from different materials to achieve a predetermined performance. In some embodiments, second section 1882 can be made of an elastomer to provide enhance flexibility to accommodate for variations in output layer 408 and enhanced wiping performance of wiper member 1844.

Surface Treatment

In some embodiments, portions of filling apparatus 400 that are intended to contact assay 1000, such as assay input ports 402, microfluidic channels 406, the plurality of staging capillaries 410, and the like, can be hydrophilic. Likewise, in some embodiments, surfaces not intended to contact assay 1000 can be hydrophobic.

In some embodiments, filling apparatus 400 comprises a treatment to increase surface energy thereof to improve flow and/or capillary action of any surface of filling apparatus 400 exposed to assay 1000, such as assay input ports 402, microfluidic channels 406, staging capillaries 410, microfluidic channels 406, depression 454, upper surface 456, etc. In some embodiments, surface energy can be improved, for example, when using a polymer material in the manufacture of filling apparatus 400, through surface modification of the polymer material via Michael addition of acrylamide or PEO-acrylate onto laminated surface; surface grafting of acrylamide or PEO-acrylate via atom transfer radical polymerization (ARTP); surface grafting of acrylamide via Ce(IV) mediated free radical polymerization; surface initiated living radical polymerization on chloromethylated surface; coating of negatively charged polyelectrolytes; plasma CVD of acrylic acid, acrylamide, and other hydrophilic monomers; or surface adsorption of an ionic or non-ionic surfactant. In some embodiments, surfactants, such as those set forth in Tables 2 and 3, can be used.

TABLE 2

Surfactants for Coating

| No | Name | MW | Hydrophile-Lipophile Balance (HLB) |
|---|---|---|---|
| 1 | Tetronic 901 | 4700 | 3 |
| 2 | Tetronic 1107 | 1500 | 24 |
| 3 | Tetronic 1301 | 6800 | 2 |
| 4 | Poly(styrene-b-ethylene oxide) | Mn: 3600-67000 | |
| 5 | Poly(styrene-b-sodium acrylate) | Mn: 1800-42500 | |
| 6 | Triton X-100 | | 13.5 |
| 7 | Triton X 100 reduced | | |
| 8 | Tween 20 | 1228 | 16.7 |
| 9 | Tween 85 | 1839 | 11 |
| 10 | Span 83 | 1109.56 | 3.7 |
| 11 | Span 80 | 428.62 | 4.3 |
| 12 | Span 40 | 402.58 | 6.7 |

Tetronic:

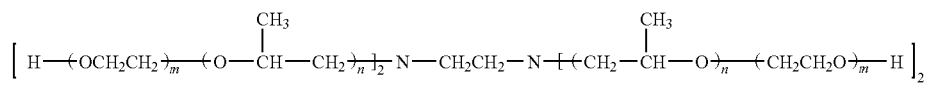

Triton X-100:

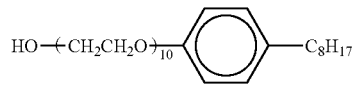

Triton X-100 reduced:

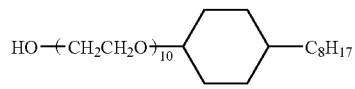

Span 80:

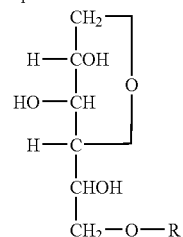

(R = —COC$_{17}$H$_{33}$ oleate)

TABLE 2-continued

Surfactants for Coating

| No | Name | MW | Hydrophile-Lipophile Balance (HLB) |
|---|---|---|---|

Spam 83:

$$\begin{array}{c} CH_2\text{—COR} \\ | \\ H\text{—COR} \\ | \quad\quad O \\ RO\text{—CH} \\ | \\ H\text{—C} \\ | \\ CHOH \\ | \\ CH_2\text{—O—R} \end{array}$$

(R = —COC$_{17}$H$_{33}$ oleate)

Spam 20:

$$\begin{array}{c} CH_2\text{—COH} \\ | \\ H\text{—COH} \\ | \quad\quad O \\ HO\text{—CH} \\ | \\ H\text{—C} \\ | \\ CHOH \\ | \\ CH_2\text{—O—R} \end{array}$$

(R = —COC$_{11}$H$_{23}$ laurate)

Tween:
Poly(oxyethylene) sorbitan monolauate

TABLE 3

Surfactants for Wetting Polypropylene

Acids:

| | |
|---|---|
| Dodecyl sulfate, Na salt | $CH_2(CH_2)_{11}OSO_3^-Na^+$ |
| Octadecyl sulfate, Na salt | $CH_3(CH_2)_{17}OSO_3^-Na^+$ |

Quaternary ammonium compounds:

| | |
|---|---|
| Cetyltrimethylammonium bromide | $CH_3(CH_2)_{15}\overset{+}{N}(CH_3)_3\ Br^-$ |
| Octadecyltrimethyl ammonium bromide | $CH_3(CH_2)_{17}\overset{+}{N}(CH_3)_3\ Br^-$ |

Ethers:

| | |
|---|---|
| Brij-52 | $CH_3(CH_2)_{15}(OCH_2CH_2)_2OH$ |
| Brij 56 | $CH_3(CH_2)_{15}(OCH_2CH_2)_{10}OH$ |
| Brij 58 | $CH_3(CH_2)_{15}(OCH_2CH_2)_{20}OH$ |
| Brij 72 | $CH_3(CH_2)_{17}(OCH_2CH_2)_2OH$ |
| Brij 76 | $CH_3(CH_2)_{17}(OCH_2CH_2)_{10}OH$ |
| Brij 78 | $CH_3(CH_2)_{17}(OCH_2CH_2)_{20}OH$ |

Esters:

| | |
|---|---|
| Poly(ethylene glycol) monolaurate | $CH_3(CH_2)_{10}CO(OCH_2CH_2)_{4.5}OH$ |
| Poly(ethylene glycol) distearate | $CH_3(CH_2)_{16}\text{—CO—}(OCH_2)_9\text{—O—CO—}(CH_2)_{16}CH_3$ |
| Poly(ethylene glycol) dioleate | $CH_3(CH_2)_7CH=CH(CH_2)_7\text{—CO—}(OCH_2)_9\text{—O—CO—}(CH_2)_7CH=CH(CH_2)_7CH_3$ |

In some embodiments, filling apparatus 400 can comprise polyolefins; poly(cyclic olefins); polyethylene terephthalate; poly(alkyl (meth)acrylates); polystyrene; poly(dimethyl siloxane); polycarbonate; structural polymers, for example, poly(ether sulfone), poly(ether ketone), poly(ether ether ketone), and liquid crystalline polymers; polyacetal; polyamides; polyimides; poly(phenylene sulfide); polysulfones; poly(vinyl chloride); poly(vinyl fluoride); poly(vinylidene fluoride); copolymers thereof; and mixtures thereof.

In some embodiments, a co-agent can be employed to enhance the hydrophilicity and/or improve the shelf life of filling apparatus 400. Co-agents can be, for example, a water-soluble or slightly water-soluble homopolymer or copolymers prepared by monomers comprising, for example, (meth) acrylamide; N-methyl (methyl)acrylamide, N,N-dimethyl (methyl)acrylamide, N-ethyl (meth)acrylamide, N-n-propyl (meth)acrylamide, N-iso-propyl (meth)acrylamide, N-ethyl-N-methyl (meth)acrylamide, N,N-diethyl (meth)acrylamide, N-hydroxymethyl (meth)acrylamide, N-(3-hydroxypropyl) (meth)acrylamide, N-vinylformamide, N-vinylacetamide, N-methyl-N-vinylacetamide, vinyl acetate that can be hydrolyzed to give vinylalcohol after polymerization, 2-hydroxyethyl (meth)acrylate, 3-hydroxypropyl (meth)acrylate, N-vinylpyrrolidone, poly(ethylene oxide) (meth)acrylate, N-(meth)acryloxysuccinimide, N-(meth)acryloylmorpholine, N-2,2,2-trifluoroethyl (meth)acrylamide, N-acetyl (meth)acrylamide, N-amido(meth)acrylamide, N-acetamido (meth)acrylamide, N-tris(hydroxymethyl)methyl (meth) acrylamide, N-(methyl)acryloyltris(hydroxymethyl)methylamine, (methyl)acryloylurea, vinyloxazolidone, vinylmethyloxazolidone, and combinations thereof. In some embodiments, the co-agent can be poly(acrylic acid-co-N,N-dimethylacrylamide) or poly(N,N-dimethyl acrylamide-co-styrene sulfonic acid).

Microplate Sealing Cover

In some embodiments, such as illustrated in FIGS. 26 and 27, sealing cover 80 can be generally disposed across microplate 20 to seal assay 1000 within each of the plurality of wells 26 of microplate 20 along a sealing interface 92 (see FIGS. 4, 5, 26, and 27). That is, sealing cover 80 can seal (isoloate) each of the plurality of wells 26 and its contents (i.e. assay 1000) from adjacent wells 26, thus maintaining sample integrity between each of the plurality of wells 26 and reducing the likelihood of cross contamination between wells. In some embodiments, sealing cover 80 can be positioned within an optional depression 94 (FIG. 30) formed in main body 28 of microplate 20 to promote proper positioning of sealing cover 80 relative to the plurality of wells 26.

In some embodiments, sealing cover 80 can be made of any material conducive to the particular processing to be done. In some embodiments, sealing cover 80 can comprise a durable, generally optically transparent material, such as an optically clear film exhibiting abrasion resistance and low fluorescence when exposed to an excitation light. In some embodiments, sealing cover 80 can comprise glass, silicon, quartz, nylon, polystyrene, polyethylene, polycarbonate, copolymer cyclic olefin, polycyclic olefin, cellulose acetate, polypropylene, polytetrafluoroethylene, metal, and combinations thereof.

In some embodiments, sealing cover 80 comprises an optical element, such as a lens, lenslet, and/or a holographic feature. In some embodiments, sealing cover 80 comprises features or textures operable to interact with (e.g., by interlocking engagement) circular rim portion 32 or square-shaped rim portion 38 of the plurality of wells 26. In some embodiments, sealing cover 80 can provide resistance to distortion, cracking, and/or stretching during installation. In some embodiments, sealing cover 80 can comprise water impermeable-moisture vapor transmission values below 0.5 (cc-mm)/(m2-24 hr-atm). In some embodiments, sealing cover 80 can maintain its physical properties in a temperature range of 4° C. to 99° C. and can be generally free of inclusions (e.g. light blocking specks) greater than 50 μm, scratches, and/or striations. In some embodiments, sealing cover 80 can comprise a liquid such as, for example, oil (e.g., mineral oil).

In some embodiments, such sealing material can comprise one or more compliant coatings and/or one or more adhesives, such as pressure sensitive adhesive (PSA) or hot melt adhesive. In some embodiments, a pressure sensitive adhesive can be readily applied at low temperatures. In some embodiments, the pressure sensitive adhesive can be softened to facilitate the spreading thereof during installation of sealing cover 80. In some embodiments, such sealing maintains sample integrity between each of plurality of wells 26 and prevents wells cross-contamination of contents between wells 26. In some embodiments, adhesive 88 exhibits low fluorescence.

In some embodiments, the sealing material can provide sufficient adhesion between sealing cover 80 and microplate 20 to withstand about 2.0 lbf per inch or at least about 0.9 lbf per inch at 95° C. In some embodiments, the sealing material can provide sufficient adhesion at room temperature to contain assay 1000 within each of the plurality of wells 26. This adhesion can inhibit sample vapor from escaping each of the plurality of wells 26 by either direct evaporation or permeation of water and/or assay 1000 through sealing cover 80. In some embodiments, the sealing material maintains adhesion between sealing cover 80 and microplate 20 in cold storage at 2° C. to 8° C. range (non-freezing conditions) for 48 hours.

In some embodiments, in order to improve sealing of the plurality of wells 26 of microplate 20, various treatments to microplate 20 can be used to enhance the coupling of sealing cover 80 to microplate 20. In some embodiments, microplate 20 can be made of a hydrophobic material or can be treated with a hydrophobic coating, such as, but not limited to, a fluorocarbon, PTFE, or the like. The hydrophobic material or coating can reduce the number of water molecules that compete with the sealing material on sealing cover 80. As discussed above, grooves 52, 54 can be used to provide seal adhesion support on the outer edges of sealing cover 80. In these embodiments, for example, a pressure chamber gasket can be sealed against grooves 52, 54 for improved sealing.

Turning now to FIG. 28, in some embodiments, sealing cover 80 can comprise multiple layers, such as a friction reduction film 82, a base stock 84, a compliant layer 86, a pressure sensitive adhesive 88, and/or a release liner 90. In some embodiments, friction reduction film 82 can be Teflon or a similar friction reduction material that can be peeled off and removed after sealing cover 80 is applied to microplate 20 and before microplate 20 is placed in high-density sequence detection system 10. In some embodiments, base stock 84 can be a scuff resistant and water impermeable layer with low to no fluorescence. While in some embodiments, compliant layer 86 can be a soft silicone elastomer or other material known in the art that is deformable to allow pressure sensitive adhesive 88 to conform to irregular surfaces of microplate 20, increase bond area, and resist delamination of sealing cover 80. In some embodiments, pressure sensitive adhesive 88 and compliant layer 86 can be a single layer, if the pressure sensitive adhesive exhibit sufficient compliancy. Release liner 90 is removed prior to coupling pressure sensitive adhesive 88 to microplate 20.

Compatibility of Cover and Assay

In some embodiments, adhesive 88 can selected so as to be compatible with assay 1000. For example, in some embodiments adhesive 88 is free of nucleases, DNA, RNA and other assay components, as discussed below. In some embodiments, sealing cover 80 comprises one or more materials that are selected so as to be compatible with detection probes in assay 1000. In some embodiments, adhesive layer 88 is selected for compatibility with detection probes.

Methods of matching a detection probe with a compatible sealing cover 80 include, in some embodiments, varying compositions of sealing cover 80 by different weight percents of components such as polymers, crosslinkers, adhesives, resins and the like. These sealing covers 80 can then be tested as a function of their corresponding fluorescent intensity level for different dyes. In such embodiments, comparison can be analyzed at room temperature as well as at elevated temperatures typically employed with PCR. Comparisons can be analyzed over a period of time and in some embodiments, the time period can be, for example, up to 24 hours. Data can be collected for each of the varying compositions of sealing cover 80 and plotted such that fluorescence intensity of the dye is on the X-axis and time is on the Y-axis. Some embodiments of the present teachings include a method of testing compatibility of the detection probe comprising an oligonucleotide and a fluorophore to a composition of a sealing cover. In such embodiments, the method includes depositing a quantity of the fluorophore into a plurality of containers, providing a plurality of sealing covers that have different compositions and sealing the containers with the sealing covers. Methods also include exciting the fluorophore in each of the containers and then measuring an emission intensity from the fluorophore in each of the containers. In such embodiments, the method can also include an evaluation of the emission intensity from the fluorophore of each of the containers and then a determination of which sealing cover composition is compatible with the fluorophore. In some embodiments, the method includes holding a temperature of the containers constant. The method can include measuring the emission intensity from the fluorophore in each container over a period of time, for example, as long as about 24 hours. In some embodiments, the method includes heating the containers to a temperature above about 20° C., optionally to a temperature from about 55° C. to about 100° C. In some embodiments, the method includes cycling the temperature of the plurality of containers. The temperature of the containers can be cycled according to a typical PCR temperature profile. Table 4 shows exemplary data that can be generated for such a comparison. In this example, a dye is evaluated by comparing it at non-heated and heated temperatures to a cyclic olefin copolymer (COC) and glue material with varying percentages of a crosslinker.

TABLE 4

Percentage of Flourescence Signal Loss

| Sealing Cover Composition | Percentage of Fluorescence Signal Loss Post Incubation with Dye (20 hrs; 59° C.) | |
|---|---|---|
| | Fresh Material (Room Temperature) | Material Heated (24 hrs; 70° C.) |
| Control (No COC, glue, or crosslinker) | 0% Loss | 0% Loss |
| COC/Glue/0% crosslinker | 0% Loss | 0% Loss |
| COC/Glue/0.5% crosslinker | 87% Loss | 76% Loss |
| COC/Glue/1% crosslinker | 86% Loss | 12.5% Loss |
| COC/Glue/3% crosslinker | 55% Loss | 0% Loss |
| COC/Glue/5% crosslinker | 97% Loss | 95% Loss |

In some embodiments, kits are provided, comprising, for example, a sealing cover 80 and one or more compatible detection probes that are compatible (e.g., emission intensity does not degrade when in contact) with sealing cover 80. In some embodiments, a kit can comprise one or more detection probes that are compatible (e.g., do not degrade over time when in contact) with adhesive 88 of sealing cover 80. Kits may comprise a group of detection probes that are compatible with sealing cover 80 comprising adhesive 88 and microplate 20. In some embodiments, the present teachings include methods for matching a group of detection probes that are compatible with sealing cover 80 and spotting into at least some of plurality of wells 26 of microplate 20.

Microplate Sealing Cover Roll

As can be seen in FIGS. 181 and 182, in some of the embodiments, sealing cover 80 can be configured as a roll 512. The use of sealing cover roll 512 can provide, in some embodiments, and circumstances, improved ease in storage and application of sealing cover 80 on microplate 20 when used in conjunction with a manual or automated sealing cover application device, as discussed herein. In some embodiments, sealing cover roll 512 can be manufactured using a laminate comprising a protective liner 514, a base stock 516, an adhesive 518, and/or a carrier liner 520. During manufacturing, protective liner 514 can be removed and discarded. Base stock 516 and adhesive 518 can then be kiss-cut, such that base stock 516 and adhesive 518 are cut to a desired shape of sealing cover 80, yet carrier liner 520 is not cut. Excess portions of base stock 516 and adhesive 518 can then be removed and discarded. In some embodiments, base stock 516 can be a scuff resistant and water impermeable layer with low to no fluorescence.

In some embodiments, carrier liner 520 can then be punched or otherwise cut to a desired shape and finally the combination of carrier liner 520, base stock 516, and adhesive 518 can be rolled about a roll core 522 (see FIG. 182). Roll core 522 can be sized so as not to exceed the elastic limitations of base stock 516, adhesive 518, and/or carrier liner 520. In some embodiments, adhesive 518 is sufficient to retain base stock 516 to carrier liner 520, yet permit base stock 516 and adhesive 518 to be released from carrier liner 520 when desired. In some embodiments, base stock 516, adhesive 518, and carrier liner 520 are rolled upon roll core 522 such that base stock 516 and adhesive 518 face toward roll core 522 to protect base stock 516 and adhesive 518 from contamination and reduce the possibility of premature release.

As can be seen in FIG. 182, in some embodiments, such a desired shape of carrier liner 520 can comprise a plurality of drive notches 524 formed along and slightly inboard of at least one of the elongated edges 526. The plurality of drive notches 524 can be shaped, sized, and spaced to permit cooperative engagement with a drive member to positively drive sealing cover roll 512 and aid in the proper positioning of sealing cover 80 relative to microplate 20. In the some embodiments, the desired shape of carrier liner 520 can further comprise a plurality of staging notches 528 to be used to permit reliable positioning of sealing cover 80. In some embodiments, the plurality of staging notches 528 can be formed along at least one elongated edge 526. In some embodiments, the plurality of staging notches 528 can be shaped and sized to permit detection by a detector, such as an optical detector, mechanical detector, or the like. An end/start of roll notch or other feature 530 can further be used in some embodiments to provide notification of a first and/or last sealing cover 80 on sealing cover roll 512. Similar to the plurality of staging notches 528, end/start of roll notch 530 can be shaped and sized to permit detection by a detector, such as an optical detector, mechanical detector, or the like. It should be appreciated that the foregoing notches and features can have other shapes than those set forth herein or illustrated in the attached figures. It should also be appreciated that other features, such as magnetic markers, non-destructive markers (e.g. optical and/or readable markers), or any other indicia may be used on carrier liner 520. To facilitate such detection with an optical detector to avoid physical contact, in some embodiments, carrier liner 520 can be opaque. However, in some embodiments, carrier liner can be generally opaque only near elongated edges 526 with generally clear center sections 532 to aid in in-process adhesive inspection.

Sealing Cover Applicator

In some embodiments, sealing cover 80 can be laminated onto microplate 20 using a hot roller apparatus 540, as illustrated in FIG. 29. In some embodiments, hot roller apparatus 540 comprises a heated top roller 542 heated by a heating element 544 and an unheated bottom roller 546. A first plate guide 548 can be provided for guiding microplate 20 into hot roller apparatus 540, while similarly a second plate guide 550 can be provided for guiding microplate 20 out of hot roller apparatus 540.

During sealing, sealing cover 80 can be placed on top of microplate 20 and the combination can be fed into hot roller apparatus 540 such that sealing cover 80 is in contact with first plate guide 548. As sealing cover 80 and microplate 20 pass and engage heated top roller 542, heat can be applied to sealing cover 80 to laminate sealing cover 80 to microplate 20. This laminated combination can then exit hot roller apparatus 540 as it passes second plate guide 550. In some embodiments, the heat from heated top roller 542 reduces the viscosity of the adhesive of sealing cover 80 to allow the adhesive to better adhere to microplate 20.

In some embodiments, hot roller apparatus 540 can variably control the amount of heat applied to sealing cover 80. In this regard, sufficient heat can be supplied to provide adhesive flow or softening of the adhesive of sealing cover 80 without damaging assay 1000. In some embodiments, hot roller apparatus 540 can variably control a drive speed of heated top roller 542 and unheated bottom roller 546. In some embodiments, hot roller apparatus 540 can variably control a clamping force between heated top roller 542 and unheated bottom roller 546. By varying these parameters, optimal sealing of sealing cover 80 to microplate 20 can be achieved with minimal negative effects to assay 1000.

Manual Sealing Cover Applicator

In some embodiments, sealing cover 80 can be laminated onto microplate 20 using a manual sealing cover applicator 552, such as illustrated in FIG. 183. In some embodiments, manual sealing cover applicator 552 can be used in conjunction with a fixture 554, such as illustrated in FIG. 184. In some embodiments, fixture 554 can comprise a generally planar substrate 556 comprising a recessed portion 558. Recessed portion 558, in some embodiments, can be longitudinally aligned with generally planar substrate 556 and sized to receive microplate 20 therein. In some embodiments, fixture 554 can comprise an alignment feature 560 that can be complementary to alignment feature 58 on microplate 20. In some embodiments, alignment feature 560 can comprise a corner chamfer, a pin, a slot, a cut corner, an indentation, a graphic, a nub, a protrusion, and/or other unique feature that can be capable of interfacing with alignment feature 58 or other feature of microplate 20. In some embodiments, fixture 554 can comprise one or more recesses 562 formed in generally planar substrate 556 to permit, among other things, improved grasping of microplate 20 for ease of insertion and withdrawal of microplate 20 from fixture 554. In some embodiments, one or more recesses 562 can be positioned along opposing ends of microplate 20.

Referring now to FIGS. 183 and 185-187, in some embodiments, manual sealing cover applicator 552 comprises a hinged housing 564 sized to receive sealing cover roll 512 therein. In some embodiments, hinged housing 564 comprises a base section 566 and at least one cover section 568. In some embodiments, at least one cover section 568 can be pivotally coupled to base section 566 about axis 570. In some embodiments, at least one cover section 568 comprises a pair of apertures 572 (only one illustrated) formed in sidewalls 574 that can each be sized to receive a pin 576 extending from an applicator roller 578 to permit pivotal movement of at least one cover section 568 relative to base section 566. In some embodiments, a latch member 580 can be used to releasably couple base section 566 to at least one cover section 568. Latch member 580 can be pivotally coupled to one of base section 566 and at least one cover section 568 and positionable in a locked position (FIG. 186), coupling base section 566 and at least one cover section 568, and an unlocked position (FIG. 187), permitting relative pivotal movement of base section 566 and at least one cover section 568.

As illustrated in FIGS. 185-187, in some embodiments, base section 566 comprises at least one of applicator roller 578, a support structure 582, a roll hub 584, a stretcher 586, a plane assembly 588, an intermediate roller 590, a drive roller assembly 592, a pressure roller 594, and a waste gate 596. In some embodiments, applicator roller 578 can comprise a generally cylindrical member comprising the pair of pins 576 disposed on opposing ends thereof along axis 570. In some embodiments, the pair of pins 576 can engage support structure 582 to permit rotating movement of applicator roller 578 relative thereto. In some embodiments, applicator roller 578 can be made of, at least in part, a compliant material to permit applicator roller 578 to accommodate variations in fixture 554 and/or microplate 20.

In some embodiments, roll hub 584 can be fixedly coupled to support structure 582 to support sealing cover roll 512 thereon and permit relative rotation therebetween. In some embodiments, roll hub 584 comprises a pair of friction legs 598 extending outwardly from tangential sections 600 of a central portion 602. In some embodiments, the pair of friction legs 598 can each extend along only a portion of roll hub 584. The pair of friction legs 598 can be sized to frictionally engage an inner surface of roll core 522 of sealing cover roll 512 to provide drag and/or positively retain sealing cover roll 512 on roll hub 584.

In some embodiments, stretcher 586 comprises a bracket portion 604 and an engaging portion 606. In some embodiments, bracket portion 604 can be fixedly coupled to support structure 582 to provide a generally rigid support. In some embodiments, engaging portion 606 comprises a mounting section 608 and one or more finger members 610 extending from mounting section 608. The one or more finger members 610 can comprise an upturned end 612 to form an engaging corner 614 to contact sealing cover roll 512 as it passes thereby. In some embodiments, mounting section 608 can be fixedly coupled to bracket portion 604 via conventional fasteners and/or a tab member interface 616 (FIG. 185).

Still referring to FIGS. 185-187, in some embodiments, plane assembly 588 comprises a plate member 618 and a plane roller 620 rotatably coupled to plate member 618 along axis 622. In some embodiments, plane roller 620 can be a generally cylindrical member comprising a pair of pins 624 disposed on opposing ends thereof along axis 622. In some embodiments, the pair of pins 624 can engage apertures formed in plate member 618 to permit rotating movement of plane roller 620 relative thereto. In some embodiments, plane roller 620 can be made of, at least in part, a compliant material to permit plane roller 620 accommodate variations in fixture 554 and/or microplate 20. In some embodiments, plane roller 620 can carry carrier liner 520 of sealing cover roll 512. In some embodiments, plane roller 620 can be sized to apply a force on a backside of carrier liner 520 and, consequently, on sealing cover 80 to adhere sealing cover 80 to microplate 20 during application. In some embodiments, carrier liner 520 can then travel along plate member 618 to intermediate roller 590. It should be appreciated that plane roller 620 can comprise posts (not illustrated) formed thereon to engage the plurality of drive notches 524 formed on some embodiments of carrier liner 520 to aid in alignment.

In some embodiments, intermediate roller 590 can comprise a generally cylindrical member comprising a pair of pins 626 disposed on opposing ends thereof along axis 628. In some embodiments, the pair of pins 626 can engage apertures formed in support structure 582 to permit rotating movement of intermediate roller 590 relative thereto. In some embodiments, intermediate roller 590 can be comprises of, at least in part, a compliant material to permit intermediate roller 590 to accommodate variations in fixture 554 and/or microplate 20. In some embodiments, intermediate roller 590 can carry carrier liner 520 of sealing cover roll 512. In some embodiments, intermediate roller 590 can be tapered along its longitudinal length to a reduced cross-section area at about a longitudinal midpoint of intermediate roller 590. This tapered configuration can aid in maintaining carrier liner 520 generally centered on intermediate roller 590. In some embodiments, intermediate roller 590 can be sized to apply a force on a backside of carrier liner 520 and, consequently, on sealing cover 80 to adhere sealing cover 80 to microplate 20 during application.

As best seen in FIG. 185, in some embodiments, drive roller assembly 592 comprises at least one knob portion 630 disposed on at least one end of a drive roller 632. In some embodiments, drive roller 632 can comprise a generally cylindrical member comprising a pair of pins 634 (illustrated hidden in FIG. 185) disposed on opposing ends thereof along axis 636. In some embodiments, the pair of pins 634 can engage apertures formed in support structure 582 to permit rotating movement of drive roller 632 relative thereto. In some embodiments, the pair of pins 634 can further engage the at least one knob portion 630. In some embodiments, a pair of knob portions 630 can be used and disposed on opposing ends of drive roller 632 to permit both left-handed and right-handed operation. Knob portion 630 can be manually manipulated by a user to manually advance carrier liner 520 of sealing cover roll 512. In some embodiments, drive roller 632 can be comprised of, at least in part, a compliant material to permit drive roller 632 to accommodate variations in fixture 554 and/or microplate 20. In some embodiments, drive roller 632 can be sized to apply a force on a backside of carrier liner 520 and, consequently, on sealing cover 80 to adhere sealing cover 80 to microplate 20 during application.

In some embodiments, drive roller 632 can be sized to operably engage pressure roller 594 to receive carrier liner 520 of sealing cover roll 512 therebetween (see FIG. 185). In some embodiments, pressure roller 594 can be a generally cylindrical member comprising a pair of pins 638 disposed on opposing ends thereof along axis 640. In some embodiments, the pair of pins 638 can engage apertures formed in a support bracket 642 to permit rotating movement of pressure roller 594 relative thereto. In some embodiments, support bracket 642 can be fixedly mounted to or integrally formed with at least one cover section 568. In some embodiments, pressure roller 594 can be biased to apply a force against drive roller 632 to, at least in part, positively grab, and/or advance carrier liner 520.

Finally, in some embodiments, carrier liner 520 of sealing cover roll 512 can be fed from a lower portion of sealing cover roll 512 forward along a top side of plate member 618. Carrier liner 520 can then be fed around plane roller 620, along an bottom side of plate member 618, around intermediate roller 590, between pressure roller 594 and drive roller 632, and finally out of waste gate 596.

In some embodiments, during operation, a user can manually manipulate at least one knob portion 630 until an edge of sealing cover 80 can be advanced to a predetermined seal position. In some embodiments, manual sealing cover applicator 552 can then be placed on top of fixture 554 having microplate 20 mounted thereon. In some embodiments, the user can then apply a downward force on, at least in part, a handle member 640 and push/pull manual sealing cover applicator 552 from one end of microplate 20 to an opposing end of microplate 20. This motion and the construction of manual sealing cover applicator 552 causes sealing cover 80 to engage and be mounted to microplate 20. In some embodiments, the downward force applied to manual sealing cover applicator 552 activates adhesive 518. This motion, in some embodiments, serves to expel the waste (i.e. carrier liner 520 having no sealing cover 80) out of waste gate 596.

In some embodiments, sealing cover roll 512 can be loaded in manual sealing cover applicator 552 by positioning latch member 580 in the unlocked position (FIG. 187) and pivoting at least one cover section 568 upward. Sealing cover roll 512 can then be place on roll hub 584. Carrier liner 520 can then be routed through manual sealing cover applicator 552 as described above.). In some embodiments, closing of the at least one cover section 568 causes pressure roller 594 to apply a force on carrier liner 520. In some embodiments, drive roller 632 and/or knob section 630 can be ratcheted to maintain carrier liner 520 under tension.

It should be appreciated that this arrangement can provide reduced possibility of sealing cover application defects, improved sealing cover placement accuracy, reduced operator skill, and faster sealing cover application.

Automated Sealing Cover Applicator—Roll

In some embodiments, as illustrated in FIGS. 188-192, sealing cover 80 can be laminated onto microplate 20 using an automated sealing cover applicator 1100. In some embodiments, automated sealing cover applicator 1100 comprises a housing 1102 sized to receive sealing cover roll 512 therein. In some embodiments, housing 1102 can comprise a base section 1104 and cover section 1106 connectable therewith. In some embodiments, cover section 1106 can comprise an opening 1108 for receiving a sealing cover cassette 1110 therein.

Referring now to FIGS. 189 and 190, in some embodiments, base section 1104 comprises at least one of a microplate tray assembly 1112, a tray drive system 1114, a sealing cover drive system 1116 for at least in part alignment control of sealing cover roll 512, a heated roller assembly 1118, and an applicator control system 1120.

In some embodiments, microplate tray assembly 1112 comprises a generally planar tray member 1122 that can be movable between an extended position (FIGS. 188-190) and a retracted position. In some embodiments, generally planar tray member 1122 comprises a recessed portion 1124. Recessed portion 1124, in some embodiments, can be sized to receive microplate 20 therein. In some embodiments, microplate tray assembly 1112 comprises an alignment feature 1126 that can be complementary to alignment feature 58 on microplate 20. In some embodiments, alignment feature 1126 can a corner chamfer, a pin, a slot, a cut corner, an indentation, a graphic, a nub, a protrusion, or other unique feature that can be capable of interfacing with alignment feature 58 or other feature of microplate 20. In some embodiments, microplate tray assembly 1112 comprises one or more recesses 1128 formed in generally planar tray member 1122 to permit, among other things, improved grasping of microplate 20 for ease of insertion and withdrawal of microplate 20 from microplate tray assembly 1112. In some embodiments, one or more recesses 1128 can be positioned along opposing ends of microplate 20. In some embodiments, generally planar tray member 1122 comprises a uniquely sized and/or shaped insert 1130 that can be fastened within recessed portion 1124 to accommodate varying sizes of microplates or other devices.

As can be seen in FIG. 190, in some embodiments, microplate tray assembly 1112 can be moved between the extended position and the retracted position via tray drive system 1114. In some embodiments, tray drive system 1114 comprises at least one of a drive motor 1132 and a drive track member 1134. In some embodiments, drive track member 1134 can be a threaded member, such as but not limited to a worm gear, threadedly engaging a receiver 1136 fixedly coupled to microplate tray assembly 1112. Drive motor 1132 can be actuated by a control switch and/or applicator control system 1120 to rotatably turn drive track member 1134. In turn, microplate tray assembly 1112 can travel relative to drive track member 1134 between the extended and retracted positions. During such travel, microplate tray assembly 1112 can be guided via at least one guide member 1137 mounted within base section 1104. It should be appreciated that tray drive system 1114 comprises a cable drive system, a track drive system, a rack and pinion system, a hydraulic system, a pneumatic system, a solenoid system, or the like.

In some embodiments, as illustrated in FIGS. 189-192, sealing cover cassette 1110 comprises at least one of a support structure 1138, a cover member 1140, a roll hub 1142, a plane roller 1144, at least one feed roller 1146, a sprocket drive member 1148, and a waste gate 1150.

In some embodiments, roll hub 1142 can be fixedly coupled to support structure 1138 to support sealing cover roll 512 thereon and permit relative rotation therebetween. In some embodiments, roll hub 1142 comprises pair of friction legs 598 extending outwardly from tangential sections 600 of central portion 602 as discussed herein. In some embodiments, roll hub 1142 can comprise a cylindrical support member 1152.

In some embodiments, plane roller 1144 can be a generally cylindrical member rotatably supported by support structure 1138 to permit rotating movement of plane roller 1144 relative thereto. In some embodiments, plane roller 1144 can be made of, at least in part, a compliant material to permit plane roller 1144 to accommodate variations in microplate tray assembly 1112 and/or microplate 20. In some embodiments, plane roller 1144 can be sized and/or positioned to engage microplate tray assembly 1112 and/or microplate 20 to apply a compressing force upon sealing cover 80 and microplate 20 to impart at least an initial sealing engagement.

In some embodiments, the at least one feed roller 1146 can comprise a pair of cylindrical members rotatably supported by support structure 1138 to permit rotating movement of feed roller 1146 relative thereto. In some embodiments, feed rollers 1146 can be made of a material to, at least in part, positively grab and/or advance carrier liner 520. Feed roller 1146 can also be configured to impart a drag force on carrier liner 520 opposing a driving force by sprocket drive member 1148 to ensure carrier liner 520 and sealing cover 80 disposed thereon are generally flat between feed roller 1146 and sprocket drive member 1148.

As best seen in FIG. 185, in some embodiments, sprocket drive member 1148 can be a generally cylindrical member comprising at least one sprocket portion 1154 disposed on at least one end of a support rod 1156 (FIG. 189) rotatable about an axis 1157. In some embodiments, a pair of sprocket portions 1154 can be provided such that each of the pair of sprocket portions 1154 can be disposed on opposing ends of support rod 1156. In some embodiments, support rod 1156 can be rotatably coupled to support structure 1138. The pair of sprocket portions 1154 can each comprise a plurality of engaging portions 1158 that are each sized and spaced to enmesh with each of the plurality of drive notched 524 formed on carrier liner 520 of sealing cover roll 512.

In some embodiments, sprocket drive member 1148 can be driven by sealing cover drive system 1116. In some embodiments, sealing cover drive system 1116 can comprise a drive motor 1160 (FIG. 189) enmeshingly engaging a drive gear 1162 (FIG. 191) fixed coupled at an end of support rod 1156 of sprocket drive member 1148 (FIG. 191). In some embodiments, drive motor 1160 can be actuated by a control switch and/or applicator control system 1120 to rotatably turn sprocket drive member 1148 and drive carrier liner 520 of sealing cover roll 512. In some embodiments, drive motor 1160 can be fixedly mounted within base section 1104. In some embodiments, a vibration isolation member 1164 can be disposed between drive motor 1160 and a support structure 1166 within base section 1104.

As best seen in FIG. 192, in some embodiments, carrier liner 520 of sealing cover roll 512 can be fed from sealing cover roll 512 downward between feed roller 1146 and around sprocket drive members 1148 and out waste gate 1150. To aid in initial feeding of carrier liner 520 around sprocket drive members 1148, a guide wall 1168 can be provided to direct an end of carrier liner 520 toward waste gate 1150.

In some embodiments, as illustrated in FIGS. 190 and 192, sealing cover cassette 1110 can further comprise a latch system 1170 for operably coupling sealing cover cassette 1110 to cover section 1106. In some embodiments, latch system 1170 comprises a lip member 1172 disposed on one end of cover member 1140 and at least one biasing members 1174. As best seen in FIG. 192, lip member 1172 can engage an underside of cover section 1106. Similarly, at least one biasing member 1174 can be generally U-shaped and have a retaining feature 1177 that can be sized to engage an underside of cover section 1106. In this regarding, at least one biasing member 1174 can impart a locking force such that retaining feature 1177 remains engaged with the underside of cover section 1106 until a user overcomes the biasing force to disengage retaining feature 1177 from cover section 1106. To install sealing cover cassette 1110 into cover section 1106, one can simply insert lip member 1172 under cover section 1106 and pivot a front end of sealing cover cassette 1110 downward until the at least one biasing member 1174 engages cover section 1106. This motion can further engage drive gear 1162 with drive motor 1160.

As illustrated in FIG. 190, in some embodiments, heated roller assembly 1118 can be used to apply at least one of heat and pressure to sealing cover 80 and/or microplate 20 as tray generally planar tray member 1122 passed therebelow. In some embodiments, heat and/or pressure can be used to activate adhesive 518 on sealing cover 80 to effect sealing interface 112. In some embodiments, heated roller assembly 1118 comprises a heated roller 1178 rotatably supported within a removable housing 1180. In some embodiments, heated roller 1178 can be heated internally via a heating member 1182 and/or heated externally via a heating device 1184. In some embodiments, heating member 1182 and/or heating device 1184 can be controlled by applicator control system 1120. It should be appreciated that heated roller assembly 1118 can be manufactured as a sub-assembly to permit easy retrofitting of existing automated sealing cover applicators 1100 for use with heat sensitive adhesives. It should also be appreciated that in some embodiments, heating device 1184 can serve as a convective and/or indirect heater of sealing cover 80 as microplate 20 passes therebelow. In such embodiments, heated roller 1178 can be eliminated.

In some embodiments, applicator control system 1120 can be operable to control tray drive system 1114 and/or sealing cover drive system 1116 to apply sealing cover 80 to microplate 20. Applicator control system 1120 comprises an electrical circuit operable to output various control signals to drive motor 1132 and/or drive motor 1160 in response to a program mode of operation and/or data input. In some embodiments, applicator control system 1120 can receive data input from at least one sensor disposed in automated sealing cover applicator 1100, such as, but not limited to, a tray drive sensor for detecting encumbered operation of microplate tray assembly 1112, a sealing cover drive sensor for detecting encumbered operation of sealing cover cassette 1110, a sealing cover position sensor for detecting one of the plurality of staging notches 528 formed in carrier liner 520, an end/start of roll sensor for detecting end/start of roll notch 530, a temperature sensor for detecting a temperature of heated roller 1178, or any other sensor for detecting a desired operating parameter of automated sealing cover applicator 1100. In some embodiments, applicator control system 1120 can be response to at least one of a power switch 1186, a tray activation button 1188, and/or a seal application button 1190 (FIG. 188). Still further, in some embodiments, applicator control system 1120 can output a control status indicia 1192 that can include, but is not limited to, a TEMP alert indicia, a SEAL EMPTY alert indicia, a TRAY JAM alert indicia, a SEAL JAM alert indicia, a POWER alert indicia, a READY alert indicia, or the like. In some embodiments, the TEMP alert indicia can be used to indicate when a desired temperature has been reached. In some embodiments, the SEAL EMPTY alert indicia can be used to indicate when sealing cover roll 512 is at or near empty of sealing covers 80. In some embodiments, the TRAY JAM alert indicia can be used to indicate when microplate tray assembly 1112 is encumbered. In some embodiments, the SEAL JAM alert indicia can be used to indicate when at least one sealing cover 80 is encumbered.

It should be appreciated that this arrangement can provide reduced possibility of sealing cover application defects, improved sealing cover placement accuracy, reduced operator skill, and faster sealing cover application.

Automated Sealing Cover Applicator—Single Sheet

Turning now to FIGS. 193-201, in some embodiments, automated sealing cover applicator 1100 comprises a single sheet applicator assembly 1194. In some embodiments, single sheet applicator assembly 1194 comprises at least one of a plate member 1196, a cartridge receiving assembly 1198, a sealing cover cartridge 1200, and a planer drive system 1202.

As can be seen in FIGS. 195 and 197, in some embodiments, sealing cover cartridge 1200 comprises at least one of a top cover 1204, a bottom cover 1206, a separator 1208, at least one wheel member 1210, and a sealing cover carrier assembly 1212. In some embodiments, sealing cover carrier assembly 1212 comprises a carrier liner 1214 and a sealing cover 80 disposed on carrier liner 1214. In some embodiments, carrier liner 1214 can be sized larger than sealing cover 80 to define a flap 1216 along a leading edge of carrier liner 1214. In some embodiments, carrier liner 1214 can be similar in material to carrier liner 520.

In some embodiments, top cover 1204 can be generally planar in construction and comprises a pair of feed slots 1218 formed along a leading edge 1220 thereof. The pair of feed slots 1218 can be sized to reveal a portion of sealing cover carrier assembly 1212, specifically flap 1216, for later use in dispensing sealing cover 80.

In some embodiments, bottom cover 1206 can be generally planar in construction and can comprise a pair of feed slots 1222 formed along a leading edge 1224 thereof. The pair of feed slots 1222 can be sized to generally align with the pair of feed slots 1218 of top cover 1204 to reveal a portion of sealing cover carrier assembly 1212, specifically flap 1216, for later use in dispensing sealing cover 80.

In some embodiments, separator 1208 can be generally planar in construction and can be sized to be generally received within top cover 1204 and bottom cover 1206. In some embodiments, separator 1208 can comprise at least one rib 1226 extending about a periphery of separator 1208 and/or traversing thereabout to support sealing cover carrier assembly 1212 thereon. Separator 1208 can further comprise at least one coupling member 1228 for retaining at least one wheel member 1210. In some embodiments, the at least one coupling member 1228 can be a C-shaped members sized to engage and retain a reduced cross-section portion 1230 of at least one wheel member 1210. In some embodiments, the outer diameter of the at least one coupling member 1228 can be less than the outer diameter the at least one wheel member 1210 to reduce interference between the at least one coupling member 1228 and sealing cover carrier assembly 1212.

In some embodiments, top cover 1204, separator 1208, and bottom cover 1206 can be coupled together to encapsulate sealing cover carrier assembly 1212 and sealing cover 80 therein, as illustrated in FIG. 196. Bottom cover 1206 can comprise at least one mounting stud 1232 formed on an interior side thereof. Top cover 1204 and separator 1208 can comprise at least one aperture 1234 generally aligned with the at least one mounting stud 1232 to receive a threaded fastener therethrough. However, it should be appreciate that other coupling systems, such as a snap-lock interface, can be used. As illustrated in FIG. 196, in some embodiments, a slot 1236 can be formed between top cover 1204 and bottom cover 1206. Slot 1236 can be generally aligned with a tangent of sealing cover carrier assembly 1212 such that as carrier liner 1214 can be driven about the at least one wheel member 1210, sealing cover 80 can be encouraged to delaminate from carrier liner 1214 and be urged from sealing cover cartridge 1200 for application upon microplate 20.

As best seen in FIGS. 193, 194, and 198-201, in some embodiments, sealing cover 80 can be urged from sealing cover cartridge 1200 for application upon microplate 20 by first inserting sealing cover cartridge 1200, having sealing cover 80 disposed therein, into cartridge receiving assembly 1198. In some embodiments, cartridge receiving assembly 1198 comprises a removable cartridge support 1238. Removable cartridge support 1238 can be sized to receive sealing cover cartridge 1200 therein for insertion into automated sealing cover applicator 1100. Automated sealing cover applicator 1100 comprises an opening 1240 formed in a cover section 1242. In some embodiments, cover section 1242 can have an inwardly-extending angled lip portion 1244. Angled lip portion 1244 can support and retain an adjustable handle member 1246 via a fastener 1247. In some embodiments, adjustable handle member 1246 comprises a grasping portion 1248 and an urging member 1250 disposed on an opposing end of adjustable handle member 1246 relative to grasping portion 1248. In some embodiments, urging member 1250 can be operable to engage a backside of removable cartridge support 1238 and urge sealing cover cartridge 1200 toward planer drive system 1202.

In some embodiments, planer drive system 1202 comprises a generally triangular mounting block 1252 and at least one drive roller 1254 mounted thereto that can be sized and generally aligned with at least one feed slot 1218, 1222 to operably engage flap 1216 of carrier liner 1214 to drive sealing cover carrier assembly 1212 and urge sealing cover 80 out of slot 1236. In some embodiments, at least one drive roller 1254 can be operably driven via a drive motor, such as drive motor 1160, through a gear assembly 1256 (FIG. 194).

With particular reference to FIGS. 198-201, planer drive system 1202 can further comprise a plane roller 1258. In some embodiments, plane roller 1258 can be a generally cylindrical member rotatably supported by support structure 1166 to permit rotating movement of plane roller 1258 relative thereto. In some embodiments, plane roller 1258 can be made of, at least in part, a compliant material to permit plane roller 1258 to accommodate variations in microplate tray assembly 1112 and/or microplate 20. In some embodiments, plane roller 1258 can be sized and/or positioned to engage microplate tray assembly 1112 and/or microplate 20 to apply a compressing force upon sealing cover 80 and microplate 20 to impart at least an initial sealing engagement. In some embodiments, plane roller 1258 can be heated.

Figure 198:
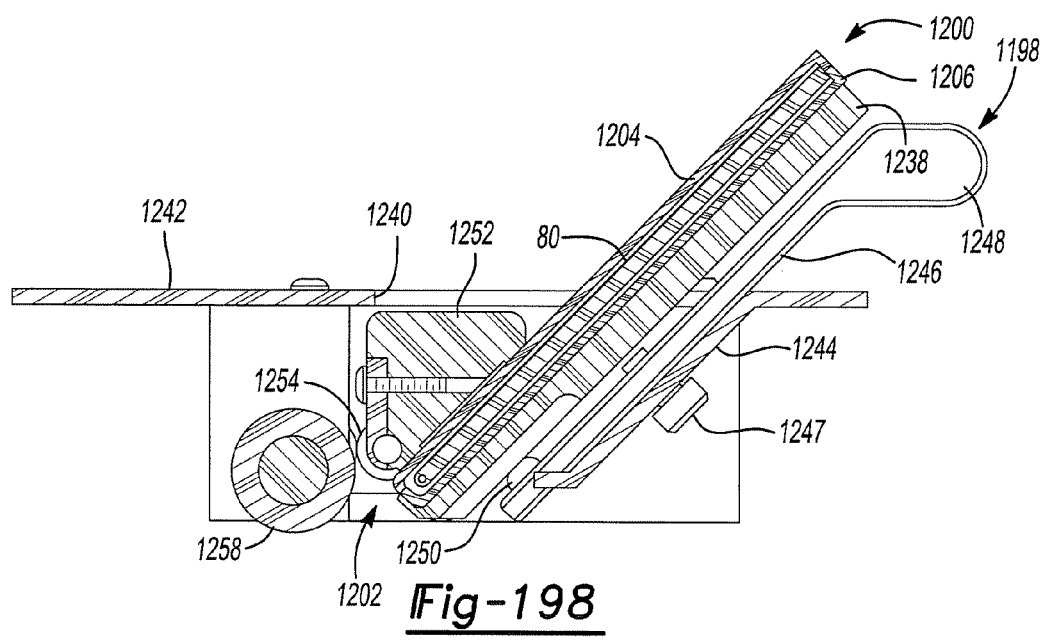
Figure 199:
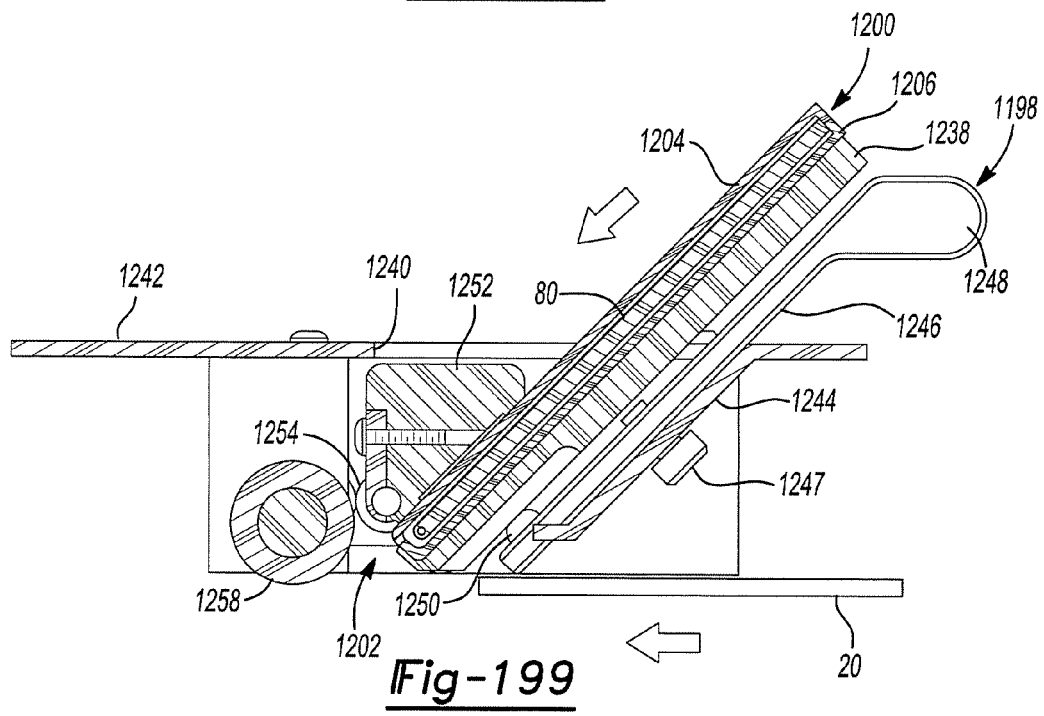
Figure 200:
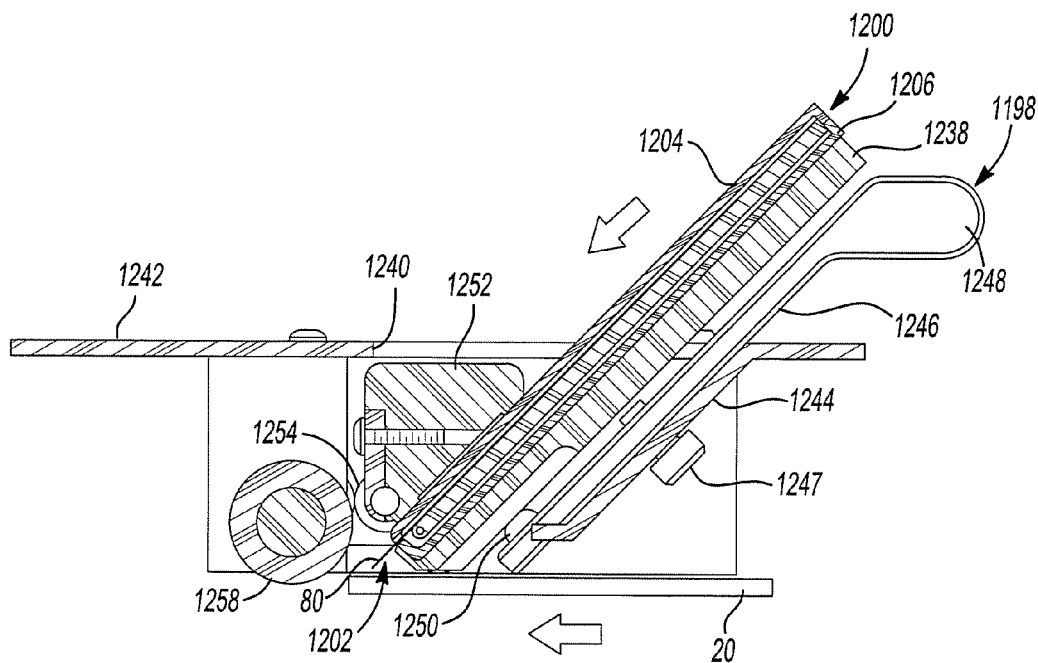
Figure 201:
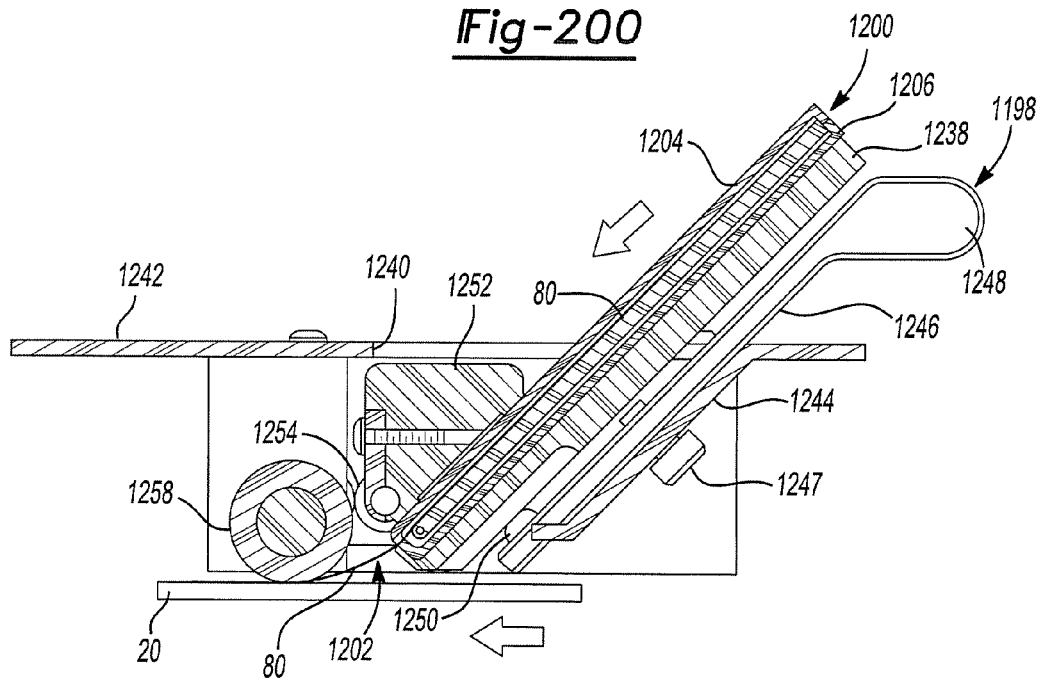

During operation, in some embodiments, sealing cover carrier assembly 1212, carrying a single sealing cover 80, can be preloaded or loaded by a user into sealing cover cartridge 1200 such that flap 1216 of carrier liner 1214 can be exposed through at least one feed slot 1218, 1222. This arrangement can provide reduced contamination of sealing cover 80 and microplate 20. As illustrated in FIG. 198, sealing cover cartridge 1200 can then be loaded into removable cartridge support 1238 and inserted into opening 1240 of cover section 1242 until urging member 1250 engages removable cartridge support 1238 such that flap 1216 can be urged against at least one drive roller 1254 of planer drive system 1202. Microplate 20 can be loaded into microplate tray assembly 1112. As illustrated in FIG. 199, microplate tray assembly 1112 can then be either manually or automatically driven into automated sealing cover applicator 1100. At least one drive roller 1254 can then be actuated at a predetermined time to drive flap 1216 of carrier liner 1214 about at least one wheel member 1210. However, because of, at least in part, the radius of the at least one wheel member 1210, sealing cover 80 can be delaminated from carrier liner 1214 and urged out of slot 1236, as illustrated in FIG. 200. Finally, sealing cover 80 can generally engage microplate 20 and plane roller 1258 applies a compressing force upon sealing cover 80 and microplate 20 to impart at least an initial sealing engagement between sealing cover 80 and microplate 20. This arrangement can provide reduced possibility of sealing cover application defects, improved sealing cover placement accuracy, reduced operator skill, and faster sealing cover application.

Thermocycler System

With reference to FIGS. 30-44, 47, and 48, in some embodiments, thermocycler system 100 comprises at least one thermocycler block 102. Thermocycler system 100 provides heat transfer between thermocycler block 102 and microplate 20 during analysis to vary the temperature of a sample to be processed. It should be appreciated that in some embodiments thermocycler block 102 can also provide thermal uniformity across microplate 20 to facilitate accurate and precise quantification of an amplification reaction. In some embodiments, a control system 1010 (FIGS. 30, 41, and 42) can be operably coupled to thermocycler block 102 to output a control signal to regulate a desired thermal output of thermocycler block 102. In some embodiments, the control signal of control system 1010 can be varied in response to an input from a temperature sensor (not illustrated).

In some embodiments, thermocycler block 102 comprises a plurality of fin members 104 (FIGS. 42 and 44) disposed along a side thereof to dissipate heat. In some embodiments, thermocycler block 102 comprises at least one of a forced convection temperature system that blows hot and cool air onto microplate 20; a system for circulating heated and/or cooled gas or fluid through channels in microplate 20; a Peltier thermoelectric device; a refrigerator; a microwave heating device; an infrared heater; or any combination thereof. In some embodiments, thermocycler system 100 comprises a heating or cooling source in thermal connection with a heat sink. In some embodiments, the heat sink can be configured to be in thermal communication with microplate 20. In some embodiments, thermocycler block 102 continuously cycles the temperature of microplate 20. In some embodiments, thermocycler block 102 cycles and then holds the temperature for a predetermined amount of time. In some embodiments, thermocycler block 102 maintains a generally constant temperature for performing isothermal reactions upon or within microplate 20.

Multiple Thermocyclers

In some embodiments, a plurality of thermocycler blocks 102 can be employed to thermally cycle a plurality of microplates 20 to permit higher throughput of microplates 20 through high-density sequence detection system 10. In some embodiments, each of the plurality of thermocycler blocks 102 can thermally cycle a separate microplate 20 to increase the overall duty cycle of detection system 300 and, in turn, high-density sequence detection system 10. In other words, during a typical PCR analysis, temperature cycles are used, at least in part, to denature (at a high temperature, e.g. about 95° C.) and then extend (at a low temperature, e.g., about 60° C.) a DNA target. Conventional detection systems can then measure a resultant emission while at the low temperature. However, as can be appreciated, during these temperature cycles, conventional detection systems are idle until the next low temperature portion of the cycle. For instance, in cases where about 40 temperature cycles are completed over a 2-hour period, the conventional detection system is active to measure the resultant emission about 40 times. The remaining time the conventional detection system is idle. Therefore, it should be appreciated that conventional thermocycler systems limit the duty cycle of conventional excitation systems and/or conventional detection systems.

In some embodiments, for example, the plurality of thermocycler blocks 102 can be synchronized to provide offset temperature cycles. In some embodiments, the plurality of thermocycler blocks 102 can be synchronized to maximize or provide at or near 100% usage of detection system 300. The exact number of thermocycler blocks 102 to be used is, at least in part, dependent on the time required to measure all the samples on a single thermocycler and the degree of time offset between the cycling profiles of each thermocycler system.

In some embodiments, detection system 300 can comprise a driving device to position detection system 300 and, in some embodiments, excitation system 200 above one of the plurality of thermocycler blocks 102 to measure a resultant emission from the corresponding microplate 20. In some embodiments, detection system 300 can comprise a movable mirror to permit measurement of the resultant emission of multiple microplates 20 from a fixed position. In some embodiments, each of the plurality of thermocycler blocks 102 can be positioned on a carousel or track system for movement relative to detection system 300. It should be appreciated that any system, in addition to those described herein, can be used to permit detection of resultant emission from one or more microplates 20 positioned on the plurality of thermocycler blocks 102 by a single detection system 300 to increase the duty cycle thereof.

Thermal Compliant Pad

With reference to FIG. 33, thermal compliant pad 140 can be disposed between thermocycler block 102 and any adjacent component, such as microplate 20 or a sealing cover 80. It should be understood that thermal compliant pad 140 is optional. Thermal compliant pad 140 can better distribute heating or cooling through a contact interface between thermocycler block 102 and the adjacent component. This arrangement can reduce localized hot spots and compensate for surface variations in thermocycler block 102, thereby providing improved thermal distribution across microplate 20.

Pressure Clamp System

As will be further described herein, according to some embodiments, pressure clamp system 110 can apply a clamping force upon sealing cover 80, microplate 20, and thermocycler block 102 to, at least in part, operably seal assay 1000 within the plurality of wells 26 during thermocycling and further improve thermal communication between microplate 20 and thermocycler block 102. Pressure clamp system 110 can be configured in any one of a number of orientations, such as described herein. Additionally, pressure clamp system 110 can comprise any one of a number of components depending upon the specific orientation used. Therefore, it should be understood that variations exist that are still regarded as being within the scope of the present teachings.

Transparent Bag

As illustrated in FIGS. 30-33, in some embodiments, pressure clamp system 110 can comprise an inflatable transparent bag 116 positioned between and in engaging contact with a transparent window 112 and sealing cover 80. In the embodiment illustrated in FIG. 30, transparent window 112 and thermocycler block 102 are fixed in position against relative movement. Inflatable transparent bag 116 comprises an inflation/deflation port 118 that can be fluidly coupled to a pressure source 122, such as an air cylinder, which can be controllable in response to a control input from a user or control system 1010. It should be understood that in some embodiments inflatable transparent bag 116 can comprise a plurality of inflation/deflation ports to facilitate inflation/deflation thereof.

Upon actuation of pressure source 122, pressurized fluid, such as air, can be introduced into inflatable transparent bag 116, thereby inflating transparent bag 116 in order to exert a generally uniform force upon transparent window 112 and upon sealing cover 80 and microplate 20. In some embodiments, such generally uniform force can serve to provide a reliable and consistent sealing engagement between sealing cover 80 and microplate 20. This sealing engagement can substantially prevent water evaporation or contamination of assay 1000 during thermocycling. In some embodiments, inflatable transparent bag 116 can be part of the transparent window 112, thereby forming a bladder.

Still referring to FIG. 30, it should be appreciated that in some embodiments transparent window 112, inflatable transparent bag 116, and sealing cover 80 permit free transmission therethrough of an excitation light 202 generated by an excitation system 200 and the resultant fluorescence emission. Transparent window 112, inflatable transparent bag 116, and sealing cover 80 can be made of a material that is non-fluorescent or of low fluorescence. In some embodiments, transparent window 112 can be comprised of Vycor®, fused silica, quartz, high purity glass, or combination thereof. By way of non-limiting example, window 112 can be comprised of Schott Q2 quartz glass. In some embodiments, window 112 can be from about ¼ to about ½ inch thick; e.g., in some embodiments, about ⅜ inch thick. In some embodiments, a broadband anti-reflective coating can be applied to one or both sides of window 112 to reduce glare and reflections. In some embodiments, the transparent window 112 can comprise optical elements such as a lens, lenslets, and/or a holographic feature.

In some embodiments, as illustrated in FIG. 31, transparent window 112 can be movable to exert a generally uniform force upon transparent bag 116 and, additionally, upon sealing cover 80 and microplate 20. In this embodiment as in others, transparent bag 116 can comprise a fixed internal amount of fluid, such as air. Transparent window 112 can be movable using any moving mechanism (not illustrated), such as an electric drive, mechanical drive, hydraulic drive, or the like.

Pressure Chamber

In some embodiments, as illustrated in FIGS. 34-40, pressure clamp system 110 can further employ a pressure chamber 150 in place of transparent bag 116.

Pressure chamber 150 can be a pressurizable volume generally defined by transparent window 112, a frame 152 that can be coupled to transparent window 112, and a circumferential chamber seal 154 disposed along an edge of frame 152. Circumferential chamber seal 154 can be adapted to engage a surface to define the pressurizable, airtight, or at least low leakage, pressure chamber 150. Transparent window 112, frame 152, circumferential chamber seal 154, and the engaged surface bound the actual volume of pressure chamber 150. Circumferential chamber seal 154 can engage one of a number of surfaces that will be further discussed herein. A port 120, in fluid communication with pressure chamber 150 and pressure source 122, can provide fluid to pressure chamber 150.

In the interest of brevity, it should be appreciated that the particular configuration and arrangement of sealing cover 80 and microplate 20 illustrated in FIGS. 34-40 can be similar to that illustrated in FIGS. 30-33.

In some embodiments, as illustrated in FIGS. 34 and 36, circumferential chamber seal 154 can be positioned such that it engages a portion of sealing cover 80. A downward force from transparent window 112 can be exerted upon microplate 20 to maintain a proper thermal engagement between microplate 20 and thermocycler block 102. Additionally, such downward force can further facilitate sealing engagement of sealing cover 80 and microplate 20. Still further, pressure chamber 150 can then be pressurized to exert a generally uniform force upon sealing cover 80 and sealing interface 92. Such generally uniform force can provide a reliable and consistent sealing engagement between sealing cover 80 and microplate 20. This sealing engagement can reduce water evaporation or contamination of assay 1000 during thermocycling.

With particular reference to FIG. 37, it should be appreciated that in some embodiments circumferential chamber seal 154 of pressure chamber 150 can be positioned to engage thermocycler block 102, rather than microplate 20. Microplate 20 can be positioned within pressure chamber 150. As pressure chamber 150 is pressurized, force is exerted upon sealing cover 80, thereby providing a sealing engagement between sealing cover 80 and microplate 20.

In some embodiments, as illustrated in FIG. 39, to improve thermal contact between microplate 20 and thermocycler block 102, optional posts 156 can be employed. Optional posts 156 can be adapted to be coupled with transparent window 112 and downwardly extend therefrom. Optional posts 156 can then engage at least one of microplate 20 or sealing cover 80 to ensure proper contact between microplate 20 and thermocycler block 102 during thermocycling.

Inverted Orientation

In some embodiments, as illustrated in FIGS. 27, 32, 35, 41, 44, 47, and 48, microplate 20 can be inverted such that each of the plurality of wells 26 is generally inverted, such that the opening of each of the plurality of wells 26 is directed downwardly. Among other things, this arrangement can provide improved fluorescence detection. As illustrated in FIG. 27, this inverted arrangement causes assay 1000 to collect adjacent sealing cover 80 and, thus, addresses the occurrence of condensation effecting fluorescence detection and improves optical efficiency, because assay 1000 is now disposed adjacent to the opening of each of the plurality of wells 26.

In some embodiments, as illustrated in FIG. 32, thermocycler block 102 remains stationary and is positioned above microplate 20 and transparent window 112 is positioned below microplate 20. Inflatable transparent bag 116 can then be positioned in engaging contact between transparent window 112 and sealing cover 80. It should be appreciated that transparent window 112, inflatable transparent bag 116, and sealing cover 80 can permit free transmission therethrough of excitation light 202 generated by excitation system 200 positioned below transparent window 112 and the resultant fluorescence therefrom. In some embodiments, detection system 300 can be positioned below microplate 20 to detect such fluorescence generated in response to excitation light 202 of excitation system 200.

In some embodiments, as illustrated in FIG. 35, microplate 20 can be positioned in an inverted orientation, similar to that described in connection with FIG. 32, and further employ pressure chamber 150. Circumferential chamber seal 154 can then be positioned such that it engages a portion of sealing cover 80. A force from transparent window 112 can be exerted upon microplate 20 to maintain a proper thermal engagement between microplate 20 and thermocycler block 102 and sealing engagement between sealing cover 80 and microplate 20. Pressure chamber 150 can then be pressurized to exert a generally uniform force across sealing cover 80.

Vacuum Channels

As illustrated in FIG. 38, some embodiments can comprise a vacuum assist system 170. In this regard, in some embodiments, port 120 can be eliminated. Vacuum assist system 170 can comprise a pressure/vacuum source 172 fluidly coupled to at least one vacuum channel 174, which extends throughout thermocycler block 102. Vacuum channel 174 can comprise grooves or, alternatively or in addition, can comprise a porous or permeable section of thermocycler block 102. Vacuum channel 174 can be evacuated so as to form a vacuum within a volume 176 defined by transparent window 112, an O-ring 178, and thermocycler block 102. Upon actuation of pressure source 172, a vacuum can be formed in vacuum channel 174. This vacuum can vacate volume 176 causing outside air pressure to exert a clamping force on transparent window 112, thereby clamping sealing cover 80 against microplate 20 to ensure a proper seal and further clamping microplate 20 to thermocycler block 102 to ensure a proper thermal contact. It should be understood that in some embodiments vacuum assist system 170 can be formed in transparent window 112.

Relief Port

Turning now to FIG. 40, in some embodiments a relief port 158 can be in fluid communication with pressure chamber 150. Relief port 158 can be operable to slowly bleed gas in pressure chamber 150 and/or simultaneously remove water vapor from pressure chamber 150 to reduce condensation. Removal of water vapor can, in some circumstances, improve fluorescence detection. Relief port 158 can be used in connection with any of the embodiments described herein.

Window Heating Device

In some embodiments, as illustrated in FIG. 41, transparent window 112 can comprise a heating device 160. Heating device 160 can be operable to heat transparent window 112, which in turn heats each of the plurality of wells 26 to reduce the formation of condensation within each of the plurality of wells 26. In some cases, condensation can reduce optical performance and, thus, reduce the efficiency and/or stability of fluorescence detection.

In some embodiments, heating device 160 can comprise a layer member 162 that can be laminated to transparent window 112. In some embodiments, layer member 162 can comprise a plurality of heating wires (not illustrated) distributed uniformly throughout layer member 162, which can each be operable to heat an adjacent area. In some embodiments, layer member 162 can be an indium tin oxide coating that is applied uniformly across transparent window 112. A pair of bus bars 164 can be disposed on opposing ends of transparent window 112. Electrical current can then be applied between bus bars 164 to heat the indium tin oxide coating, which provides a consistent and uniform heat across transparent window 112 without interfering with fluorescence transmission. Bus bars 164 can be controlled in response to control system 1010. In some embodiments, heating device 160 can be on both sides of transparent window 112.

Clamp Mechanism

In some embodiments, as seen in FIGS. 202-206, pressure chamber 150 can be used with a clamp mechanism 1400 (best illustrated in FIGS. 204-206). Clamp mechanism 1400 can retain pressure chamber 150 in a clamped position against thermocycler system 100.

Turning now to FIGS. 202 and 203, one of some embodiments of pressure chamber 150 is illustrated. A chamber body 1402 has a first side 1404 and a second side 1406. In some embodiments, chamber body 1402 can be formed from aluminum or other materials such as steel, stainless steel, standard plastic, or fiber-reinforced plastic compound, such as a resin or polymer, and mixtures thereof. An opening 1408 extends through first side 1404 and second side 1406.

A chamber cover 1410 has an opening 1412 surrounded by circumferential chamber seal 154. Circumferential chamber seal 154 can have a peripheral lip that 1413 that defines a sealing plane abutting sealing cover 80 of microplate 20. In some embodiments, peripheral lip 1413 can be positioned radially inward of a periphery of opening 1412. A reactive surface 1415 can span between opening 1412 and peripheral lip 1413. Reactive surface 1415 can react to fluid pressure in pressure chamber 150 by increasingly urging peripheral lip 1413 against sealing cover 80 as the fluid pressure increases from zero to about 25 pounds per square inch (PSI). In some embodiments, chamber cover 1410 is formed from stainless steel. In some embodiments, a gasket 1414 (FIG. 203) can fit in a groove 1416 formed in a periphery of opening 1408 and provide a seal between chamber cover 1410 and chamber body 1402. Chamber cover 1410 can be as thin as practicable and have a lower thermal mass than said chamber body to reduce heat flow between microplate 20 and chamber body 1402. In some embodiments, frame 152 (also seen in FIG. 35) can comprise chamber cover 1410 and chamber body 1402.

In some embodiments, a thin film heater 1418 can be positioned on chamber cover 1410 to further reduce heat flow into chamber body 1402. Thin film heater 1418 can have a heater signal input 1420 to receive heater power from control system 1010. In some embodiments, a thermocouple 1422 can be positioned on chamber cover 1410 and provide a cover temperature signal 1424, by way of non-limiting example, via leads or other signal transmission medium, to control system 1010. Thermocouple 1422 can comprise, by way of non-limiting example, a type E, type J, type K, or type T thermocouple. Control system 1010 can use cover temperature signal 1424 to control heater power applied to thin film heater 1418 and thereby reduce temperature differences across microplate 20. In some embodiments, thin film heater 1418 can have a power dissipation of at least 50 watts.

In some embodiments, circumferential chamber seal 154 can be molded from a silicone material. In some embodiments, circumferential chamber seal 154 can be insert-molded with chamber cover 1410. An alignment ring 1426 can be fastened to chamber body 1402 through chamber cover 1410, and secure chamber cover 1410 to second side 1406. Microplate 20 can fit within an inner periphery of alignment ring 1426. Alignment ring 1426 can locate microplate 20 with respect to thermocycler system 100. In some embodiments, an alignment feature 1428 can interface with alignment feature 58 of microplate 20. In some embodiments, recesses 1430 can be formed in the inner periphery of alignment ring 1426. Recesses 1430 reduce a contact area between alignment ring 1426 and microplate 20 and can thereby reduce heat flow between microplate 20 and alignment ring 1426.

On first side 1404, a flange 1432 can protrude radially inward from the periphery of opening 1408 and support a window seal 1434. In some embodiments, flange 1432 can be about ¼" wide. A surface of transparent window 112 can abut window seal 1434. In some embodiments, for example when window seal 1434 is a non-adhesive type seal, a window-retaining ring 1436 can be secured to chamber body 1402 and clamp transparent window 112 against window seal 1434. A connector 1438 can provide a connection to port 120 (FIGS. 34-37, 39-40) that is in fluid communication with the internal volume of pressure chamber 150.

At least one catch 1440 can be positioned on frame 152. In some embodiments, a pair of catches 1440 can be positioned on opposing sides of a perimeter of frame 152. Each of the pair of catches 1440 can have a centering feature 1442.

Referring now to FIGS. 204-206, thermocycler system 100 and clamp mechanism 1400 are illustrated fixedly mounted to a support structure 1444. In some embodiments, support structure 1444 can be generally planar in construction and adapted to be mounted within housing 1008 (FIG. 1). Clamp mechanism 1400 can be movable to between a locked condition (FIG. 204) and an unlocked condition (FIG. 205) and can be adapted to selectively clamp pressure chamber 150 against thermocycler system 100. An opening can be provided in support structure 1444 to allow contact between pressure chamber 150 and thermocycler system 100. In the locked condition, clamp mechanism 1400 can secure pressure chamber 150 in a clamped position against thermocycler system 100. In the clamped position, circumferential chamber seal 154 can be pressed against sealing cover 80 (best seen in FIG. 203). In the unlocked condition, clamp mechanism 1400 can allow pressure chamber 150 to be moved to an unclamped position away from thermocycler system 100. In some embodiments, the unclamped position can provide a gap of ⅜ inch between thermocycler block 102 (FIG. 203) and microplate 20. In some embodiments, clamp mechanism 1400 can be actuated manually. In other embodiments, clamp mechanism 1400 can be actuated by pneumatics, hydraulics, electric machines and/or motors, electromagnetics, or any other suitable means.

In some embodiments, clamp mechanism 1400 can have a clamp frame 1446 fixedly mounted to support structure 1444. An over-center link 1448 can pivot about a first end 1450 that can be pivotally connected to clamp frame 1446. A bellcrank 1452 can pivot about a pivot pin 1454 connected to clamp frame 1446. A lever arm 1456 can have a clamp end 1458 pivotally connected to an input end 1460 of bellcrank 1452. Lever arm 1456 can have an intermediate portion 1462 pivotally connected to a second end 1464 of over-center link 1448. An input end 1466 of lever arm 1456 can be pivotally connected to a telescoping end 1468 of a pneumatic cylinder 1470. A ball joint 1472 can pivotally connect telescoping end 1468 to input end 1466. A mounting end 1474 of pneumatic cylinder 1470 can pivotally connect to support structure 1444. In various other embodiments, mounting end 1474 of pneumatic cylinder 1470 can pivotally connect to clamp frame 1446. Bellcrank 1452 can have a clamp end 1476. A clamp pin 1478 can project from clamp end 1476 and engage centering feature 1442 when clamp mechanism 1400 is in the locked condition. It should be appreciated that the clamp mechanism 1400 on one side of thermocycler system 100 has been described. A second clamp mechanism 1401 can be positioned on the other side of thermocycler system 100 (FIG. 206). Second clamp mechanism 1401 can be symmetrical with the side just described and operate similarly. A transverse member 1479 can connect lever arm 1456 to the lever arm of the other side.

Operation of the clamp assembly 1400 embodiment illustrated in FIGS. 204-206 will now be described. Pneumatic cylinder 1470 can be movable between an extended condition (FIG. 205) and a contracted condition (FIGS. 204 and 206). As pneumatic cylinder 1470 moves to the contracted condition, it can cause lever arm 1456 to pivot as indicated by a curved arrow A. Lever arm 1456 can in turn cause bellcrank 1452 to pivot as indicated by a curved arrow B, thereby moving clamp pin 1478 towards centering feature 1442. Clamp pin 1478 can then become centered in centering feature 1442. As bellcrank 1452 completes rotating in the direction of arrow B, it can cause clamp pin 1478 to move chamber 150 from an unclamped position towards the clamped position against thermocycler assembly 100. This can cause circumferential chamber seal 154 to press against microplate 20 (best seen in FIG. 203). A clamping pressure between chamber seal 154 and microplate 20 can be adjusted by varying the pivot location of first end 1450 of over-center link 1448. In some embodiments, an adjustment mechanism 1477, such as, by way of non-limiting example, a screw, can be used to vary the pivot location as indicated by arrows A (FIG. 205).

Moving clamp mechanism 1400 to the unlocked condition will now be described. As pneumatic cylinder 1470 moves to the extended condition, it can cause lever arm 1456 to pivot in a direction opposite curved arrow A. Lever arm 1456 can in turn cause bellcrank 1452 to pivot in a direction opposite curved arrow B, thereby relieving the clamping pressure between clamp pin 1478 and catch 1440. Clamp pin 1478 can then disengage from centering feature 1442. As bellcrank 1452 completes rotating in the direction opposite curved arrow B, it can cause clamp pin 1478 to move away from catch 1440, allowing chamber 150, with microplate 20, to move to the unclamped position away from thermocycler system 100.

In some embodiments, a pair of rails 1480 can be used to traverse pressure chamber 150 between a thermocycler position adjacent thermocycler system 100 (FIG. 204) and a loading position away from thermocycler system 100 (FIG. 205). In some embodiments, the loading position can be external of housing 1008. In such embodiments, housing 1008 has an aperture that allows pressure chamber 150 and rails 1480 to pass therethrough. In some embodiments, a position sensor 1487 can be positioned on support structure 1440 and provide a position signal indicative of pressure chamber 150 being in the thermocycler position. In some embodiments, position sensor can be of an infrared, limit switch, contactless proximity, or ultrasonic type. Rails 1480 can be slidably mounted to support structure 1444. In some embodiments, optical sensor 1491 can read marking indicia 94 (FIG. 16) on microplate 20 as it is moved to the thermocycler position. Optical sensor 1491 can provide a marking data signal indicative of marking indicia 94 to control system 1010.

In some embodiments, rails 1480 can be telescoping rails. Rails 1480 can be moved manually or can be motorized. In some motorized embodiments, a rack gear 1482 can be positioned on at least one of rails 1480. A rotating actuator 1484 can be adapted with a pinion gear 1486 that engages rack gear 1482. Rotating actuator 1484 can rotate in response to control signals from control system 1010. In some embodiments, rotating actuator 1484 can be an electric motor, such as a stepper motor. For example, actuator 1484 can be a Vexta PK245-02AA stepper motor available from Oriental Motor U.S.A. Corp. In other embodiments, rotating actuator 1484 can be pneumatic or hydraulic. Pressure chamber 150 can be attached between rails 1480.

In some embodiments, a lost motion mechanism 1488 can be positioned between rails 1480 and pressure chamber 150. Lost motion mechanism 1488 can allow pressure chamber 150 limited perpendicular movement with respect to rails 1480. The limited perpendicular movement facilitates moving pressure chamber 150 between the clamped and unclamped positions as clamp assembly 1400 moves between the locked and unlocked conditions, respectively.

In some embodiments, lost motion mechanism 1488 can include shoulder bolts 1490 threaded into rails 1480. Catches 1440 can have through holes 1492 that slidingly engage shoulder bolts 1490. In some embodiments, springs 1494 can be positioned between catches 1440 and rails 1480. Springs 1494 can bias pressure chamber 140 toward the unclamped position and facilitate moving it away from thermocycler assembly 100 when clamp assembly 1400 moves to the unlocked condition.

Pneumatic System

Referring now to FIGS. 207 and 208, a pneumatic system 1500 is illustrated in accordance with some embodiments. Pneumatic system 1500 can provide pneumatic control for various pneumatic devices used in sequence detection system 10. By way of non-limiting example, the pneumatic devices can include, alone or in any combination, pressure chamber 150, pneumatic cylinders 1470, and vacuum source 172.

An input coupling 1502 can provide a connection point for a supply of compressed fluid, such as, by way of non-limiting example, air, but can also comprise nitrogen, argon, or helium. Input coupling 1502 can be accessible from an exterior of housing 1008 (FIG. 1). In some embodiments, a pressure relief valve 1504 can be in fluid communication with input coupling 1502. In some embodiments, pressure relief valve 1504 can have a maximum pressure of 120 PSI. In some embodiments, a particle filter 1506 can be in fluid communication with pressure relief valve 1504. In some embodiments, a condensation separator 1508 can be in fluid communication with particle filter 1508. Alternatively, condensation separator 1508 can be in fluid communication with pressure relief valve 1504. Particle filter 1506 and condensation separator 1508 can provide a conditioned fluid supply 1510 to a remainder of pneumatic system 1500.

In some embodiments, a first pressure regulator 1512 can be in fluid communication with conditioned fluid supply 1510. First pressure regulator 1512 can provide a first fluid supply 1516 to a chamber pressurization subsystem 1518 and/or to other subsystems.

In chamber pressurization subsystem 1518, a check valve 1520 can be connected in series with first pressure regulator 1512. Check valve 1520 can reduce a risk of depressurization of the internal volume of pressure chamber 150 in the event conditioned fluid supply 1510 is interrupted. A ballast tank 1522 can be in fluid communication with the first fluid supply 1516 and increase a fluid volume of chamber pressurization subsystem 1518. The increased volume can reduce pressure variations of the first fluid supply 1516. Ballast tank 1522 can also provide a fluid reserve to help maintain pressure in the event first fluid supply 1516 is interrupted. One side of a charge valve 1524 can be in fluid communication with the first fluid supply 1516. The other side of charge valve 1524 can be in fluid communication with the internal volume of pressure chamber 150. A flexible fluid line can connect chamber pressurization subsystem 1518 to connector 1438 of chamber 150. Charge valve 1524 can be controlled by control system 1010 in accordance with a method described later herein. In some embodiments, charge valve 1524 can be a part number MKH0NBG49A available from Parker-Hannifin Corp.

A pressure sensor 1526 can be in fluid communication with the internal volume of pressure chamber 150 and can provide a chamber pressure signal 1527 to control system 1010. In some embodiments, pressure sensor 1526 can be a part number MPS-P6N-AG available from Parker-Hannifin Corp. A chamber pressure relief valve 1528 can be in fluid communication with the internal volume of pressure chamber 150 and establish a maximum pressure that can be applied thereto. In some embodiments, the maximum pressure of 1528 chamber pressure relief valve can be less than, or equal to, 30 PSI.

Pressurization subsystem 1518 can also comprise a release valve 1530 in fluid communication with the internal volume of pressure chamber 150. The other side of release valve 1530 can be vented to atmosphere. Release valve 1530 can be controlled by control system 1010 in accordance with a method described later herein. In some embodiments, release valve 1530 can be a part number MKH0NBG49A available from Parker-Hannifin Corp. In some embodiments, the charge and release valves 1524, 1530 can maintain chamber pressure at about 18 PSI while the microplate temperature is greater than 40 degrees Celsius. This combination of pressure and temperature conditions can help reduce a possibility of pressure within wells 26 overcoming the chamber pressure and causing wells 26 to leak between sealing cover 80. A first silencer 1532 can be in fluid communication with the other side of release valve 1530 to reduce noise as fluid is vented.

In some embodiments, a second pressure regulator 1534 can be in fluid communication with conditioned fluid supply 1510. Second pressure regulator 1534 can provide a second fluid supply 1536 to a cylinder control subsystem 1538. Second pressure regulator 1540 can also provide second fluid supply 1536 to a vacuum control subsystem 1540. A pressure transducer 1542 can be in fluid communication with second fluid supply 1536 and provide a pressure signal 1544 to control system 1010. In some embodiments, pressure transducer 1542 can comprise a part number MPS-P6N-AG available from Parker-Hannifin Corp. In some embodiments, second fluid supply 1536 is greater than, or equal to, 50 PSI.

In cylinder control subsystem 1538, a cylinder valve 1546 can have a pressure port 1548, an exhaust port 1550, a first port 1552, and a second port 1554. Cylinder valve 1546 can be referred to as a 3-position, 2-port valve, commonly referred to as a 3/2 valve. In some embodiments, cylinder valve 1546 can comprise a part number P2MISGEE2CV2DF7 available from Parker-Hannifin Corp. or a part number B360BA549C available from Parker-Hannifin Corp. Pressure port 1548 can be in fluid communication with second fluid supply 1536. Exhaust port 1550 can be vented to atmosphere. Cylinder silencer 1556 can be in fluid communication with exhaust port 1550 to reduce noise when fluid is vented from pneumatic cylinder 1470. First port 1552 can be in fluid communication with first port 1558 of pneumatic cylinder 1470. Second port 1554 can be in fluid communication with second port 1559 of pneumatic cylinder 1470. Cylinder valve 1546 can be manually controlled. In some embodiments, cylinder valve 1546 is a servovalve controlled by control system 1010 in accordance with a method described later herein.

Cylinder valve 1546 can have three positions that route fluid between ports 1548-1554. A first position can route pressure port 1548 to first port 1552 and route second port 1554 to exhaust port 1550. A second position can block pressure port 1548 and route first and second ports 1552, 1554 to exhaust port 1550. A third position can route pressure port 1548 to second port 1554 and route first port 1552 to exhaust port 1550. The first, second, and third positions of cylinder valve 1546 can be referred to as the lock, release, and unlock positions, respectively.

When cylinder valve 1546 is in the lock position, fluid routing through cylinder valve 1546 can cause pneumatic cylinder 1470 to move to the contracted condition, thereby moving clamp mechanism 1400 to the locked condition (FIG. 204). When cylinder valve 1546 is in the unlock position, the fluid routing through cylinder valve 1546 can cause pneumatic cylinder 1470 to move to the extended condition, thereby moving clamp mechanism 1400 to the unlocked condition (FIG. 205). When cylinder valve 1546 is in the release position, the fluid routing through cylinder valve 1546 can cause pneumatic cylinder 1470 to be freely extended or contracted by an outside influence, thereby allowing clamp mechanism 1400 to be manually moved between the closed and open positions. It should be noted that over-center link 1448 can maintain clamp mechanism in the locked condition when cylinder valve 1546 is moved to the release position. A first limit switch 1560 can sense, either directly or indirectly, when pneumatic cylinder 1470 is in the extended condition and provide a corresponding signal 1562 to control system 1010. A second limit switch 1564 can be used to sense, either directly or indirectly, when pneumatic cylinder 1470 is in the contracted condition and provide a corresponding signal 1566 to control system 1010. In some embodiments, first and second limits switches 1560, 1564 can be integral to pneumatic cylinder 1470. In some embodiments, pneumatic cylinder 1470 can be a Parker-Hannifin Corp. SRM Series pneumatic cylinder with piston sensing capability. In some embodiments, pneumatic cylinder 1470 can be a part number L06DP-SRMBSY400 from Parker-Hannifin Corp.

In some embodiments, vacuum control system 1540 selectively actuates vacuum source 172. Vacuum generated by vacuum source 172 can be provided to thermocycler system 100 or other systems. Vacuum control system 1572 can comprise a vacuum control valve 1568. In some embodiments, vacuum control valve 1568 can comprise a part number P2MISDEE2CV2BF7 available from Parker-Hannifin Corp.

Vacuum control valve 1568 can have a pressure port 1570, an exhaust port 1572, a first port 1574, and a second port 1576. Vacuum control valve 1568 can be referred to as a 3-position, 2-port valve, commonly referred to as a 3/2 valve. Pressure port 1570 can be in fluid communication with second fluid supply 1536. In some embodiments, exhaust port 1572 can be blocked. In other embodiments, exhaust port 1572 can be vented to atmosphere. First port 1574 can be in fluid communication with vacuum source 172. Second port 1576 can be blocked in some embodiments having exhaust port 1572 vented to atmosphere. In other embodiments, second port 1576 can be vented to atmosphere. Vacuum control valve 1568 can be manually controlled. In some embodiments, vacuum control valve 1568 is a servovalve controlled by control system 1010 in accordance with a method described later herein.

Vacuum control valve 1568 can have three positions that route fluid between ports 1570-1576. A first position can route pressure port 1570 to first port 1574, and can block exhaust port 1572 and second port 1576. A second position can block pressure port 1570, and route first and second ports 1574, 1576 through exhaust port 1572. A third position can route pressure port 1570 to second port 1576, and block first port 1574 and exhaust port 1572. The first, second, and third positions of vacuum control valve 1568 can also be referred to as the vacuum on, vacuum off, and vent positions, respectively.

When vacuum control valve 1568 is in the vacuum on position, the fluid routing through vacuum control valve 1568 can flow through vacuum source 172. Vacuum source 172 generates a vacuum in response thereto that can be fluidly coupled to the thermocycler system 100 or other systems. When vacuum control valve 1568 is in the vacuum off position, second fluid supply 1536 is disconnected from vacuum source 172 and vacuum source 172 can be routed to atmosphere through exhaust port 1572 and/or second port 1576. When vacuum control valve 1568 is in the vent position, second fluid supply 1536 can be purged to atmosphere through second port 1576.

Referring now to FIG. 209, a method 1580 is illustrated, according to some embodiments, for clamping pressure chamber 150 to thermocycler system 100. Method 1580 can be executed by control system 1010 when pressure chamber 150 is placed in proximity to thermocycler block 102. Method 1580 can begin in step 1582 and can proceed to decision step 1584 to determine whether pressure chamber 150 is properly located within clamp mechanism 1400. Position signal 1489 (FIG. 204) can be used to make the determination. When pressure chamber 150 is properly located, method 1580 can proceed to step 1586 and move cylinder valve 1546 to the lock position. Method 1580 can then proceed to decision step 1588 and determine whether pneumatic cylinder 1470 has moved to the contracted condition, thereby placing clamp mechanism 1400 in the locked condition. Decision step 1588 can make the determination by using signal 1566 (FIG. 207) from second limit switch 1570. Method 1580 can execute decision step 1588 until pneumatic cylinder 1470 moves to the contracted condition. Method 1580 can then proceed to step 1590 and can perform a leak test 1590 as described later herein. Method 1580 can then proceed to decision step 1592 and determine, from results of leak test 1590, whether leak test 1590 passed. If leak test 1590 passed, then method 1580 can proceed to step 1594 and exit. If leak test 1590 failed, then method 1580 can proceed to step 1610 and release chamber 150 according to a method described later herein.

Returning to decision step 1584, if method 1580 determines that chamber 150 is improperly located within clamp mechanism 1400, then method 1580 can proceed to step 1596. In step 1596, method 1580 can indicate that chamber 150 is improperly located within clamp mechanism 1400. Method 1580 can then proceed to method 1610 and assure clamp mechanism 1400 is in the unlocked condition. Method 1580 can indicate the improper location of chamber 150 though, by way of example, a buzzer, lamp, writing to a computer memory in control system 1010, or any other suitable means.

Referring now to FIG. 210, method 1590 is illustrated, according to some embodiments of the invention, for performing the leak test on chamber 150. Method 1590 can be executed by control system 1010 when chamber 150 is in the clamped position. Method 1590 can begin at step 1591 and can proceed to step 1593. In step 1593, method 1590 can pressurize chamber 150 by opening charge valve 1524 and closing release valve 1530 (FIG. 207). Method 1590 can then proceed to decision step 1595 and determine a chamber leak rate of pressure chamber 150. In one of some embodiments, the chamber leak rate can be determined by determining a difference in air pressure, as indicated by pressure transducer 1526, over a predetermined amount of time. In one example, the chamber leak rate can be expressed in units of PSI/minute. In decision step 1595, method 1590 can compare the chamber leak rate to a predetermined leak rate. If the chamber leak rate is less than the predetermined leak rate, method 1590 can proceed to step 1598, indicating that the leak test has passed. Method 1590 can then proceed to step 1600 and open charge valve 1524 to connect ballast tank 1536 to the internal volume of pressure chamber 150. In step 1600, method 1590 can also provide an indication to control system 1010 that thermocycling can begin.

Returning now to decision step 1595, if the chamber leak rate is greater than, or equal to, the predetermined leak rate, method 1590 can proceed to step 1602, indicating that the leak test has failed. Method 1590 can then proceed to step 1604 and indicate the failure though, by way of example, a buzzer, lamp, writing to the computer memory in control system 1010, or any other suitable means. Method 1590 can exit at step 1606 from either step 1600 or step 1604.

Referring now to FIG. 211, method 1610 of unclamping pressure chamber 150 from thermocycler system 100 is illustrated according to one of several embodiments. Method 1610 can be executed by control system 1010. In some embodiments, method 1612 can be called by method 1580. Method 1610 can also be executed after thermocycling is completed. Method 1610 can begin in step 1612 and then can proceed to step 1614. In step 1614, method 1610 can move cylinder valve 1546 to the unlock position, which can cause pneumatic cylinder 1470 to begin moving to the extended condition and changing clamp mechanism to the unlocked condition. Method 1610 can then proceed to decision step 1616 and determine whether pneumatic cylinder 1470 has moved to the extended condition. Decision step 1616 can make the determination by using signal 1562 (FIG. 207) from first limit switch 1560. Method 1610 can execute decision step 1616 until pneumatic cylinder 1470 moves to the extended condition. Method 1610 can then proceed to step 1618 and exit.

Excitation System

In some embodiments, as illustrated in FIGS. 42-49, excitation system 200 generally comprises a plurality of excitation lamps 210 generating excitation light 202 in response to control signals from control system 1010. Excitation system 200 can direct excitation light 202 to each of the plurality of wells 26 or across the plurality of wells 26. In some embodiments, excitation light 202 can be a radiant energy comprising a wavelength that permits detection of photo-emitting detection probes in assay 1000 disposed in at least some of the plurality of wells 26 of microplate 20 by detection system 300.

By way of background, it should be understood that the quantitative analysis of assay 1000, in some embodiments, can involve measurement of the resultant fluorescence intensity or other emission intensity. In some embodiments of the present teachings, fluorescence from the plurality of wells 26 on microplate 20 can be measured simultaneously using a CCD camera. In an idealized optical system, if all of the plurality of wells 26 have the same concentration of dye, each of the plurality of wells 26 would produce an identical fluorescence signal. In some prior conventional designs, wells near the center of the microplate may appear significantly brighter (i.e. output more signal) than those wells near the edge of the microplate, despite the fact that all of the wells may be outputting the same amount of fluorescence. There are several reasons for this condition in some current designs—vignetting, shadowing, and the particular illumination/irradiance profile.

With respect to vignetting, camera lenses can collect more light from the center of the frame relative to the edges. This can reduce the efficiency of certain prior, conventional detection systems. Additionally, in certain prior, conventional designs, the irradiance profile is sometimes not uniform. Most commercially available irradiance sources have a greater irradiance value (watts/meter$^2$) near the center compared to the edges of the irradiance zone. In PCR, it has been found that for a given dye, until the dye saturates or bleaches, the amount of fluorescence can be proportional to the irradiance of the illumination source. Therefore, if the excitation light is brighter at the center, then the fluorescence signal from a well near the edge of the irradiance zone would be less than an identical well near the center. Shadowing can occur due to the depth of the wells. Unless the excitation light is perpendicular to the microplate, some part of the well may not be properly illuminated. In other words, the geometry of the well may block some of the light from reaching the bottom of the well. In addition, the amount of fluorescence emitted, which can be collected, may vary from center to edge. As should be appreciated by one skilled in the art, noise sources are often constant across the field of view of the camera. Therefore, for wells near the edges of microplate 20 that output a smaller amount of fluorescence, the signal to noise ratio can be adversely effected, thereby reducing the efficiency of high-density sequence detection system 10. As illustrated in FIG. 50, a graph illustrates the relative intensity or light transmission versus well location on a plate. As can be seen from the graph, the effects of vignetting and shadowing causes the light intensity to drop off along the edges of the field of view of the plate.

The present teachings, at least in part, address these effects so that identical wells output generally identical fluorescence irrespective of their location on microplate 20. By using the profile from FIG. 50, the optimum irradiance profile can be calculated. With reference to FIG. 51, a corresponding irradiance profile, represented by a dashed line, can provide a higher irradiance along the edges. This irradiance profile, when coupled with the effects of vignetting and shadowing, creates generally uniform signal strength across all of the plurality of wells 26 of microplate 20.

Excitation Sources

In some embodiments, as illustrated in FIGS. 42-49, the plurality of excitation lamps 210 of excitation system 200 can be fixedly mounted to a support structure 212. In some embodiments, the plurality of excitation lamps 210 can be removably mounted to support structure 212 to permit convenient interchange, exchange, replacement, substitution, or the like. In some embodiments, support structure 212 can be generally planar in construction and can be adapted to be mounted within housing 1008 (FIG. 1). The plurality of excitation lamps 210 can be arranged in a generally circular configuration and directed toward microplate 20 to promote uniform excitation of assay 1000 in each of the plurality of wells 26. The present teachings permit a generally uniform excitation that is substantially free of shadowing. In some embodiments, the plurality of excitation lamps 210 can be arranged in a generally circular configuration about an aperture 214 formed in support structure 212. Aperture 214 permits the free transmission of fluorescence therethrough for detection by detection system 300, as described herein.

In some embodiments, as illustrated in FIGS. 52-56, each of the plurality of excitation lamps 210 can be configured to achieve the desired irradiance profile. In some embodiments, as seen schematically in FIG. 52, each of the plurality of excitation lamps 210 can comprise a lens 216. Lens 216 can be shaped to provide a desired irradiance profile (see FIG. 51). The exact shape of lens 216 can depend, at least in part, upon one or more of the desired irradiance profile at microplate 20, the illumination/irradiance profile at each of the plurality of excitation lamps 210, and the size and position of microplate 20 relative to the plurality of excitation lamps 210. The shape of lens 216 can be calculated in response to the particular application using commercially available software, such as ZEMAX and/or ASAP.

In some embodiments, as seen schematically in FIG. 53, each of the plurality of excitation lamps 210 can comprise a mirror 218. Mirror 218 can be shaped to provide a desired irradiance profile (see FIG. 51). The exact shape of mirror 218 can be dependent, at least in part, upon the desired irradiance profile at microplate 20, the illumination/irradiance profile at each of the plurality of excitation lamps 210, and the size and position of microplate 20 relative to the plurality of excitation lamps 210. The shape of mirror 218 can be calculated in response to the particular application using commercially available software, such as ZEMAX and/or ASAP.

In some embodiments, as illustrated in FIG. 54, each of the plurality of excitation lamps 210 can comprise a combination of lens 216 and mirror 218 to achieve the desired irradiance profile. Again, lens 216 and mirror 218 can be calculated in response to the particular application using commercially available software, such as ZEMAX and/or ASAP.

Turning now to FIG. 55, in some embodiments, each of the plurality of excitation lamps 210 can be aligned such that their optical centers converge on a single point 220. Additionally, in some embodiments, a desired irradiance profile (see FIG. 51) can be achieved by directing each of the plurality of excitation lamps 210 at a predetermined location 222a-222n on microplate 20, as illustrated in FIG. 56. In some embodiments, each of the plurality of excitation lamps 210 can comprise lens 216 and/or mirror 218 and can further be aligned as illustrated in FIG. 56 to achieve more complex irradiance profiles. As can be appreciated, employing any of the above techniques described herein can provide improved irradiance across microplate 20, thereby improving the resultant signal to noise ratio of the plurality of wells 26 along the edge of microplate 20.

It is anticipated that the plurality of excitation lamps 210 can be any one of a number of sources. In some embodiments, the plurality of excitation lamps 210 can be a laser source having a wavelength of about 488 nm, an Argon ion laser, an LED, a halogen bulb, or any other known source. In some embodiments, the LED can be a MR16 from Opto Technologies (Wheeling Ill.; http://www.optotech.com/MR16.htm). In some embodiments, the LED can be provided by LumiLEDS. In some embodiments, the halogen bulb can be a 75 W, 21 V DC lamp or a 50 W, 12 V DC lamp.

As discussed above, each of the plurality of excitation sources 210 can be removably coupled to support structure 212 to permit convenient interchange, exchange, replacement, substitution, or the like thereof. In some embodiments, the particular excitation source(s) employed can be selected by one skilled in the art to exhibit desired characteristics, such as increased power, better efficiency, improved uniformity, multi-colors, or having any other desired performance criteria. In embodiments employing multi-color and/or multi-wavelength excitation sources, additional detection probes and/or dyes can be used to, in some circumstances, increase throughput of high-density sequence detection system 10 by including multiple assays in each of the plurality of wells 26.

In some embodiments, the temperature of the plurality of excitation lamps 210 can be controlled to decrease the likelihood of intensity and spectral shifts. In such embodiments, the temperature control can be, for example, a cooling device. In some embodiments, the temperature control can maintain each of the plurality of excitation lamps 210 at an essentially constant temperature. In some embodiments, the intensity can be controlled via a photodiode feedback system, utilizing pulse width modulation (PWM) control to modulate the power of the plurality of excitation lamps 210. In some embodiments, the PWM can be digital. In some embodiments, shutters can be used to control each of the plurality of excitation lamps 210. It should be appreciated that any of the excitation assemblies 200 illustrated in FIGS. 42-49 and described above can be interchanged with each other.

Detection Systems

In some embodiments, as illustrated in FIGS. 42-44, 47, and 48, detection system 300 can be used to detect and/or gather fluorescence emitted from assay 1000 during analysis. In some embodiments, detection system 300 can comprise a collection mirror 310, a filter assembly 312, and a collection camera 314. After excitation light 202 passes into each of the plurality of wells 26 of microplate 20, assay 1000 in each of the plurality of wells 26 can be illuminated, thereby exciting a detection probe disposed therein and generating an emission (i.e. fluorescence) that can be detected by detection system 300.

In some embodiments, collection mirror 310 can collect the emission and/or direct the emission from each of the plurality of wells 26 towards collection camera 314. In some embodiments, collection mirror 310 can be a 120 mm-diameter mirror having ¼ or ½ wave flatness and 40/20 scratch dig surface. In some embodiments, filter assembly 312 comprises a plurality of filters 318. During analysis, microplate 20 can be scanned numerous times—each time with a different filter 318.

In some embodiments, collection camera 314 comprises a multi-element photo detector 324, such as, but not limited to, charge coupled devices (CCDs), diode arrays, photomultiplier tube arrays, charge injection devices (CIDs), CMOS detectors, and avalanche photodiodes. In some embodiments, the emission from each of the plurality of wells 26 can be focused on collection camera 314 by a lens 316. In some embodiments, collection camera 314 is an ORCA-ER cooled CCD type available from Hamamatsu Photonics. In some embodiments, lens 316 can have a focal length of 50 mm and an aperture of 2.0. In some embodiments, collection camera 314 can be mounted to, and prealigned with, lens 316.

In some embodiments, detection system 300 can comprise a light separating element, such as a light dispersing element. Light dispersing element can comprise elements that separate light into its spectral components, such as transmission gratings, reflective gratings, prisms, beam splitters, dichroic filters, and combinations thereof that are can be used to analyze a single bandpass wavelength without spectrally dispersing the incoming light. In some embodiments, with a single bandpass wavelength light dispersing element, a detection system can be limited to analyzing a single bandpass wavelength. Therefore, one or more light detectors, each comprising a single bandpass wavelength light dispersing element, can be provided.

In some embodiments, as seen in FIG. 212, an alignment mount 320 can mate collection camera 314 and lens 316. Alignment mount 320 can provide a mechanism to adjust an axial alignment and a distance between an optic assembly 322 and multi-element photo detector 324. Lens 316 can receive optic assembly 322 and can mount to a mounting face 326 of a base plate 328. Base plate 328 can have an aperture 330 formed therein that can allow light to pass from optic assembly 322 to multi-element photo detector 324. In some embodiments, base plate 328 can be formed from a metal, such as steel, stainless steel, or aluminum.

Collection camera 314 can contain multi-element photo detector 324 and can mount to a camera mounting plate 332. Mounting plate 332 can have an aperture 334 that can align with aperture 330. Mounting plate 332 can have a face 336 generally parallel to a mating face 338 of base plate 328. In some embodiments, mounting plate 332 can be formed from a metal, such as steel, stainless steel, or aluminum. At least one resilient member 340 can attach to mounting plate 332 and to base plate 328. Resilient member 340 can be formed, by non-limiting example, from a spring and/or other elastic structure. Resilient member 340 can provide a bias force that urges face 336 towards mating face 338. A planarity adjustment feature, such as, by way of non-limiting example, at least one setscrew 342, can be positioned between face 336 and mating face 338. At least one setscrew 342 can apply a force opposite the bias force provided by resilient member 340 and maintain face 336 in a spaced relationship from mating face 338.

In some embodiments, at least one set screw 342 can have a thread pitch between 80 and 100 threads per inch (TPI), inclusive. In some embodiments, at least one setscrew 342 can be a ball-end type. In some embodiments, three setscrews 342 can be radially spaced around mounting plate 332. In some embodiments, the planarity adjustment feature can comprise cams, motorized screws, fluid-containing bags, or inclined planes. In some embodiments, the space between face 336 and mating face 338 can be less than ⅛ inch. In some embodiments, a light blocking gasket 344 can be positioned in the space between face 336 and mating face 338. In some embodiments, light blocking gasket 344 can be formed from closed cell foam. Light blocking gasket 344 can have apertures formed therein that align with apertures 330 and 334, and with the planarity adjustment feature.

In some embodiments, at least one of collection camera 314 and lens 316 can have a mount comprising a threaded mount or a bayonet mount. The threaded mount can comprise, for example, a C-mount or a CS-mount. The bayonet mount can comprise, for example, an F-mount or a K-mount. In some embodiments, collection camera 314 can be mounted to mounting plate 332 using a mounting ring 346 and a retaining ring 348. In some embodiments, mounting plate 332 can be formed from a metal, such as steel, stainless steel, or aluminum. Collection camera 314 can be secured to mounting ring 346. Mounting ring 346 can fit into a groove 350 formed around a periphery of aperture 334. Retaining ring 348 can fasten to mounting plate 332 and can cover at least a portion of groove 350 and a portion of mounting ring 346, thereby retaining mounting ring 346 within groove 350. In some embodiments, retaining ring 348 can be formed from a metal, such as steel, stainless steel, or aluminum. In some embodiments, a concentricity adjustment feature, such as at least one set screw 352, can protrude radially into groove 350 and can press against an outer periphery 354 of mounting ring 346. The concentricity adjustment feature can locate mounting ring 350 in an x-y plane of groove 350. The x-y plane can be illustrated by a coordinate system 356. In some embodiments, at least one setscrew 352 can have a thread pitch between 80 TPI and 100 TPI, inclusive. In some embodiments, at least one setscrew 352 can be a ball-end type. The concentricity adjustment feature in other embodiments can include cams, motorized screws, fluid-containing bags, and/or inclined planes.

A line segment 358 can represent an image plane of optic assembly 322. An arrow 360 can be centered on optic assembly 322 and normal to its image plane 358. A line segment 362 can represent an image plane of multi-element photo detector 324. An arrow 364 can be centered on multi-element photo detector 324 and normal to its image plane 362.

In operation, the planarity adjustment feature, such as at least one set screw 342, can be used to tilt mounting plate 332 such that image plane 362 can become parallel with image plane 322. The planarity adjustment feature can also used to adjust the distance between optic assembly 322 and multi-element photo detector 324.

The concentricity adjustment feature, such as at least one setscrew 352, can translate mounting ring 346 in the x-y plane. Translating mounting ring 346 can adjust arrow 364 concentrically with arrow 360.

In some embodiments, alignment features 368 can align base plate 328 with support structure 212. Locations of alignment features 368 and dimensions of alignment mount 320 can be selected to place the arrow 360 concentric with a center of microplate 20. Locations of alignment features 356 and dimensions of alignment mount 320 can be selected to place image plane 358 in parallel with an image plane of microplate 20. In some embodiments having collection mirror 310 (of FIGS. 42 and 43), locations of alignment features 356 and dimensions of alignment mount 320 can be selected to place image plane 358 perpendicular with the image plane of microplate 20. In some embodiments, base plate 328 can include a foot plate 366. By way of non-limiting example, alignment features 368 can comprise any combination of dowels and keys.

Control System

In some embodiments, control system 1010 can be operable to control various portions of high-density sequence detection system 10 and to collect data. In such embodiments, control system 1010 can comprise software and devices operable to collect and analysis data; control operation of electrical, mechanical, and optical portions of high-density sequence detection system 10; and thermocycling. In some embodiments, such data analysis can comprise organizing, manipulating, and reporting of data and derived results to determine relative gene expression within assay 1000, between various test samples, and across multiple test runs.

In some embodiments, control system 1010 can archive data within a database, database retrieval, database analysis and manipulation, and bioinformatics. In some embodiments, control system 1010 can be operable to analyze raw data and among other actions, control operation of high-density sequence detection system 10. Such analysis of raw data can comprise compensating for point spread (PSF), background or base emissions, a unique intensity profile, optical crosstalk, detector and/or optical path variability and noise, misalignment, or movement during operation. This can be accomplished, in some embodiments, by utilizing internal controls in several of the plurality of wells 26, as well as calibrating high-density sequence detection system 10. In some embodiments, data analysis can comprise difference imaging, such as comparing an image from one point in time to an image at a different point in time, or image subtracting. In some embodiments, data analysis can comprise curve fitting based on a specific gene or a gene set. Still further, in some embodiments, data analysis can comprise using no template control (NTC) background or baseline correction. In some embodiments, data analysis can comprise error estimation using confidence values derived in terms of CT. See U.S. patent application Ser. No. 60/517,506 filed Nov. 4, 2003 and U.S. patent application Ser. No. 60/519,077 filed Nov. 10, 2003.

In some embodiments, the present teachings can provide a method for reducing signal noise from an array of pixels of a segmented detector for biological samples. The signal noise comprises a dark current contribution and readout offset contribution. The method can comprise providing a substantially dark condition for the array of pixels, wherein the dark condition comprises being substantially free of fluorescent light emitted from the biological samples, providing a first output signal from a binned portion of the array of pixels by collecting charge for a first exposure duration, transferring the collected charge to an output register and reading out the register, wherein transferring of the collected charge from the binned pixels comprises providing a gate voltage to a region near the binned pixels to move collected charge from the binned pixels, and wherein the collected charge can be transferred in a manner that causes the collected charge to be shifted to the output register, providing a second output signal from each pixel by collecting charge for a second exposure duration, transferring the collected charge to the output register, and reading out the register, providing a third output signal by resetting and reading out the output register, determining the dark current contribution and the readout offset contribution from the first output signal, the second output signal, and the third output signal.

In some embodiments, the present teachings can provide a method of characterizing signal noise associated with operation of a charge-coupled device (CCD) adapted for analysis of biological samples, wherein the signal noise comprises a dark current contribution, readout offset contribution, and spurious change contribution. The method can comprise providing a plurality of first data points associated with first outputs provided from the CCD under a substantially dark condition during a first exposure duration, providing a plurality of second data points associated with second outputs provided from the CCD under the substantially dark condition during a second exposure duration wherein the second duration is different from the first duration, providing a plurality of third data points associated with third outputs provided from a cleared output register of the CCD without comprising charge transferred thereto, determining the dark current contribution per unit exposure time by comparing the first data points and the second data points, determining the readout offset contribution from the third data points, and determining the spurious charge contribution based on the dark current contribution and the readout offset contribution. See U.S. patent application Ser. No. 10/913,601 filed Aug. 5, 2004; U.S. patent application Ser. No. 10/660,460 filed Sep. 11, 2003, and U.S. patent application Ser. No. 10/660,110 filed Sep. 11, 2003.

Methods of Use and Analysis

Polynucleotide Amplification

In some embodiments, a high-density sequence detection system or components thereof are used for the amplification of polynucleic acids, such as by PCR. Briefly, by way of background, PCR can be used to amplify a sample of target Deoxyribose Nucleic Acid (DNA) for analysis. Typically, the PCR reaction involves copying the strands of the target DNA and then using the copies to generate additional copies in subsequent cycles. Each cycle doubles the amount of the target DNA present, thereby resulting in a geometric progression in the number of copies of the target DNA. The temperature of a double-stranded target DNA is elevated to denature the DNA, and the temperature is then reduced to anneal at least one primer to each strand of the denatured target DNA. In some embodiments, the target DNA can be a cDNA. In some embodiments, primers are used as a pair—a forward primer and a reverse primer—and can be referred to as a primer pair or primer set. In some embodiments, the primer set comprises a 5' upstream primer that can bind with the 5' end of one strand of the denatured target DNA and a 3' downstream primer that can bind with the 3' end of the other strand of the denatured target DNA. Once a given primer binds to the strand of the denatured target DNA, the primer can be extended by the action of a polymerase. In some embodiments, the polymerase can be a thermostable DNA polymerase, for example, a Taq polymerase. The product of this extension, which sometimes may be referred to as an amplicon, can then be denatured from the resultant strands and the process can be repeated. Temperatures suitable for carrying out the reactions are well known in the art. Certain basic principles of PCR are set forth in U.S. Pat. Nos. 4,683,195, 4,683,202, 4,800,159, and 4,965,188, each issued to Mullis et al.

In some embodiments, PCR can be conducted under conditions allowing for quantitative and/or qualitative analysis of one or more target DNA. Accordingly, detection probes can be used for detecting the presence of the target DNA in an assay. In some embodiments, the detection probes can comprise physical (e.g., fluorescent) or chemical properties that change upon binding of the detection probe to the target DNA. Some embodiments of the present teaching can provide real time fluorescence-based detection and analysis of amplicons as described, for example, in PCT Publication No. WO 95/30139 and U.S. patent application Ser. No. 08/235,411.

In some embodiments, assay 1000 can be a homogenous polynucleotide amplification assay, for coupled amplification and detection, wherein the process of amplification generates a detectable signal and the need for subsequent sample handling and manipulation to detect the amplified product is minimized or eliminated. Homogeneous assays can provide for amplification that is detectable without opening a sealed well or further processing steps once amplification is initiated. Such homogeneous assays 1000 can be suitable for use in conjunction with detection probes. For example, in some embodiments, the use of an oligonucleotide detection probe, specific for detecting a particular target DNA can be included in an amplification reaction in addition to a DNA binding agent of the present teachings. Homogenous assays among those useful herein are described, for example, in commonly assigned U.S. Pat. No. 6,814,934.

In some embodiments, methods are provided for detecting a plurality of targets. Such methods include those comprising forming an initial mixture comprising an analyte sample suspected of comprising the plurality of targets, a polymerase, and a plurality of primer sets. In some embodiments, each primer set comprises a forward primer and a reverse primer and at least one detection probe unique for one of the plurality of primer sets. In some embodiments, the initial mixture can be formed under conditions in which one primer elongates if hybridized to a target.

In some embodiments, the location of a fluorescent signal on a solid support, such as microplate 20, can be indicative of the identity of a target comprised by the analyte sample. In some embodiments, a plurality of detection probes are distributed to identify loci of at least some of the plurality of wells 26 of microplate 20. A signal deriving from a detection probe, such as, for example, an increase in fluorescence intensity of a fluorophore at a particular locus can be detected if an amplification product binds to a detection probe and is then amplified. The location of the locus can indicate the identity of the target, and the intensity of the fluorescence can indicate the quantity of the target.

In some embodiments, reagents are provided comprising a master mix comprising at least one of catalysts, initiators, promoters, cofactors, enzymes, salts, buffering agents, chelating agents, and combinations thereof. In some embodiments, reagents can include water, a magnesium catalyst (such as MgCl2), polymerase, a buffer, and/or dNTP. In some embodiments, specific master mixes can comprise AmpliTaq® Gold PCR Master Mix, TaqMan® Universal Master Mix, TaqMan® Universal Master Mix No AmpErase® UNG, Assays-by-DesignSM, Pre-Developed Assay Reagents (PDAR) for gene expression, PDAR for allelic discrimination and Assays-On-Demand®, (all of which are marketed by Applied Biosystems). However, the present teachings should not be regarded as being limited to the particular chemistries and/or detection methodologies recited herein, but may employ Taqman®; Invader®; Taqman Gold®; protein, peptide, and immuno assays; receptor binding; enzyme detection; and other screening and analytical methodologies.

In some embodiments, high-density sequence detection system 10 is operable for analysis of materials (e.g., polynucleotides) comprising or derived from genetic materials from organisms. In some embodiments, such materials comprise or are derived from substantially the entire genome of an organism. In some embodiments, such organisms include, for example, humans, mammals, mice, *Arabidopsis* or any other plant, bacteria, fungi, or animal species. In some embodiments, assay 1000 comprises at least one of a homogenous solution of a DNA sample, at least one primer set for detection of a polynucleotide comprising or derived from such genetic materials, at least one detection probe, a polymerase, and a buffer. In some embodiments, assay 1000 comprises at least one of a plurality of different detection probes and/or primer sets to perform multiplex PCR, which can be particularly useful when analyzing a whole genome having, for example, about 30,000 different genes. In some embodiments, analysis of substantially the entire genome of an organism is conducted on a single microplate 20, or on multiple microplates (e.g., two, three, four or more) each comprising subparts of such materials comprising or derived from the genetic materials of the organism. In some embodiments using multiple microplates, a plurality of plates contain a plurality of assay 1000 having essentially identical materials and a plurality of assay 1000 having different materials. In some embodiments, a plurality of plates do not contain assay 1000 having essentially identical materials. In some embodiments, microplate 20 comprises a fixed subset of a genome. It should also be recognized that the present teachings can be used in connection with genotyping, gene expression, or other analysis.

In various some embodiments, the microplate can be covered with a sealing liquid prior to performance of analysis or reaction of assay 1000. For example, in some embodiments, a sealing liquid is applied to the surface of a microplate comprising reaction spots comprising an assay 1000 for amplification of polynucleotides. In some embodiments, a sealing liquid can be a material which substantially covers the material retention regions (e.g., reaction spots) on the microplate so as to contain materials present in the material retention regions, and substantially prevent movement of material from one reaction region to another reaction region on the substrate. In some embodiments, the sealing liquid can be any material which is not reactive with assay 1000 under normal storage or usage conditions. In some embodiments, the sealing liquid can be substantially immiscible with assay 1000. In some embodiments, the sealing liquid can be transparent, have a refractive index similar to glass, have low or no fluorescence, have a low viscosity, and/or be curable. In some embodiments the sealing liquid can comprise a flowable, curable fluid such as a curable adhesive selected from the group consisting of: ultra-violet-curable and other light-curable adhesives; heat, two-part, or moisture activated adhesives; and cyanoacrylate adhesives. In some embodiments, the sealing liquid can be selected from the group consisting of mineral oil, silicone oil, fluorinated oils, and other fluids which are substantially non-miscible with water.

In some embodiments, the sealing liquid can be a fluid when it is applied to the surface of the microplate and in some embodiments, the sealing liquid can remain fluid throughout an analytical or chemical reaction using the microplate. In some embodiments, the sealing liquid can become a solid or semi-solid after it is applied to the surface of the microplate.

Other Amplification Methods

As should be appreciated from the discussion above, the present teachings can find utility in a wide variety of amplification methods, such as PCR, Reverse Transcription PCR (RT-PCR), Ligation Chain Reaction (LCR), Nucleic Acid Sequence Based Amplification (NASBA), self-sustained sequence replication (3SR), strand displacement activation (SDA), Q (3replicase) system, isothermal amplification methods, and other known amplification method or combinations thereof. Additionally, the present teachings can find utility for use in a wide variety of analytical techniques, such as ELISA; DNA and RNA hybridizations; antibody titer determinations; gene expression; recombinant DNA techniques; hormone and receptor binding analysis; and other known analytical techniques. Still further, the present teachings can be used in connection with such amplification methods and analytical techniques using not only spectrometric measurements, such as absorption, fluorescence, luminescence, transmission, chemiluminescence, and phosphorescence, but also calorimetric or scintillation measurements or other known detection methods. It should also be appreciated that the present teachings may be used in connection with microcards and other principles, such as set forth in U.S. Pat. Nos. 6,126,899 and 6,124,138.

In some embodiments, the reagents can comprise first and second oligonucleotides effective to bind selectively to adjacent, contiguous regions of target DNA and that can be ligated covalently by a ligase enzyme or by chemical means. Such oligonucleotide ligation assays (OLA) are described, for example, in U.S. Pat. No. 4,883,750; and Landegren, U., et al., *Science* 241:1077 (1988). In this approach, the two oligonucleotides (oligonucleotides) are reacted with the target under conditions effective to ensure specific hybridization of the oligonucleotides to their targets. When the oligonucleotides have base-paired with their targets, such that confronting end subunits in the oligonucleotides are base paired with immediately contiguous bases in the target, the two oligonucleotides can be joined by ligation, e.g., by treatment with ligase. After the ligation step, microplate 20 is heated to dissociate unligated detection probes, and the presence of ligated, target-bound detection probe is detected by reaction with an intercalating dye or by other means. The oligonucleotides for OLA can also be designed to bring together a fluorescer-quencher pair, as discussed above, leading to a decrease in a fluorescence signal when the analyte sequence is present. In some embodiments of the OLA ligation method, the concentration of a target region from an analyte polynucleotide can be increased, if desired, by amplification with repeated hybridization and ligation steps. Simple additive amplification can be achieved using the analyte polynucleotide as a target and repeating denaturation, annealing, and ligation steps until a desired concentration of the ligated product is achieved.

In other embodiments, the ligated product formed by hybridization and ligation can be amplified by ligase chain reaction (LCR). In this approach, two complementary sets of sequence-specific oligonucleotide detection probes are employed for each target DNA. One of the two sets of sequence-specific oligonucleotide detection probes comprises first and second oligonucleotides designed for sequence-specific binding to adjacent, contiguous regions of a first strand of target DNA. The second of the two sets of sequence-specific oligonucleotide detection probes comprises first and second oligonucleotides designed for sequence-specific binding to adjacent, contiguous regions of a second strand of target DNA. With continued cycles of denaturation, reannealing, and ligation in the presence of the two complementary oligonucleotide sets, the target DNA is amplified exponentially, allowing small amounts of target DNA to be detected and/or amplified. In a further modification, the oligonucleotides for OLA or LCR assay bind to adjacent regions in a target that are separated by one or more intervening bases, and ligation is effected by reaction with (i) a DNA polymerase, to fill in the intervening single stranded region with complementary nucleotides, and (ii) a ligase enzyme to covalently link the resultant bound oligonucleotides.

Detection Probes

In some embodiments, a detection probe comprises a moiety that facilitates detection of a nucleic acid sequence, and in some embodiments, quantifiably. In some embodiments, a detection probe can comprise, for example, a fluorophore such as a fluorescent dye, a hapten such as a biotin or a digoxygenin, a radioisotope, an enzyme, or an electrophoretic mobility modifier. In some embodiments, the level of amplification can be determined using a fluorescently labeled oligonucleotide. In some embodiments, a detection probe can comprise a fluorophore further comprising a fluorescence quencher.

In some embodiments, a detection probe can comprise a fluorophore and can be, for example, a 5'-exonuclease assay probe such as a TaqMan® probe (marketed by Applied Biosystems), a stem-loop Molecular Beacon (see, e.g., U.S. Pat. Nos. 6,103,476 and 5,925,517, *Nature Biotechnology* 14:303-308 (1996); Vet et al., *Proc Natl Acad Sci USA*. 96:6394-6399 (1999)), a stemless or linear molecular beacon (see., e.g., PCT Patent Publication No. WO 99/21881), a Peptide Nucleic Acid (PNA) Molecular Beacon™ (see, e.g., U.S. Pat. Nos. 6,355,421 and 6,593,091), a linear PNA Molecular Beacon (see, e.g., Kubista et al., *SPIE* 4264:53-58 (2001)), a flap endonuclease probe (see, e.g., U.S. Pat. No. 6,150,097), a Sunrise®/Amplifluor® probe (see, e.g., U.S. Pat. No. 6,548,250), a stem-loop and duplex Scorpion™ probe (see, e.g., Solinas et al., *Nucleic Acids Research* 29:E96 (2001), and U.S. Pat. No. 6,589,743), a bulge loop probe (see, e.g., U.S. Pat. No. 6,590,091), a pseudo knot probe (see, e.g., U.S. Pat. No. 6,589,250), a cyclicon (see, e.g., U.S. Pat. No. 6,383,752), an MGB Eclipse™ probe (Marketed by Epoch Biosciences), a hairpin probe (see, e.g., U.S. Pat. No. 6,596, 490), a peptide nucleic acid (PNA) light-up probe, a self-assembled nanoparticle probe, or a ferrocene-modified probe described, for example, in U.S. Pat. No. 6,485,901; Mhlanga et al., *Methods* 25:463-471 (2001); Whitcombe et al., *Nature Biotechnology* 17:804-807 (1999); Isacsson et al., *Molecular Cell Probes* 14:321-328 (2000); Svanvik et al., *Anal. Biochem.* 281:26-35 (2000); Wolffs et al., *Biotechniques* 766: 769-771 (2001), Tsourkas et al., *Nucleic Acids Research* 30:4208-4215 (2002); Riccelli et al., *Nucleic Acids Research* 30:4088-4093 (2002); Zhang et al., Sheng Wu Hua Xue Yu Sheng Wu Li Xue Bao (Shanghai) (*Acta Biochimica et Biophysica Sinica*) 34:329-332 (2002); Maxwell et al., *J. Am. Chem. Soc.* 124:9606-9612 (2002); Broude et al., *Trends Biotechnol.* 20:249-56 (2002); Huang et al., *Chem. Res. Toxicol*. 15:118-126 (2002); Yu et al., *J. Am. Chem. Soc* 14:11155-11161 (2001). In some embodiments, a detection probe can comprise a sulfonate derivative of a fluorescent dye, a phosphoramidite form of fluorescein, or a phosphoramidite forms of CY5. Detection probes among those useful herein are also disclosed, for example, in U.S. Pat. Nos. 5,188,934, 5,750, 409, 5,847,162, 5,853,992, 5,936,087, 5,986,086, 6,020,481, 6,008,379, 6,130,101, 6,140,500, 6,140,494, 6,191,278, and 6,221,604. Energy transfer dyes among those useful herein include those described in U.S. Pat. Nos. 5,728,528, 5,800, 996, 5,863,727, 5,945,526, 6,335,440, 6,849,745, U.S. Patent Application Publication No. 2004/0126763 A1, PCT Publication No. WO 00/13026A1, PCT Publication No. WO 01/19841A1, U.S. patent application Ser. No. 60/611,119, filed Sep. 16, 2004, and U.S. patent application Ser. No. 10/788,836, filed Feb. 26, 2004. In some embodiments, a detection probe can comprise a fluorescence quencher such as a black hole quencher (marketed by Metabion International AG), an Iowa Black™ quencher (marketed by Integrated DNA Technologies), a QSY quencher (marketed by Molecular Probes), and Dabsyl and Eclipse™ Dark Quenchers (marketed by Epoch).

In some embodiments, a detection probe can comprise a fluorescent dye. In such embodiments, the fluorescent dye can comprise at least one of rhodamine green (R110), 5-carboxyrhodamine, 6-carboxyrhodamine, N,N'-diethyl-2',7'-dimethyl-5-carboxy-rhodamine (5-R6G), N,N'-diethyl-2',7'-dimethyl-6-carboxyrhodamine (6-R6G), 5-carboxy-2',4',5', 7',-4,7-hexachlorofluorescein, 6-carboxy-2',4',5',7',4,7-hexachloro-fluorescein, 5-carboxy-2',7'-dicarboxy-4',5'-dichlorofluorescein, 6-carboxy-2',7'-dicarboxy-4',5'-dichlorofluorescein, 5-carboxy-2',4',5',7'-tetrachlorofluorescein, 1',2'-benzo-4'-fluoro-7',4,7-trichloro- 5-carboxyfluorescein, 1',2'-benzo-4'-fluoro-7',4,7-trichloro-6-carboxy-fluorescein, 1',2',7',8'-dibenzo-4,7-dichloro-5-carboxyfluorescein, or those dyes set forth in Table 5.

TABLE 5

| Fluorescent Dye | Absorbance (nm) | Emission (nm) | Extinction Coefficient |
| --- | --- | --- | --- |
| 5-Fluorescein[1] | 495 | 520 | 73000 |
| 5-Carboxyfluorescein (5-FAM ™)[1] | 495 | 520 | 83000 |
| 6-Carboxyfluorescein (6-FAM ™)[1] | 495 | 520 | 83000 |
| 6-Carboxyhexachlorofluorescein (6-HEX ™)[1] | 535 | 556 | 73000 |
| 6-Carboxytetrachlorofluorescein (6-TET ™)[1] | 521 | 536 | 73000 |
| JOE ™[1] | 520 | 548 | 73000 |
| LightCycler® Red 640[2] | 625 | 640 | |
| LightCycler® Red 705[2] | 685 | 705 | |
| Oregon Green® 488[1] | 496 | 516 | 76000 |
| Oregon Green® 500[1] | 499 | 519 | 84000 |
| Oregon Green® 514[1] | 506 | 526 | 85000 |
| BODIPY® FL-X[1] | 504 | 510 | 70000 |
| BODIPY® FL[1] | 504 | 510 | 70000 |
| BODIPY®-TMR-X[1] | 544 | 570 | 56000 |
| BODIPY® R6G[1] | 528 | 547 | 70000 |
| BODIPY® 650/665[1] | 650 | 665 | 101000 |
| BODIPY® 564/570[1] | 563 | 569 | 142000 |
| BODIPY® 581/591[1] | 581 | 591 | 136000 |
| BODIPY® TR-X[1] | 588 | 616 | 68000 |
| BODIPY® 630/650[1] | 625 | 640 | 101000 |
| BODIPY® 493/503[1] | 500 | 509 | 79000 |
| 5-Carboxyrhodamine 6G[1] | 524 | 557 | 102000 |
| 5(6)-Carboxytetramethylrhodamine (TAMRA)[1] | 546 | 576 | 90000 |
| 6-Carboxytetramethylrhodamine (TAMRA)[1] | 544 | 576 | 90000 |
| 5(6)-Carboxy-X-Rhodamine (ROX)[1] | 576 | 601 | 82000 |
| 6-Carboxy-X-Rhodamine (ROX)[1] | 575 | 602 | 82000 |
| AMCA-X (Coumarin)[1] | 353 | 442 | 19000 |
| Texas Red®-X[1] | 583 | 603 | 116000 |
| Rhodamine Red ™-X[1] | 560 | 580 | 129000 |
| Marina Blue®[1] | 362 | 459 | 19000 |
| Pacific Blue ™[1] | 416 | 451 | 37000 |
| Rhodamine Green ™-X[1] | 503 | 528 | 74000 |
| 7-diethylaminocoumarin-3-carboxylic acid[1] | 432 | 472 | 56000 |
| 7-methoxycoumarin-3-carboxylic acid[1] | 358 | 410 | 26000 |
| Cy3®[3] | 552 | 570 | 150000 |
| Cy3B®[3] | 558 | 573 | 130000 |
| Cy5®[3] | 643 | 667 | 250000 |
| Cy5.5®[3] | 675 | 694 | 250000 |
| DY-505[4] | 505 | 530 | 85000 |
| DY-550[4] | 553 | 578 | 122000 |
| DY-555[4] | 555 | 580 | 100000 |
| DY-610[4] | 606 | 636 | 140000 |
| DY-630[4] | 630 | 655 | 120000 |
| DY-633[4] | 630 | 659 | 120000 |
| DY-636[4] | 645 | 671 | 120000 |
| DY-650[4] | 653 | 674 | 77000 |
| DY-675[4] | 674 | 699 | 110000 |
| DY-676[4] | 674 | 699 | 84000 |
| DY-681[4] | 691 | 708 | 125000 |
| DY-700[4] | 702 | 723 | 96000 |
| DY-701[4] | 706 | 731 | 115000 |
| DY-730[4] | 734 | 750 | 113000 |
| DY-750[4] | 747 | 776 | 45700 |
| DY-751[4] | 751 | 779 | 220000 |
| DY-782[4] | 782 | 800 | 102000 |
| Cy3.5®[3] | 581 | 596 | 150000 |
| EDANS[1] | 336 | 490 | 5700 |
| WellRED D2-PA[5] | 750 | 770 | 170000 |
| WellRED D3-PA[5] | 685 | 706 | 224000 |
| WellRED D4-PA[5] | 650 | 670 | 203000 |
| Pyrene | 341 | 377 | 43000 |
| Cascade Blue ™[1] | 399 | 423 | 30000 |
| Cascade Yellow ™[1] | 409 | 558 | 24000 |
| PyMPO[1] | 415 | 570 | 26000 |
| Lucifer Yellow[1] | 428 | 532 | 11000 |
| NBD-X[1] | 466 | 535 | 22000 |
| Carboxynapthofluorescein[1] | 598 | 668 | 42000 |
| Alexa Fluor® 350[1] | 346 | 442 | 19000 |
| Alexa Fluor® 405[1] | 401 | 421 | 35000 |
| Alexa Fluor® 430[1] | 434 | 541 | 16000 |
| Alexa Fluor® 488[1] | 495 | 519 | 71000 |
| Alexa Fluor® 532[1] | 532 | 554 | 81000 |
| Alexa Fluor® 546[1] | 556 | 573 | 104000 |
| Alexa Fluor® 555[1] | 555 | 565 | 150000 |
| Alexa Fluor® 568[1] | 578 | 603 | 91300 |
| Alexa Fluor® 594[1] | 590 | 617 | 73000 |
| Alexa Fluor® 633[1] | 632 | 647 | 100000 |
| Alexa Fluor® 647[1] | 650 | 665 | 239000 |
| Alexa Fluor® 660[1] | 663 | 690 | 132000 |
| Alexa Fluor® 680[1] | 679 | 702 | 184000 |
| Alexa Fluor® 700[1] | 702 | 723 | 192000 |
| Alexa Fluor® 750[1] | 749 | 775 | 240000 |
| Oyster 556®[6] | 556 | 570 | 155000 |
| Oyster 645®[6] | 645 | 666 | 250000 |
| Oyster 656®[6] | 656 | 674 | 220000 |
| 5(6)-Carboxyeosin[1] | 521 | 544 | 95000 |
| Erythrosin[1] | 529 | 544 | 90000 |

[1]Marketed by Molecule Probes;
[2]Marketed by Roche Applied Science;
[3]Marketed by Amersham Biosciences;
[4]Marketed by Synthegen, LLC;
[5]Marketed by Beckman Coulter, Inc.;
[6]Marketed by Denovo Biolabels;

In some embodiments, amplified sequences can be detected in double-stranded form by a detection probe comprising an intercalating or a crosslinking dye, such as ethidium bromide, acridine orange, or an oxazole derivative, for example, SYBR Green® (marketed by Molecular Probes, Inc.), which exhibits a fluorescence increase or decrease upon binding to double-stranded nucleic acids. In some embodiments, a detection probe comprises SYBR Green® or Pico Green® (marketed by Molecular Probes, Inc.).

In some embodiments, a detection probe can comprise an enzyme that can be detected using an enzyme activity assay. An enzyme activity assay can utilize a chromogenic substrate, a fluorogenic substrate, or a chemiluminescent substrate. In some embodiments, the enzyme can be an alkaline phosphatase, and the chemiluminescent substrate can be (4-methoxyspiro[1,2-dioxetane-3,2'(5'-chloro)-tricyclo [3.3.1.13, 7]decan]-4-yl)phenylphosphate. In some embodiments, a chemiluminescent alkaline phosphatase substrate can be CDP-Star® chemiluminescent substrate or CSPD® chemiluminescent substrate (marketed by Applied Biosystems).

In some embodiments, the present teachings can employ any of a variety of universal detection approaches involving real-time PCR and related approaches. For example, the present teachings contemplate embodiments in which an encoding ligation reaction is performed in a first reaction vessel (such as for example, an eppendorf tube), and a plurality of decoding reactions are then performed in microplate 20 described herein. For example, a multiplexed oligonucleotide ligation reaction (OLA) can be performed to query a plurality of target DNA, wherein each of the resulting reaction products is encoded with, for example, a primer portion, and/or, a universal detection portion. By including a distinct primer pair in each of plurality of wells 26 of microplate 20 corresponding to the primers sequences encoded in the OLA, a given encoded target DNA can be amplified by that distinct primer pair in a given well of plurality of wells 26. Further, a universal detection probe (such as, for example, a nuclease cleavable TaqMan® probe) can be included in each of plurality of wells 26 of microplate 20 to provide for universal detection of a single universal detection probe. Such approaches can result in a universal microplate 20, with its attendant benefits including, among other things, one or more of economies of scale, manufacturing, and/or ease-of-use. The nature of the multiplexed encoding reaction can comprise any of a variety of techniques, including a multiplexed encoding PCR pre-amplification or a multiplexed encoding OLA. Further, various approaches for encoding a first sample with a first universal detection probe, and a second sample with a second universal detection probe, thereby allowing for two sample comparisons in a single microplate 20, can also be performed according to the present teachings. Illustrative embodiments of such encoding and decoding methods can be found for example in PCT Publication No. WO2003US0029693 to Aydin et al., PCT Publication No. WO2003US0029967 to Andersen et al., U.S. Provisional Application Nos. 60/556,157 and 60/630,681 to Chen et al., U.S. Provisional Application No. 60/556,224 to Andersen et al., U.S. Provisional Application No. 60/556,162 to Livak et al., and U.S. Provisional Application No. 60/556,163 to Lao et al.

Single Nucleotide Polymorphism (SNP)

In some embodiments, the detection probes can be suitable for detecting single nucleotide polymorphisms (SNPs). A specific example of such detection probes comprises a set of four detection probes that are identical in sequence but for one nucleotide position. Each of the four detection probes comprises a different nucleotide (A, G, C, and T/U) at this position. The detection probes can be labeled with probe labels capable of producing different detectable signals that are distinguishable from one another, such as different fluorophores capable of emitting light at different, spectrally resolvable wavelengths (e.g., 4-differently colored fluorophores). In some embodiments, for example SNP analysis, two colors can be used for two known variants.

In some embodiments, at least one of the forward primer and the reverse primer can further comprise a detection probe. A detection probe (or its complement) can be situated within the forward primer between the first primer sequence and the sequence complementary to the target DNA, or within the reverse primer between the second primer sequence and the sequence complementary to the target DNA. A detection probe can comprise at least about 10 nucleotides up to about 70 nucleotides and, more particularly, about 15 nucleotides, about 20 nucleotides, about 30 nucleotides, about 50 nucleotides, or about 60 nucleotides. In some embodiments, a detection probe (or its complement) can further comprise a Zip-Code™ sequence (marketed by Applied Biosystems). In some embodiments, a detection probe can comprise an electrophoretic mobility modifier, such as a nucleobase polymer sequence that can increase the size of a detection probe, or in some embodiments, a non-nucleobase moiety that increases the frictional coefficient of the detection probe, such as those mobility modifier described in commonly-owned U.S. Pat. Nos. 5,514,543, 5,580,732, 5,624,800, and 5,470,705 to Grossman. A detection probe comprising a mobility modifier can exhibit a relative mobility in an electrophoretic or chromatographic separation medium that allows a user to identify and distinguish the detection probe from other molecules comprised by the sample. In some embodiments, a detection probe comprising a sequence complementary to a detection probe and an electrophoretic mobility modifier can be, for example, a ZipChute™ detection probe (marketed by Applied Biosystems). In these embodiments, hybridization of a detection probe with an amplicon, followed by electrophoretic analysis, can be used to determine the identity and quantity of the target DNA.

RT-PCR

In some embodiments, the present teaching provide methods and apparatus for Reverse Transcriptase PCR(RT-PCR), which include the amplification of a Ribonucleic Acid (RNA) target. In some embodiments, assay 1000 can comprise a single-stranded RNA target, which comprises the sequence to be amplified (e.g., an mRNA), and can be incubated in the presence of a reverse transcriptase, two primers, a DNA polymerase, and a mixture of dNTPs suitable for DNA synthesis. During this process, one of the primers anneals to the RNA target and can be extended by the action of the reverse transcriptase, yielding an RNA/cDNA doubled-stranded hybrid. This hybrid can be then denatured and the other primer anneals to the denatured cDNA strand. Once hybridized, the primer can be extended by the action of the DNA polymerase, yielding a double-stranded cDNA, which then serves as the double-stranded target for amplification through PCR, as described herein. RT-PCR amplification reactions can be carried out with a variety of different reverse transcriptases, and in some embodiments, a thermostable reverse-transcriptions can be used. Suitable thermostable reverse transcriptases can comprise, but are not limited to, reverse transcriptases such as AMV reverse transcriptase, MuLV, and Tth reverse transcriptase.

Amplifications for MicroRNA and Small Interfering RNA

In some embodiments, assay 1000 can be an assay for the detection of RNA, including small RNA. Detection of RNA molecules can be, in various circumstances, very important to molecular biology, in research, industrial, agricultural, and clinical settings. Among the types of RNA that are of interest in some embodiments are, for example, naturally occurring and synthetic regulatory RNAs such as small RNA molecules (Lee, et al., Science 294: 862-864, 2001; Ruvkun, Science 294: 797-799; Pfeffer et al., 304: Science 734-736, 2004; Ambros, Cell 107: 823-826, 2001; Ambros et al., RNA 9: 277-279, 2003; Carrington and Ambros, *Science* 301: 336-338, 2003; Reinhart et al., *Genes Dev.* 16: 1616-1626, 2002 Aravin et al., Dev. Cell 5: 337-350, 2003, Tuschel et al., Science 294: 853-858, 2001; Susi P. et al., Plant Mol. Biol. 54: 157-174, 2004; Xie et al., PLoS Biol. 2: E104, 2004). Small RNA molecules, such as, for example, micro RNAs (miRNA), short interfering RNAs (siRNA), small temporal RNAs (stRNA) and short nuclear RNAs (snRNA), can be, typically, less than about 40 nucleotides in length and can be of low abundance in a cell. With appropriate detection probes, high-density sequence detection system 10 can detect miRNA expression found in, for instance, cell samples taken at different stages of development. In some embodiments, coexpression patterns can be analyzed across microplate 20 with TaqMan sensitivity, specificity, and dynamic range. In some embodiments, such methods obviate the need for running further assays to validate the expression levels. In some embodiments, high-density sequence detection system 10 can be used to validate that siRNA molecules have successfully, post-translationally regulated the gene expression patterns of interest. In some embodiments, such methods may be useful during the manipulation of gene expression patterns using siRNAs in order to elucidate gene function and/or inter-relationships amongst genes. In some embodiments, gene expression patterns can be introduced into living cells, cellular assays can be seen on high-density sequence detection system 10 and can reveal gene functions. In some embodiments, analysis for small RNA can be run on high-density sequence detection system 10 allowing for a high number of simultaneous assays 1000 on a single sample with performance that obviates the need for secondary assays to validate the gene expression results.

In some embodiments, the methods of the present teachings can include forming a detection mixture comprising a detection probe set ligation sequence, and a primer set. In such embodiments, any detection probe set ligation sequence comprised by the detection mixture can be amplified using PCR on high-density sequence detection system 10 and thereby form an amplification product. In such embodiments, detection of amplification of any detection probe ligation sequence of an analyte. In some embodiments, detection of amplification by high-density sequence detection system 10 can comprise detection of binding of a detection probe to a detection probe hybridization sequence comprised by a probe set ligation sequence or an amplification product thereof. In some configurations, detecting can comprise contacting a PCR amplification product such as an amplified probe set ligation sequence with a detection probe comprising a label under hybridizing conditions.

Pre-Amplification and Multiplex Methods

In some embodiments for amplification of a polynucleotide, assay 1000 can comprise a preamplification product, wherein one or more polynucleotides in an analyte has been amplified prior to being deposited in at least one of the plurality of wells 26. In some embodiments, these methods can further comprise forming a plurality of preamplification products by subjecting an initial analyte comprising a plurality of polynucleotides to at least one cycle of PCR to form a detection mixture comprising a plurality of preamplification products. The detection mixture of preamplification products can be then used for further amplification using microplate 20 and high-density sequence detection system 10. In some embodiments, preamplification comprises the use of isothermal methods.

In some embodiments, a two-step multiplex amplification reaction can be performed wherein the first step truncates a standard multiplex amplification round to boost a copy number of the DNA target by about 100-1000 or more fold. Following the first step, the resulting product can be divided into optimized secondary single amplification reactions, each containing one or more of the primer sets that were used previously in the first or multiplexed booster step. The booster step can occur, for example, using an aqueous target or using a solid phase archived nucleic acid. See, for example, U.S. Pat. No. 6,605,452, Marmaro.

In some embodiments, preamplification methods can employ in vitro transcription (IVT) comprising amplifying at least one sequence in a collection of nucleic acids sequences. The processes can comprise synthesizing a nucleic acid by hybridizing a primer complex to the sequence and extending the primer to form a first strand complementary to the sequence and a second strand complementary to the first strand. The primer complex can comprise a primer complementary to the sequence and a promoter region in anti-sense orientation with respect to the sequence. Copies of anti-sense RNA can be transcribed off the second strand. The promoter region, which can be single or double stranded, can be capable of inducing transcription from an operably linked DNA sequence in the presence of ribonucleotides and a RNA polymerase under suitable conditions. Suitable promoter regions may be prokaryote viruses, such as from T3 or T7 bacteriophage. In some embodiments, the primer can be a single stranded nucleotide of sufficient length to act as a template for synthesis of extension products under suitable conditions and can be poly (T) or a collection of degenerate sequences. In some embodiments, the methods involve the incorporation of an RNA polymerase promoter into selected cDNA molecule by priming cDNA synthesis with a primer complex comprising a synthetic oligonucleotide containing the promoter. Following synthesis of double-stranded cDNA, a polymerase generally specific for the promoter can be added, and anti-sense RNA can be transcribed from the cDNA template. The progressive synthesis of multiple RNA molecules from a single cDNA template results in amplified, anti-sense RNA (aRNA) that serves as starting material for cloning procedures by using random primers. The amplification, which will typically be at least about 20-40, typically to 50 to 100 or 250-fold, but can be 500 to 1000-fold or more, can be achieved from nanogram quantities or less of cDNA.

In some embodiments, a two stage preamplification method can be used to preamplify assay 1000 in one vessel by IVT and, for example, this preamplification stage can be 100× sample. In the second stage, the preamplified product can be divided into aliquots and preamplified by PCR and, for example, this preamplification stage can be 16,000× sample or more. Although the above preamplification methods can be used in microplate 20, these are only examples and are non-limiting.

In some embodiments, the preamplification can be a multiplex preamplification, wherein the analyte sample can be divided into a plurality of aliquots. Each aliquot can then be subjected to preamplification using a plurality of primer sets for DNA targets. In some embodiments, the primer sets in at least some of the plurality of aliquots differ from the primer sets in the remaining aliquots. Each resulting preamplification product detection mixture can then be dispersed into at least some of the plurality of wells 26 of microplate 20 comprising an assay 1000 having corresponding primer sets and detection probes for further amplification and detection according to the methods described herein. In some embodiments, the primer sets of assay 1000 in each of the plurality of wells 26 can correspond to the primer sets used in making the preamplification product detection mixture. The resulting assay 1000 in each of the plurality of wells 26 thus can comprise a preamplification product and primer sets and detection probes for amplification for DNA targets, which, if present in the analyte sample, have been preamplified.

Since a plurality of different sequences can be amplified simultaneously in a single reaction, the multiplex preamplification can be used in a variety of contexts to effectively increase the concentration or quantity of a sample available for downstream analysis and/or assays. In some embodiments, because of the increased concentration or quantity of target DNA, significantly more analyses can be performed with multiplex amplified samples than can be performed with the original sample. In many embodiments, multiplex amplification further permits the ability to perform analyses that require more sample or a higher concentration of sample than was originally available. In such embodiments, multiplex amplification enables downstream analysis for assays that could not have been possible with the original sample due to its limited quantity. In some embodiments, the plurality of aliquots can comprise 16 aliquots with each of the 16 aliquots comprising about 1536 primer sets. In such embodiments, a sample comprising a whole genome for a species, for example a human genome, can be preamplified. In some embodiments, the plurality of aliquots can be greater than 16 aliquots. In some embodiments, the number of primer sets can be greater than 1536 primer sets. In some embodiments, the plurality of aliquots can be less than 16 aliquots and the number of primer sets can be greater than 1536 primer sets.

For examples of such embodiments, see PCT Publication No. WO 2004/051218 to Andersen and Ruff.

Multiplex Methods

In some embodiments, multiplex methods are provided wherein assay 1000 comprises a first universal primer that binds to a complement of a first target, a second universal primer that binds to a complement of a second target, a first detection probe comprising a sequence that binds to the sequence comprised by the first target, and a second detection probe comprising a sequence that binds to a sequence comprised by the second target. In some embodiments, at least some of the plurality of wells 26 of microplate 20 comprise a solution operable to perform multiplex PCR. The first and second detection probes can comprise different labels, for example, different fluorophores such as, in non-limiting example, VIC and FAM. Sequences of the first and second detection probes can differ by as little as one nucleotide, two nucleotides, three nucleotides, four nucleotides, or greater, provided that hybridization occurs under conditions that allow each detection probe to hybridize specifically to its corresponding detection probe.

In some embodiments, multiplex PCR can be used for relative quantification, where one primer set and detection probe amplifies the target DNA and another primer set and detection probe amplifies an endogenous reference. In some embodiments, the present teaching provide for analysis of at least four DNA targets in each of the plurality of wells 26 and/or analysis of a plurality of DNA targets and a reference in each of the plurality of wells 26.

Kits

In some embodiments, kits can be provided comprising materials suitable for carrying out polynucleotide amplification. In some embodiments, such kits can comprise microplate 20 and at least a master mix, such as described above herein.

In some embodiments, such kits can comprise solutions packaged for preamplification of targets for downstream or subsequent analysis including by multiplex PCR. In some embodiments, the kits can comprise a plurality of primer sets. In some embodiments, the kits can further comprise a set of amplification primers suitable for pre-amplifying a sample of target DNA disposed in at least some of the plurality of wells 26. In some embodiments, the primers comprised in each of the plurality of wells 26 can, independently of one another, be the same or a different set of primers.

In some embodiments, the kit can comprise at least one primer and at least one detection probe disposed in at least some of the plurality of wells 26. In some embodiments, the kit can comprise a forward primer, a reverse primer, and at least one FAM labeled MGB quenched PCR detection probe disposed in at least some of the plurality of wells 26. In some embodiments, the kit can comprise at least one detection probe, at least one primer, and a polymerase. In some embodiments, the kit can comprise at least one forward primer, at least one reverse primer, at least one labeled MGB quenched detection probe, at least one labeled MGB quenched detection probe used as a endogenous control, and a polymerase disposed in at least some of the plurality of wells 26. In some embodiments, a ROX labeled detection probe can be used as a passive internal reference. Some embodiments comprise other detection probes to be used as a passive internal reference. In some embodiments, the kit can comprise reagents for preamplification. In some embodiments, reaction vessels, separate from microplate 20, can contain any of the above reagents in a dried form, which can be coated to or directed to the bottom of at least some of the plurality of wells 26. In some embodiments, the user can add a universal master mix, water, and a sample of target DNA to each of the plurality of wells 26 before analysis.

In some embodiments, a kit comprises a container containing assay reagents and a separate data storage medium that contains data about the assay reagents. The assay reagents can be adapted to perform an allelic discrimination or expression analysis reaction when mixed with at least one target polynucleotide. The other reagents can be, for example, components conventionally used for PCR and can comprise non-reactive components. In some embodiments, the assay reagents container can have a machine-readable label that provides information about the contents of the container.

In some embodiments, the data stored on the data storage medium can comprise computer-readable code that can be used to adjust, calibrate, direct, set, run, or otherwise control an apparatus, for example, high-density sequence detection system 10. In some embodiments, the data stored on the date storage medium can be used to control high-density sequence detection system 10 to automatically perform PCR or RT-PCR of assay 1000. See, for example, U.S. Patent Application Publication No. 2004/0072195.

Data Analysis

In some embodiments, as seen in FIG. 58, a plurality of microplates 20 having assay 1000 filled thereon can be analyzed as described herein with high-density sequence detection system 10 to generate data. In some embodiments, this data can be stored in a gene expression analysis system database 736. Software can then be used to generate gene expression analysis information 738.

In some embodiments, a gene expression analysis system can utilize computer software that organizes analysis sessions into studies and stores them in database 738. An analysis session can comprise the results of running microplate 20 in high-density sequence detection system 10. To analyze session data, one can load an existing study that contains analysis session data or create a new study and attach analysis session data to it. Studies can be opened and reexamined an unlimited number of times to reanalyze the analysis session data or to add other analysis sessions to the analysis.

In some embodiments, gene expression analysis system database 736 stores the analyzed data for each microplate 20 run on high-density sequence detection system 10 as an analysis session in database 736. The software can identify each analysis session by marking indicia 64 of the associated microplate 20 and the date on which it was created. Once analysis sessions have been assigned to a study, various functions can be performed. These functions comprise, but are not limited to, designating replicates, removing outliers, filtering data out of a particular view or report, correction of preamplification values via stored values, and computation of gene expression values.

In some embodiments, real time PCR is adapted to perform quantitative real time PCR (qRT-PCR). In some embodiments, two different methods of analyzing data from qRT-PCR experiments can be used: absolute quantification and relative quantification. In some embodiments, absolute quantification can determine an input copy number of the target DNA of interest This can be accomplished, for example, by relating a signal from a detection probe to a standard curve. In some embodiments, relative quantification can describe the change in expression of the target DNA relative to a reference or a group of references such as, for an example, an untreated control, an endogenous control, a passive internal reference, an universal reference RNA, or a sample at time zero in a time course study. When determining absolute quantification, the expression of the target DNA can be compared across many samples, for example, from different individuals, from different tissues, from multiple replicates, and/or serial dilution of standards in one or more matrices. In some embodiments of the present teachings, qRT-PCR can be performed using relative quantification and the use of standard curve is not required. Relative quantification can compare the changes in steady state target DNA levels of two or more genes to each other with one of the genes acting as an endogenous reference, which may be used to normalize a signal from a sample gene. In some embodiments, in order to compare between experiments, resulting fold differences from the normalization of sample to the reference can be expressed relative to a calibrator sample. In some embodiments, the calibrator sample is included in each assay 1000. The gene expression analysis system can determine the amount of target DNA, normalized to a reference, by determining $$\Delta C_T = C_{Tq} - C_{Tendo}$$

where $C_T$ is the threshold cycle for detection of a fluorophore in real time PCR; $C_{Tq}$ is the threshold cycle for detection of a fluorophore for a target DNA in assay 1000; and $C_{Tendo}$ is the threshold cycle for detection of a fluorophore for an endogenous reference or a passive internal reference in assay 1000.

In some embodiments, a gene expression analysis system can determine the amount of target DNA, normalized to a reference and relative to a calibrator, by determining:

$$\Delta\Delta C_T = \Delta C_{T,q} - \Delta C_{T,cb}$$

where $C_{T,q}$ is the threshold cycle for detection of a fluorophore for the target DNA in assay 1000; $C_{T,cb}$ is the threshold cycle for detection of a fluorophore for a calibrator sample; $\Delta C_{T,q}$ is a difference in threshold cycles for the target DNA and an endogenous reference; and $\Delta C_{T,cb}$ is a difference in threshold cycles for the calibrator sample and the endogenous reference If $\Delta\Delta C_T$ is determined, the relative quantity of the target DNA can be determined using a relationship of relative quantity of the target DNA can be equal to $2^{-\Delta\Delta C_T}$. In some embodiments, $\Delta\Delta C_T$ can be about zero. In some embodiments, $\Delta\Delta C_T$ can be less than ±1. In some embodiments, the above calculations can be adapted for use in multiplex PCR (See, for example, Livak et al. Applied Biosystems User Bulletin #2, updated October 2001 and Livak and Schmittgen, *Methods* (25) 402-408 (2001).

Triple Delta Analysis

In some embodiments, assay 1000 can be preamplified, as discussed herein, in order to increase the amount of target DNA prior to distribution into the plurality of wells 26 of microplate 20. In some embodiments, assay 1000 can be collected, for example, via a needle biopsy that typically yields a small amount of sample. Distributing this sample across a large number of wells can result in variances in sample distribution that can affect the veracity of subsequent gene expression computations. In such situations, assay 1000 can be preamplified using, for example, a pooled primer set to increase the number of copies of all target DNA simultaneously.

In some embodiments, preamplification processes can be non-biased, such that all target DNA are amplified similarly and to about the same power. In such embodiments, each target DNA can be amplified reproducibly from one input sample to the next input sample. For example, if target DNA X is initially present in sample A at 100 target molecules, then after 10 cycles of PCR amplification (1000-fold), 100,000 target molecules should be present. Continuing the example, if target DNA X is initially present in sample B at 500 target molecules, then after 10 cycles of PCR amplification (1000-fold), 500,000 target molecules should be present. In this example, the ratio of target DNA X in samples A/B remains constant before and after the amplification procedure.

In some embodiments, a minor proportion of all target DNA can have an observed preamplification efficiency of less than 100%. In such embodiments, if the amplification bias is reproducible and consistent from one input sample to another, then the ability to accurately compute comparative relative quantitation between any two samples containing different relative amounts of target can be maintained. Continuing the example from above and assuming 50% reproducible amplification efficiency, if target DNA X is initially present in sample A at 100 target molecules, then after 10 cycles of PCR amplification (50% of 1000-fold), 50,000 target molecules should be present. Further continuing the example, if target X is initially present in sample B at 500 target molecules, then after 10 cycles of PCR amplification (50% of 1000-fold), 250,000 target molecules should be present. In this example, the ratio of template X in samples A/B remains constant before and after the amplification procedure and is the same ratio as the 100% efficiency scenario.

In some embodiments, an unbiased amplification of each target DNA (x, y, z, etc.) can be determined by calculating the difference in $C_T$ value of the target DNA (x,y,z, etc.) from the $C_T$ value of a selected endogenous reference, and such calculation is referred to as the $\Delta C_T$ value for each given target DNA, as described above. In some embodiments, a reference for a bias calculation can be non-preamplified, amplified target DNA and an experimental sample can be a preamplified amplified target DNA. In some embodiments, the standard sample and experimental sample can originate from the same sample, for example, same tissue, same individual, and/or same species. In some embodiments, comparison of $\Delta C_T$ values between the non-preamplified amplified target DNA and preamplified amplified target DNA can provide a measure for the bias of the preamplification process between the endogenous reference and the target DNA (x, y, z, etc.).

In some embodiments, the difference between the two $\Delta C_T$ values ($\Delta\Delta C_T$) can be zero and as such there is no bias from preamplification. This is illustrated below with reference to FIG. 213. In some embodiments, the gene expression analysis system can be calibrated for potential differences in preamplification efficiency that can arise from a variety of sources, such as the effects of multiple primer sets in the same reaction. In some embodiments, calibration can be performed by computing a reference number that reflects preamplification bias. Reference number similarity for a given target DNA across different samples is indicative that the preamplification reaction $\Delta C_T$s can be used to achieve reliable gene expression computations.

In some embodiments of the present teaching, a gene expression analysis system can compute these reference numbers by collecting a sample (designated as Sample A and $S_A$) and processing it with one or more protocols. A first protocol comprises running individual PCR gene expression reactions for each target DNA ($T_x$) relative to an endogenous reference (endo), such as, for example, 18s or GAPDH. These reactions can yield cycle threshold values for each target DNA relative to the endogenous control; as computed by:

$$\Delta C_{T\,not\,preamplified} T_x S_A = C_{T\,not\,preamplified} T_x S_A - C_{T\,notpreamplified}\,endo$$

A second protocol can comprise running a single PCR preamplification step on assay 1000 with, for example, a pooled primer set. In some embodiments, the pooled primer set can contain primers for each target DNA. Subsequently, the preamplified product can be distributed among plurality of wells 26 of microplate 20. PCR gene-expression reactions can be run for each preamplified target DNA (Tx) relative to an endogenous reference (endo). These counts can yield cycle threshold values for each preamplified target DNA relative to the endogenous control, as computed by:

$$\Delta C_{T\,preamplified}T_xS_A = C_{T\,preamplified}T_xS_A - C_{T\,preamplified\,endo}$$

A difference between these $\Delta C_{T\,not\,preamplified}\,T_xS_A$ and $\Delta C_{T\,preamplified}\,T_xS_A$ can be computed by:

$$\Delta\Delta C_T T_x S_A = \Delta C_{T\,not\,preamplified}T_xS_A - \Delta C_{T\,preamplified}T_xS_A$$

In some embodiments, a value for $\Delta\Delta C_T T_x S_A$ can be zero or close to zero, which can indicate that there is no bias in the preamplification of target DNA $T_x$. In some embodiments, a negative $\Delta\Delta C_T\,T_xS_A$ value can indicate the preamplification process was less than 100% efficient for a given target DNA ($T_x$). For example, when using an IVT process, a percentage of target DNA with a $\Delta\Delta C_T$ of +/−1 $C_T$ of zero can be ~50%. In another example, when using a multiplex preamplification process, a percentage of target DNA with a $\Delta\Delta C_T$ of +/−1 $C_T$ of zero can be ~90%.

In some embodiments, an amplification efficiency can be less than 100% for a particular target DNA, therefore $\Delta\Delta C_T$ is less than zero for the particular target DNA. An example can be an evaluation of $\Delta\Delta C_T$ values for a group of target DNA from a 1536-plex for the multiplex preamplification process including four different human sample input sources: liver, lung, brain and an universal reference tissue composite. In this example, most $\Delta\Delta C_T$ values are near zero, however, some of the target DNA have a negative $\Delta\Delta C_T$ value but these negative values are reproducible from one sample input source to another. In some embodiments, a gene expression analysis system can determine if a bias exists for target DNA analyzed for different sample inputs.

In some embodiments of the present teachings, a gene expression analysis system can use $\Delta\Delta C_T$ values computed for the same target DNA but in different samples (Sample A ($S_A$) and Sample B ($S_B$)) in order to determine the accuracy of subsequent relative expression computations. This results in the equation, $$\Delta\Delta\Delta C_T T_x = \Delta\Delta C_T T_x S_A - \Delta\Delta C_T T_x S_B$$

In some embodiments a value for $\Delta\Delta\Delta C_T T_x$ can be zero or reasonably close to zero which can indicate that the preamplified $\Delta C_T$ values for $T_x$ ($\Delta C_{T\,preamplified}\,T_xS_A$ and $\Delta C_{T\,preamplified}\,T_xS_B$) can be used for relative gene expression computation between different samples via a standard relative gene expression calculation.

In some embodiments, a standard relative gene expression calculation can determine the amount of the target DNA. In some embodiments, a standard relative gene expression calculation employs a comparative $C_T$. In some embodiments, the above methods can be practiced during experimental design and once the conditions have been optimized so that the $\Delta\Delta\Delta C_T T_x$ is reasonably close to zero, subsequent experiments only require the computation of the $\Delta C_T$ value for the preamplified reactions. In some embodiments, $\Delta\Delta C_T T_x S_A$ values can be stored in a database or other storage medium. In such embodiments, these values can then be used to convert $\Delta\Delta C_{T\,preamplified}T_xS_A$ values to $\Delta\Delta C_{T\,not\,preamplified}T_xS_A$ values. In such embodiments, the $\Delta\Delta C_{T\,preamplified}T_xS_y$ values can be mapped back to a common domain. In some embodiments, a not preamplified domain can be calculated using other gene expression instrument platforms such as, for example, a microarray. In some embodiments, the $\Delta\Delta C_T T_x S_A$ values need not be stored for all different sample source inputs ($S_A$) if it can be illustrated that the $\Delta\Delta C_{T\,preamplified}T_x$ is reasonably consistent over different sample source inputs.

In some embodiments, after microarray sample-to-sample differences are in a $\Delta\Delta C_T$ format, then real-time PCR data can be directly compared to data from other platforms. In some embodiments, a $\Delta\Delta\Delta C_T$ calculation can be a validation tool to confirm that relative quantitation data can be compared from one amplification/detection process to another. In some embodiments, $\Delta\Delta\Delta C_T$ calculation can be a validation tool to confirm that relative quantitation data can be compared from one sample input source to another sample input source, for example, comparing a sample from liver to a sample from brain in the same individual. In some embodiments, $\Delta\Delta\Delta C_T$ calculation can be a validation tool to confirm that relative quantitation data can be compared from one high-density sequence detector system 10 to another high-density sequence detection system 10. In some embodiments, $\Delta\Delta\Delta C_T$ calculation can be a validation tool to confirm that relative quantitation data can be compared from one platform to another, for example, data from real time PCR to data from a hybridization array is especially valuable for cross-platform validation. In some embodiments, real time PCR and hybridization array data can be directly compared. In some embodiments, the TaqMan $\Delta\Delta C_T$ can be compared to a microarray output converted to the $\Delta\Delta C_T$ format. In such embodiments, the resultant $\Delta\Delta\Delta C_T$, if within +/−1 $C_T$ of zero, can determine a high-degree of confidence that the actual fold difference observed within each of the two platforms is correlative.

Assay Controls

In some embodiments, high-density sequence detection system 10 measures the relative quantities of target DNA using the $C_T$ value from a PCR growth curve, as described herein. The measured $C_T$ value for target DNA for a given assay may vary depending on the system and/or microplate 20 in which the assay 1000 is measured. That is, such variation may arise from manufacturing differences in high-density sequence detection system 10 and/or thermal non-uniformity from variances in production of microplate 20.

In some embodiments, normalization may be the adjusting of a set of raw measurements. For example, a variable storing target DNA levels, quantities may be represented in copy numbers, according to some transformation function in order to make such data compatible between different samples. For example, adjusting copy numbers for a target DNA quantity will produce measurements normalized against a quantity of total RNA and therefore such data can be expressed in specific meaningful and/or compatible units. Without relevant normalization, raw measurements may not carry information that is easily interpretable.

In some embodiments, several of the plurality of wells 26 of microplate 20 can be allocated for controls. In some embodiments, the control comprises a template. The template can be, for example, a synthetic oligonucleotide or plasmid, genomic DNA, or other natural DNA or RNA. In some embodiments, the template can contain analogs of naturally occurring nucleotides with modifications to the base, sugar, or phosphate backbone, such as PNAs.

In some embodiments, exogenous templates can be used as controls and such templates can be introduced into assay 1000 in one of the following ways:

(i) the template at a known concentration can be introduced into a reverse transcription reaction along with the sample;

(ii) the template at a known concentration can be introduced into a preamplification reaction along with the sample;

(iii) the template at a known concentration can be introduced into assay 1000 along with the sample; or (iv) the template at a known concentration can be spotted onto at least one of a plurality of wells 26.

In some embodiments, the exogenous template can be spotted and dried into at least some of the plurality of wells 26 at a known and defined concentration and the $C_T$ value measured from those of the plurality of wells 26 comprising the control. This $C_T$ value can be used to correct for high-density sequence detection system 10, microplate 20, and sample filling/pipetting variations. In these embodiments, assay 1000 can be used to fill at least some of the plurality of wells 26, but assay 1000 would not contain any exogenous template that would be amplified. In some embodiments, the template can be filled into at least some of the plurality of wells 26 at a known and defined concentration and the $C_T$ value can be measured from the plurality of wells 26 comprising the control to correct for variations from sample filling and pipetting. Templates can also be detected in some of the plurality of wells 26 as an internal control. In such embodiments, the detection probe for the template would produce a different signal than the detection probe for the target DNA. In some embodiments that include a preamplification method to amplify targets prior to PCR, the template can also be designed such that it can be preamplified. Thus, if the template is introduced to assay 1000 prior to preamplification and subsequently measured on microplate 20, its $C_T$ value could be used to correct for variations in the efficiency of sample preamplification as well as filling/pipetting errors.

In some embodiments, the plurality of wells 26 used for controls on microplate 20 can be allocated to contain at least one fluorescent dye that can be spotted and dried down into microplate 20 and hydrolyzed at the time of sample filling. Such plurality of wells 26 can be used to improve calibration of detection system 300 for optical aberrations. In some embodiments, a dye can be used at known concentration and the signals therefrom can be used to optimize the detection sensitivity of high-density sequence detection system 10 (such as the exposure time of the CCD in a detection system 300). In some embodiments, the plurality of wells 26 comprising a series dilution of control wells can be used for such calibrations and optimizations. In some embodiments, some of the plurality of wells 26 can be used as controls for identification of the position of the plurality of wells 26. In some embodiments, at least some of the plurality of wells 26 on microplate 20 can comprise a passive internal reference dye (PIR), such as for example, ROX. The signal from the PIR can be used to locate the plurality of wells 26 by detection system 300. In some embodiments, prior to beginning PCR, background signals from quenching dyes can be used to determine the locations of the plurality of wells 26 by detection system 300. In some embodiments, controls can be used to determine filling errors. That is, signals from the PIR can be used to determine if sample filling errors have occurred by looking for an absent or an abnormally high or low signal in the PIR detection image or channel. These signals can indicate an empty well, or an overfilled or under filled well, respectively. In some embodiments, controls can be used to determine spotting errors. The background signals from quenching dyes can be used to determine if spotting errors occurred by looking for an absent or an abnormally high or low signal in the quenching detection image or channel.

In some embodiments, controls can be used as quality control for spotting reagents onto microplate 20. Controls can be measured (by imaging or scanning) for the weak background fluorescence of the dried down reagents to determine if the plurality of wells 26 were spotted correctly and/or in the correct orientation. In some embodiments, one or more fluorescent, infrared, ultraviolet, or visible dyes are introduced into the reagents prior to spotting. When dried down, the fluorescent dyes can be measured to determine if spotting was performed correctly. In some embodiments, the addition of extra dyes to the spotting reagents can be useful for spotting reagents that do not have an inherent fluorescent signal, such as for example the use of reagents comprising SYBR® detection probes. In such embodiments, these additional dyes could also be used as internal controls for identifying filling and pipetting errors.

In some embodiments, the plurality of wells 26 without detection probes or primers and/or the plurality of wells 26 that are completely empty or filled with buffer or other solution not containing dye can be used for background correction. The plurality of wells 26 comprising controls without templates (no template controls (NTC)) can also be used for background correction and/or for confirming lack of contamination of the plurality of wells 26 by other samples. In some embodiments, the plurality of wells 26 comprising controls without assay 1000 can be used to confirm lack of contamination during spotting. In some embodiments, the plurality of wells 26 containing varying amounts of a single or multiple dyes can be used to determine if high-density sequence detection system 10 is capable of detecting signals within the expected dynamic range independent of assay performance. In some embodiments, the plurality of wells 26 containing varying amounts of a single or multiple dyes can be used to correct for optical crosstalk or other means of signal correction or normalization. Examples include serial dilutions, multiple titration points, dye ladders, as well as replicates and combinations thereof. In some embodiments, pin hole arrays are used for optical calibration. The controls described above, individually or in combinations thereof, can be incorporated into a single microplate 20 to be used to verify high-density sequence detection system 10 performance in the field at the time of installation or during manufacture.

In some embodiments, a procedure for calibration of spectral sensitivity can employ a reference standard to apply a correction to a spectrum such that each of the plurality of wells 26 signal for each filter is normalized to a specific value. In some embodiments, the reference standard can comprise serial dilutions, multiple titration points or dye ladders, as well as replicates and combinations thereof. In some embodiments, the reference comprises multiple dyes (e.g., two, three, four, five, or more) in some of the plurality of wells 26 of microplate 20. In some embodiments, the value should be identical across all instruments and time periods in order to preserve the calibration. In some embodiments, a reference can be fluorescent reference standard. In some embodiments, the reference can be used in normalizing a single high-density sequence system 10. In some embodiments, the reference can be used to normalize a group of high-density sequence systems 10. In some embodiments, the procedure normalizes thresholds and baselines over a group of high-density sequence detector systems 10 so that $C_T$ values are similar across the group for the same assay 1000. In some embodiments, the controls are templates.

In some embodiments, the templates are introduced into a mixture comprising a sample prior to reverse transcription and the resulting $C_T$ values generated from the templates are used to correct for variations in the efficiency of the reverse transcription reaction relative to the expected $C_T$ value. In some embodiments, templates are introduced into a mixture comprising a sample prior to preamplification and the resulting $C_T$ values generated from the templates are used to correct for variations in efficiency of the preamplification reaction. In some embodiments, the templates are introduced into a mixture comprising the sample prior to amplification and the resulting $C_T$ values generated from the templates are used to correct for variations in efficiency of amplification. In some embodiments, different templates are introduced into the mixture comprising a sample at the three different steps (i) reverse transcription, (ii) preamplification and (iii) amplification and the resulting $C_T$ values generated from the templates are calculated for each of the three steps. In such embodiments, the resulting $C_T$ value generated from the templates can be used to determine which of the three steps can be responsible for large deviations of $C_T$ measurements from the expected values. Multiple exogenous templates with varying relative concentrations can be added to a sample mixture in any of the three steps or all of the steps. In some embodiments, a standard plot for absolute quantitation of a sample run on microplate 20 can be calculated. The standard plot can be used to normalize data attained from different microplates 20 or from different samples on the same microplate 20.

In some embodiments, a control can comprise an endogenous template or a set of endogenous templates within a sample that can be used in a wide range of tissues. In some embodiments, the endogenous template can be selected so that the average signal produced during amplification is consistent from sample to sample. In some embodiments, the appropriately selected endogenous template can be used to normalize for variations in sample quantity in the plurality of wells 26. In some embodiments, results from endogenous controls can be compared from results from exogenous control to distinguish variations in sample quantity and variations in assay performance. A dataset can be normalized by using a function of multiple endogenous templates as controls. For example, a regression of the mean expression values from multiple endogenous controls and can be chosen to be expressed across the entire expression range. Other examples of normalization using a function include functions of the mean signal across microplate 20, median normalization, quantile normalization, and lowness normalization. In some embodiments, the endogenous controls are relatively invariantly expressed across standard experimental conditions or biological conditions, for example, a tumor, or non-tumor tissue. In some embodiments, the endogenous controls are relatively, invariantly expressed across different tissue types, for example, brain and lung. In some embodiments, a single endogenous control can be used for normalization. In some embodiments, multiple endogenous controls are used for normalization.

In some embodiments, microplate 20 comprising a calibrated dilution series of DNA targets and single exon assays can be run on high-density sequence detection system 10 and the data collected can be used to calibrate for absolute quantity or copy number estimations or as in comparison to other array platforms. In such embodiments, microplate 20 can comprise a combination of replicated bacterial DNA and human DNA. For example, microplate 20 can be spotted with 96 different primer sets and 64 replications of the ten-fold primer sets. The human sample can be split and then spiked with bacterial targets to make a set of four ten-fold dilutions. Microplate 20 comprising 96 primer sets with 64 replications can be filled with the set of four ten-fold dilutions and run in high-density sequence detection system 10 producing data for 16 replications of each dilution of the set. The data collected can be used for calculation of high-level performance parameters such as tabulating bad data, calibrating random error model, estimating systematic errors, and estimating starting copy number.

In some embodiments, controls can be used for spatial normalization that compensates between at least two channels of signal that is being collected by detections system 300. The channels for which a signal can be being collected and imaged can be different band passes and the optical performance can change with wavelength and detection probe. In some embodiments, spatial normalization can be accomplished by calibration images of each of the at least two channels collected from a mixture of a pure detection probe spotting to the channel. In some embodiments, a control comprising a mixture of dyes can be spotted onto microplate. In such embodiments, the control comprising a mixture of dyes produces a high signal to noise ratio when detected in detection system 300 of high-density sequence detection system 10. In such embodiments, spatial normalization correction can be calculated by the use of spatial trends of the measurements of the controls. The controls comprising a mixed dye can be placed in the grid throughout microplate 20. In some embodiments, to correct all extracted normalization intensities for the spatial trends, a coarse image can be collected and normalized to a 1, 2D median smoothed inner plated under every feature collected is then divided into the image of the extracted normalized intensities. In some embodiments, spatial normalization allows for platform comparisons of data, removes specific instrument effects, or improves cross instrument and cross platform comparisons. In some embodiments, any of the controls discussed above can be adapted for genotyping applications.

Assay Selection and Polynucleotide Library

In some embodiments, a method is provided for supplying a user with assays useful in obtaining structural genomic information, such as the presence or absence of one or more SNPs, and functional genomic information, such as the expression or amount of expression of one or more genes. As such, in some embodiments, the assays can be configured to detect the presence or expression of genetic material in the sample.

In some embodiments, a method of compiling a library of polynucleotide data sets can be provided. In such embodiments, the data sets can correspond to polynucleotides that each function as a primer for producing a nucleic acid sequence that can be complementary to at least one target SNP, as a detection probe for rendering detectable the at least one target SNP, or as both. According to some embodiments, the method can comprise selecting for the library polynucleotide data sets that each correspond to a respective polynucleotide that contains a sequence that is complementary to a respective first allele in each of the at least one target, if, under a set of reaction conditions a number of parameters are met by each polynucleotide corresponding to the data sets in the library.

In some embodiments, the method can comprise determining a background signal value by calculating a first normalized ratio of a fluorescence intensity of a respective polynucleotide that contains a sequence that is complementary to a first allele comprised in the at least one target nucleic acid sequence, reacted with first assay reactants in the absence of the target nucleic acid sequence, and under first conditions of fluorescence excitation, to a dye fluorescence intensity of a passive-reference dye under the first conditions. The method can comprise comparing a difference between a second normalized ratio of the fluorescence intensity of the respective polynucleotide reacted with the first assay reactants in the presence of the target nucleic acid sequence, to the dye fluorescence intensity, and the background signal value. The method can comprise comparing a difference between a third normalized ratio of the fluorescence intensity of the respective polynucleotide reacted with second assay reactants that contain a second allele comprised in the at least one target nucleic acid sequence to the dye fluorescence intensity, wherein the second allele differs from the first allele, and the background signal value.

In some embodiments, the method can comprise determining whether at least one individual from a population of individuals has a genotype identifiable under the first conditions that result from reacting the respective polynucleotide with the first assay reactants and in the presence of the target nucleic acid sequence, wherein the population comprises at least one individual that has the identifiable genotype and at least one individual that does not have the identifiable genotype. The method can comprise determining whether at least one individual from the population has an identifiable minor allele of the identifiable genotype, under the first conditions that result from reacting the respective polynucleotide with the first assay reactants in the presence of the target nucleic acid sequence. See U.S. Patent Application Publication No. 2003/0190652 to De La Vega et al.

Other Applications and Methods

In some embodiments, high-density sequence detection system 10 can be used for a variety of biological applications, or assays, other than PCR. In some embodiments, high-density sequence detection system 10 comprising optical illumination and detection system 300 can be used in imaging microplates that fit a SBS standard footprint from low density microplates, for example, 96, 384, or 1536 well microplates to high-density microplates, for example, 6144 or 31104 well microplate. In some embodiments, using lower density microplates high-density sequence detection system 10 can detect multiple, discrete events within a well, for example, for imaging fluorescently tagged antibodies binding to receptors on the surface of a cell for high-throughput cell-based screening. In some embodiments, high-density sequence detection system 10 is not limited to imaging only microplate 20 but can be used in the imaging of gels, blots, nitrocellulose membranes, and the like with features at high-density.

In some embodiments, high-density sequence detection system 10 can image microplates, nitrocellulose membranes, gels, films, blots, and the like. Detection can be, in some embodiments, for isotopic changes, chemiluminescent emissions, chemifluorescent emissions, fluorescent emissions, calorimetric changes, and time-lapse studies of any of the above detection methods. In some embodiments, high-density sequence detection system 10 can be used as a spectrophotometer or spectrofluorometer for samples contained in microplate 20. For example, high-density sequence detection system can be used for methods for the measurement and/or analysis of absorbance (UV-Vis-NIR) by adding a detector to opposite side from excitation side of microplate 20; for methods for the measurement and/or analysis of fluorescence intensity; for methods for the measurement and/or analysis of fluorescence polarization by adding at least one polarizing filter to detection system 300; or for methods for the measurement and/or analysis of time resolved fluorescence. In some embodiments of high-density sequence detection system 10 can be modified to increase read out speed of CCD pixels. In some embodiments, high-density sequence detection system 10 can be used for methods for the measurement and/or analysis of luminescence. In some embodiments, high-density sequence detection system 10 can be used for time-limited chemiluminescent reactions and in such embodiments, high-density sequence detection system 10 can be modified to manipulate reagents in microplate 20 to begin the reactions.

Isothermal Amplification

According to some embodiments, high-density sequence detection system 10 can be used to perform various isothermal procedures in, for example, the areas of molecular diagnostics, genotyping, gene expression monitoring, and drug screening. Such isothermal procedures can include, for example, those useful in genetic, biochemical, and bioanalytic processes, such as processes for detecting a target DNA, processes for detecting a mutation, processes for detecting a polymorphism, processes for detecting a single base insertion or deletion, and for processes for identifying SNPs. In some embodiments, the high-density sequence detection system 10 can be used to perform isothermal amplification according to U.S. Pat. No. 6,692,917.

In some embodiments, processes for identifying SNPs can include, for example, assays for single-base discrimination and/or quantitative detection of DNA or RNA sequences, for example, SNPs and mutations (single base changes, insertions or deletions in DNA and RNA molecules), from samples containing genomic DNA, total RNA, cell lysates, purified DNA, purified RNA, or nucleic acid amplification products, for example, PCR or RT-PCR products. Other assays that can be carried out using high-density sequence detection system 10 of the present teachings include the processes and methods taught in U.S. Pat. No. 6,692,917.

In some embodiments, the assays can be performed using a high-density sequence detection system 10 wherein assay 1000 comprises reaction components, including, for example, the first oligonucleotide, the detection probe, or both the first oligonucleotide and the detection probe. In some embodiments, such components can be attached to microplate 20, directly or through a spacer and/or linker molecule, including for example, a carbon chain, a polynucleotide, biotin, or a polyglycol. In some embodiments, the assays can be performed alone or in combination with nucleic acid amplification assays, including for example, standard or multiplex PCR.

Protein Assays

In some embodiments, high-density sequence detection system 10 can be used to detect the binding activity of primary antibody reagents as direct labeled conjugates or indirect conjugate forms, for example, conjugate enzymes or conjugate Quantum Dots (Qdots). Cells from a variety of sources can be used including in vitro tissue culture and peripheral blood leukocytes. In some embodiments, binding events can be detected or imaged from microplate 20, or alternatively, on nitrocellulose membranes with high-density separation channels and/or bands, for example, using a Western blot technique. In some embodiments, when using a Western blot, one protein in a mixture of any number of proteins can be detected while also providing information about the size of the protein and such information can indicate how much protein has accumulated in cells.

Referring to an illustrative example, first proteins are separated using SDS-polyacrylamide gel electrophoresis (SDS-PAGE) which separates the proteins by size. Nitrocellulose membrane is placed on the gel and the protein bands are electrokinetically transported onto the nitrocellulose membrane. This results in a nitrocellulose membrane imprinted with the same protein bands as the gel. The nitrocellulose membrane is then incubated with a primary antibody made by inoculating a rabbit and diluting the antisera (from blood).

The primary antibody sticks to the protein and forms an antibody-protein complex with the protein of interest. The nitrocellulose membrane is then incubated with a secondary antibody, an antibody enzyme conjugate. The secondary antibody is an antibody against the primary antibody and has the ability to stick to the primary antibody. The conjugate enzyme can comprise a molecular flare stuck onto the antibodies so they can be visualized. The enzyme is incubated in its specific reaction mix resulting in bands wherever there is a protein-primary antibody-secondary antibody-enzyme complex such as wherever the protein of interest is located. In some embodiments, high-density sequence detection system 10 can be used to detect a flash of light that is given off by the enzyme and, in some embodiments, detection system 300 of high-density sequence detection system 10 can be customized for the particular conjugated labels.

By way of example in some embodiments, Green Fluorescent Protein (GFP) is extracted from *Aequorea Victoria*. GFP is a small protein (about 27 Kd) and the DNA sequences coding for GFP can be manipulated by recombinant DNA technology to create gene fusions between GFP and any protein of interest. Such DNA constructs can then be introduced into living cells to express the GFP fluorescent tags on the protein of interest. The GFP fluorescent tag can be used to localize a protein of interest to a specific cell type and/or subcellular localization in living cells and organisms. In some embodiments, high-density sequence detection system 10 optics can be modified to enable 2-40× magnification of individual wells or a small number of wells, adding an x-y stage and adding z-axis autofocus. In some embodiments, high-density sequence detection system 10 can be used to perform GFP-based protein localization assays using microplate 20. In some embodiments, for gene expression, the GFP DNA coding sequence can be placed behind a promoter and/or regulatory DNA sequence of interest, and introduced into cells and this can be used to perform promoter studies in living organisms.

In some embodiments, fluorescence resonance energy transfer (FRET) assays can be used to determine the exact time and place of colocalization. Energy transfers from the excited fluorophore to the nearby acceptor fluorophore. In some embodiments, donor and acceptor molecules are less than 10 nm apart and the emission spectra of the donor fluorophore overlap the excitation spectra of the acceptor fluorophore. The farther apart the molecules are, the weaker the transfer energy. Extremely low light levels require, in some embodiments, a highly sensitive cooled CCD with high quantum efficiency and fast readout rates. FRET images can be taken at different wavelengths. In some embodiments, high-density sequence detection system 10 can be modified to perform FRET assays in microplate 20. High-density sequence detection system 10 optics can be modified to enable magnification (e.g., 2-40×) of individual wells or a small number of wells, adding an x-y stage, and adding z-axis autofocus. In some embodiments, high-density sequence detection system 10 can be used to perform FRET assays using microplate 20. In some embodiments, high-density sequence detection system 10 can produce a series of time lapse images for FRET.

Assays Using QDots as Labels

Quantum dots (QDots) are fluorescent nanoparticles made of inorganic molecules, for example, CdSe and an emission wavelength of a QDot is determined by its physical size. In general, QDots have large stokes shifts, with excitation wavelengths on the order of 408 nm and emission wavelengths starting at around 520 nm and In some embodiments, Qdots can have greater photostability, greater spectral separation, and brighter emission relative to organic fluorescent dyes. It is possible to label, or conjugate QDots to molecules of interest for molecular biology assays, such as antibodies. Further, mixtures of QDots can be employed to provide multiplexing capability. Some embodiments include the use of beads coated with different QDot nanocrystals to detect gene expression levels. For example, 9 μm paramagnetic beads can be coated with mixtures of QDot nanocrystals. Unique spectral codes can be created using four different fluorescent colors of QDot nanocrystals coated onto the beads at defined ratios. Then an outer protective coat can be applied and cross-linked. In some embodiments, gene-specific oligonucleotide probes are conjugated to the bead surface and each gene-specific bead can be identified by its unique QDot nanocrystal spectral code. Gene-specific beads can be combined to form custom gene panels. In some embodiments, many beads of each different type are added to each well 26 with the different bead types having been coated with the spectral code corresponding to the different target DNA.

Referring to an illustrative example, total RNA is isolated from cells or tissue and the sample can then be labeled with biotin. Unbound biotin can be separated from the biotynilated-sample complex by washing, size exclusion, or any of a number of other well-known processes. The cleanly separated biotin labeled sample can then be added to the bead mixtures in microplate 20 and allowed to hybridize to the beads. A reporter can be created by attaching streptavidin to a fifth QDot nanocrystal label. Unattached streptavidin can be separated from the QDot labeled streptavidin in a manner similar to that used for separating the unbound biotin, as before. Cleanly separated streptavidin can then be added to the mix. This fifth QDot (the reporter) provides quantitative information on gene expression. The QDot nanocrystal-labeled streptavidin can bind to the biotinylated targets. To separate any unbound, non-specific biotin and streptavidin, another wash step, or size exclusions step, can be added to separate them from the biotin-streptavidin complexes (sample-biotin to bead-oligo-streptavidin complex). Alternatively, the beads can be allowed to settle to the bottom of wells 26 of microplate 20, which is then imaged. For example, QDots have been linked to immunoglobulin G (IgG) and streptavidin to label the breast cancer marker Her2 on the surface of fixed and live cancer cells, to stain actin and microtubule fibers in the cytoplasm, and to detect nuclear antigens inside the nucleus. In some embodiments, each bead can be identified by reading its spectral code and can quantify the amount of target hybridized to each coded bead. In some embodiments, high-density sequence detection system 10 can be optimized for the excitations and emissions of QDots. In some embodiments, with the multiplexing capabilities afforded by spectral codes, a whole genome gene expression analysis can be completed on a microplate 20.

Cellular Assays

In some embodiments, with the addition of humidity control and $CO_2$ to the existing temperature control-chamber, high-density sequence detection system 10 can accommodate live cell assays in microplate 20. In some embodiments, high-density sequence detection system 10 is modified to comprise magnification (e.g., 2-40×) and an x-y stage. In some embodiments, throughput can be increased by imaging more than one well at a time, with lower resolution and/or lower magnification images.

In some embodiments, using a lower magnification and/or image resolution, high-density sequence detection system 10 can simultaneously read multiple wells in real time. This can be useful, for example, for optimizing assay conditions and determining dose response curves. In some embodiments using microplate 20, more such assays can be run in shorter time leading to better optimizations and more accurate IC50 value determinations.

In some embodiments, microplate 20 can be modified using coatings, activations, and the like to make it more amenable to a particular assay. For example, for growing and staining adherent cells, for example, high protein binding (affinity to molecules for hydrophobic and hydrophilic domains—high binding of antibodies), and for low binding capacity (affinity to molecules of hydrophobic domains).

In some embodiments, high-density sequence detection system 10 comprising microplate 20 can be used to analyze cell differentiation such as identifying morphological changes following membrane dye incorporation; analyze cell cycle employing the detection of G1, S and G2/M phases of a cell cycle; determine mitotic index by detection using antibodies to identify M-phase specific marker; identify cell adhesion by detecting attachment and morphology; or monitor colony formation by detecting the enumeration of one or more colonies. In some embodiments, high-density sequence detection system 10 comprising microplate 20 can be used to study slow ion channels by employing, for example, detection of ion flux fluorescent DiBAC4(3) reporter. In some embodiments, high-density sequence detection system 10 comprising microplate 20 can be used to study protein kinase by using standard antibody methods; study translocation by identifying movement of proteins between plasma membrane, cytoplasm, and the nucleus; study fluorescent proteins such as EGFP and Reef Coral Fluorescent Protein in multiplex assays; identify quantum dots using limited spectral overlap from distinct conjugates; or to study cell based screening such as data lactamase, adipogenesis, hybridoma, expression cloning and/or lectin binding. In some embodiments, high-density sequence detection system 10 comprising microplate 20 can be used to study G-protein coupled receptors. In such embodiments, the membrane proteins are encoded by about 20% of genes and most organisms and are critical for cellular communication, electrical and ion balances, structural integrity of cells and their adhesions, as well as other like functions. In some embodiments, high-density sequence detection system 10 can be used for the analysis of DNA/RNA/protein quantitation and purity; PicoGreen/Nanoorange and Bradford assays; analysis of ELISA and/or enzyme kinetics; analysis of drug dissolution profiles; analysis of caspase-3 and protease assays; analyzing Catch Point cAMP assays; analysis of IMAP kinase assays; analysis of intrinsic tryptophan fluorescence; analysis of membrane permeability assays; analysis of FluoroBlok cell migration assays; analysis of delfia assays; analysis of immunohistochemistry; analysis of tissue staining; analysis of hybridization arrays; or analysis of amino assay.

Dielectric Spectroscopy of Molecular Biology Assays

In some embodiments of high-density sequence detection system 10, an electrically conductive circuitry can be added to microplate 20 to transform a plurality of wells 26 into resonant cavities. In some embodiments, a terminal antenna can be placed in close proximity to a sample in each of the plurality of wells 26, such as a coplanar waveguide device. Such circuitry can deliver electrical signals in the Hz-GHz frequency ranges, for example in the microwave ranges, to the samples. In some embodiments, an electrical connector can be added to microplate 20 in order to connect it to the generated and measured electrical signals from external sources, such as an Agilent vector network analyzer. Such a system can be used to measure changes in the dielectric properties of the samples contained in the plurality of wells 26 of microplate 20. Examples of events that cause changes in dielectric properties, which can be detected or monitored by such a system, include monitoring cell growth and/or death, detecting DNA hybridization, detecting protein-protein and protein-small molecule interactions, detecting protein conformational changes, detecting ion channel flux in cells, and monitoring bulk properties such as pH, and salt concentration.

Monitoring Surface Plasmon Resonance in Real-Time

In some embodiments of high-density sequence detection system 10, microplate 20 can be modified to have an electrically conductive thin layer which can be, for example, gold, on bottom wall 36 of plurality of wells 26. In some embodiments, surface plasmon resonance (SPR) can occur when polarized light incident at an angle for total internal reflection strikes the electrically conductive layer at the interface between media of different refractive index, for example, microplate material with high refractive index and the assay 1000 with low refractive index. In some embodiments, an evanescent wave of electric field intensity can be generated and interacts with (is absorbed by) free electron clouds in the gold layer. In some embodiments, this interaction can generate electron charge density waves called plasmons and can cause a reduction in the intensity of the reflected light. High-density sequence detection system 10 can be modified to illuminate microplate 20 with incident polarized light covering a range of incident angles. In some embodiments with further modifications, high-density sequence detection system 10 can measure reflected light at different angles of transmission from microplate 20. In some embodiments, the resonance angle at which the intensity minimum occurs can be a function of the refractive index of the solution close to the gold layer, for example, a biological sample flowing over the gold layer in the plurality of the wells 26 of microplate 20. In some embodiments, modified high-density sequence detection system 10 can be used to detect SPR analysis such as protein interactions, small molecule (drug candidates) interactions with their targets, membrane-bound receptor interactions, DNA and RNA hybridization, interactions between whole cells and viruses, recognition of cell surface carbohydrates and molecular interactions, such as binding and dissociation.

Determining Presence of Specific DNA Oligonucleotide Sequences using Bioelectronic Detection In some embodiments, high-density array of gold electrodes can be incorporated into microplate 20. In some embodiments, capture probes and signal probes can be designed and manufactured for a specific target DNA. In some embodiments, capture probes can be coated onto the gold electrodes forming a monolayer on the gold surface. In some embodiments, signal probes can be tagged with ferrocenes. In some embodiments, the target DNA can be amplified by PCR and when added to the monolayers on the gold electrodes, specific target DNA can hybridize to the capture probe. An electrochemical signal can be generated when the amplicon hybridizes to the capture probe and the ferrocene-labeled signal probe, thereby bringing a reporter molecule, ferrocene, into contact with the monolayer on the gold electrode. In some embodiments, an AC voltammogram is obtained when the specific target DNA is detected in a sample, but no electronic signal is registered when the specific target DNA is absent from the sample.

Optical Planar Waveguides

In some embodiments, microplate 20 can comprise a high-density array of planar waveguides to selectively excite only fluorophores located at or near the surface of the waveguide. The waveguide can be constructed by depositing a high refractive index material onto a low refractive index material. In some embodiments, a parallel laser light beam is coupled into the waveguiding film by a diffractive grating which is etched into the substrate material of microplate 20. In some embodiments, the light propagates within the waveguiding film and creates a strong evanescent field perpendicular to the direction of propagation into the adjacent medium, for example, one of plurality of wells 26 in microplate 20. In some embodiments, the field strength of the evanescent wave can decay exponentially with distance, so only fluorophores at or near the surface are excited. In some embodiments, selective detection of DNA hybridization, immunoaffinity reactions, and membrane receptor based assays can be analyzed using microplate 20 comprising a high-density array of planar waveguides.

Microplate Applications for Localized Heating, Gradient Thermocycling

In some embodiments, microplate 20 can comprise heat generating electronics and such electronics can be associated with, or in proximity to, one or more of plurality of wells 26 in microplate 20. In some embodiments, temperatures in a plurality of wells 26 or subsets thereof can be controlled to create a gradient thermocycler. In some embodiments, microplate 20 comprising heat generating electronics can be used, for example, to determine optimum assay parameters such as oligo melting point temperatures and/or can be used to improve synchronization of thermal cycling with detection system 300 in high-density sequence detection system 10. In some embodiments, when detection system 300 is limited to reading only a portion of microplate 20 at a time, thermal cycling reactions can be started or stopped selectively by use of microplate 20 comprising heat generating electronics to correspond with optical detection.

Portals

In some embodiments, a web-based user interface can be provided that comprises a web-based gene exploration system operable to provide information to assist a user in selecting one or both of a stock assay and a custom assay. In some embodiments, the web-based gene exploration system can comprise a search function operable to identify genetic material based on a portion of known data. The search function can provide one or more parameters identifying gene structure or function for selection by the user.

In some embodiments, systems are provided comprising a web-based user interface configured for ordering stock assays and/or requesting custom designed assays. Such assays can then be delivered to the user. In some embodiments, such assays are configured to detect presence or expression of genetic material. Assays that detect the presence or expression of genetic material can comprise assays for detecting SNPs or for detecting expressed genes. In some embodiments, the web-based user interface can be configured to receive criteria related to the SNP or to the expressed transcript for which an assay is ordered. Such methods, kits, assays, web interfaces, and the like are disclosed in U.S. Patent Application Publication No. 2004/0018506 to Koehler et al.

What is claimed is:

1. A method of normalizing spectral sensitivity from an instrument, the instrument using a microplate having a plurality of reaction chambers, the instrument having a plurality of filters, the method comprising:

depositing a first reference standard into a first of the plurality of reaction chambers in the microplate, the first reference standard outputting a first reference standard signal;

depositing a sample aliquot and at least one dye into a second of the plurality of reaction chambers, the sample aliquot having at least a portion of a polynucleotide sample, the dye outputting a data signal representative of the polynucleotide sample;

subjecting the sample aliquot and the first reference standard to a testing regimen, wherein the polynucleotide sample in the sample aliquot is amplified, the first reference standard signal is emitted from the first of the plurality of reaction chambers containing the first reference standard, and the data signal is emitted from the second of the plurality of reaction chambers;

collecting and analyzing the first reference standard signal relative to a predetermined level to generate a normalization bias; and normalizing the data signal relative to the normalization bias.

2. The method according to claim 1, further comprising:

depositing a second reference standard into a second of the plurality of reaction chambers in the microplate, the second reference standard outputting a second reference standard signal.

3. The method according to claim 2 wherein the collecting and analyzing the first reference standard signal relative to a predetermined level to generate a normalization bias comprises collecting and analyzing the first and second reference standard signals relative to a predetermined level to generate a normalization bias.

4. The method according to claim 1 wherein the at least one dye comprises a series dilution.

5. The method according to claim 1 wherein the at least one dye comprises multiple titration points.

6. The method according to claim 1 wherein the at least one dye comprises dye ladders.

7. The method according to claim 1 further comprises performing reverse transcription on the sample aliquot.

8. A method of normalizing data output from an instrument, the instrument using a microplate having a plurality of reaction chambers, the method comprising:

providing a first of the plurality of reaction chambers in the microplate, the first of the plurality of reaction chambers being free from a fluorescing substance;

depositing a sample aliquot and at least one dye into a second of the plurality of reaction chambers, the sample aliquot having at least a portion of a polynucleotide sample, the dye outputting a data signal in response to the polynucleotide sample;

collecting and analyzing a signal from the first of the plurality of reaction chambers to determine a level of background correction to generate a normalization bias; and normalizing the data signal relative to the normalization bias.

9. The method according to claim 8, further comprising:

depositing a non-template control in the first of the plurality of reaction chambers.

10. The method according to claim 8 wherein the at least one dye comprises a series dilution.

11. The method according to claim 8 wherein the at least one dye comprises multiple titration points.

12. The method according to claim 8 wherein the at least one dye comprises dye ladders.

13. A method of normalizing data output from an instrument, the instrument using a microplate having a plurality of reaction chambers, the method comprising:

depositing a first control into a first of the plurality of reaction chambers in the microplate, the first control outputting a first control signal, the first of the plurality of reaction chambers being free of a polynucleotide sample;

depositing a sample aliquot and at least one dye into a second of the plurality of reaction chambers, the sample aliquot having at least a portion of a polynucleotide sample, the dye outputting a data signal in response to the polynucleotide sample;

collecting and analyzing the first control signal relative to a predetermined level to generate a normalization bias; and normalizing the data signal relative to the normalization bias.

14. The method according to claim 13, further comprising:

depositing a non-template control in the first of the plurality of reaction chambers.

15. The method according to claim 13 wherein the at least one dye comprises a series dilution.

16. The method according to claim 13 wherein the at least one dye comprises multiple titration points.

17. The method according to claim 13 wherein the at least one dye comprises dye ladders.

* * * * *